US008710195B2

(12) United States Patent
Inouye

(10) Patent No.: US 8,710,195 B2
(45) Date of Patent: *Apr. 29, 2014

(54) FLUORESCENT PROTEINS

(75) Inventor: Satoshi Inouye, Kanagawa (JP)

(73) Assignee: JNC Corporation, Tokyo (JP)

( * ) Notice: Subject to any disclaimer, the term of this patent is extended or adjusted under 35 U.S.C. 154(b) by 1623 days.

This patent is subject to a terminal disclaimer.

(21) Appl. No.: 10/567,857

(22) PCT Filed: Aug. 12, 2004

(86) PCT No.: PCT/JP2004/011870
§ 371 (c)(1),
(2), (4) Date: Dec. 5, 2006

(87) PCT Pub. No.: WO2005/014633
PCT Pub. Date: Feb. 17, 2005

(65) Prior Publication Data
US 2011/0070656 A1    Mar. 24, 2011

(30) Foreign Application Priority Data

Aug. 12, 2003  (JP) ................................ 2003-207397
Mar. 3, 2004    (JP) ................................ 2004-059611

(51) Int. Cl.
*C07K 1/13*       (2006.01)
*G01N 33/533*  (2006.01)
*C07D 241/00*  (2006.01)

(52) U.S. Cl.
USPC ............ 530/400; 436/546; 530/409; 544/336

(58) Field of Classification Search
None
See application file for complete search history.

(56) References Cited

U.S. PATENT DOCUMENTS

| 5,139,937 A | 8/1992 | Inouye et al. |
| 7,241,864 B2 | 7/2007 | Inouye |
| 2003/0212259 A1 | 11/2003 | Inouye |

FOREIGN PATENT DOCUMENTS

| EP | 0 303 817 A2 | 2/1989 |
| EP | 0 316 933 | 5/1989 |
| JP | 61-135586 | 6/1986 |
| JP | 64-047379 | 2/1989 |
| JP | 01-132397 | 5/1989 |
| JP | 2001-270899 | 10/2001 |
| JP | 2004-000143 | 1/2004 |
| JP | 2004-035449 | 2/2004 |
| JP | 2004-061281 | 2/2004 |
| JP | 2004-156017 | 6/2004 |
| WO | WO 97/29319 | 8/1997 |

OTHER PUBLICATIONS

Kurose et al. Bioluminescence of the Ca2+ -binding photoprotein aequorin after cystein modification. PNAS 1989, vol. 86, pp. 80-84.*
European Search Report, dated Sep. 5, 2007, from corresponding application EP 04 77 1831.

Hirano, Takashi et al., *Chemiluminenscence of Coelenterazine Analogues—Structures of Emitting Species*—Tetrahedron Letters, vol. 33, No. 39, pp. 5771-5774, 1992.
Inouye, Satoshi et al., *Aequorea green fluorescent protein Expression of the gene and fluorescence characteristics of the recombinant protein*, FEBS Letters 341 (Mar. 21, 1994) 277-280.
Kojima, Satoshi et al., *Mechanism of the Redox Reaction of the Aequorea Green Fluorescent Protein (GFP)*, Tetrahedron Letters, vol. 38, No. 16, pp. 2875-2878, Apr. 21, 1997.
English Translation of the International Preliminary Report on Patentability for International Application No. PCT/JP2004/011870, dated May 8, 2006, 5 pages.
Head, J. F. et al., "The Crystal Structure of the Photoprotein Aequorin at 2.3 Å Resolution," Nature, vol. 405, pp. 372-376 (2000).
Inouye, S. et al.," Overexpression and Purification of the Recombinant $Ca^{2+}$-Binding Protein, Apoaequorin," vol. 105, No. 3, pp. 473-477 (1989).
Inouye, S. et al., "High-Level Expression and Purification of Apoaequorin," vol. 2, No. 2, pp. 122-126 (1991).
Inouye, S., "Calcium-Activated Photoprotein Aequorin," Wako Junyaku Jihou, vol. 69, No. 4, pp. 24-26 (2001).
Inouye, S. et al., "Structure of Calcium-Activated Photoprotein Aequorin," Protein, Nucleic Acid and Enzyme, vol. 46, No. 3, pp. 220-227 (2001).
Inouye, S., "Technique of Biophoton 'Aequorin'," Japan Energy and Technology Intelligence, vol. 51, No. 7, pp. 10-13 (2003).
Notice of Reasons of Rejection mailed Jan. 5, 2010, in corresponding Japanese Patent Application No. 2005-513049 (5 pages), and English language translation thereof (5 pages).
Notice of Reasons of Rejections mailed Feb. 22, 2011, in corresponding Japanese Patent Application No. 2005-513049 (7 pages), and English language translation thereof (8 pages).
Shimomura, O., "Cause of Spectral Variation in the Luminescence of Semisynthetic Aequorins," Biochem. J., vol. 306, pp. 537-543 (1995).
Shimomura, O. et al., "Calcium Binding, Quantum Yield, and Emitting Molecule in Aequorin Bioluminescence," Nature, vol. 227, pp. 1356-1357 (Sep. 1970).
Shimomura, O. et al., "Regeneration of the Photoprotein Aequorin," Nature, vol. 256, pp. 236-238 (Jul. 1975).
Shimomura, O. et al., "The in Situ Regeneration and Extraction of Recombinant Aequorin from *Escherichia coli* Cells and the Purification of Extracted Aequorin," Protein Expression and Purification, vol. 16, pp. 91-95 (1999).
Shimomura, O. et al., "Chemical Nature of the Light Emitter in Bioluminescence of Aequorin," Tetrahedron Letters, No. 31, pp. 2963-2966 (1973).

* cited by examiner

*Primary Examiner* — Shafiqul Haq
(74) *Attorney, Agent, or Firm* — Finnegan, Henderson, Farabow, Garrett & Dunner, LLP

(57) ABSTRACT

A fluorescent protein (bFP) having chemiluminescence activity is a complex composed of the apoprotein of a calcium-binding photoprotein, coelenteramid or an analog thereof, and calcium ions or divalent or trivalent ions that can be substituted for the calcium ions. In the complex, the ratio of the number of molecules of the apoprotein to that of the coelenteramid is 1:1 and the ratio of the number of molecules of the apoprotein to that of the divalent or trivalent ions is 1:1 to 1:4. The fluorescent protein is used as a marker because it catalyzes luminescence of coelenterazine and has fluorescence capability. Removal of calcium ions etc. from this fluorescent protein (bFP) having luminescence activity provides a novel fluorescent protein (gFP). Mixing this gFP with the coelenterazine provides a calcium-binding photoprotein, which emit light instantaneously, enabling use as a marker.

21 Claims, 4 Drawing Sheets

SEQUENCE LISTING

<160> NUMBER OF SEQ ID NOS: 4

<210> SEQ ID NO 1
<211> LENGTH: 189
<212> TYPE: PRT
<213> ORGANISM: Aequorea aequorea
<220> FEATURE:
<223> OTHER INFORMATION: Inventor: Inouye, Satoshi

<400> SEQUENCE: 1

Val Lys Leu Thr Ser Asp Phe Asp Asn Pro Arg Trp Ile Gly Arg His
1               5                   10                  15

Lys His Met Phe Asn Phe Leu Asp Val Asn His Asn Gly Lys Ile Ser
            20                  25                  30

Leu Asp Glu Met Val Tyr Lys Ala Ser Asp Ile Val Ile Asn Asn Leu
        35                  40                  45

```
Gly Ala Thr Pro Glu Gln Ala Lys Arg His Lys Asp Ala Val Glu Ala
        50                  55                  60

Phe Phe Gly Gly Ala Gly Met Lys Tyr Gly Val Glu Thr Asp Trp Pro
 65                  70                  75                  80

Ala Tyr Ile Glu Gly Trp Lys Lys Leu Ala Thr Asp Glu Leu Glu Lys
                 85                  90                  95

Tyr Ala Lys Asn Glu Pro Thr Leu Ile Arg Ile Trp Gly Asp Ala Leu
                100                 105                 110

Phe Asp Ile Val Asp Lys Asp Gln Asn Gly Ala Ile Thr Leu Asp Glu
            115                 120                 125

Trp Lys Ala Tyr Thr Lys Ala Ala Gly Ile Ile Gln Ser Ser Glu Asp
        130                 135                 140

Cys Glu Glu Thr Phe Arg Val Cys Asp Ile Asp Glu Ser Gly Gln Leu
145                 150                 155                 160

Asp Val Asp Glu Met Thr Arg Gln His Leu Gly Phe Trp Tyr Thr Met
                165                 170                 175

Asp Pro Ala Cys Glu Lys Leu Tyr Gly Gly Ala Val Pro
            180                 185

<210> SEQ ID NO 2
<211> LENGTH: 195
<212> TYPE: PRT
<213> ORGANISM: Obelia longissima

<400> SEQUENCE: 2

Met Ser Ser Lys Tyr Ala Val Lys Leu Lys Thr Asp Phe Asp Asn Pro
  1               5                  10                  15

Arg Trp Ile Lys Arg His Lys His Met Phe Asp Phe Leu Asp Ile Asn
                 20                  25                  30

Gly Asn Gly Lys Ile Thr Leu Asp Glu Ile Val Ser Lys Ala Ser Asp
             35                  40                  45

Asp Ile Cys Ala Lys Leu Glu Ala Thr Pro Glu Gln Thr Lys Arg His
        50                  55                  60

Gln Val Cys Val Glu Ala Phe Phe Arg Gly Cys Gly Met Glu Tyr Gly
 65                  70                  75                  80

Lys Glu Ile Ala Phe Pro Gln Phe Leu Asp Gly Trp Lys Gln Leu Ala
                 85                  90                  95

Thr Ser Glu Leu Lys Lys Trp Ala Arg Asn Glu Pro Thr Leu Ile Arg
                100                 105                 110

Glu Trp Gly Asp Ala Val Phe Asp Ile Phe Asp Lys Asp Gly Ser Gly
            115                 120                 125

Thr Ile Thr Leu Asp Glu Trp Lys Ala Tyr Gly Lys Ile Ser Gly Ile
        130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
                180                 185                 190

Gly Val Pro
        195

<210> SEQ ID NO 3
<211> LENGTH: 198
<212> TYPE: PRT
<213> ORGANISM: Clytia gregarium
```

```
<400> SEQUENCE: 3

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 4
<211> LENGTH: 198
<212> TYPE: PRT
<213> ORGANISM: Mitrocoma cellularia

<400> SEQUENCE: 4

Met Ser Met Gly Ser Arg Tyr Ala Val Lys Leu Thr Thr Asp Phe Asp
1               5                   10                  15

Asn Pro Lys Trp Ile Ala Arg His Lys His Met Phe Asn Phe Leu Asp
            20                  25                  30

Ile Asn Ser Asn Gly Gln Ile Asn Leu Asn Glu Met Val His Lys Ala
        35                  40                  45

Ser Asn Ile Ile Cys Lys Lys Leu Gly Ala Thr Glu Glu Gln Thr Lys
50                  55                  60

Arg His Gln Lys Cys Val Glu Asp Phe Phe Gly Gly Ala Gly Leu Glu
65                  70                  75                  80

Tyr Asp Lys Asp Thr Thr Trp Pro Glu Tyr Ile Glu Gly Trp Lys Arg
                85                  90                  95

Leu Ala Lys Thr Glu Leu Glu Arg His Ser Lys Asn Gln Val Thr Leu
            100                 105                 110

Ile Arg Leu Trp Gly Asp Ala Leu Phe Asp Ile Ile Asp Lys Asp Arg
        115                 120                 125

Asn Gly Ser Val Ser Leu Asp Glu Trp Ile Gln Tyr Thr His Cys Ala
130                 135                 140

Gly Ile Gln Gln Ser Arg Gly Gln Cys Glu Ala Thr Phe Ala His Cys
145                 150                 155                 160
```

```
Asp Leu Asp Gly Asp Gly Lys Leu Asp Val Asp Glu Met Thr Arg Gln
                165                 170                 175
His Leu Gly Phe Trp Tyr Ser Val Asp Pro Thr Cys Glu Gly Leu Tyr
            180                 185                 190
Gly Gly Ala Val Pro Tyr
        195
```

FLUORESCENT PROTEINS

CROSS REFERENCE TO RELATED APPLICATIONS

This application claims the benefit of priority to Japan Patent Application No. 2003-207397, filed on Aug. 12, 2003, and Japan Patent Application No. 2004-59611, filed on Mar. 3, 2004, which are incorporated herein by reference.

TECHNICAL FIELD

The present invention relates to two kinds of proteins generated from calcium-binding photoproteins. More particularly, it relates to a fluorescent protein having chemiluminescence activity that can be used as a photogen in the field of amusement or as a marker in biological experiments, and to another fluorescent protein formed from the protein.

First, the present invention relates to a novel complex that not only has function (enzymatic function) to make a luminescence substrate emit light but also emits fluorescence in response to excitation of light, i.e., a novel fluorescent protein having chemiluminescence activity. This fluorescent protein (hereinafter described as bFP) can be obtained by reacting a calcium ion-binding photoprotein with calcium ions etc. extremely slowly. This fluorescent protein is composed of coelenteramid or its analog coordinated inside the apoprotein of a calcium-binding photoprotein and calcium ions etc. bound to this apoprotein. The term "fluorescent protein," as used herein, means a "complex that emits fluorescence in response to excitation of light," as described above.

The other protein is another novel fluorescent protein (hereinafter described as gFP) obtained by removing calcium ions etc. from the above-mentioned fluorescent protein (bFP) having chemiluminescence activity. Since this fluorescent protein (gFP) turns into a calcium-binding photoprotein by mixing it with coelenterazine or its analog, it can be used as a marker in biological experiments.

BACKGROUND ART

A representative bioluminescence reaction is the oxidation reaction of a luminescent substrate, "luciferin" (a low-molecular organic compound), catalyzed by an enzyme (protein) called "luciferase." Luminescence is the release of energy in the form of light (photons), produced when excited oxyluciferin molecules generated immediately after the oxidation reaction of luciferin return to the ground state. Thus, luminescence in which molecules formed by reaction are excited by chemical reaction energy and emit visible light when returning from the excited state to the ground state is called chemiluminescence. In almost all cases, this chemical reaction is an oxidation reaction.

On the other hand, fluorescence is the phenomenon in which a certain kind of substance absorbs the energy of light such as ultraviolet radiation or visible light and emits light. In this process, energy produced when excited molecules return to the ground state by absorption of light energy is released as light (photons). Thus, prompt reemission of excitation energy absorbed by energy-absorbing functional groups (fluorescence chromophores) as light (photons) is fluorescence.

However, the presence of substances having both chemiluminescence activity and fluorescence-generating ability has not yet been known. If such a substance is created, both measurement or detection using chemiluminescence and measurement or detection using fluorescence will become possible in the same molecules. Undoubtedly, that will make a significant contribution to industry.

In addition, chemilumimescent enzymes isolated so far are unstable to heat. For example, when treated at 90° C. for 5 min, they have lost chemiluminescence activity and never been recovered. Development of a heat-resistant chemilumimescent enzyme has been strongly desired. Meanwhile, calcium ion-binding photoproteins react specifically with calcium or strontium ions etc. and emit light instantaneously. Currently, aequorin, clytin, obelin, mitrocomin, mineopsin, bervoin, etc. are known as the calcium ion-binding photoprotein family. Table 1 lists the calcium ion-binding photoproteins whose apoprotein has been isolated.

TABLE 1

| Name | Species, scientific name | GeneBank Acc. No. | Authors (year) |
|---|---|---|---|
| Aequorin | Aequorea victoria | L29571 | Inouye et al. (1985) |
| Aequorin | Aequorea victoria | | Charbonnueau et al. (1985) |
| Aequorin | Aequorea victoria | M16103 | Prasher et al. (1987) |
| Aequorin | Aequorea parva | AY013822 | Luo et al. (2000) |
| Aequorin | Aequorea macrodactyla | AY013823 | Luo et al. (2000) |
| Clytin (=Phialidin) | Clytia(=Phialidium) gregarium | L13247 | Inouye & Tsuji (1993) |
| Mitrocomin (=Halistarin) | Mitrocoma(=Halistaura) cellularia | L31623 | Fagan et al. (1993) |
| Obelin | Obelia longissima | U07128 | Illarionov et al. (1995) |
| Obelin | Obelia geniculata | AF394688 | Markova et al. (2002) |

Among the calcium-binding photoproteins, aequorin has been studied especially in detail. Aequorin is a protein complex that binds specifically only with a trace amount of calcium ions and emits light instantaneously. It has been clarified from the crystal structures analyzed with X ray that aequorin is present as a complex (coelenterazine peroxide) composed of apoaequorin (apoprotein), which is the protein portion consisting of 189 amino acids, coelenterazine corresponding to a luminescent substrate, and molecular oxygen (Head, J. F., Inouye, S., Teranishi, K. and Shimomura, O. (2000) Nature, 405, 372-376). The light-emitting reaction and regeneration reaction of aequorin are shown below.

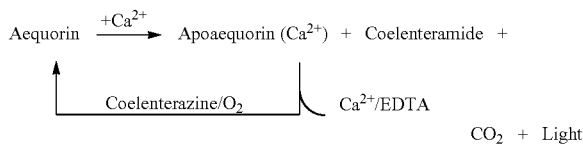

That is, when calcium ions bind to aequorin, a blue light (maximum wave length: 465-470 nm) emission takes place instantaneously; coelenteramid, an oxide of a coelenterazine, dissociates from apoaequorin; and carbon dioxide is released. (Shimomura, O. and Johnson, F. H. (1975) Nature 256, 236-238).

On the other hand, apoaequorin that has bound to calcium ions and emitted light can be regenerated to aequorin having instantaneous light-emitting ability. This regeneration is realized by dissociating calcium ions bound to apoaequorin with a chelating agent such as EDTA and incubating with coelenterazine and oxygen in the presence of a reducing agent (dithiothreitol, 2-mercaptoethanol, etc.) at low temperatures (Shimomura, C. and Johnson, F. H (1970), Nature, 227, 1356-1357).

It has been reported that feeble continuous luminescence is observed in process of the experiment in which natural aequorin is reacted with calcium ions and caused to emit light, and subsequently regenerated to aequorin in the presence of a chelating agent, a reducing agent, and coelenterazine that a luminescent substrate (Shimomura, O. and Johnson, F. H. (1975) Nature 256, 236-238). Further, it has been predicted that a molecular species exhibiting feeble luciferase-like activity would be present in a aequorin solution after having emitted light. However, as to substances involved in feeble luminescence predicted to be present after the light-emitting reaction, participation of complexes etc. of calcium-apoaequorin-coelenteramid, apoaequorin-coelenteramid, and calcium-apoaequorin was not confirmed. In addition, the amount of coelenteramid that is still present after a light-emitting reaction was 17% for natural apoaequorin and 33% for recombinant apoaequorin. That is, although the presence of the complex of calcium ion-apoaequorin-coelenteramid was predicted, it was not isolated and purified, or confirmed. As for the mechanism of feeble continuous luminescence, calcium-apoaequorin-coelenteramid, apoaequorin-coelenteramid, and calcium-apoaequorin have not been isolated or identified, either. The presence of these complexes was not predicted based on the precise fact, and was only speculated (Shimomura, O. (1995) Biochem. J. 306, 537-543).

On the other hand, the inventors have already reported that the mere addition of coelenterazine to calcium-bound apoaequorin (calcium-apoaequorin) without coelenteramid exhibits feeble continuous luminescence (Japanese Laid-Open Application No. 1989-47379). However, it has not been known what kind of substance it is that emits feeble luminescence.

An object of the present invention is to provide a novel luminescent substance and a novel fluorescent substance. It turned out, surprisingly, that the substances produced for that purpose are the first that have both chemiluminescence activity and fluorescence-generating ability.

Accordingly, the first object of the present invention is to provide a fluorescent protein having chemiluminescence activity. Specifically, it is to provide a novel fluorescent protein (bFP) having chemiluminescence activity, generated from a calcium-binding photoprotein, and further, a method for producing such a protein together with its specific use.

The second object is to produce another novel fluorescent protein (gFP) from the fluorescent protein (bFP) having chemiluminescence activity and to provide its specific use.

DISCLOSURE OF THE INVENTION

Fluorescent Protein Having Chemiluminescence Activity

The present invention provides a novel fluorescent protein having chemiluminescence activity (enzyme activity). This is the substance based on a novel concept, which has never existed before, having the activity catalyzing light-emitting reaction of a luminescent substrate combined with fluorescence-generating ability.

This novel substance is extremely useful in industry because of having both chemiluminescence activity and fluorescence-generating ability, enabling both measurement or detection using chemiluminescence and measurement or detection using fluorescence in one substance. To be specific, it is possible to, while measuring the intensity of fluorescence emitted by irradiating excitation light, measure that luminescence intensity by adding a luminescent substrate to the same sample. For example, both of the following methods for detecting a target substance will be possible: (a) a ligand (e.g., an antibody, biotin, a receptor, etc.) for the target substance to be detected is bound to the fluorescent protein having chemiluminescence activity according to the present invention, the fluorescent protein is bound to the target substance to be detected via the ligand, and then a luminescent substrate is added, so that generated light is detected. (b) excitation light is irradiated, so that generated fluorescence can is detected. Use of these two kinds of highly-sensitive detection systems will realize detection, tracking, and so forth of the target substance.

The substance that is specifically prepared in the present invention is derived from a calcium-binding photoprotein, and its fluorescence spectrum is identical to the emission spectrum of the originating photoprotein.

The specific fluorescent protein (bFP) having a chemiluminescence activity provided by the present invention is composed of the apoprotein of a calcium-binding photoprotein, coelenteramid or its analog, and calcium ions or divalent or trivalent ions that can be substituted for the calcium ions. In the complex of apoprotein and coelenteramid or its analog, the ratio of the number of molecules of the former to that of the latter is preferably 1:1. In the complex of apoprotein and calcium ions or divalent or trivalent ions that can be substituted for the calcium ions, the ratio of the number of molecules of the former to that of the latter is preferably 1:1 to 1:4, more preferably 1:2 to 1:3.

The apoprotein of a calcium-binding photoprotein constituting the fluorescent protein (bFP) having a desirable chemiluminescence activity is selected from the group consisting of apoaequorin, apoclytin, apoobelin, apomitrocomin, apomineopsin, and apobervoin.

Apoaequorin, apoclytin, apoobelin, and apomitrocomin have the amino acid sequences of SEQ ID NOs: 1, 2, 3, and 4, respectively, in the sequence listing. These may be mutants in which one or more amino acids are deleted, substituted, or added in the sequences in the sequence listing. The apoprotein of a calcium-binding photoprotein may be a mutant apoprotein in which at least one of at least two free sulfhydryl groups possessed by the apoprotein may be substituted with a hydroxyl group so that disulfide bonds cannot be formed.

Coelenteramid or its analog constituting the fluorescent protein (bFP) having chemiluminescence activity is represented by the following formula (1) or (2):

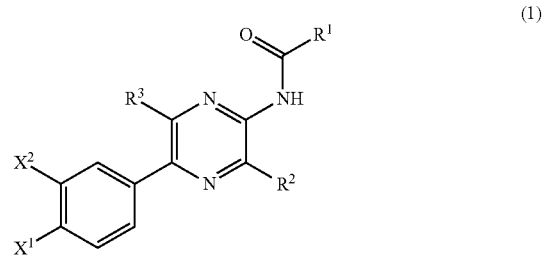

(1)

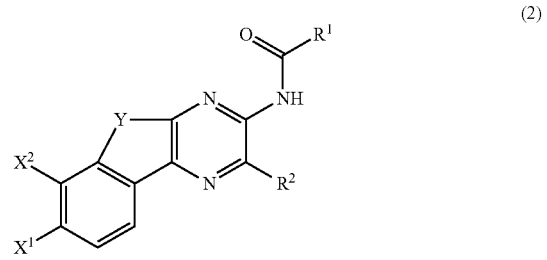

(2)

wherein $R^1$ is a substituted or unsubstituted aryl group, a substituted or unsubstituted arylated alkyl group, or a straight or branched chain alkyl group that may be substituted by an aliphatic cyclic group; preferably an unsubstituted aryl group, an unsubstituted-arylated alkyl group, an arylated alkyl group substituted by a hydroxyl group or a halogen atom, or a straight or branched chain alkyl group that may be substituted by a cyclohexyl group; and more preferably a phenyl group, a benzyl group, a p-hydroxybenzyl group, a p-fluorobenzyl group, a p-chlorobenzyl group, a p-bromobenzyl group, a p-iodinebenzyl group, a 3,4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group.

$R^2$ is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group; preferably an unsubstituted aryl group, an aryl group substituted by a hydroxyl group, an unsubstituted arylated alkyl group, an arylated alkyl group substituted with a hydroxyl group, an unsubstituted aryl alkenyl group, an unsubstituted straight or branched chain alkyl group, a straight chain alkyl group that may be substituted by an aliphatic cyclic group, a branched chain alkenyl group, a heterocyclic group containing sulfur; and more preferably a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

$R^3$ is a hydrogen atom, a substituted or unsubstituted alkyl group, preferably a hydrogen atom, a methyl group, or 2-hydroxyethyl group.

$X^1$ is a hydrogen atom, a hydroxyl group, a halogen atom, an alkoxyl group, or an amino group, particularly preferably a hydrogen atom, a hydroxyl group, a fluorine atom, a methoxy group, or an amino group.

$X^2$ is a hydrogen atom or a hydroxyl group.

Y is a divalent hydrocarbon group having 1 to 4 carbon atoms, preferably a methylene group, ethylene group, a propylene group, or a vinylene group.

Calcium ions or divalent or trivalent ions that can be substituted for the calcium ions constituting the fluorescent protein (bFP) having chemiluminescence activity according to the present invention is preferably calcium ions, strontium ions, and lead ions.

The present invention provides a fluorescent protein (bFP) having chemiluminescence activity, in which a ligand for a target substance to be detected is bound to the a poprotein of a calcium-binding photoprotein. This ligand can be covalently bound to a free sulfhydryl group or amino group of an a poprotein either directly or via a spacer, but the binding method is not limited thereto.

The fluorescent protein (bFP) having chemiluminescence activity according to the present invention is caused to emit light by catalytically degrading coelenterazine or its analog. The light-emitting reaction lasts longer in the presence of a reducing agent.

Coelenterazine or its analog used for the light-emitting reaction is represented in the following formula (3) or (4):

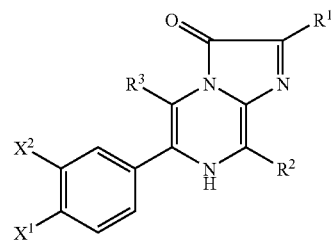

(3)

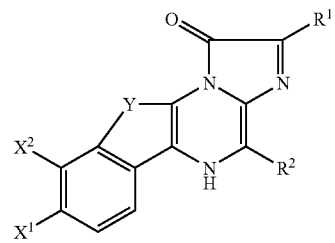

(4)

($R^1, R^2, R^3, X^1, X^2$ and Y in the formulas are identical to those in formulae (1) and (2)).

When detecting a target substance using a fluorescent protein, the fluorescent protein having chemiluminescence activity to which the ligand for the target substance to be detected is bound to the target substance via the ligand, a luminescent substrate is added to trigger light emission, and at the same time fluorescence is used for detecting the target substance.

The fluorescent protein (bFP) having chemiluminescence activity according to the present invention can have its thermal stability enhanced by adding a reducing agent into its solution. A particularly preferred reducing agent is dithiothreitol or mercaptoethanol.

The present invention provides a luminescence kit that combines a fluorescent protein (bFP) having chemiluminescence activity with coelenterazine or its analog. At least one of the reagents containing the fluorescent protein (bFP) having chemiluminescence activity or a coelenterazine or its analog included in the kit preferably contains a reducing agent. However, the reducing agent may be provided as an independent reagent of the aforementioned reagents in the kit. The luminescence kit may be used in the field of amusement, but the field of use is not limited thereto.

The present invention provides methods for producing a fluorescent protein (bFP) having chemiluminescence activity. The fluorescent protein (bFP) having chemiluminescence activity according to the present invention can be produced by reacting under gentle conditions a calcium-binding photoprotein with a solution of calcium ions or divalent or trivalent ions that can be substituted for the calcium ions.

"Gentle conditions," as used herein refers to conditions in which the reaction is performed such that substantially all of the coelenteramid or its analog formed remains coordinated into the apoprotein to substantially prevent de novo formation of disulfide bonds. The fluorescent protein (bFP) can be produced by, for example, reacting a calcium-binding photoprotein with a solution of $10^{-7}$ M or less of calcium ions or divalent or trivalent ions that can be substituted for the calcium ions.

The fluorescent protein (bFP) having the chemiluminescence activity according to the present invention can also be produced by reacting a solution of calcium ions or divalent or trivalent ions that can be substituted for the calcium ions with a fluorescent protein (gFP) consisting of the apoprotein of a calcium-binding photoprotein and coelenteramid or its analog, which will be described later.

Fluorescent Protein (gFP)

The present invention further provides a novel fluorescent protein (gFP) that can be formed from a fluorescent protein (bFP) having chemiluminescence activity and that does not contain calcium ions. The fluorescent protein (gFP) consists of the apoprotein of a calcium-binding photoprotein and coelenteramid or its analog. In the complex of an apoprotein and coelenteramid or its analog, the molar ratio of the number of molecules of the former to that of the latter is preferably, 1:1.

The apoprotein of a calcium-binding photoprotein that constitutes a fluorescent protein (gFP) is the same as explained above as the apoprotein of a fluorescent protein (bFP) having chemiluminescence activity, which was previously mentioned. Coelenteramid or its analog that constitutes a fluorescent protein (gFP) is the same as explained above for a fluorescent protein (bFP) having chemiluminescence activity, which was previously mentioned.

The present invention also provides a fluorescent protein (gFP) in which, when detecting a target substance, a ligand for the target substance to be detected is bound to the apoprotein of a calcium-binding photoprotein. The ligand can be covalently bound to a free sulfhydryl group or amino group of an apoprotein either directly or via a spacer.

When the fluorescent protein (gFP) according to the present invention reacts with calcium ions or ions that can be substituted for the calcium ions, the wavelength of the fluorescence emitting light changes. Taking advantage of such changes in fluorescence wavelength therefore enables detection and quantification of calcium ions or ions that can be substituted for the calcium ions. Thus, the present invention provides reagents for detection and quantification of calcium ions or ions that can be substituted for the calcium ions, including a fluorescent protein (gFP)

Making coelenterazine or its analog react on the fluorescent protein (gFP) according to the present invention turns the protein into a calcium-binding photoprotein. The present invention can therefore provide a method for producing a calcium-binding photoprotein in which coelenterazine or its analog is made to react on the fluorescent protein (gFP). In this production method, it is desirable to make them react in the presence of a reducing agent.

Coelenterazine or its analog used for the production method of a calcium-binding photoprotein is the same as explained for the previously-mentioned fluorescent protein (bFP) having chemiluminescence activity.

A kit for producing a calcium-binding photoprotein, which combines the fluorescent protein (gFP) according to the present invention with coelenterazine or its analog, is provided. At least one of the reagents containing the fluorescent protein (gFP) or a coelenterazine or its analog in the calcium-binding photoprotein production kit preferably contains a reducing agent. However, the reducing agent may be provided as an independent reagent in the kit.

In detecting a target substance using a fluorescent protein (gFP), binding of the fluorescent protein (gFP) to which a ligand for the target substance to be detected has been bound to the target substance to be detected via the ligand and then adding of coelenterazine or its analog results in formation of a calcium-binding photoprotein. Subsequent addition of calcium ions or divalent or trivalent ions that can be substituted for the calcium ions makes the calcium-binding photoprotein emit light instantaneously. This instantaneous light emission can be used as a marker in detection of a target substance. Further, since a fluorescent protein (gFP) that remains unreacted has fluorescence-generating ability, it is possible to continue detection of a target substance by using the fluorescence.

The fluorescent protein (gFP) according to the present invention may be produced by treating the previously-described fluorescent protein (bFP) having chemiluminescence activity (a protein complex composed of the apoprotein of a calcium-binding photoprotein, coelenteramid or its analog, and calcium ions or divalent ions that can be substituted for the calcium ions) with a chelating agent to remove calcium ions or divalent ions that can be substituted for the calcium ions.

Relationship among a Fluorescent Protein (bFP) Having Chemiluminescence Activity, a Fluorescence Protein (gFP), and Aequorin A fluorescent protein (bFP) having chemiluminescence activity, a fluorescence protein (gFP), and aequorin will be explained using FIG. 4. In the figure, CTM, CTZ, and EDTA represent coelenteramid, coelenterazine, and ethylenediaminetetraacetic acid, respectively.

Aequorin is a kind of calcium-binding photoprotein and present as a complex (coelenterazine peroxide) composed of molecular oxygen and coelenterazine coordinated inside apoaequorin that is an apoprotein. To produce the fluorescent protein (bFP) having chemiluminescence activity according to the present invention, an aequorin solution is overlaid with an extremely weak calcium ion solution and reacted for typically 24 hours or longer, though time required until completion of a reaction varies depending on the quantity of the protein. In this case, aequorin continues to emit feeble light and coelenterazine, the substrate, is decomposed into coelenteramid and carbon dioxide.

The fluorescent protein (bFP) having chemiluminescence activity according to the present invention is obtained by making calcium ions react on aequorin under extremely gentle conditions; the product obtained is different from that when aequorin is caused to instantaneously emit light, as conventionally performed. Aequorin caused to instantaneously emit light, as conventionally performed, reacts with excessive calcium ions all at once. In this case, a rapid change occurs in the conformation of apoaequorin that is an apoprotein, preventing most of the coelenteramid from remaining inside the apoaequorin. However, in the fluorescent protein (bFP) having chemiluminescence activity obtained under extremely gentle conditions according to the present invention, the coelenteramid remains coordinated inside the apoaequorin, so that the ratio of the number of molecules is 1:1 in the complex.

Treatment of a fluorescent protein (bFP) having chemiluminescence activity with EDTA results in the removal of calcium ions to provide an fluorescent protein (gFP). Addition of calcium ions to the resulting fluorescent protein (gFP) returns it to the original fluorescent protein (bFP) having chemiluminescence activity. Addition of coelenterazine to this fluorescent protein (gFP) causes substitution of the coelenteramid within apoaequorin for coelenterazine to form aequorin. This aequorin is capable of emitting light instantaneously upon reaction with calcium ions.

The wavelengths of fluorescence radiated from a fluorescent protein (bFP) having chemiluminescence activity and a fluorescent protein (gFP) formed by removing the calcium ion etc. from bFP, from a bFP are determined depending on the kind of the chromophore contained in them, i.e., coelenteramid or its analog.

Addition of coelenterazine to a fluorescent protein (bFP) having chemiluminescence activity triggers a light-emitting reaction in the fluorescent protein (bFP). In this case, the coelenterazine added is incorporated into the apoaequorin to be catalytically oxidized. The persistence time of the luminescence catalytic activity is fairly long, though it depends on the conditions such as the presence or absence of a reducing agent. In the absence of a reducing agent, the sulfhydryl groups in an apoaequorin molecule forms a disulfide bond in a relatively short time to lose its chemiluminescence activity. In the presence of a reducing agent, since disulfide bond formation is inhibited, the chemiluminescence activity continues typically for 2 hours or longer. It is known that mutated aequorin, having a mutated apoaequorin in which cysteine residues are deleted or substituted with other amino acids, has activity equal to that of the wild-type aequorin. It is highly likely that the fluorescent protein (bFP) having chemiluminescence activity prepared from such the mutated aequorin does not require the addition of a reducing agent.

Calcium ions, shown in the figure to be bound to the EF-hands of aequorin, do not need to be bound to all of the three. In addition, calcium ions may be divalent or trivalent ions that can be substituted for them.

BEST MODE FOR CARRYING OUT THE INVENTION

Figure 1:
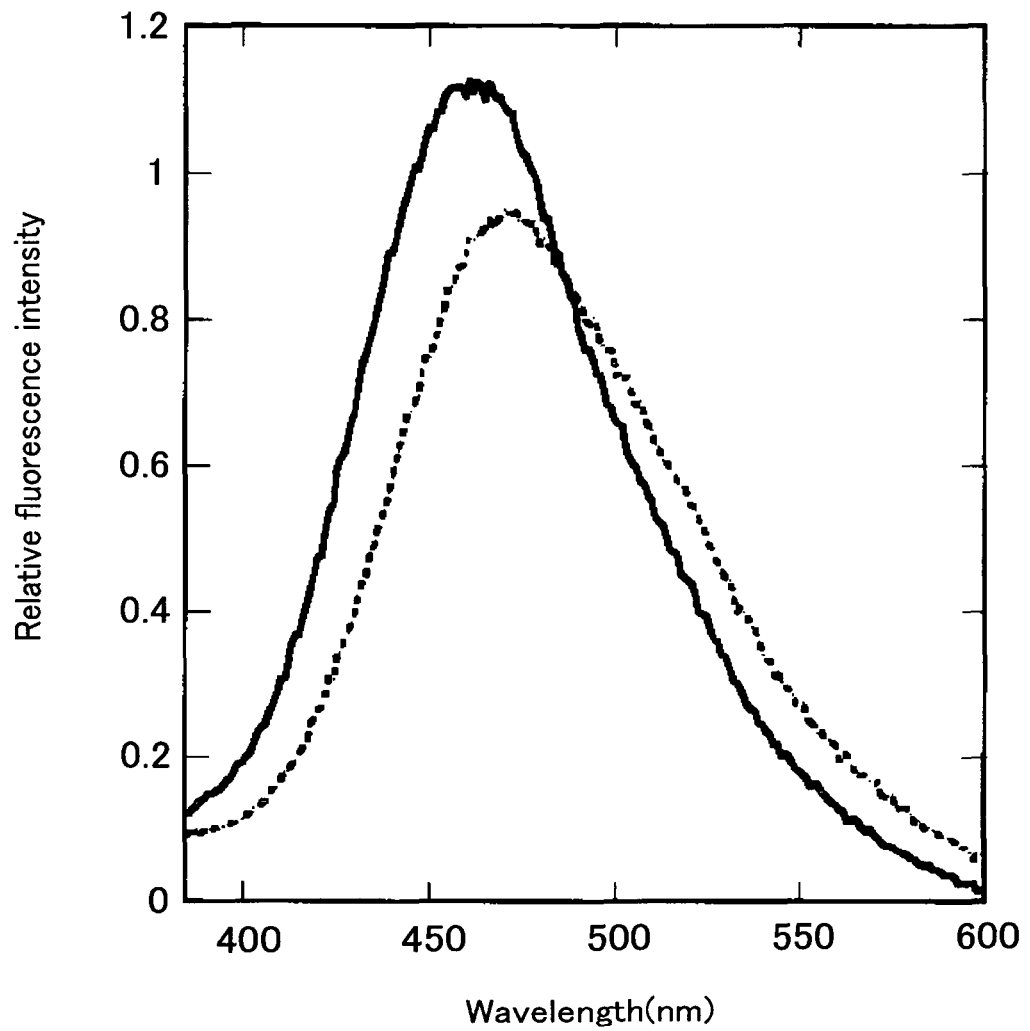
FIG. 1 shows the fluorescence spectrum of bFP-aq (solid line) and the fluorescence spectrum of gFP-aq (dotted line).

1. Fluorescent Protein Having Chemiluminescence Activity
1-1. Composition and Conformation of a Fluorescent Protein (bFP) Having Chemiluminescence Activity Calcium-binding photoproteins are used for detection of calcium by taking advantage of sensitive instantaneous luminescence generated when they encounter calcium ions. In the detection, the calcium-binding photoprotein instantaneously reacts with the calcium ions and the conformation of the apoprotein is changed all at once. As a result, most coelenteramid generated inside the apoprotein is released from the inside of the apoprotein (Shimomura (1995), Biochem J. 306, 537-543). Simultaneously, the free sulfhydryl group of the apoprotein is oxidized to form a disulfide bond. Since conformational change is instantaneous, the composition and conformation of a responsible substance could not be identified, though feeble chemiluminescence activity (luciferase-like activity) or fluorescence-generating ability has been so far detected after causing a calcium-binding photoprotein such as aequorin to emit light using calcium.

The inventors succeeded in identifying a novel fluorescent protein (bFP) having chemiluminescence activity by reacting a calcium-binding photoprotein with calcium ions under the reaction condition completely different from the conventional reaction conditions of a calcium-binding photoprotein with calcium ions, i.e., under an extremely gentle reaction condition.

The fluorescent protein (bFP) having chemiluminescence activity according to the present invention is composed of the apoprotein of a calcium-binding photoprotein, coelenteramid or its analog, and calcium ions or divalent or trivalent ions that can be substituted for the calcium ions. The ratio of the number of molecules in the complex, of the apoprotein to the coelenteramid or its analog, is preferably 1:1. The ratio of the number of molecules in the complex, of the apoprotein to the calcium ions or divalent or trivalent ions that can be substituted for the calcium ions, is preferably 1:1 to 1:4, more preferably 1:2 to 1:3, and still more preferably 1:3. In this complex, coelenteramid or its analog is coordinated inside the apoprotein, and calcium ions are bound mainly to the EF-hands of the apoprotein.

As will be shown in Examples, having an excellent thermal stability as compared with luciferase, a representative photoprotein, the fluorescent protein (bFP) having chemiluminescence activity according to the present invention is applicable to the fields in which luciferase could never be used.

1-2. Production of a Fluorescent Protein (bFP) Having Chemiluminescence Activity A fluorescent protein (bFP) having chemiluminescence activity can be produced by reacting a calcium-binding photoprotein with calcium ions or divalent or trivalent ions that can be substituted by calcium ions under an extremely gentle (i.e., extremely slow in reaction velocity) condition. "Reacting under an gentle condition" in the present invention refers to reacting under conditions such that after a calcium-binding photoprotein is reacted with calcium ions etc., coelenteramid or its analog remains coordinated to the apoprotein and disulfide bonds are not substantially formed.

For example, a highly viscous solution of a calcium-binding photoprotein may be overlaid with an extremely thin solution of calcium ions etc. and reacted at low temperature for a long time. In this case, the reaction temperature is preferably 0 to 30° C., more preferably 4° C. The reaction time is preferably 24 hours or longer, though it varies depending on the concentration of the protein.

On that occasion the concentration of calcium ions is preferably lower. This is because the lower the concentration of calcium ions the less frequently calcium ions contact (react) with a calcium-binding photoprotein. On the contrary, the concentration of a calcium-binding photoprotein solution is preferably higher. This is because the higher the concentration of a protein complex solution the higher the viscosity of the protein complex solution and the more slowly the mixing of the calcium ion solution and the protein complex solution proceeds.

Specifically, an aqueous solution of calcium ions or divalent or trivalent ions that can be substituted for the calcium ions at a concentration of $10^{-7}$ M (mol/l) or lower is added so that its molar ratio to a calcium ion-binding photoprotein is 1 to 4. The molar ratio of ions, such as calcium ions, to a calcium-binding photoprotein may be equal to or greater than the ratio of the number of molecules (e.g., 4 or greater) in the fluorescent protein (bFP) having chemiluminescence activity of interest, as long as the reaction proceeds slowly. To attain reaction conditions required for the present invention, variations in reaction vessel design changes, selection of solvents, and use of a semipermeable membrane, etc. are possible, and the descriptions herein should not be construed as limitations on the scope of the invention.

1-3. Apoprotein that Constitutes a Fluorescent Protein (bFP) Having Chemiluminescence Activity The apoprotein of a calcium-binding photoprotein is used as an apoprotein that constitutes the fluorescent protein (bFP) having chemiluminescence activity according to the present invention. "A calcium-binding photoprotein" as used herein refers to a protein complex that reacts with calcium ions or divalent or trivalent ions equivalent thereto and emits light. The examples include aequorin, clytin, obelin, mitrocomin, mineopsin, and bervoin. These may be either prepared from the nature or produced by genetic engineering. In addition, the amino acid sequence of the calcium-binding photoprotein may be mutated by gene recombination technology, as long as it has the aforementioned luminescence activity.

The amino acid sequence of the apoaequorin that is the apoprotein of naturally-occurring aequorin, is shown in SEQ ID NO: 1 in the sequence listing. Any apoaequorin, besides the one containing amino acid sequence described in SEQ ID NO: 1, can be used even if it is a known or unknown apoaequorin mutant as long as it is capable of constituting a calcium-binding photoprotein. Accordingly, the apoaequorin used in the present invention includes the apoaequorin having the amino acid sequence described in SEQ ID NO: 1 as well as a mutant apoaequorin in which one or more amino acids are deleted, substituted, or added in the amino acid sequence described in SEQ ID NO: 1. One example of a particularly preferred mutant apoaequorin is the one in which the first Val is substituted with Ala-Asn-Ser in SEQ ID NO: 1.

The amino acid sequence of the apoclytin that is the apoprotein of the wild-type clytin, is shown in SEQ ID NO: 2 in the sequence listing. The amino acid sequence of the apoobelin that is the apoprotein of the wild-type obelin, is shown in SEQ ID NO: 3 in the sequence listing. The amino acid sequence of the apomitrocomin that is the apoprotein of the wild-type mitrocomin, is shown in SEQ ID NO: 4 in the sequence listing. These may be mutants in which one or more amino acids are deleted, substituted, or added in each of the sequences.

The fluorescent protein (bFP) having chemiluminescence activity according to the present invention will lose its chemiluminescence activity when the free sulfhydryl groups of cysteine residues in the apoprotein are oxidized to form a disulfide bond. Therefore it is considered that mutated apoproteins, in which free sulfhydryl groups are deleted or substituted, whereby a disulfide bond cannot be formed, never lose its chemiluminescence activity. For example, it is expected that a fluorescent protein (bFP) having its cysteine residue substituted with serine residue sustains its activity because the disulfide bonds is not formed.

1-4. Coelenteramid that Constitutes a Fluorescent Protein (bFP) Having Chemiluminescence Activity.

The coelenteramid or its analog that constitutes the fluorescent protein (bFP) having chemiluminescence activity according to the present invention is represented in the previously-mentioned formula (1) or (2).

Specific preferable compounds as coelenteramid or its analog will be described later.

1-5. Metal Ions that Constitute a Fluorescent Protein (bFP) Having Chemiluminescence Activity Metal ions that bind to the fluorescent protein (bFP) having chemiluminescence activity according to the present invention are calcium ions or divalent or trivalent ions that can be substituted for the calcium ions. "Ions that can be substituted for the calcium ions" as used herein refers to those ions which cause a light-emitting reaction when they react with a calcium-binding photoprotein such as aequorin in place of calcium ions. In other words, they refer to ions that exert the similar function to calcium ions on a calcium-binding photoprotein. Examples of such ions include magnesium ions ($Mg^{2+}$), strontium ions ($Sr^{2+}$), barium ions ($Ba^{2+}$), lead ions ($Pb^{2+}$), cobalt ions ($Co^{2+}$), nickel ions ($Ni^{2+}$), cadmium ions ($Cd^{2+}$), yttrium ions ($Y^{3+}$), lanthanum ions ($La^{3+}$), samarium ions ($Sm^{3+}$), europium ions ($Eu^{3+}$), dysprosium ions ($Dy^{3+}$), thulium ions ($Tm^{3+}$), and yttribium ions ($Yb^{3+}$). Among these, divalent metal ions are preferable and divalent ions of metals other than transition metals (e.g., $Ca^{2+}$, $Sr^{2+}$, and $Pb^{2+}$) are more preferable.

In addition, binding of at least one of each of these ions to the so-called EF-hands of a calcium-binding photoprotein is all that is required, but binding of two or more is preferable and binding of three is particularly preferable.

1-6. Fusion Substance of a Fluorescent Protein Having Chemiluminescence Activity and a Ligand for a Target Substance When detecting a target substance using a fluorescent protein having chemiluminescence activity, the fluorescent protein can be bound to a ligand for a target substance to be detected either directly or via a spacer. A ligand refers to a substance that specifically binds to a substance to be detected (a protein, a peptide, an enzyme, a receptor, an antigen, or an antibody) directly or indirectly when using a fluorescent protein having chemiluminescence activity as a detection marker.

For example, in detecting a receptor, humoral factors (insulin-like hormone, cytokine, TNF, Fas ligand, etc.) that bind to a receptor are the ligand. Further, in detecting a humoral factor, the proteins that constitutes its receptor are the ligand. In detecting a receptor for a drug, the drug is the ligand, and in detecting a drug, the drug receptor is the ligand.

As another example, in detecting an enzyme, its substrate is the ligand, and in detecting the substrate of an enzyme, the enzyme is the ligand. In detecting a single-stranded nucleic acid, a complementary nucleic acid may be the ligand. In detecting another substance that specifically bind to a polysaccharide, the polysaccharide is the ligand. In addition, DNA binding proteins, such as lectin and transcription factors, which can specifically bind to a blood coagulation factor, can also be the ligand.

It is also possible to indirectly detect a substance to be detected. For example, an antibody against a substance to be detected is conjugated by avidin or biotin and their partner, biotin or avidin (or streptavidin), may be used as a ligand. When avidin has been conjugated to an antibody against a target substance to be detected, indirect binding between the target substance and a fluorescent protein can be done using a fluorescent protein having chemiluminescence activity to which biotin has been bound, following binding of the antibody to the target substance.

Thus, a ligand encompasses a wide range of substances bindable either directly or indirectly to a target of detection, but various proteins, biotin, avidin, streptavidin, an antibody, nucleic acids, etc. are preferable.

A ligand can either be directly bound to the apoprotein of the fluorescent protein (bFP) having fluorescence activity according to the present invention or be bound to the apoprotein of a calcium-binding photoprotein, which is the material for production of the fluorescent protein (bFP). That is, a ligand-bound fluorescent protein (bFP) having chemiluminescence activity can be produced by any one of the following: (a) a method for directly binding a ligand to a fluorescent protein (bFP) having chemiluminescence activity; (b) a method for binding a ligand to a calcium-binding protein complex and subsequently making it react with calcium ions etc. slowly; and (c) a method for binding a ligand to an apoprotein and subsequently making it react with coelenterazine or its derivative to obtain a calcium-binding photoprotein, which is then made to react with calcium ions etc. slowly.

Many methods for binding a ligand to a protein have been reported, and any of such methods can be used in the present invention. A ligand can bind via an SH group, a hydroxyl group, an amino group, etc. in the apoprotein. Binding to a ligand may be direct in consideration of the molecular size of the apoprotein and steric hindrance to the ligand, or may be indirect via a linker or a spacer. A binding reagent can be prepared by conjugating a ligand or a ligand and a spacer to N-hydroxy succinimide, 4-nitrophenol, etc. Commercially available reagents such as succinimidyl 6-(biotinamido) hexanoate (NHS-LC-Biotin) and biotin 4-nitrophenylester can be used.

When binding a ligand to a hydroxyl group or an amino group, in order to prevent formation of —S—S— in apoprotein molecules, it is desirable to bind them in the presence of a reducing agent such as mercaptoethanol or dithiothreitol.

A ligand-bound fluorescent protein (bFP) having chemiluminescence activity can be produced by reacting a ligand-bound calcium-binding photoprotein (composed of a ligand-bound apoprotein and coelenterazine) with ions such as calcium ions under an extremely gentle condition as previously described.

1-7. Use of a Fluorescent Protein (bFP) Having Chemiluminescence Activity

The fluorescent protein (bFP) having chemiluminescence activity according to the present invention can be used as a luminescence catalyst because of acting on a luminescent substrate to make it emit light. The chemiluminescent substrate is a coelenterazine or its analog. "An analog of coelenterazine" as used herein refers to a compound, capable of constituting as an apoprotein a calcium-binding photoprotein such as aequorin, like coelenterazine. Specific analogs of coelenterazine are represented in previously-described formula (3) or formula (4).

These coelenterazine and its analogs emit light when being oxidized, when carbon dioxide is emitted, to the corresponding coelenteramid by the catalytic action of the fluorescent protein (bFP) having chemiluminescence activity according to the present invention. Luminescence resulting from addition of coelenterazine or its analog to the fluorescent protein (bFP) having chemiluminescence activity according to the present invention is continuous (sustainable). Luminescence lasts either until all the added coelenterazine is consumed up or until its catalytic activity is lost. The emission period is typically 0.5 to 3 hours, but can be longer depending on the conditions selected.

Coelehterazine and h-coelenterazine are excellent luminescent substrates, among which h-coelenterazine is preferable, as will be described in Example 16 later.

1-7-1. Maintenance of Chemiluminescence Activity by Addition of a Reducing Agent Referring to Example 13, the fluorescent protein (bFP) having chemiluminescence activity according to the present invention has chemiluminescence activity even after heating at 90° C. In this case, addition of a reducing agent such as dithiothreitol can markedly suppress a decrease in chemiluminescence activity. Further, referring to Example 14, when 15 minutes have passed after start of a light-emitting reaction at room temperature, the chemiluminescence activity begins to decrease. In the co-presence of a reducing agent, however, the luminescence intensity does not decrease even after 60 minutes have passed. Consequently, addition of a reducing agent together enables a long-time, continuous emission without decreasing luminescence intensity. It is surprising that chemiluminescence activity is thus exerted even after high temperature treatment, as compared with the bioluminescence by the conventional luciferase. For this reason, application of bFP as a marker using bioluminescence is expected in novel fields.

A reducing agent makes chemiluminescence activity last long, because it inhibits oxidation of free sulfhydryl groups in an apoprotein, thereby maintaining catalytic activity of a fluorescent protein (bFP) for a long time. Preferred reducing agents are dithiothreitol and mercaptoethanol.

1-7-2. Application of a Fluorescent Protein Having Chemiluminescence Activity to Amusement One use of photoproteins is amusement. To use for amusement, coelenterazine or its analog is mixed with the fluorescent protein (bFP) having chemiluminescence activity according to the present invention at the moment for light emission. For that purpose, it is desirable to combine the fluorescent protein (bFP) having chemiluminescence activity according to the present invention with coelenterazine or its analog into a kit. In that case, it is preferable to make a kit in which a fluorescent protein having chemiluminescence activity and coelenterazine or its analog are put in a vessel so that they can be mixed easily when used. For example, they can be placed in each of two rooms divided in a plastic tube, whose partition can be ruptured at the moment for light emission, so that they are mixed to emit light. There are already some reports on such a use (i.e., WO 97/29319), and the fluorescent protein (bFP) having chemiluminescence activity according to the present invention is applicable to any method. The chemiluminescence activity of the fluorescent protein having chemiluminescence activity (bFP) according to the present invention is stabilized with a reducing agent. For this reason, it is desirable to add a reducing agent to one or both of the fluorescent protein (bFP) having chemiluminescence activity and coelenterazine or its analog, but a reducing agent may be provided independently in the kit. Use of such a kit is not limited to the field of amusement.

1-7-3. Use of a Fluorescent Protein Having Chemiluminescence Activity as a Detection Marker The most important use of the fluorescent protein having chemiluminescence activity according to the present invention is use as a detection marker. The fluorescent protein (bFP) having chemiluminescence activity according to the present invention which has been bound to a ligand for a target of detection binds to the target (e.g., virus or a specific protein on a cell) via the ligand. Addition of coelenterazine to that triggers light emission.

To date, using fluorescence of a fluorescence substance as a marker has been known well. However, the detection sensitivity of light by the chemiluminescence of coelenterazine is 100 times or more higher compared with the detection sensitivity in fluorescence. Moreover, since this chemiluminescence is continuous, it is suitable for long-time observation.

In addition, even after coelenterazine is consumed up, fluorescence is generated by absorbing light energy, so that observation can be continued using that fluorescence. This method is expected as extremely effective means in biological experiments etc. Such a use has became possible for the first time by the fluorescent protein (bFP) having chemiluminescence activity according to the present invention having both chemiluminescence activity and fluorescence-generating ability based on the catalytic action.

In this case also, addition of a reducing agent can enhance the sustainability of chemiluminescence activity, further enabling light emission at high temperatures. It is therefore possible to detect a target substance to be detected before heating and to continue detection even after heating using the same marker. This is expected to open up application fields for unprecedented, completely new bioluminescence markers.

The wavelength (color) of fluorescence emitted by the fluorescent protein (bFP) having chemiluminescence activity according to the present invention varies depending on the kind of coelenteramid (chromophore) retained in the protein. Further, when coelenterazine or its analog emits light due to oxidation by the catalytic action of the fluorescent protein (bFP) having chemiluminescence activity according to the present invention, the wavelength of light emitted varies depending on the kind of coelenteramid (chromophore) formed.

1-7-4. Use for Producing Another Fluorescent Protein (gFP)

Calcium ions and their substitutable divalent ions that constitute the fluorescent protein (bFP) having chemiluminescence activity according to the present invention are removed by treatment with a chelating agent and turn into another completely novel fluorescent protein (gFP), which will be described later in Section 2.

1-7-5. Use for Production of a Calcium-Binding Photoprotein

A calcium-binding photoprotein such as aequorin can be produced from the fluorescent protein (bFP) having chemiluminescence activity according to the present invention. For that purpose, a fluorescent protein (bFP) having chemiluminescence activity is reacted with coelenterazine or its analog in the presence of a chelating agent for removing calcium ions or divalent or trivalent ions that can be substituted for the calcium ions. Such a chelating agent is present preferably in a little more excess than the amount equivalent to calcium ions or divalent or trivalent ions that can be substituted for the calcium ions. Although the reaction temperature is not particularly limited, 4 to 25° C. is suitable. After addition of a reducing agent such as dithiothreitol (DTT) optionally, the reaction mixture can be allowed to stand for about 1 to 30 hours. Aequorin can be isolated and purified from other unreacted bFP, gFP, coelenterazine, etc. in accordance with the known methods for purifying aequorin. That is, a reaction solution is isolated and purified by the Butyl Sepharose 4 Fast Flow column chromatography method.

A chelating agent is not particularly limited as long as it binds strongly to calcium ions or divalent or trivalent ions that can be substituted for the calcium ions. Examples of such a chelating agent include ethylenediaminetetraacetic acid (EDTA); ethyleneglycolbis (β-aminoethyl ether) N,N,N',N'-4-tetraacetic acid (EGTA); trans-1,2-diaminocyclohexane-N,N,N',N'-tetraacetic acid (CyDTA); and N-(2-hydroxyethyl) iminodiacetic acid (HIDA).

1-8. Properties of a Fluorescent Protein Having Chemiluminescence Activity 1-8-1. Excellent Thermal Stability The fluorescent protein (bFP) having chemiluminescence activity according to the present invention has an excellent thermal stability. As will be shown in Example 9, the fluorescence intensity of the fluorescent protein (bFP) having chemiluminescence activity according to the present invention do not decrease even at 40° C. The intensity decreases if bFP is kept at 45° C. for 10 min. However, the fluorescence intensity that has once decreased with heating is completely recovered by cooling, as long as the heating temperature did not exceed 65° C. Further, as will be shown in Example 10, the fluorescence intensity of the fluorescent protein (bFP) having chemiluminescence activity according to the present invention recovered 93% of its fluorescence-generating ability by making to stand at room temperature for 20 min even after heating at 90° C. for 3 min. The fluorescence-generating ability is recovered 100% when heating at 65° C. or lower.

Fluorescence proteins and luciferases known to date lose their chemiluminescence activity by heating. Calcium-binding photoproteins also lose their light-emitting ability by heating. In contrast, the fluorescent protein (bFP) having chemiluminescence activity according to the present invention recovers its chemiluminescence activity by returning to a low temperature such as room temperature even if it is temporarily maintained at a high temperature. This is a great advantage over conventional fluorescent proteins, luciferases, calcium-binding photoproteins, and so on; this fluorescent protein (bFP) having chemiluminescence activity is extremely useful.

1-8-2. Excellent Storage Stability

The fluorescent protein (bFP) having chemiluminescence activity according to the present invention has an excellent storage stability. bFP was stored at −80° C. and 4° C., without adding a stabilizing agent etc. and the fluorescence intensity after a lapse of 6 months was compared with that at the start of preservation. No change in fluorescence intensity was found at −80° C. and almost no change even at 4° C. Since calcium-binding photoproteins have a problem with storage stability, they obtain a long storage at −80° C. by the addition of a stabilizing agent etc. This indicates that the fluorescent protein (bFP) having chemiluminescence activity according to the present invention has a marked storage stability.

From the fluorescent protein (bFP) having chemiluminescence activity so far explained, another novel fluorescent protein (gFP) is produced, which will be explained hereinbelow.

2. Conformation of a Fluorescent Protein (gFP)

2-1. Conformation of a Fluorescent Protein (gFP)

The fluorescent protein (gFP) according to the present invention is composed of an apoprotein of a calcium-binding photoprotein to which coelenteramid or its analog is coordinated. In other words, gFP is the fluorescent protein (bFP) having chemiluminescence activity according to the present invention previously described that have its calcium ions or divalent or trivalent ions substitutable for the calcium ions removed.

The fluorescent protein (gFP) according to the present invention consists of an apoprotein of a calcium-binding photoprotein and coelenteramid or its analog and, in the complex, the ratio of the number of molecules of the apoprotein to the coelenteramid or its analog is 1:1.

2-2. Method for Producing a Fluorescent Protein (gFP)

The fluorescent protein (gFP) according to the present invention is obtained by removing calcium ions or divalent ions that can be substituted for the calcium ions from the fluorescent protein (bFP) having chemiluminescence activity according to the present invention previously described. Divalent ions can be removed by treating a fluorescent protein (bFP) having chemiluminescence activity with a chelating agent.

The chelating agent is not particularly limited as long as it binds strongly to calcium ions or divalent or trivalent ions that can be substituted for the calcium ions. Examples of such a chelating agent include ethylenediaminetetraacetic acid (EDTA); ethyleneglycolbis (β-aminoethyl ether)N,N,N',N'-4-tetraacetic acid (EGTA); trans-1,2-diaminocyclohexane-N,N,N',N'-tetraacetic acid (CyDTA); and N-(2-hydroxyethyl) iminodiacetic acid (HIDA).

2-3. An Apoprotein that Constitutes a Fluorescent Protein (gFP)

The explanation given to the apoprotein that constitutes the above-described fluorescent protein (bFP) having chemiluminescence activity is applied.

2-4. Coelenteramid that Constitutes a Novel Fluorescent Protein (gFP)

The explanation given to coelenteramid that constitutes the above-described fluorescent protein (bFP) having chemiluminescence activity is applied.

2-5. Fusion Substance of a Novel Fluorescent Protein (gFP) and a Ligand

The explanation given to the above-described fluorescent protein (bFP) having chemiluminescence activity and a ligand for the detection target is applied. A ligand-bound fluorescent protein (gFP) can be prepared by removing calcium ions etc. from a fluorescent protein (bFP) having chemiluminescence activity to which a ligand for the detection target has been bound. Alternatively, it is possible to bind a ligand to a fluorescent protein (gFP) prepared by removing calcium ions etc. from a fluorescent protein (bFP) having chemiluminescence activity to which a ligand is not bound.

2-6. Use of a Novel Fluorescent Protein (gFP)

2-6-1. Detection of Calcium

The fluorescent protein (gFP) according to the present invention reacts with calcium ions or ions that can be substituted for the calcium ions to turn into a substance having a different fluorescence wavelength. It is therefore possible to detect and quantify calcium ions or ions that can be substituted for calcium ions using such changes in fluorescence wavelength. Reagents for detecting and quantifying calcium ions or ions that can be substituted for the calcium ions, including a fluorescent protein (gFP), are provided by the present invention.

2-6-2. Use as a Detection Marker

A fluorescent protein (gFP) to which a ligand for a target substance to be detected in a virus or cells is bound can be used as a detection marker for the substance. A ligand-bound fluorescent protein (gFP) is bound to the target substance to be detected via the ligand. Subsequent addition of coelenterazine or its analog results in formation of a calcium-binding photoprotein. Further addition of calcium ions or divalent or trivalent ions that can be substituted for the calcium ions causes the calcium-binding photoprotein to emit light instantaneously. The instantaneous luminescence can be used as a marker. Further, since a fluorescent protein (gFP) that has not reacted with coelenterazine has fluorescence-generating ability, the detection of a target substance is continued using the fluorescence.

Alternatively, a target may be detected using only fluorescence, without addition of coelenterazine from the beginning.

Thus, it is epoch-making that both instantaneous light emission with fluorescent calcium ions etc. and fluorescence can be performed with the same marker. A wide range of applications is expected.

2-6-3. Application to Production of a Calcium-Binding Photoprotein

The fluorescent protein (gFP) according to the present invention can be converted to a calcium-binding photoprotein such as aequorin by mixing with coelenterazine or its analog, a luminescent substrate.

A calcium-binding photoprotein is generally regenerated by adding a chelating agent, a reducing agent, and coelenterazine at a low temperature to the reaction product obtained by making the calcium-binding photoprotein react with calcium ions. As for the temperature in regeneration, 4° C. is the most efficient and regeneration is hardly takes place at 37° C. Even when a calcium-binding photoprotein is newly produced from an apoprotein, the same operation is required by adding a chelating agent, a reducing agent, and a coelenterazine at a low temperature.

In contrast, production of a calcium-binding photoprotein from the fluorescent protein (gFP) according to the present invention only requires addition of coelenterazine. Regarding the temperature condition for the addition of coelenterazine, at 25° C., as in 4° C., 90% or more of the molecules is converted to calcium-binding photoproteins without addition of a reducing agent and at 37° C., about 80% of the molecules is converted to calcium-binding photoproteins by add-on of a reducing agent. Details will be described in Example 12.

Coelenterazine and its analog used for the production of a calcium-binding photoprotein were as explained previously. Specific coelenterazine and its analog are presented in the previously-mentioned formula (3) or formula (4).

In the present invention, a kit for producing a calcium-binding photoprotein combining a fluorescent protein (gFP) with coelenterazine or its analog is provided. It is preferable to include a reducing agent in one or both of the fluorescent protein (gFP) or coelenterazine or its analog of the kit for producing a calcium-binding photoprotein, but a reducing agent may be provided independently in the kit.

2-6-4. Application to Production of a Fluorescent Protein (bFP) Having Chemiluminescence Activity The previously-mentioned fluorescent protein (bFP) having chemiluminescence activity can be produced by adding calcium ions or divalent or trivalent ions that can be substituted for the calcium ions to the fluorescent protein (gFP) according to the present invention.

2-7. Fluorescent Protein (gFP) has an Excellent Storing Stability.

Fluorescent protein (gFP) according to the present invention has an excellent storing stability. gFP was stored at −80° C. and 4° C., without adding a stabilizing agent etc. and the fluorescence intensity after a lapse of 6 months was compared with that at the start of preservation. No change in fluorescence intensity was found at −80° C. and almost no change even at 4° C. Since calcium-binding photoproteins having a problem with storing stability, they obtain a long storage at −80° C. by the addition of a stabilizing agent etc. This indicates that the fluorescent protein (gFP) according to the present invention has marked storage stability.

The chemical structural formula of coelenterazine, coelenteramid, e-coelenterazine, e-coelenteramid, h-coelenterazine, and h-coelenteramid, which are of particular importance, are shown collectively below.

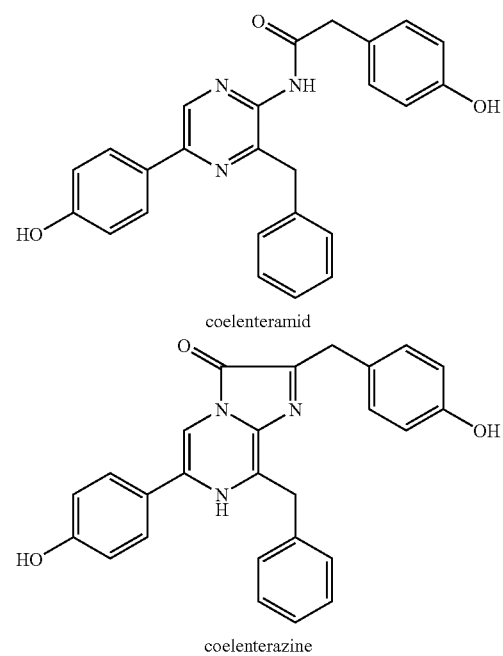

coelenteramid coelenterazine

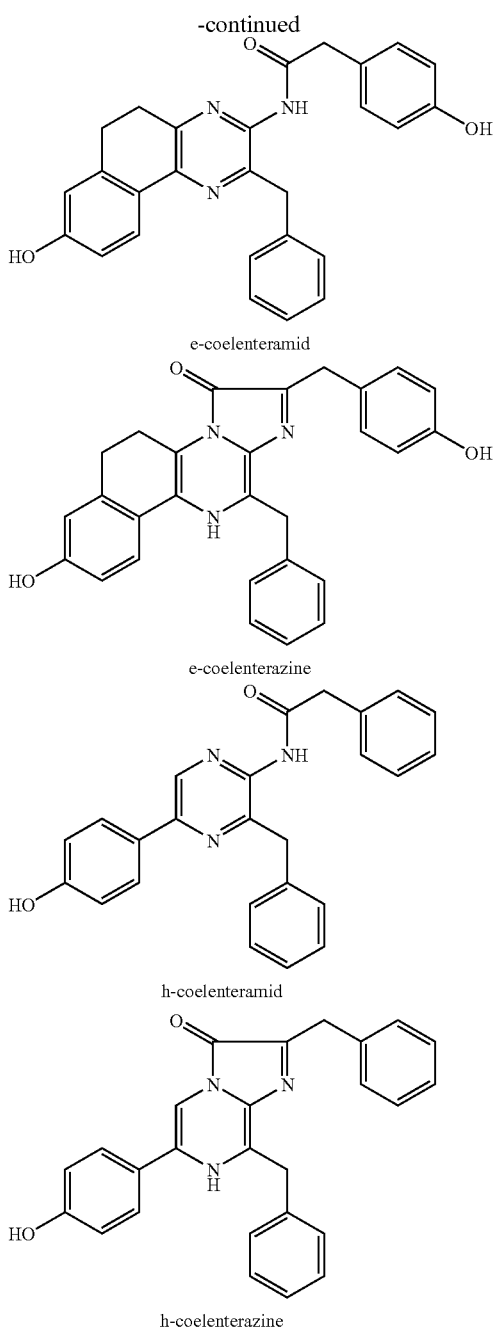

e-coelenteramid e-coelenterazine h-coelenteramid h-coelenterazine

The present invention is explained in the following examples, but these examples are not to be construed to limit the present invention.

The abbreviations as used in the following examples represent the following meaning.

CTZ: coelenterazine
e-CTZ: e-coelenterazine
h-CTZ; h-coelenterazine
CMT: Coelenteramid
AQ: aequorin containing coelenterazine (CTZ) as a luminescent substrate
e-AQ: aequorin containing e-coelenterazine (e-CTZ) as a luminescent substrate
h-AQ: the aequorin which contains h-coelenterazine (h-CTZ) as a luminescent substrate
ApoAQ-$Ca^{2+}$: substance obtained by reacting calcium ions with apoaequorin
bFP-aq: a fluorescent protein complex (bFP) having chemiluminescence activity obtained by reacting calcium ions slowly with apoaequorin (AQ) that contains coelenterazine (CTZ) as a luminescent substrate
e-bFP-aq: a fluorescent protein complex (bFP) having chemiluminescence activity obtained by reacting calcium ions slowly with apoaequorin (e-AQ) that contains e-coelenterazine (e-CTZ) as a luminescent substrate
h-bFP-aq: a fluorescent protein complex (bFP) having chemiluminescence activity obtained by reacting calcium ions slowly with apoaequorin (h-AQ) that contains h-coelenterazine (h-CTZ) as a luminescent substrate
gFP-aq: a fluorescent protein complex (gFP) obtained by removing calcium ions bFP-aq
e-gFP-aq: a fluorescent protein complex (gFP) obtained by removing calcium ions from e-bFP-aq
h-gFP-aq: a fluorescent protein complex (gFP) obtained by removing calcium ions from h-bFP-aq Example 1

Method for Preparation of Recombinant Aequorins [AQ, e-AQ, AND h-AQ]

As shown below, recombinant aequorins were obtained by expressing the recombinant apoaequorin gene in the *E. coli* described in Japanese Laid-Open Application No. 1989-132397, forming complexes as recombinant aequorins by binding the expressed product to coelenterazine, and subsequently purifying the complexes as described in Japanese Laid-Open Application No. 2001-270899. The recombinant apoaequorins obtained is composed of 191 amino acids, whose N-terminus starts from Ala-Asn-Ser-(Val- of the N-terminal of SEQ ID NO: 1 in the sequence listing has been replaces by Ala-Asn-Ser-). These specifications are incorporated herein by reference.

1) Expression of Recombination Apoaequorins in *E. coli*

To express recombinant apoaequorins in *E. coli*, the apoaequorin gene expression vector piP-HE (refer to Japanese Laid-Open Application No. 1989-132397) constructed from pAQ440 harboring the apoaequorin gene (refer to Japanese Laid-Open Application No. 1986-135586) was used. *E. coli* strain WA802 was used as the host and was transformed with piP-HE using the conventional methods. The transformant obtained was incubated at 30° C. overnight, inoculated into 50 ml of LB liquid medium (bactotrypton 1% w/v, yeast extract 0.5% w/v, sodium chloride 0.5% w/v, pH 7.2 in water) containing ampicillin (50 µg/ml), and incubated for at 30° C. for 8 hours. Subsequently, the culture was added to a fresh LB liquid media and incubated at 37° C. at day and night (18 hours), followed by isolation of the bacterial cells from the medium by low-speed centrifugation (5,000×g). Since both the bacterial cells and the medium contain expressed recombinant apoaequorins, they were stored individually as the starting material for aequorin purification.

2) Purification of Aequorin (AQ) from Cultured Bacterial Cells

Harvested bacterial cells were suspended in 400 ml buffer (50 mM Tris-HCl, pH7.6, 10 mM EDTA) containing 200 mg of a reducing agent dithiothreitol (DTT, manufactured by Wako Pure Chemicals Industries, Ltd.). The cells were crushed by treating with an ultrasonicator for 2 min under ice-cold conditions and centrifuged at 12,000×g for 20 min. Subsequently, the supernatant was recovered. Chemosynthesized coelenterazine was dissolved in a small quantity of methanol, added to the supernatant obtained at 1.2-fold molar concentration of apoaequorin to be produced, and allowed to stand at 4° C. for 5 hours. This supernatant was immediately loaded on to a Q-Sepharose column (Amersham Pharmacia Biotech, 2×10 cm diameter) pre-equilibrated with a buffer of 20 mM Tris-HCl, pH 7.6, 10 mM EDTA, to have aequorin adsorbed. The column was washed with a buffer of 20 mM Tris-HCl, pH 7.6, 10 mM EDTA, 0.1M NaCl until the absorbance of the wash flowing out from the column at 280 nm becomes 0.05 or less. Then, the apoaequorin and aequorin adsorbed on the column were eluted with a linear concentration gradient of 0.1 to 0.4 M-NaCl.

Aequorin that has formed complexes with coelenterazine was isolated from apoaequorin that has not formed complexes, using a hydrophobic chromatography with Butyl Sparse 4 Fast Flow gel. That is, the orange eluent from the Q-Sepharose column was adjusted at final ammonium sulfate concentration at 2M, and then the precipitant was removed by centrifugation. The supernatant was applied to a Butyl Sepharose 4 Fast Flow column (Amersham Pharmacia Biotech, column size: 2×10 cm diameter) pre-equilibrated with 20 mM Tris-HCl, 10 mM EDTA, pH 7.6, containing 2 M ammonium sulfate, eluted by a linear concentration gradient to a final ammonium sulfate concentration at 1 M, the aequorin fractions having chemiluminescence activity were collected. On the other hand, apoaequorin was eluted only in 20 mM Tris-HCl, pH 7.6, 10 mM EDTA.

The aequorin fractions were analyzed by SDS-PAGE using 12% polyacrylamide gel under reducing conditions. As a result, a single band with a molecular weight equivalent to that of a 25 kDa protein was detected in the purified fractions, with a purity of 98% or higher according to densitometer measurement. The recovery rate of aequorin from the bacterial cells was about 80%. A total of 80 mg of high-purity aequorin (AQ) was thus obtained.

3) Purification of Aequorin (AQ) from the Culture Medium

High-purity aequorin was purified from the culture medium according to the method described in Japanese Laid-Open Application No. 1989-132397. That is, the culture medium was subjected to acidification treatment with 0.1M acetic acid to pH 5 or below and allowed to stand at 4° C. for 60 mm or longer. The white-precipitated apoaequorin was isolated by centrifugation and dissolved in the above-mentioned buffer containing a reducing agent. Then, after forming aequorin in the same manner as in purification method from bacterial cells, aequorin equal to or greater than 98% pure was obtained by the sepharose column chromatography and the Butyl Sepharose 4 Fast Flow column chromatography. Purified aequorin obtained was analyzed by SDS-PAGE using 12% polyacrylamide gel under a reducing condition. As a result, a single band with a molecular weight equivalent to that of a 25 kDa protein was detected with a purity of 98% or higher according to densitometer measurement. A total of 45 mg of high-purity aequorin was obtained from 50 mg of apoaequorin obtained from the culture medium. The purified protein concentration was determined using a commercially available kit (manufactured by Bio-Rad Laboratories, Inc.) based on the Bradford method. Bovine serum albumin (manufactured by Pierce Laboratories Inc.) was used as the standard substance.

4) Preparation of e-AQ e-AQ, which contains e-CTZ as a luminescent substrate, was prepared in the same manner using e-coelenterazine (e-CTZ) in place of coelenterazine (CTZ).

5) Preparation of h-AQ h-AQ, which contains h-CTZ as a luminescent substrate, was prepared in the same manner using h-coelenterazine (h-CTZ) in place of coelenterazine (CTZ).

Example 2

Preparation of Fluorescent Proteins Having Chemiluminescence Activity [bFP-aq, e-bFP-aq, AND h-bFP-aq]

1) Concentration of Aequorin (AQ)

An aequorin solution with an aequorin concentration of 8 mg/ml was prepared with a buffer containing 10 mM Tris-HCl (pH7.6), 2 m MEDTA, and 1.2M ammonium sulfate, using the purified aequorin described in Example 1 as a starting material.

1 ml of this aequorin solution was centrifuged at 5000×g at 4° C. for 60 min or longer with a high speed refrigerated centrifuge (CR20B2; manufactured by Hitachi Ltd.), using a Vivaspin 2 column (Manufactured by Zartorius K.K.) having a high-speed ultrafiltration filter, a polyethersulfone membrane with a fraction molecular weight of 10,000. The solution was concentrated to a total quantity of 1 ml or smaller. Further, to lower the EDTA concentration of the concentrated solution to 0.1 μM or lower, 10 mM Tris-HCl containing 1 ml of 0.1 μM EDTA was loaded onto the Vivaspin 2 column and the total quantity was decreased by centrifuging the column under the same condition. This step was repeated at least twice to make the concentration of EDTA 0.1 μM or less. This aequorin concentrate looked yellow-red, which could be confirmed easily by the naked eye.

2) Preparation of bFP-aq bFP-aq was prepared in the following procedures. In a Vivaspin 2 column, the concentrated aequorin (AQ) solution was overlaid with 50 mM Tris-HCl (pH 7.6) containing 0.9 ml of 5 mM calcium chloride (Wako Pure Chemicals Industries, Ltd.) and 2 mM dithiothreitol (Wako Pure Chemicals Industries, Ltd.) to trigger continuous light emission. The solution was allowed to stand at 4° C. for 24 hours or longer. The end of the light-emitting reaction could also be confirmed by disappearance of the yellow-red color from the aequorin solution. Further, 50 mM Tris-HCl (pH 7.6) containing 2 ml of 5 mM calcium chloride (Wako Pure Chemicals Industries, Ltd.) and 2 mM dithiothreitol (Wako Pure Chemicals Industries, Ltd.) was loaded on to the Vivaspin 2 column and the column was centrifuged under the identical conditions and then washed. Generated bFP-aq was confirmed to emit blue fluorescence under a long wavelength UV lamp (maximum wavelength: 366 nm).

3) Preparation of e-bFP-aq and h-bFP-aq e-bFP-aq and h-bFP-aq were prepared in the same manner using e-AQ and h-AQ in place of AQ.

Example 3

Preparation of Fluorescent Proteins Generating Green Fluorescence [gFP-aq, e-gFP-aq, AND h-gFP-aq] from Fluorescent Proteins Having Chemiluminescence Activity [bFP-aq, e-bFP-aq, AND h-bFP-aq]

1) Preparation of gFP-aq gFP-aq was prepared by removing calcium with EDTA from bFP-aq prepared in Example 2. That is, 2 ml of 50 mM Tris-HCl (pH 7.6) containing 10 mM EDTA was added to the bFP-aq in the Vivaspin 2 column for centrifugation under the aforementioned identical condition. This operation was repeated three times. The product was confirmed to emit green fluorescence under a long wavelength UV lamp (maximum wavelength: 366 nm). The recovery rate of the amount of proteins was quantitive.

To remove an excessive EDTA solution from the product, 2 ml of 50 mM Tris-HCl (pH 7.6) was added and the column was centrifuged under the aforementioned identical condition. This operation was repeated five times and the excessive EDTA was removed.

2) Preparation of e-gFP-aq and h-gFP-aq e-gFP-aq and h-gFP-aq were prepared in the same manner using e-bFP-aq and h-bFP-aq in place of bFP-aq.

Example 4

Preparation of Fluorescent Proteins Having Chemiluminescence Activity [bFP-aq, e-bFP-aq, AND h-bFP-aq] from Fluorescent Proteins [gFP-aq, e-gFP-aq, AND h-gFP-aq]

1) Preparation of bFP-aq

The same bFP-aq as that prepared in Example 2 was prepared by adding a solution containing excess calcium ions to the gFP-aq prepared in Example 3. Specifically, 0.1 M calcium chloride was gradually added at room temperature to 0.5 ml (0.25 mg/ml) of the gFP-aq solution to a final calcium ion concentration of 5 mM in the sample solution. Generation of bFP-aq was confirmed by an increase in fluorescence intensity at 459 nm, the absorption peak of its fluorescence-spectrum (excited at 335 nm) together with a decrease in fluorescence intensity at 467 nm, the absorption peak (excited at 335 nm) of the fluorescence spectrum of gFP-aq. To remove excess calcium ions, the product solution was transferred to the a Vivaspin 2 column and centrifuged at 5000×g at 4° C. for 60 min or longer with a high-speed refrigerated centrifuge (CR20B2; manufactured by Hitachi Ltd.), using 2 ml of 50 mM Tris-HCl (pH7.6), so that the total quantity was condensed to 0.1 ml or smaller. Repetition of this operation three times resulted in the removal of excess calcium ions.

2) Preparation of e-bFP-aq and h-bFP-aq e-bFP-aq and h-bFP-aq were prepared in the same manner using e-gFP-aq and h-gFP-aq in place of gFP-aq.

Example 5

Spectroscopic Measurement: Measurement of Absorption/Fluorescence/Emission Spectra, and Measurement of Fluorescence Quantum Yield 1) Measurement of Absorption Spectra Absorption spectra were measured using a spectrophotometer (V-560; manufactured by JASCO Corporation), transferring bFP-aq, e-bFP-aq, and h-bFP-aq with known concentrations, prepared in Example 2; and gFP-aq, e-g FP-aq, and h-gFP-aq, prepared in Example 3 to quartz cells with an optical path length of 10 mm. The measurement conditions used were as follows: 1.0 nm band path, medium response, and 200 nm/min scanning speed, at 22 to 25° C.

2) Measurement of Fluorescence Spectra

Fluorescence spectra were measured using a spectrofluorometer (FP-777W; manufactured by JASCO Corporation), transferring the substances with known concentrations to quartz cells with an optical path length of 10 mm. The measurement conditions used were as follows: 1.5 nm band path, 1.5 sec response and 60 nm/min scanning speed, at 22 to 25° C. The correction of fluorescence spectra was performed using the operating instructions of the spectrofluorometer. The fluorescence quantum yield was calculated by making the fluorescence efficiency 0.55, which is at the excitation at 335 nm for bFP-aq and gFP-aq as well as h-bFP-aq and h-gFP-aq and at the excitation at 350 nm for e-bFP-aq and e-gFP-aq, using quinine-sulfuric acid in 0.1M sulfuric acid (Wako Pure Chemicals Industries, Ltd.) as standard.

3) Measurement of Emission Spectra

The emission spectra of bFP-aq, e-bFP-aq, and h-bFP-aq were obtained by measuring luminescence generated in the preparation process of described in Example 2. Here, continuous light emission was measured with the xenon lamp, the excitation light source of spectrofluorometer (FP-777W; manufactured by JASCO Corporation) being off. The measurement conditions used were as follows: 10 nm band path, 0.5 sec response, and 100 nm/min scanning speed, at 22 to 25° C. The results are shown in Table 2.

TABLE 2

| Spectrum analysis | bFP-aq | gFP-aq | e-bFP-aq | e-gFP-aq | h-bFP-aq | h-gFP-aq |
|---|---|---|---|---|---|---|
| Absorption spectrum | | | | | | |
| Absorption maximum(nm) Absorbance 0.1% solution | 281, 336 | 282, 336 | 282, 353 | 282, 351 | 281, 334 | 282, 339 |
| a) | 2.82 (280 nm) | 2.80 (280 nm) | 2.74 (280 nm) | 2.77 (280 nm) | 2.83 (280 nm) | 2.78 (280 nm) |
| b) | 0.56 (335 nm) | 0.65 (335 nm) | 0.72 (350 nm) | 0.75 (350 nm) | 0.55 (335 nm) | 0.62 (335 nm) |
| a/b ratio | 5.0 | 4.3 | 3.8 | 3.7 | 5.1 | 4.5 |
| Fluorescence spectrum | | | | | | |
| Fluorescence maximum(nm) | 459 (Excitation at 335 nm) | 467 (Excitation at 335 hm) | 423 (Excitation at 335 nm) | 418 (Excitation at 335 nm) | 460 (Excitation at 335 nm) | 472 (Excitation at 335 nm) |
| Half band width of fluorescence spectrum(nm) | 84 | 89 | 78 | 84 | 72 | 92 |
| Fluorescence quantum yield | 0.079 | 0.073 | 0.056 | 0.044 | 0.092 | 0.030 |
| Emission spectrum | | | | | | |
| Emission maximum(nm) | 460 | N.D. | 415, 445 | N.D. | 459 | N.D. |
| Half band width of emission spectrum(nm) | 84 | N.D. | 83 | N.D. | 97 | N.D. |

Example 6

Confirmation of Fluorescence Chromophores of bFP-aq and gFP-aq

The chromophore of the fluorescence contained in bFP-aq prepared in Example 2 and in gFP-aq prepared in Example 3 were confirmed by extracting the compounds having chromophores with methanol from each protein complex and subjecting the extract to TLC, UV irradiation, mass spectrometry, etc. That is, 0.9 ml of methanol was added to a protein complex solution (0.26 mg/0.1 ml), and the mixture was heated at 95° C. for 3 min, followed by cooling. Subsequently, methanol extract was obtained by centrifugation (12,000×g, 5 min) and subjected to analysis.

The presence of coelenteramid was confirmed in the methanol extract by the TLC method, using a chemosynthesized coelenteramid and coelenterazine preparations as standard samples. Silica gel 60F-254 (manufactured by Merck Co.) was used as TLC gel and ethyl acetate:chloroform (2:1) was used as a developing solvent. The Rf values of coelenteramid and coelenterazine under a UV lamp were 0.5 and 0.6, respectively.
It was confirmed from the Rf value that the chromophore contained in the methanol extract was coelenteramid. The absorption maximum wavelength of the absorption spectrum was 278 nm, 294 nm, and 333 nm and the absorption maximum wavelength of the fluorescence spectrum was 428 nm at the excitation at 335 nm. These values corresponded to those of the synthetic standard preparation of coelenteramid. Further, ESI-TOF mass spectrometry was performed to obtain a measured value of m/z=412.36 (the calculated value for coelenteramid $[M+H]^+$=412.45). These results confirmed that the fluorescence chromophores contained in bFP-aq and gFP-aq are coelenteramid, which is the oxide of coelenterazine.

Based on the above, the rate of the number of coelenteramid molecules in bFP-aq and gFP-aq was calculated using the molecular absorbency index $16.0 \times 10^3 M^{-1} cm^{-1}$ of coelenteramid at 335 nm. The result revealed that one apoaequorin protein to one coelenteramid molecule are present in the ratio of practically 1:1 in noncovalent bonds, indicating that coelenteramid is present in 95% or more of the apoaequorin protein.

Example 7

Mass Spectrometry of bFP-aq and gFP-aq

Mass spectrometry was performed on bFP-aq and gFP-aq prepared in Examples 2 and 3, respectively, using the matrix-assisted laser desorption time-of-flight mass spectrometry (MALDI-TOF-MS) method with a Voyager DE-PRO mass spectrometer. (PerSeptive Biosystem). Angiotensin I (m/z 1296.69), insulin (m/z 5734.59), apomyoglobin (m/z 16952.60) and an apoaequorin (m/z 2163.20) were used as molecular weight standard. Sinapic acid (Sigma-Aldrich) was used as a matrix. As a result of the measurement, a measured value of molecular weight of 21632±5 was obtained, indicating that no particular modification, for example, decarboxylation or dehydration, has occurred to apoaequorin in the fluorescence protein preparation process.

Example 8

Measurement of Fluorescence Spectra

FIG. 1 shows the fluorescence spectra of bFP-aq and gFP-aq prepared in Examples 2 and 3, respectively. In the figure, the solid line and the dotted line represent bFP-aq and gFP-aq, respectively.

These changes in the fluorescence spectrum are reversible; taking advantage of the differential spectrum of the fluorescence spectrum enables qualitative and quantitative syntheses of calcium ions. That is, a standard curve (a plot of fluorescence intensity versus calcium concentration) of the fluorescence intensity at arbitrary wavelengths is obtained by adding calcium with various known concentrations to gFP-aq. Contrasting measured values in a sample with unknown calcium concentration with the standard curve makes it possible to measure the calcium concentration.

Example 9

Temperature Dependency of Fluorescence Intensity of bFP-aq

The temperature dependency of the fluorescence generation intensity of bFP-aq prepared in Example 2 was measured. Samples (protein concentration of 0.025 mg/ml) were incubated for 10 min at 4° C., 25° C., 37° C., 40° C., 45° C., 50° C., 55° C. and 65° C., and then their fluorescence generation intensities produced by excitation at 335 nm were measured. On the basis of the fluorescence generation intensity at 4° C., the relative percent value was 100 at 25° C., 37° C., and 40° C.; 10 at 45° C.; and 0 at 50° C. or higher. Immediately after measurement, the samples were allowed to stand for 10 min or longer under ice-cold conditions and measured again for fluorescence generation intensity. The results revealed that the fluorescence intensity had been returned to the original intensity.

The temperature at which fluorescence intensity has become half that at 4° C. was calculated to be 43° C. At 40° C. or lower, bFP-aq exhibited thermal stability and the phenomenon of fluorescence generation intensity was not observed. Heating at temperatures exceeding 40° C. decreases or loses the fluorescence-generating ability of bFP-aq. As described above, however, it was confirmed that fluorescence-generating ability once decreased or lost is recovered by cooling. That is, it was clarified that bFP-aq according to the present invention exhibits recoverability of fluorescence-generating ability by cooling from decreased fluorescence-generating ability at high temperatures.

Example 10

Light-Emitting Ability Recoverability of bFP-aq

Figure 2:
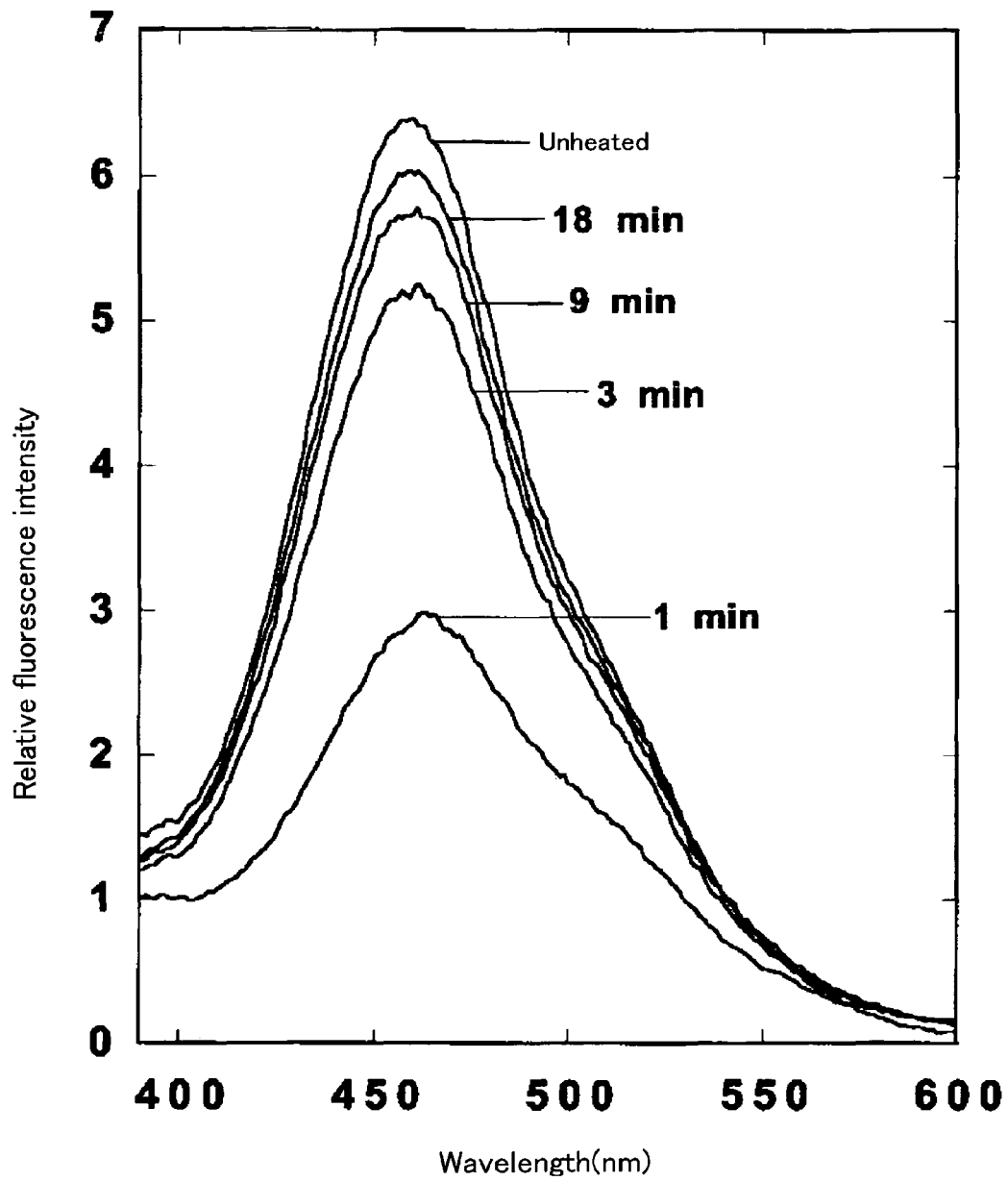
FIG. 2 shows fluorescence intensity of bFP-aq measured after being allowed to stand for 1, 3, 9, and 18 min at 24° C., following heating at 90° C. for 3 min, represented as the relative intensity to bFP-aq unheated (HEAT).

The thermal stability of bFP-aq prepared in Examples 2 was compared with that of gFP-aq prepared Example 3. The solution containing bFP-aq or gFP-aq with a protein concentration of 0.26 mg/ml was heated at 90° C. for 3 min and allowed to stand at 24° C. Subsequently, each fluorescence generation intensity was measured with a spectrofluorometer.

bFP-aq recovered its fluorescence-generating ability to 93.0% within 20 min, whereas gFP-aq recovered its fluorescence-generating ability only to 31.3% within 20 min. On the other hand, the ability of aequorin, a known calcium-binding photoprotein, to emit light due to the addition of calcium ions, has completely been lost by the aforementioned heat treatment. It was therefore clarified that bFP-aq according to the present invention has a high reversibility of heat as compared with known calcium-binding photoproteins. The measurement results of bFP-aq were shown in FIG. 2.

Example 11

Storage of bFP-aq and gFP-aq

The solutions of bFP-aq and gFP-aq prepared in Examples 2 and 3, respectively, were stored at 4° C. and −80° C. Based on each fluorescence generation intensity, each fluorescence-generating ability was measured, according to the method in Example 5. The results are shown in Table 3. 95% of fluorescence-generating ability of both bFP-aq and gFP-aq was stably maintained for six months or longer, revealing that they can be stored without a stabilizing agent, etc.

TABLE 3

Storage test

| Storage time | bFP-aq Fluorescence-generating intensity at 495 nm (%) | | gFP-aq Fluorescence-generating intensity at 467 nm (%) | |
|---|---|---|---|---|
| | temperature | | | |
| | 4° C. | −80° C. | 4° C. | −80° C. |
| 0 month | 100 | 100 | 100 | 100 |
| 6 months | 96 | 101 | 95 | 99 |

Example 12

Method for Preparing Aequorin [Aq] from Gfp-Aq

Figure 3:
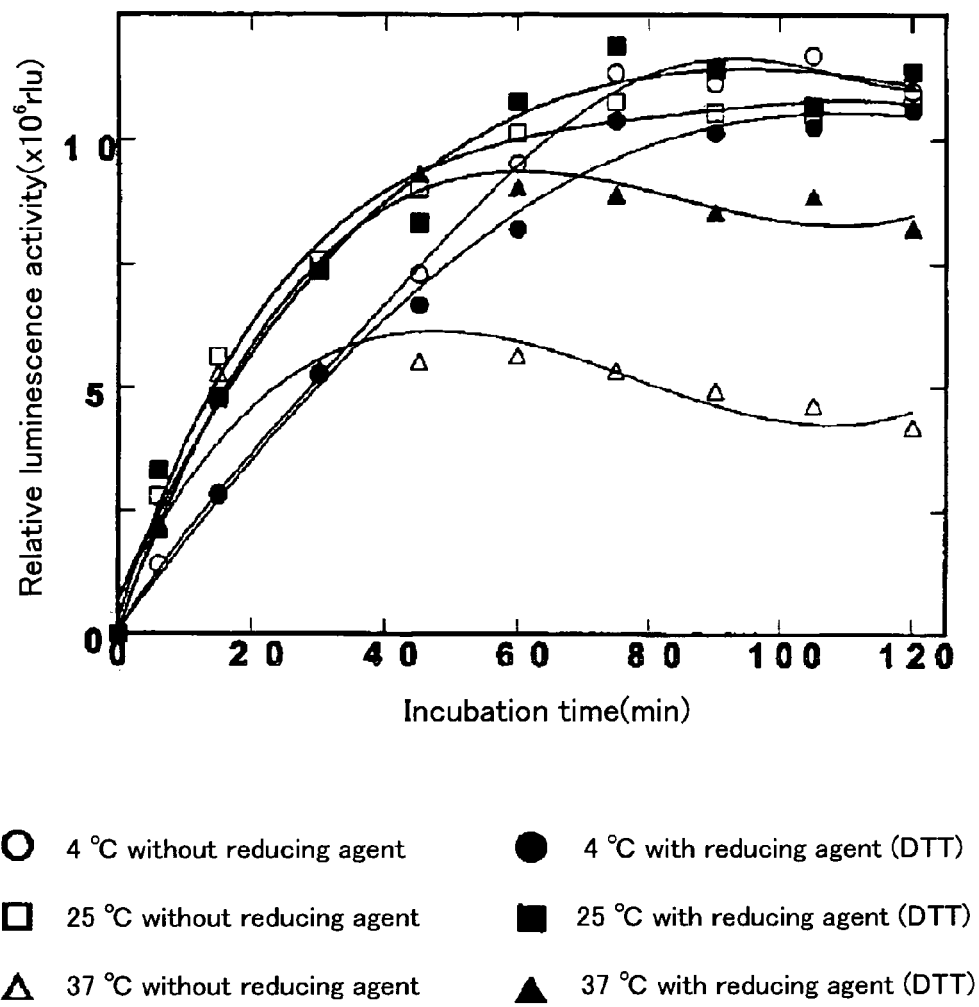
FIG. 3 shows the amount of product obtained from preparation of aequorin by adding coelenterazine to gFP-aq, measured by luminescence intensity using calcium, the amount being represented as a correlation with incubation time.
Figure 4:
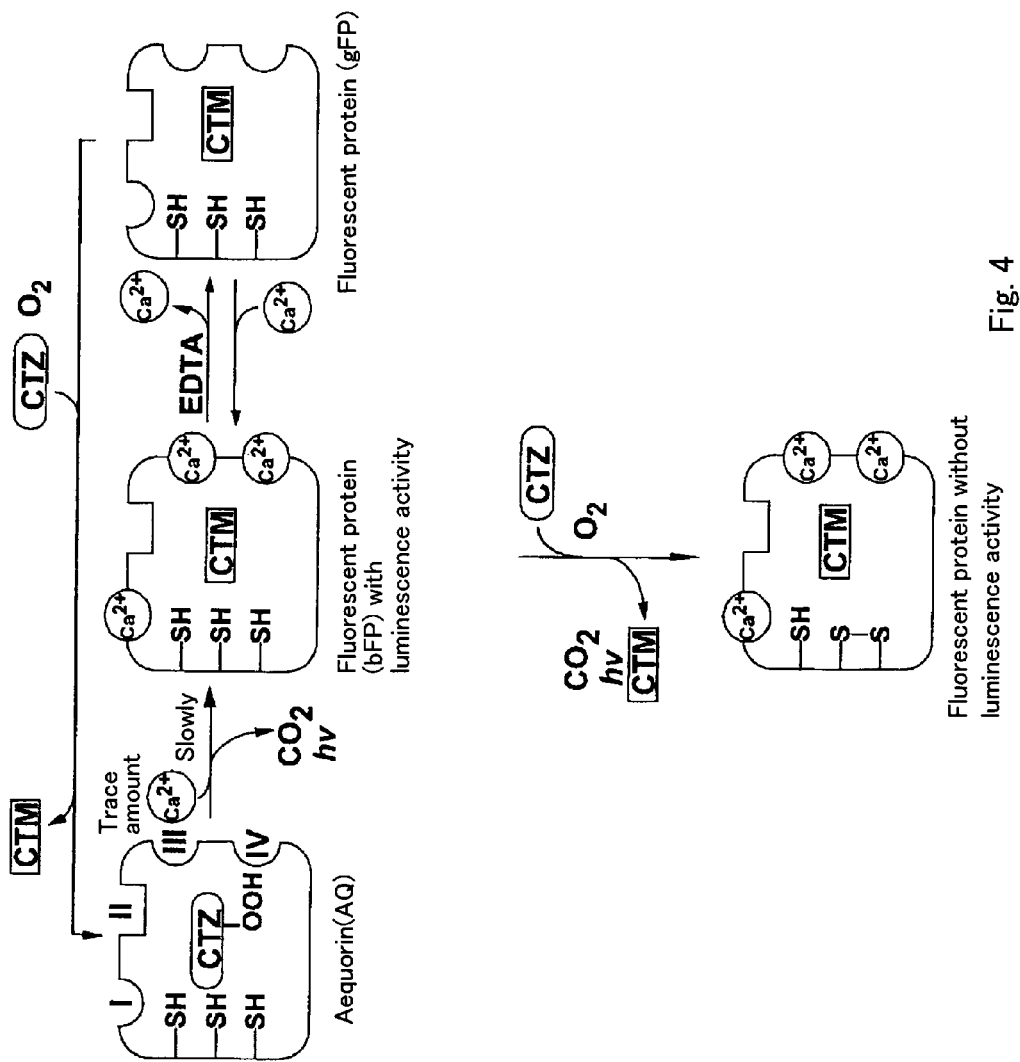
FIG. 4 shows the interrelation of a fluorescent protein (bFP) having luminescence activity, a fluorescent protein (gFP), coelenterazine (CTZ), coelenteramid (CTM), calcium ions, and aequorin (AQ).

Addition of the luminescent substrate coelenterazine to a solution of gFP-aq prepared in Example 3 enabled preparation of aequorin (AQ) having light-emitting ability. Specifically, 0.002 mg of the luminescent substrate coelenterazine dissolved in methanol was added to 0.1 ml of 50 mM Tris-HCl (pH 7.6) containing 0.02 mg of gFP-aq and 2 mM EDTA at 4° C., 25° C., and 37° C. Chemiluminescence activity of a product (aequorin) caused by addition of calcium ions was measured by varying incubation time. Simultaneously, the effect of addition of 1 mM dithiothreitol (DTT), a reducing agent, was also examined. The chemiluminescence activity of aequorin was presented as the maximum value of instantaneous luminescence (Imax) by adding 0.1 ml of 50 mM $CaCl_2$. The results are shown in FIG. 3.

At 4° C. and 25° C., gFP-aq could be efficiently converted into aequorin (AQ) without addition of 1 mM DTT, a reducing agent. The conversion yield was 90% or higher. Generation time at 25° C. was shorter than that at 4° C. At 37° C., about 80% conversion was possible by addition of 1 mM DTT, a reducing agent.

In regeneration of aequorin using a reducing agent and coelenterazine after causing aequorin to emit light with calcium, as has been done conventionally, the highest efficiency is obtained at 4° C. and almost no regeneration can take place at 37° C. It was shown that according to this method, however, addition of a reducing agent enables preparation of aequorin even at 37° C. Likewise, even the use of e-coelenterazine, a substrate analog, in place of coelenterazine, allowed preparation of e-aequorin having chemiluminescence activity by addition of calcium.

Example 13

Enhancement of Thermal Stability of bFP-aq by Addition of a Reducing Agent bFP-aq (0.25 µg) prepared in Example 2 was dissolved in 100 µl of 50 mM Tris-HCl (pH 7.6) containing 5 mM dithiothreitol (DTT) and then incubated at 90° C. for 3 min, immediately followed by cooling on ice. 1 µg/µl of coelenterazine dissolved in methanol was added to the cooled samples and its light emission was measured with a luminometer (AB-2200; manufactured by Atto Co., Ltd.) for 1 min. The measured values were represented as relative values of the maximum intensity (Imax). The results were summarized in Table 4. Obviously, the presence of DTT in heat treatment results in enhancement of thermal stability of chemiluminescence activity (a luciferase-like action).

TABLE 4

Enhancement of heat resistance of luminescence activity caused by addition of DTT

| Experiment No. | Addition of DTT | Heat treatment | Relative luminescence activity |
|---|---|---|---|
| 1 | + | − | 26888 (100) |
| 2 | + | + | 24916 (93) |
| 3 | − | − | 24670 (92) |
| 4 | − | + | 16964 (63) | rlu: relative light unit
+: with
−: without

Example 14

Stabilization of the Chemiluminescence Activity OF bFP-AQ by Addition of a Reducing Agent bFP-aq (0.25 µg) prepared in Example 2 was dissolved in 100 µl of 50 mM Tris-HCl (pH 7.6) containing or not containing 5 mM dithiothreitol (DTT), to each of which 1 µg/µl coelenterazine was added. The chemiluminescence was measured with a luminometer (AB-2200; manufactured by Atto Co., Ltd.).

The results are summarized in Table 5. In reactions for 3 min to 60 min, each luminescence intensity was monitored. Luminescence intensity sharply decreased without the addition of DTT after 15 min. On the other hand, with the addition of DTT, marked decrease in luminescence intensity is remarkably suppressed. Thus, the effect suppressing a decrease in chemiluminescence activity due to addition of a reducing agent was revealed.

TABLE 5

Stabilization of luminescence activity by addition of DTT

| Reaction time (min) | Relative luminescence activity (rlu/sec) | |
|---|---|---|
| | Without addition of DTT | With addition of DTT |
| 3 | 23321 | 31155 |
| 6 | 21983 | 45050 |
| 15 | 13653 | 46663 |
| 30 | 7014 | 43951 |
| 45 | 4173 | 42329 |
| 60 | 2129 | 40930 |

Example 15

Determination of Light-Emitting Reaction Velocity of bFP-aq

Coelenterazine was dissolved into 100 µl of 50 mM Tris-HCl (pH 7.6) containing 5 mM dithiothreitol (DTT) at final coelenterazine concentrations of 2.36 to 23.6 µM. bFP-aq (0.25 µg) prepared in Example 2 was added. Using the initial velocity of luminescence for 1 min, the maximum velocity (Vmax) was determined to be $1.32 \times 10^8$ rlu/min/mg protein, and the Km value was determined to be 13.3 μM by the Lineweaver-Burk plot method. It was thus confirmed that bFP-aq exhibits the catalytic ability of general enzymes.

Example 16

Substrate Specificity of Fluorescent Proteins Having Chemiluminescence Activity [bFP-aq, e-bFP-aq, AND h-bFP-aq]

bFP-aq, e-bFP-aq, and h-bFP-aq (0.25 μg) prepared in Example 2 were individually dissolved in 100 μl of 50 mM Tris-HCl (pH 7.6) containing 5 mM dithiothreitol (DTT) and 1 μg/μl coelenterazine and its analog were added to each solution. Each chemiluminescence in the steady reaction state (after 10 min) was measured with a luminometer (AB-2200; manufactured by Atto Co., Ltd.). It was found that h-coelenterazine, a coelenterazine substrate analog, serves as a luminescent substrate better than coelenterazine. The results are shown in Table 6.

TABLE 6

| Sub-strate analog | Substrate specificity | | | |
|---|---|---|---|---|
| | Relative luminescence activity (rlu/sec/μg protein)(%) | | | |
| | bFP-aq | h-bFP-aq | e-bFP-aq | ApoAQ-Ca$^{2+}$ |
| CTZ | 213,987 (100) | 148,732 (100) | 149,048 (100) | 39,873 (100) |
| h-CTZ | 374,664 (175) | 404,793 (272) | 339,486 (228) | 96,699 (243) |
| e-CTZ | 704 (0.3) | 588 (0.4) | 243 (0.16) | 242 (0.6) |

(Imax of 1 ng of recombination aequorin is 6.4 × 10$^4$ rlu.)

Example 17

Method for Preparing Various AQS from Various bFP Using Coelenterazine Analogs

When preparing AQ from bFP-aq, preparation is enabled by adding substrate coelenterazine after preparing gFP-aq described in Example 4. As a simple method for preparing AQ, however, it is possible to prepare AQ from bFP-aq directly, without preparing gFP-aq, by binding a substrate by adding coelenterazine at the same time as dissociating calcium by adding a chelating agent (EDTA) to a bFP-aq solution.

Specifically, making the total quantity 100 μl, CTZ, h-CTZ, and e-CTZ (1 μg/μl) individually dissolved in methanol were added to a 50 mM Tris-HCl (pH 7.5) solution containing 10 μg of bFP, 10 mM EDTA, and 1 mM DTT, and allowed to stand at 20° C. After 24 hours, 0.1 ml of 50 mM CaCl$_2$ was added to 0.1 μg-equivalent protein and chemiluminescence activity (Imax) was measured with a Lab Science model TD-4000 luminometer. Assuming that the generation efficiency of AQ in the combination of bFP-aq and CTZ is 100%, the generation efficiency of AQ, h-AQ, and e-AQ in other combinations were obtained. The results are shown in Table 7.

Evidently, not only AQ but also e-AQ and h-AQ were able to be directly prepared by replacing coelenterazine analogs from bFP-aq. This is a novel method for preparation different from that for semisynthesized aequorin e-AQ and h-AQ to be prepared from apoaequorin and coelenterazine analogs as shown in Example 1. On the other hand, using e-bFP and h-bFPas starting materials, various AQs other than e-AQ and h-AQ were prepared in the same manner.

TABLE 7

Regeneration of bFP to aequorins by coelenterazine analogs

| Protein | Type of CTZ | Regenerated aequorin | Regeneration efficiency (%) |
|---|---|---|---|
| bFP-aq | CTZ | AQ | 100.0 |
| | h-CTZ | h-AQ | 96.7 |
| | e-CTZ | e-AQ | 27.2 |
| h-bFP | CTZ | AQ | 104.6 |
| | h-CTZ | h-AQ | 96.5 |
| | e-CTZ | e-AQ | 25.7 |
| e-bFP | CTZ | AQ | 91.1 |
| | h-CTZ | h-AQ | 82.6 |
| | e-CTZ | e-AQ | 20.1 |

Preferred compounds as coelenteramide and its analogs are described below.

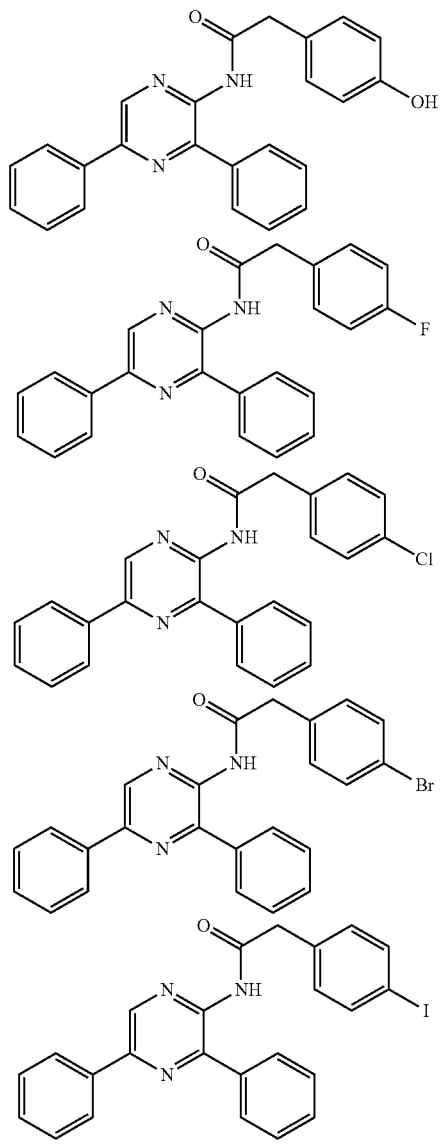

31
-continued
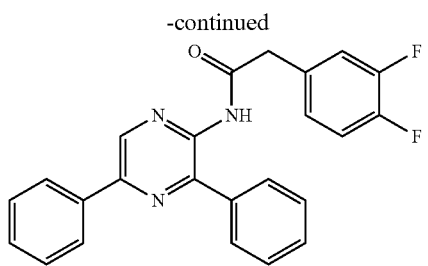
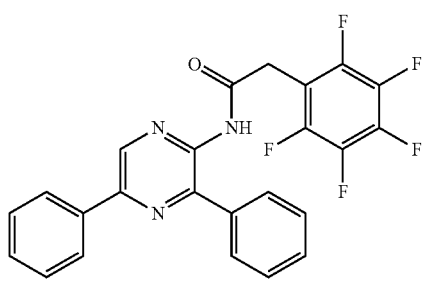
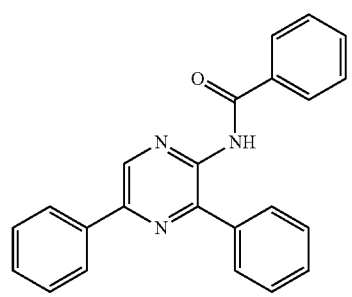
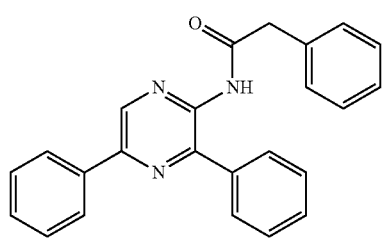
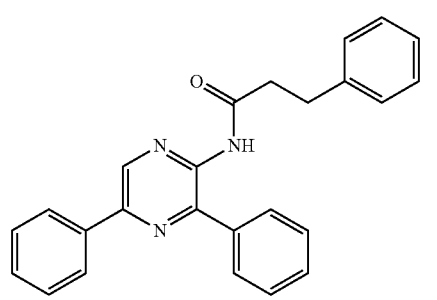
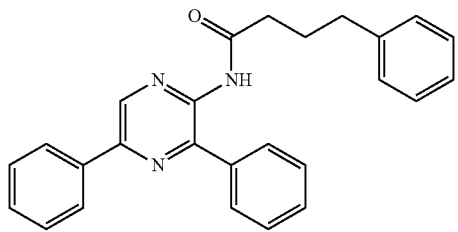
32
-continued
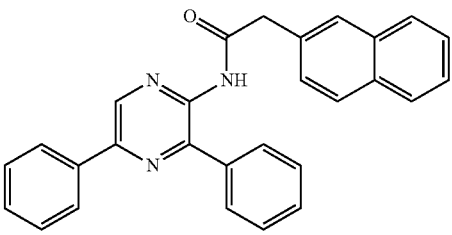
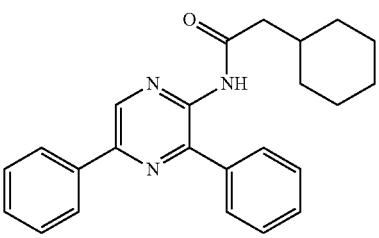
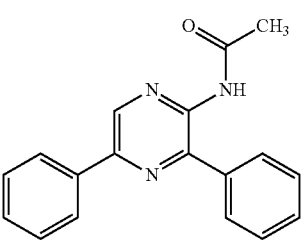
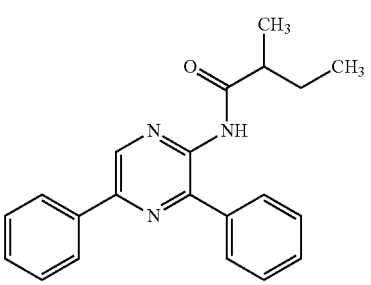
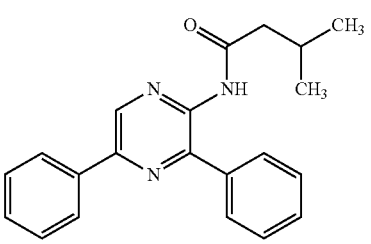
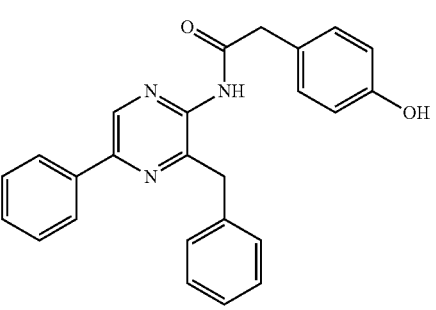

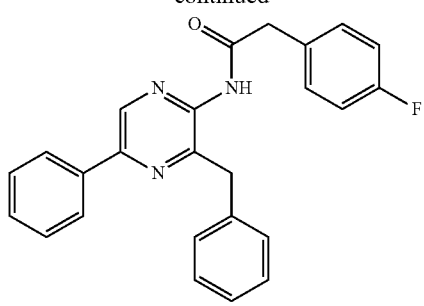
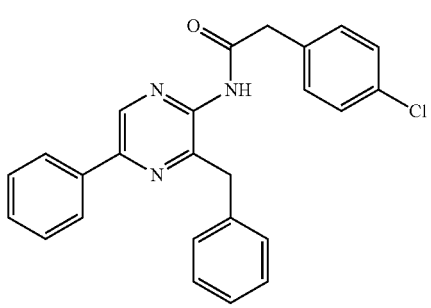
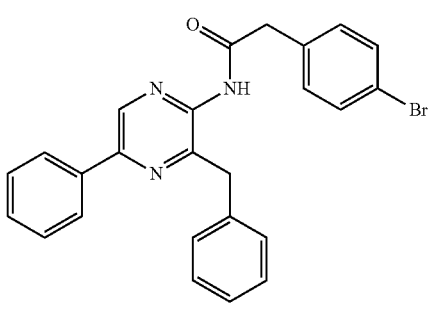
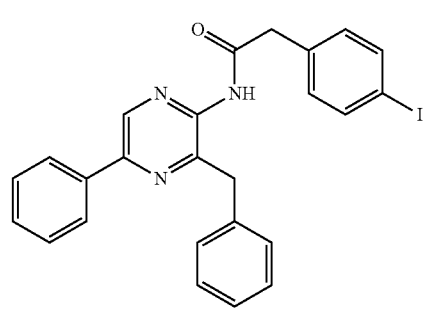
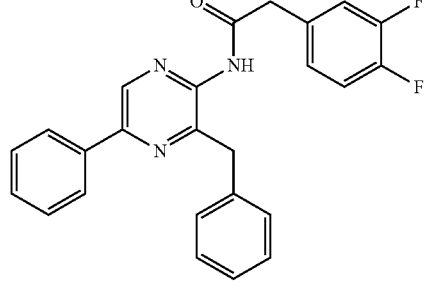
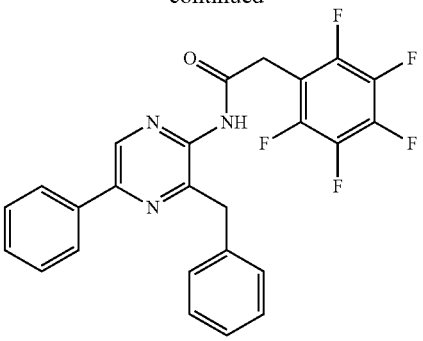
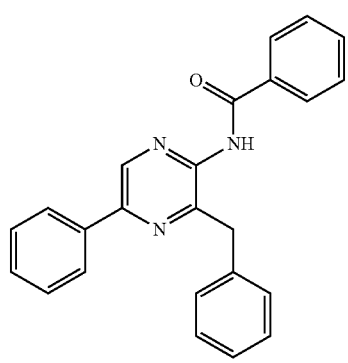
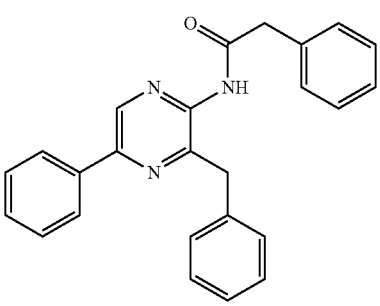
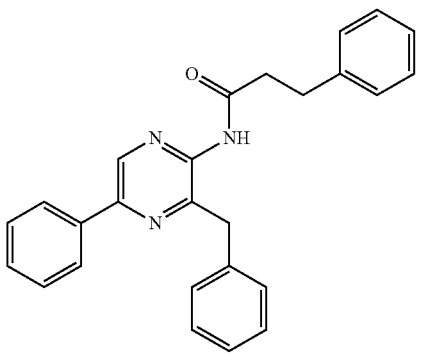
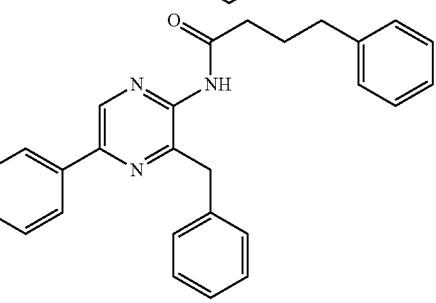

| 35 | 36 |
|---|---|
| -continued | -continued |
| 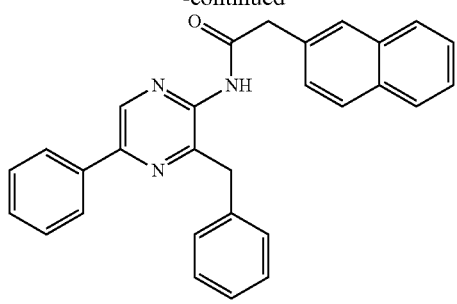 | 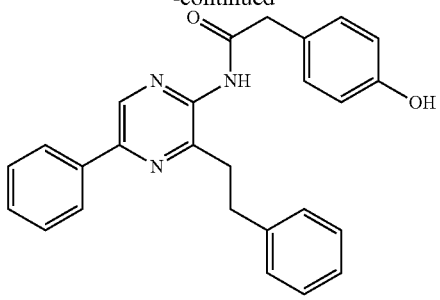 |
| 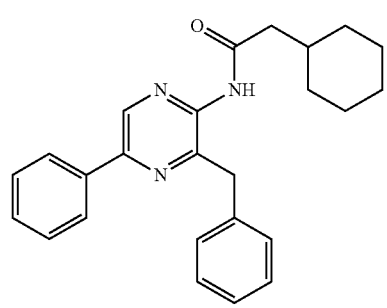 | 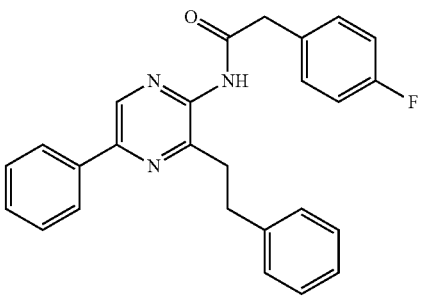 |
| 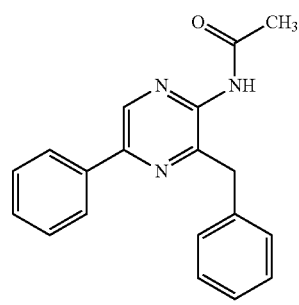 | 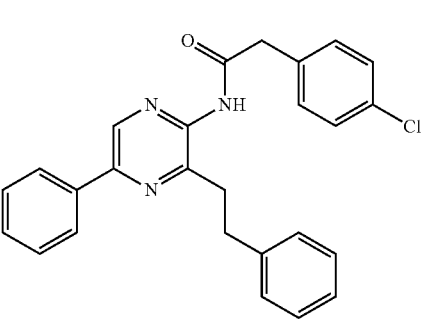 |
| 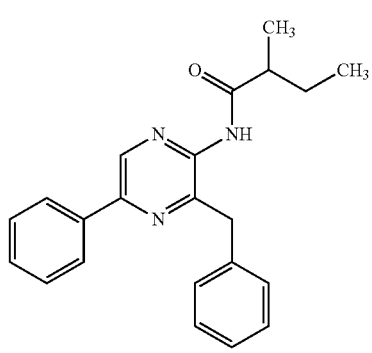 | 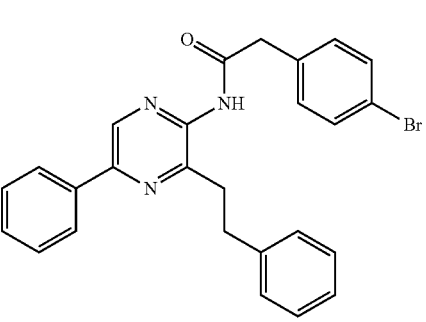 |
| 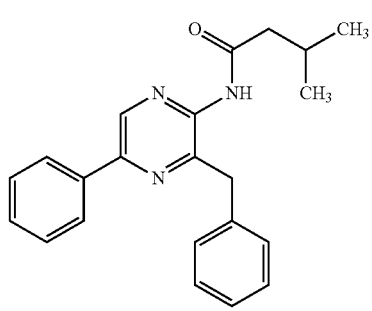 | 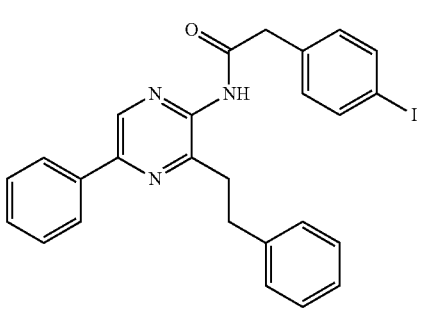 |

37
-continued
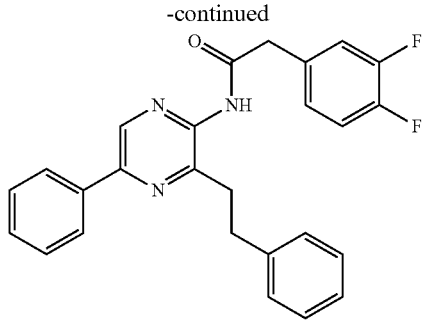
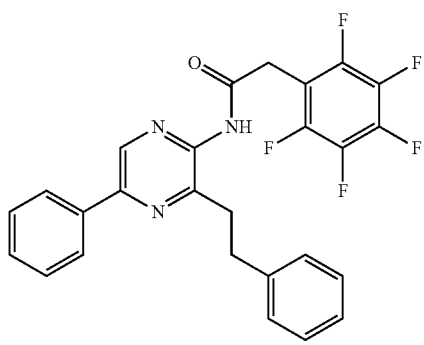
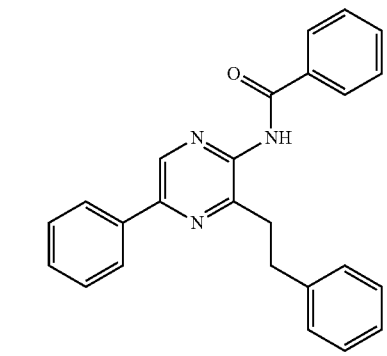
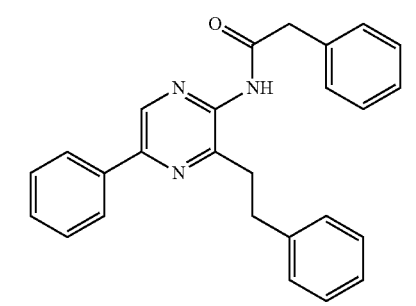
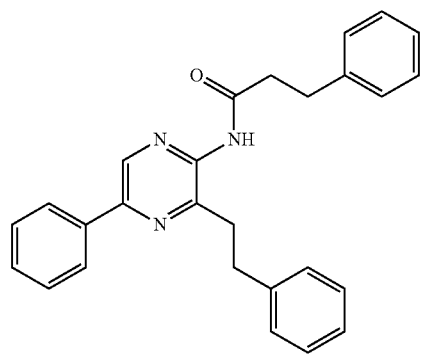
38
-continued
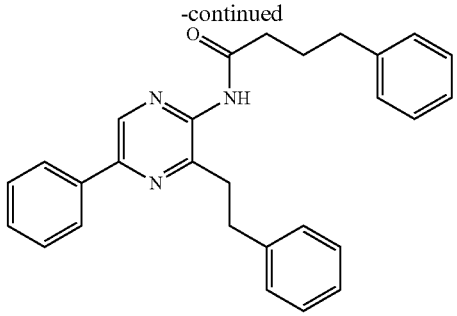
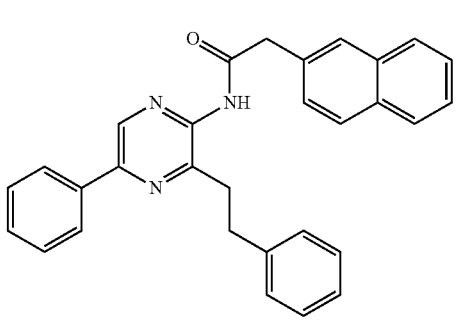
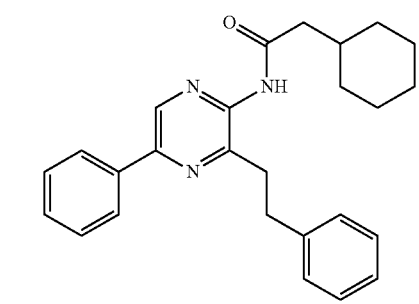
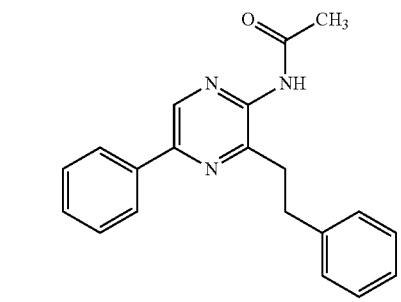
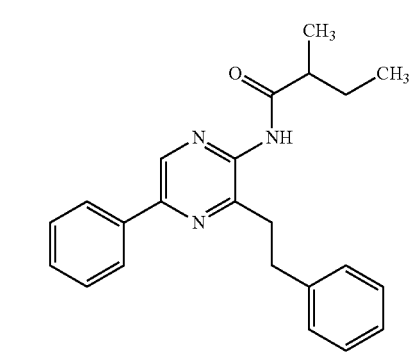

-continued
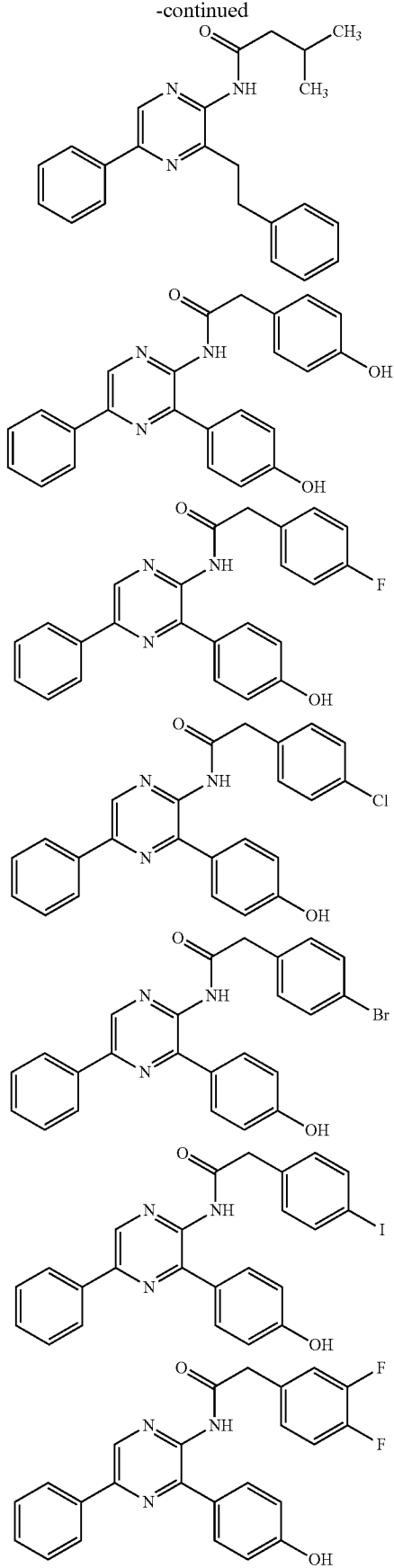
-continued
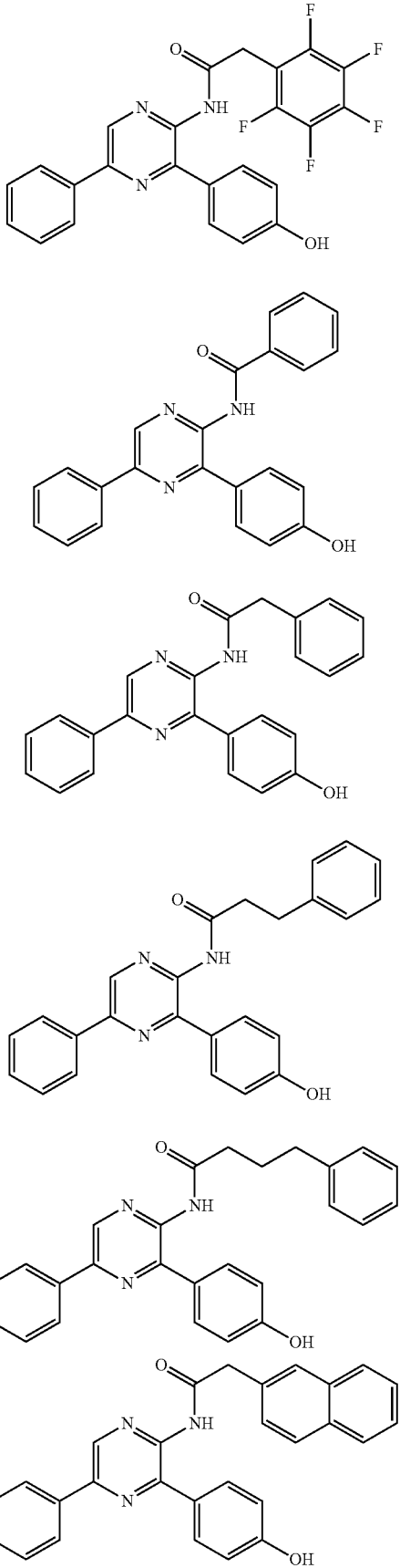

41
-continued
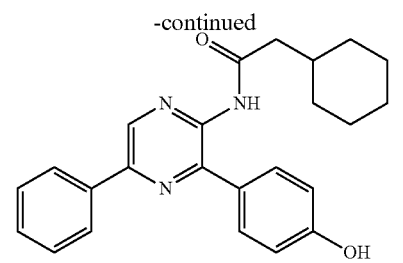
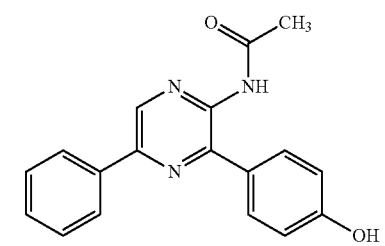
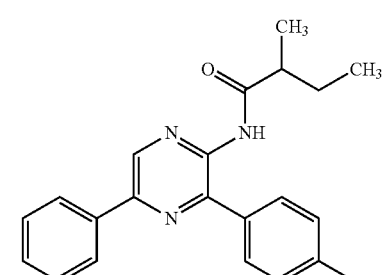
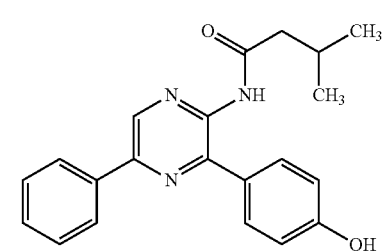
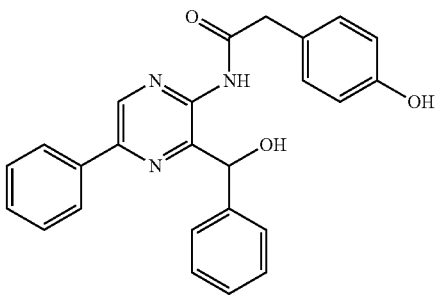
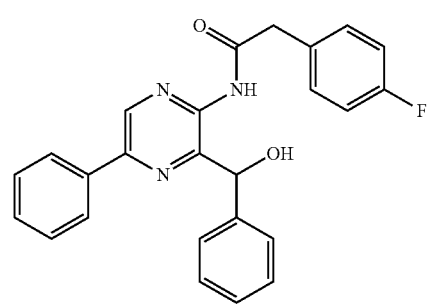
42
-continued
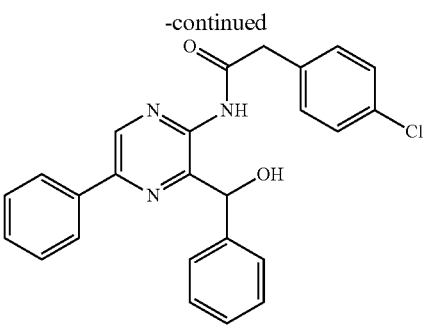
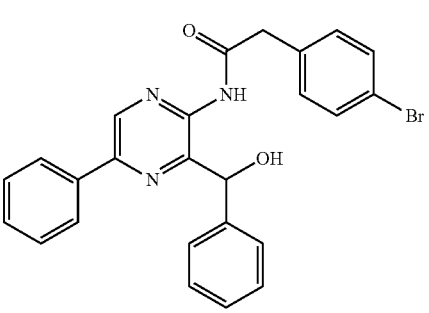
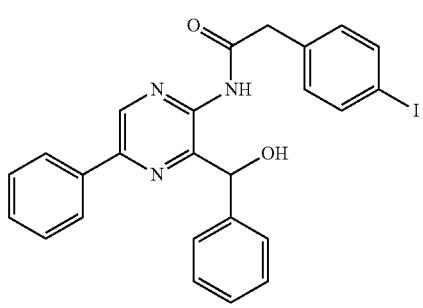
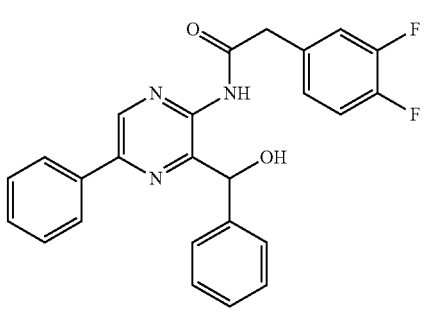
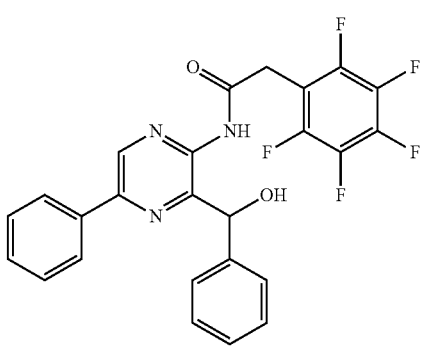

43
-continued
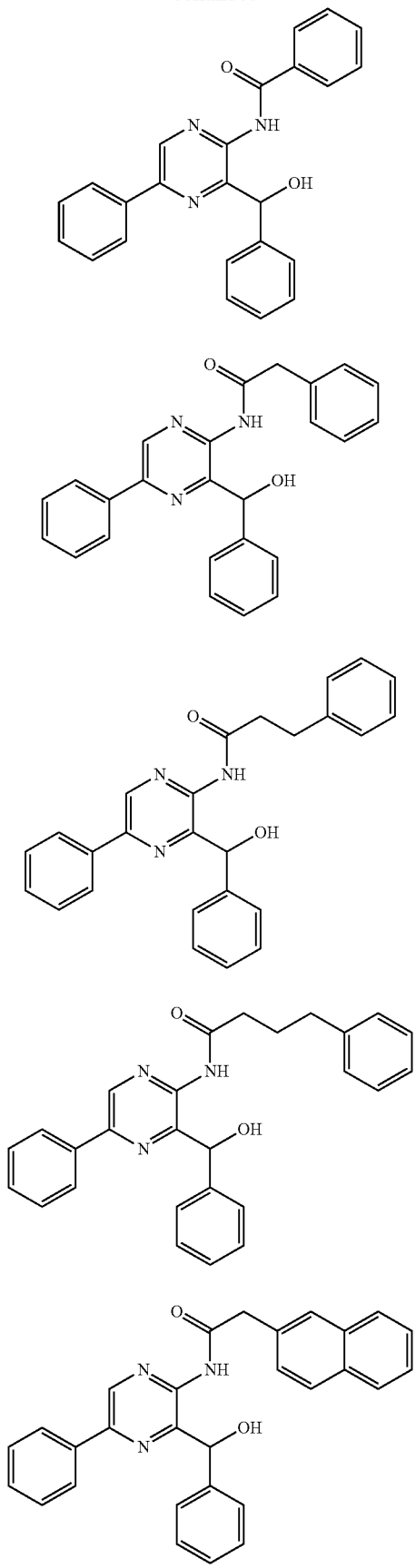
44
-continued
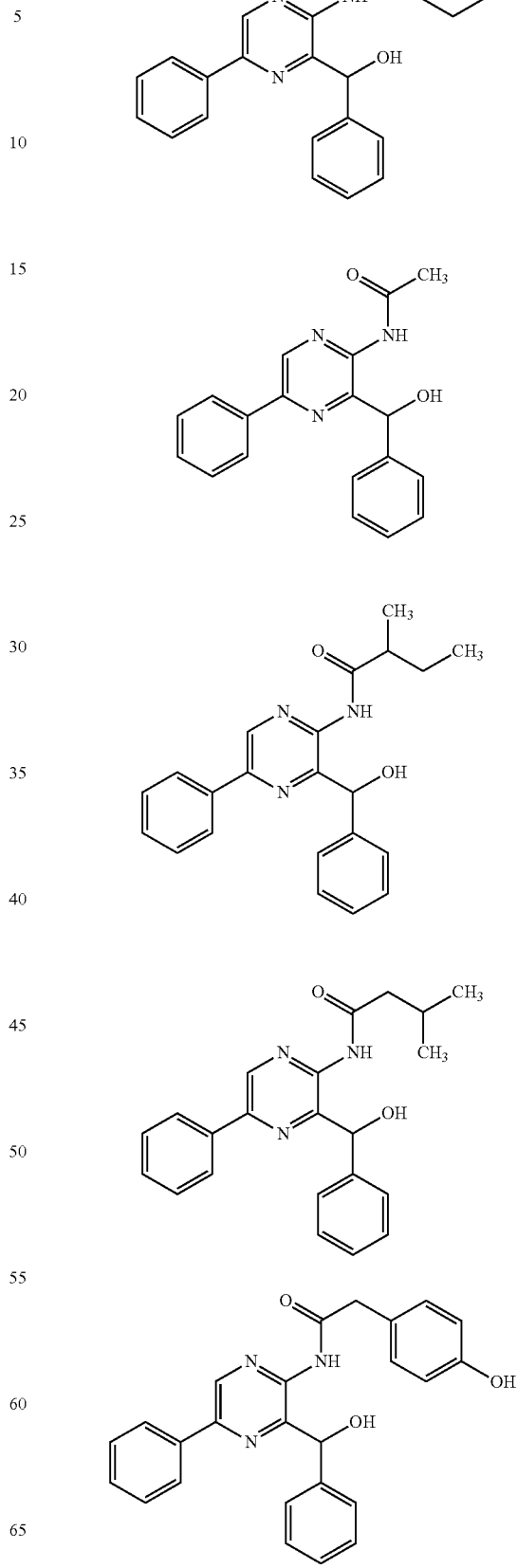

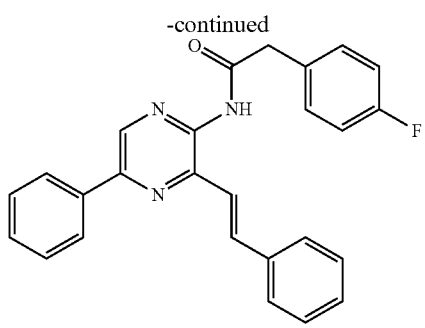
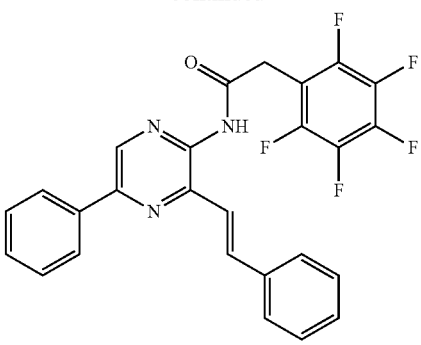
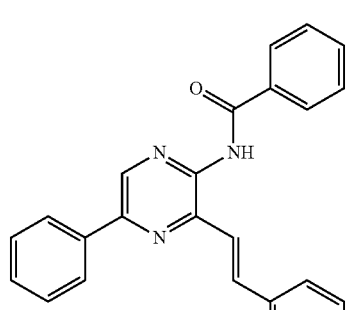
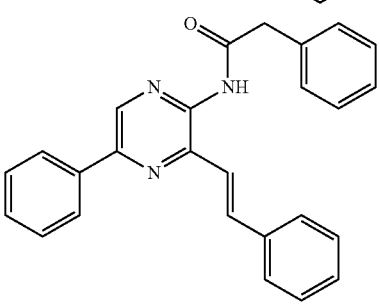
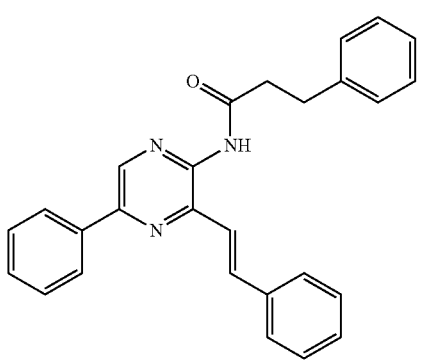
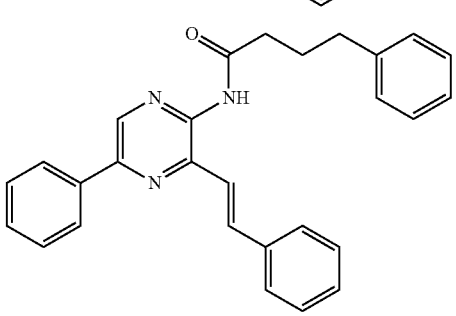

47
-continued
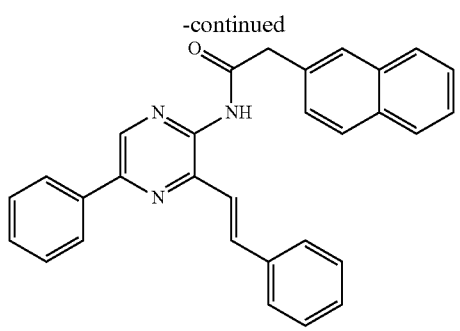
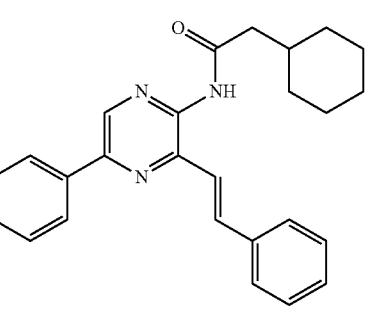
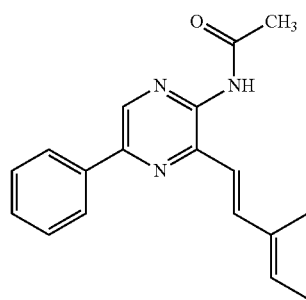
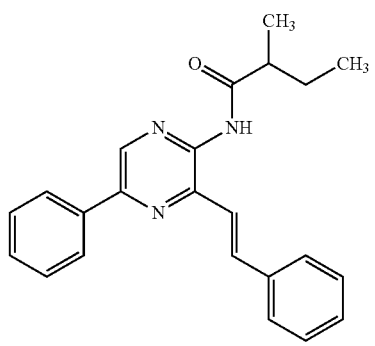
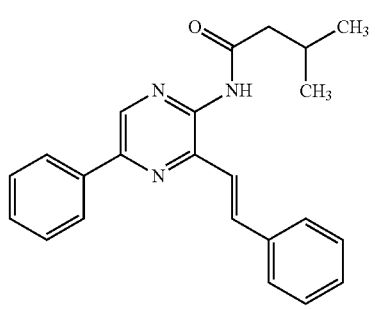
48
-continued
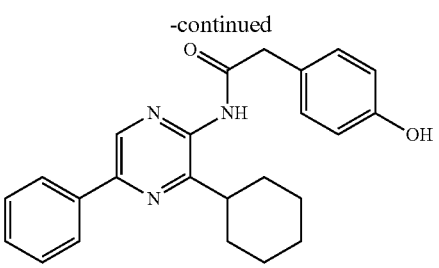
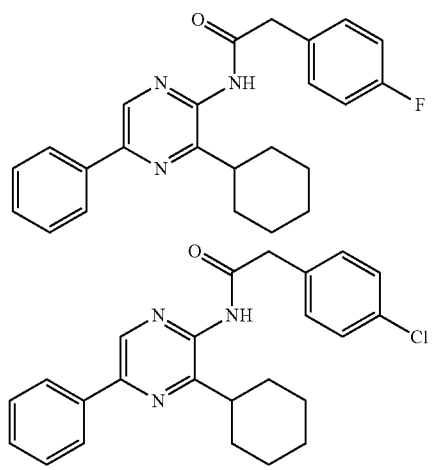
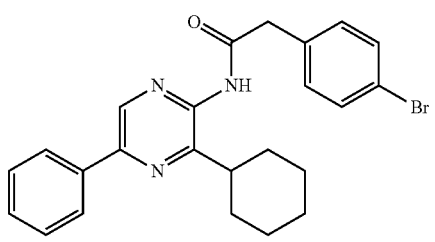
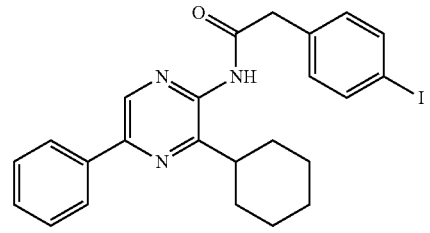
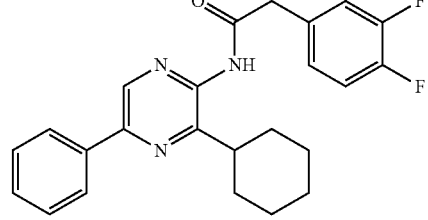
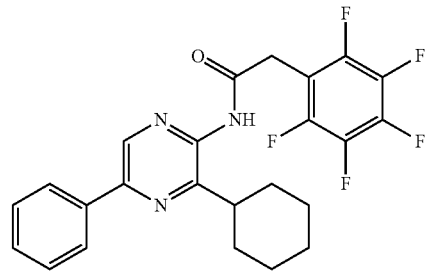

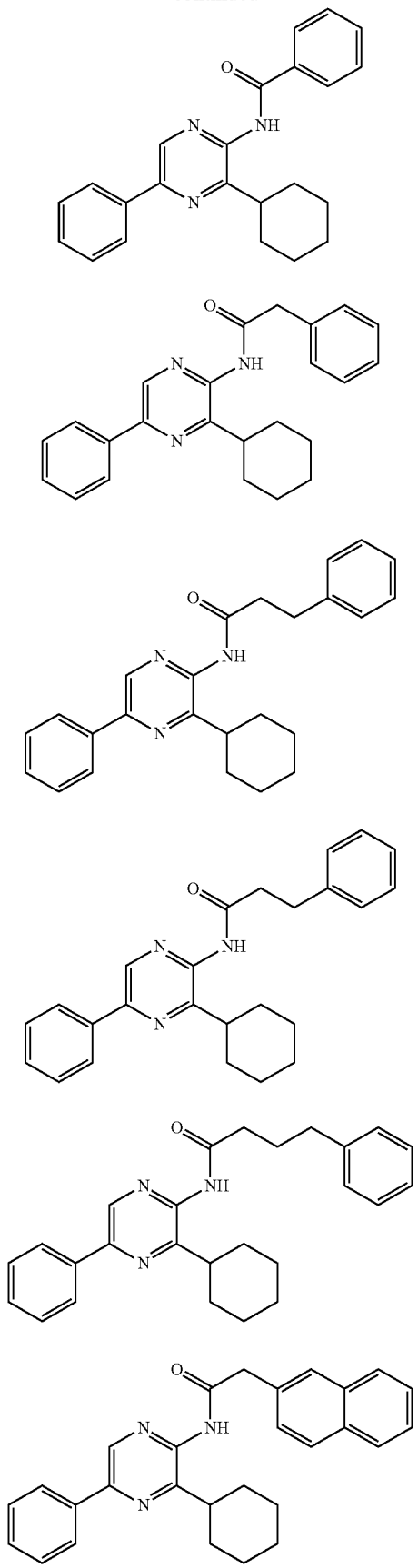
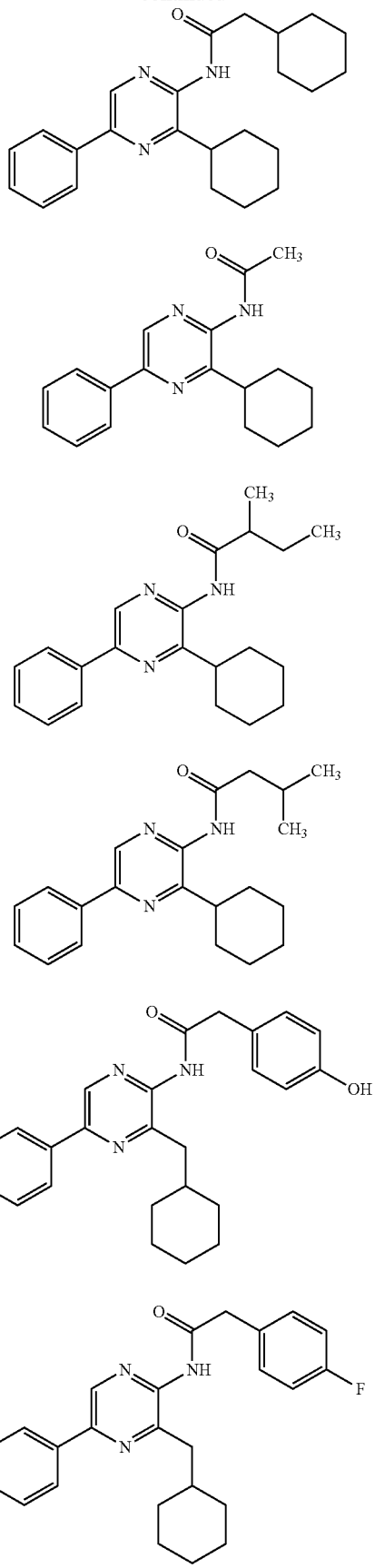

51
-continued
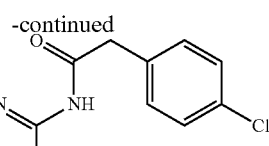
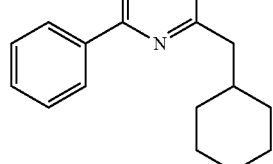
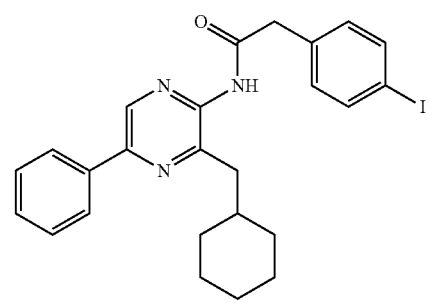
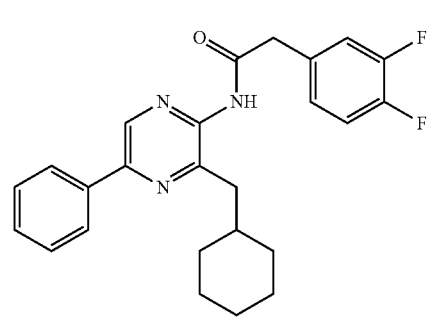
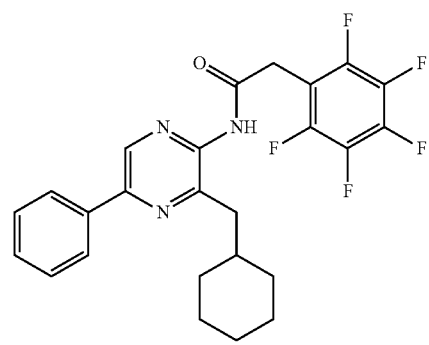
52
-continued
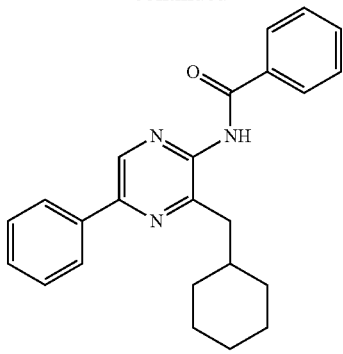
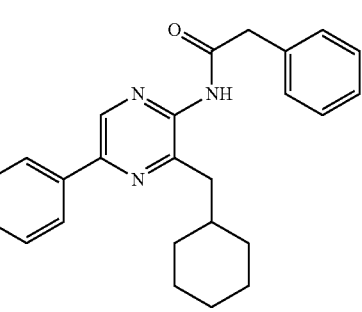
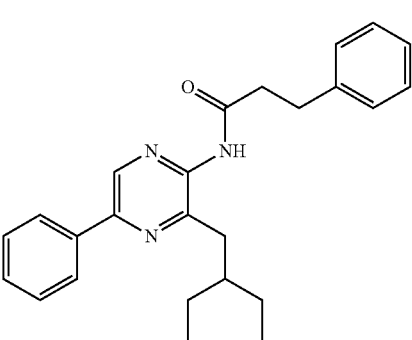
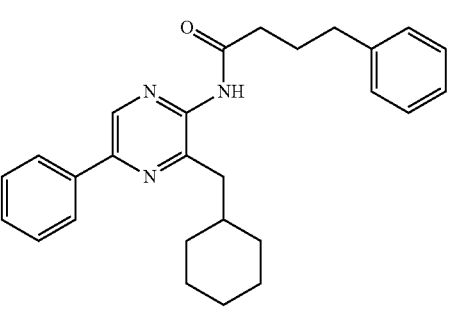
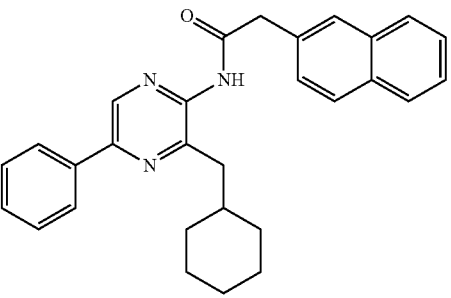

53
-continued
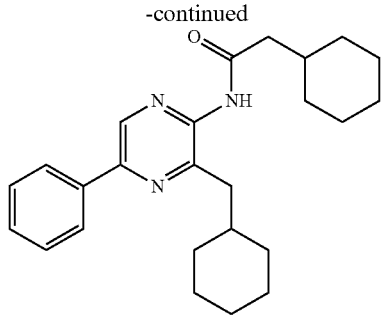
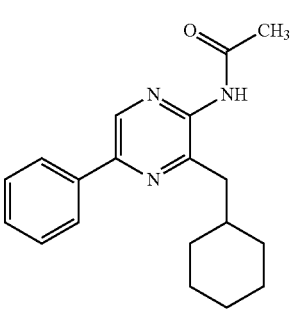
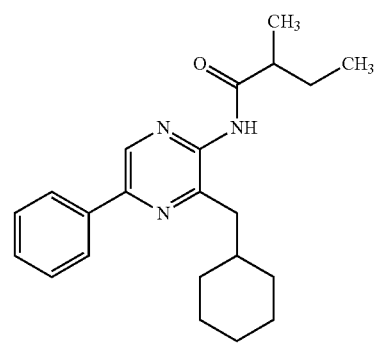
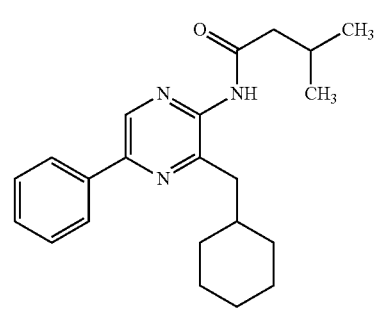
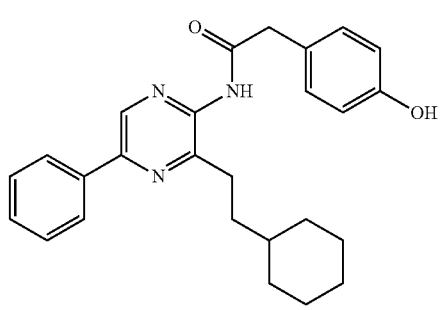
54
-continued
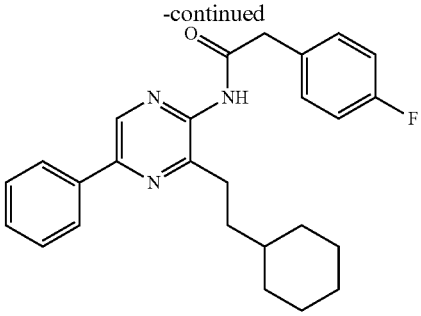
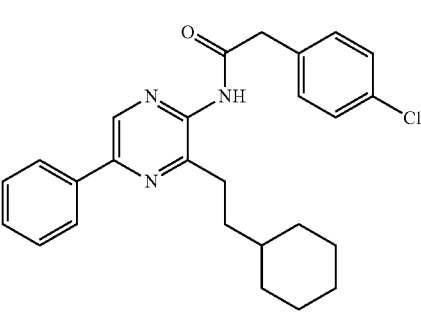
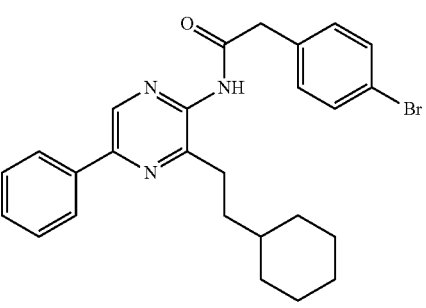
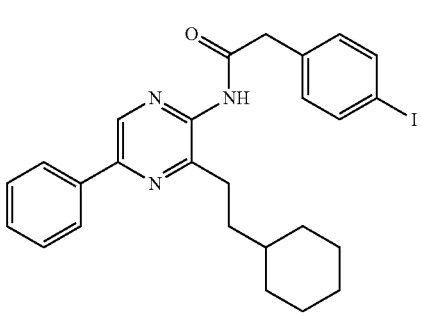
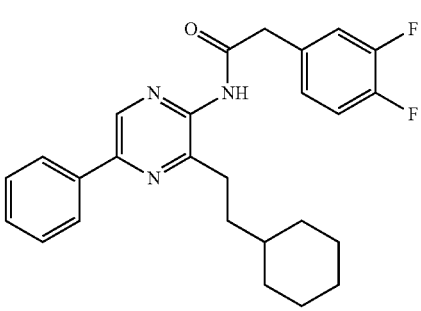

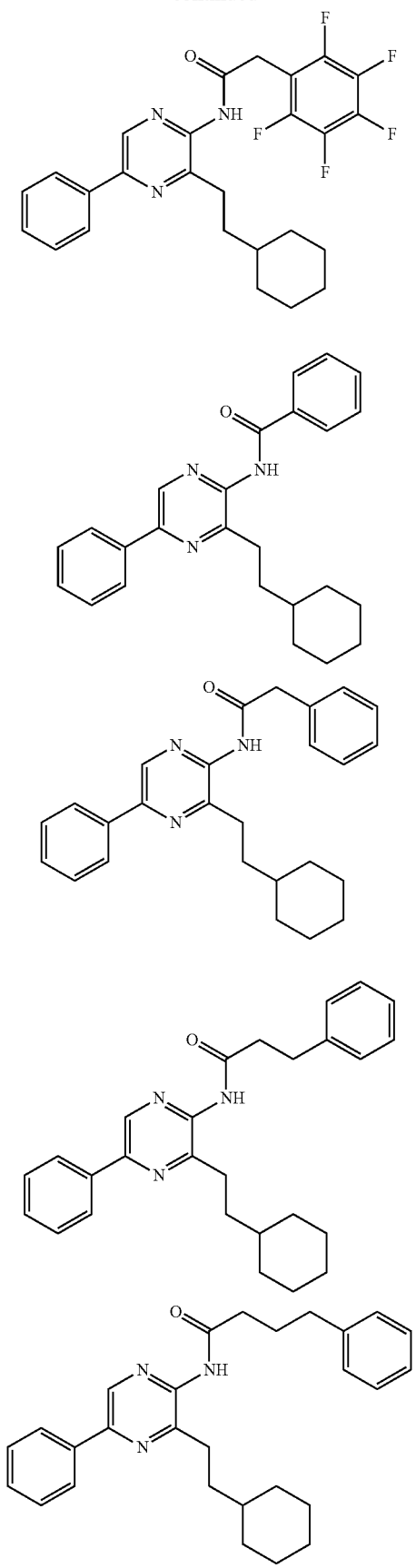
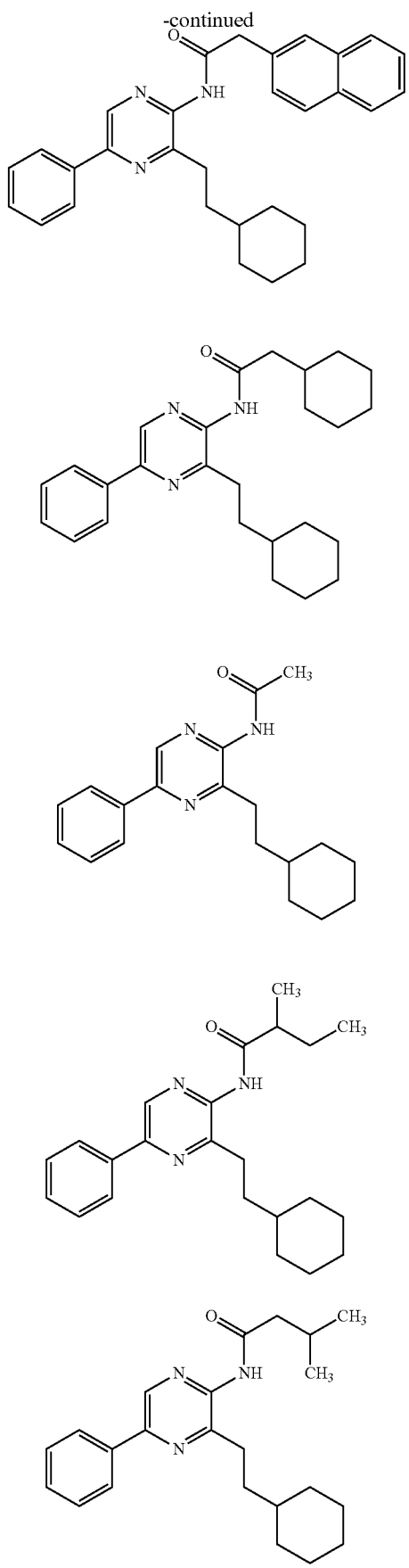

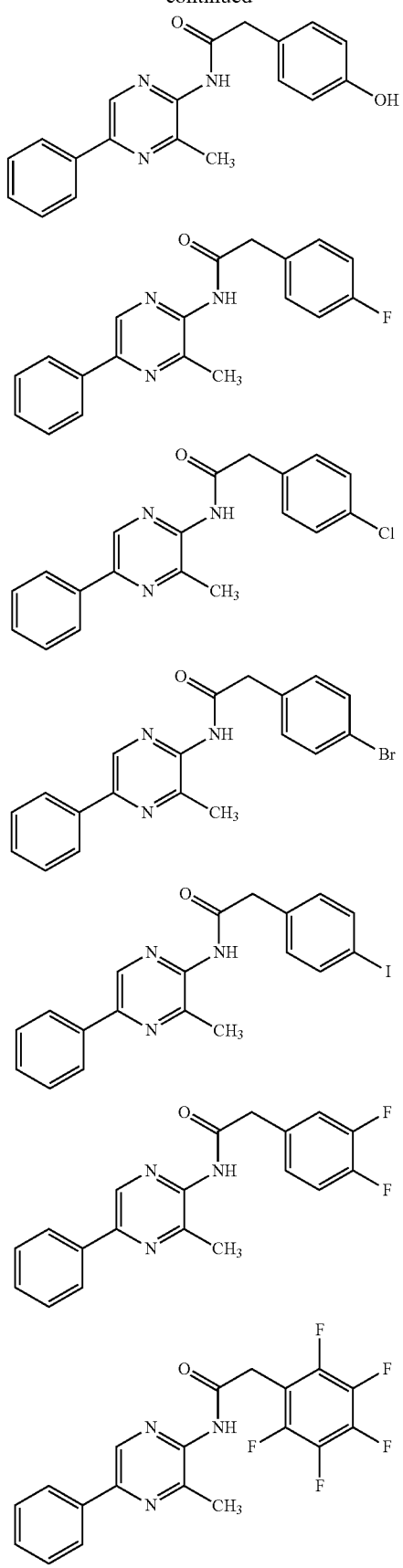
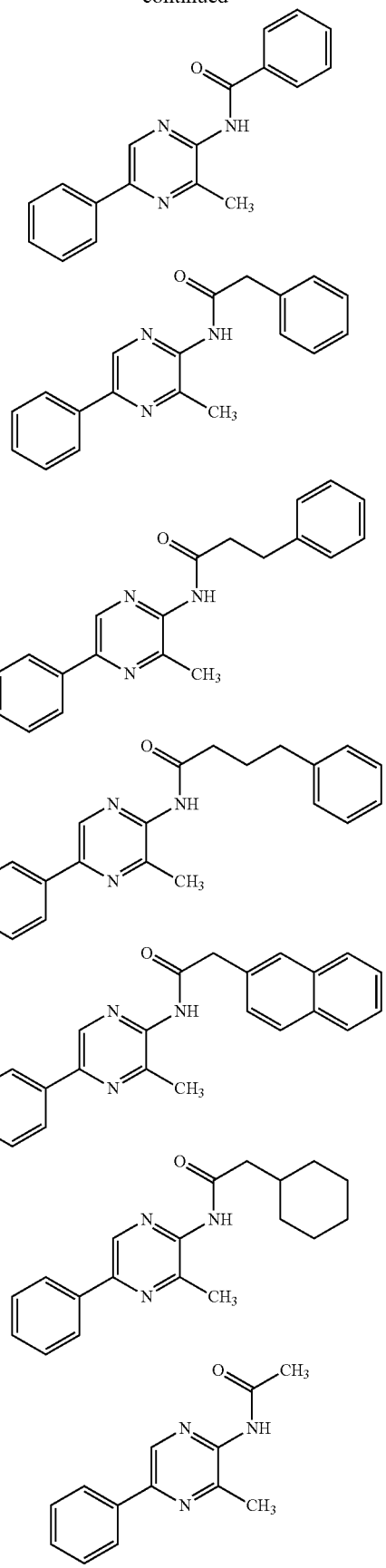

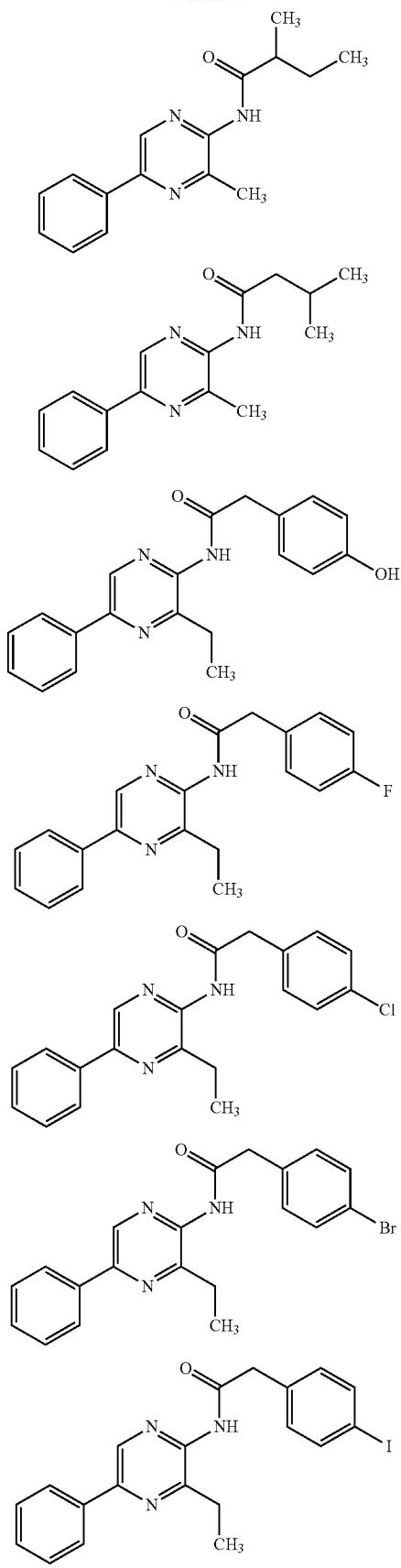
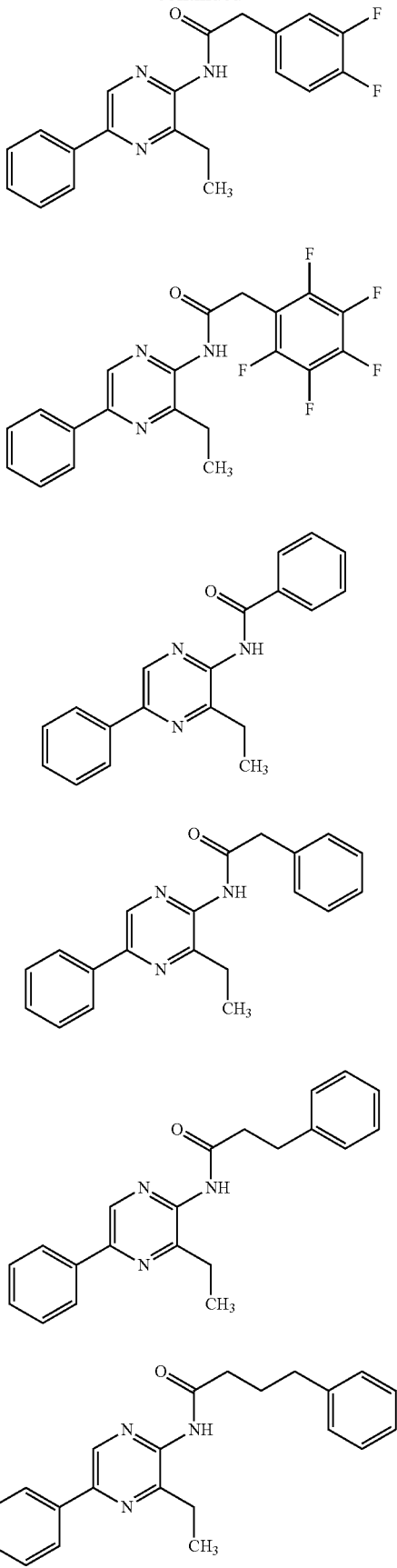

61
-continued
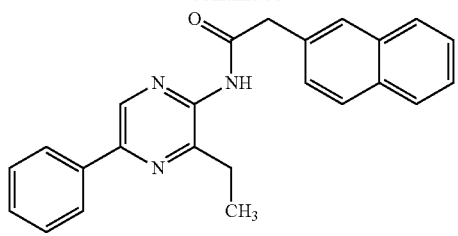
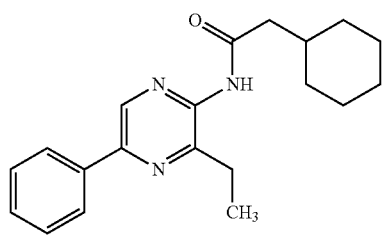
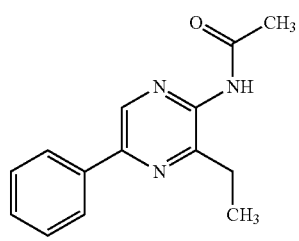
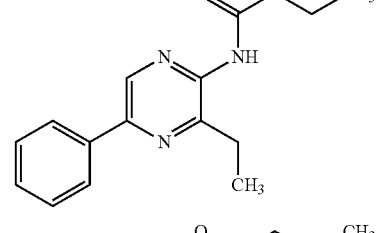
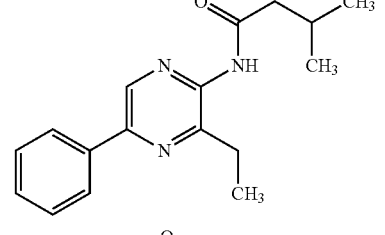
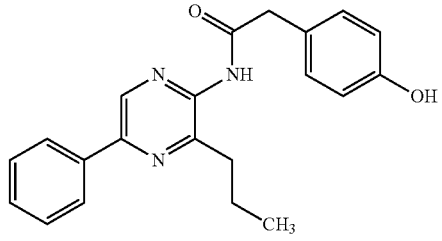
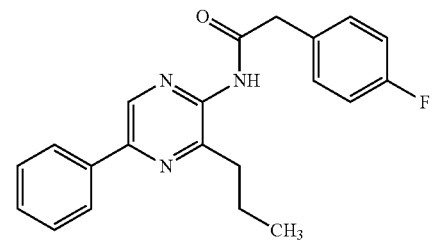
62
-continued
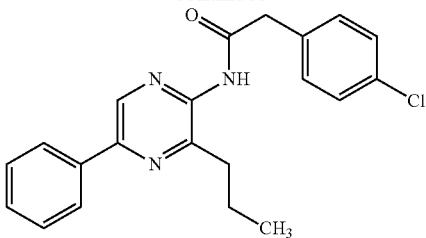
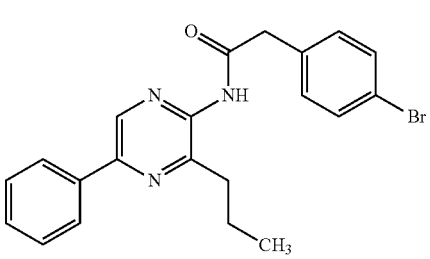
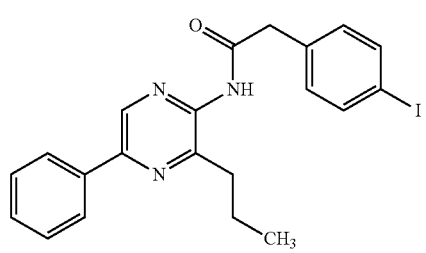
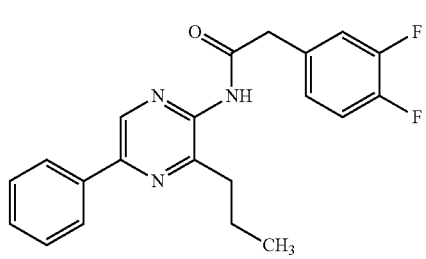
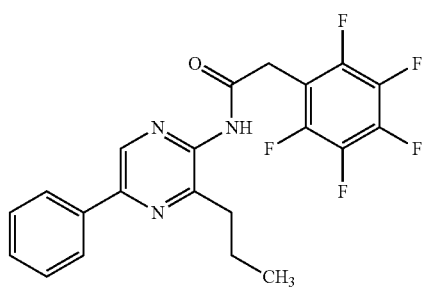

63
-continued
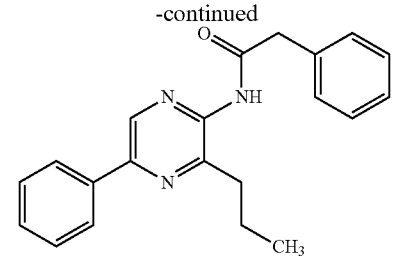
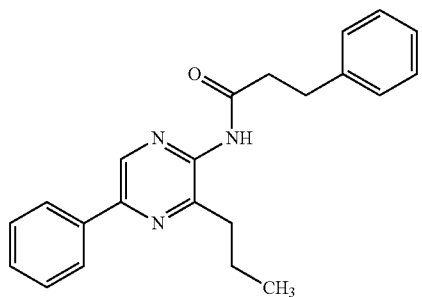
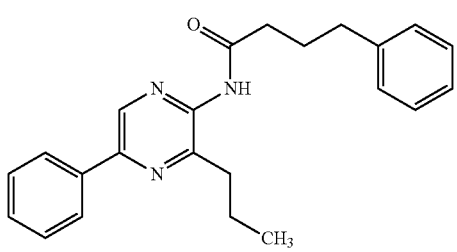
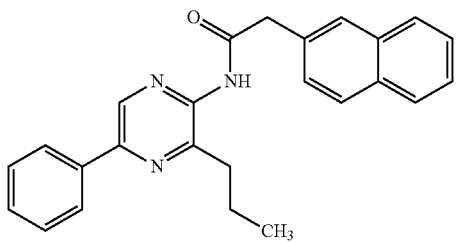
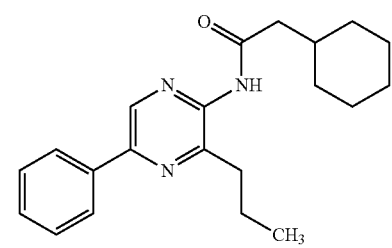
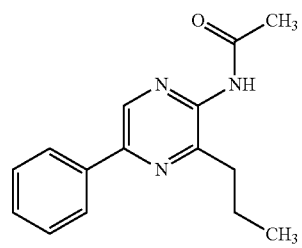
64
-continued
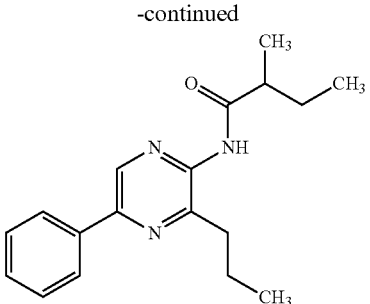
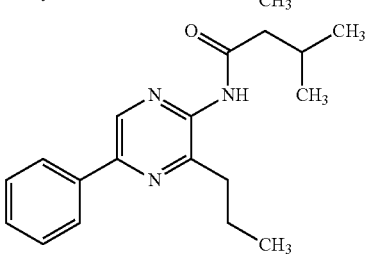
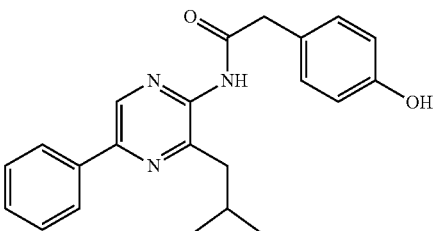
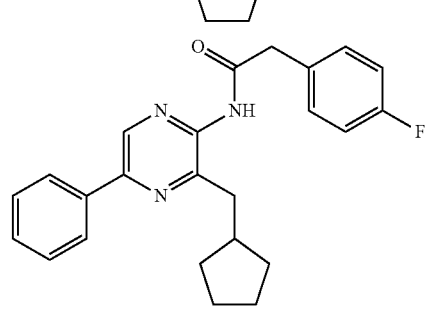
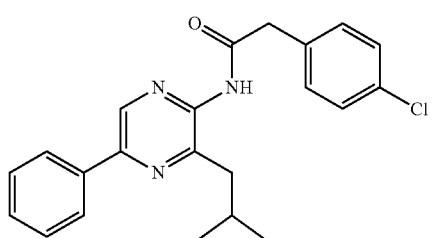
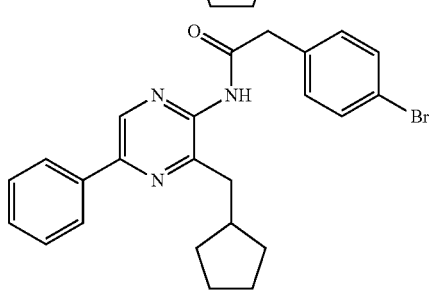

65
-continued
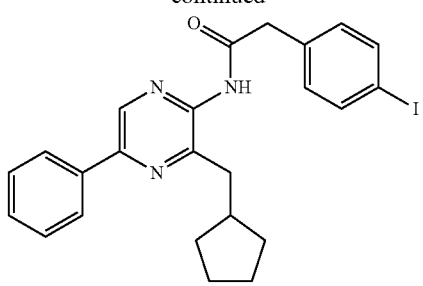
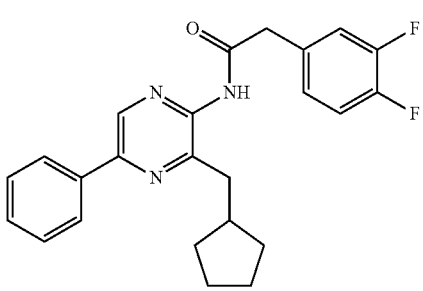
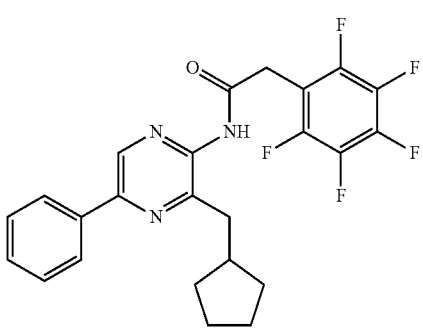
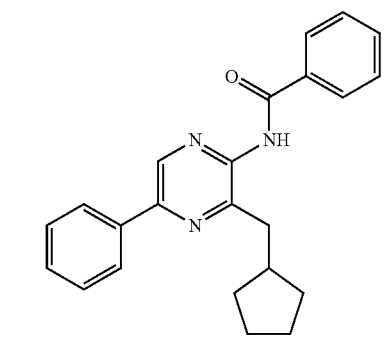 [SMILES: O=C(Nc1ncc(-c2ccccc2)nc1CC1CCCC1)c1ccccc1]
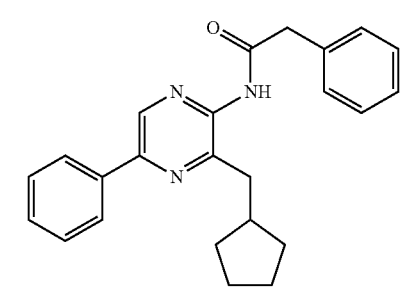
66
-continued
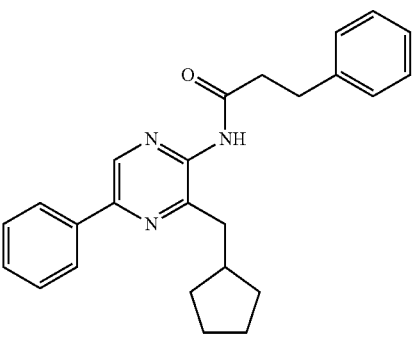
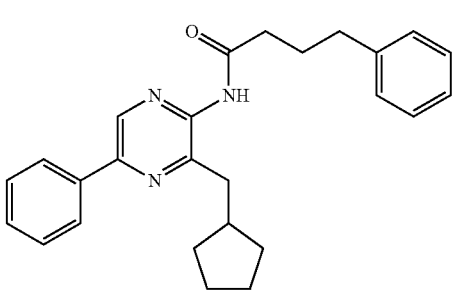
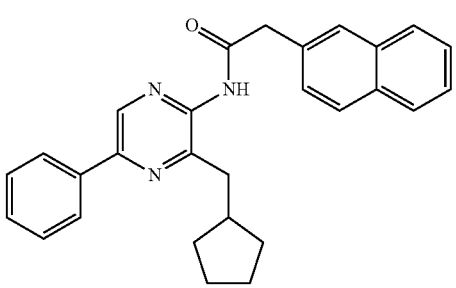
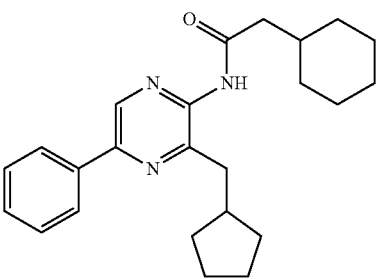
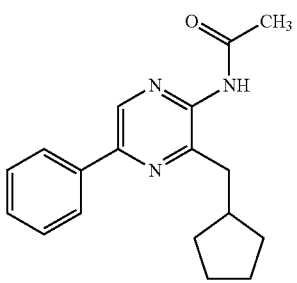

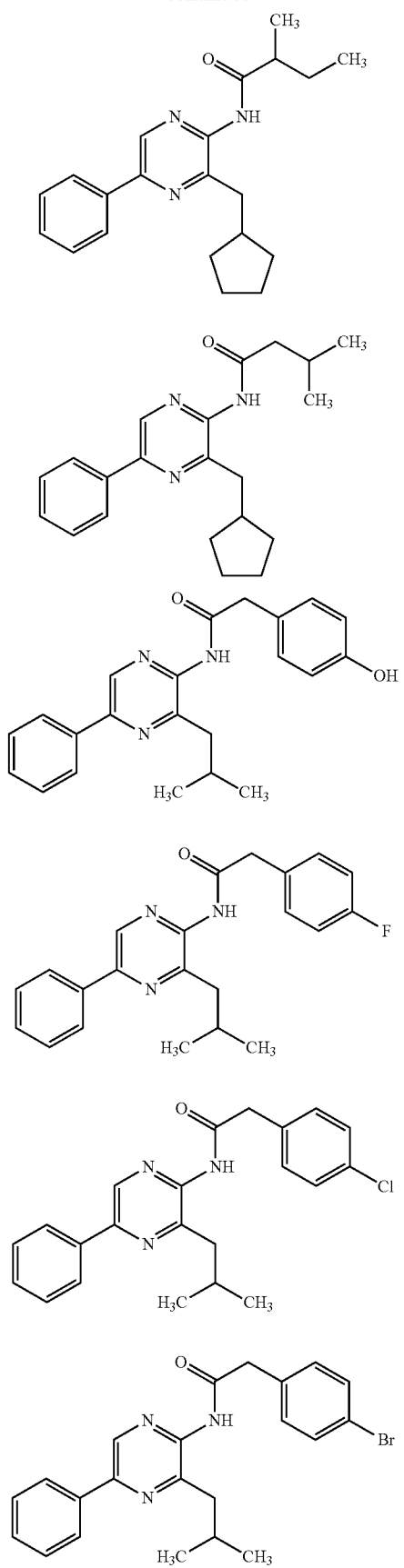
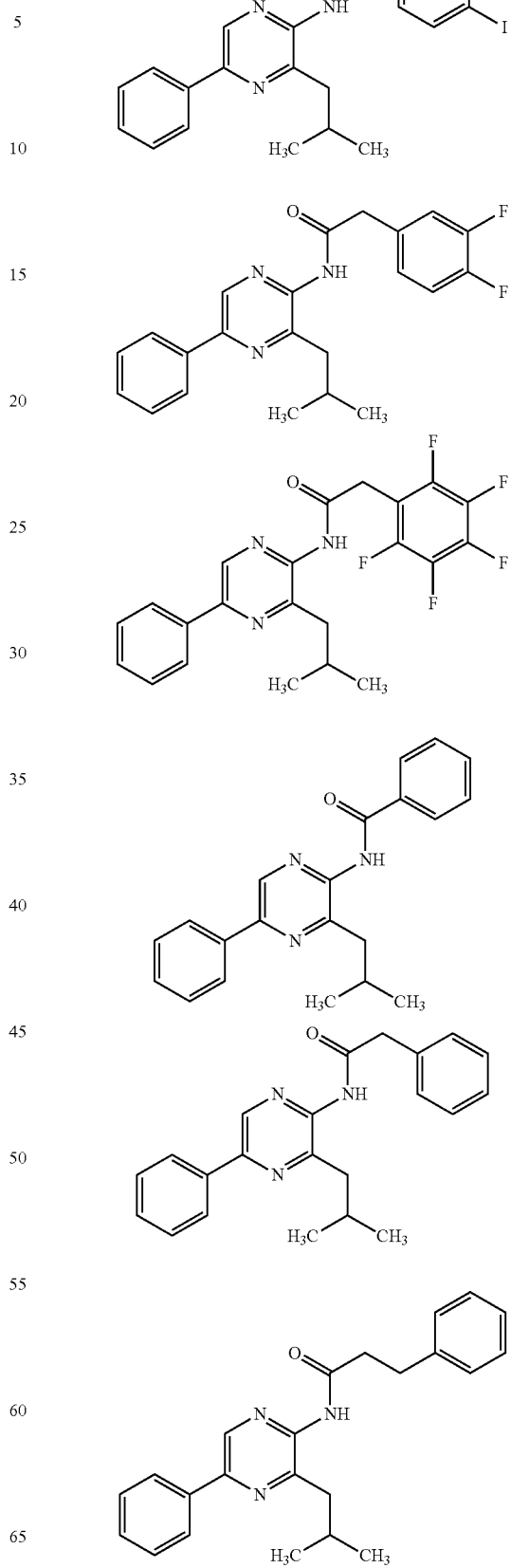

-continued
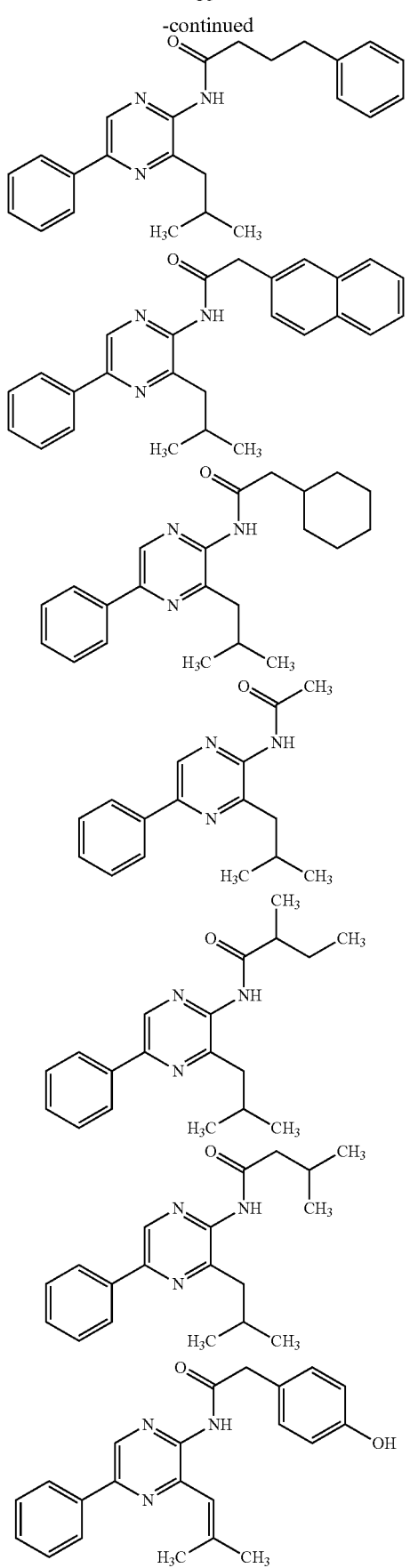
-continued
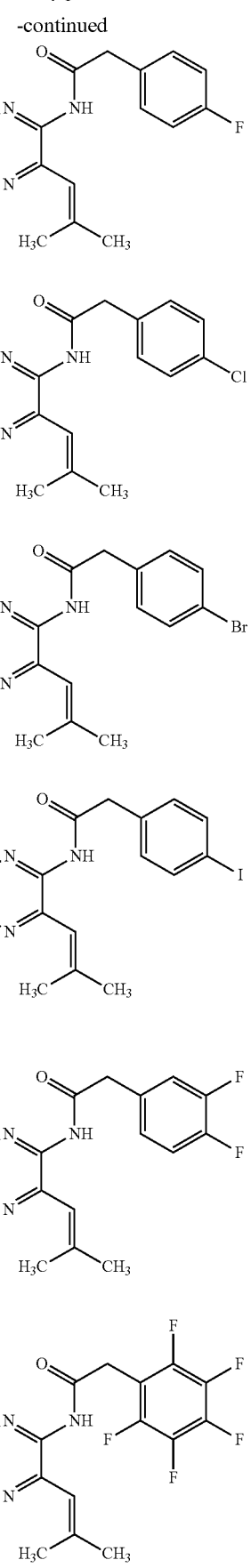

| 71 -continued | 72 -continued |
|---|---|
| 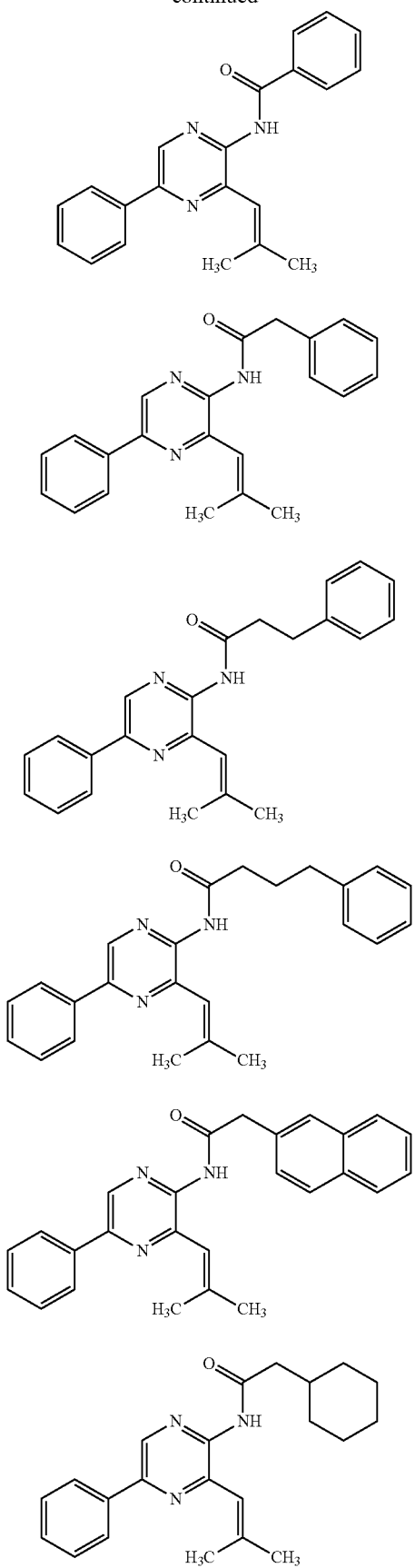 | 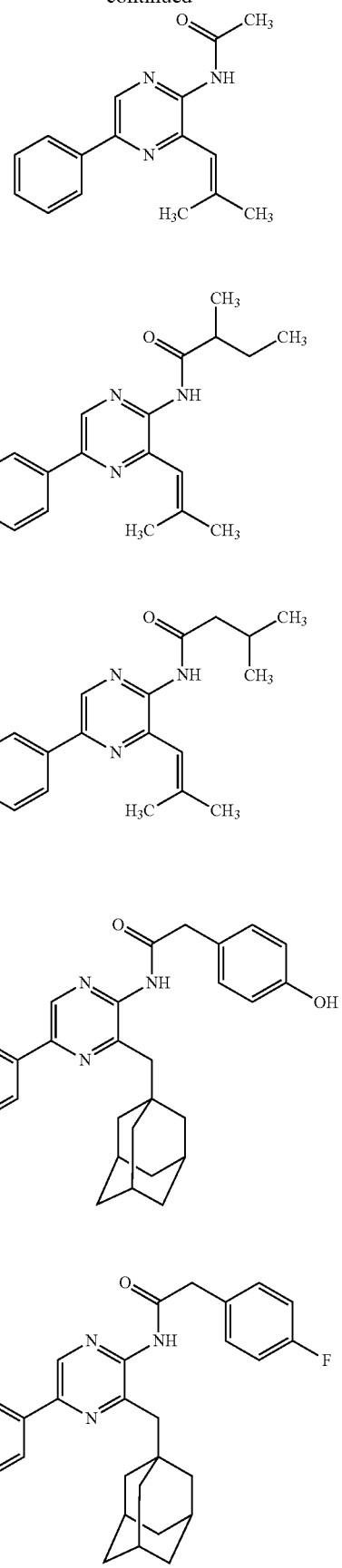 |

73
-continued
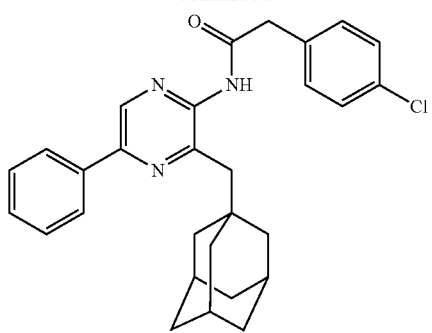
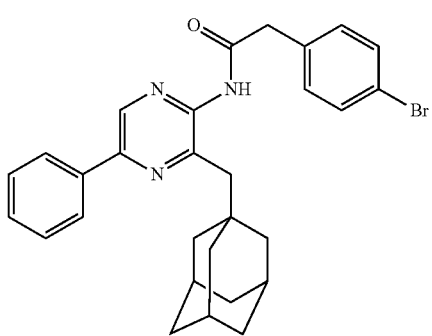
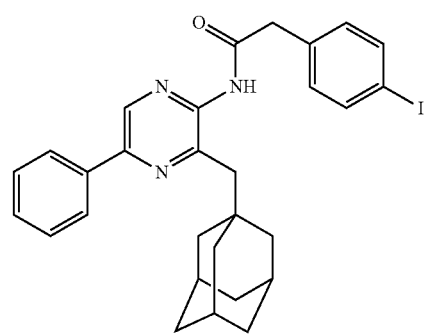
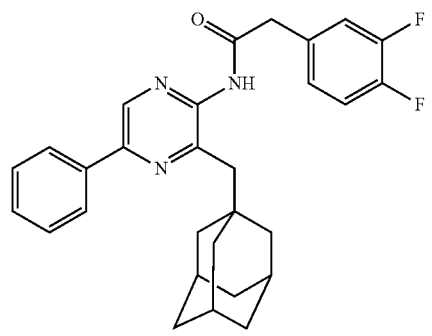
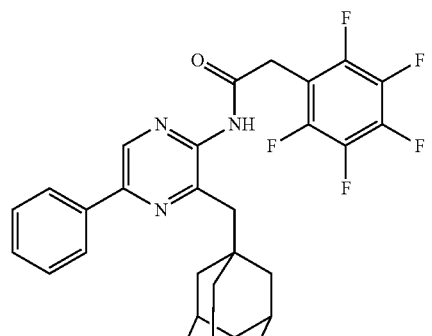
74
-continued
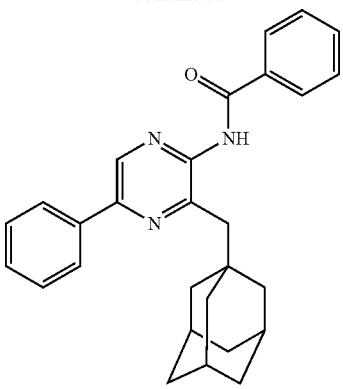
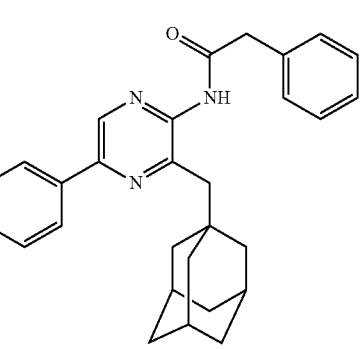
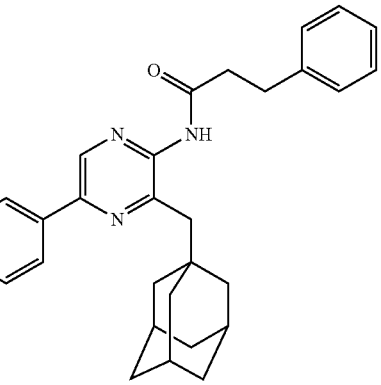
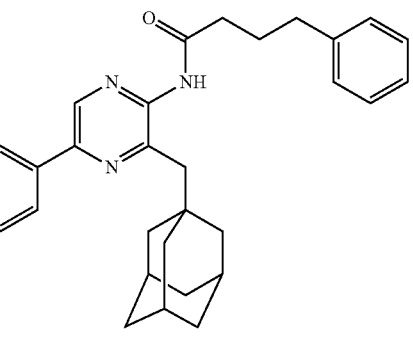

75
-continued
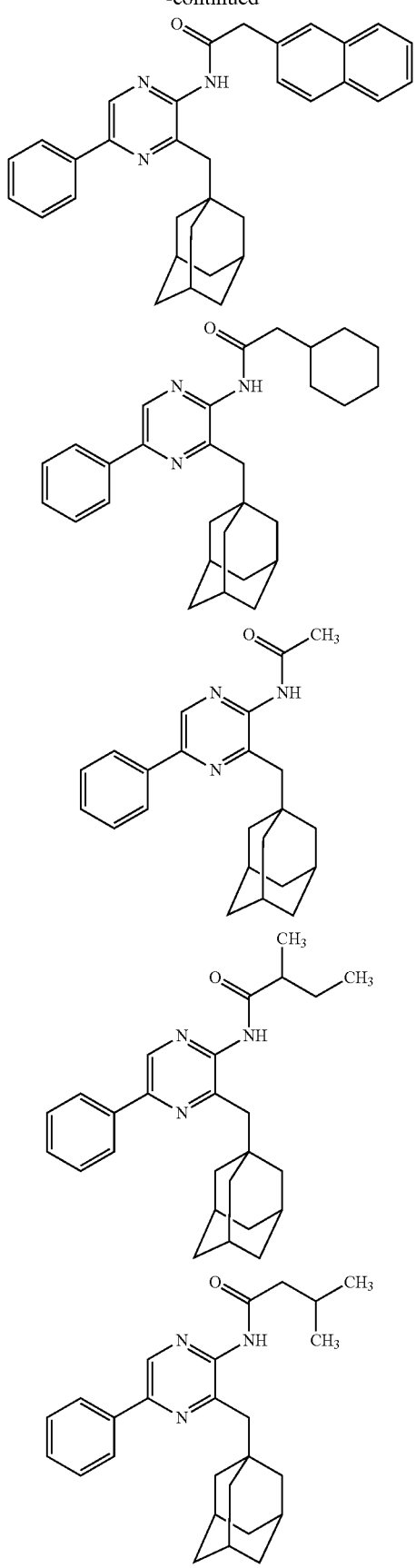
76
-continued
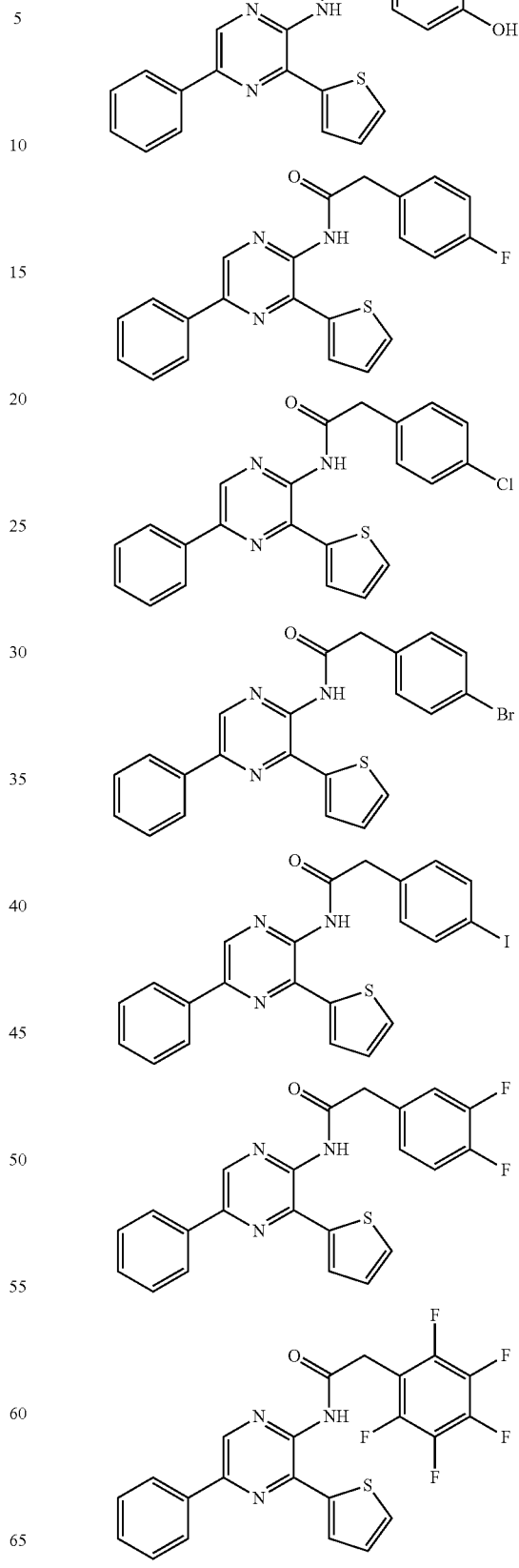

77
-continued
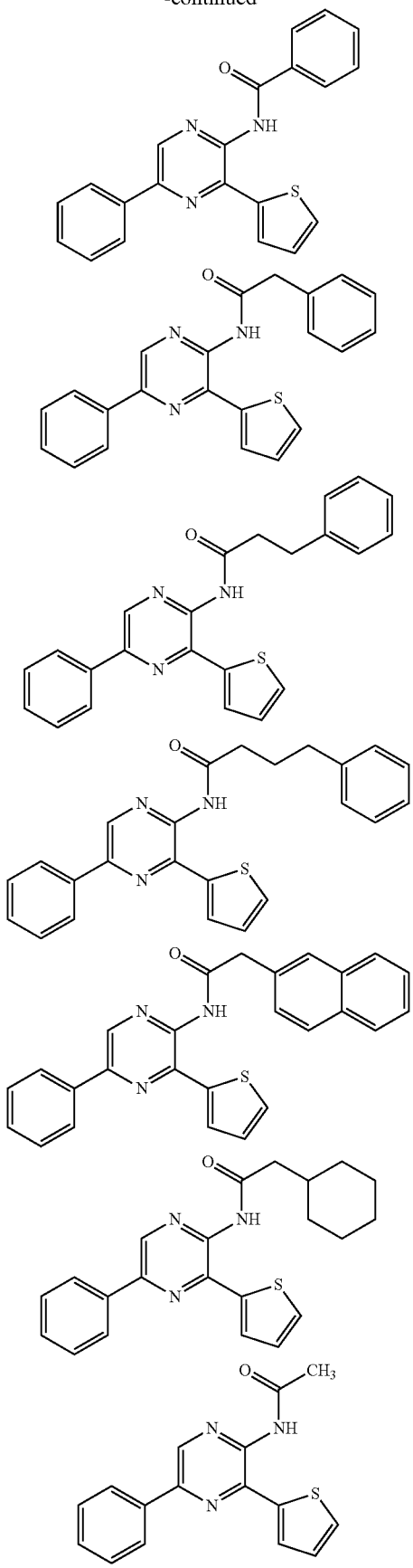
78
-continued
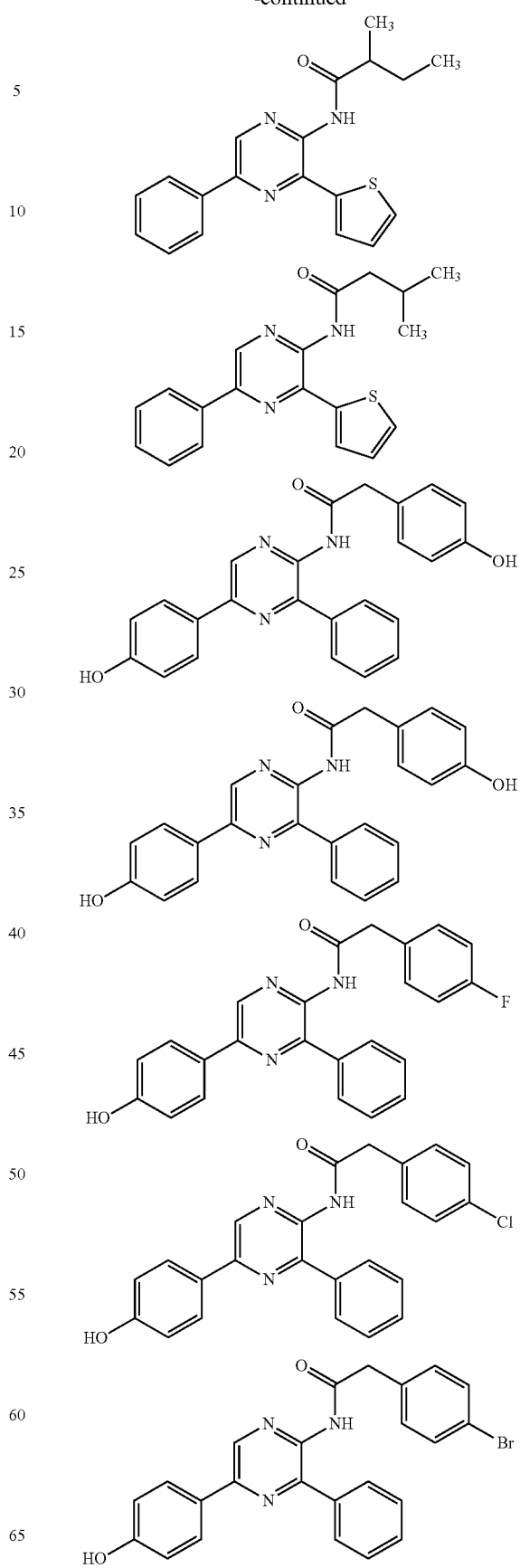

79
-continued
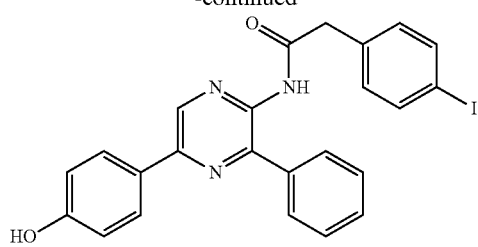
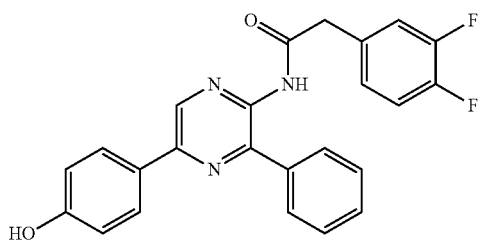
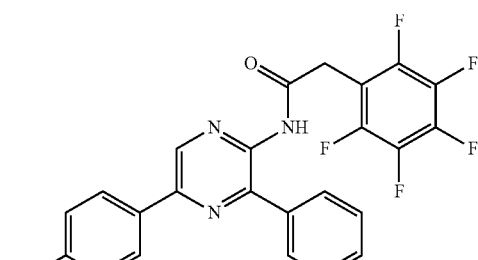
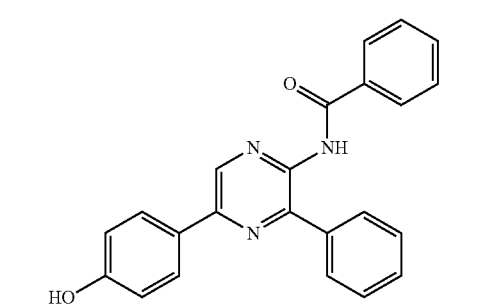
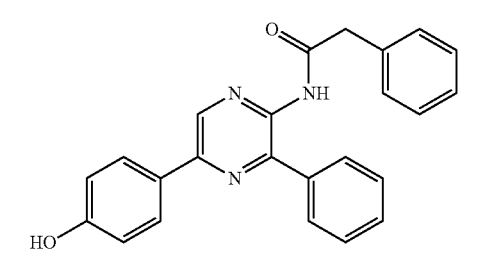
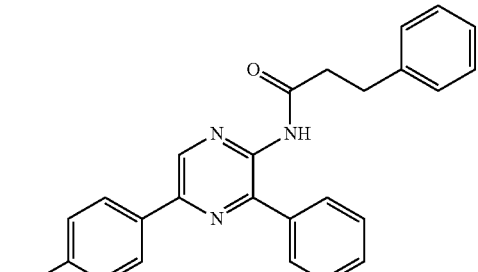
80
-continued
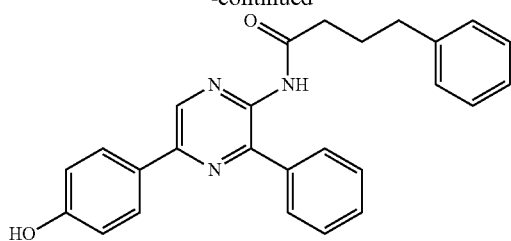
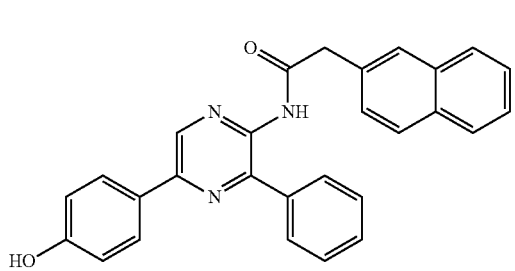
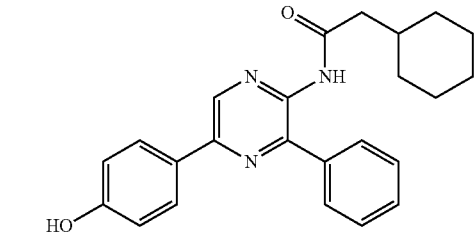
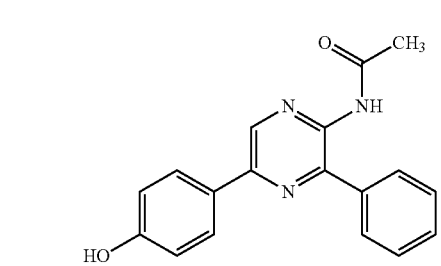
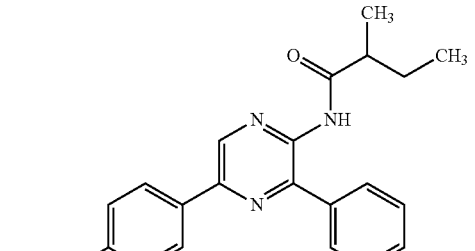
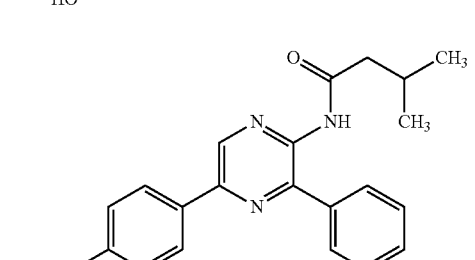

-continued
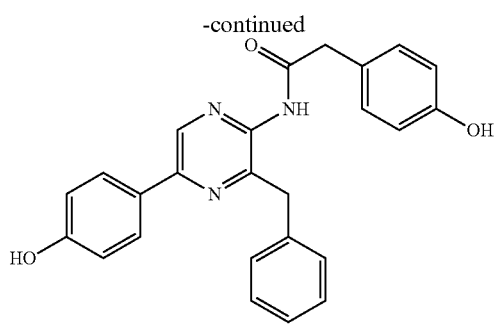
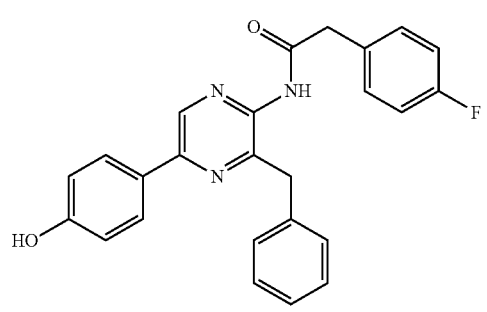
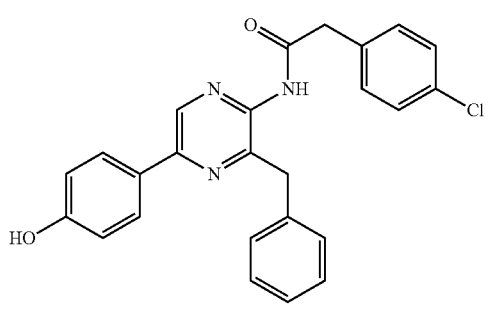
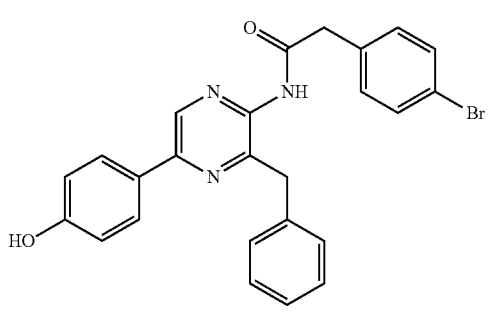
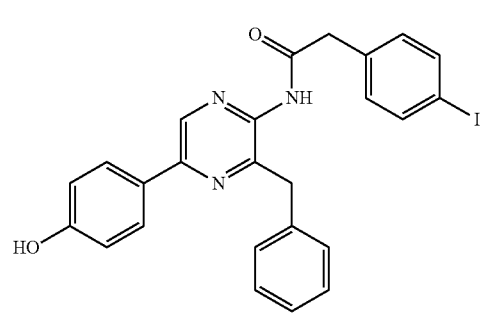
-continued
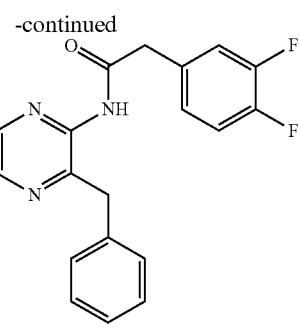
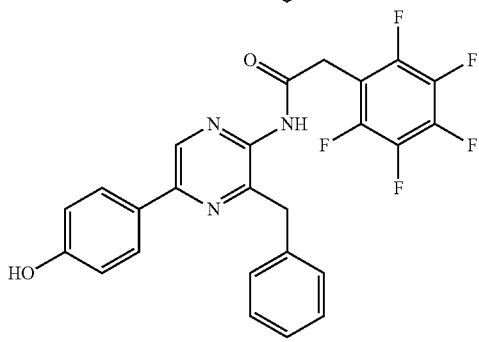
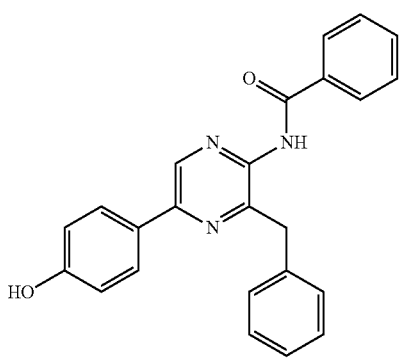
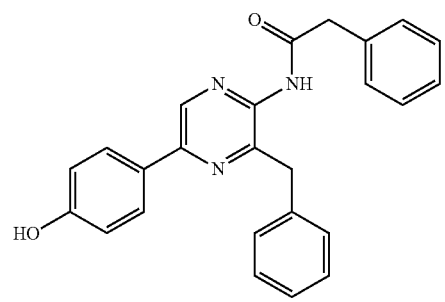
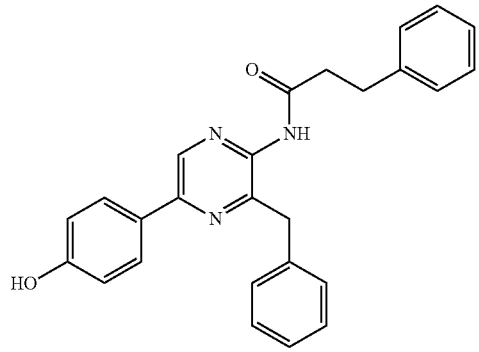

83
-continued
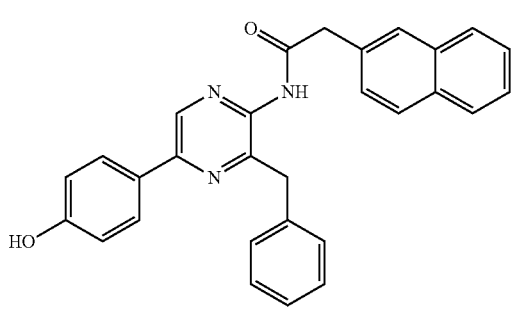
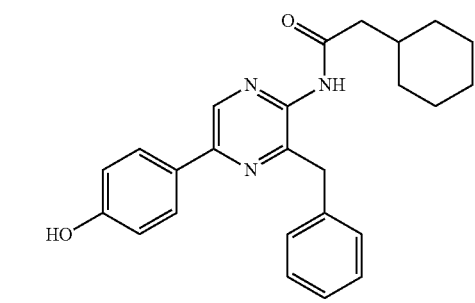
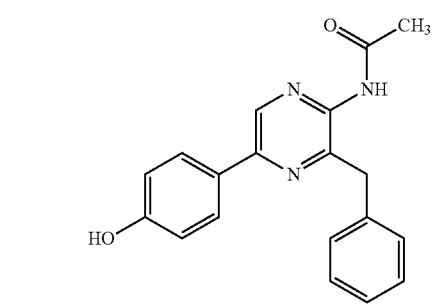
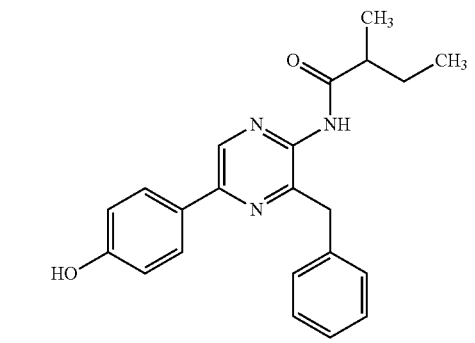
84
-continued
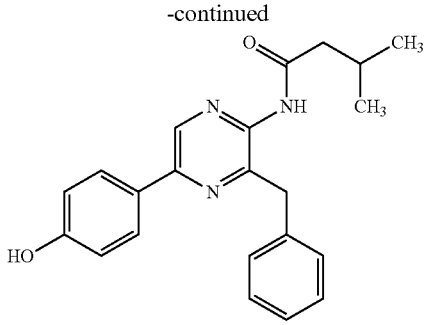
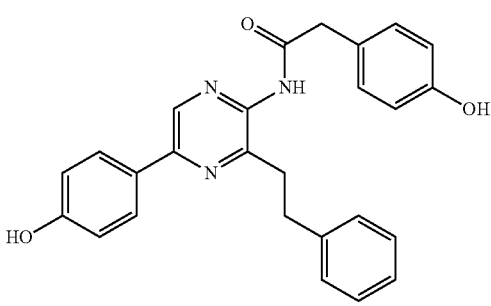
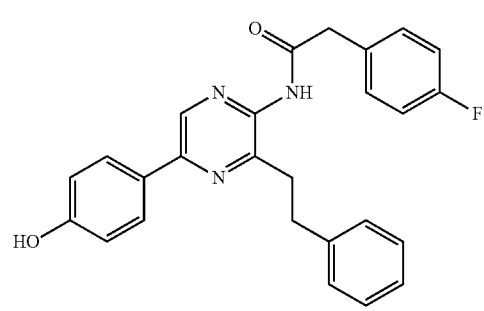
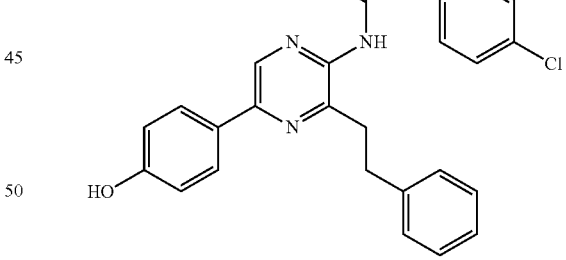
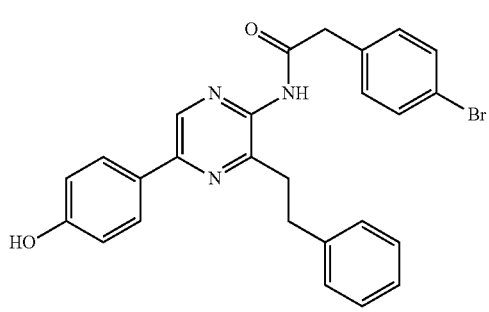

85
-continued
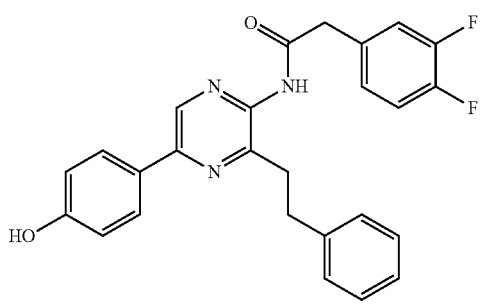
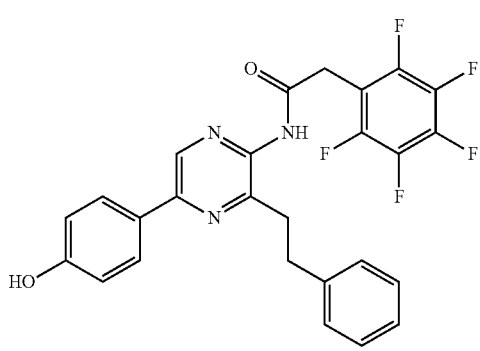
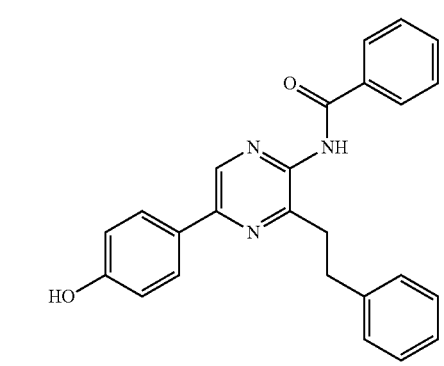
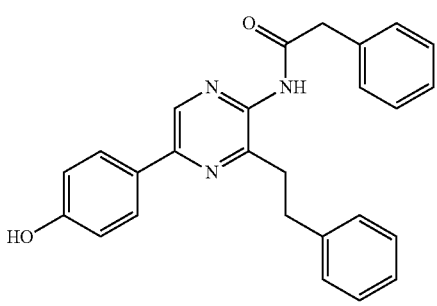
86
-continued
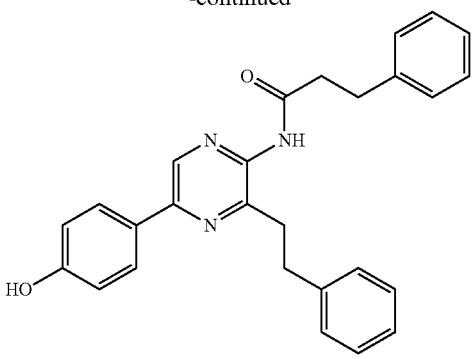
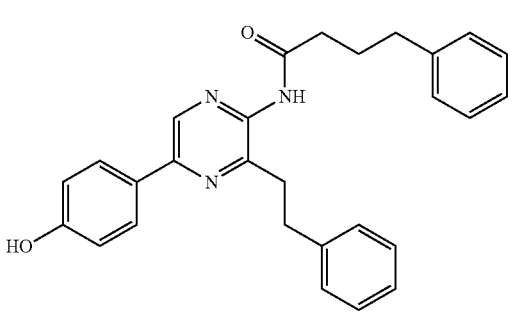
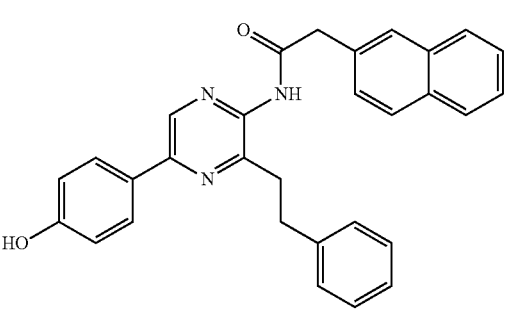
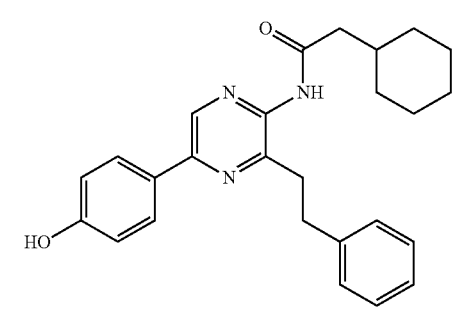
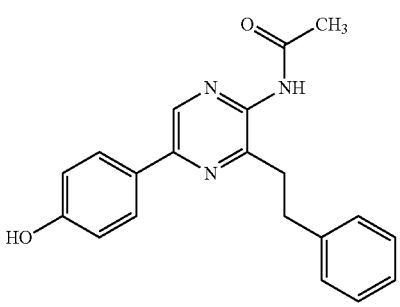

87
-continued
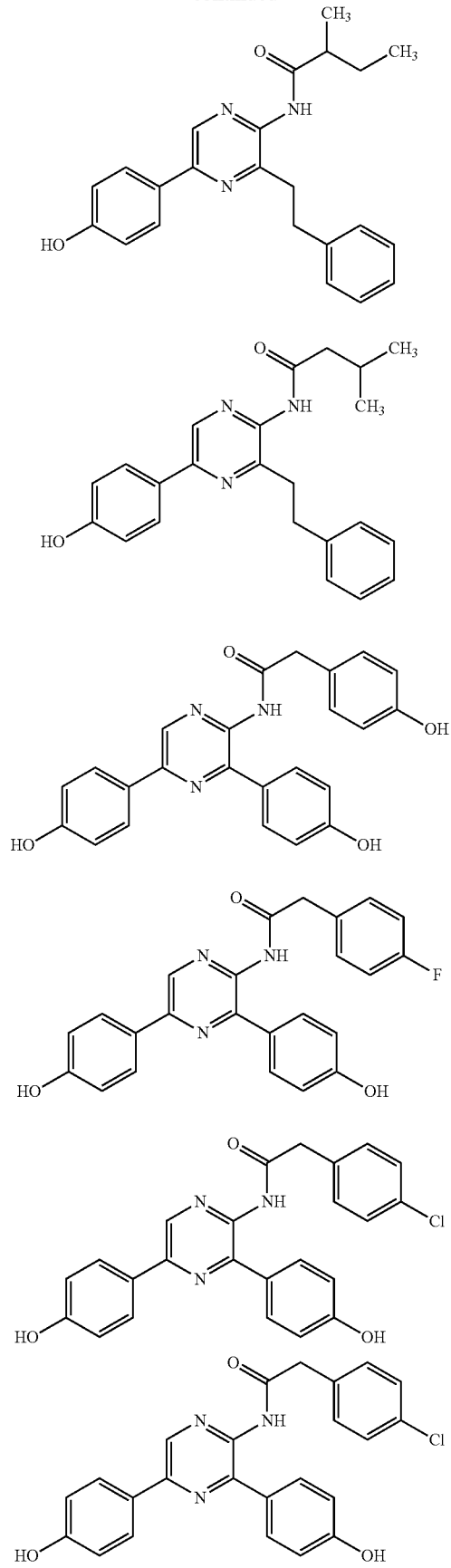
88
-continued
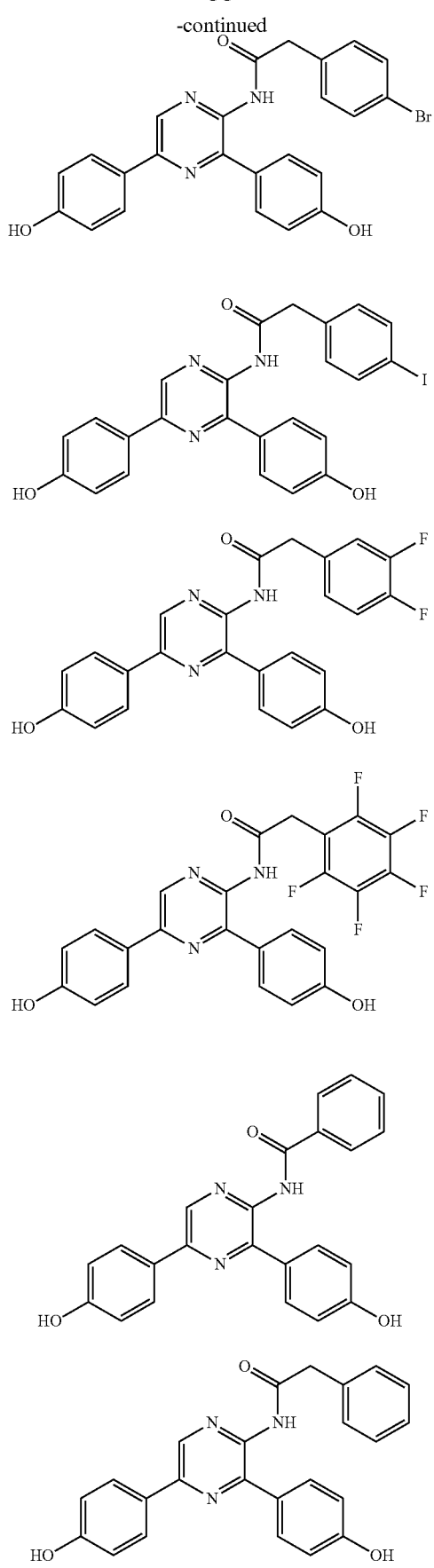

89
-continued
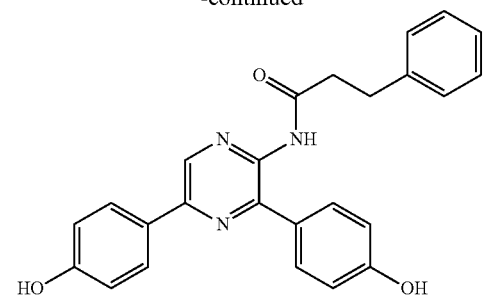
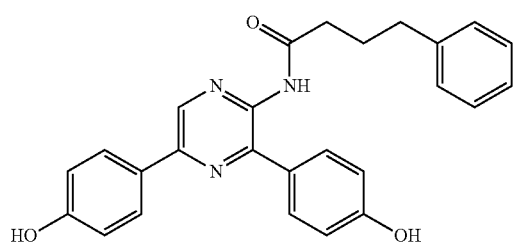
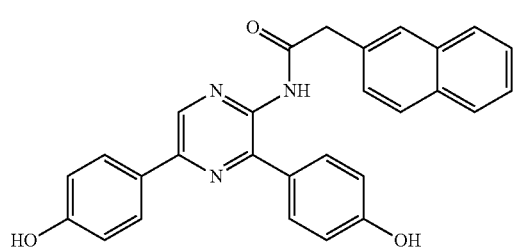
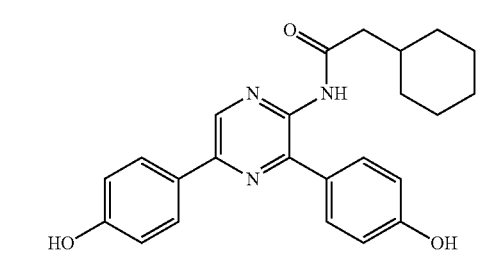
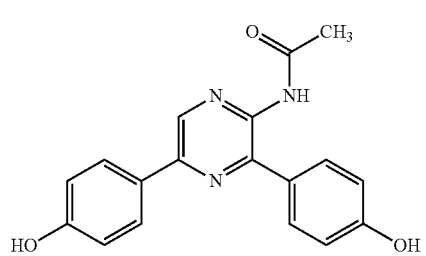
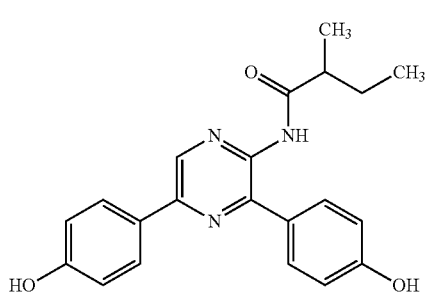
90
-continued
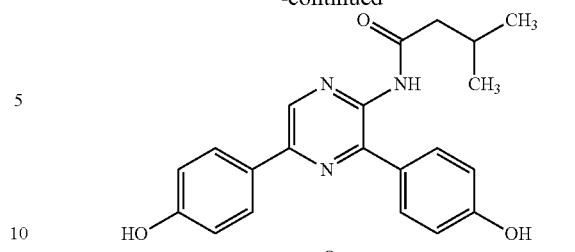
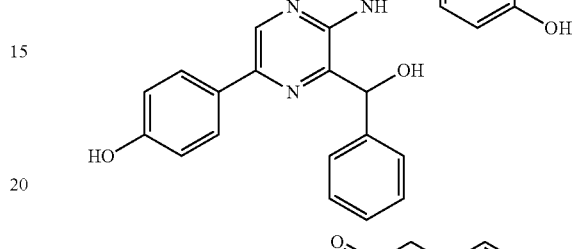
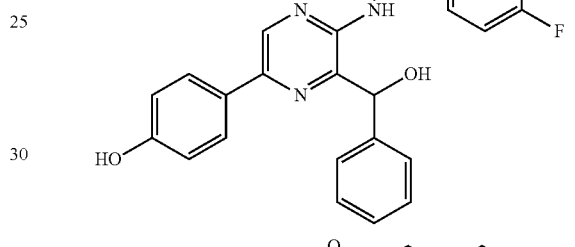
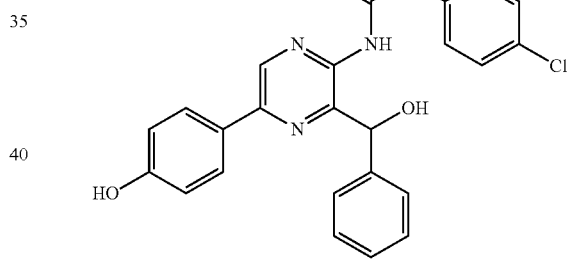
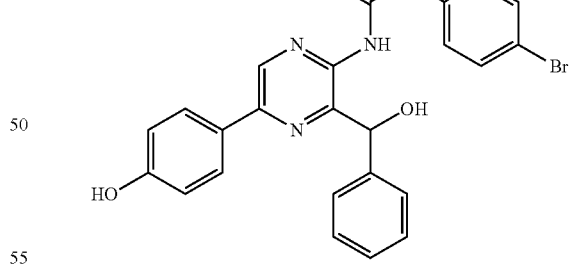
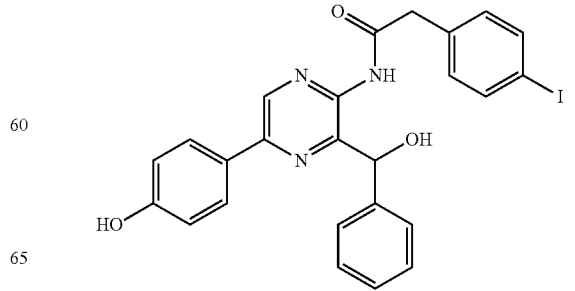

91
-continued
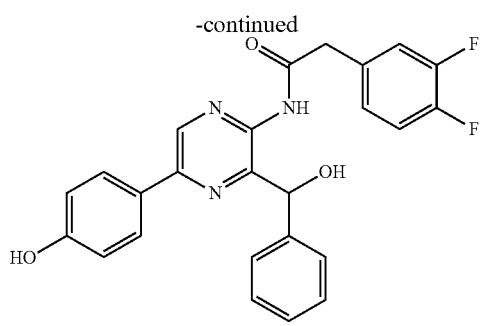
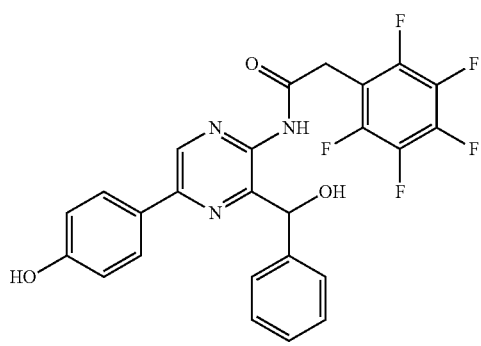
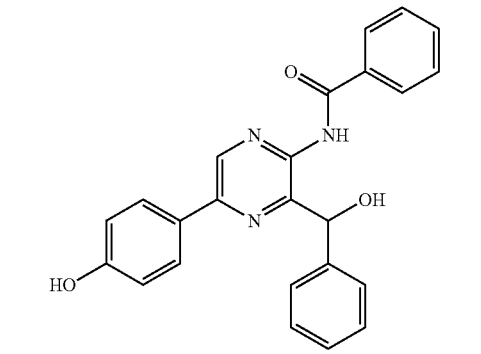
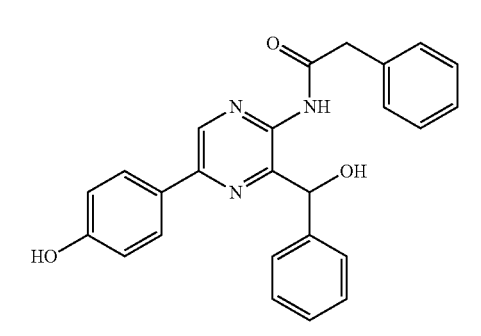
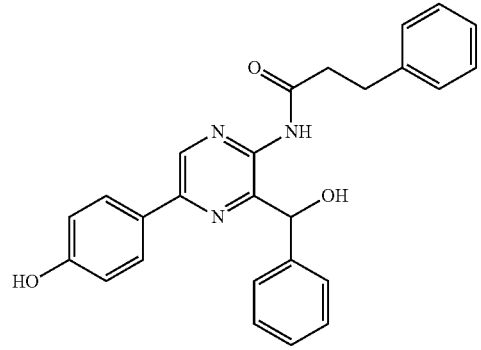
92
-continued
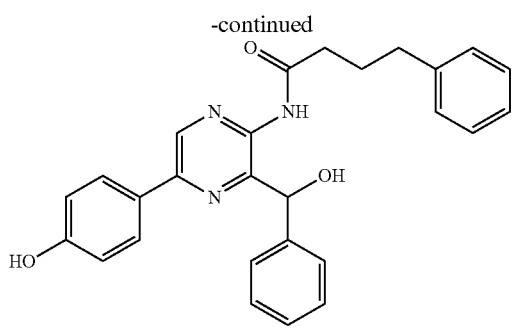
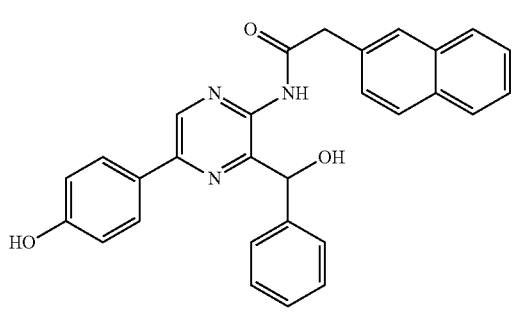
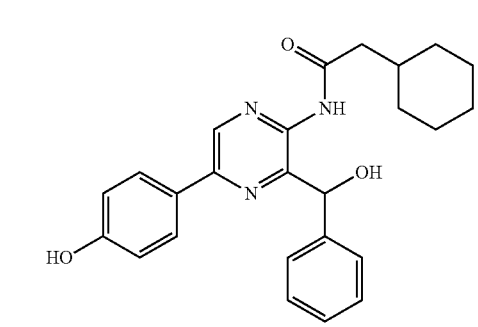
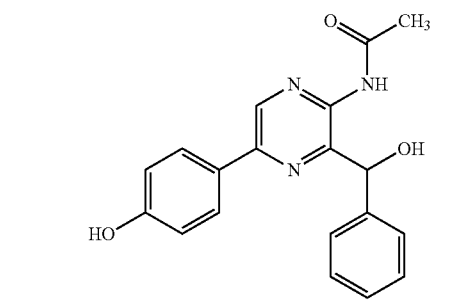
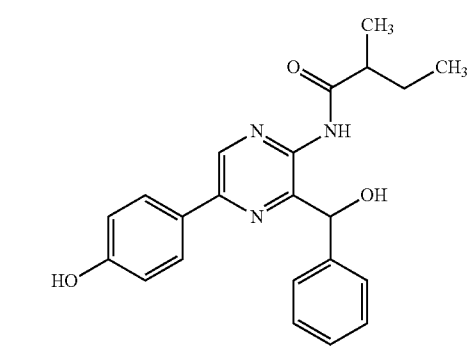

93
-continued
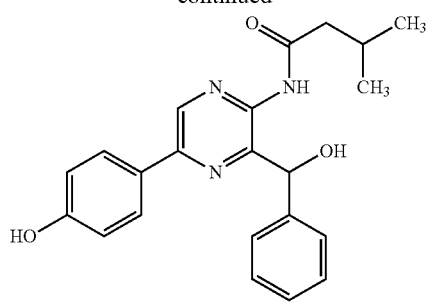
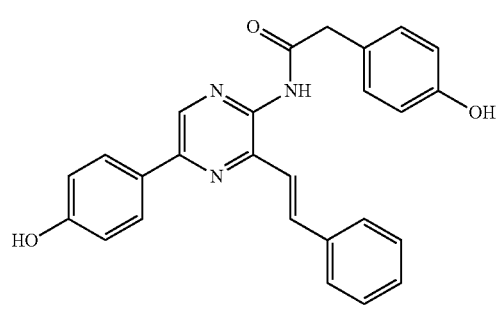
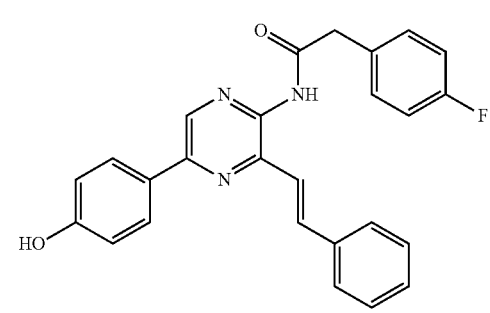
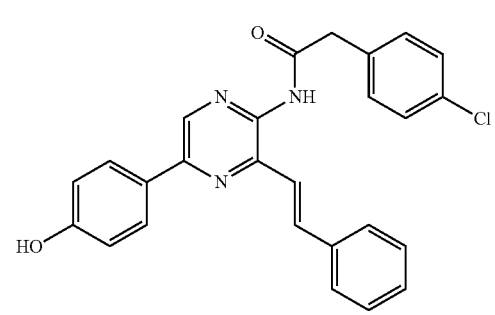
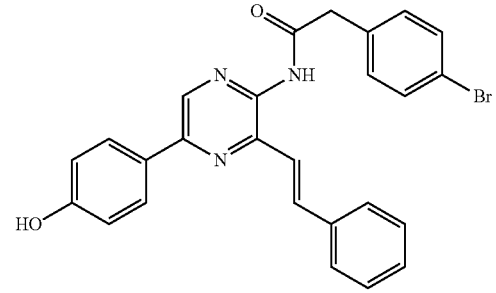
94
-continued
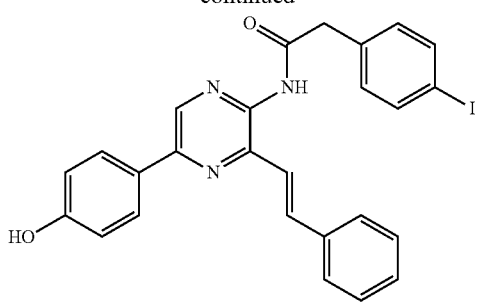
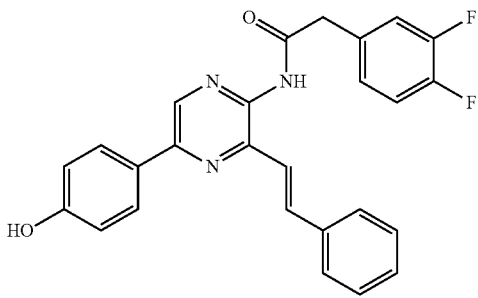
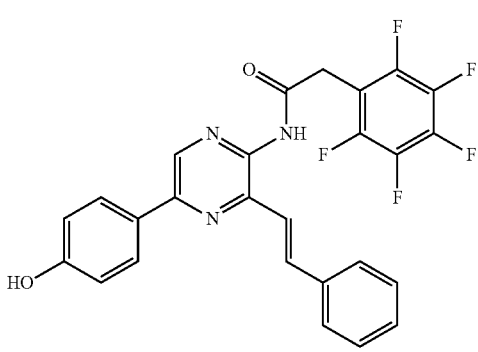
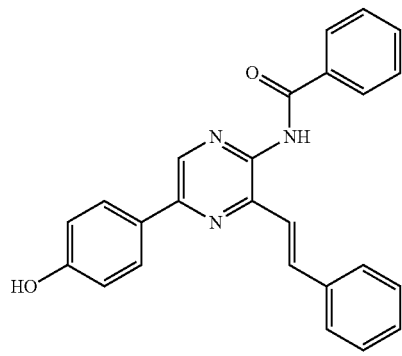
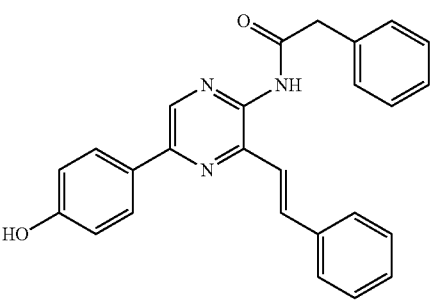

95
-continued
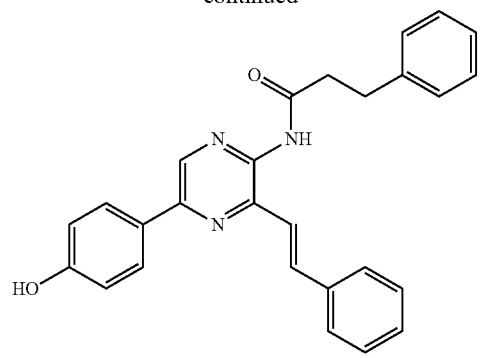
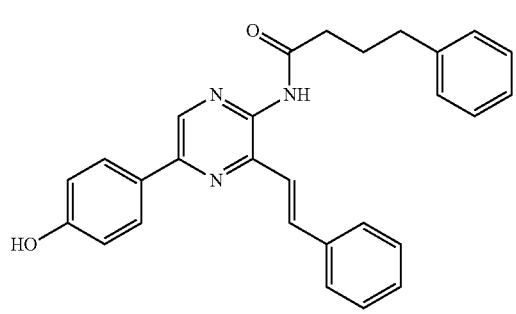
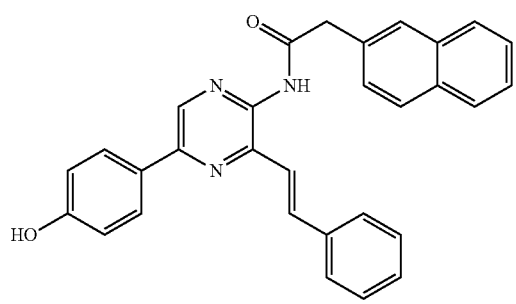
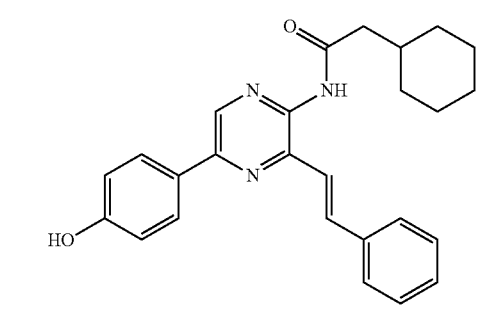
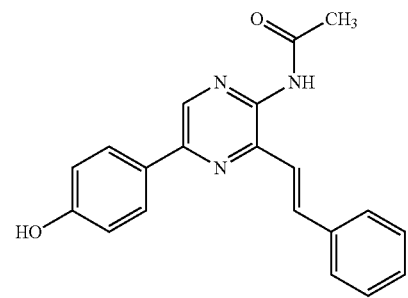
96
-continued
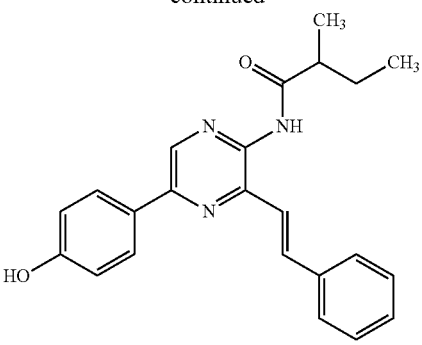
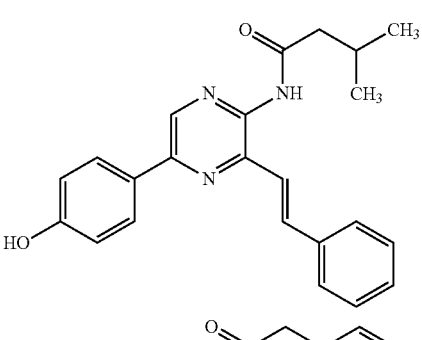
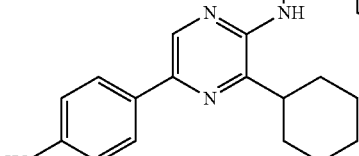
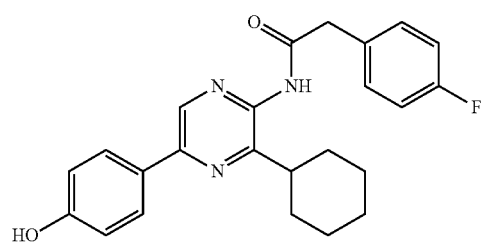
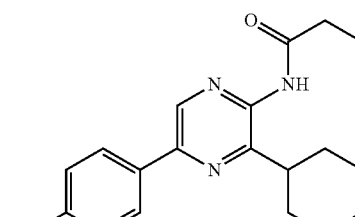
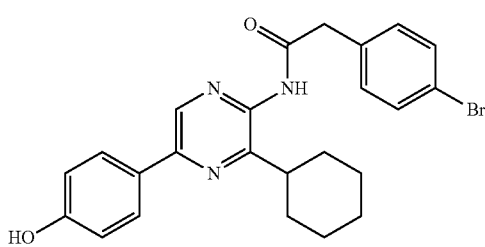

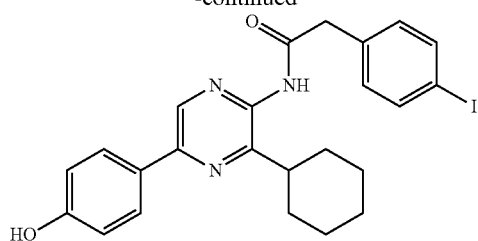
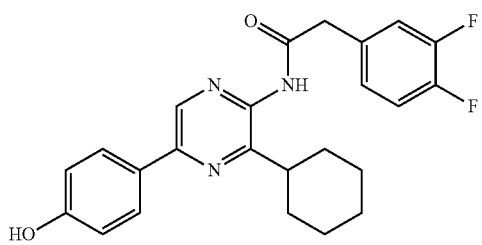
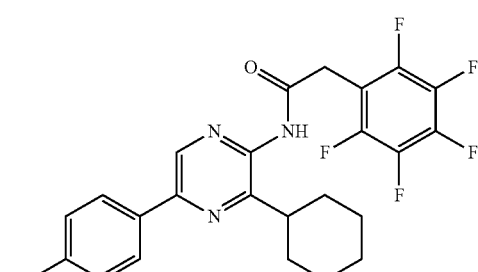
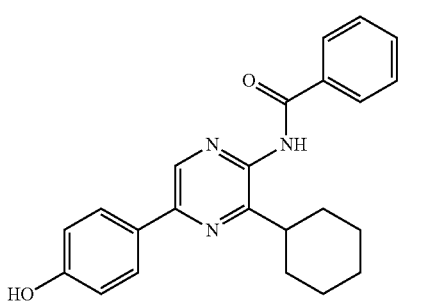
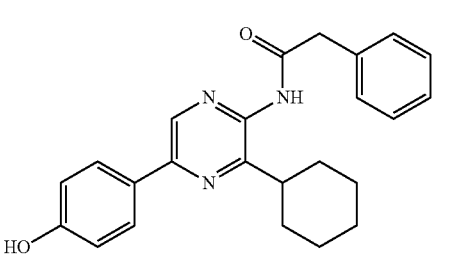
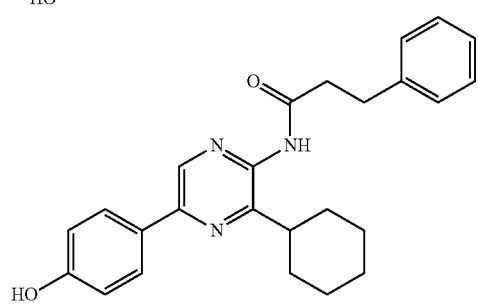
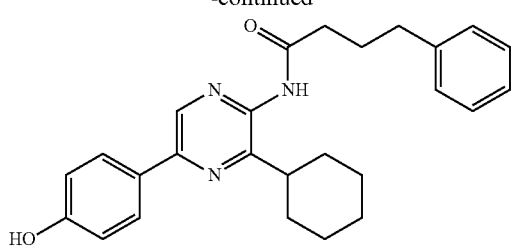
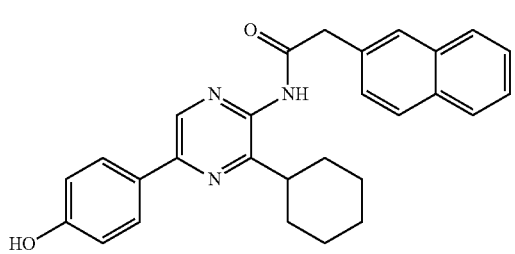
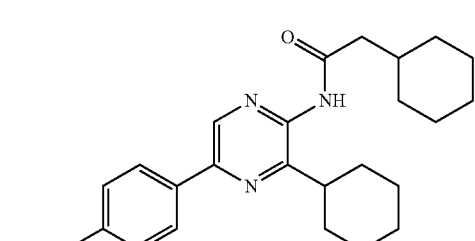
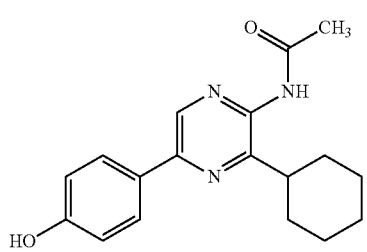
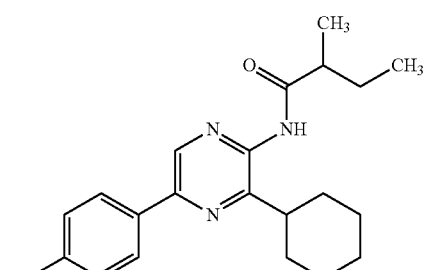
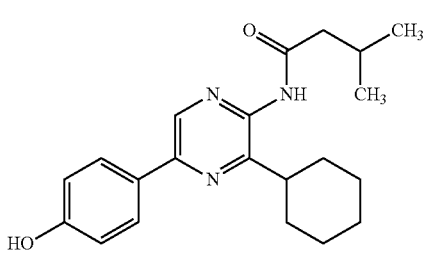

99
-continued
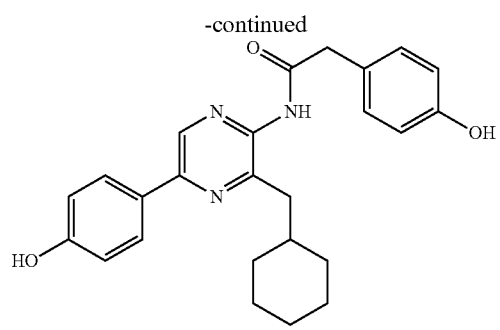
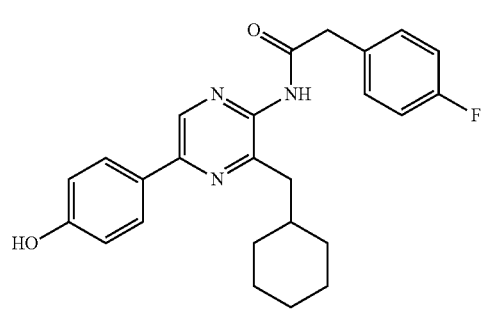
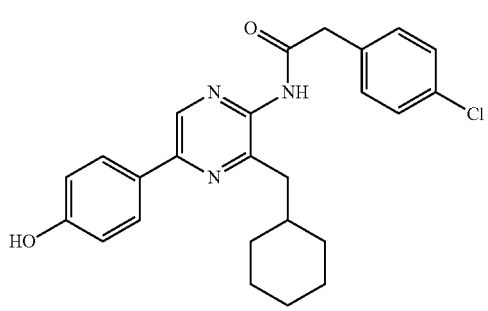
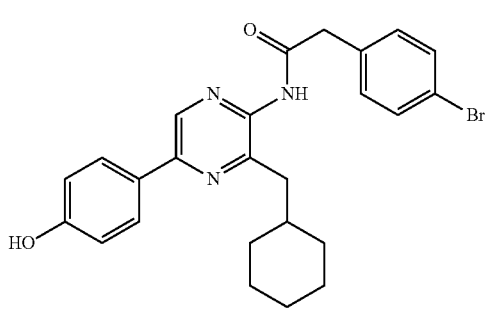
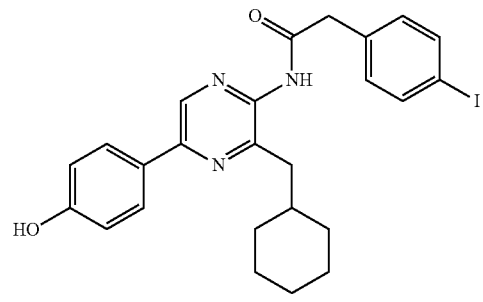
100
-continued
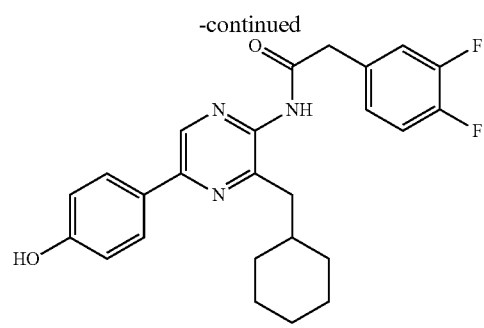
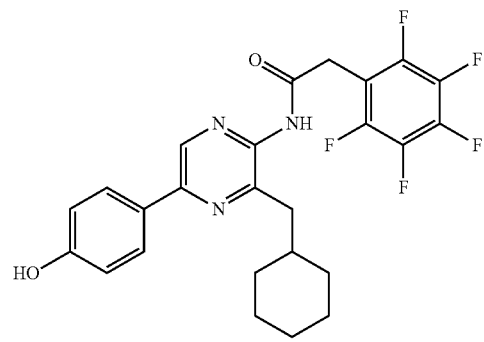
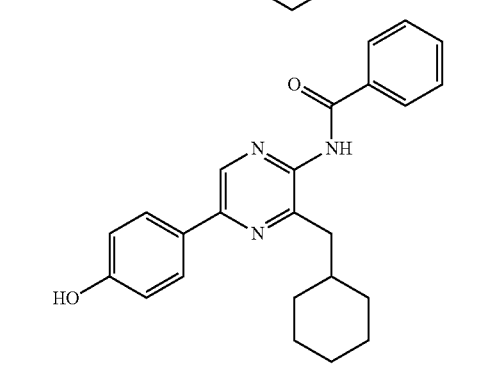
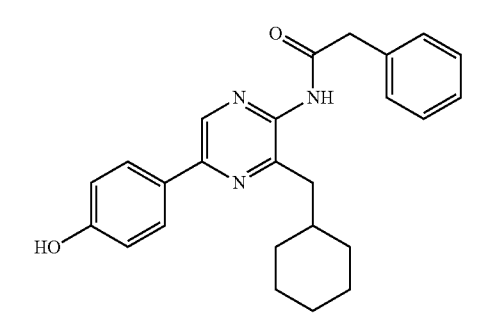
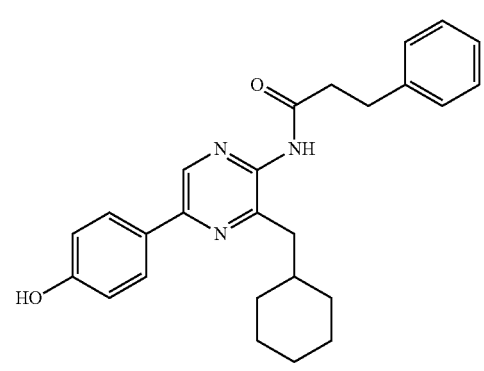

101
-continued
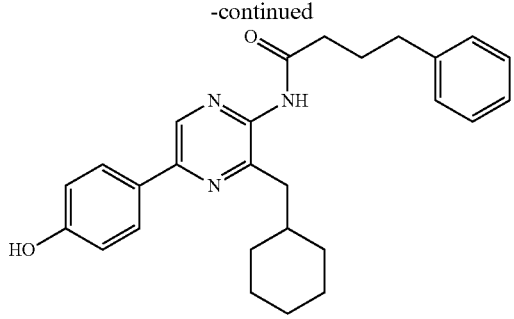
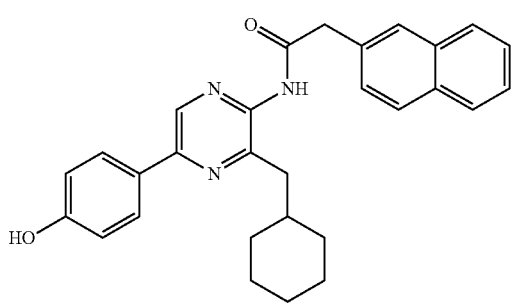
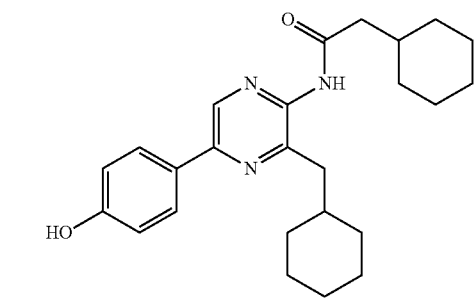
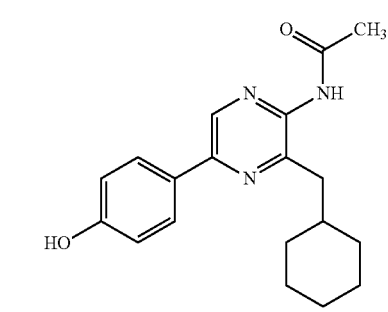
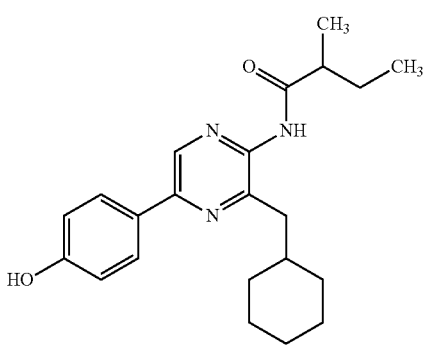
102
-continued
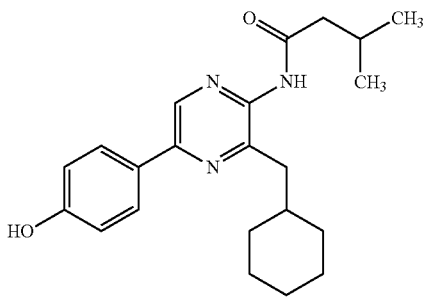
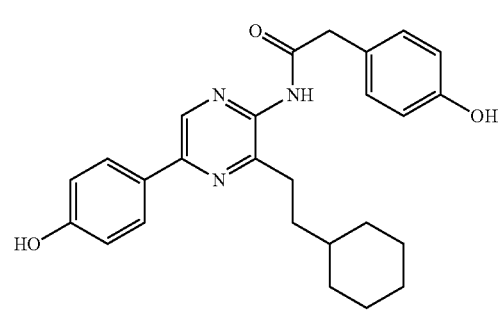
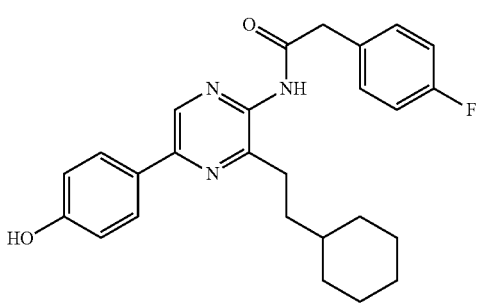
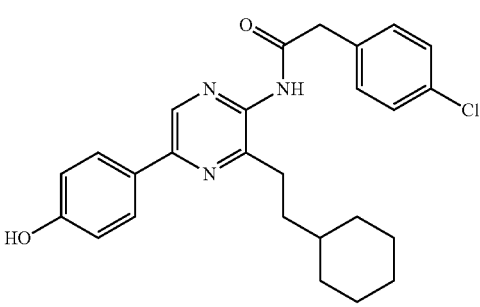
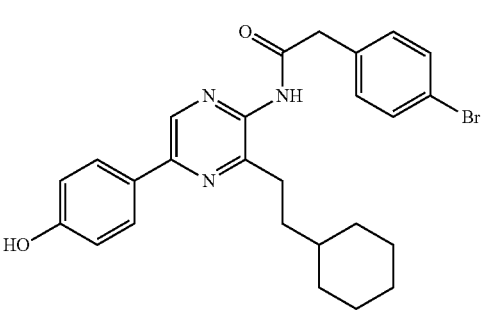

103
-continued
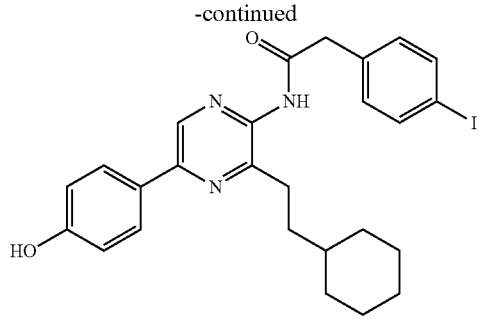
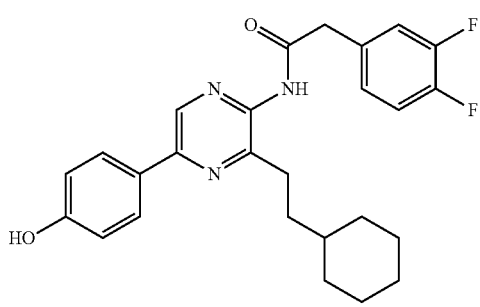
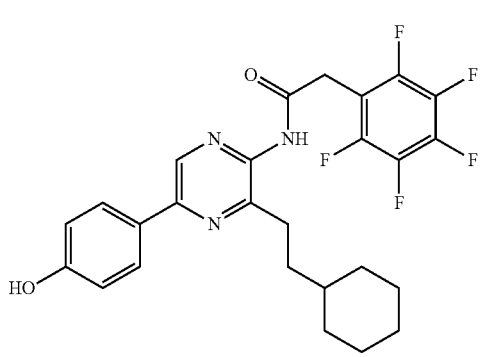
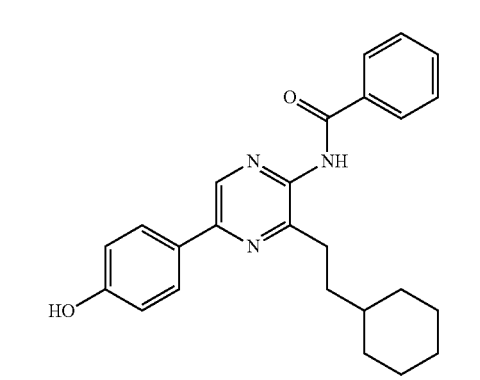
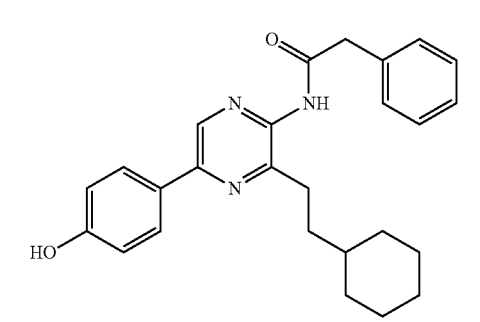
104
-continued
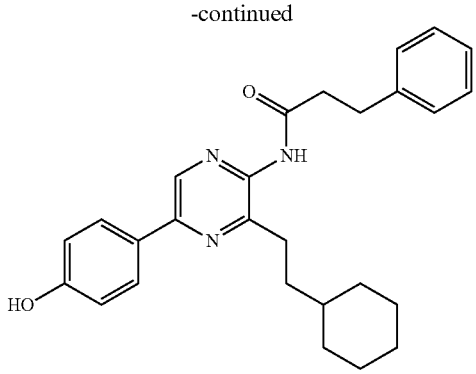
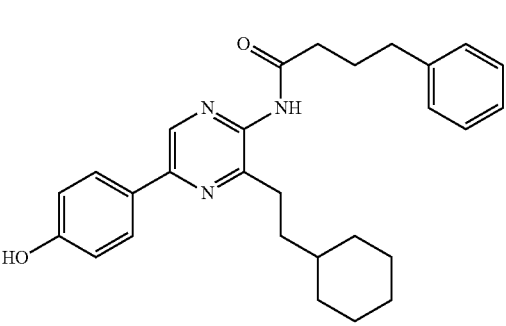
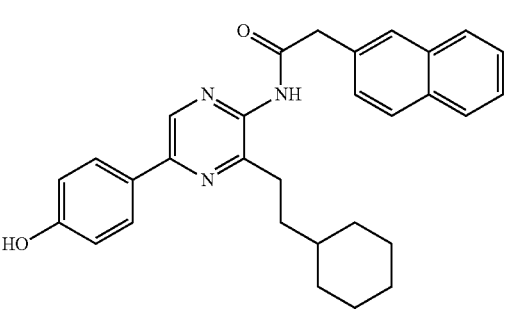
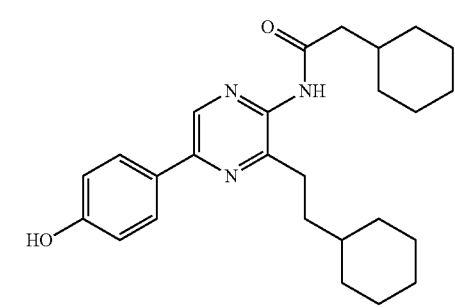
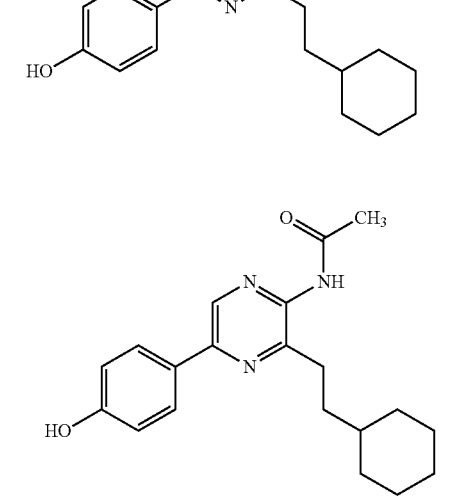

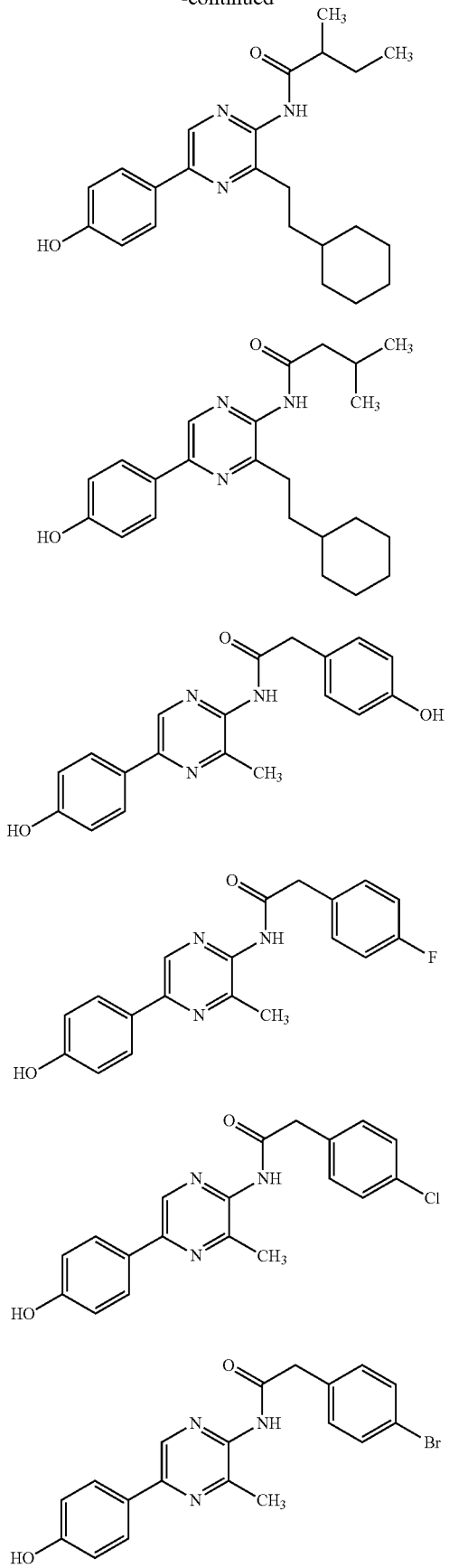
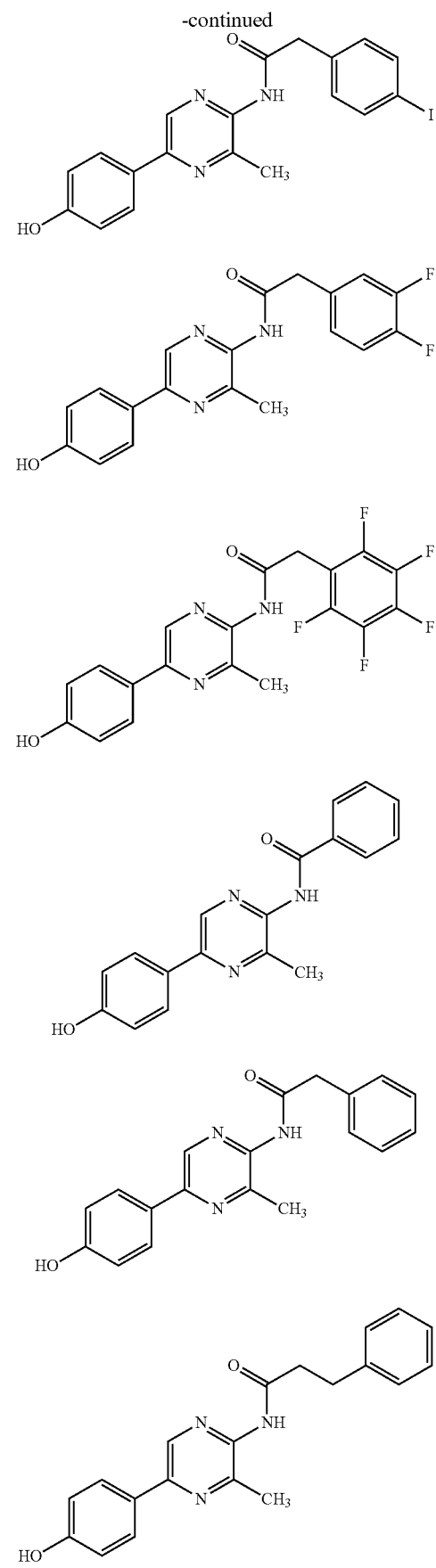

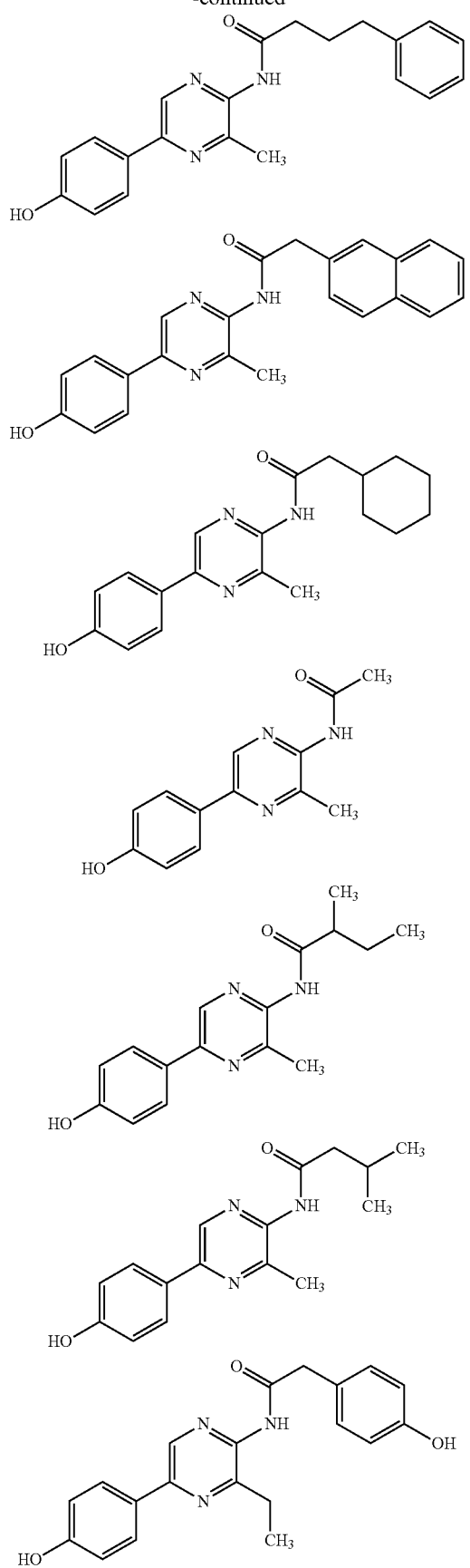
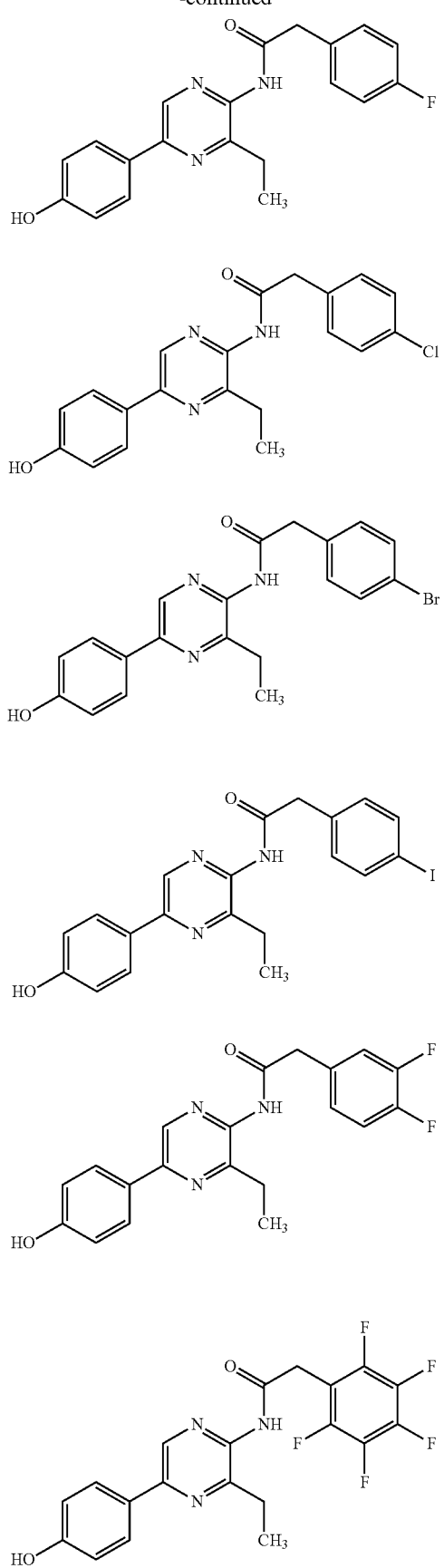

109
-continued
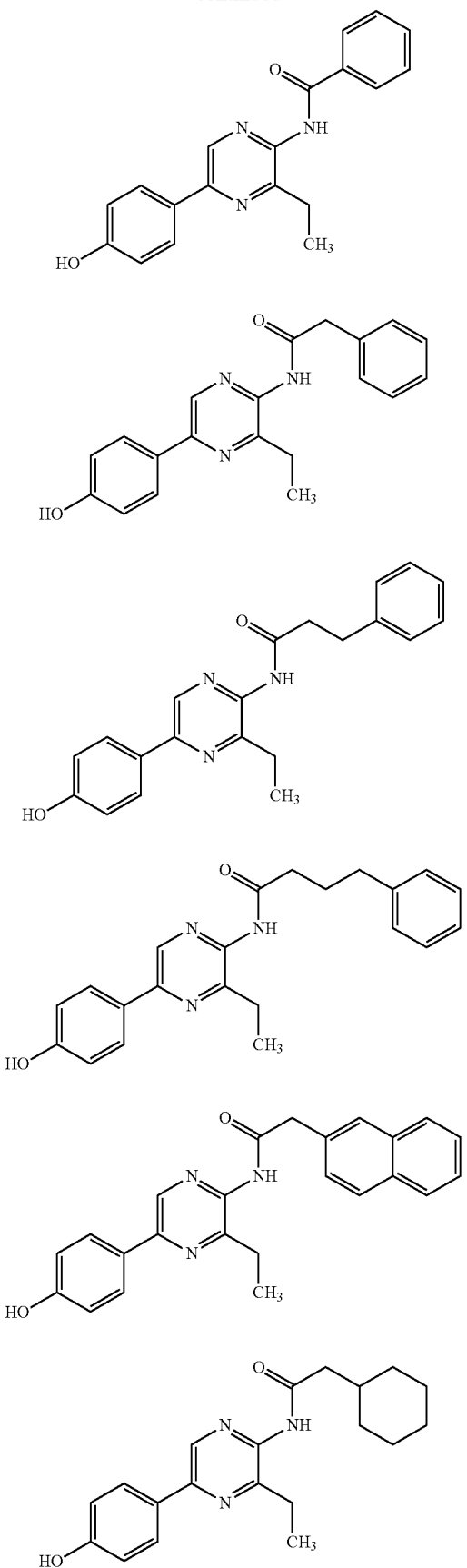
110
-continued
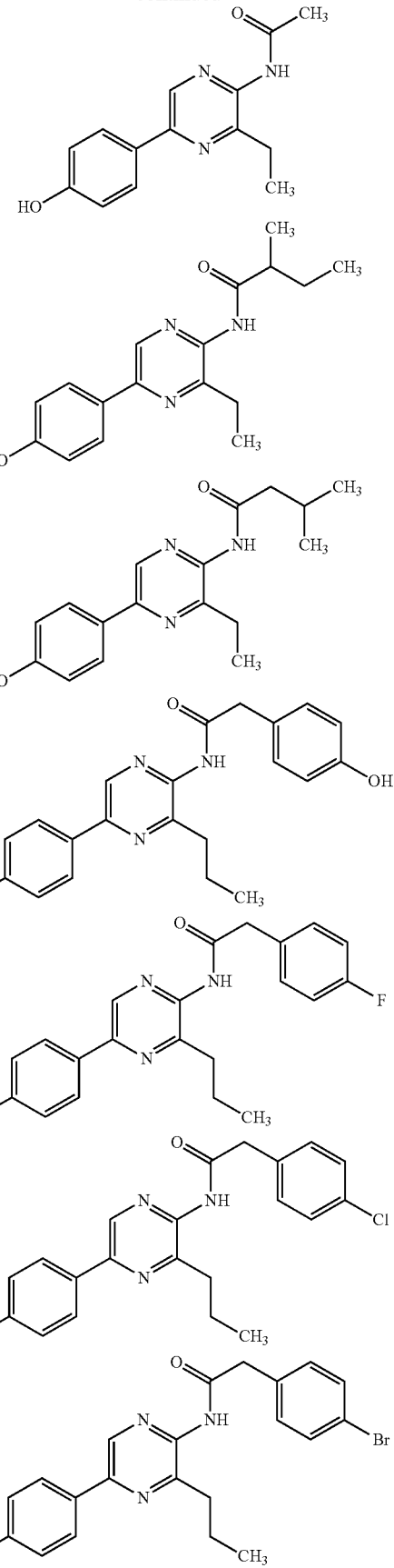

111
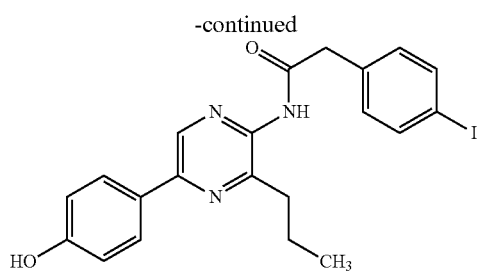
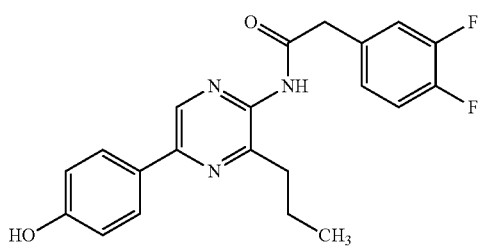
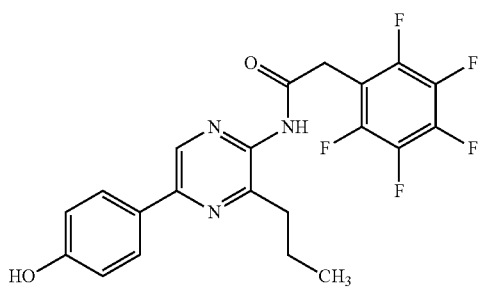
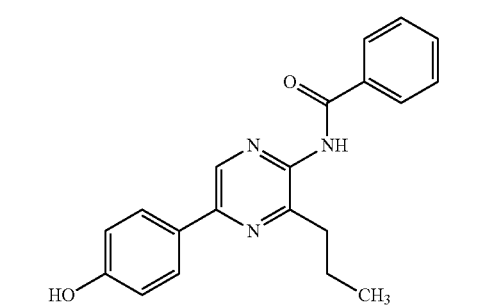
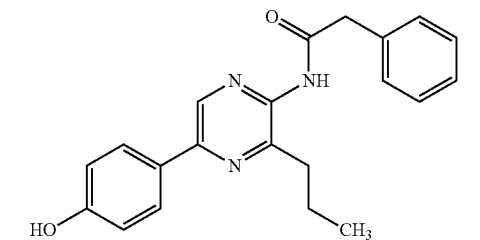
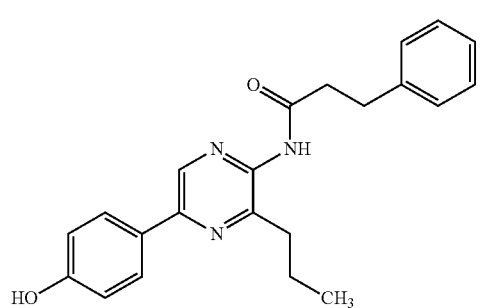
112
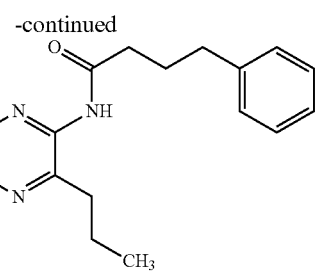
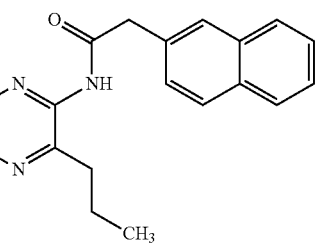
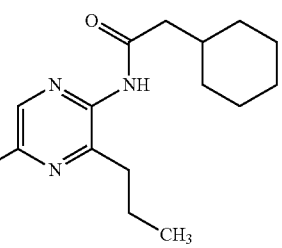
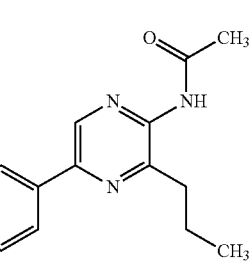
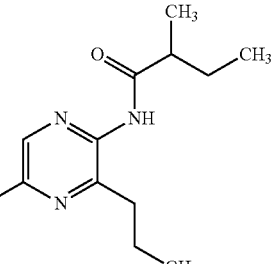
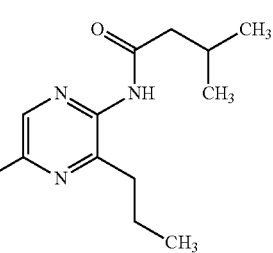

113
-continued
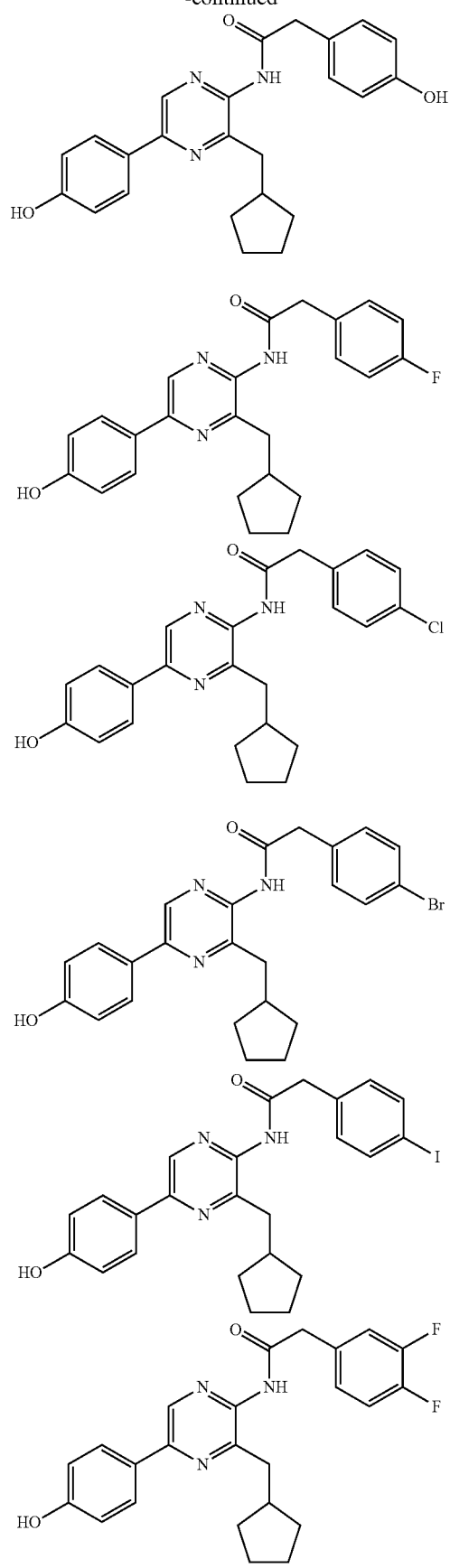
114
-continued
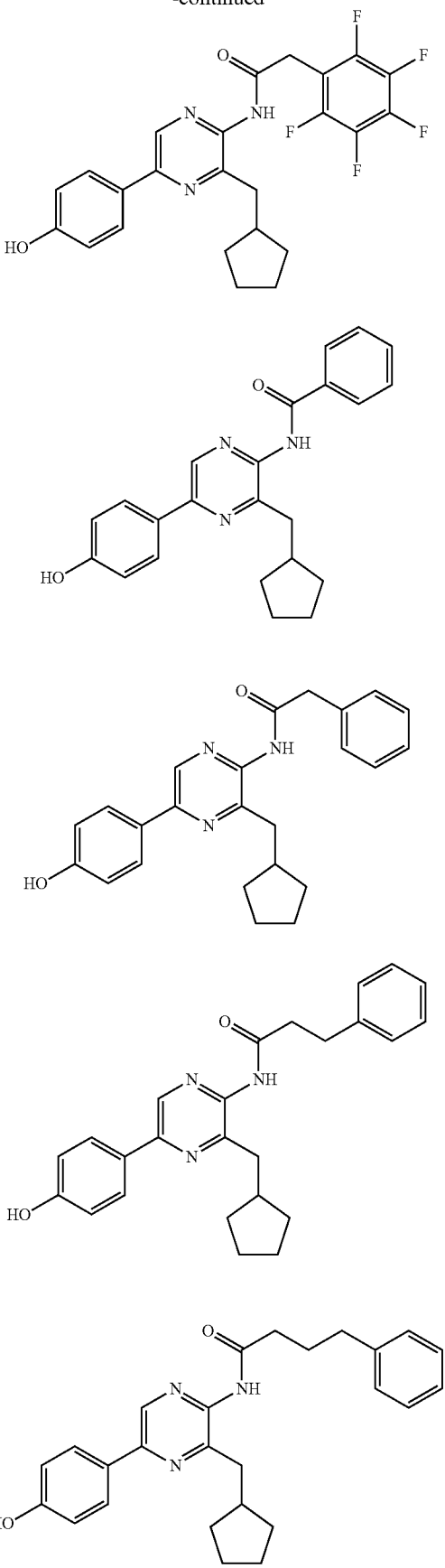

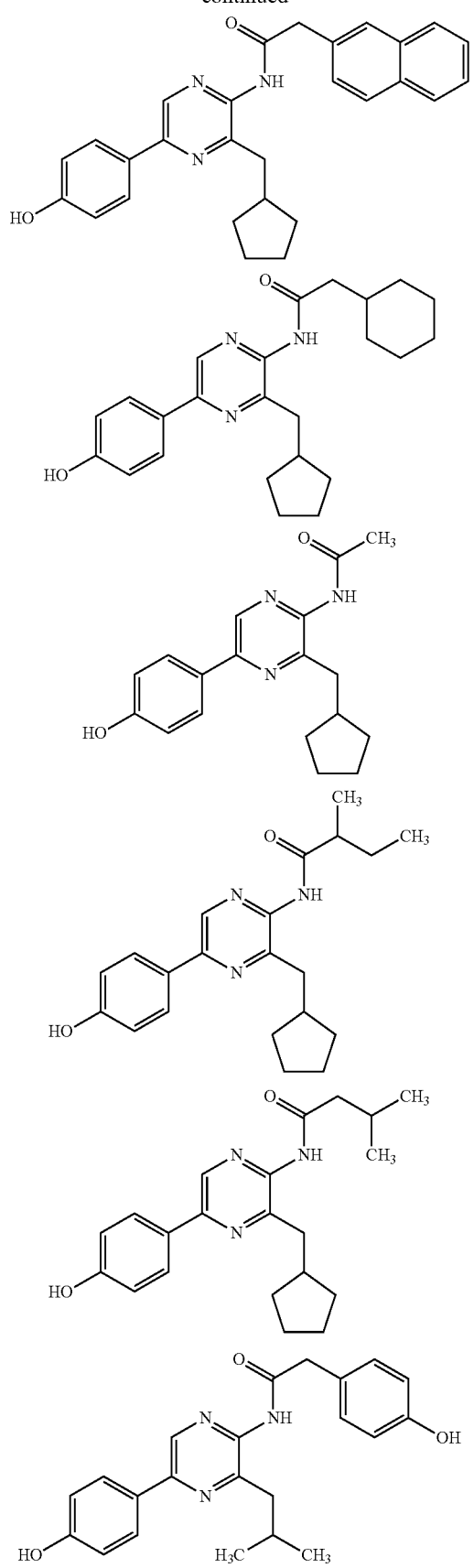
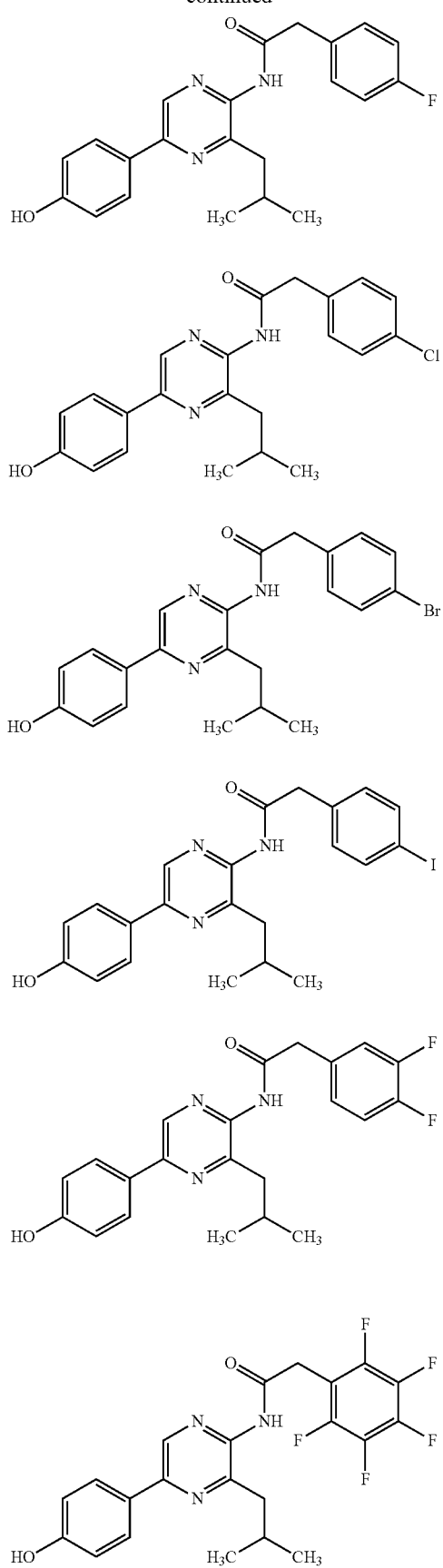

117
-continued
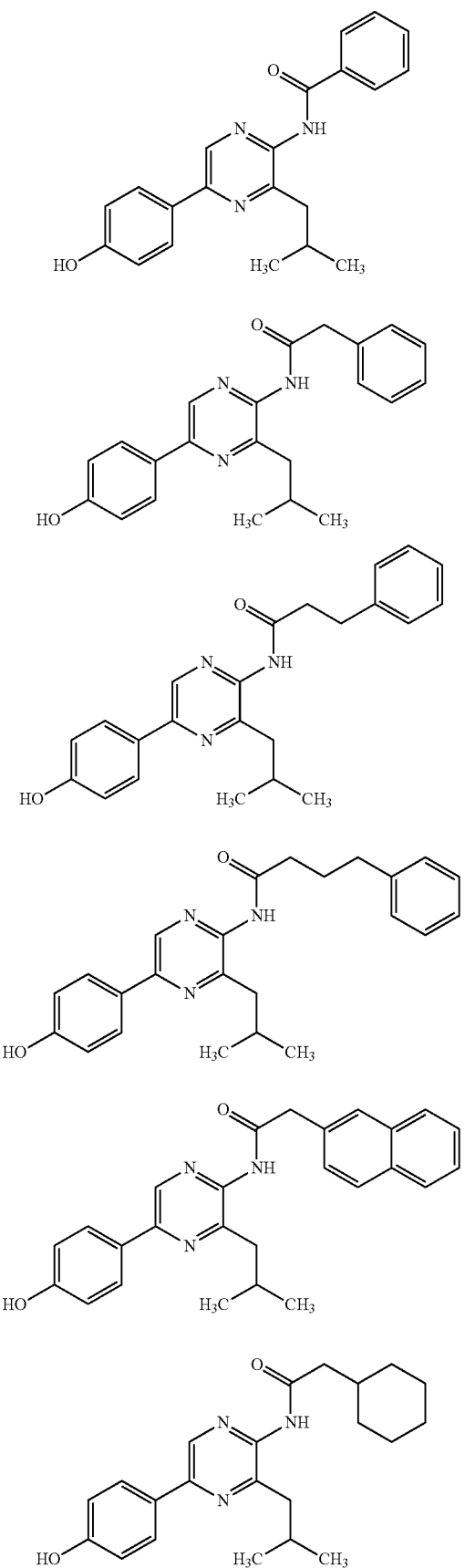
118
-continued
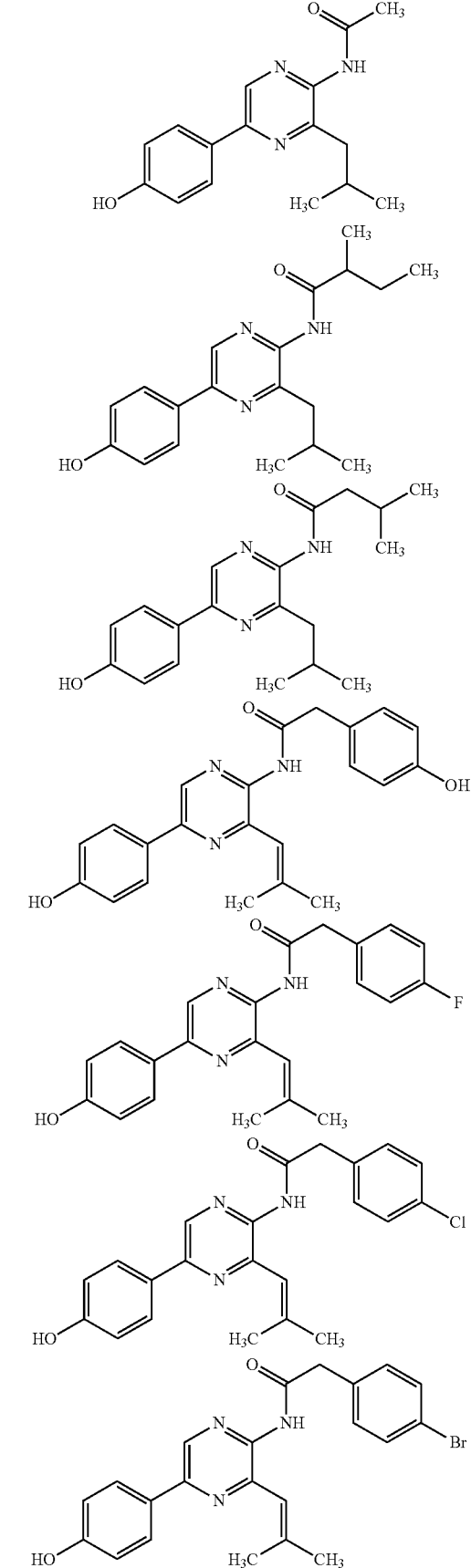

119
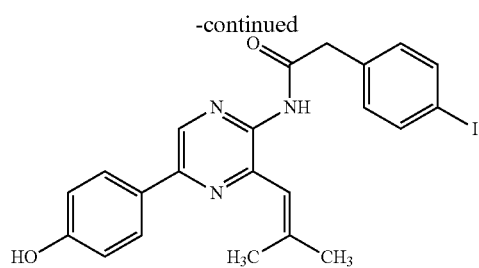
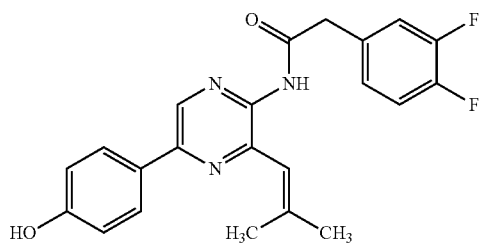
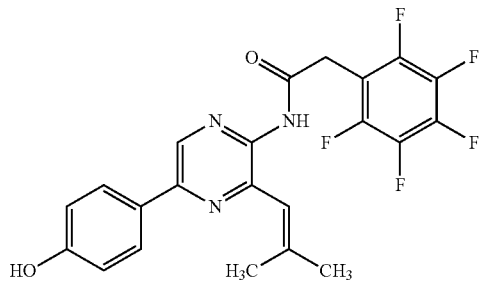
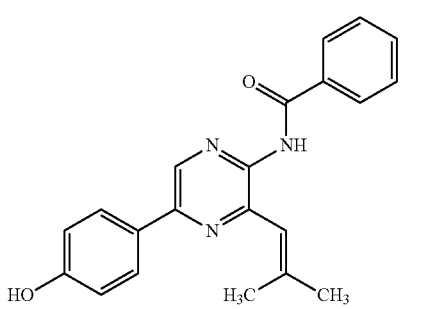
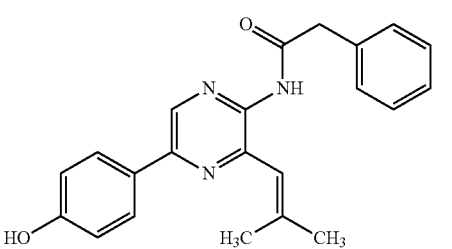
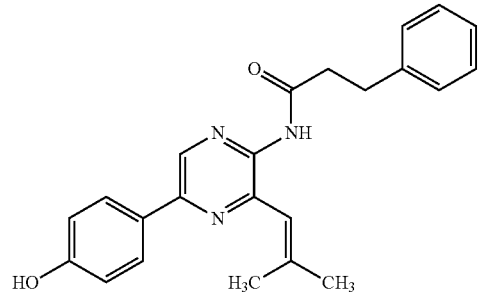
120
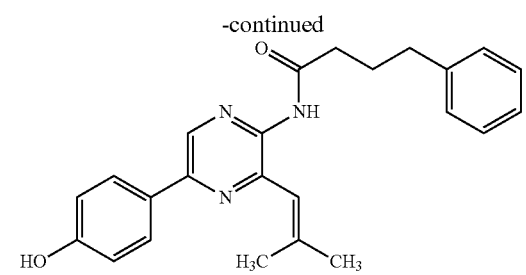
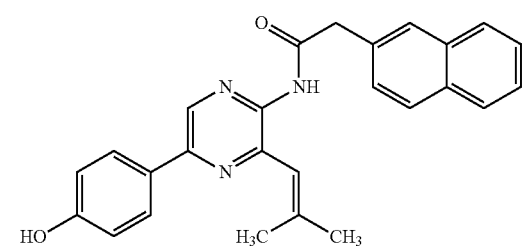
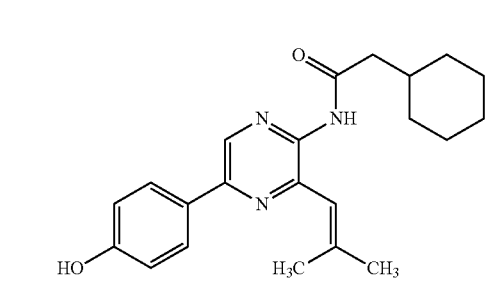
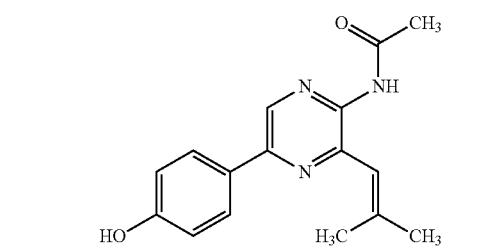
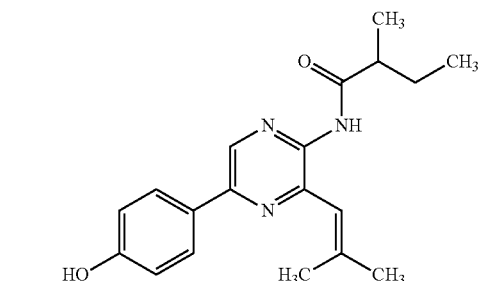
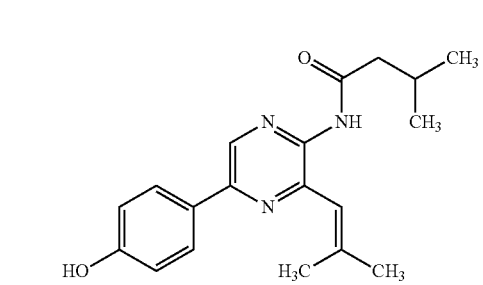

121
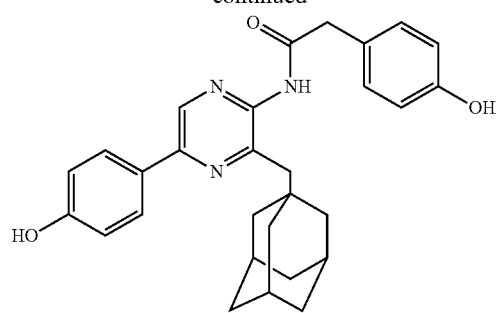
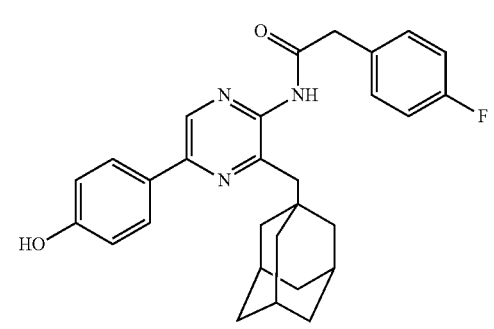
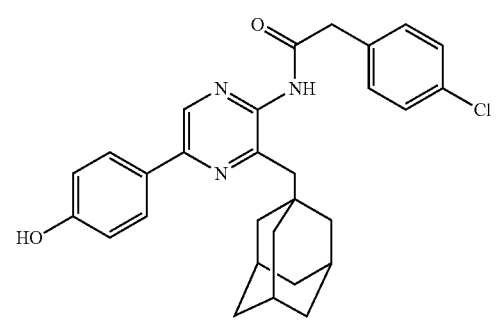
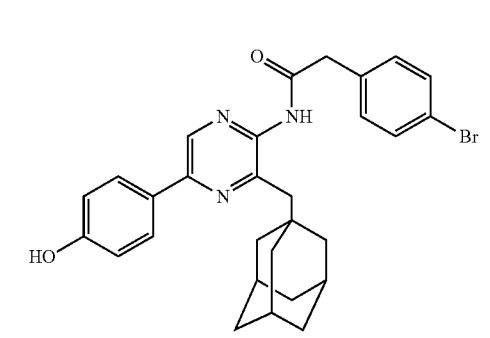
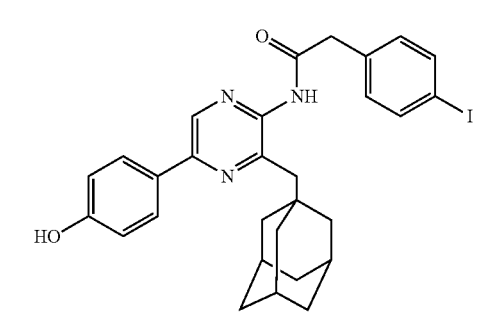
122
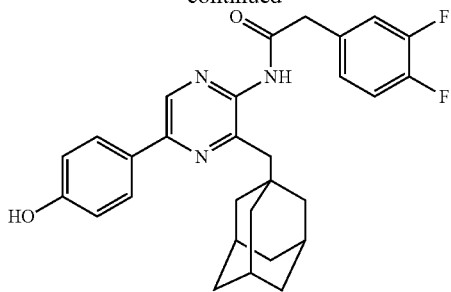
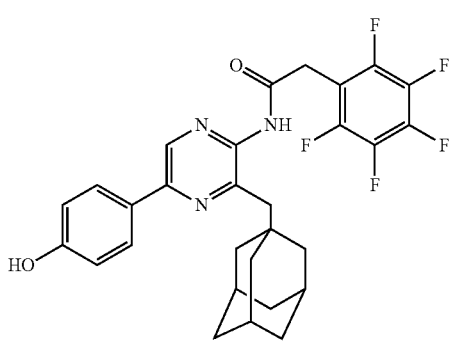
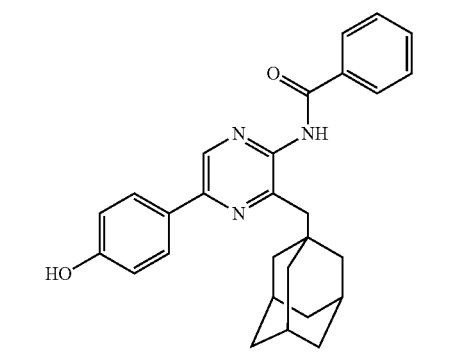
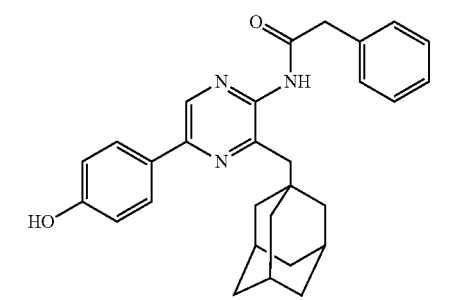
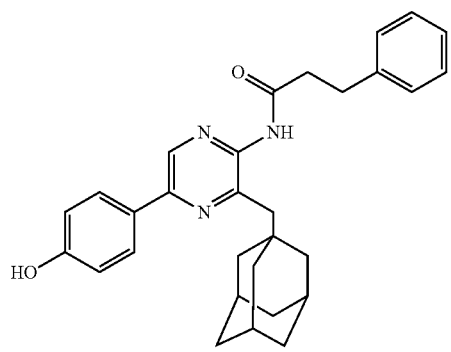

123
-continued
124
-continued
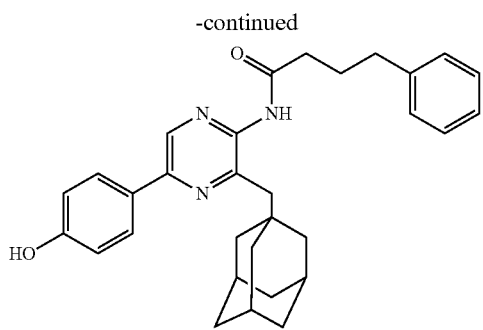
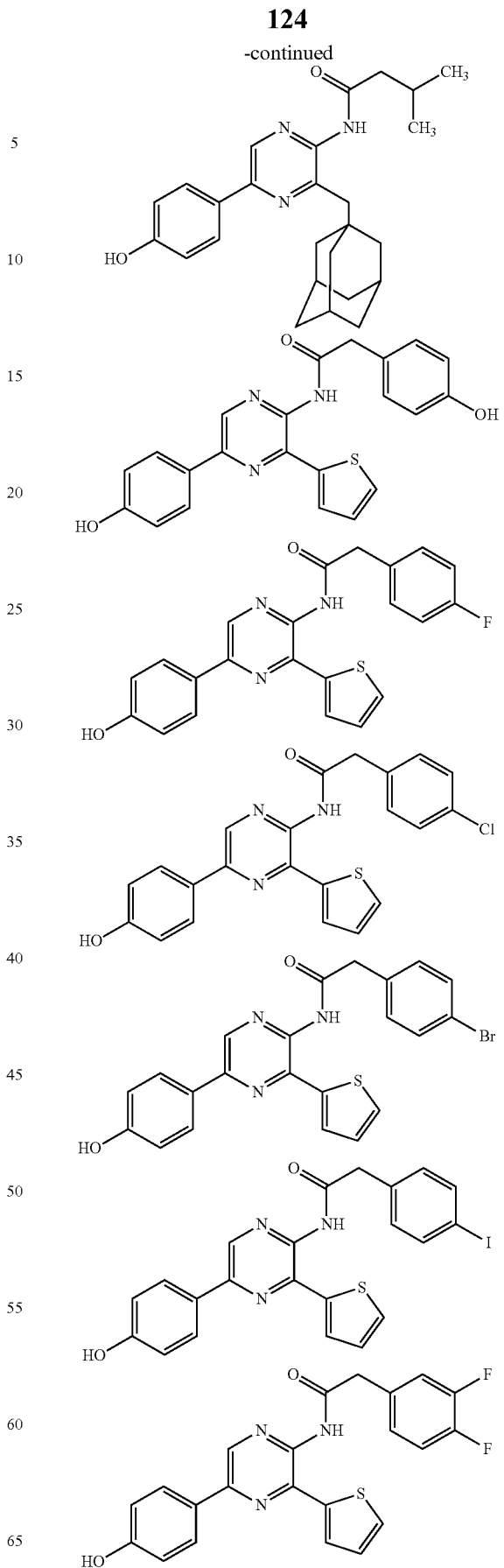

125
-continued
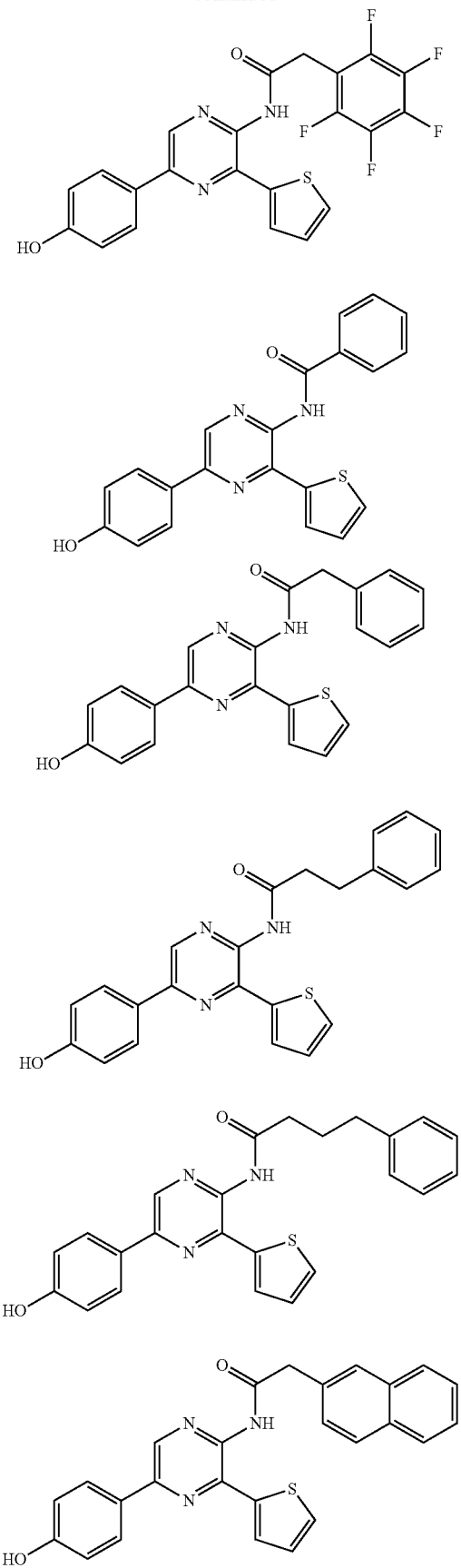
126
-continued
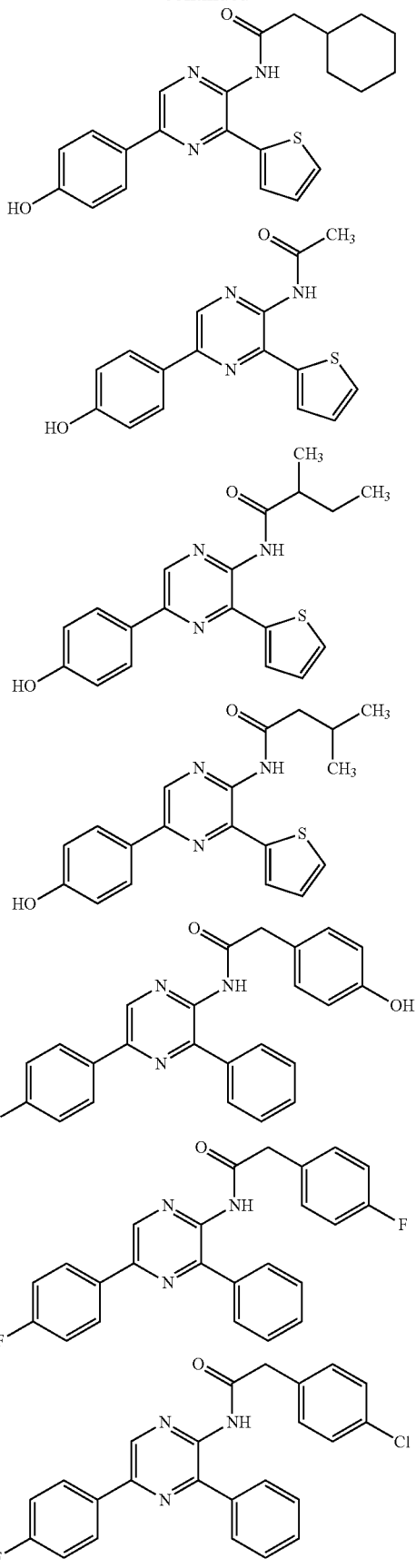

127
-continued
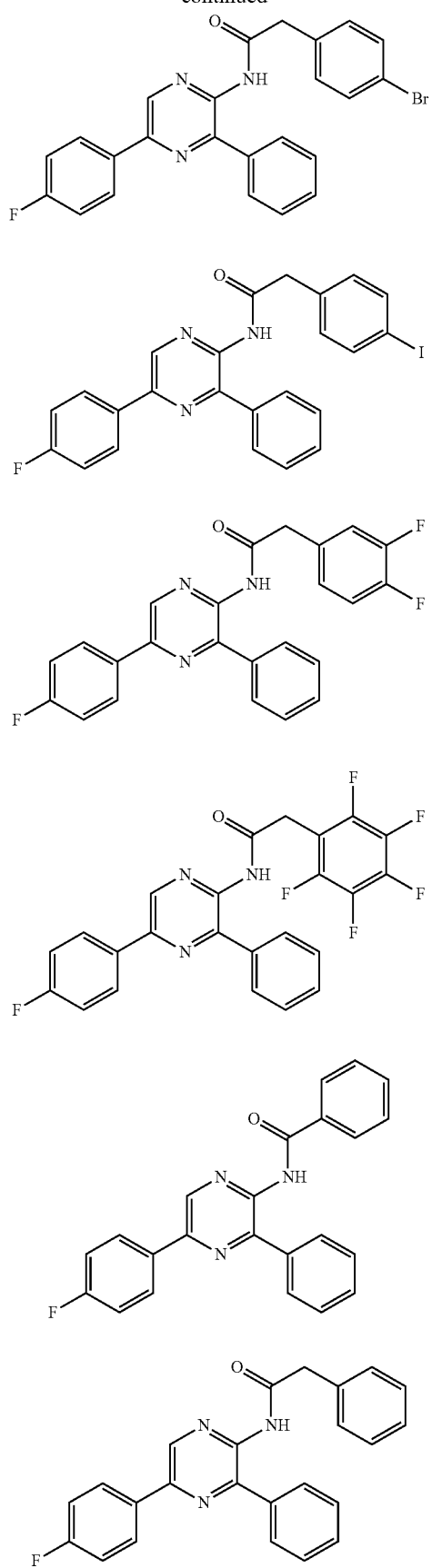
128
-continued
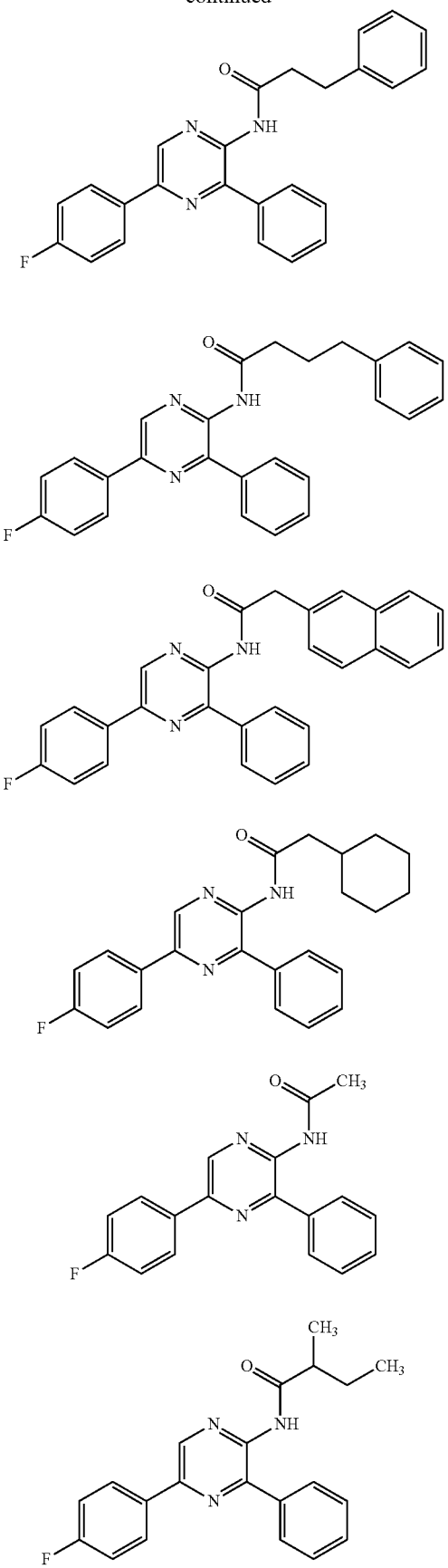

129
-continued
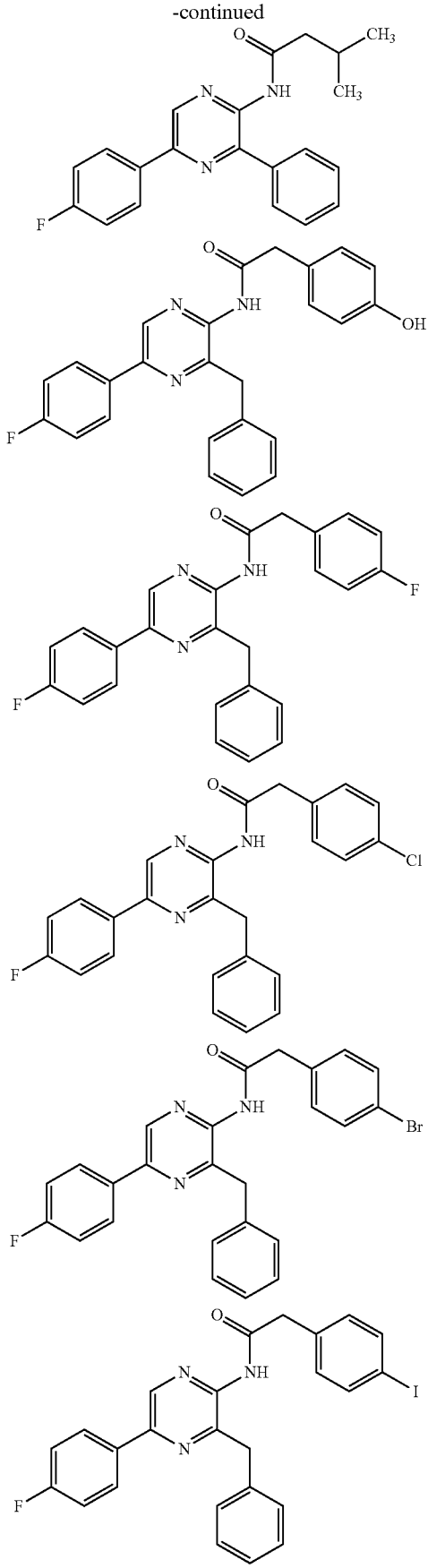
130
-continued
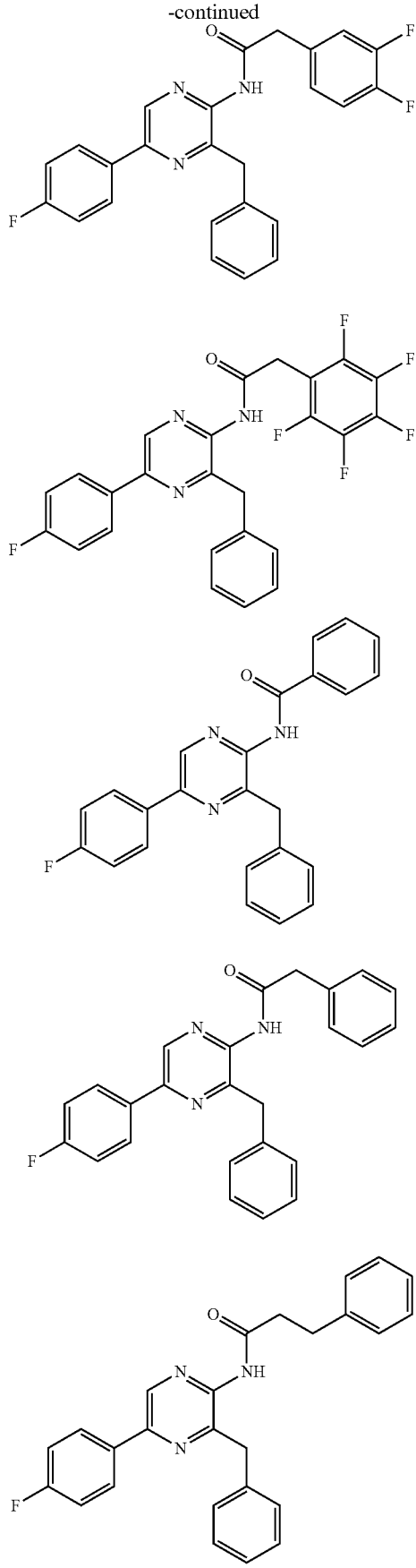

131
-continued
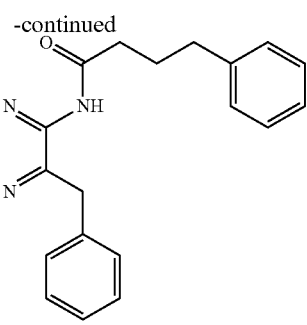
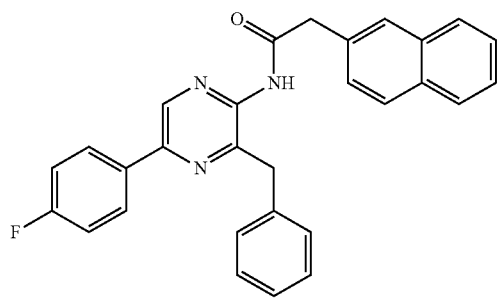
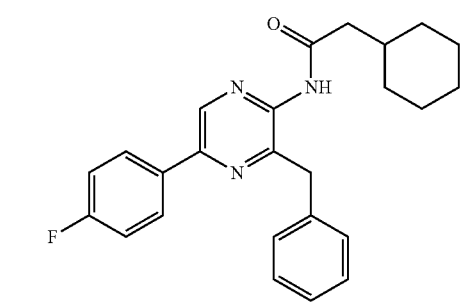
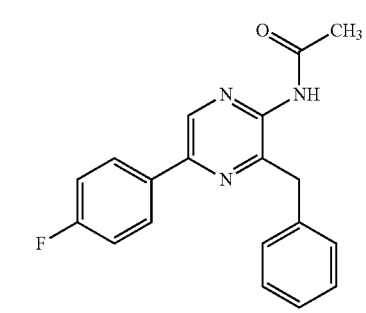
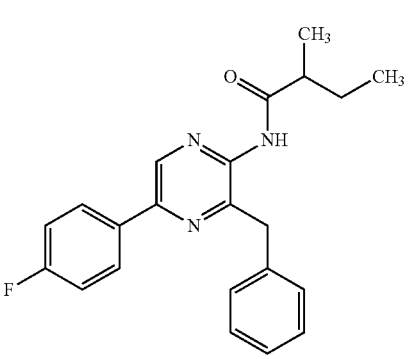
132
-continued
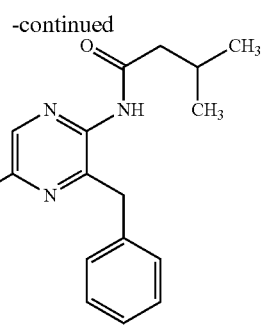
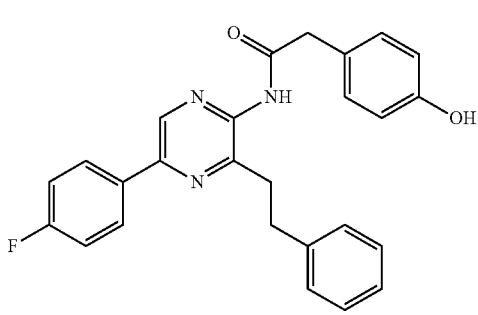
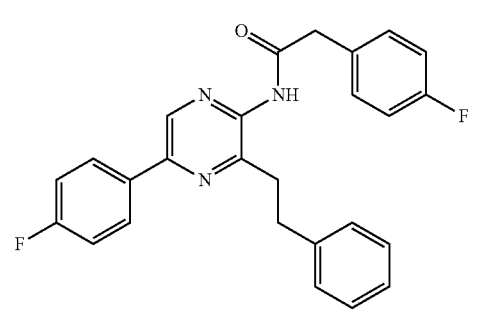
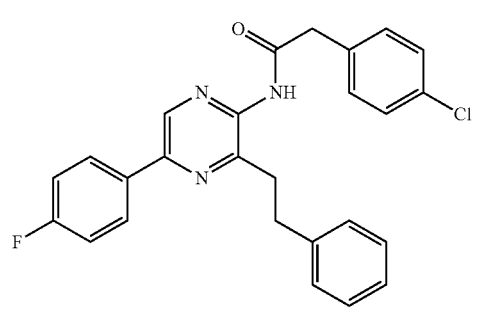
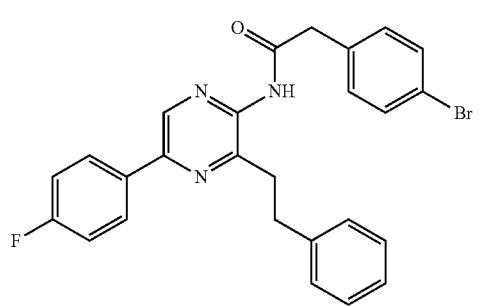

133
-continued
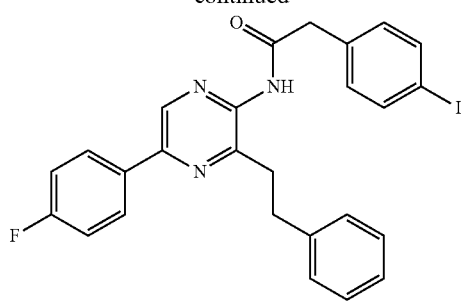
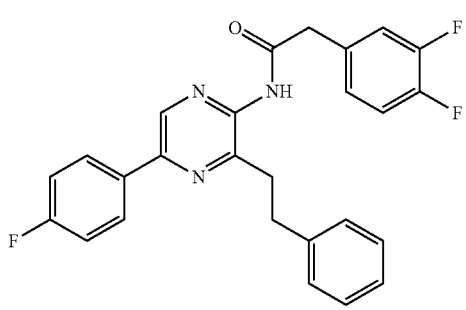
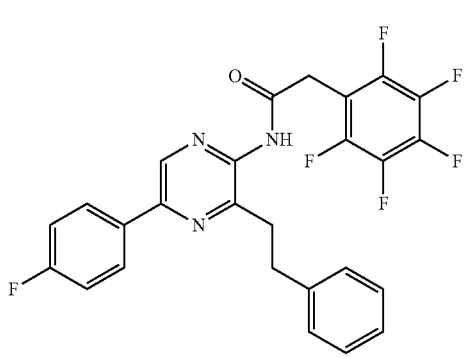
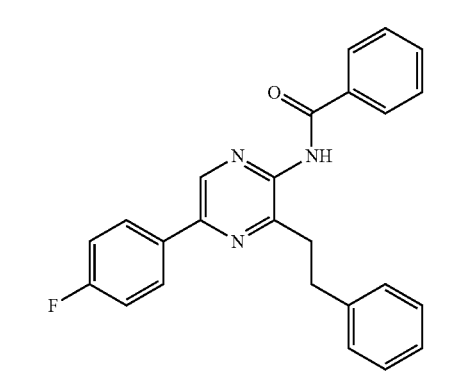
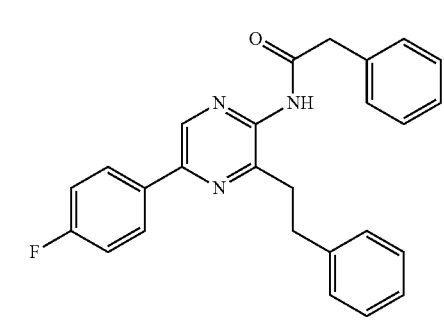
134
-continued
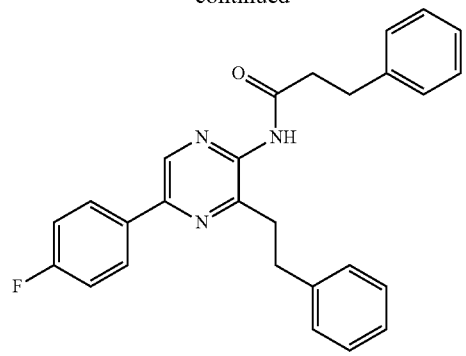
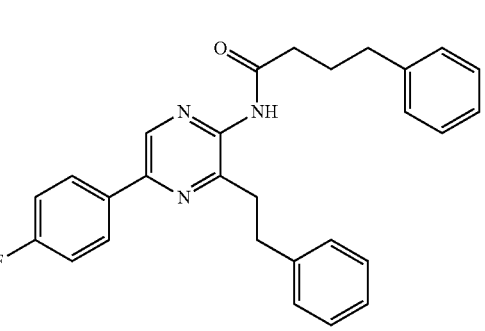
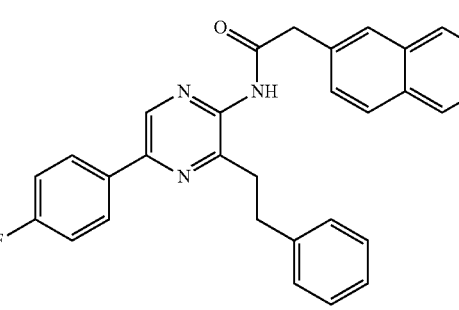
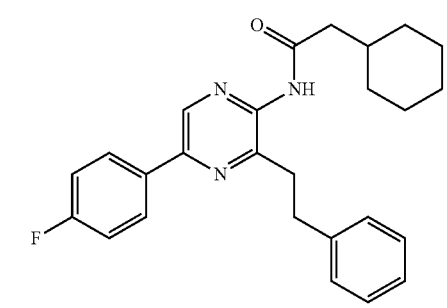
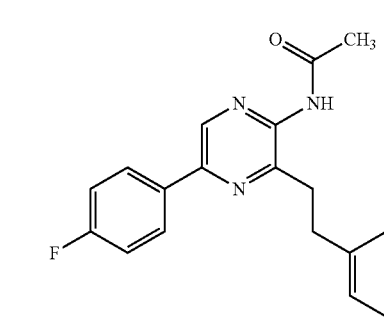

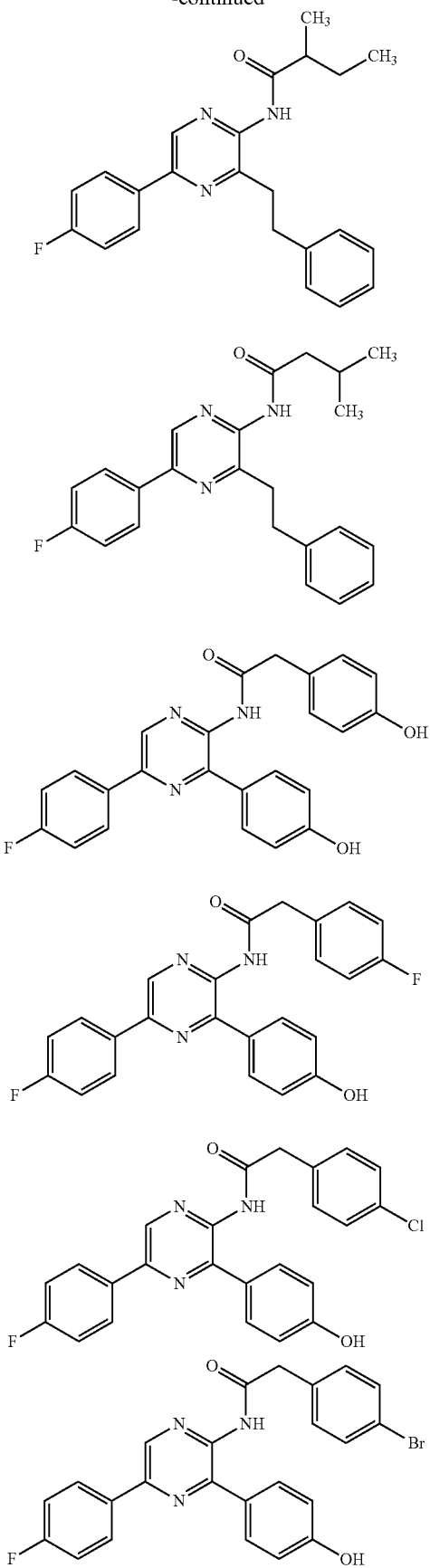
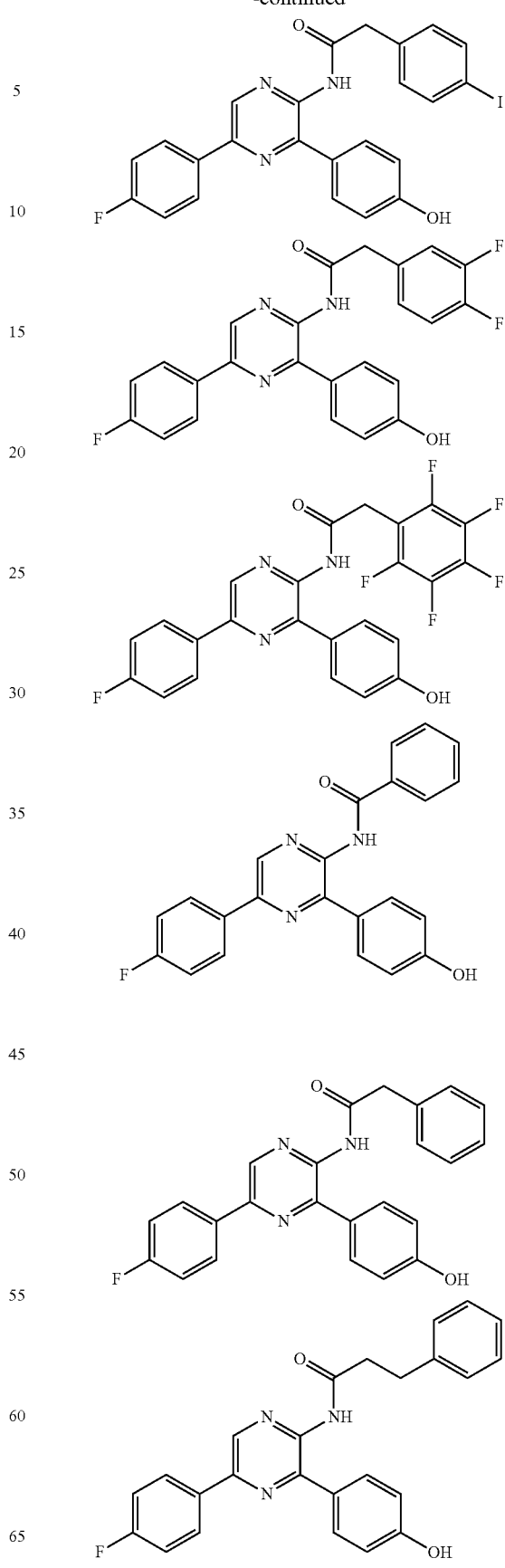

137
-continued
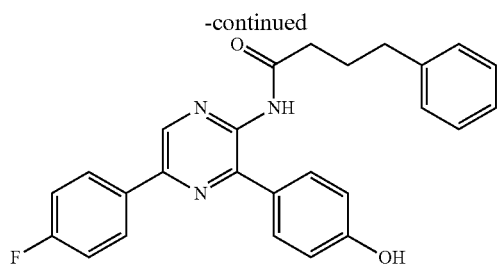
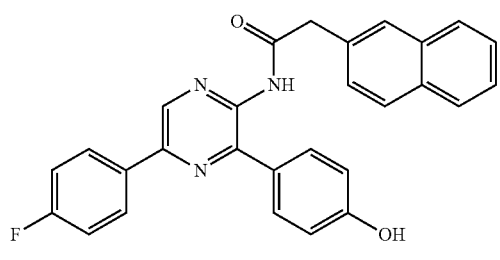
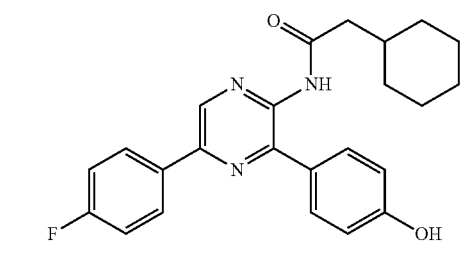
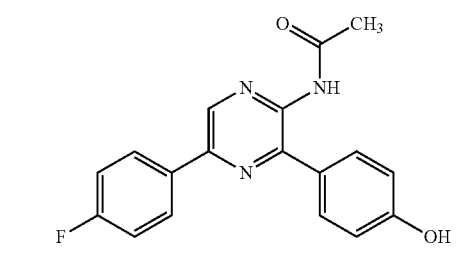
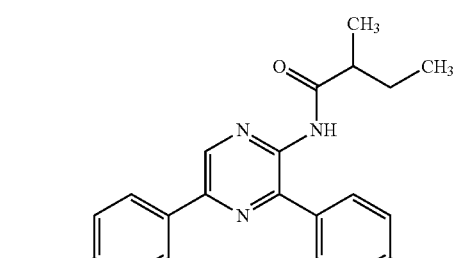
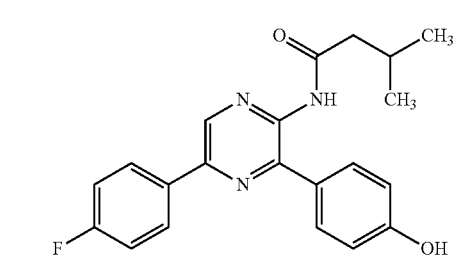
138
-continued
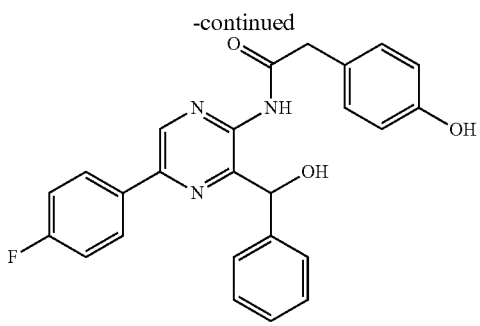
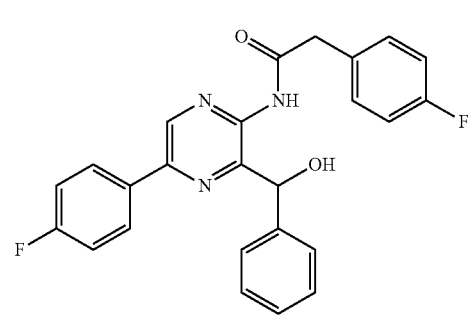
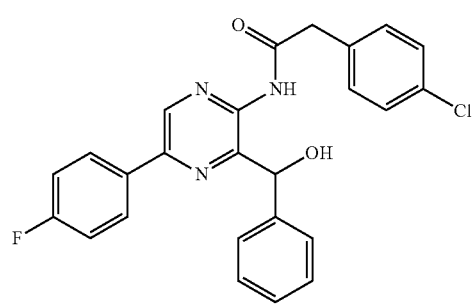
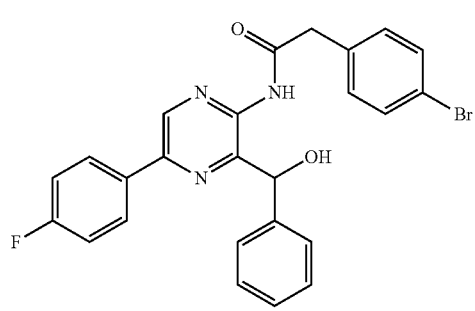

-continued
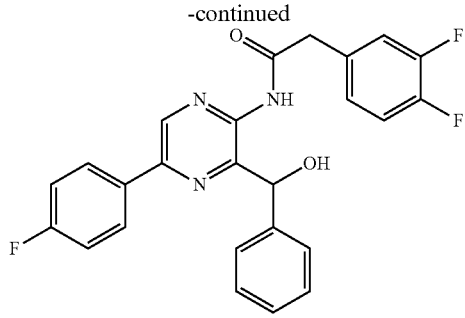
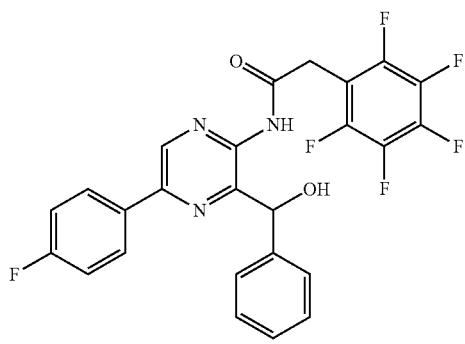
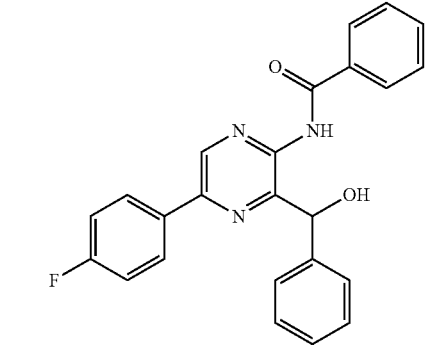
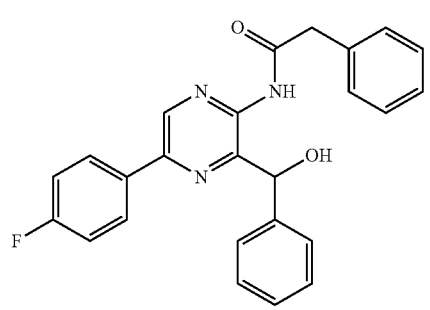
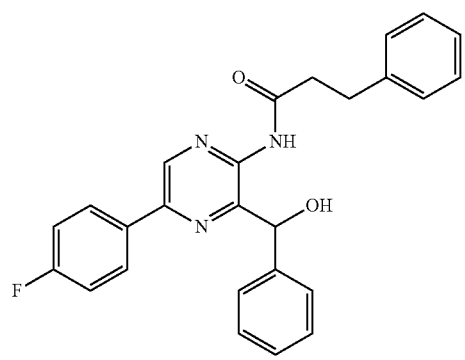
-continued
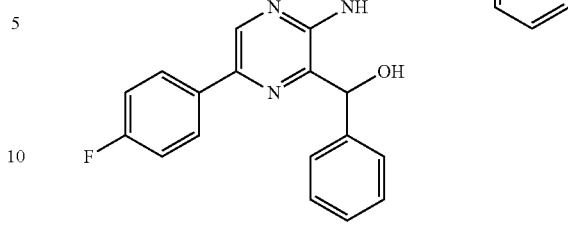
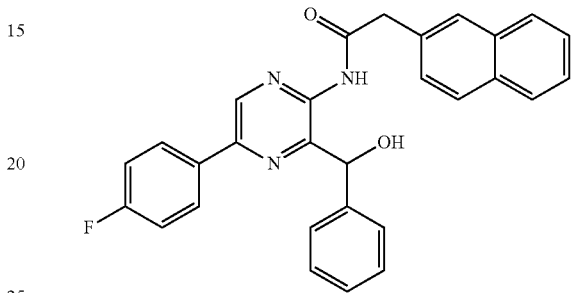
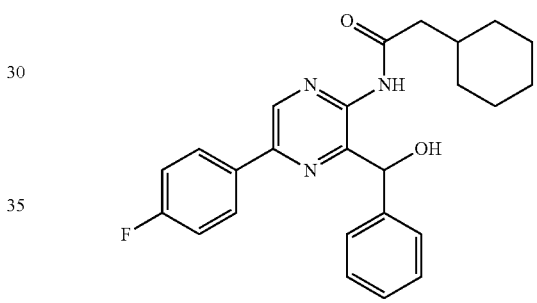
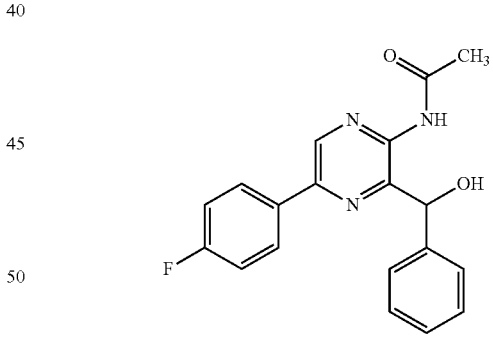
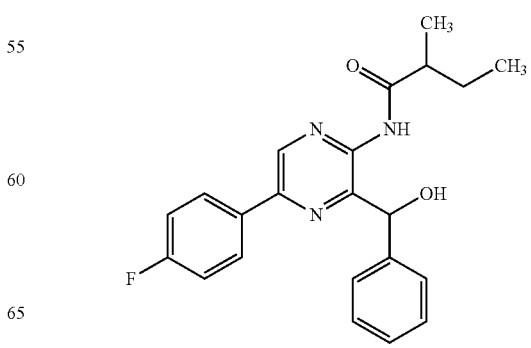

141
-continued
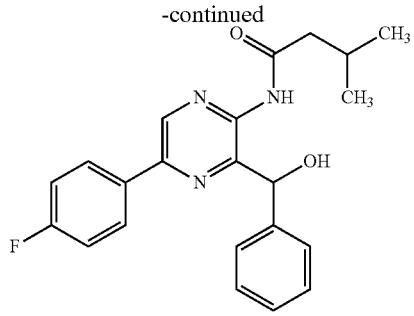
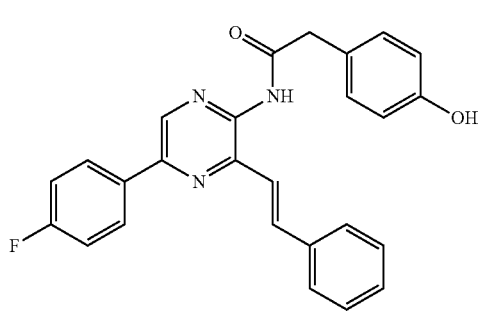
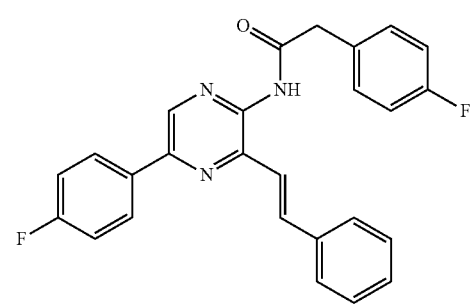
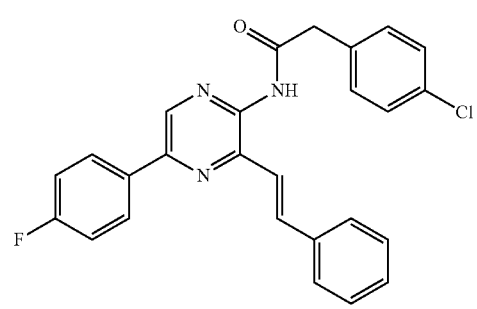
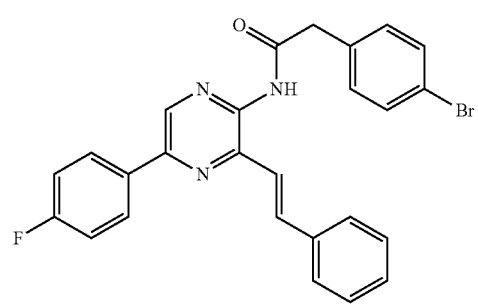
142
-continued
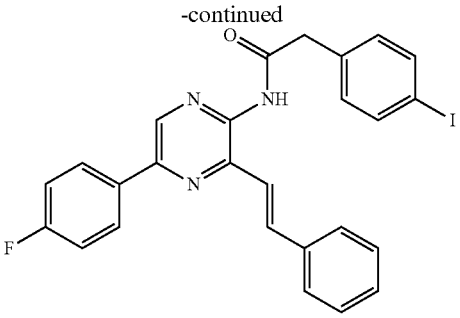
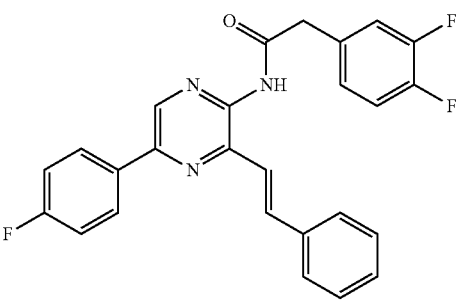
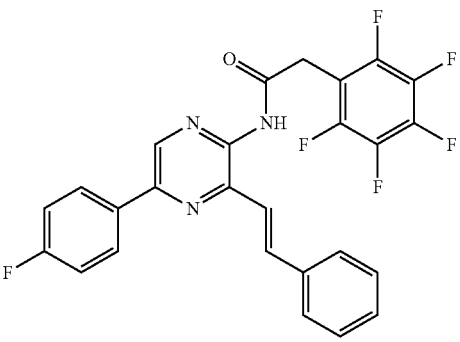
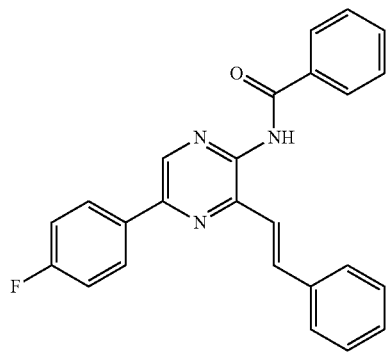
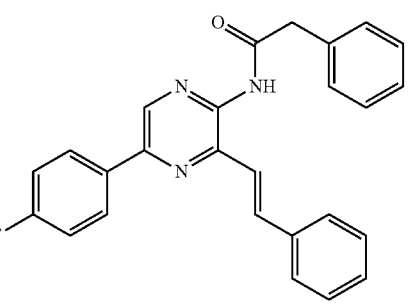

143
-continued
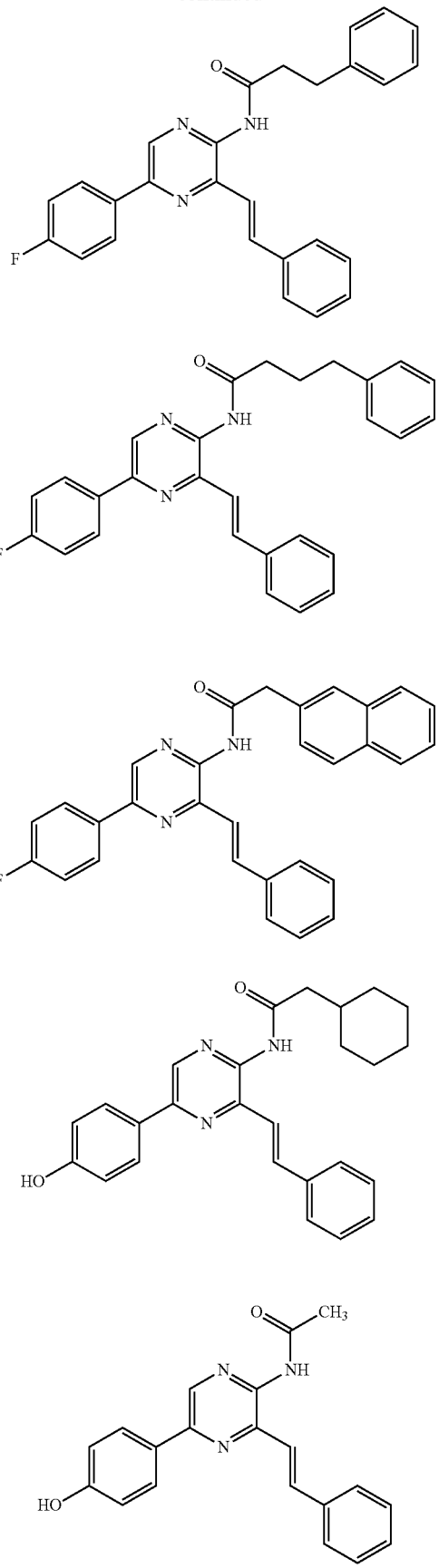
144
-continued
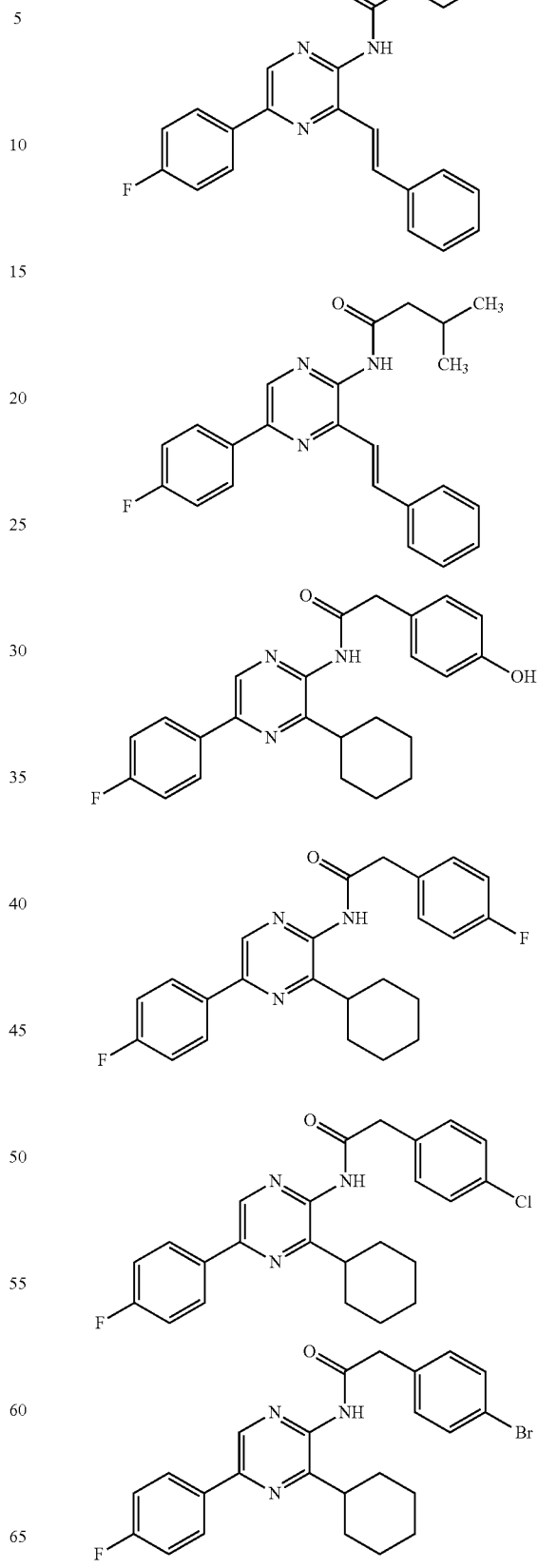

145
-continued
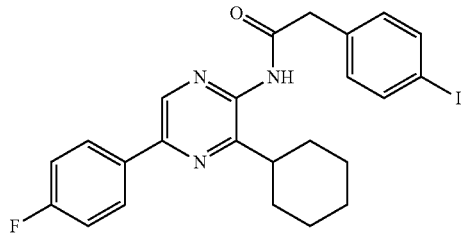
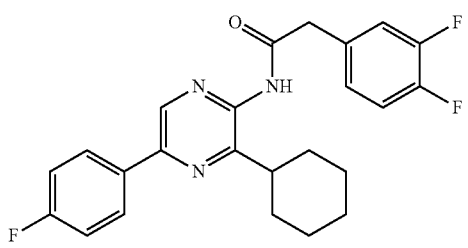
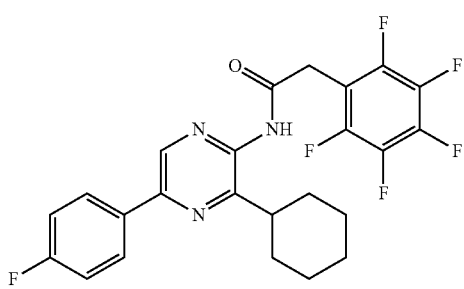
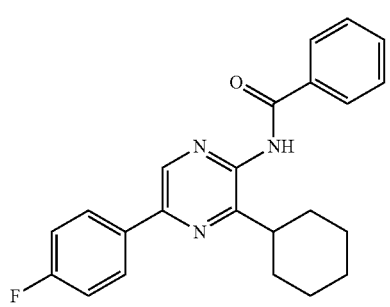
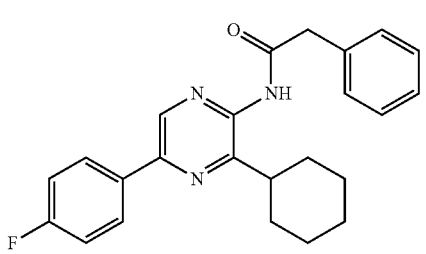
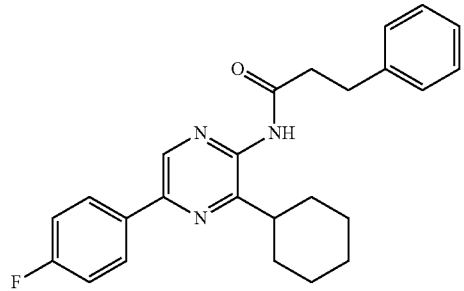
146
-continued
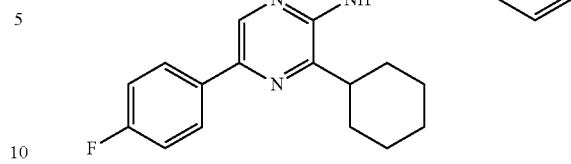
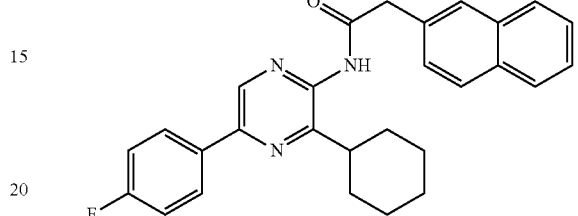
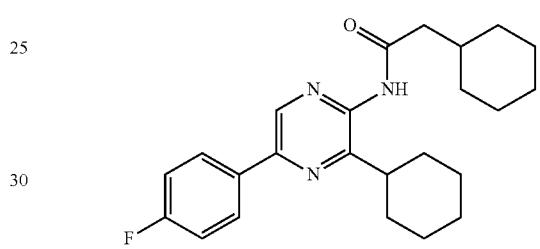
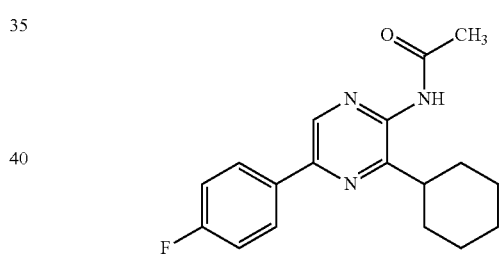
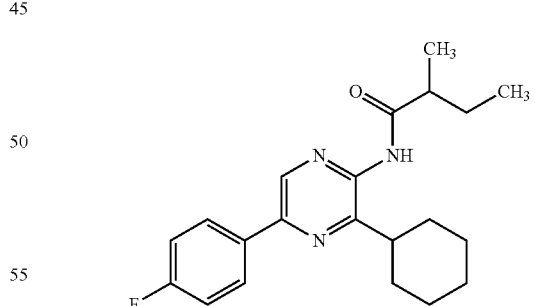
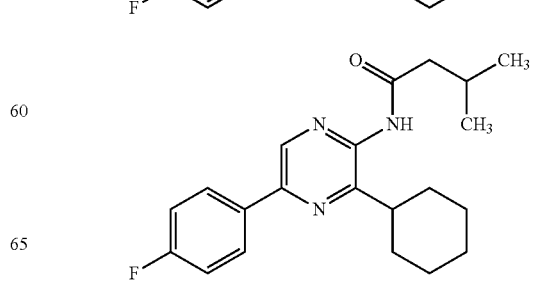

147
-continued
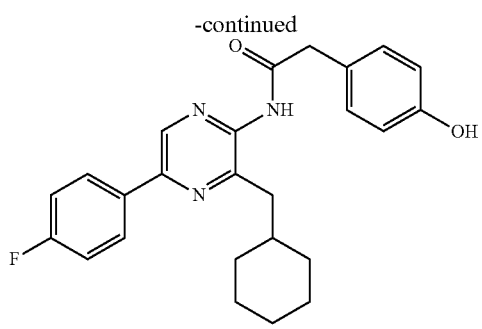
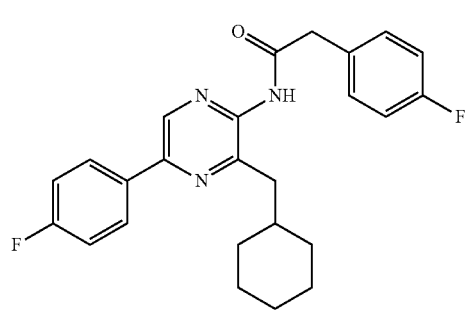
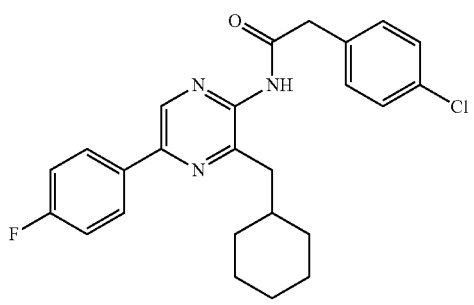
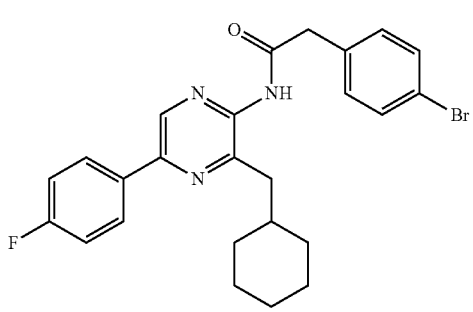
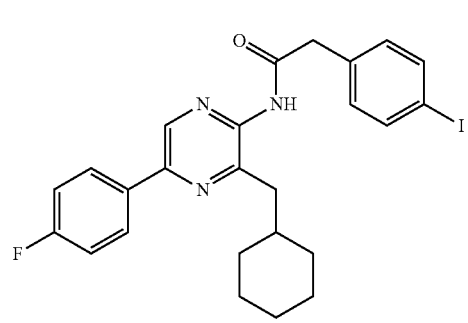
148
-continued
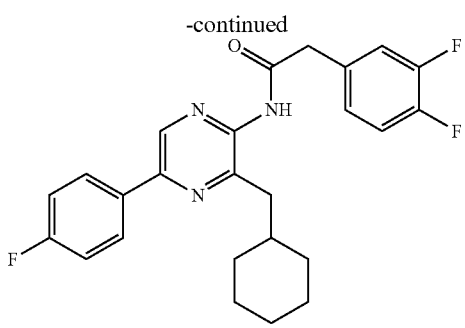
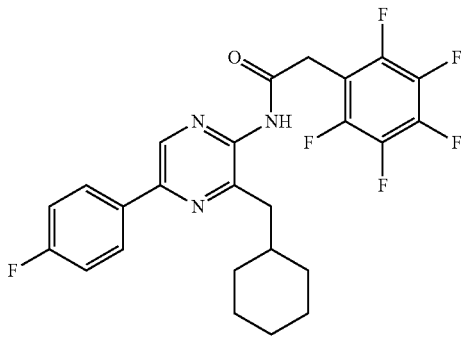
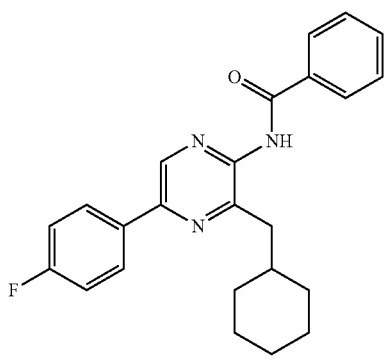
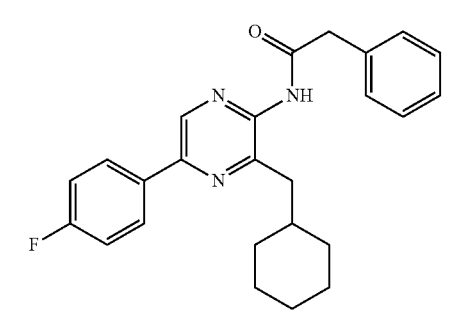
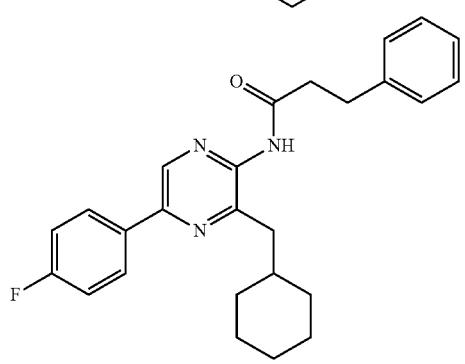

149
-continued
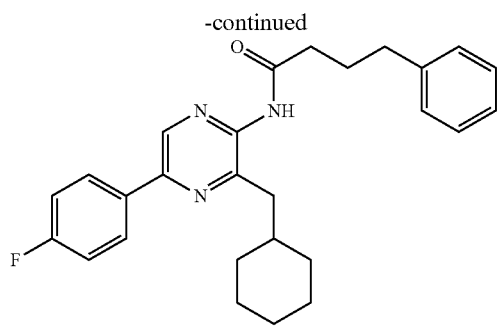
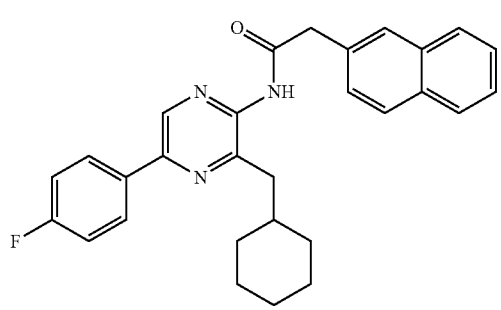
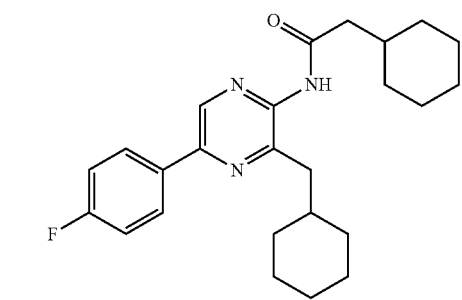
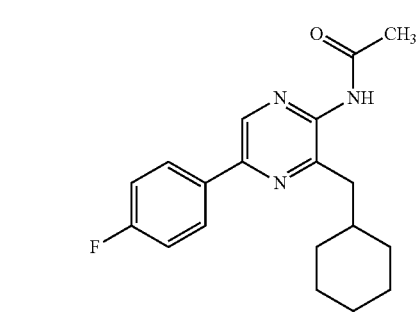
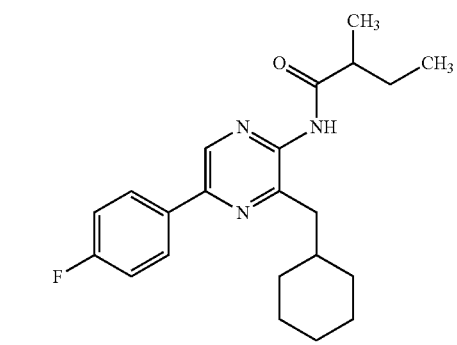
150
-continued
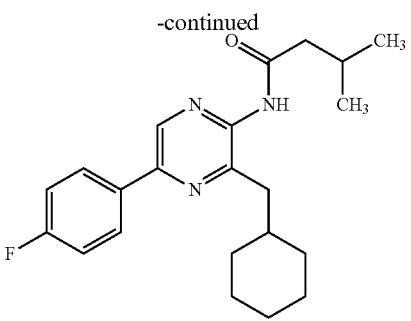
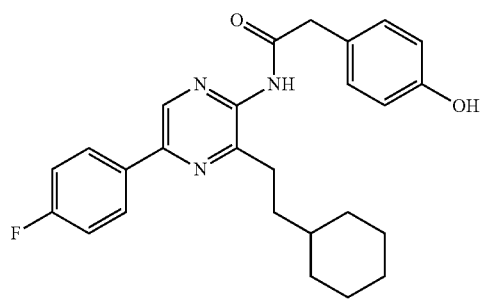
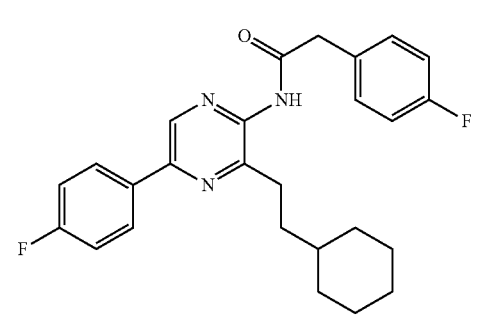
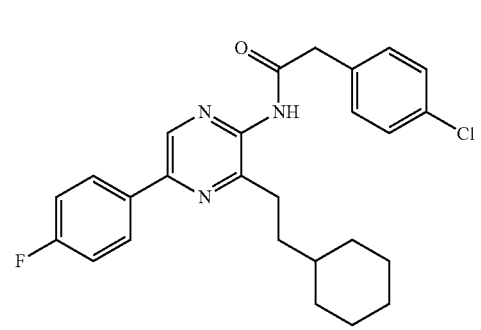
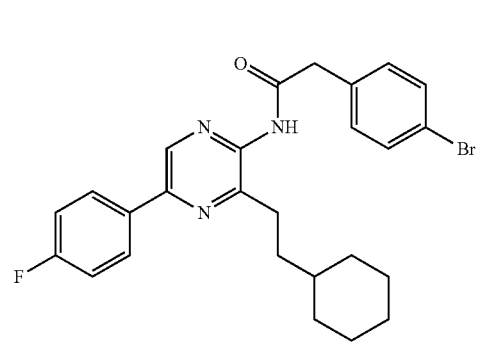

151
-continued
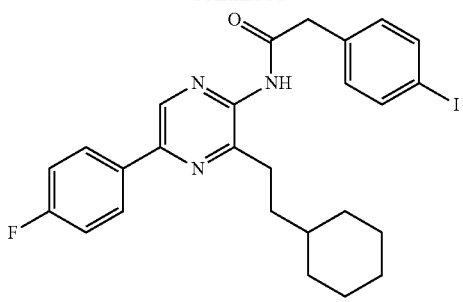
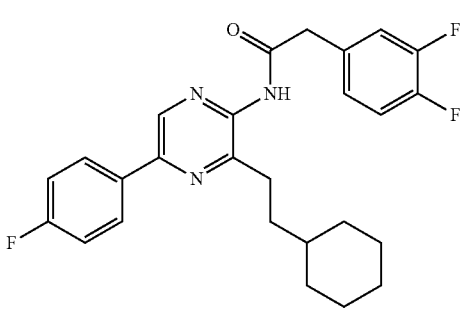
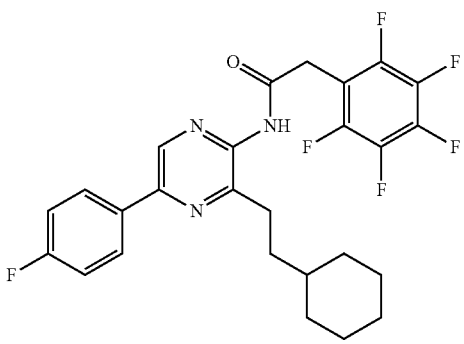
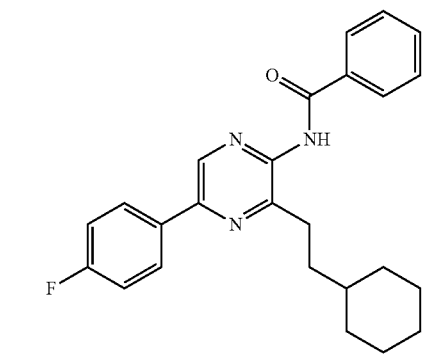
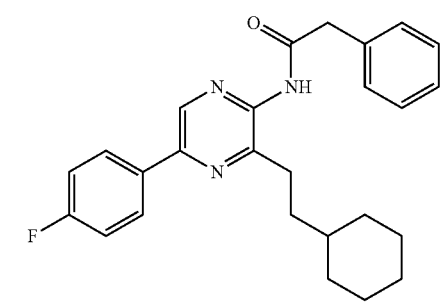
152
-continued
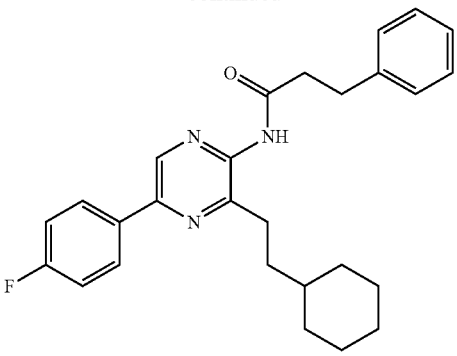
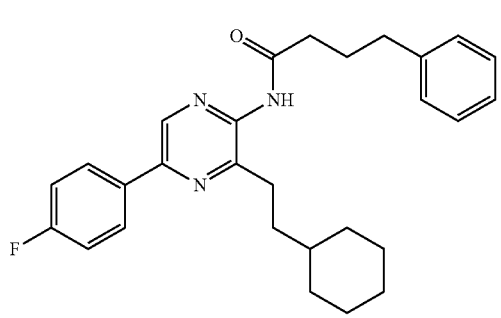
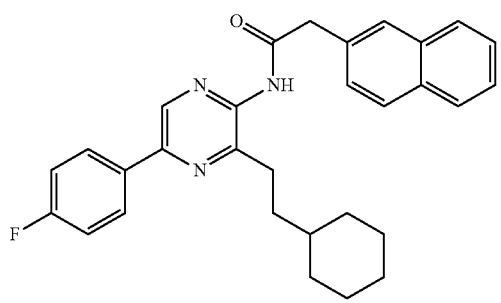
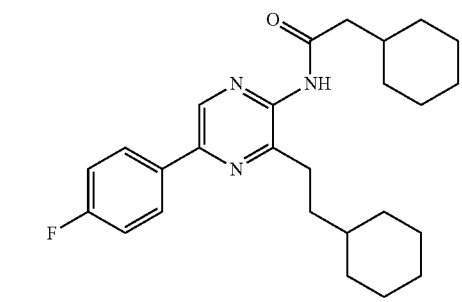
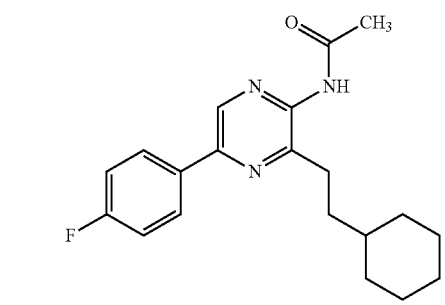

153
-continued
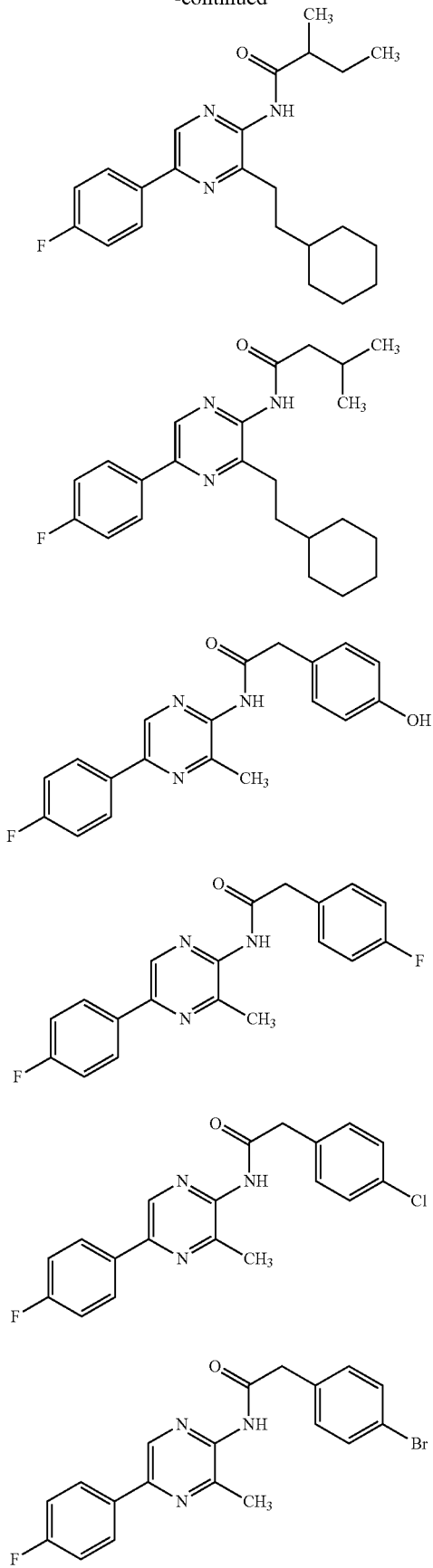
154
-continued
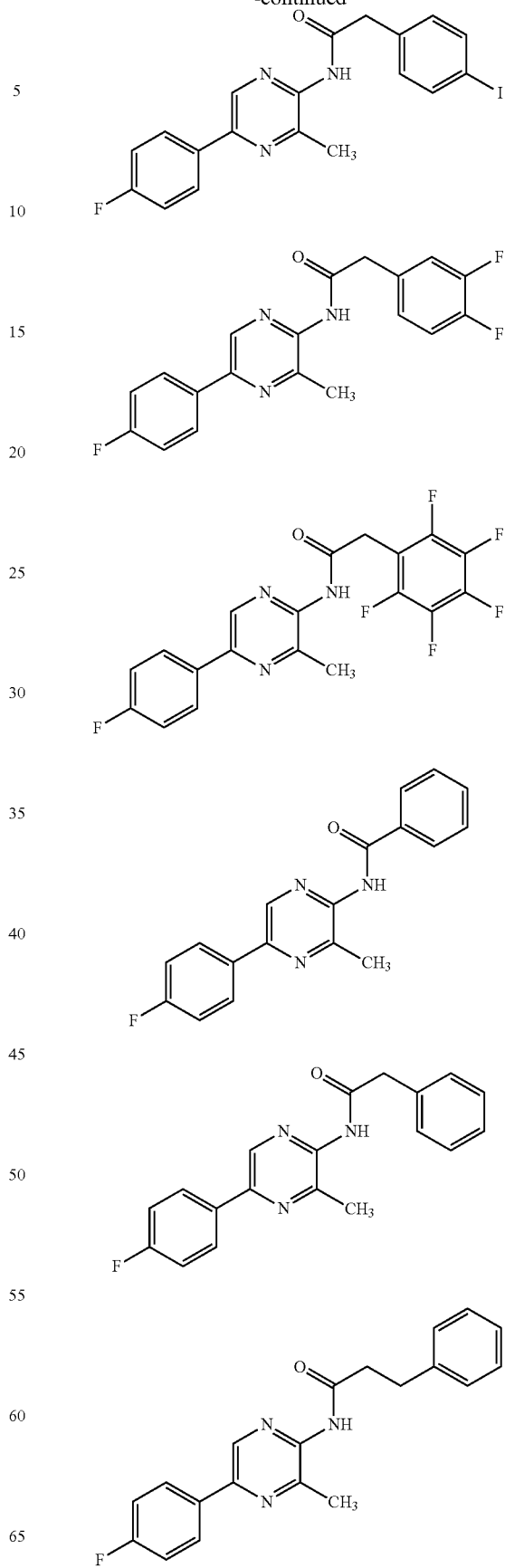

-continued
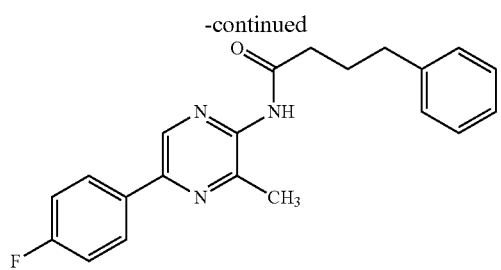
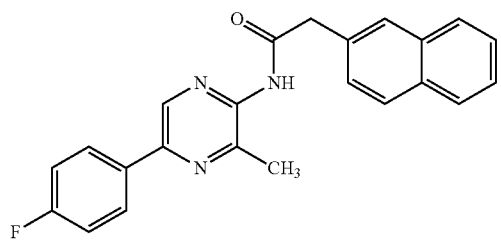
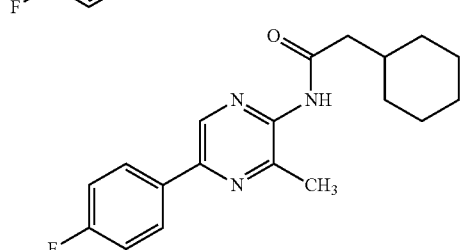
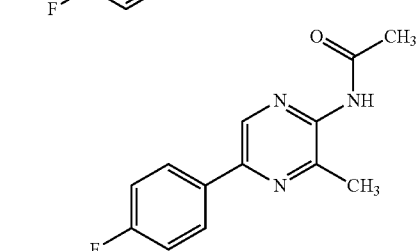
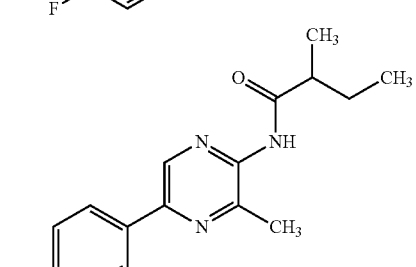
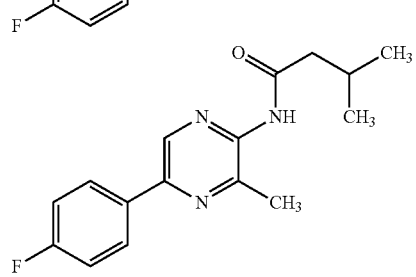
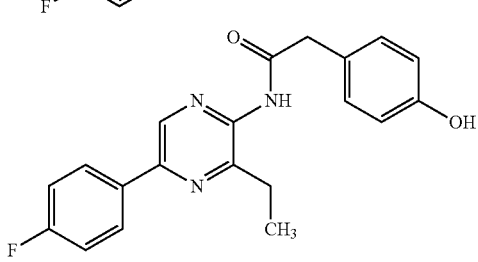
-continued
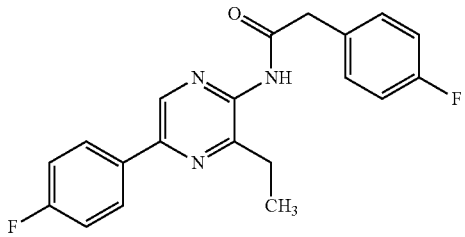
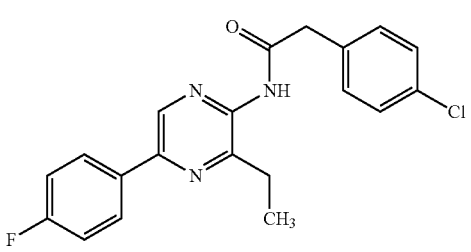
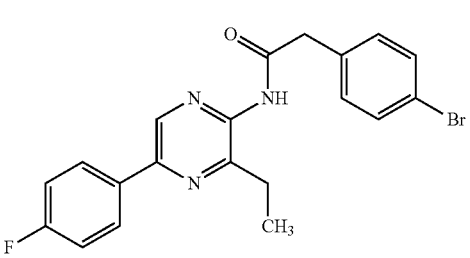
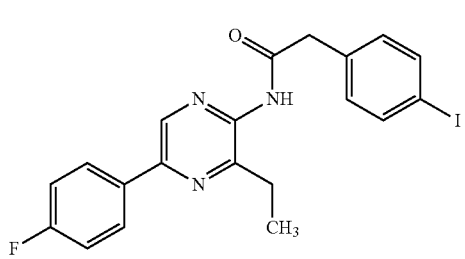
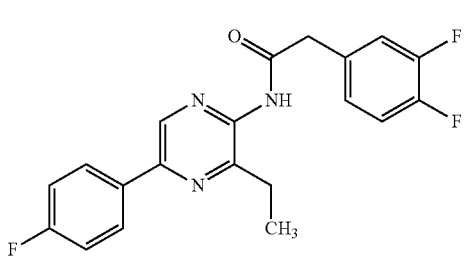
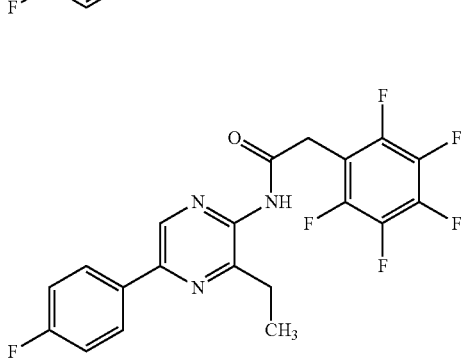

157
-continued
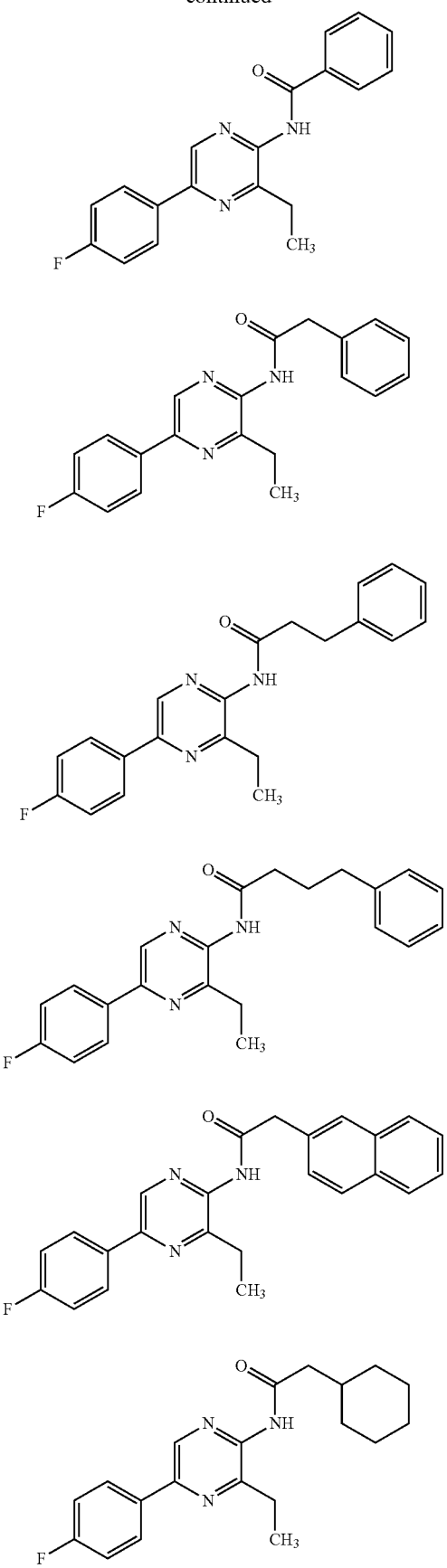
158
-continued
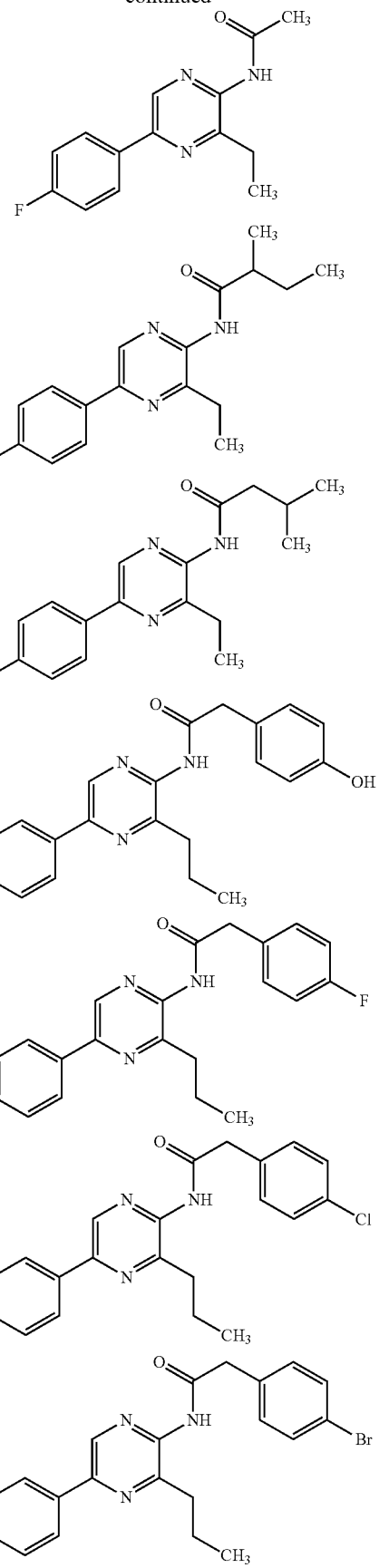

159
-continued
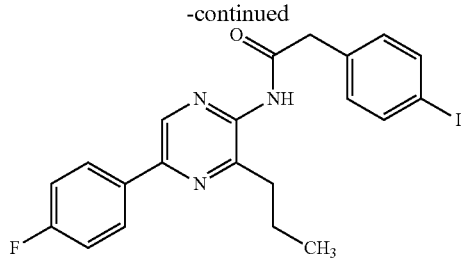
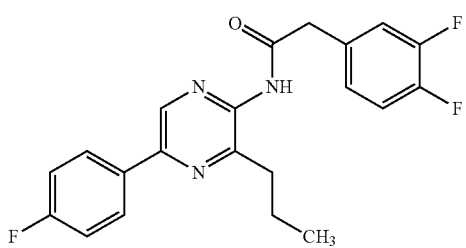
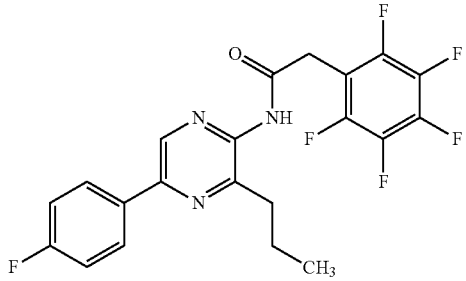
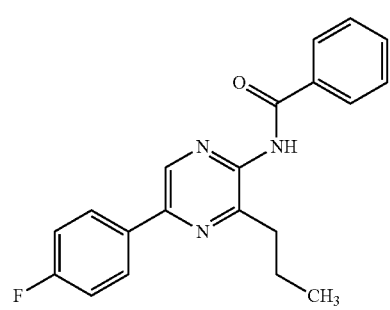
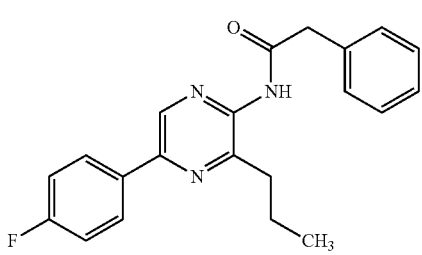
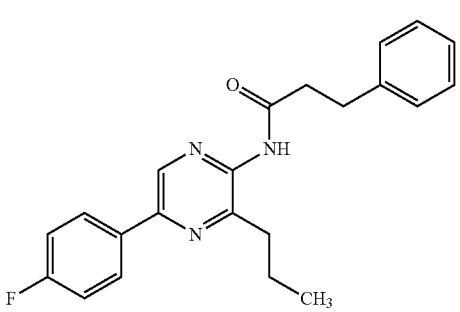
160
-continued
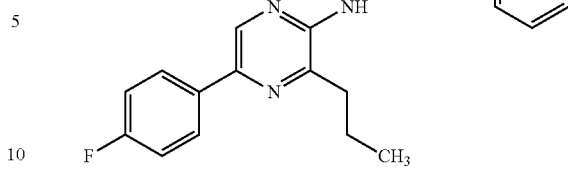
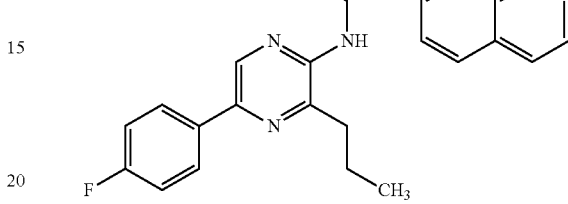
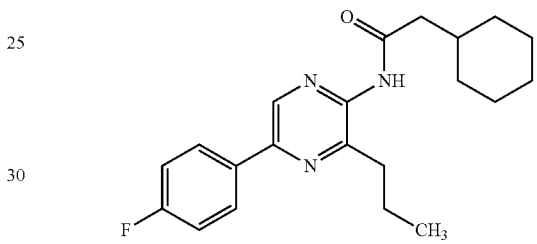
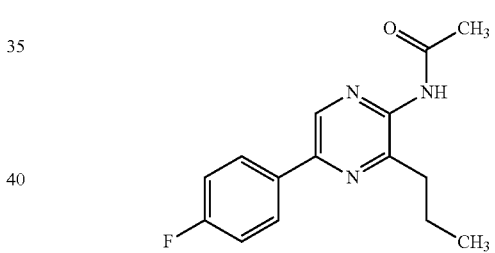
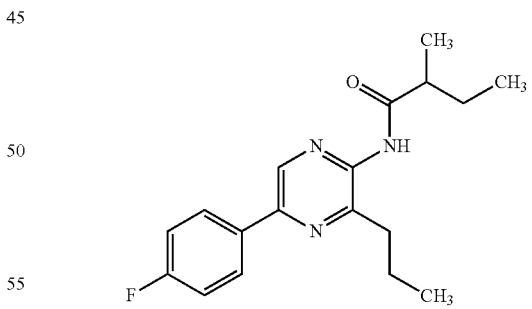

161
-continued

162
-continued
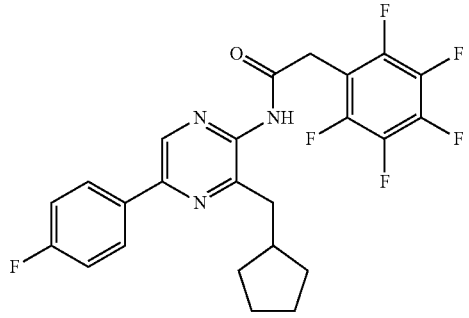
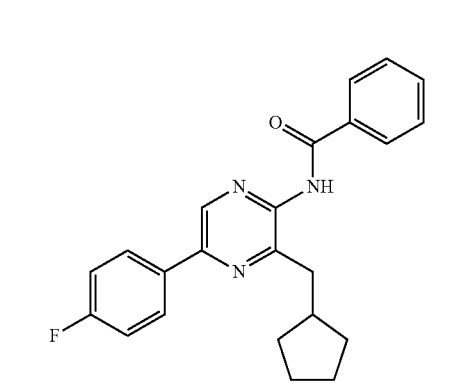
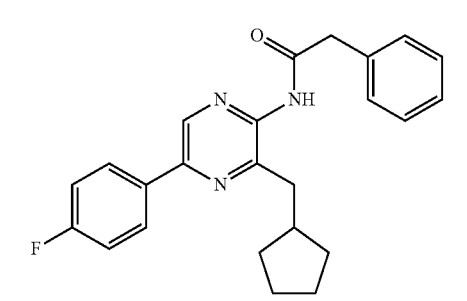
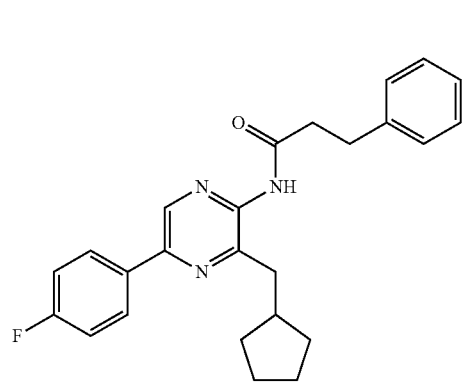
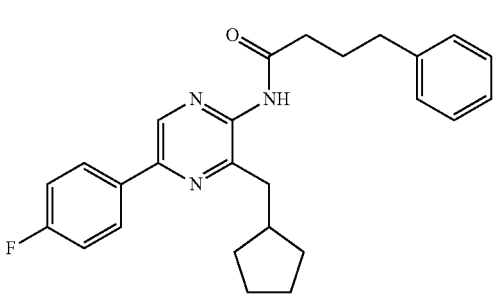

163
-continued

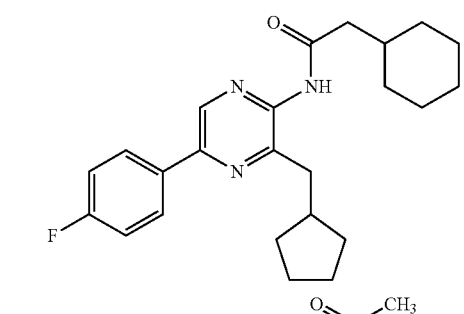
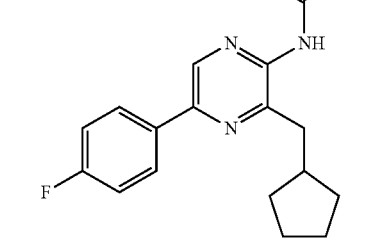
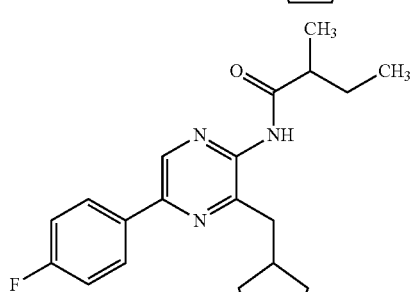
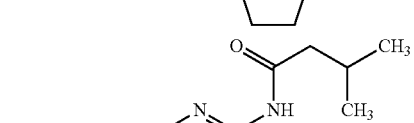
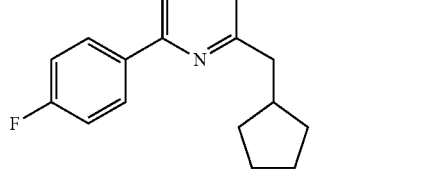
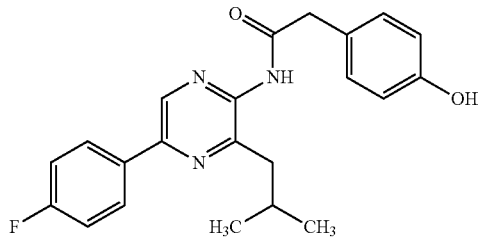
164
-continued
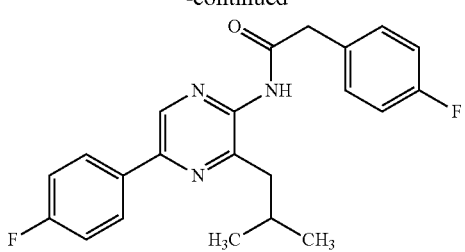
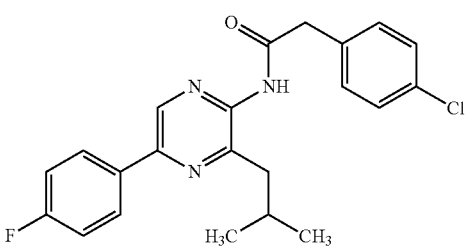
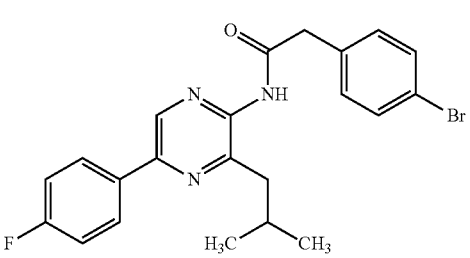
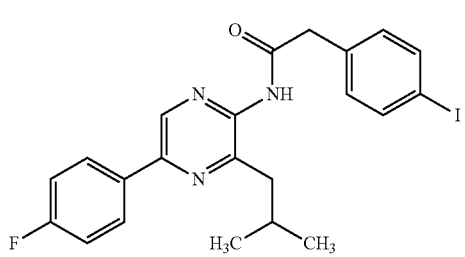
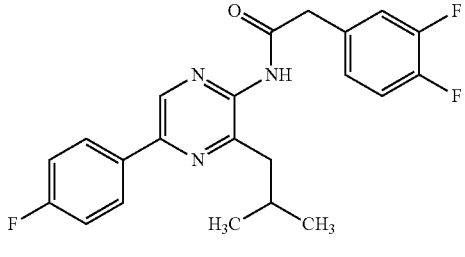
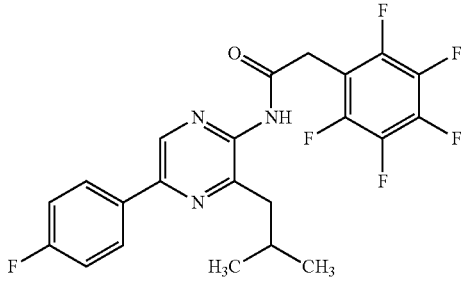

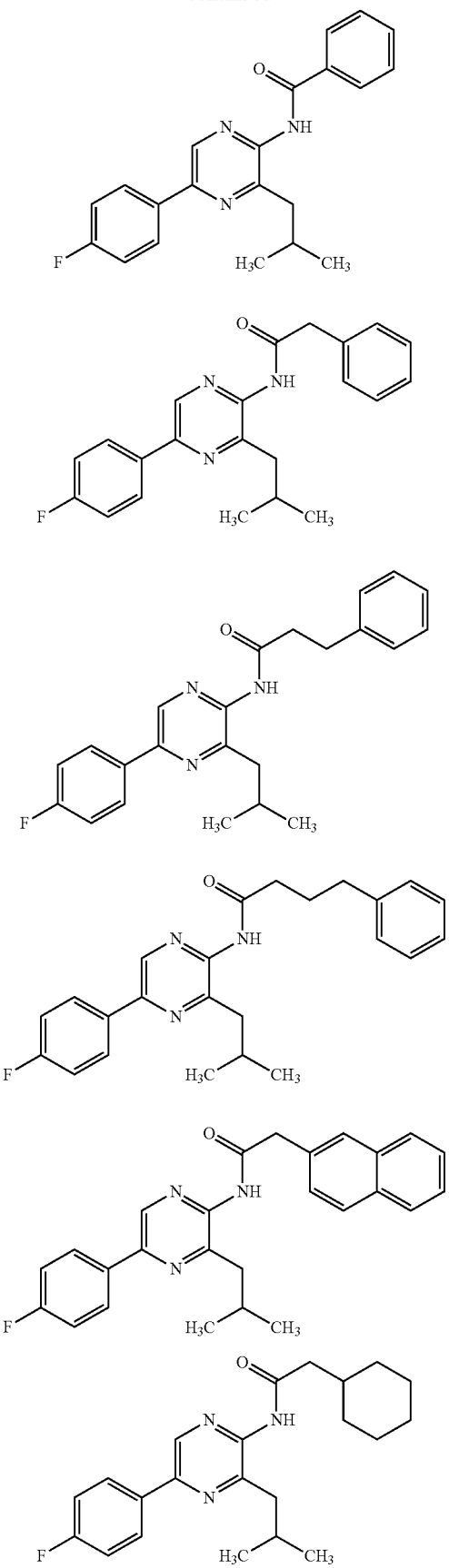
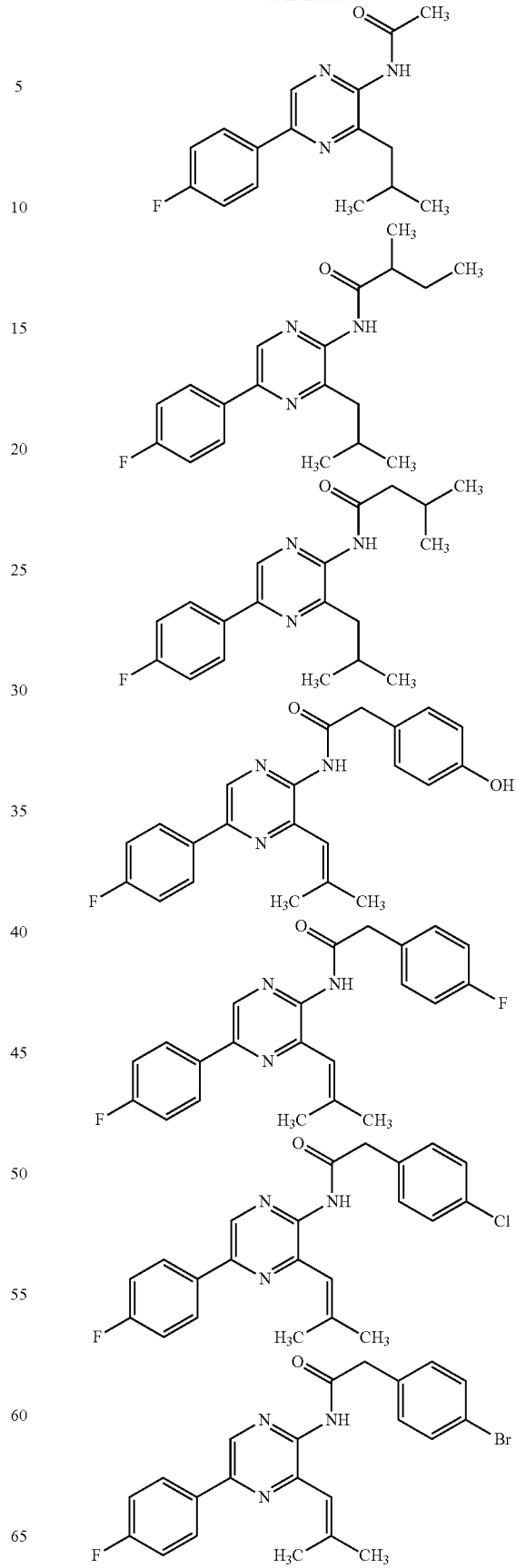

167
-continued
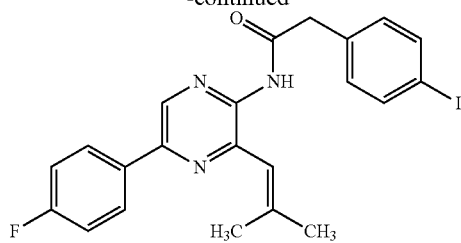
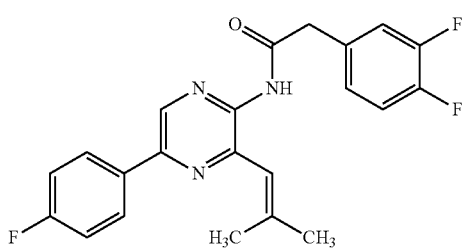
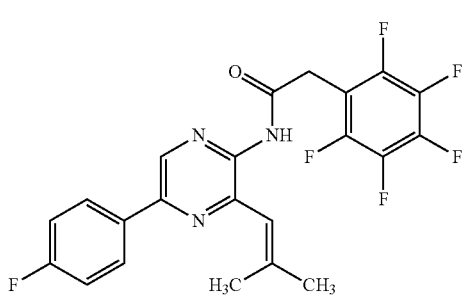
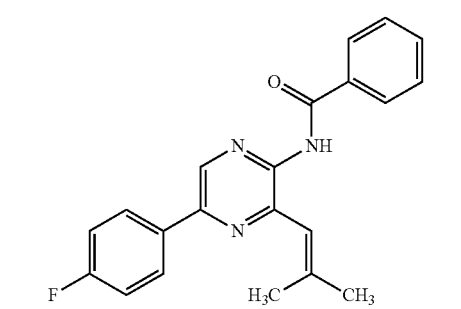
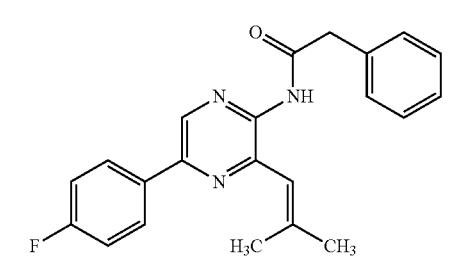
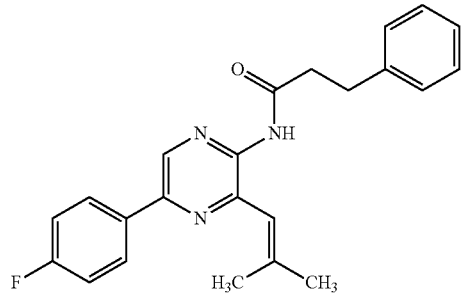
168
-continued
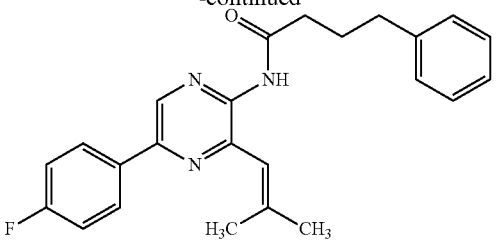
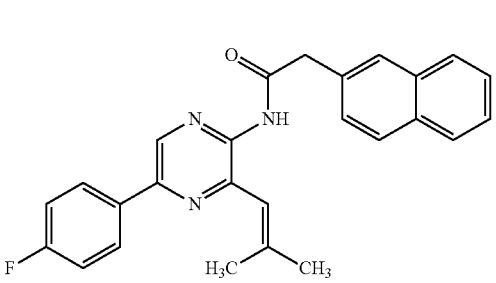
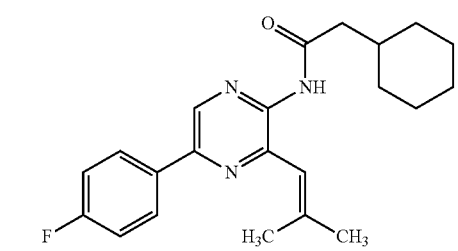
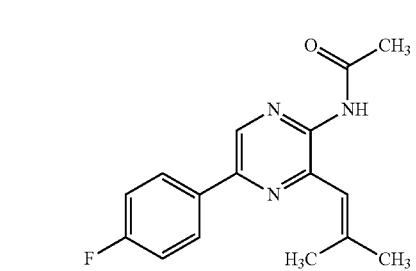
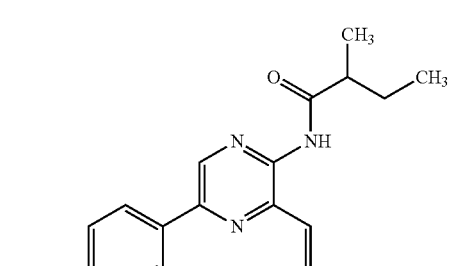
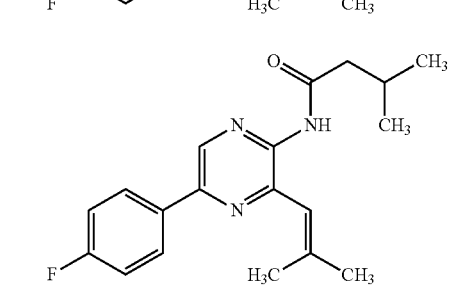

169
-continued
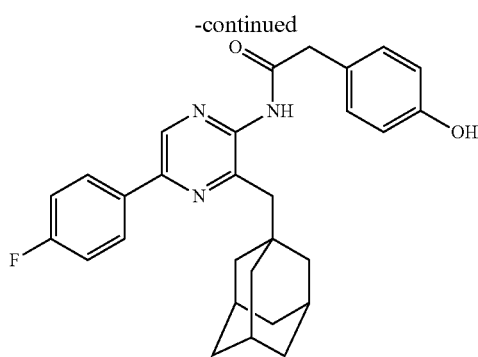
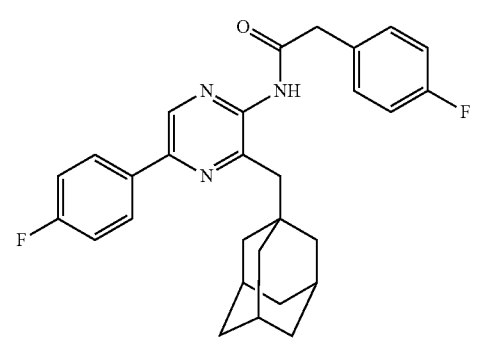
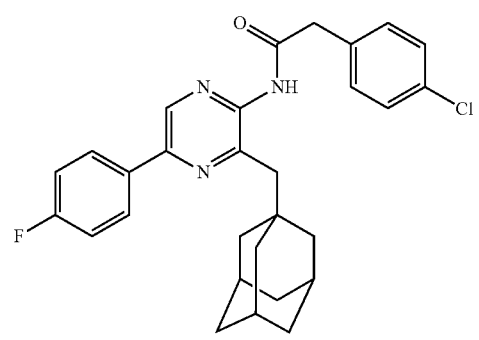
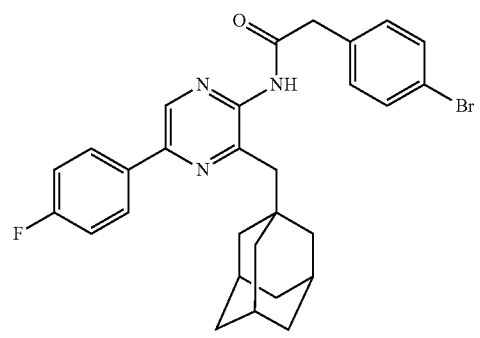
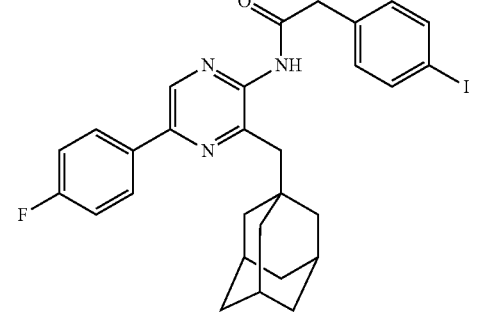
170
-continued
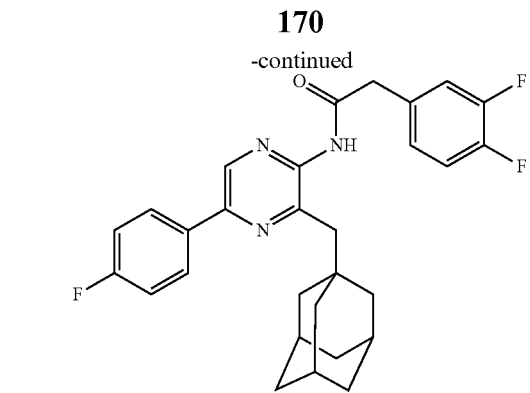
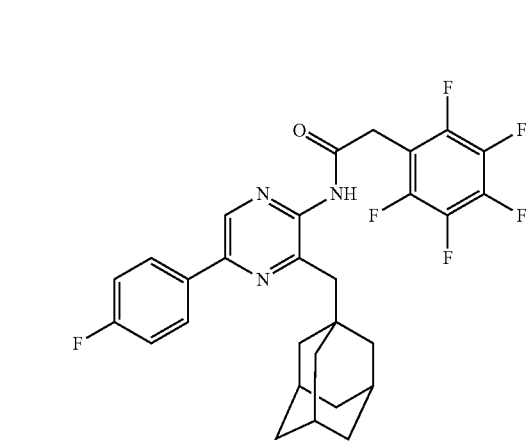
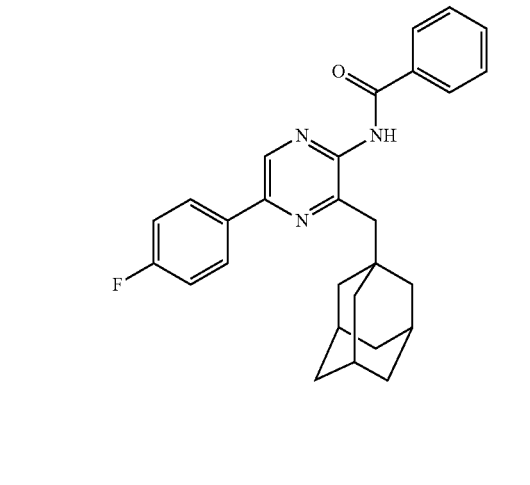
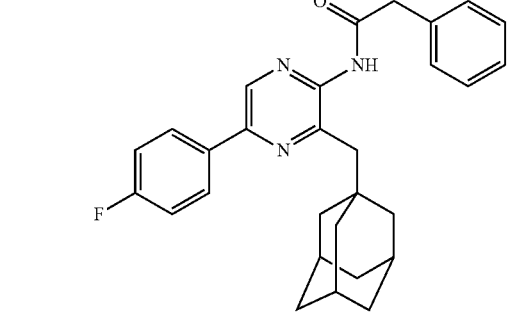

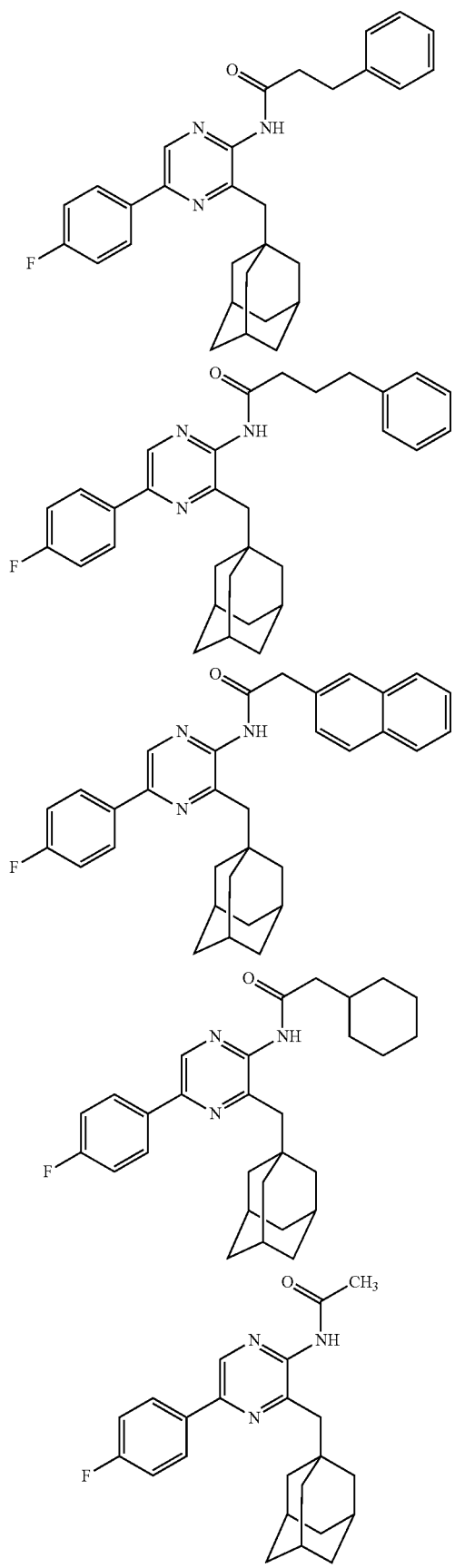
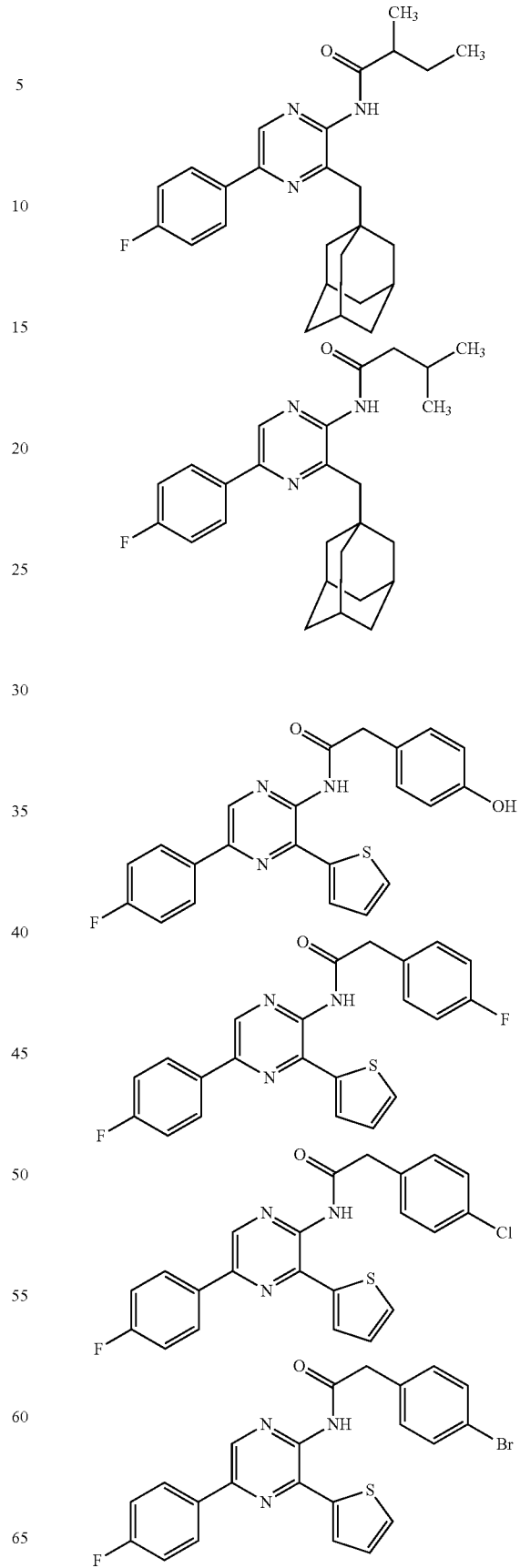

173
-continued
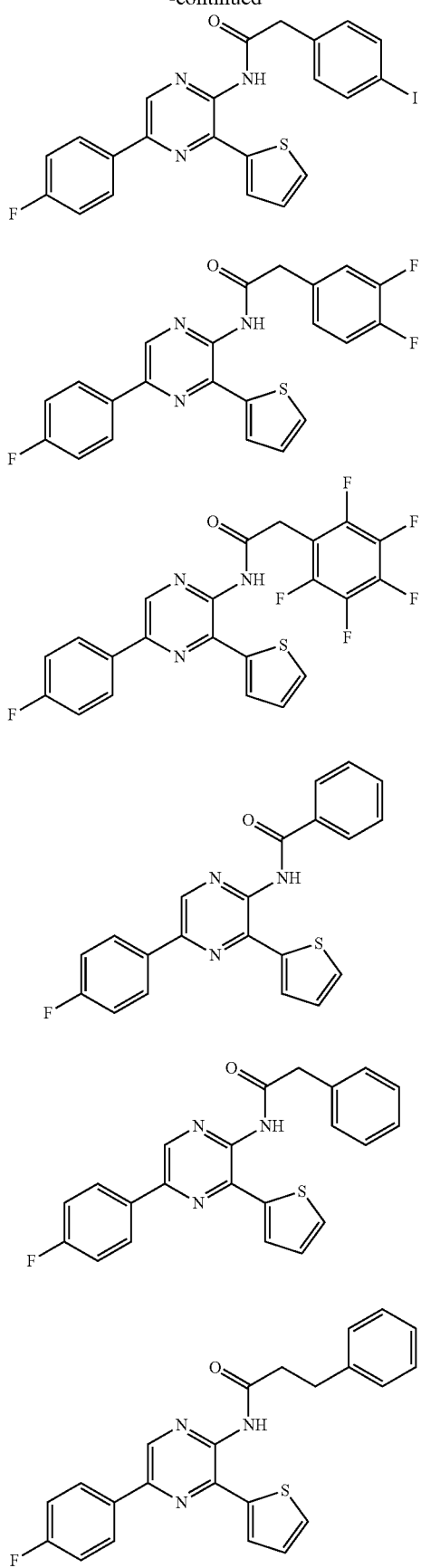
174
-continued
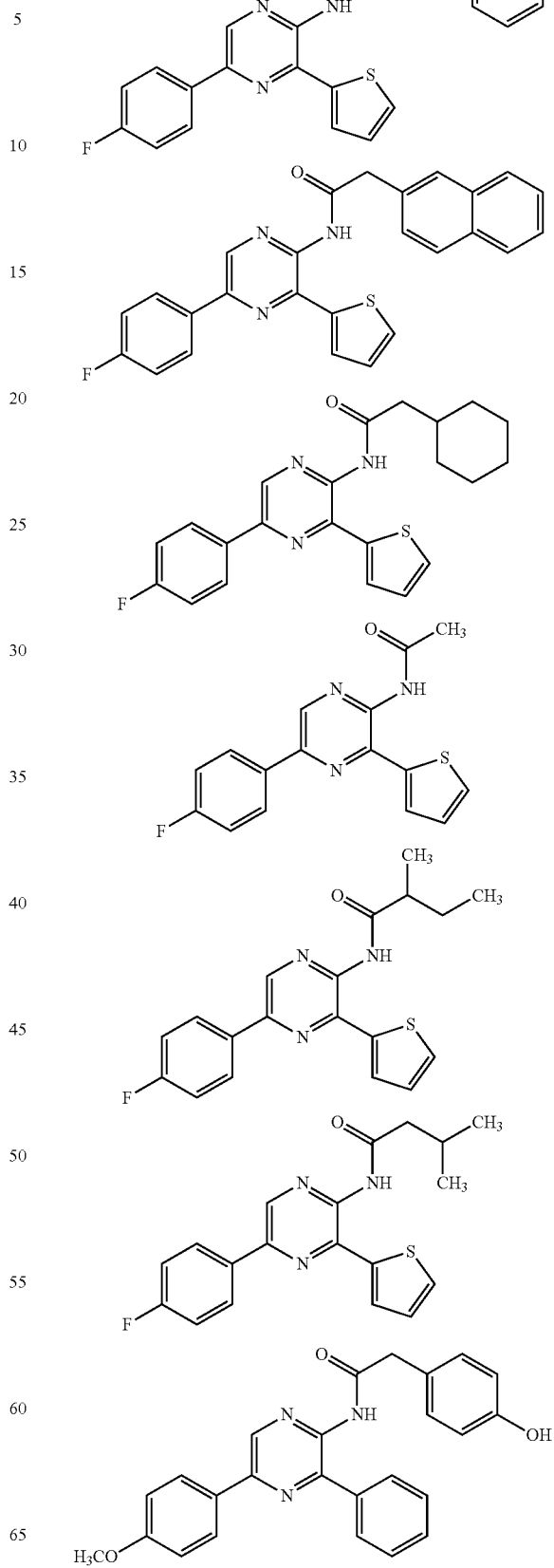

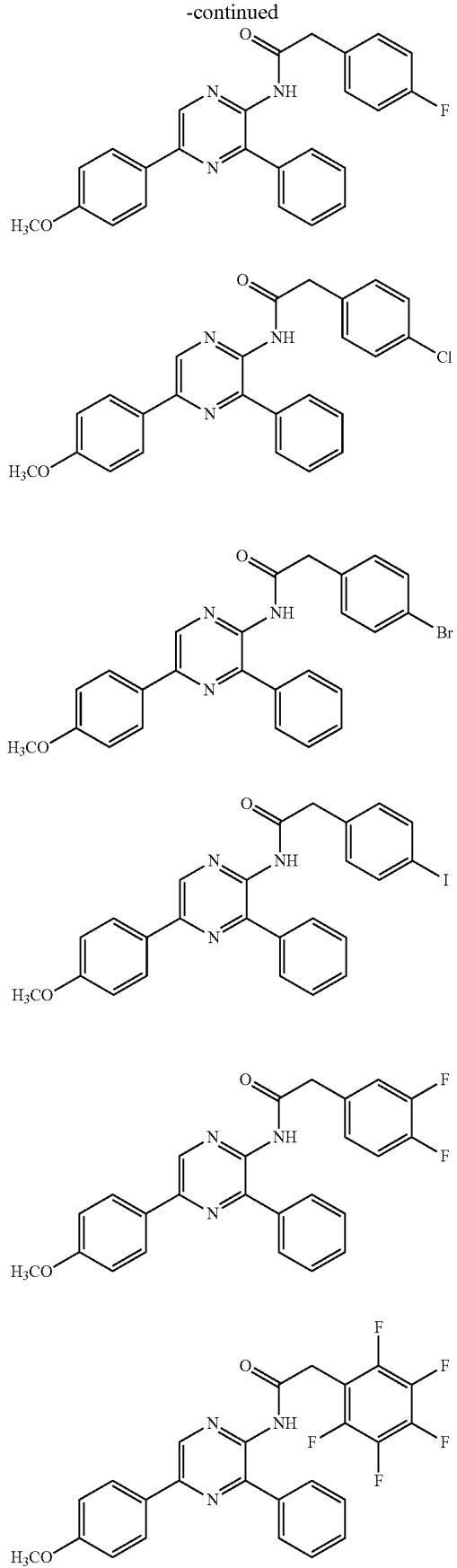
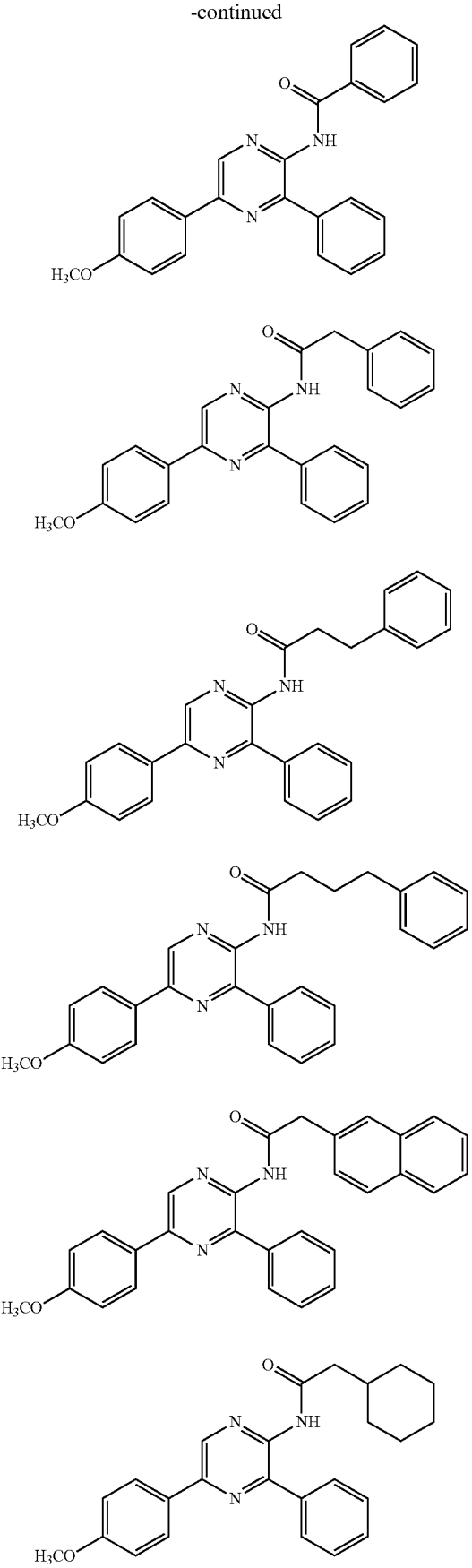

177
-continued
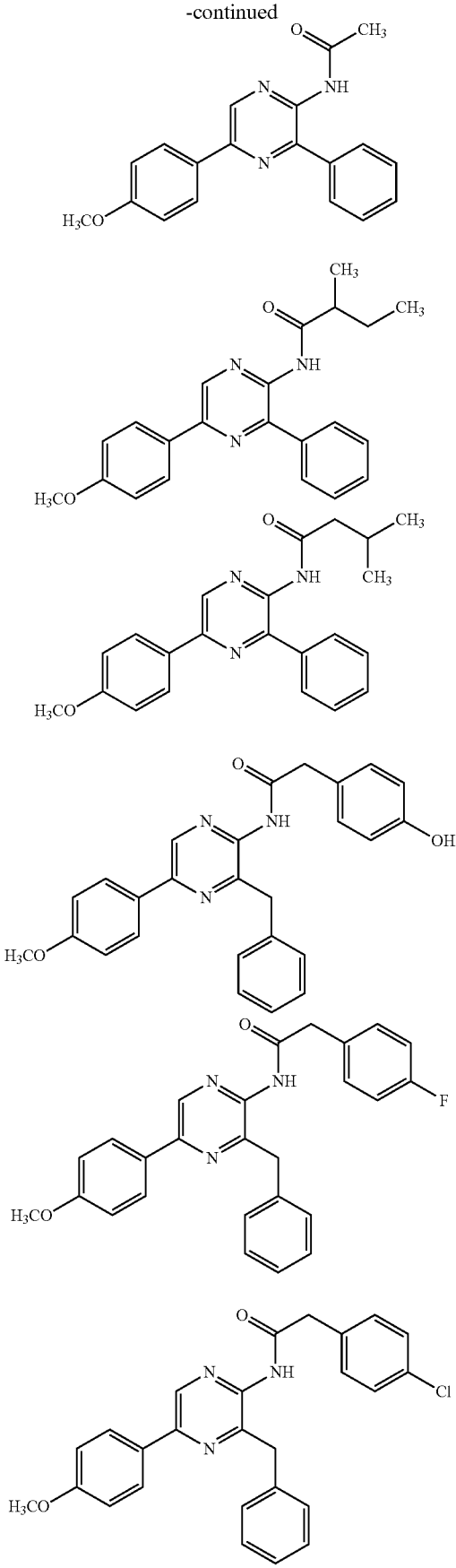
178
-continued
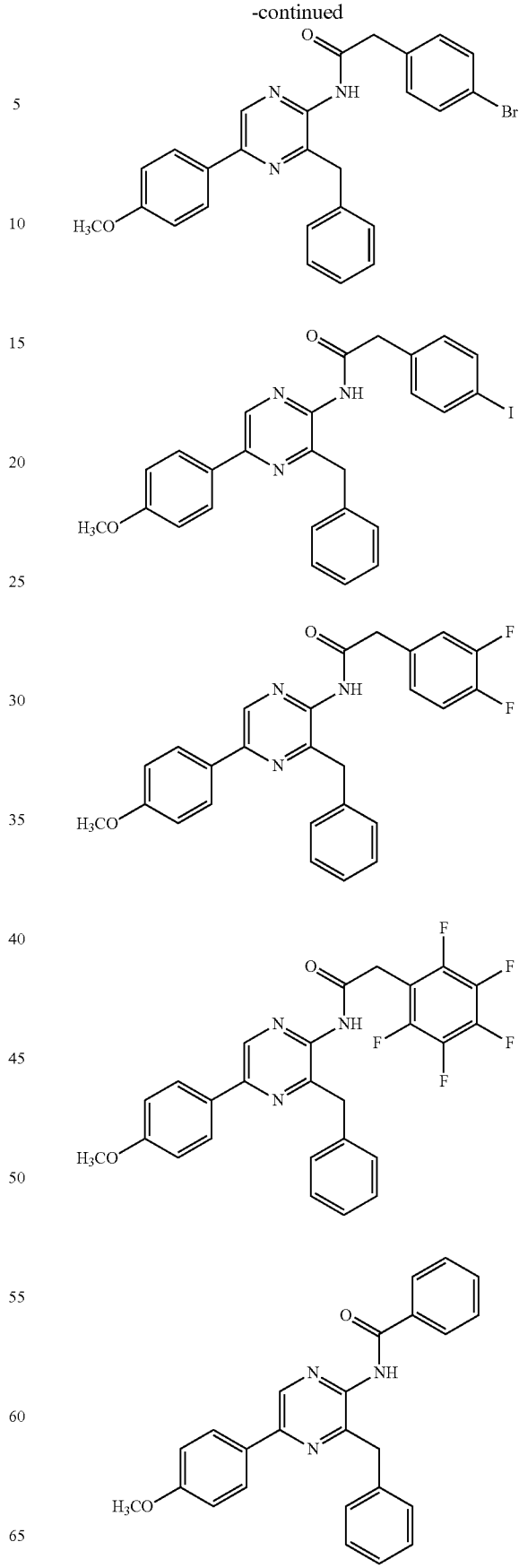

179 | 180
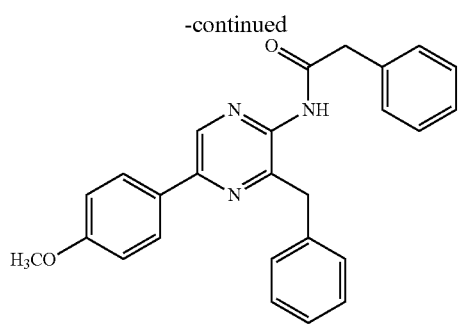
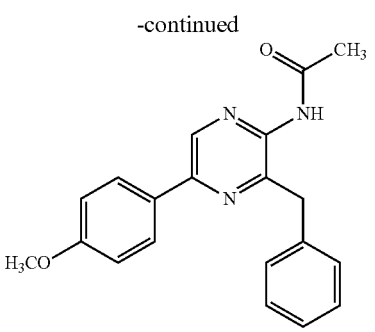
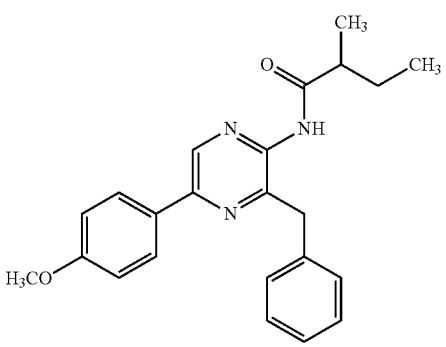
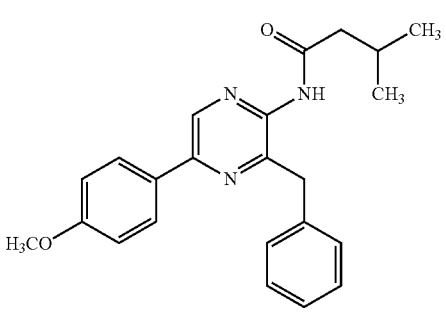
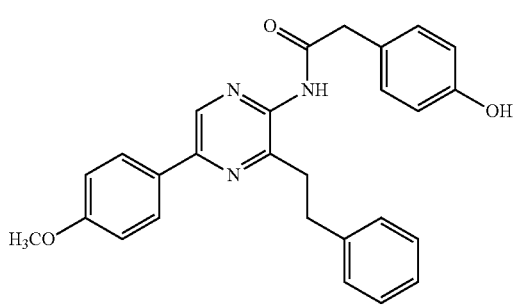
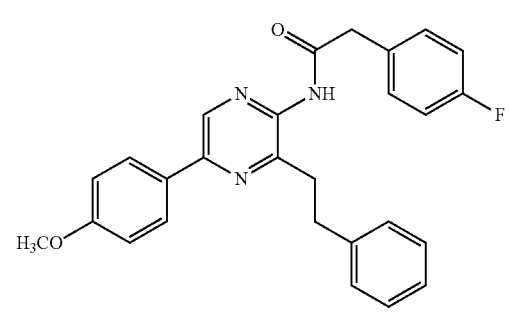

181
-continued
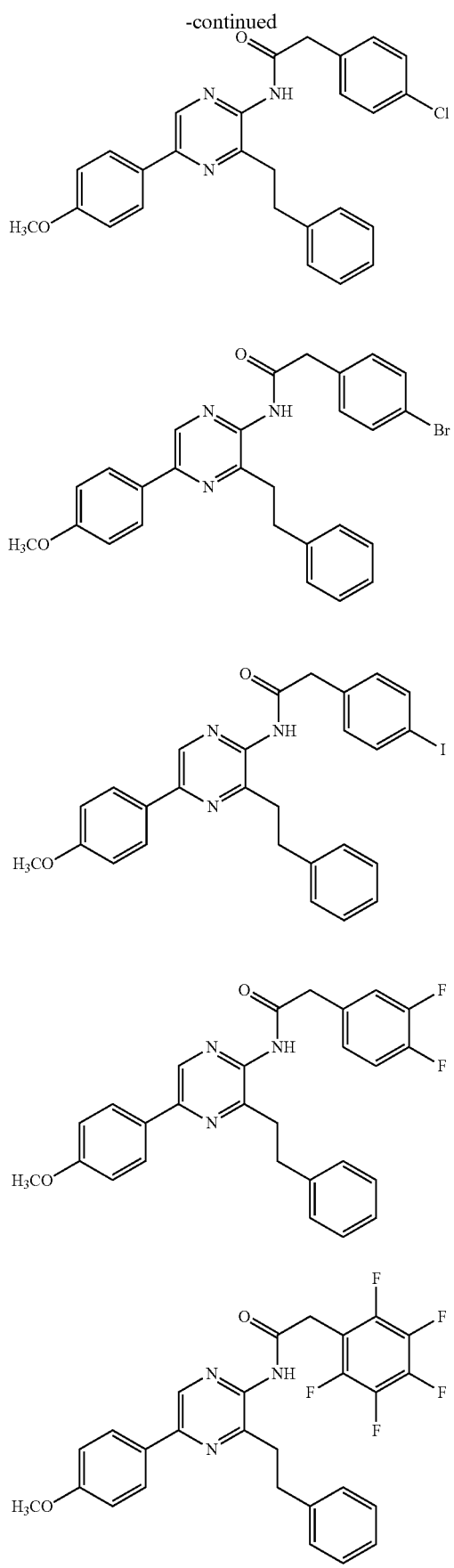
182
-continued
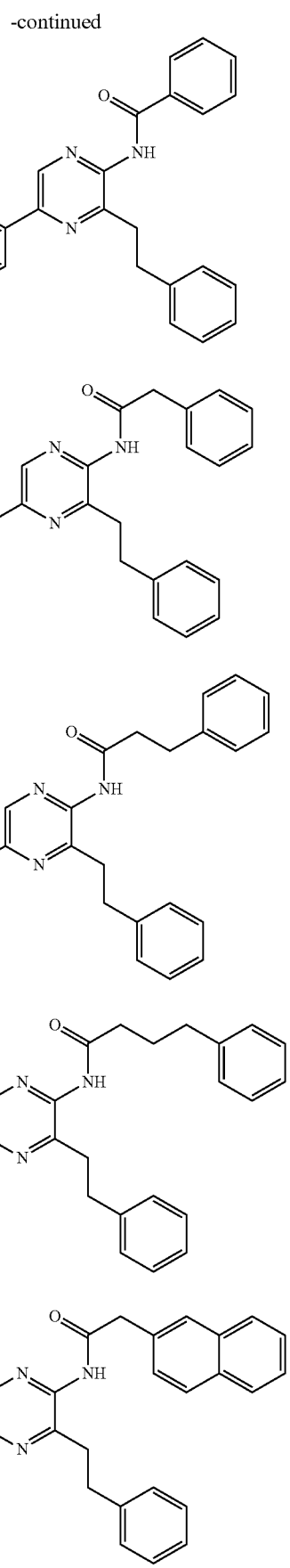

183
-continued
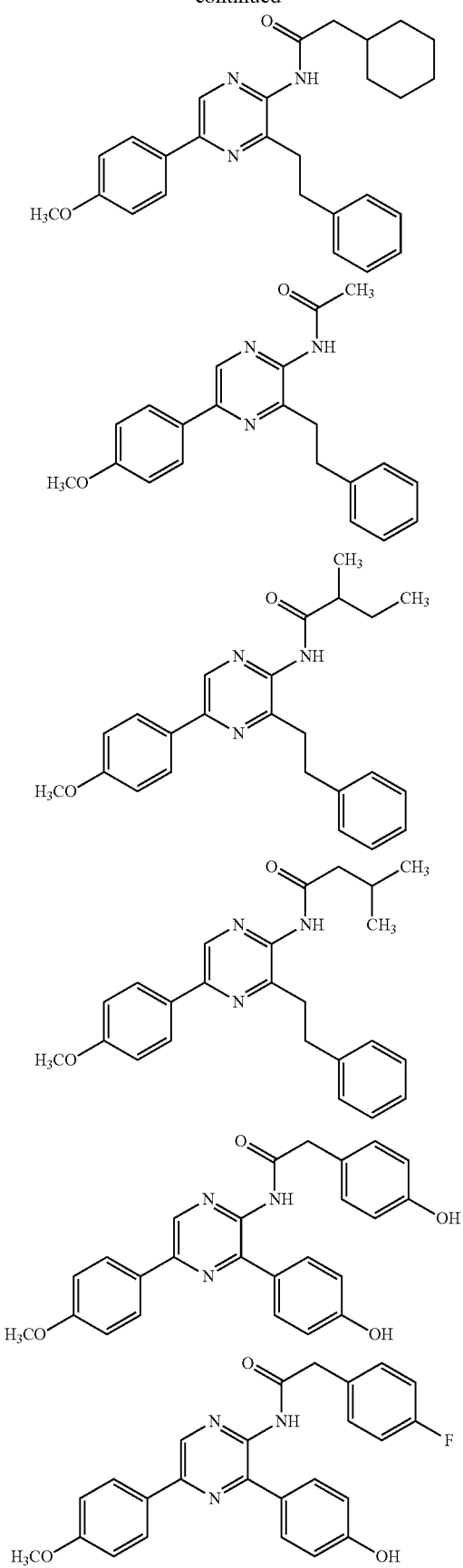
184
-continued
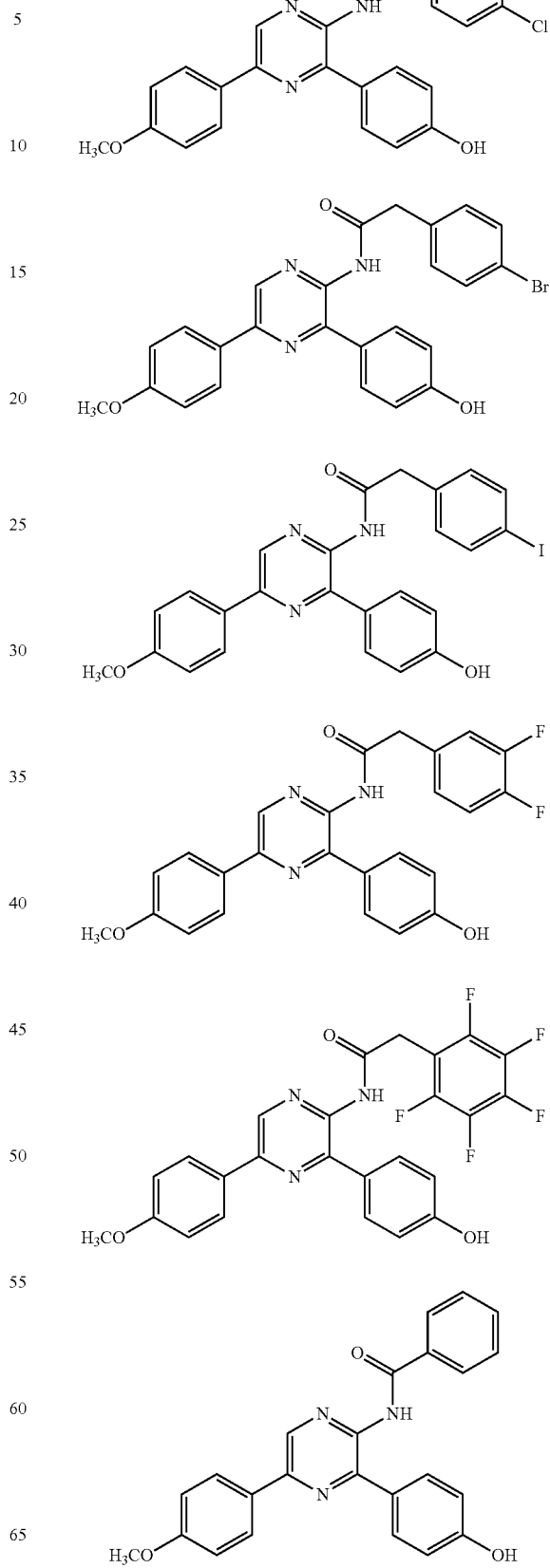

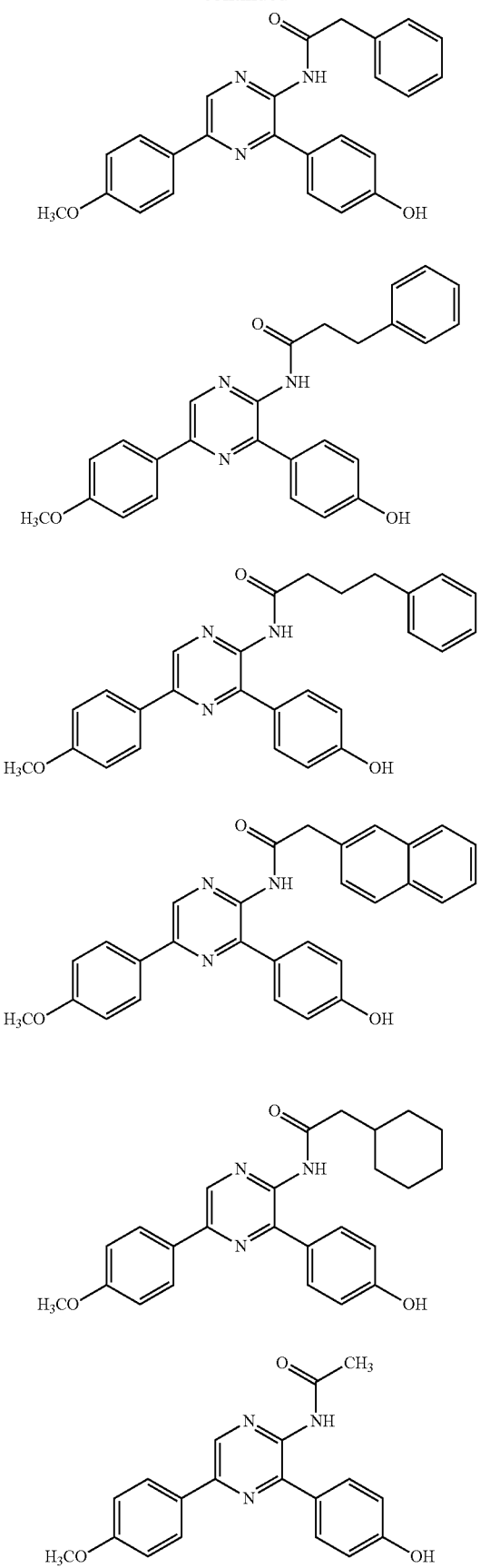
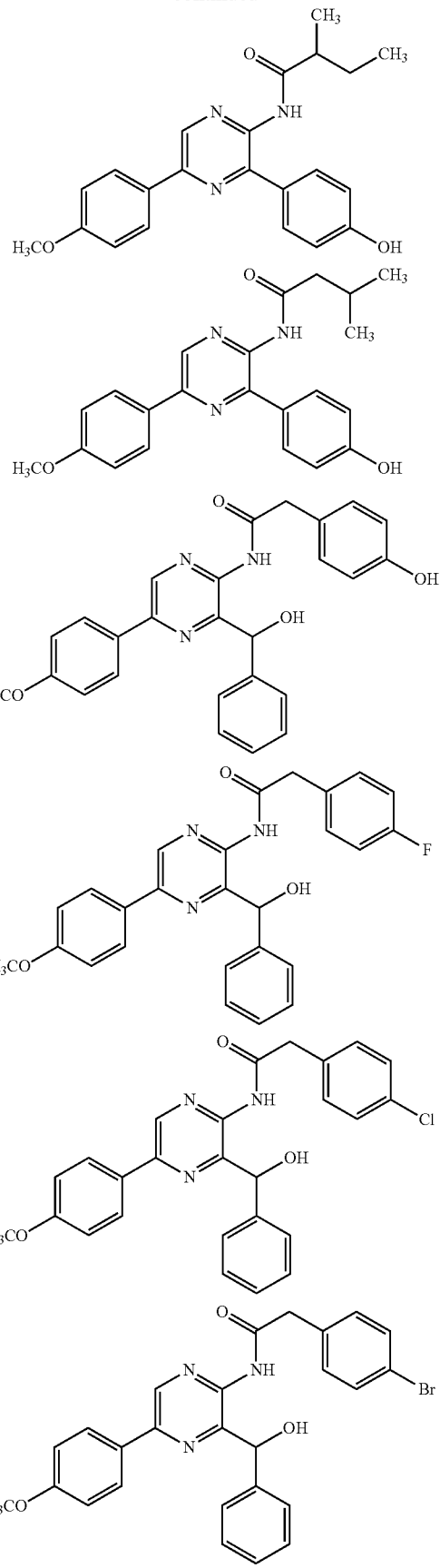

187
-continued
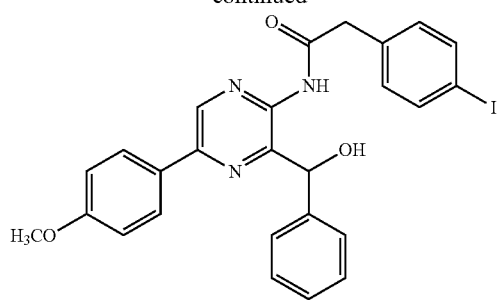
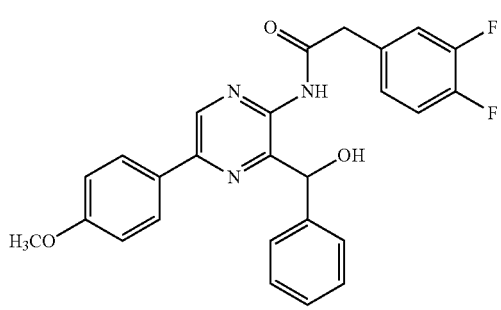
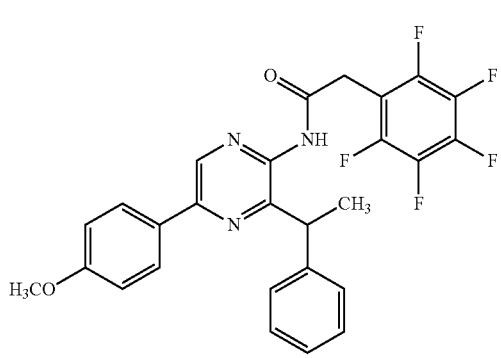
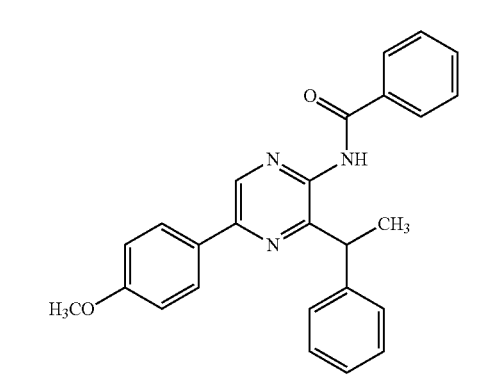
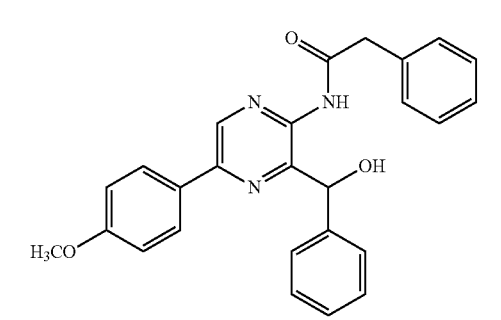
188
-continued
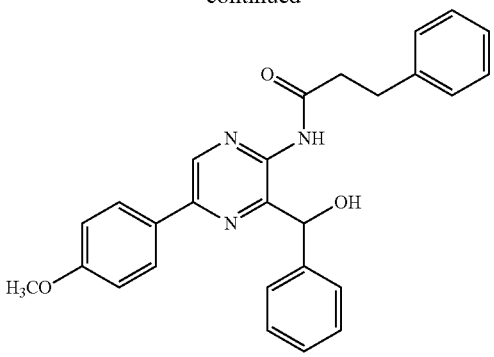
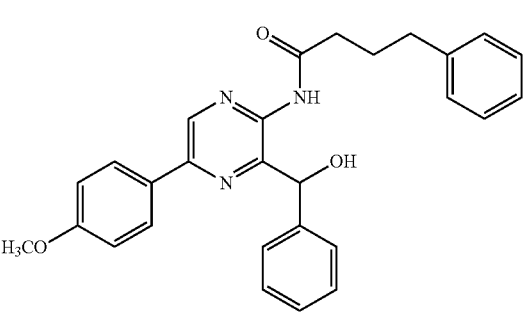
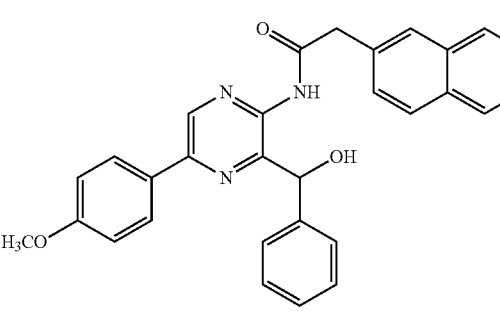
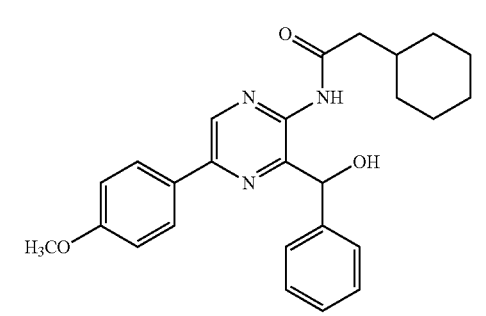
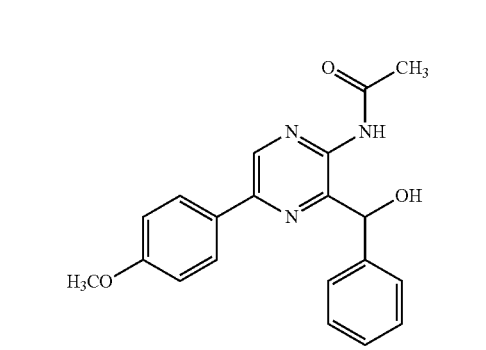

189
-continued
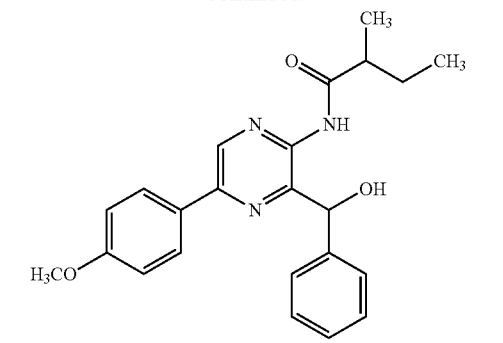
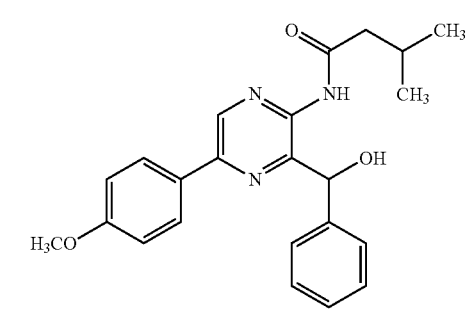
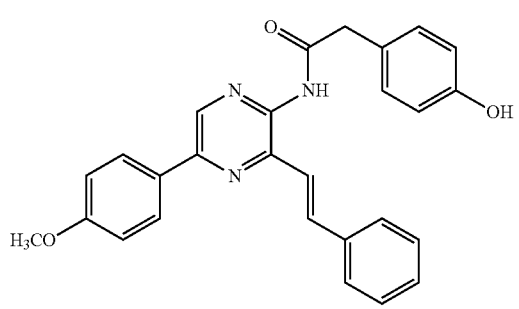
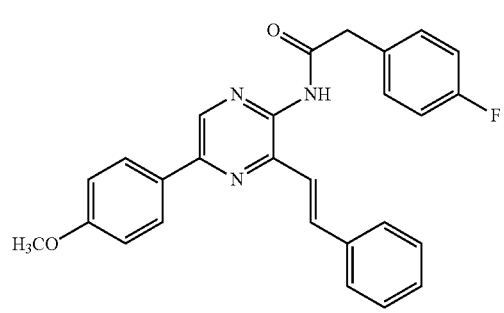
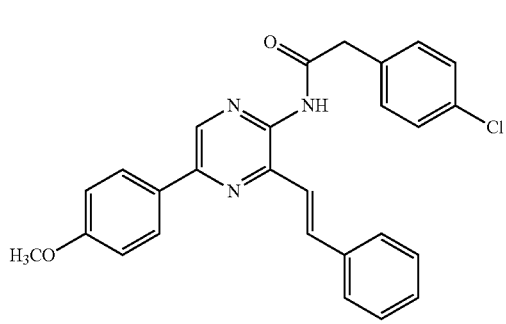
190
-continued
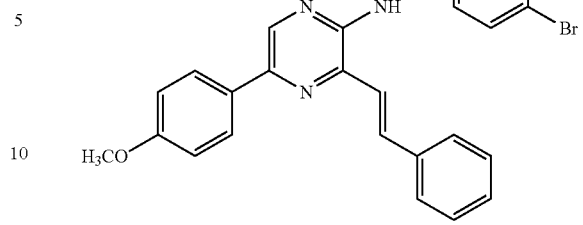
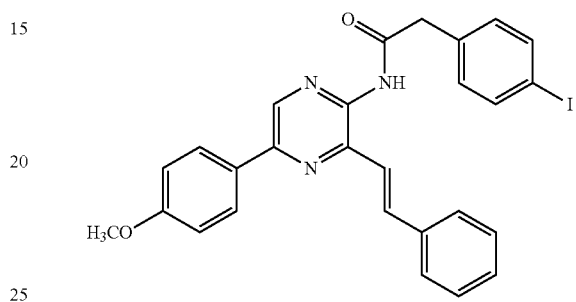
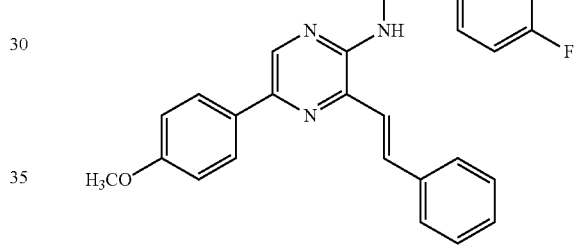
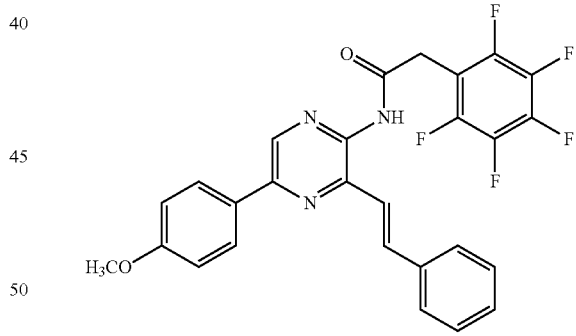
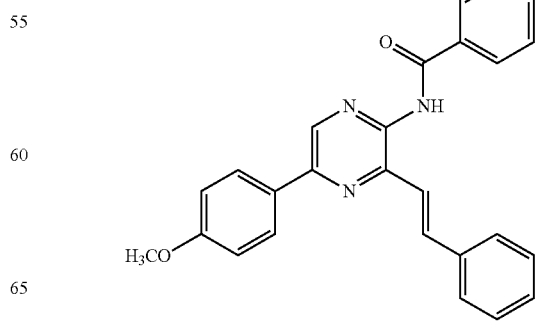

191
-continued
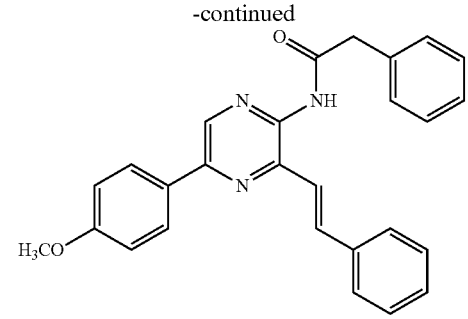
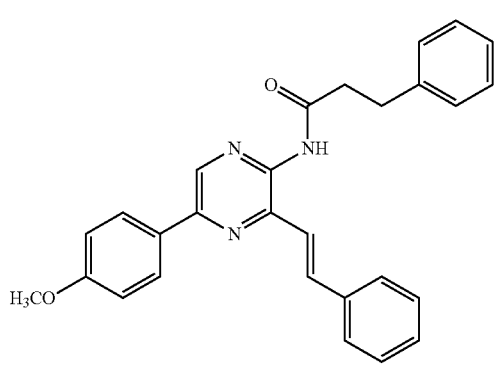
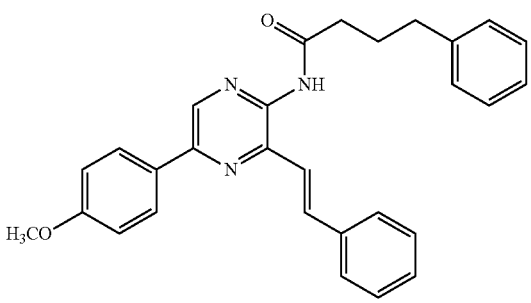
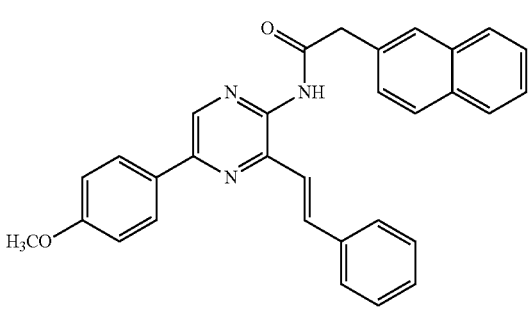
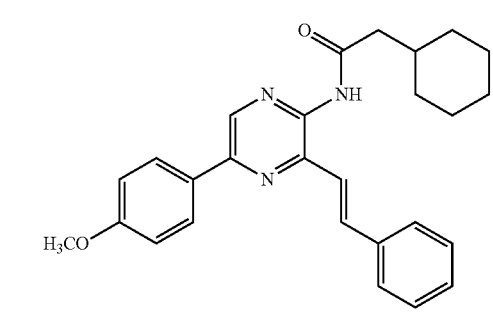
192
-continued
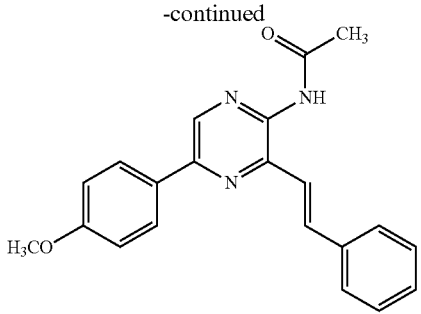
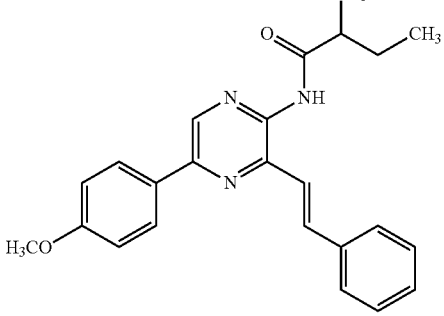
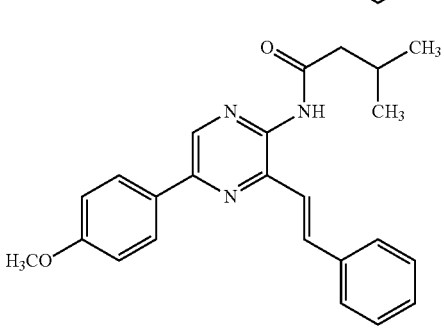
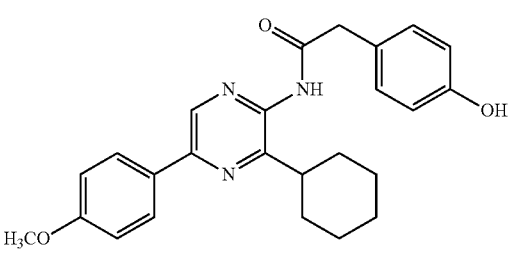
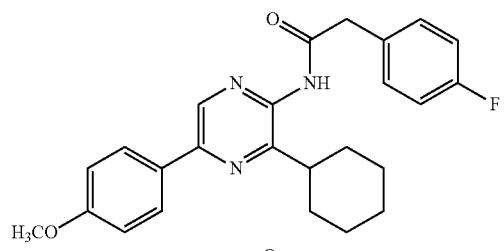
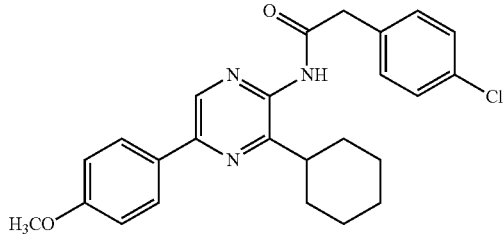

193
-continued

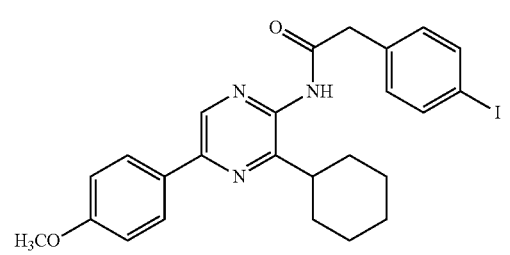
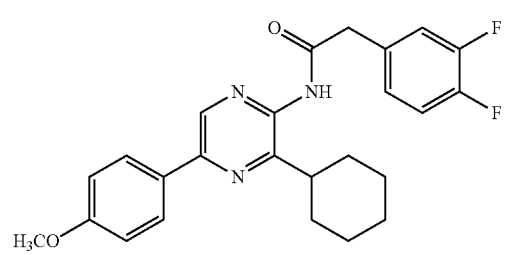
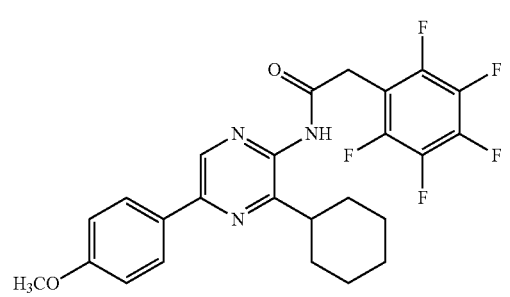
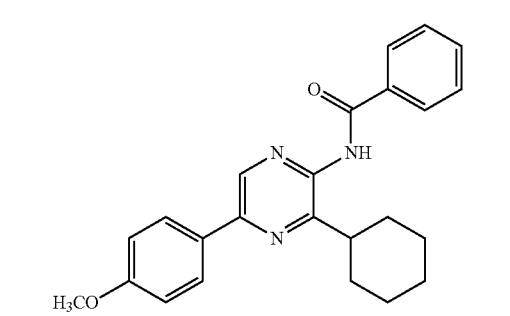
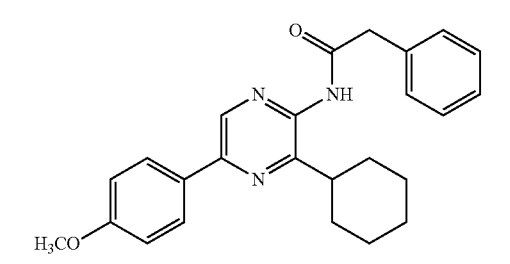
194
-continued
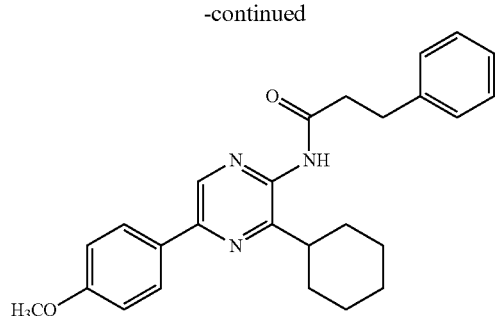
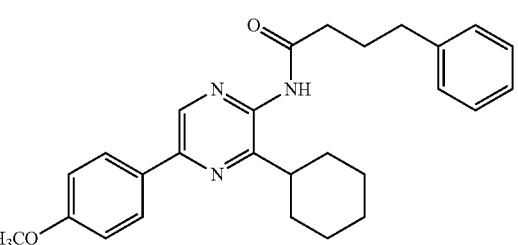
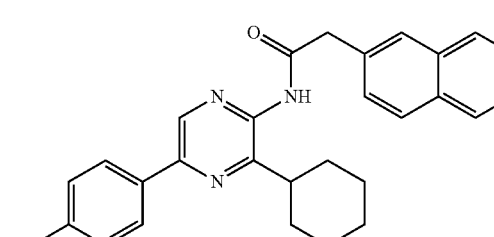
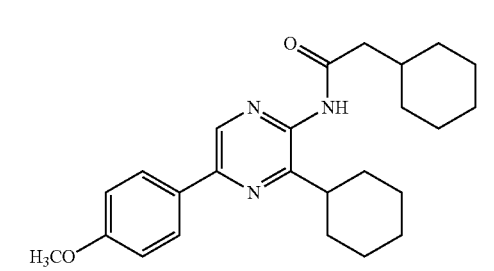
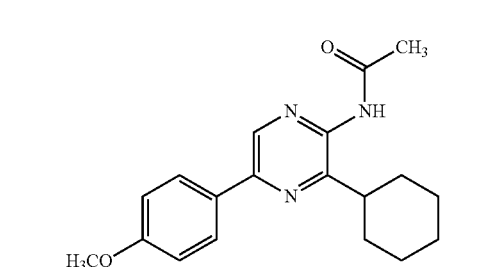
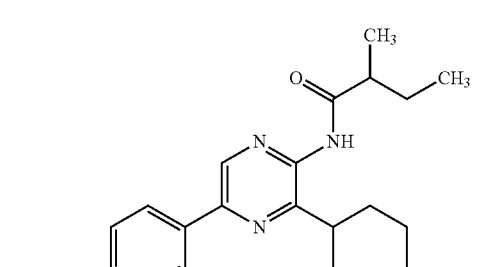

-continued
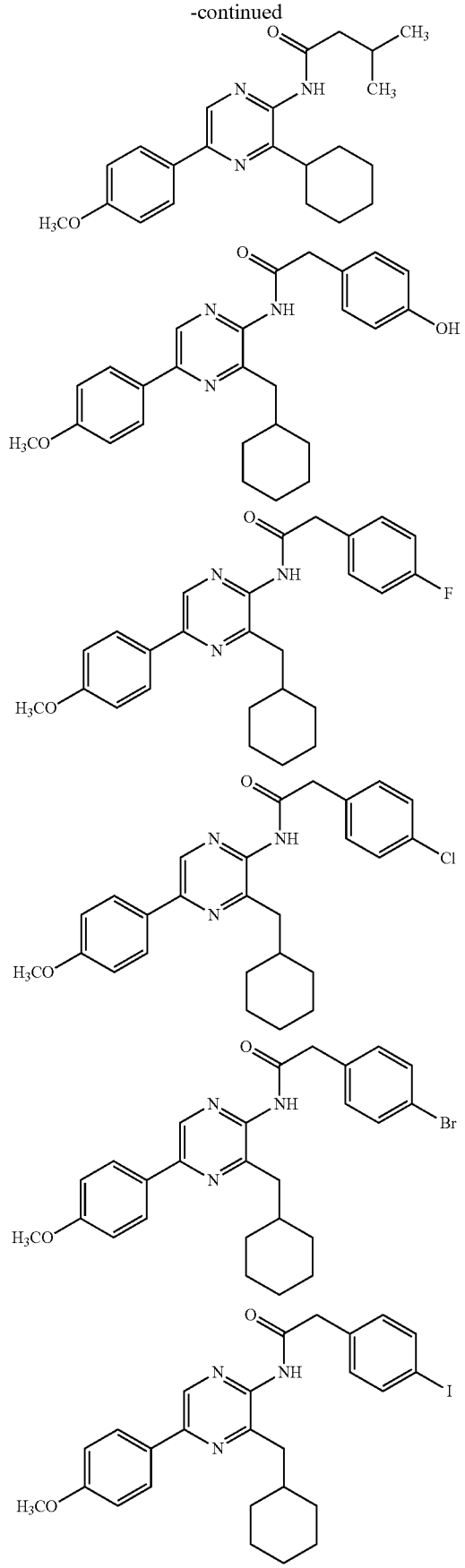
-continued
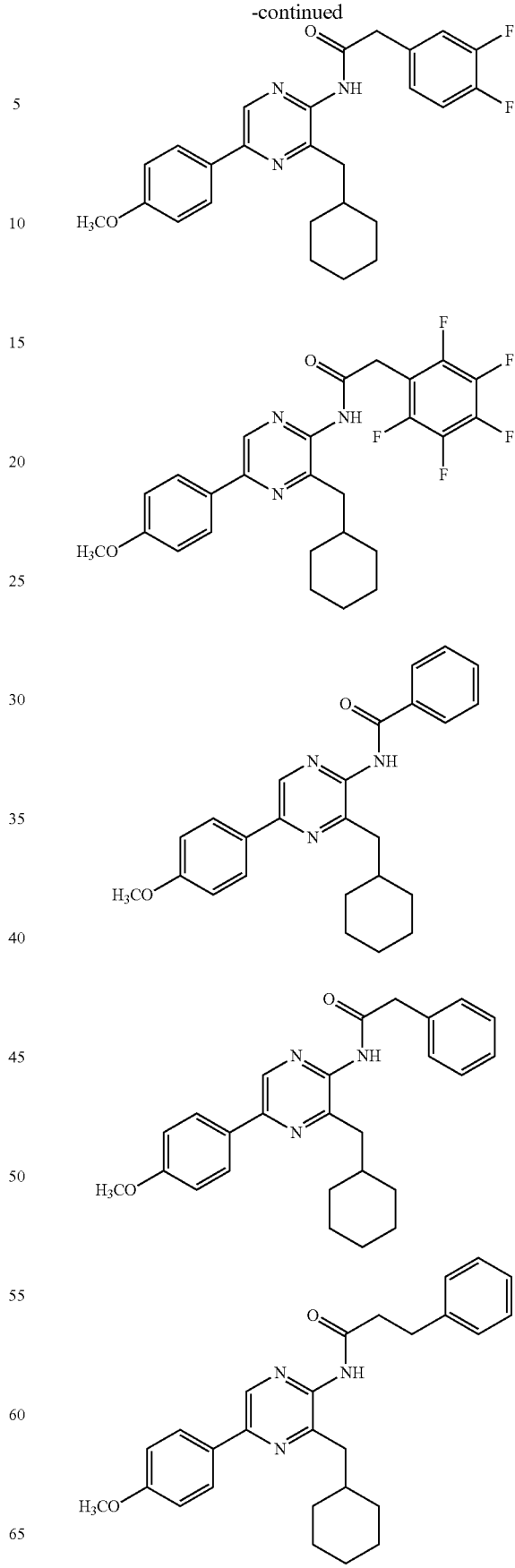

197
-continued
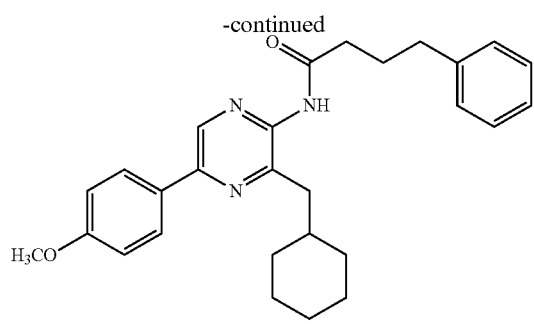
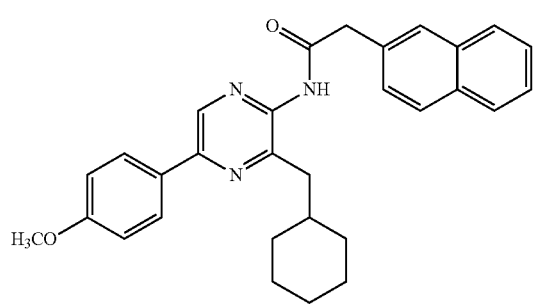
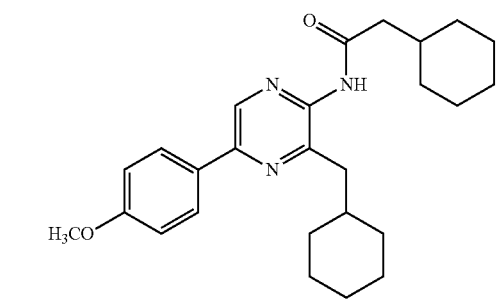
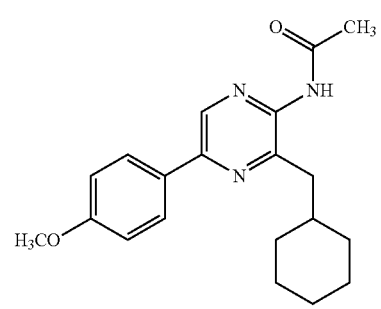
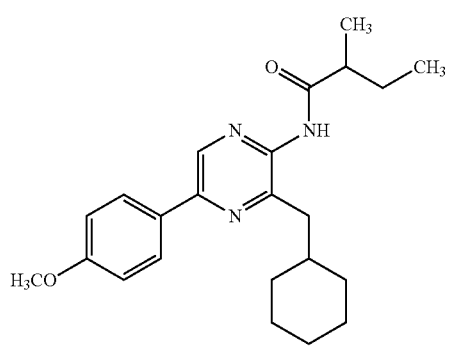
198
-continued
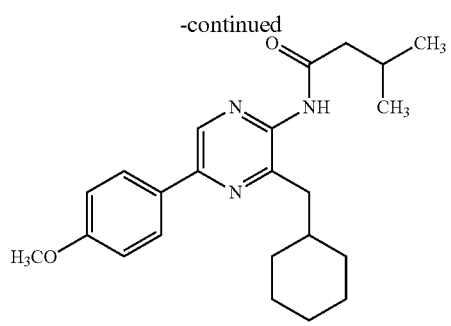
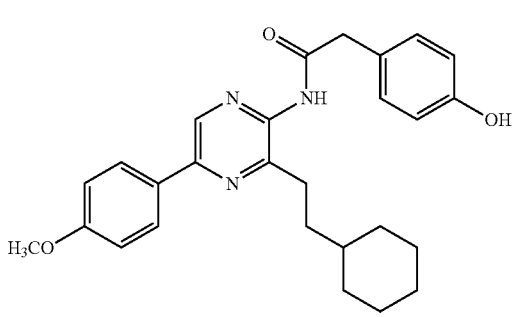
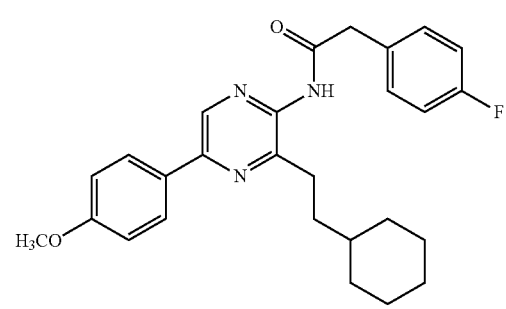
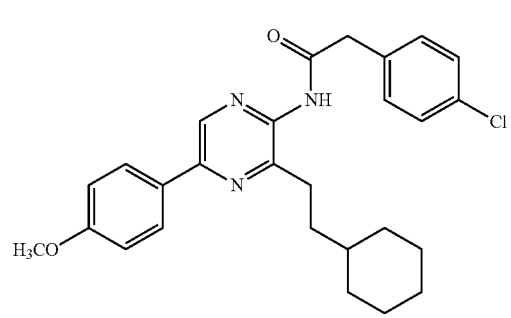
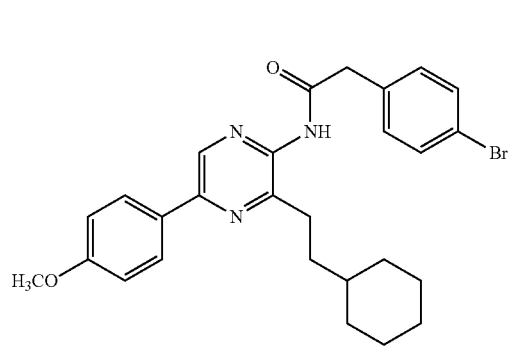

199
-continued
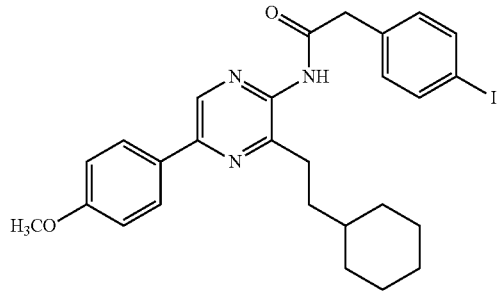
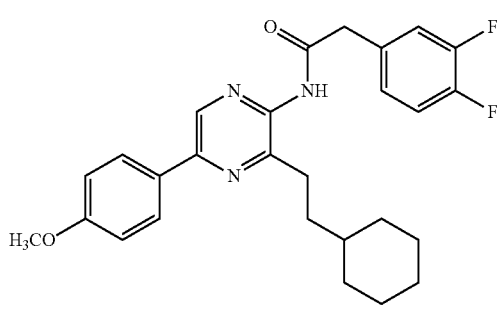
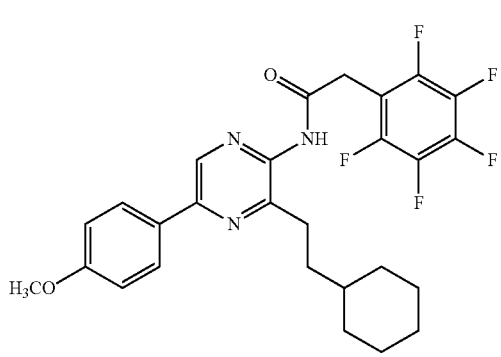
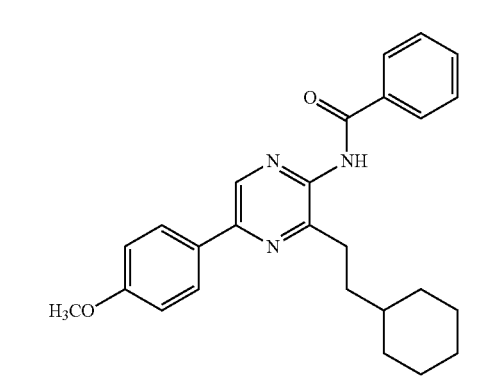
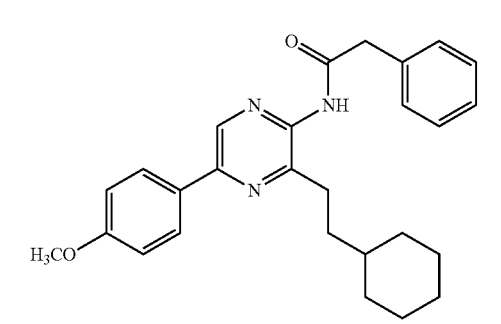
200
-continued
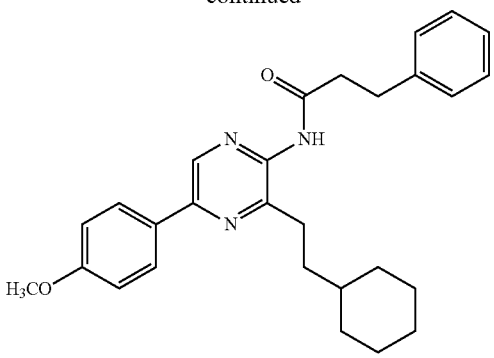
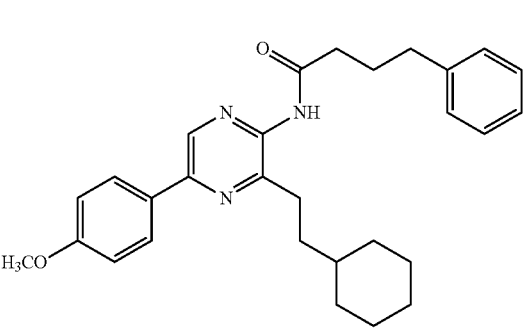
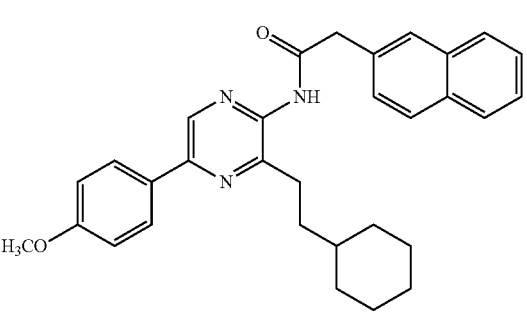
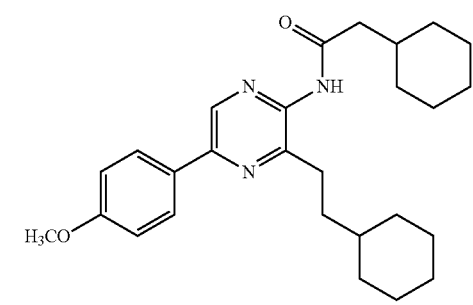
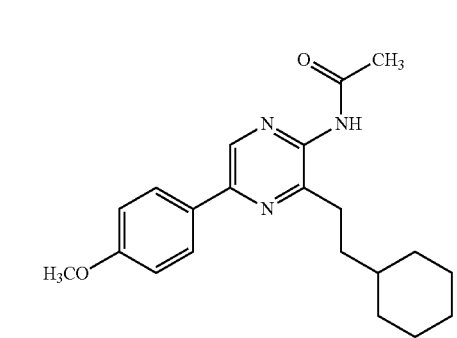

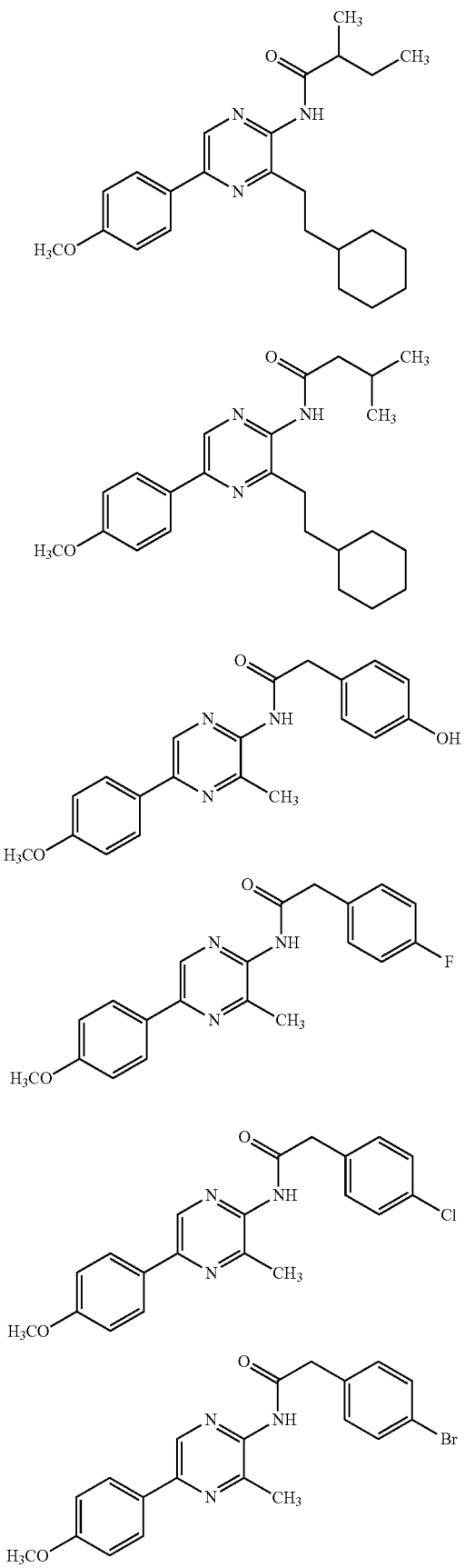
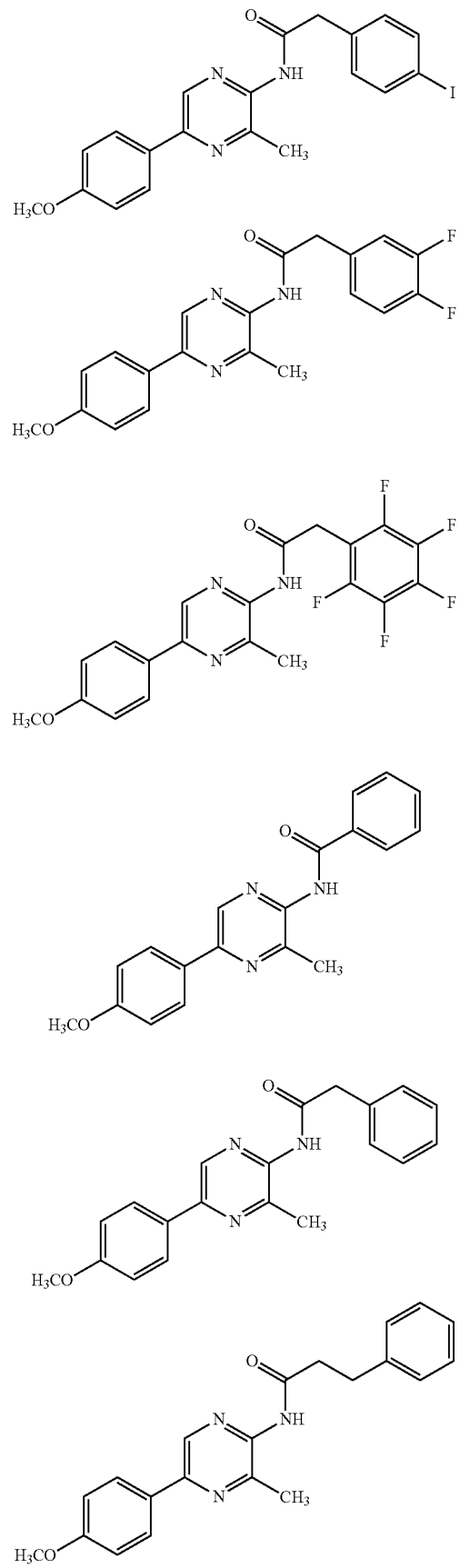

203
-continued
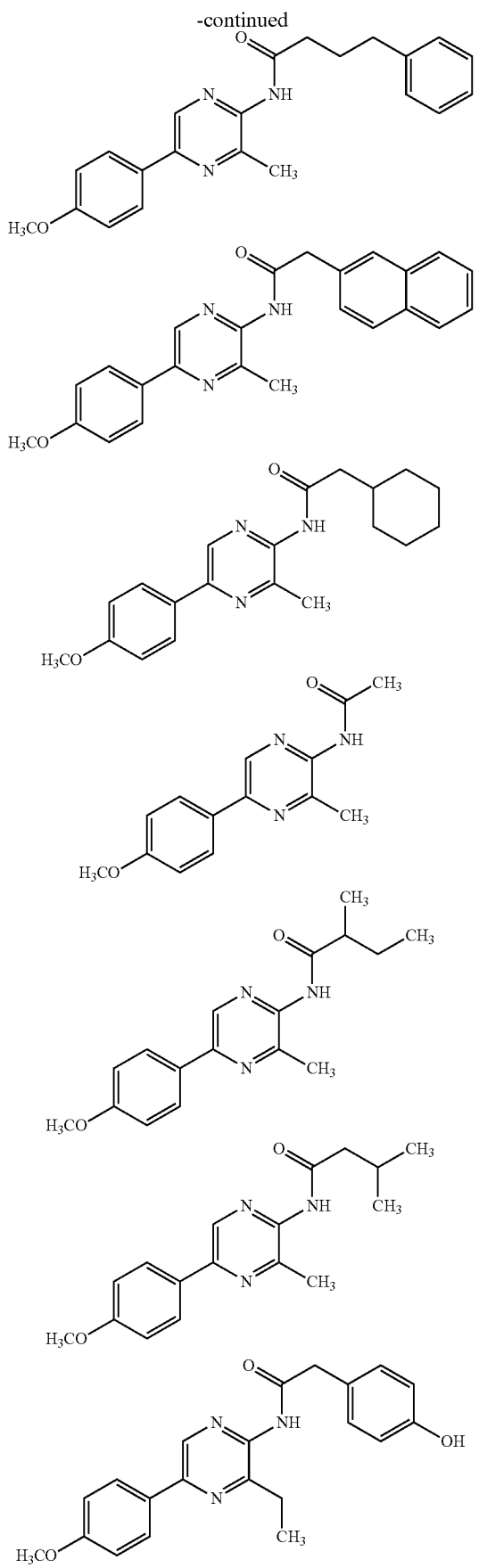
204
-continued
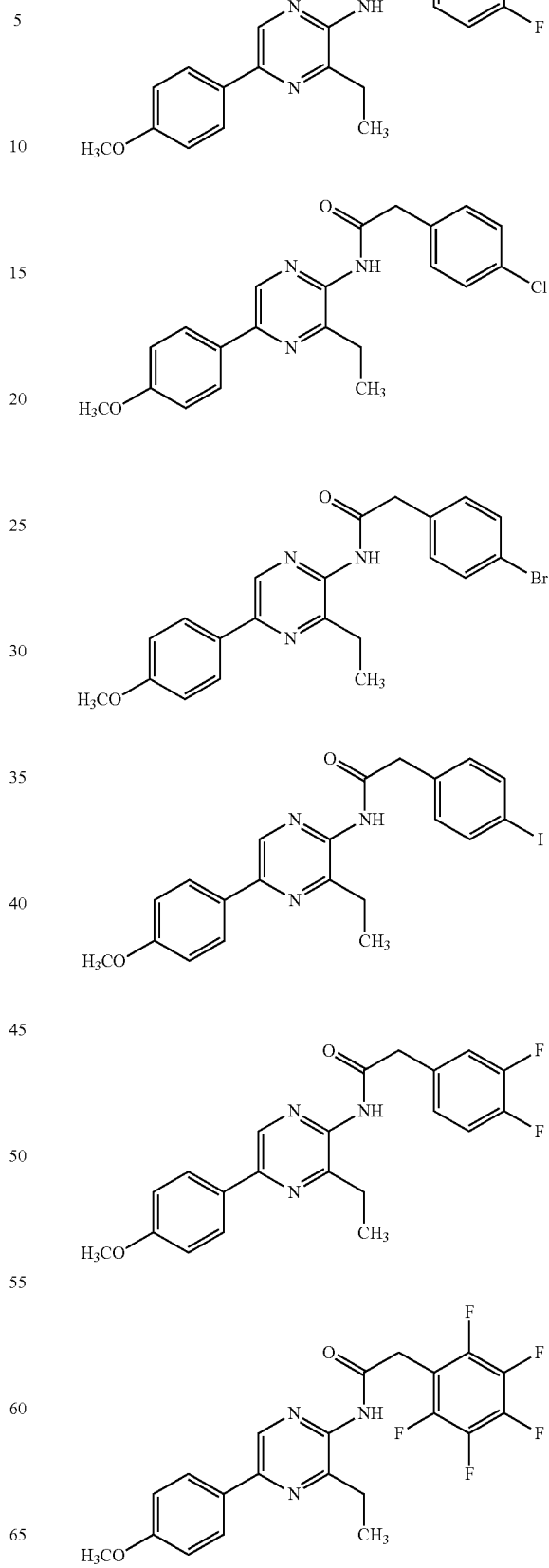

205
-continued
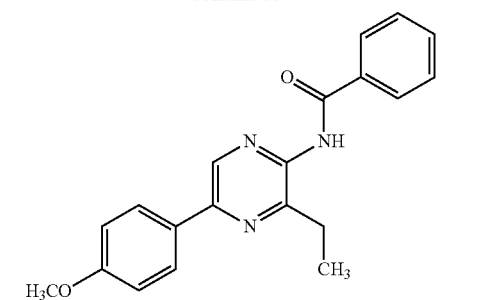
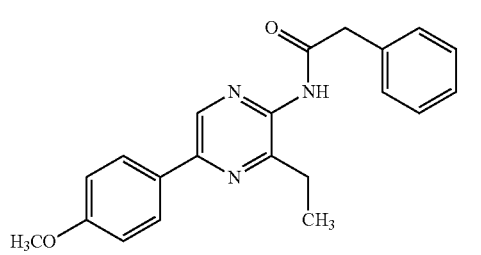
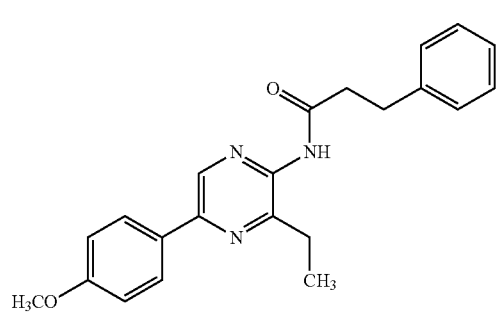
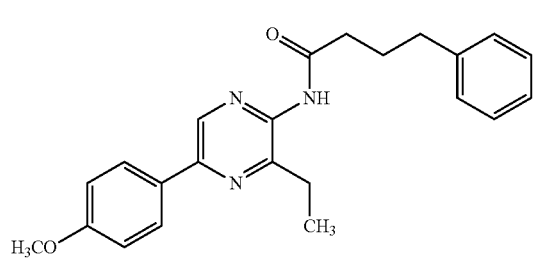
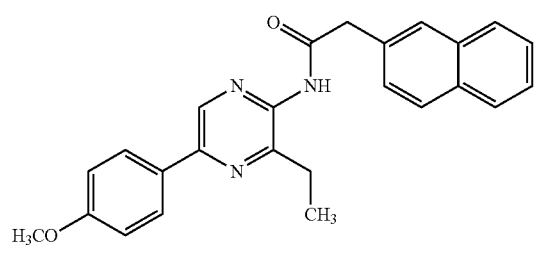
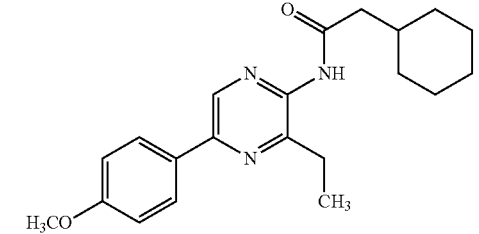
206
-continued
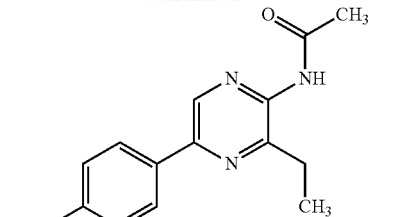
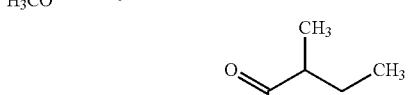
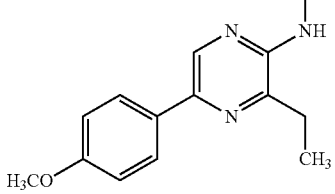
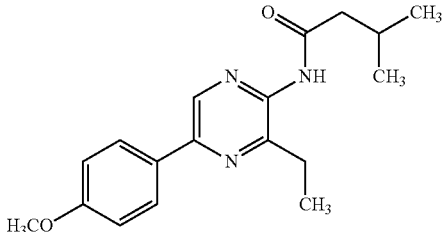
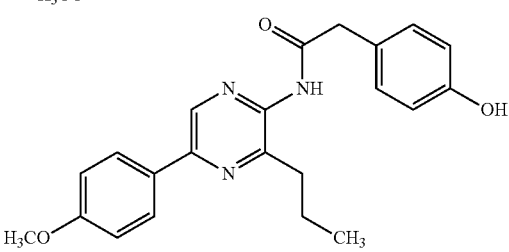
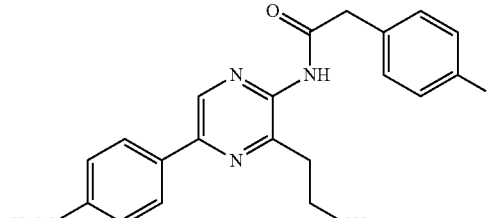
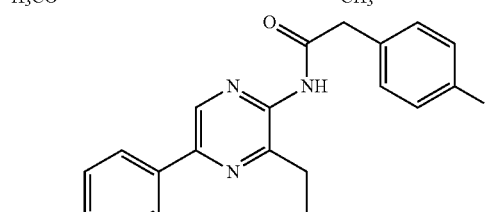
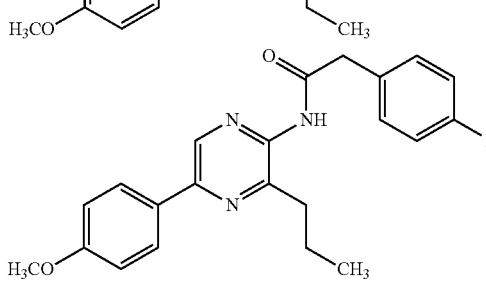

207
-continued
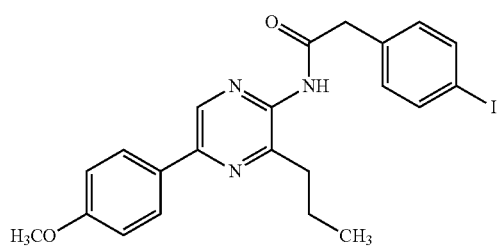
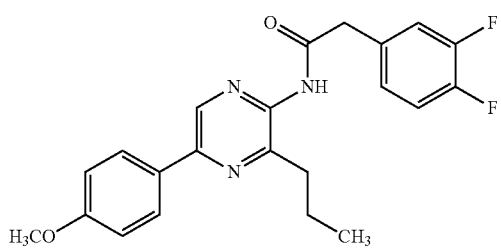
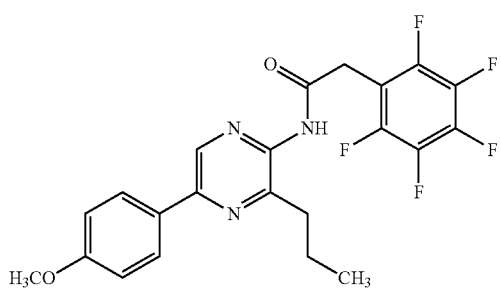
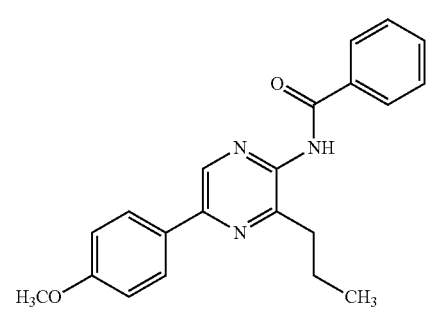
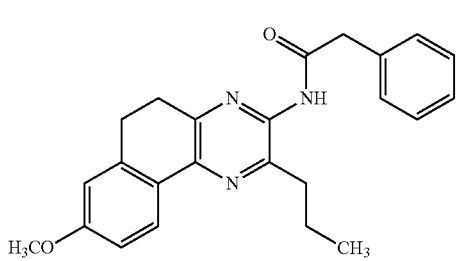
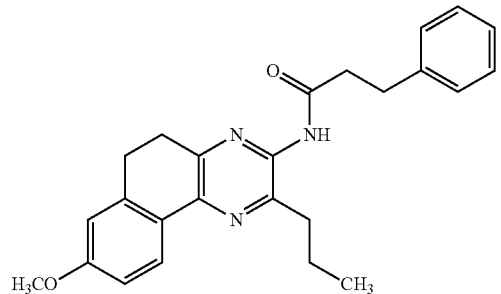
208
-continued
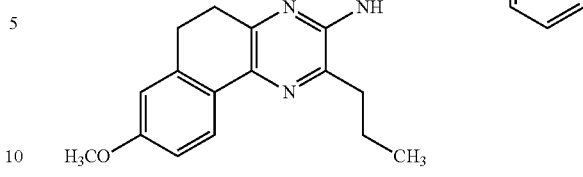
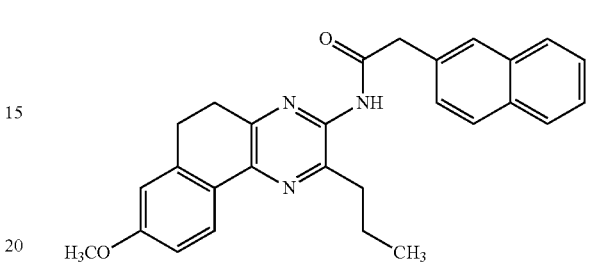
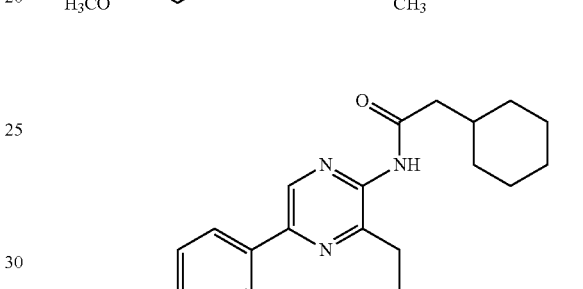
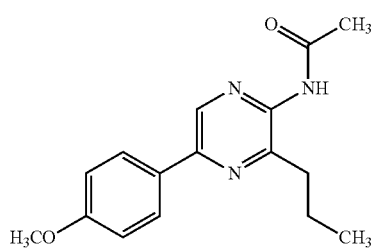
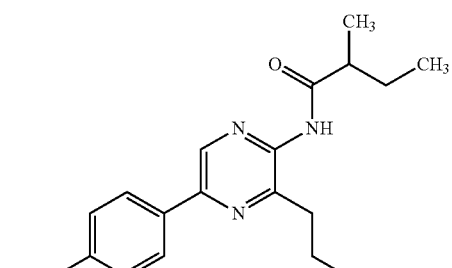
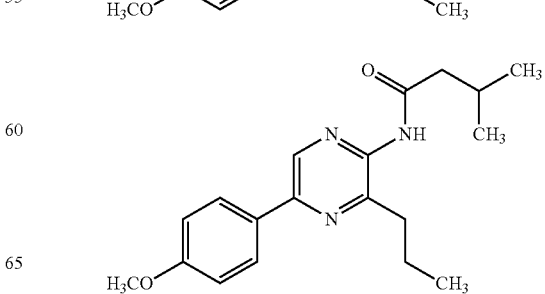

209
-continued
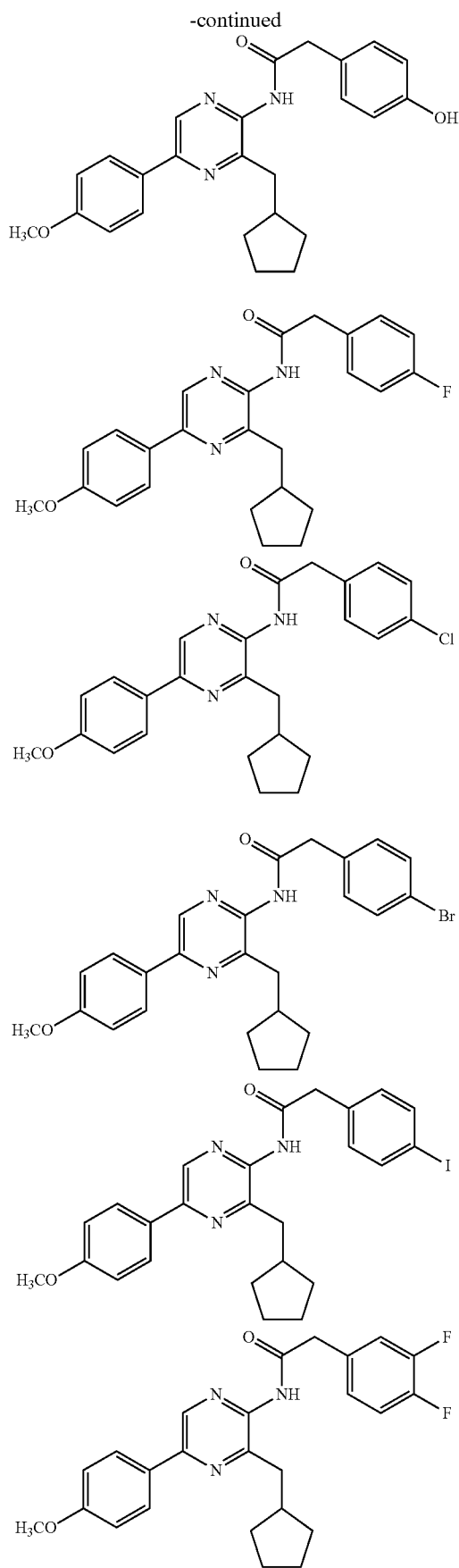
210
-continued
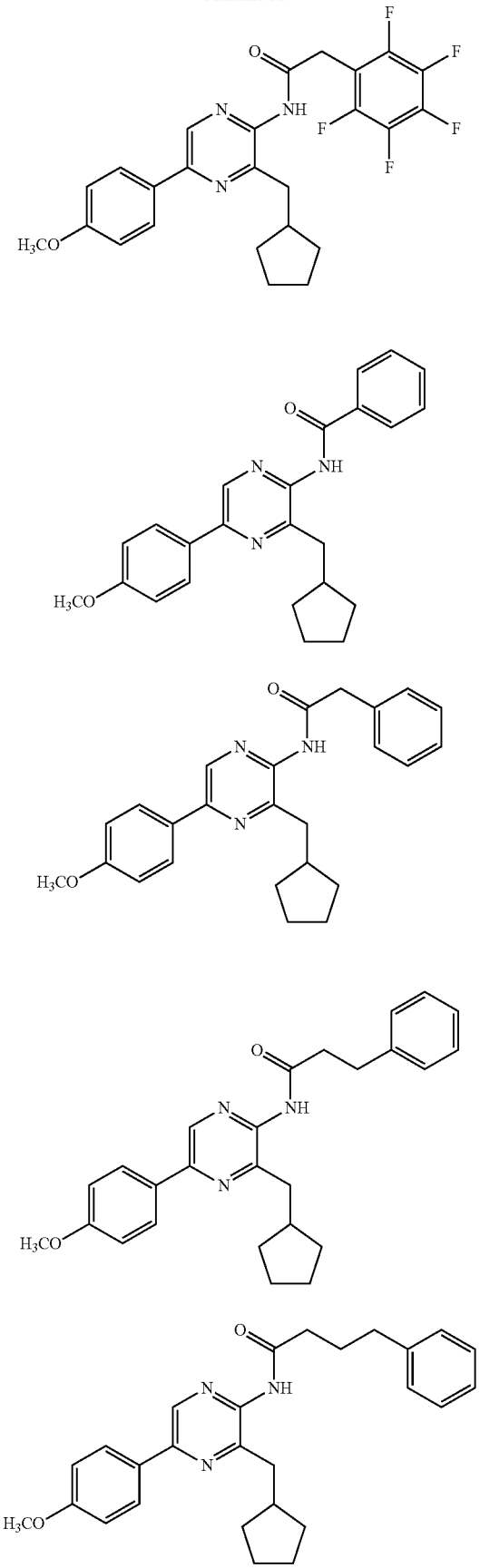

211
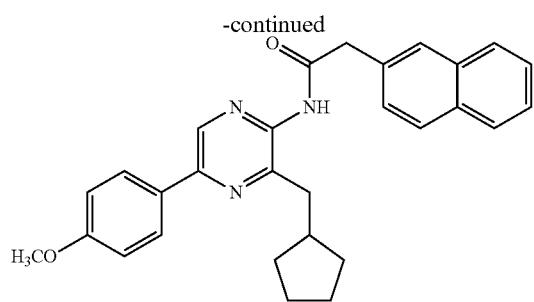
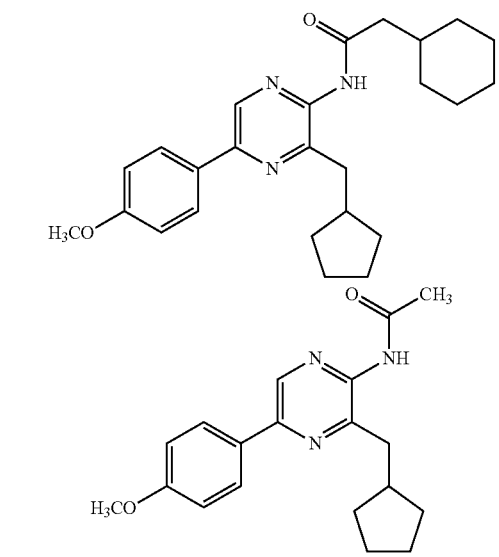
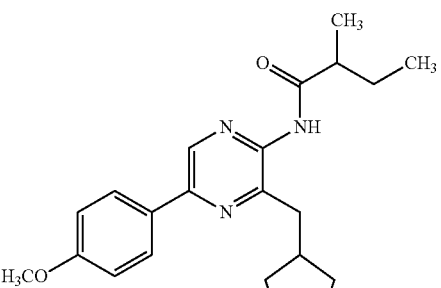
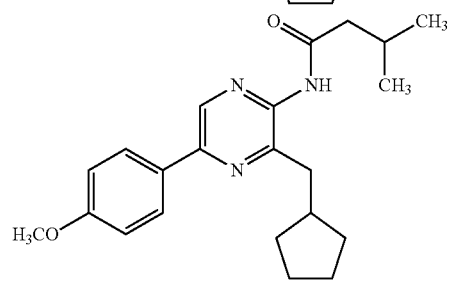
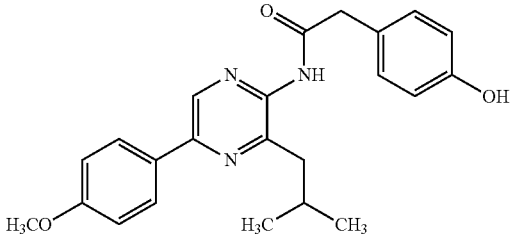
212
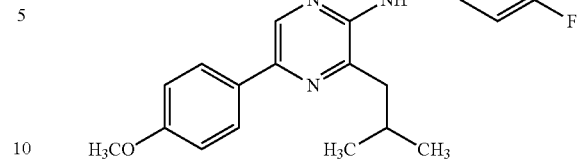
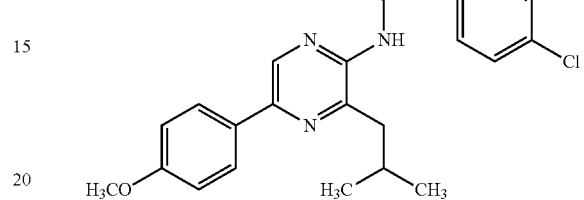
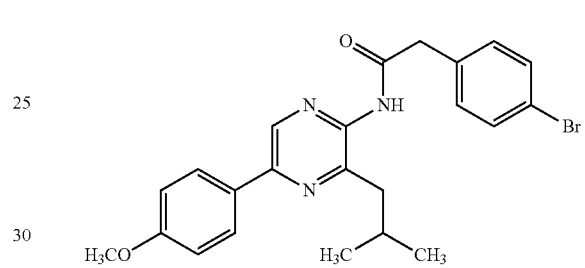
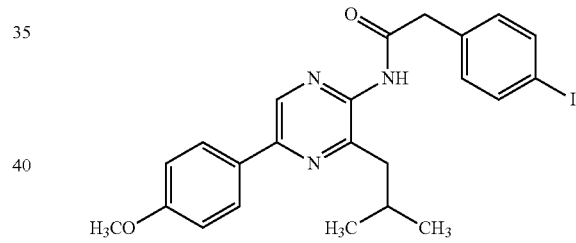
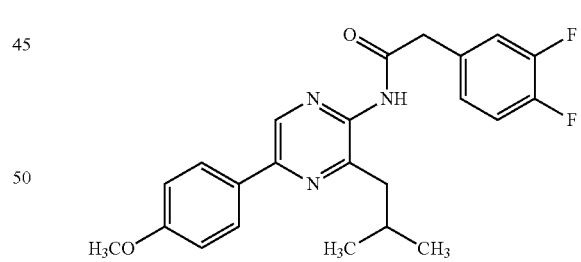
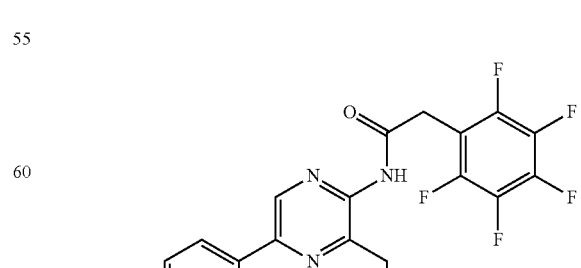

213
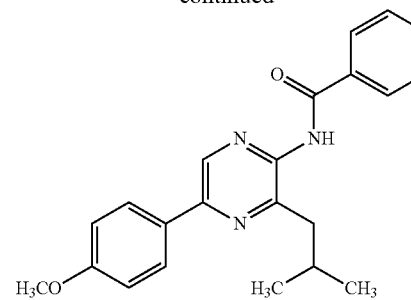
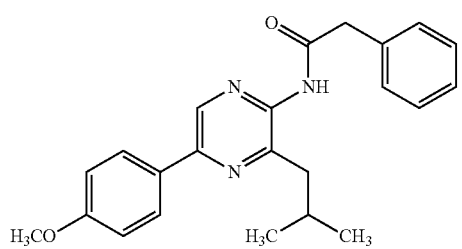
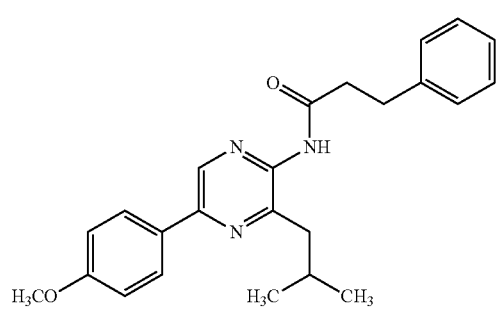
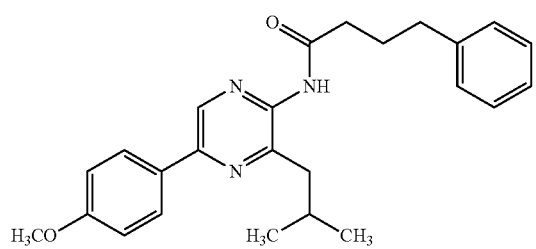
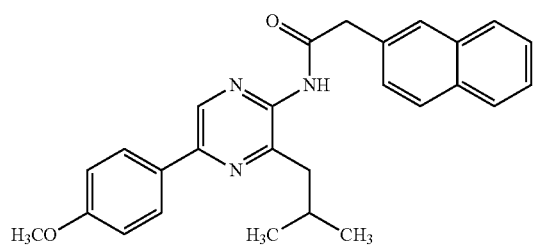
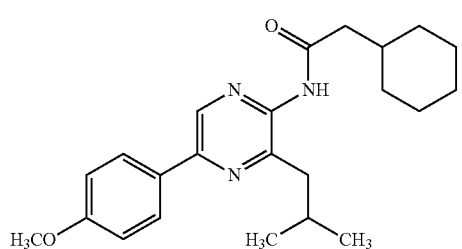
214
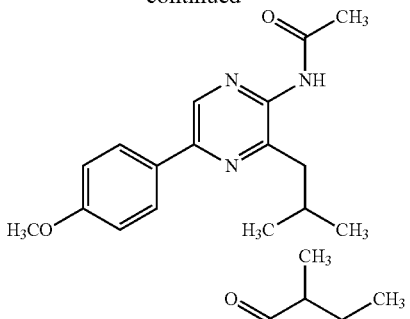
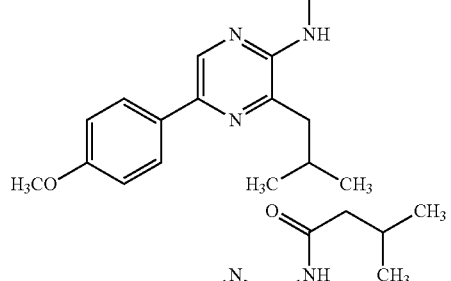
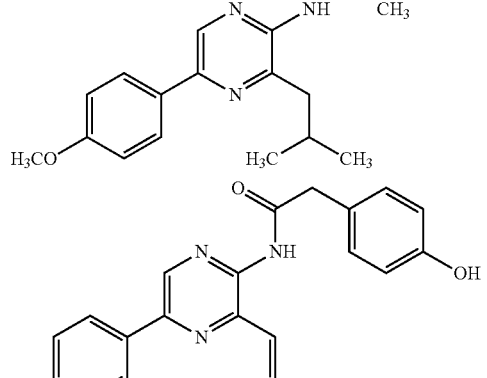
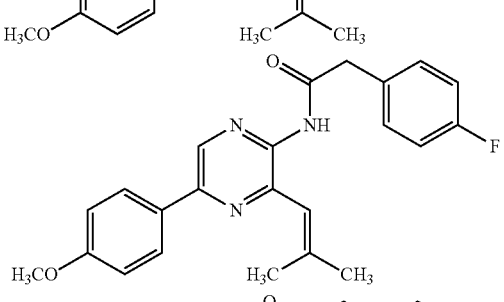
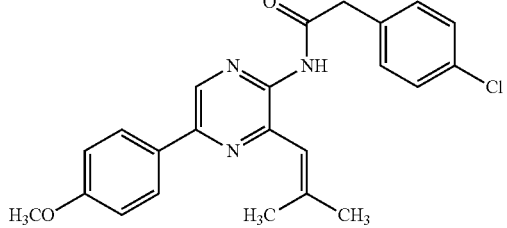
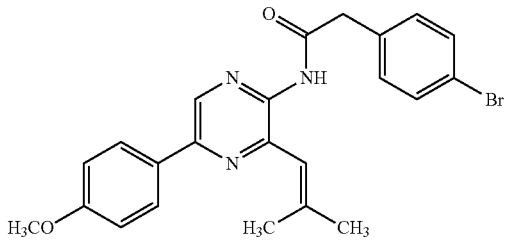

-continued

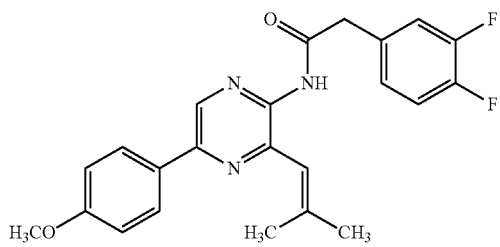
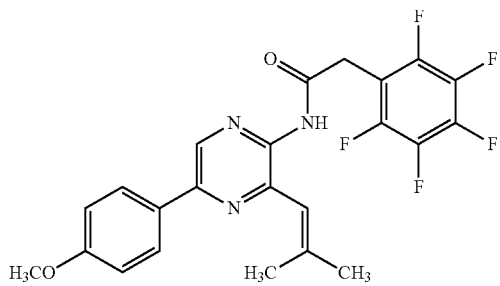
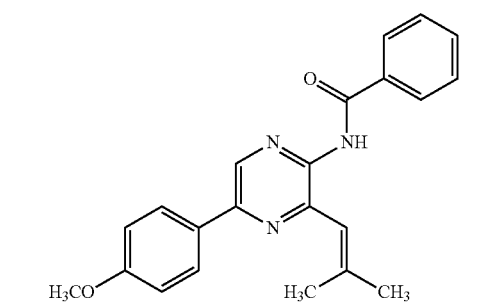
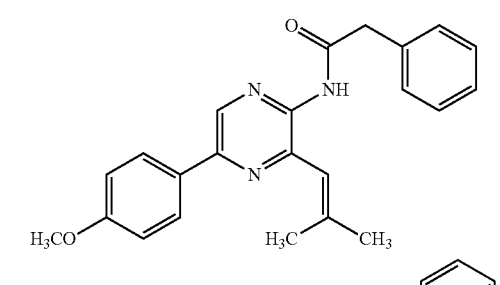
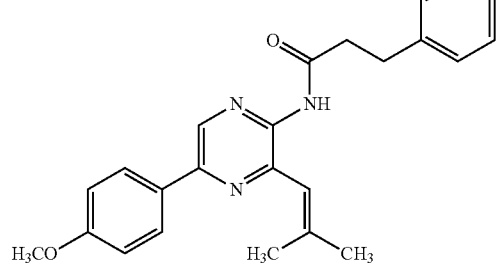
-continued
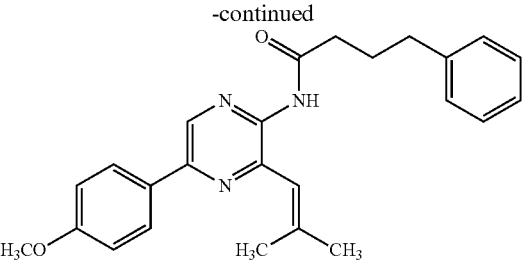
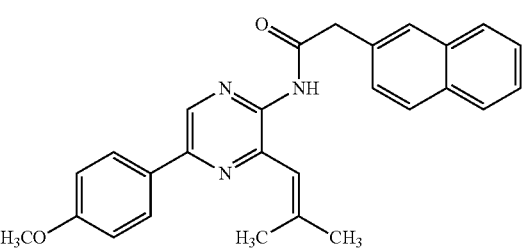
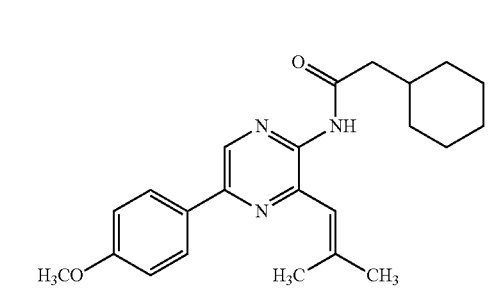
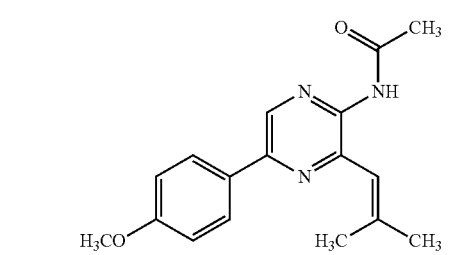
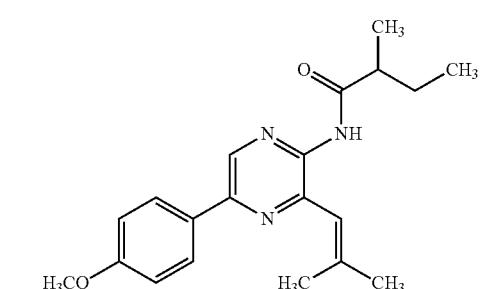
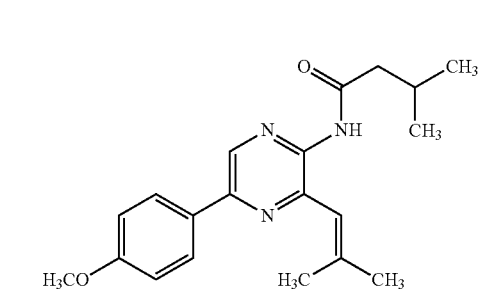

217
-continued
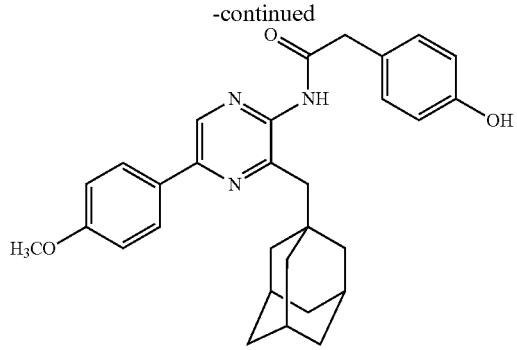
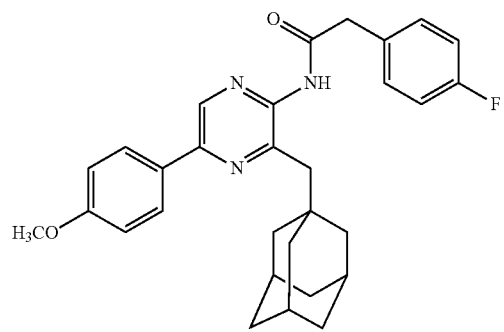
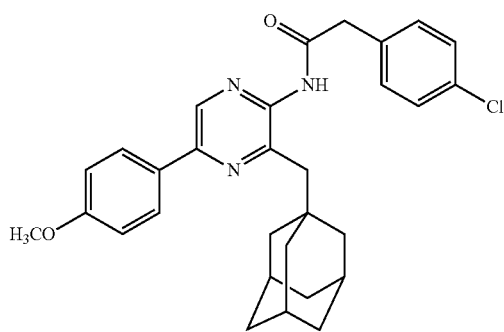
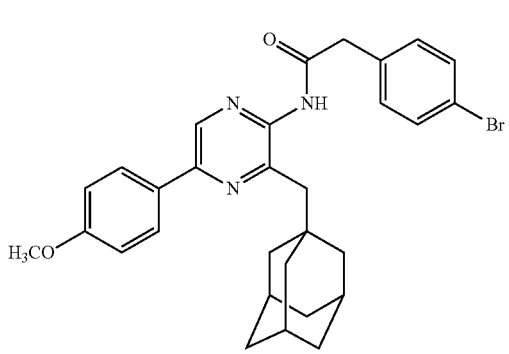
218
-continued
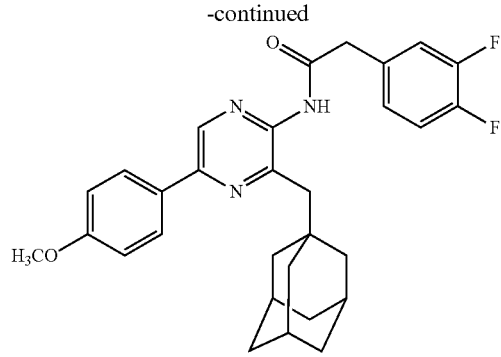
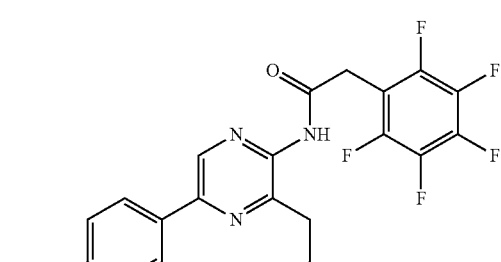
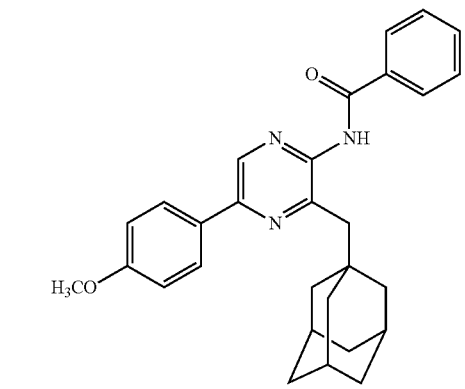
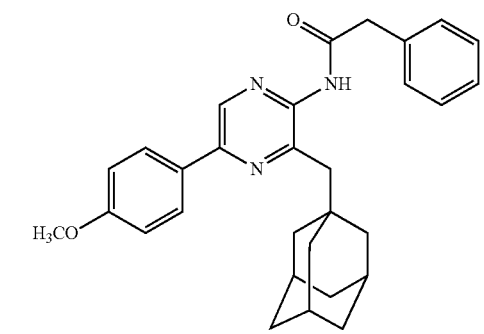

219
-continued
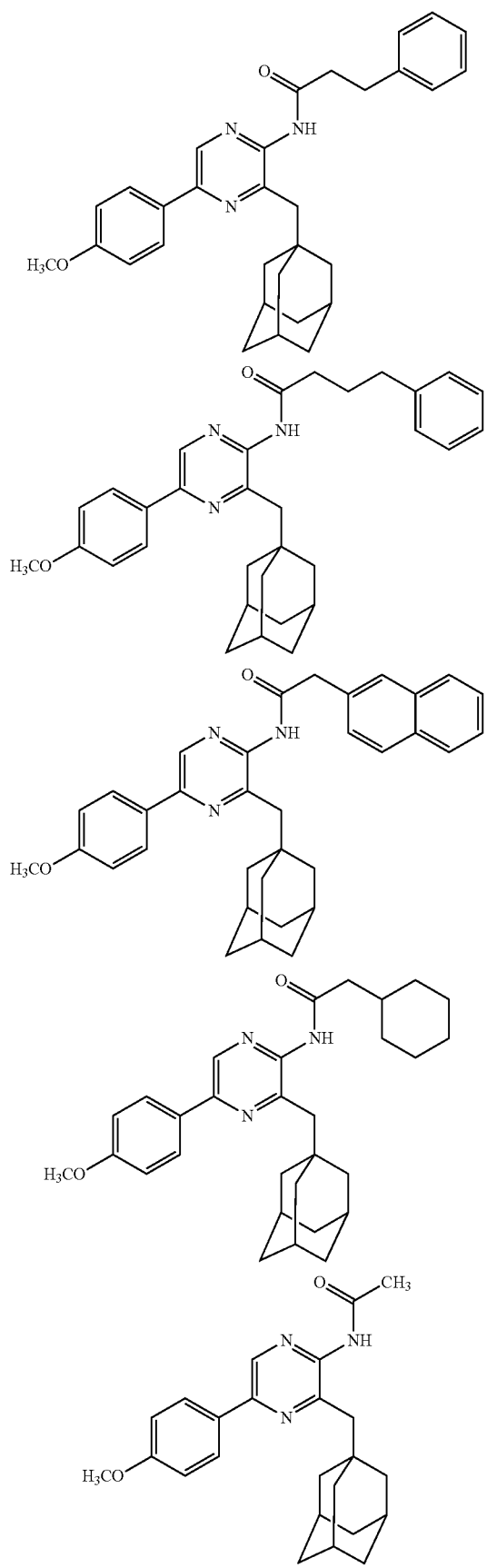
220
-continued
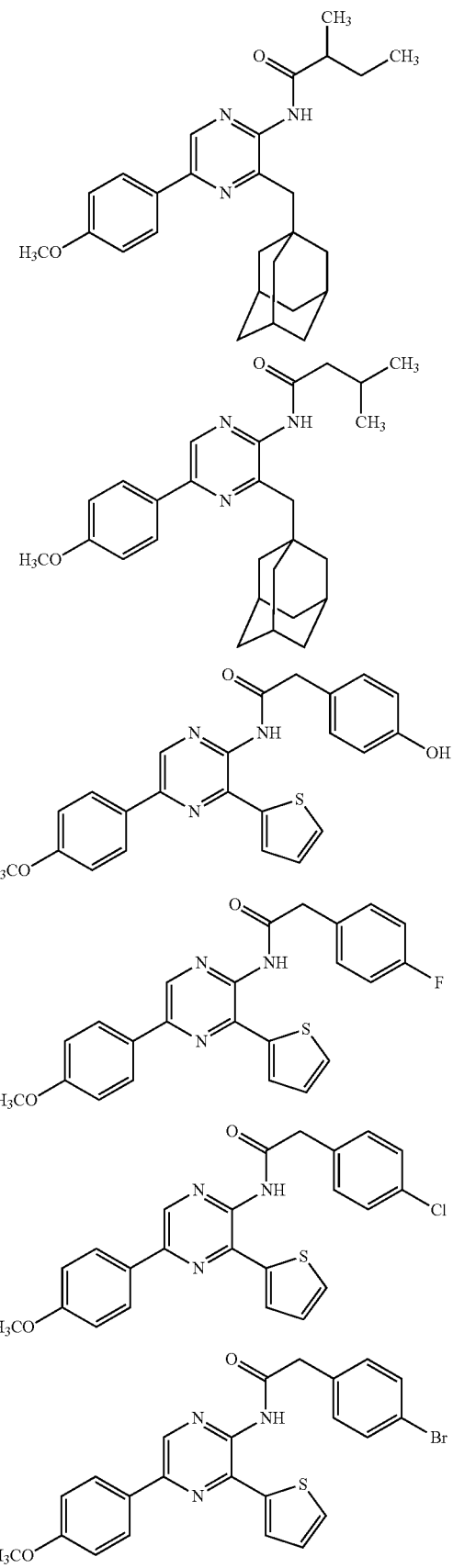

-continued
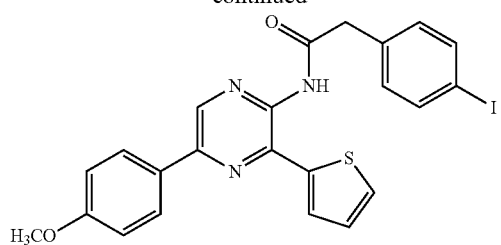
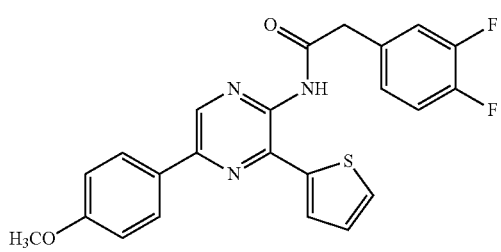
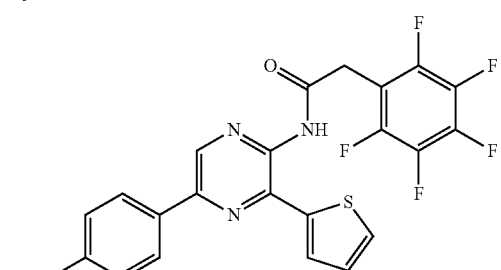
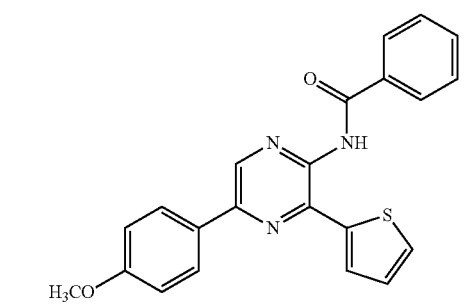
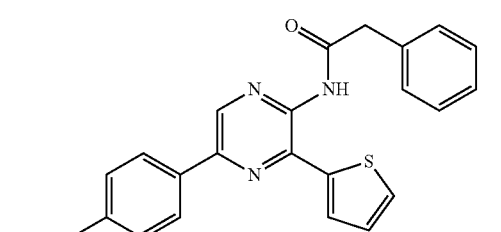
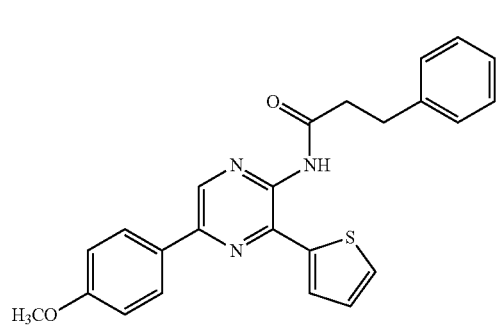
-continued
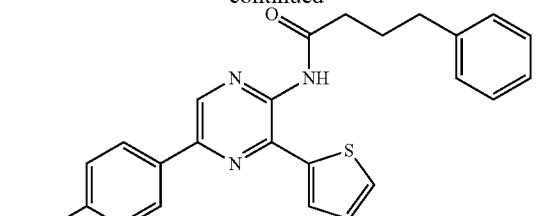
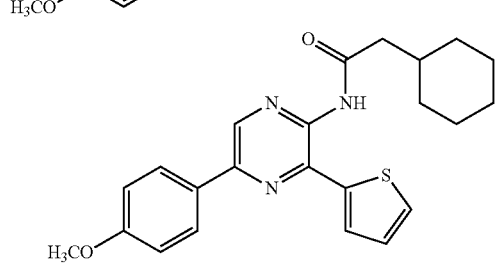
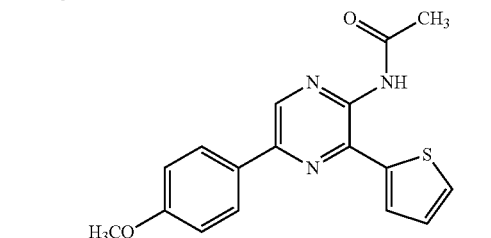
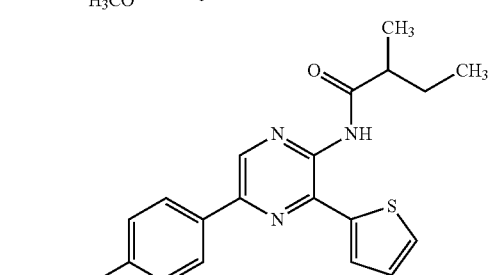
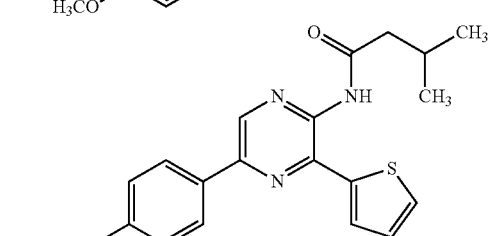
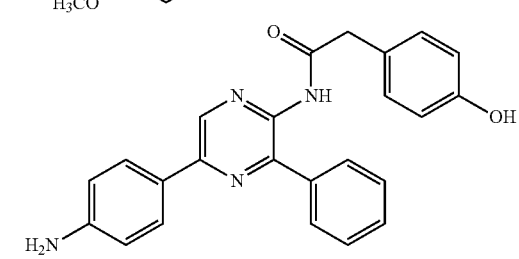

223
-continued
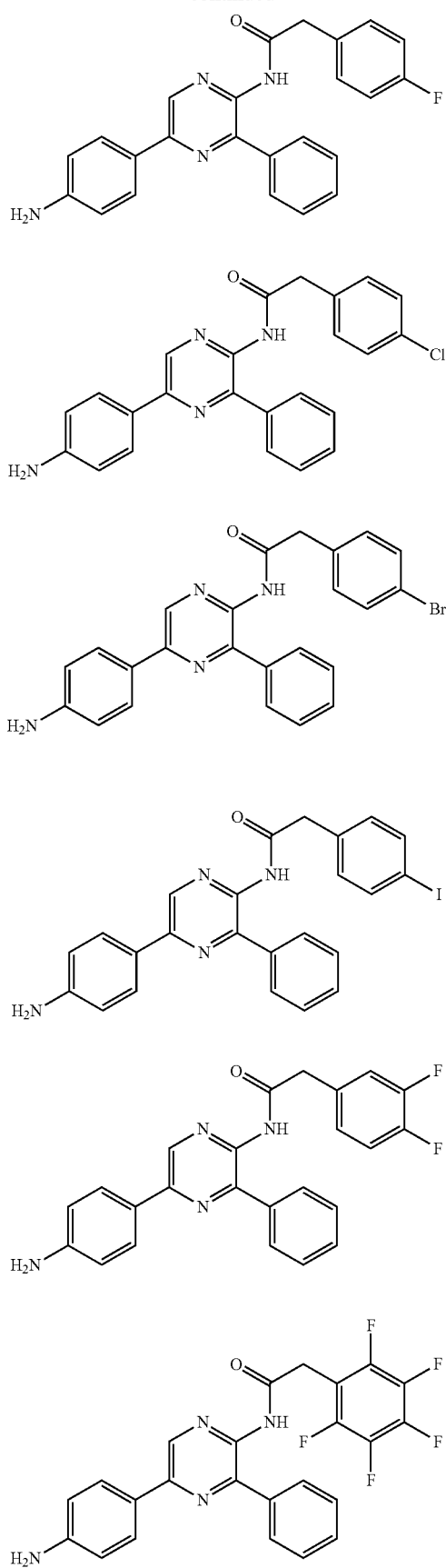
224
-continued
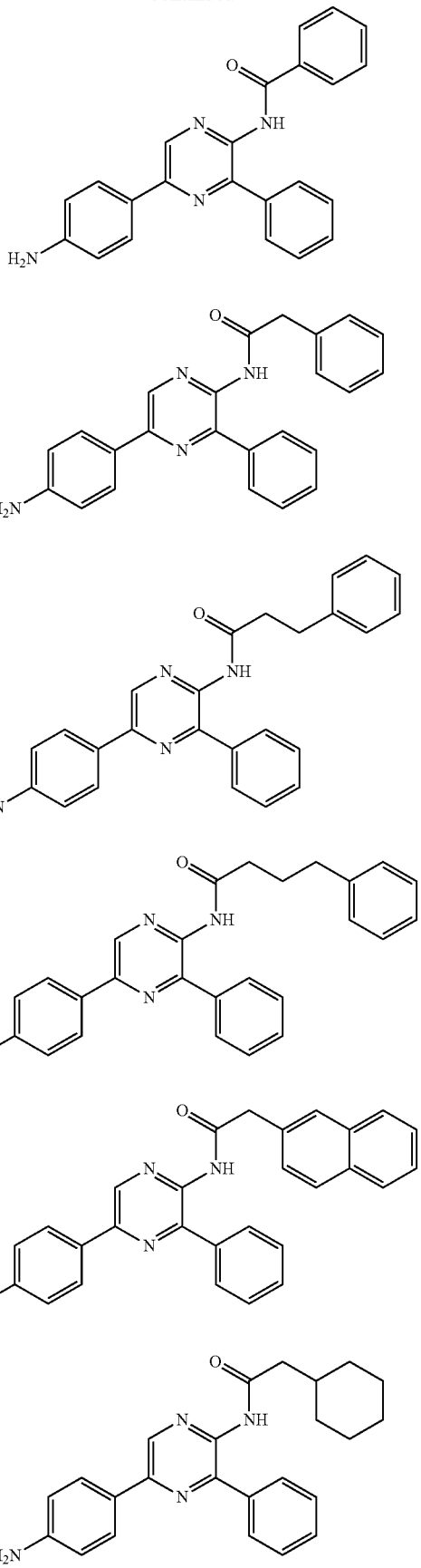

225
-continued
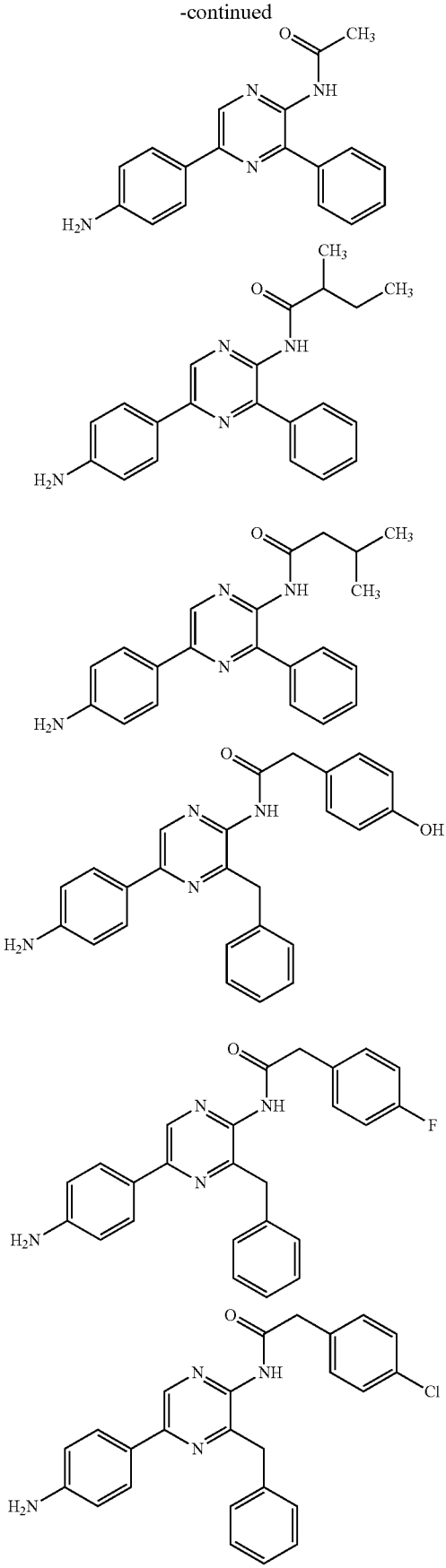
226
-continued
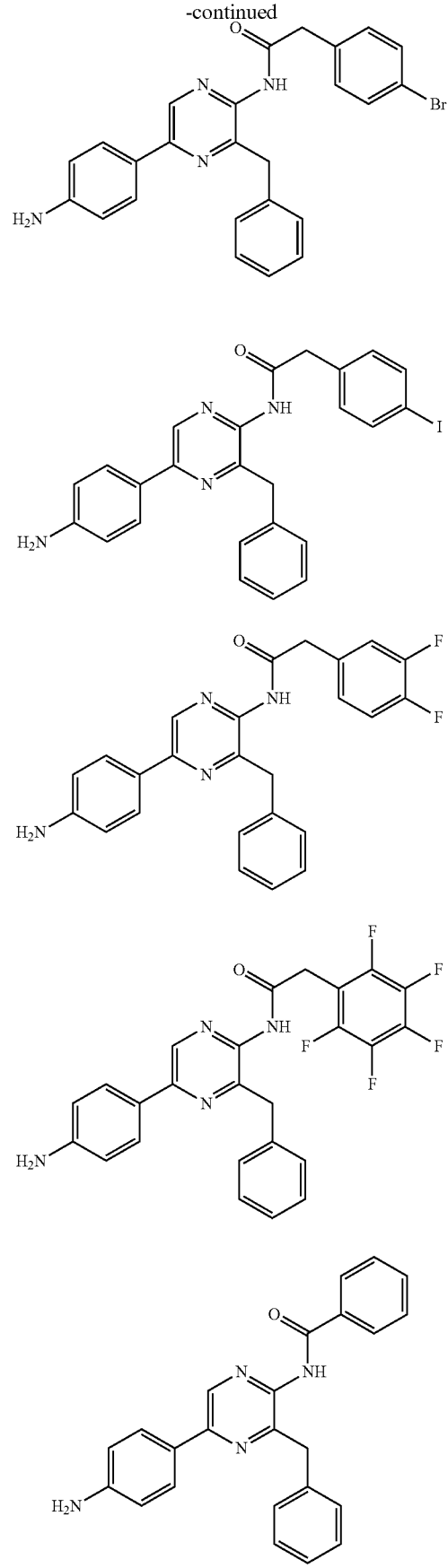

227
-continued
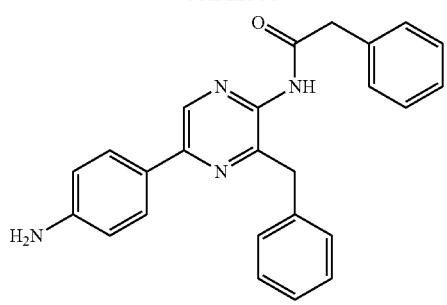
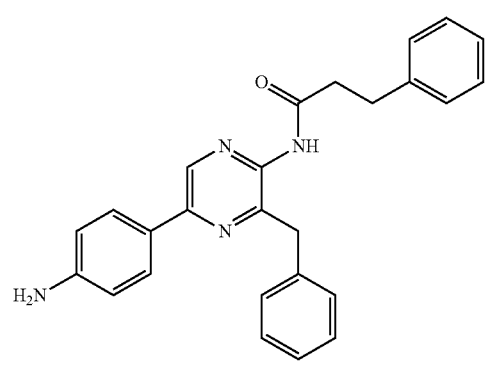
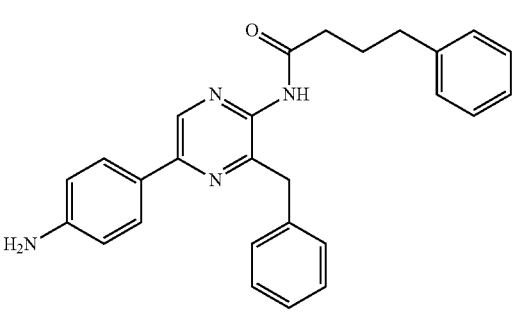
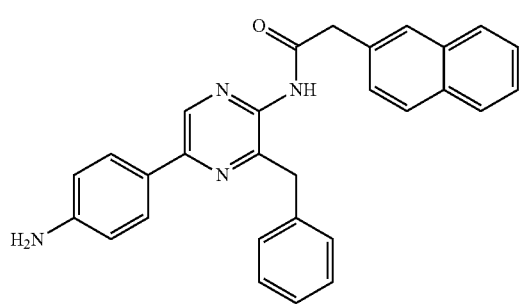
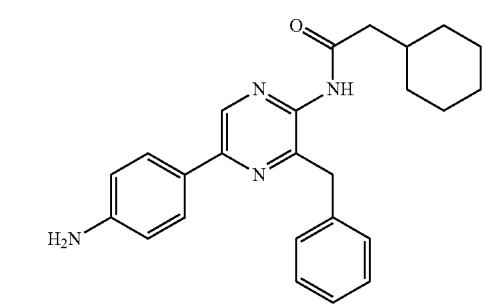
228
-continued
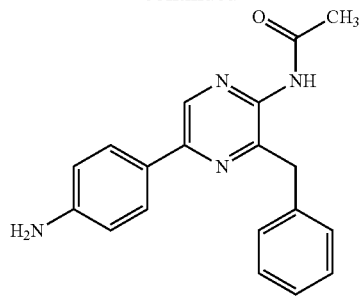
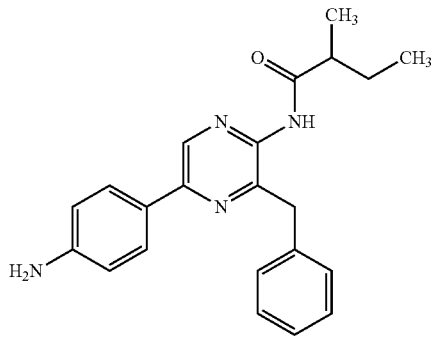
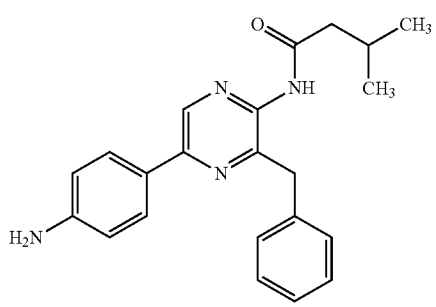
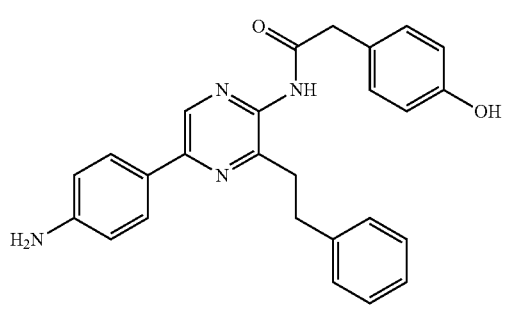
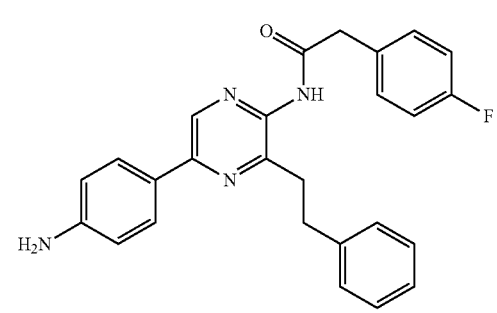

229
-continued
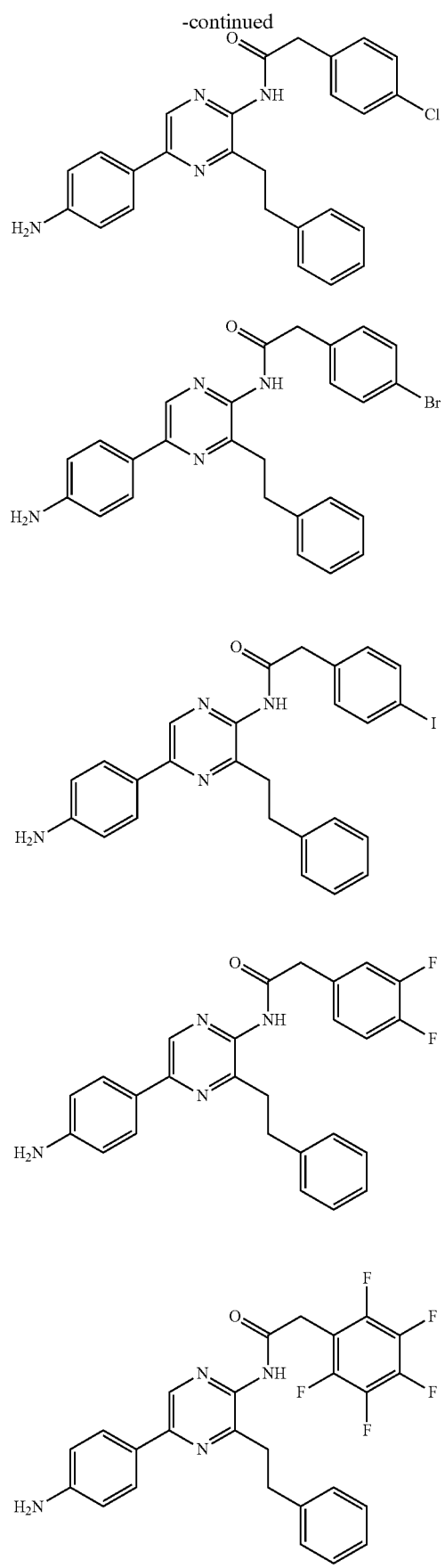
230
-continued
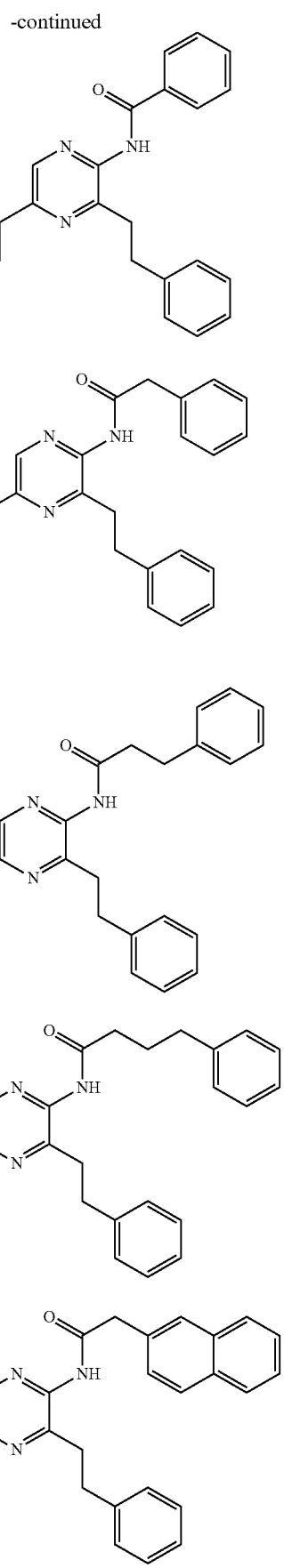

231
-continued
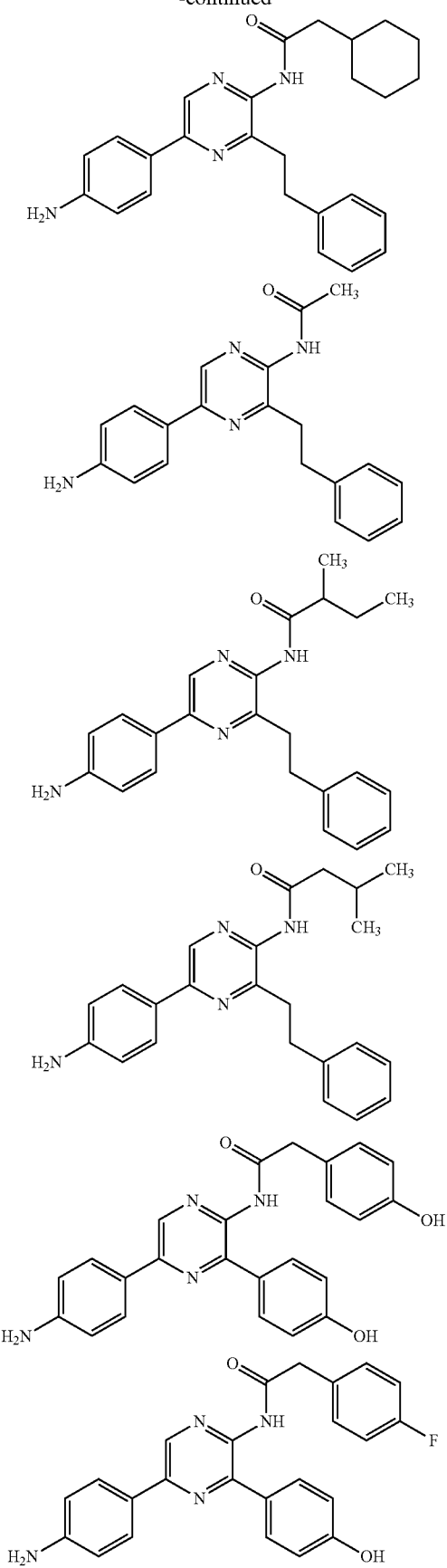
232
-continued
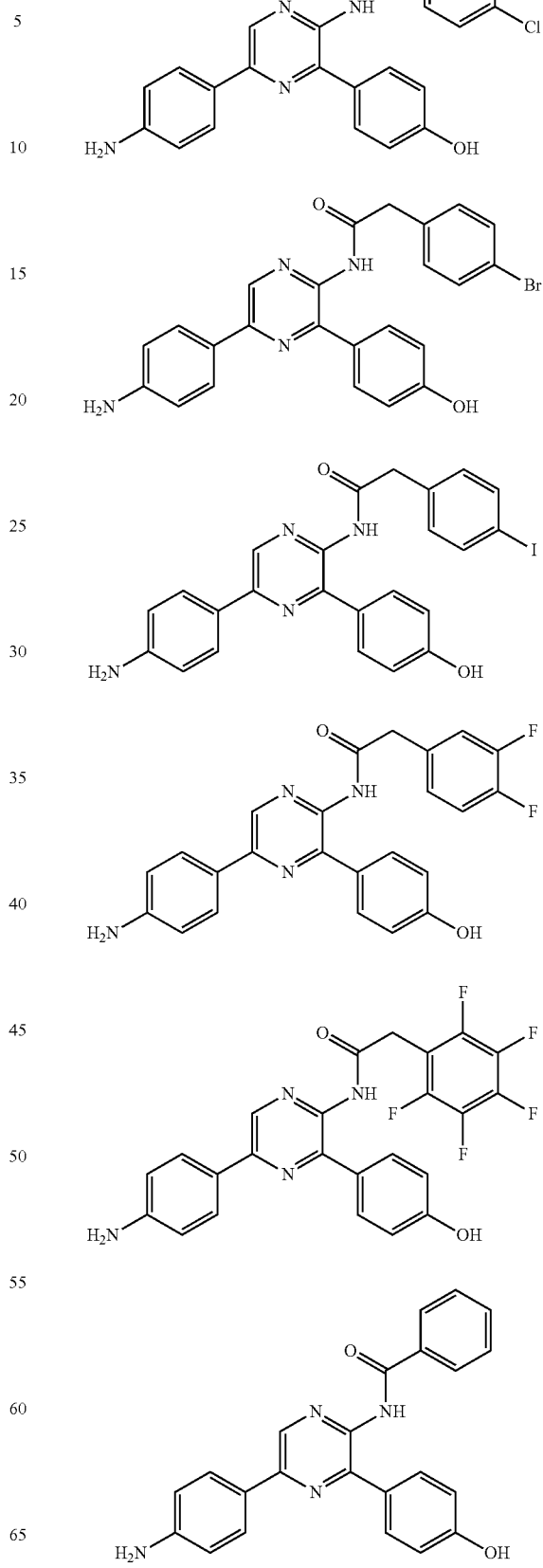

233
-continued
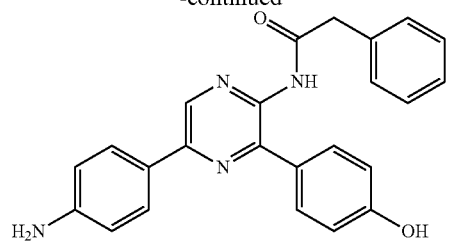
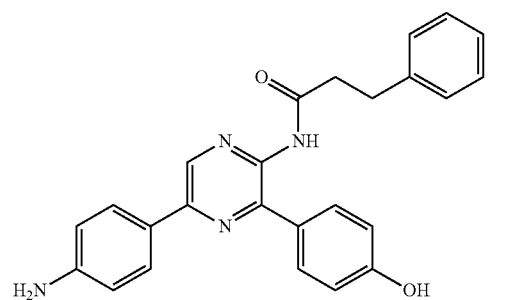
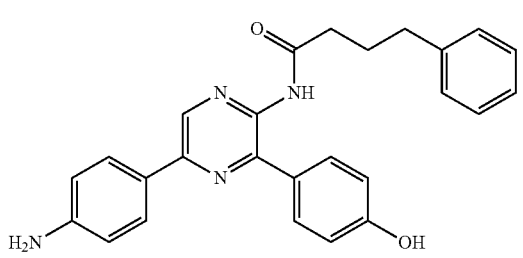
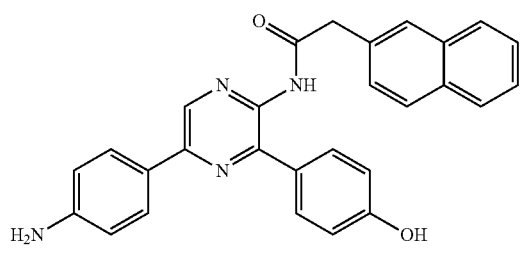
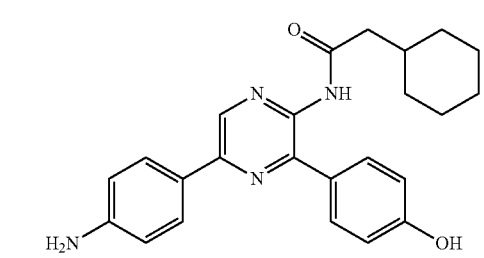
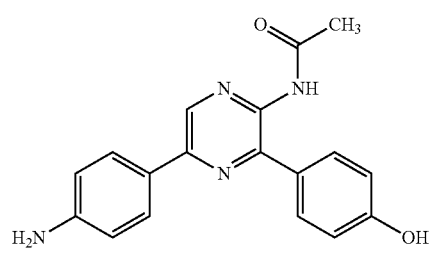
234
-continued
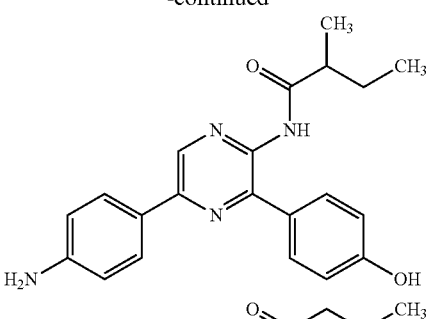
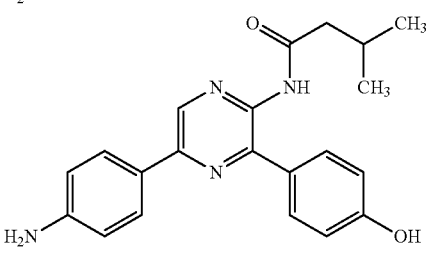
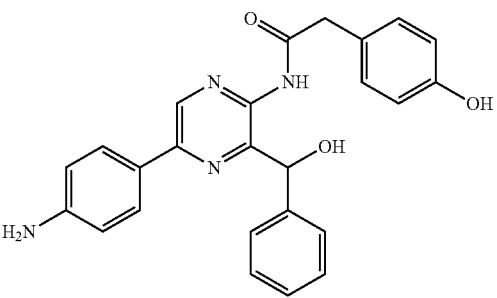
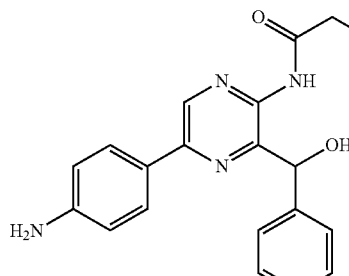
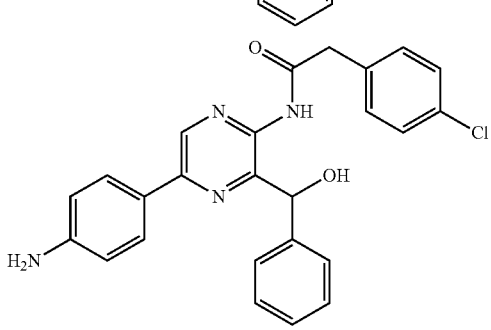
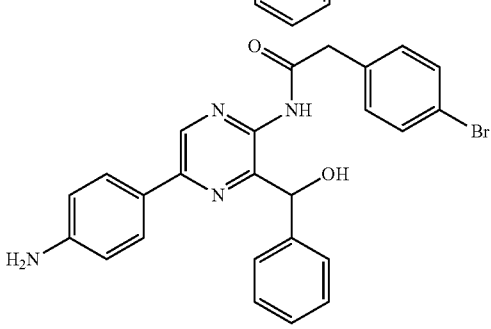

235
-continued
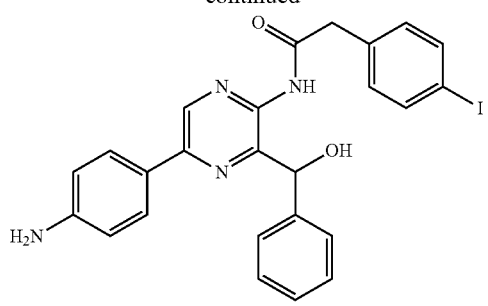
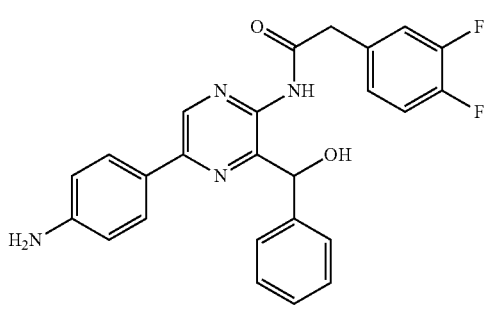
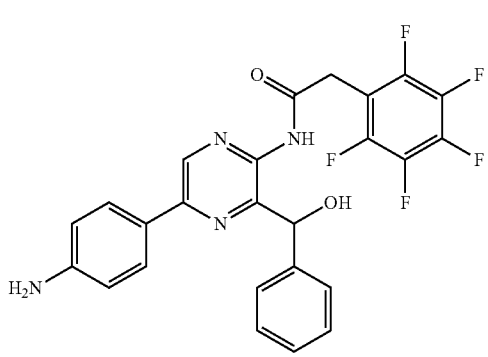
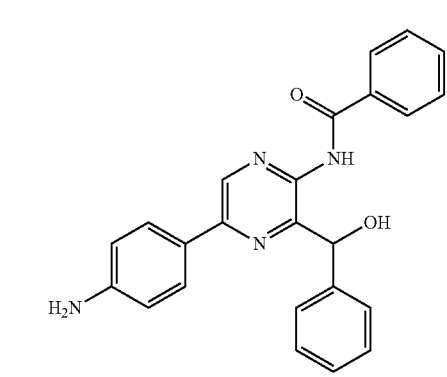
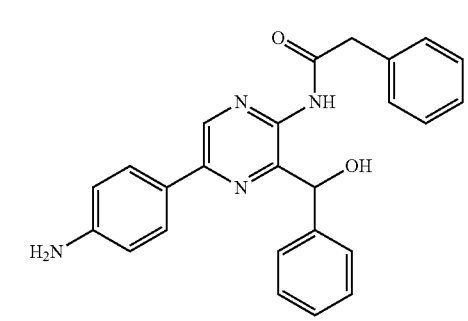
236
-continued
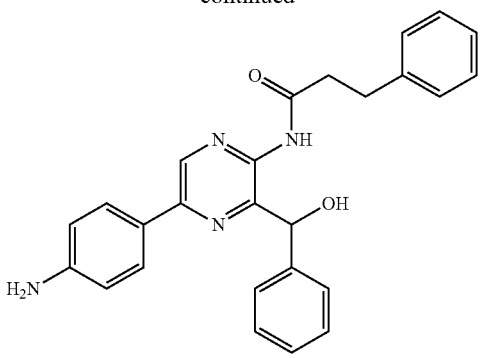
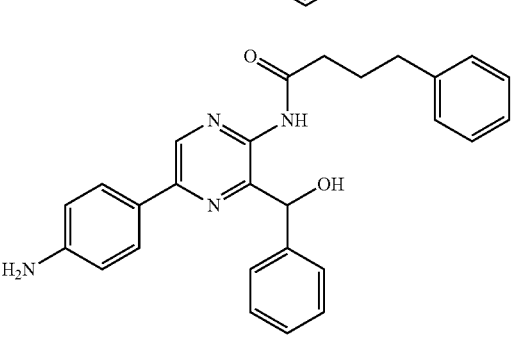
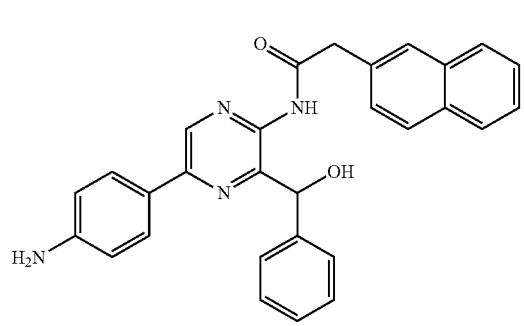
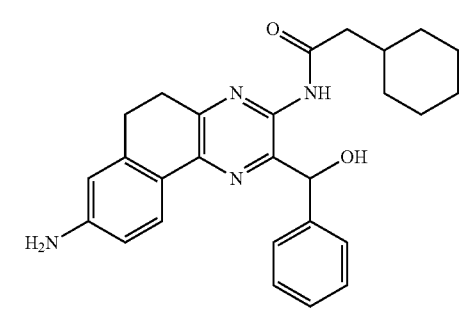
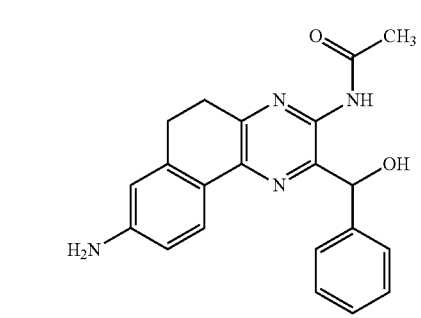

237
-continued
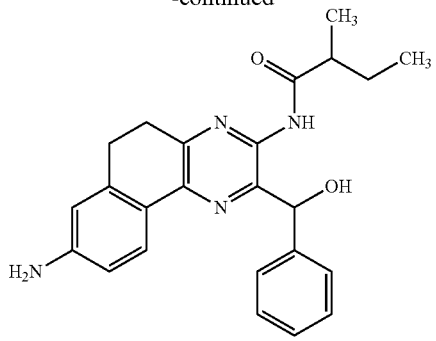
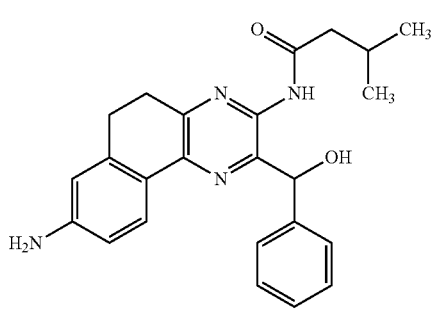
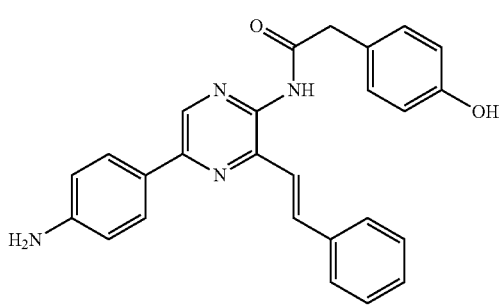
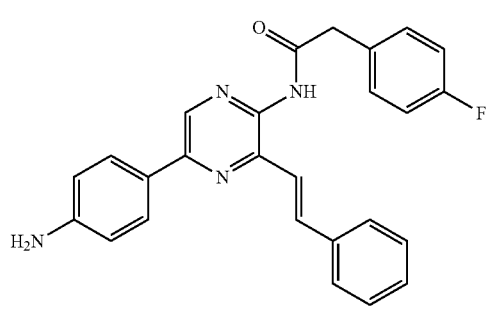
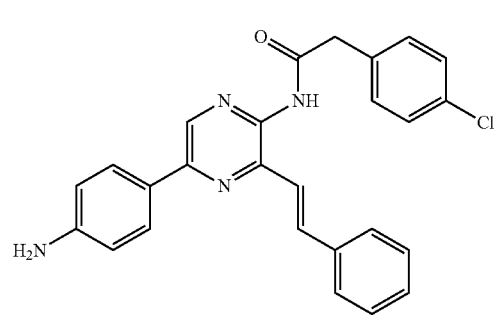
238
-continued
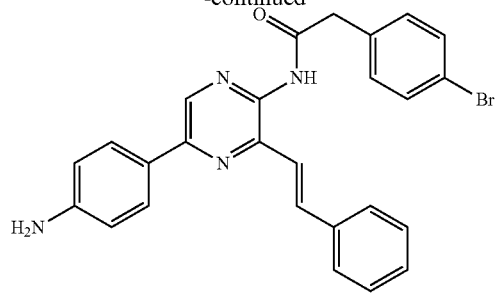
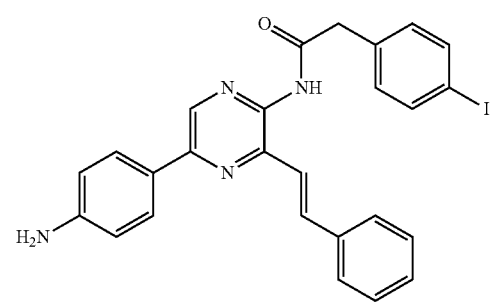
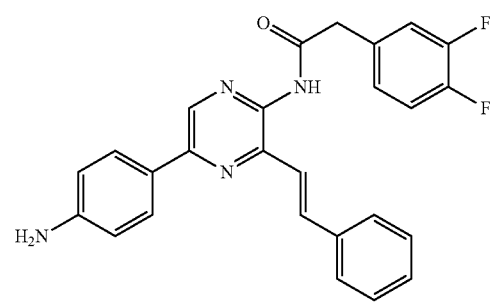
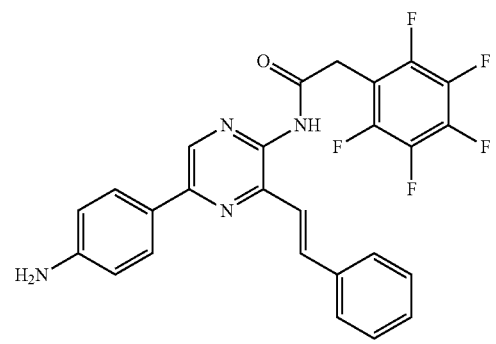
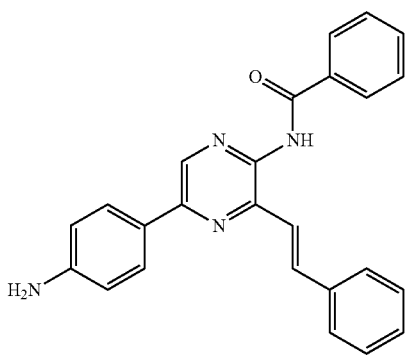

239
-continued
240
-continued
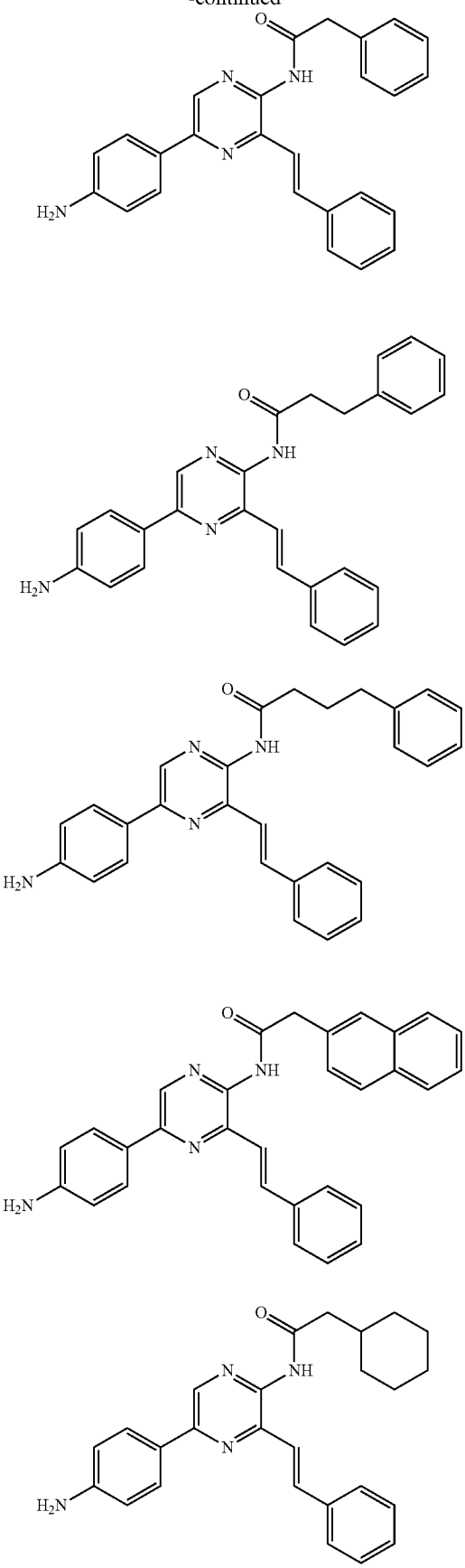
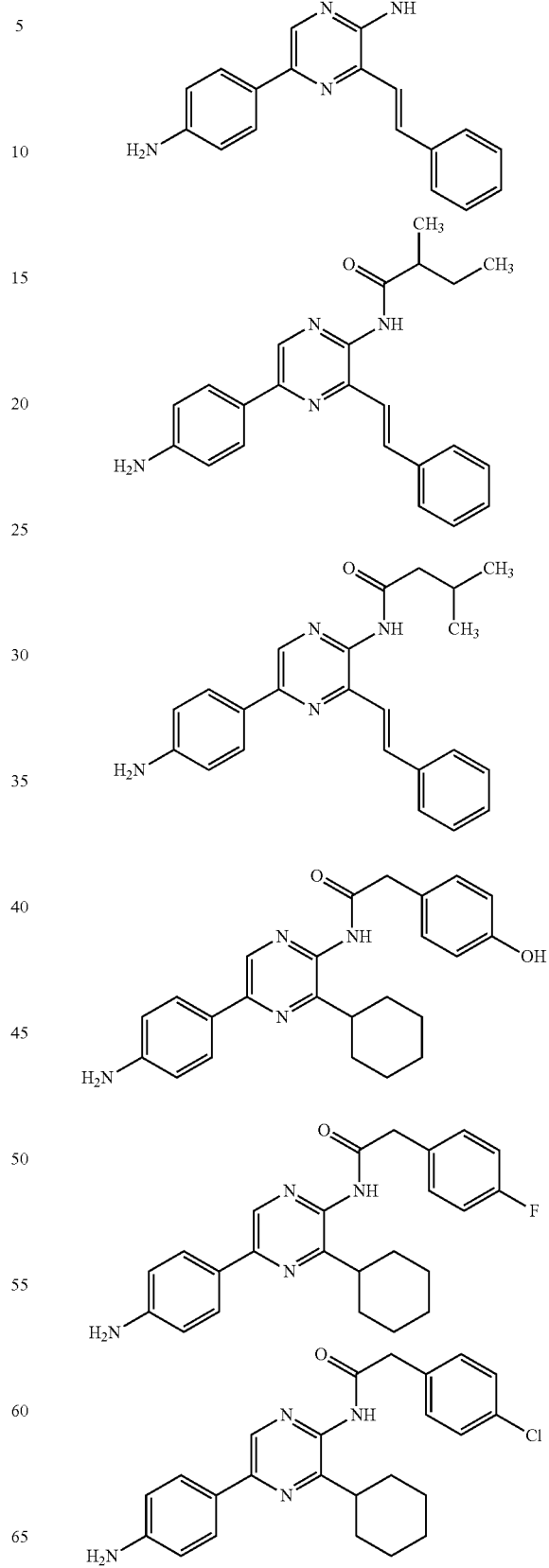

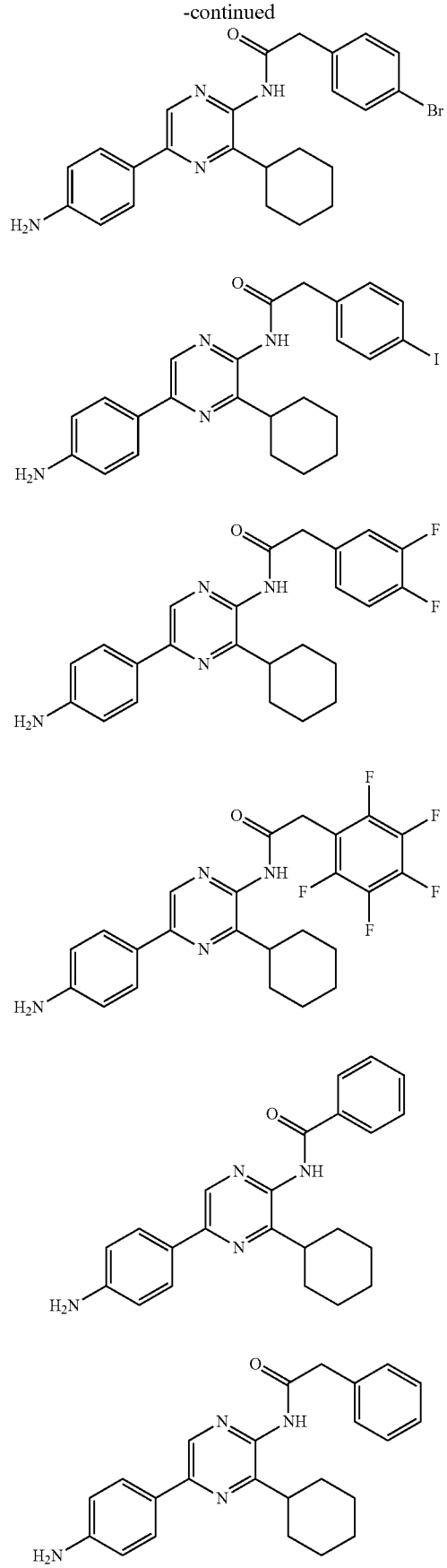
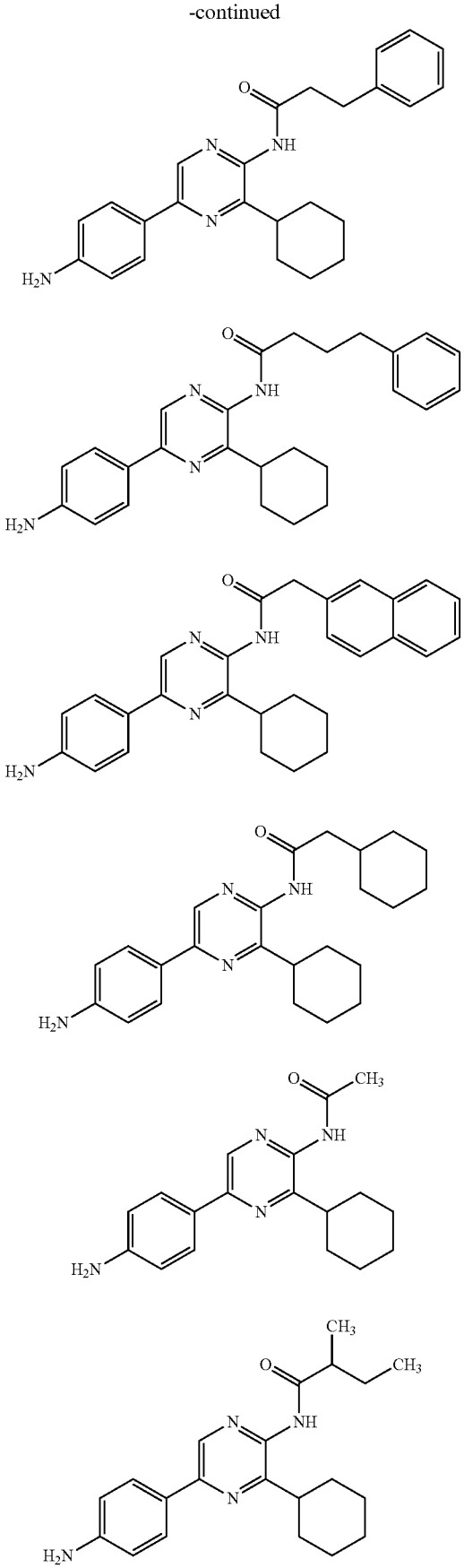

243
-continued
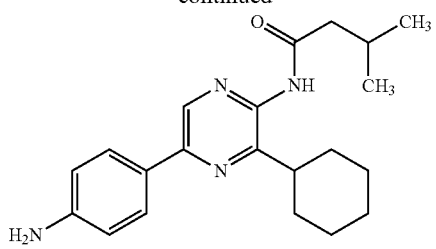
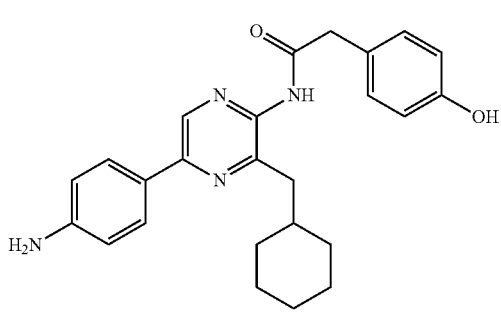
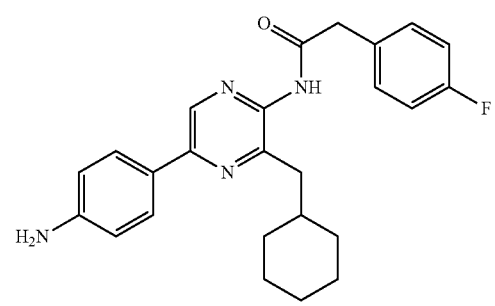
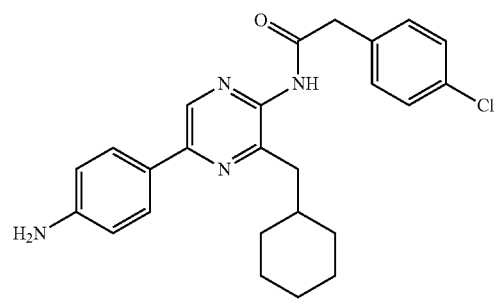
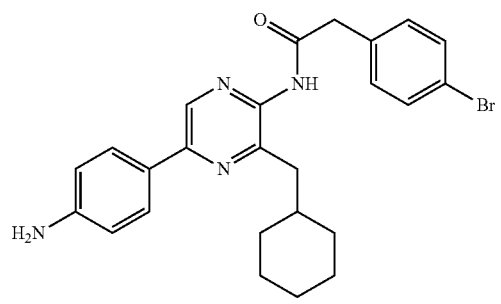
244
-continued
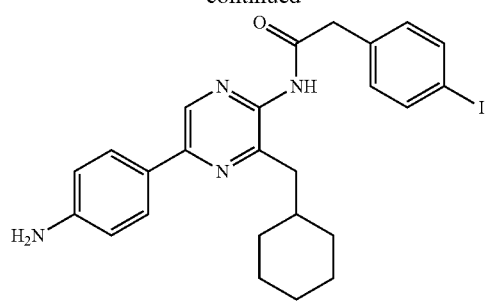
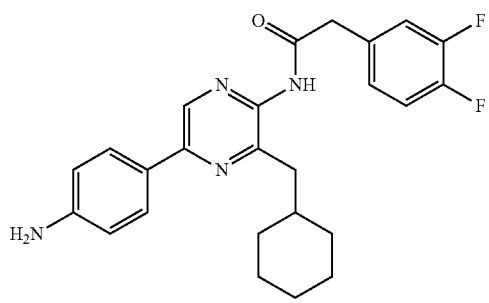
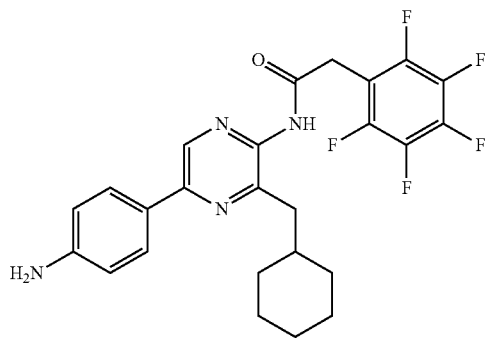
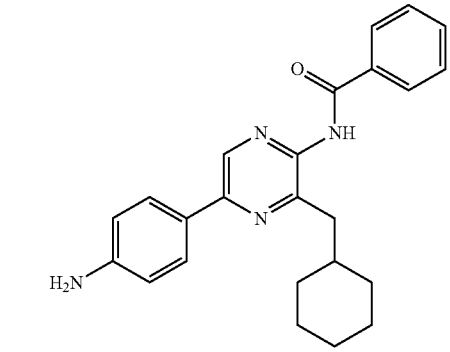
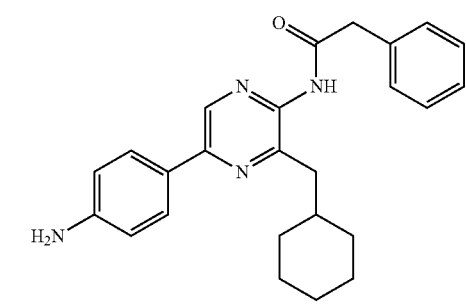

245
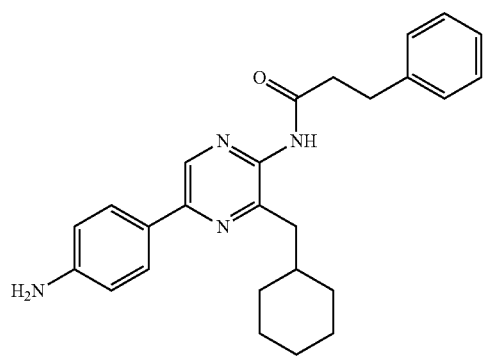
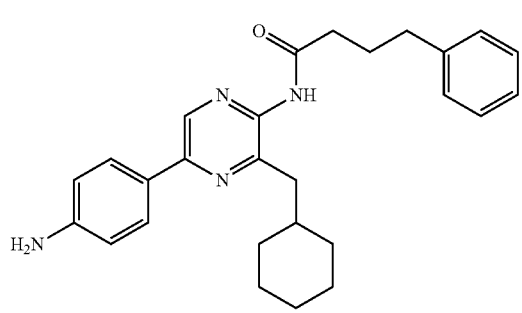
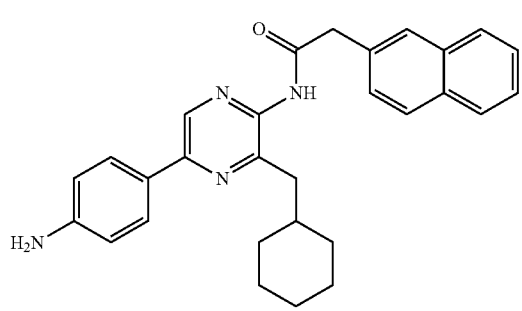
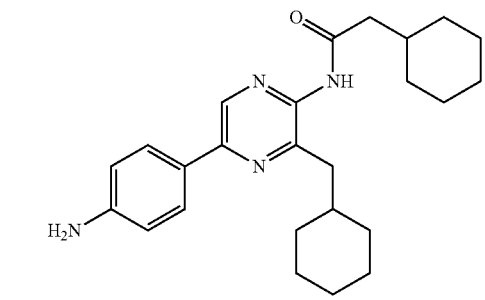
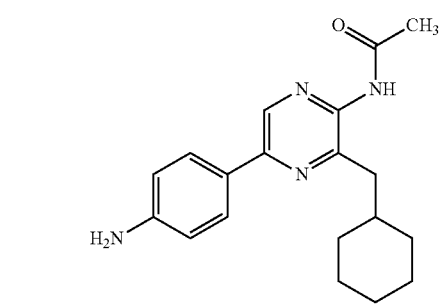
246
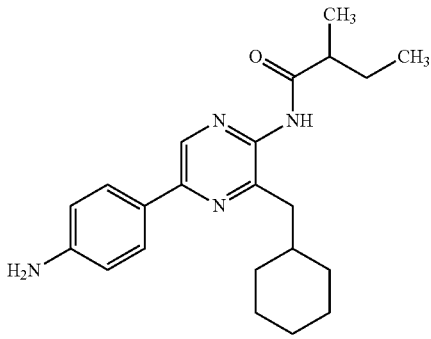
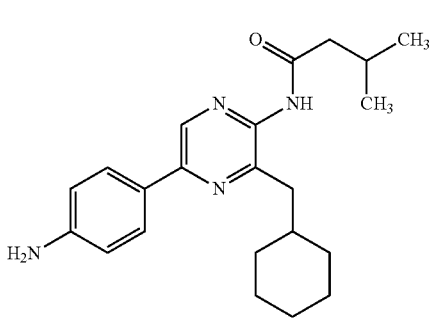
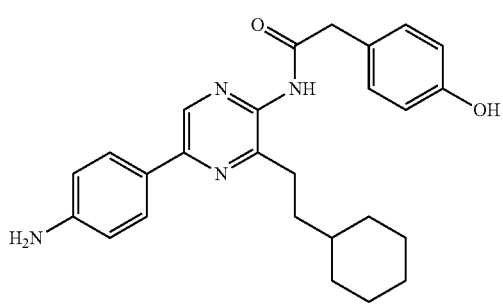
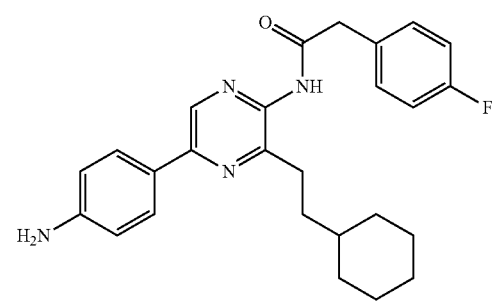
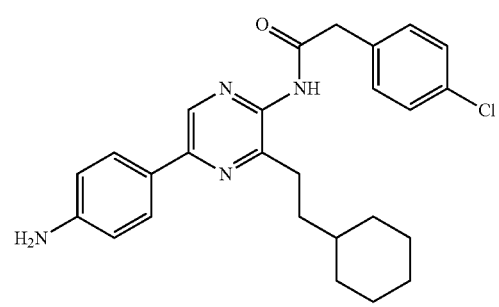

247
-continued
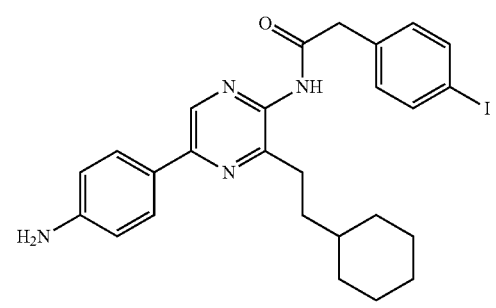
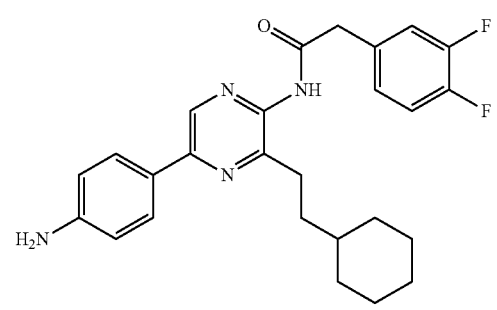
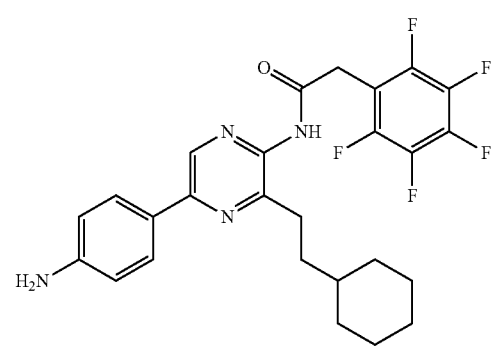
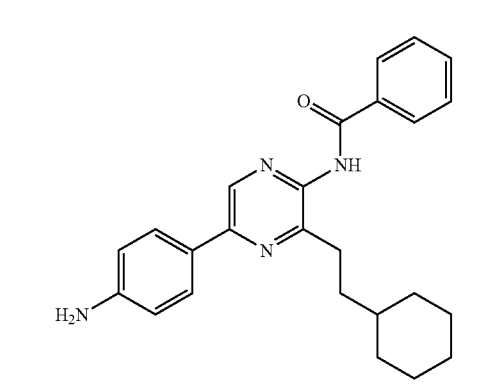
248
-continued
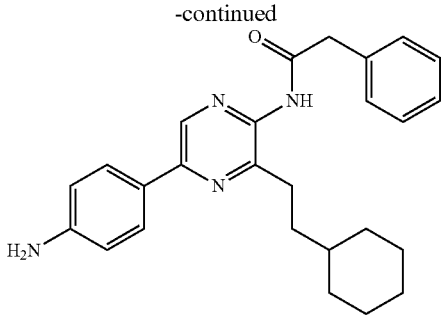
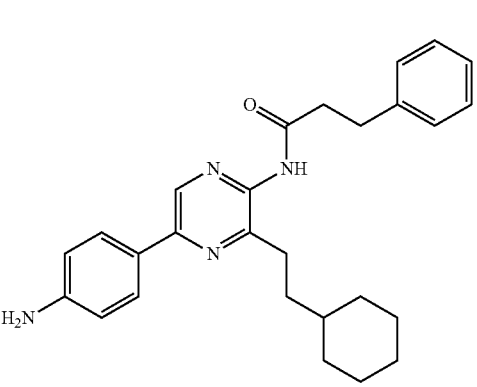
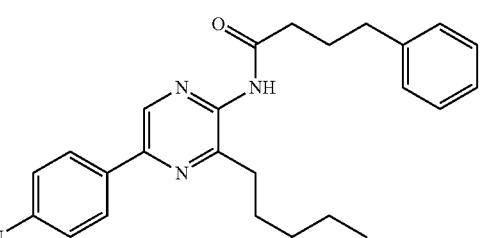
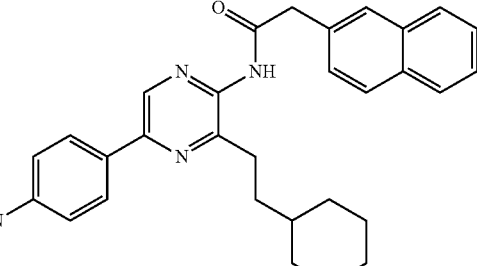
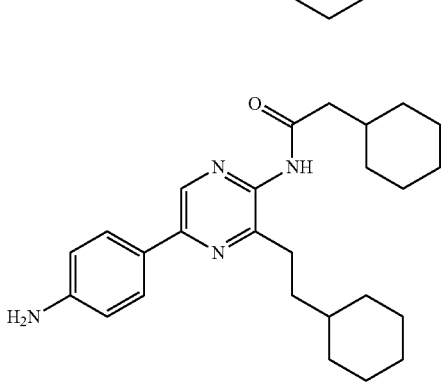

249
-continued
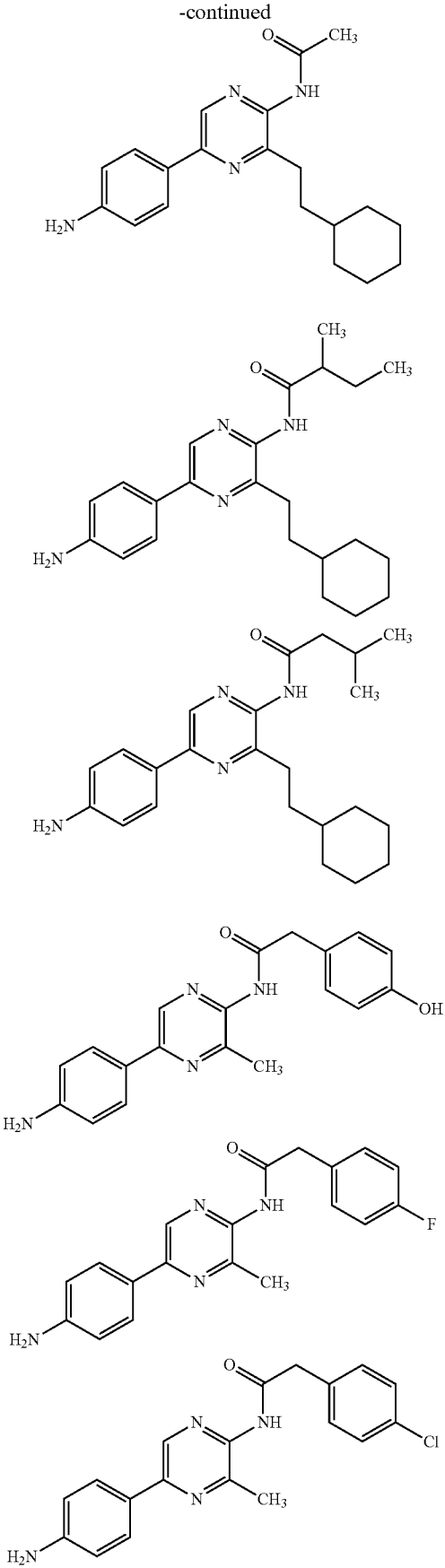
250
-continued
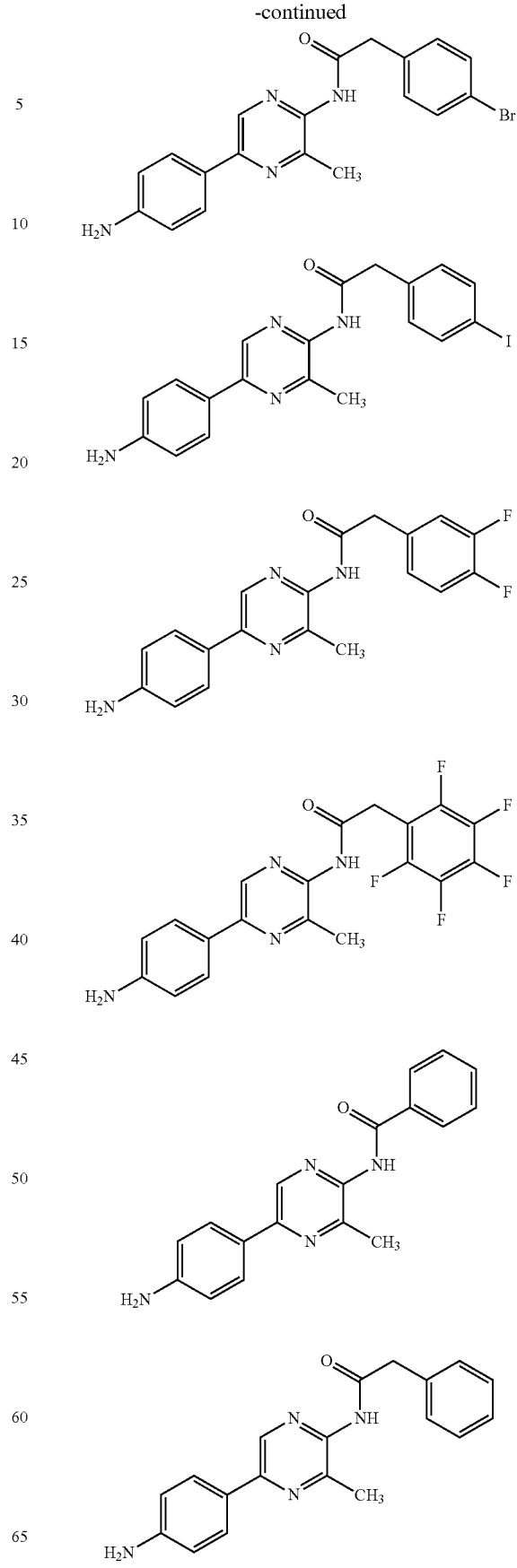

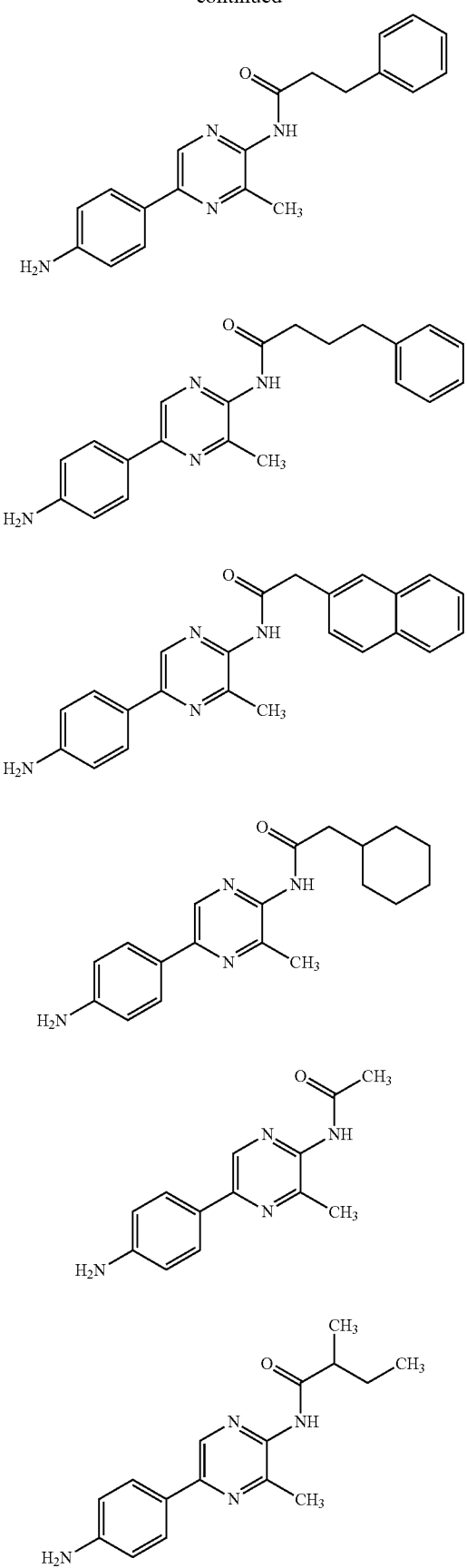
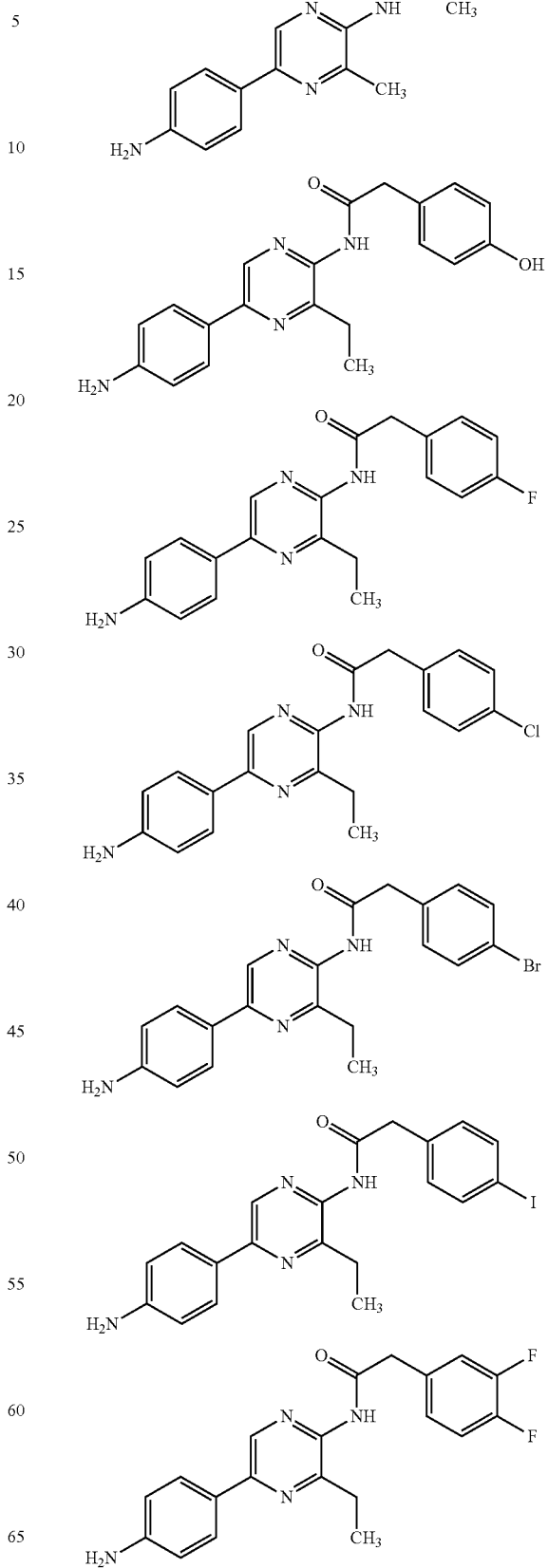

253
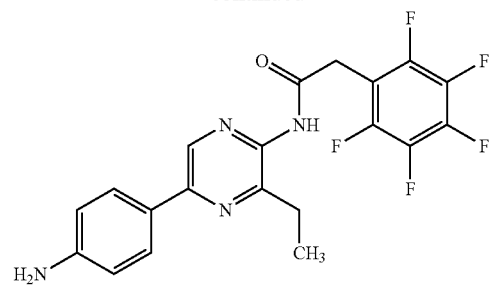
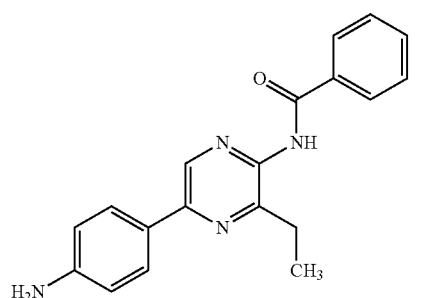
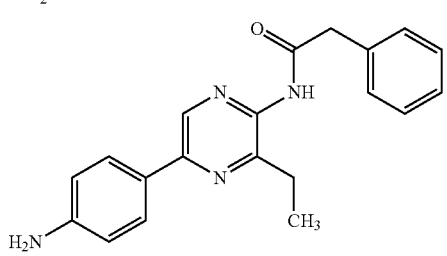
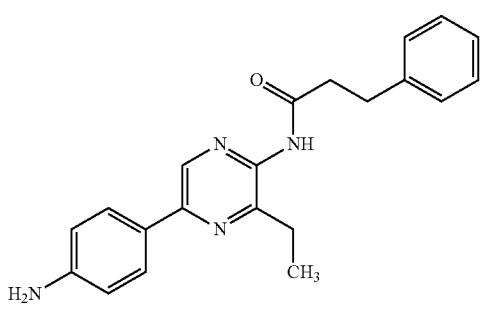
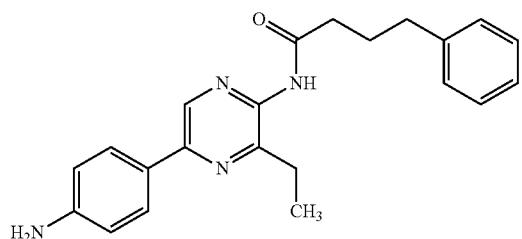
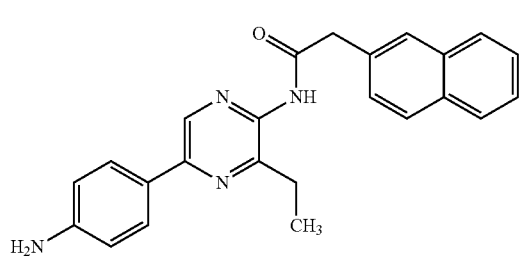
254
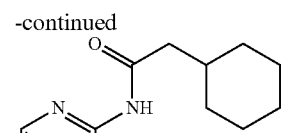
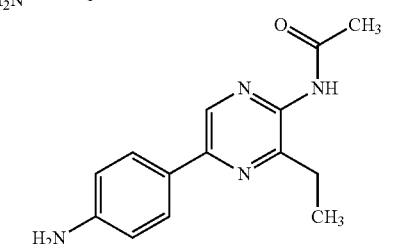
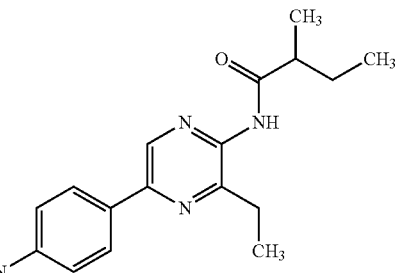
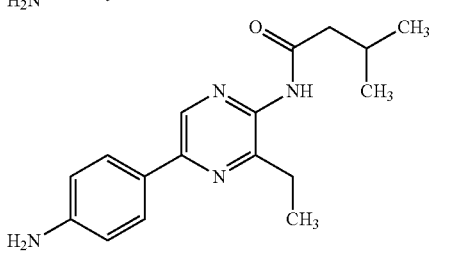
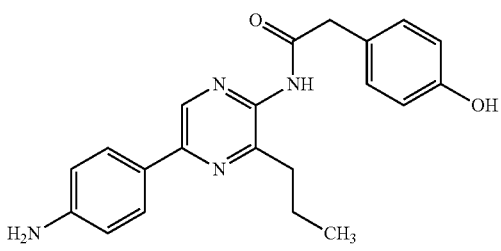
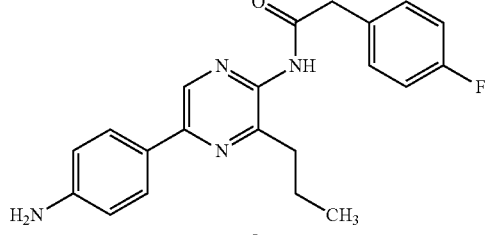
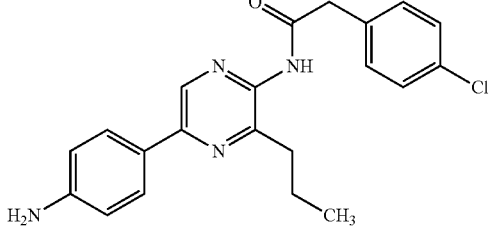

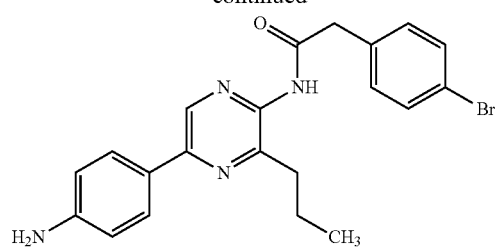
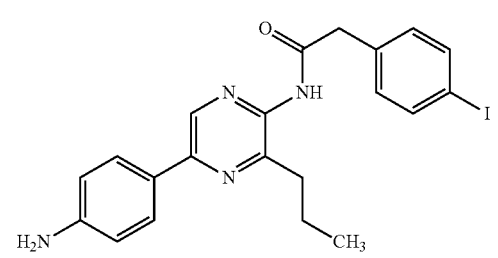
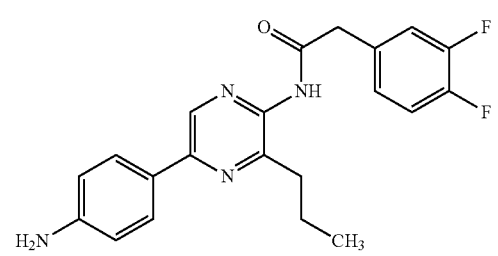
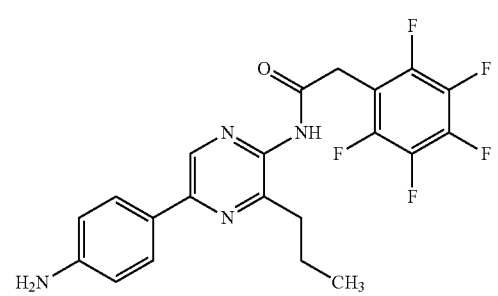
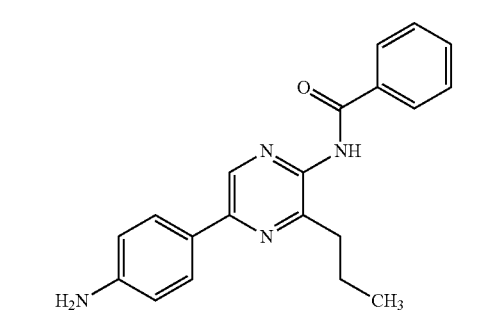
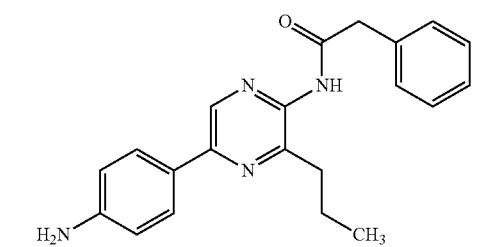
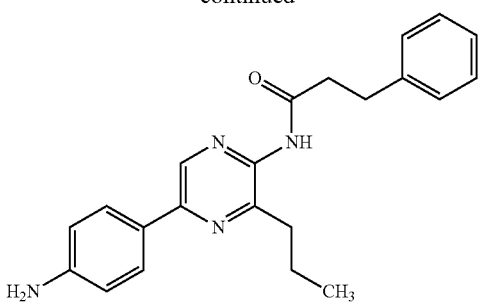
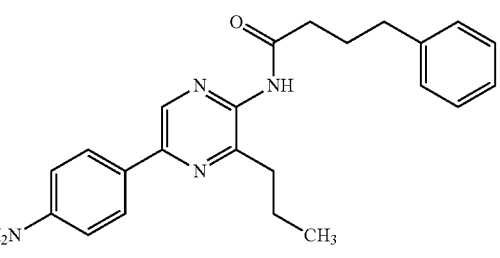
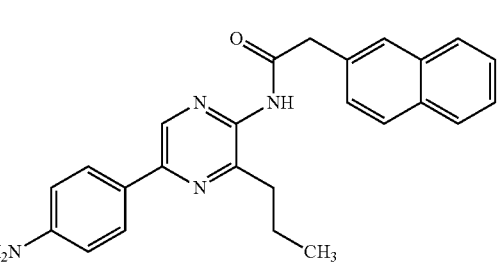
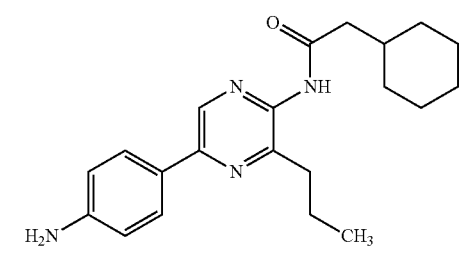
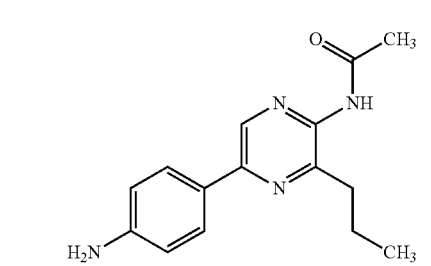
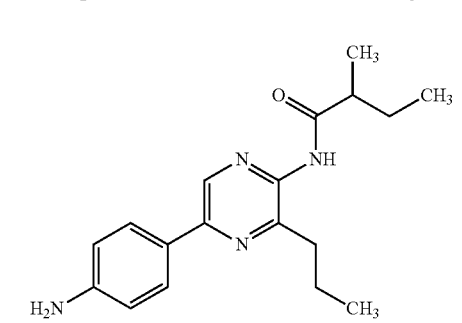

257
-continued
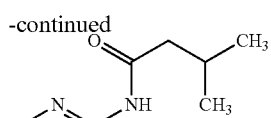
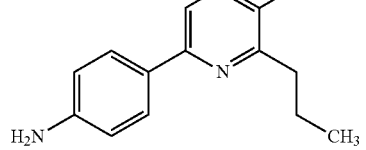
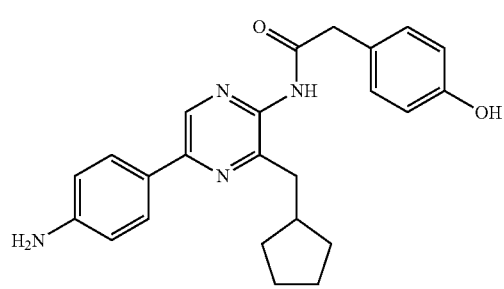
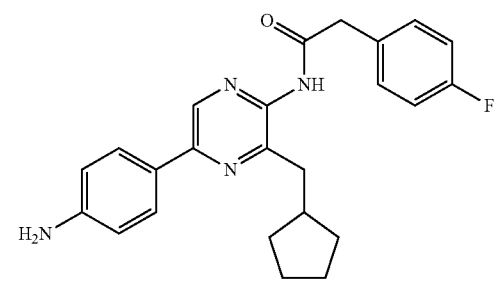
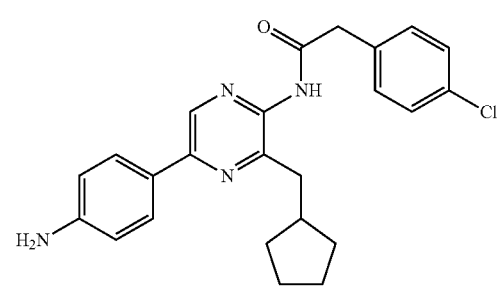
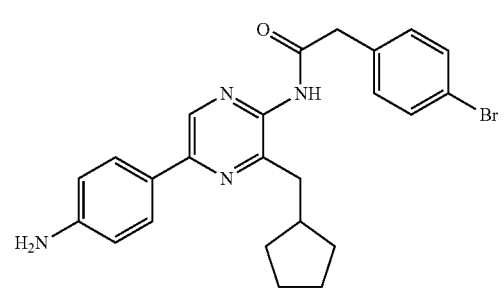
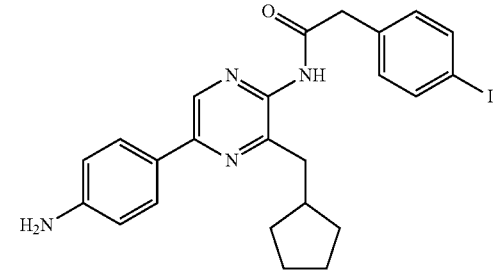
258
-continued
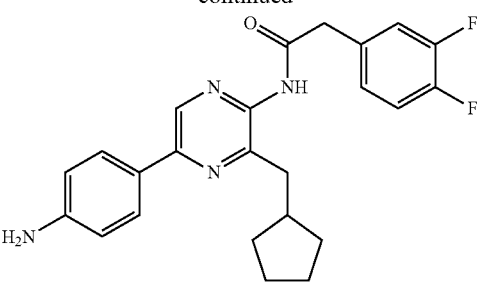
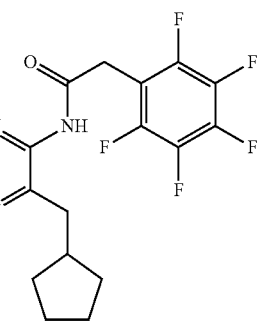
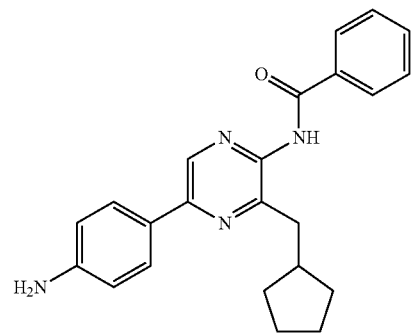
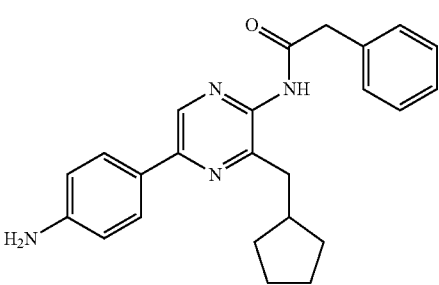
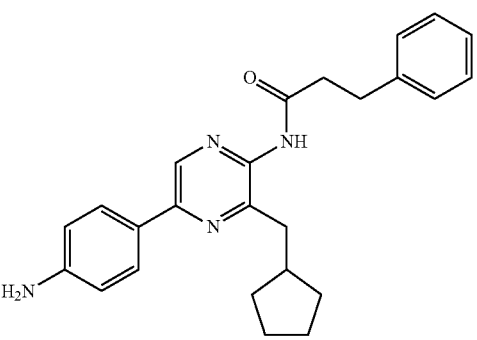

259
-continued
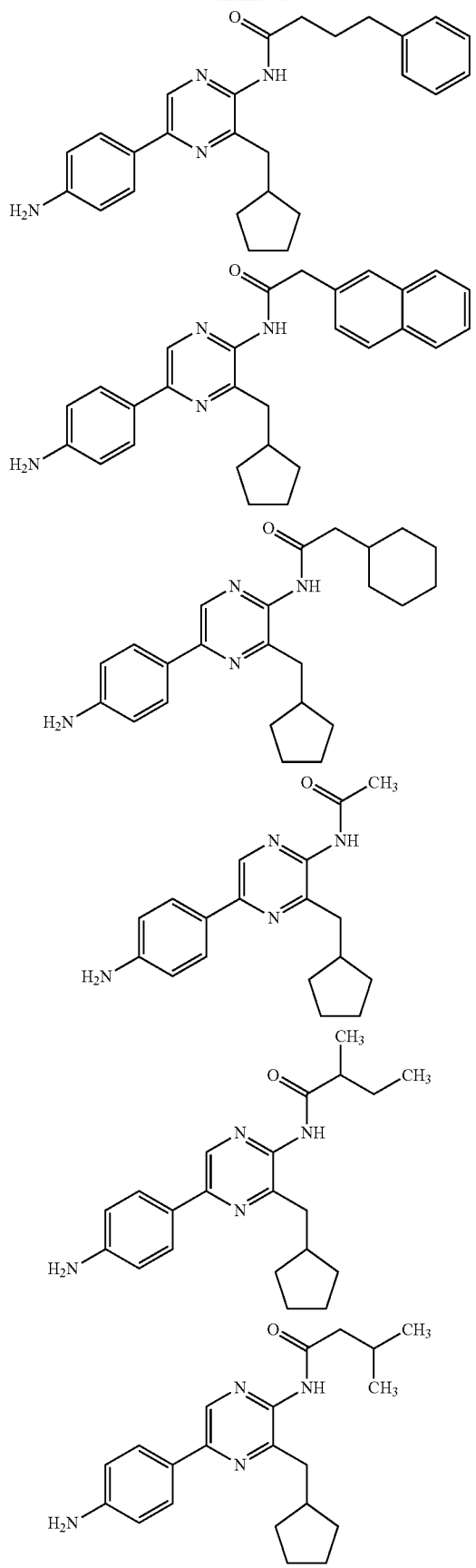
260
-continued
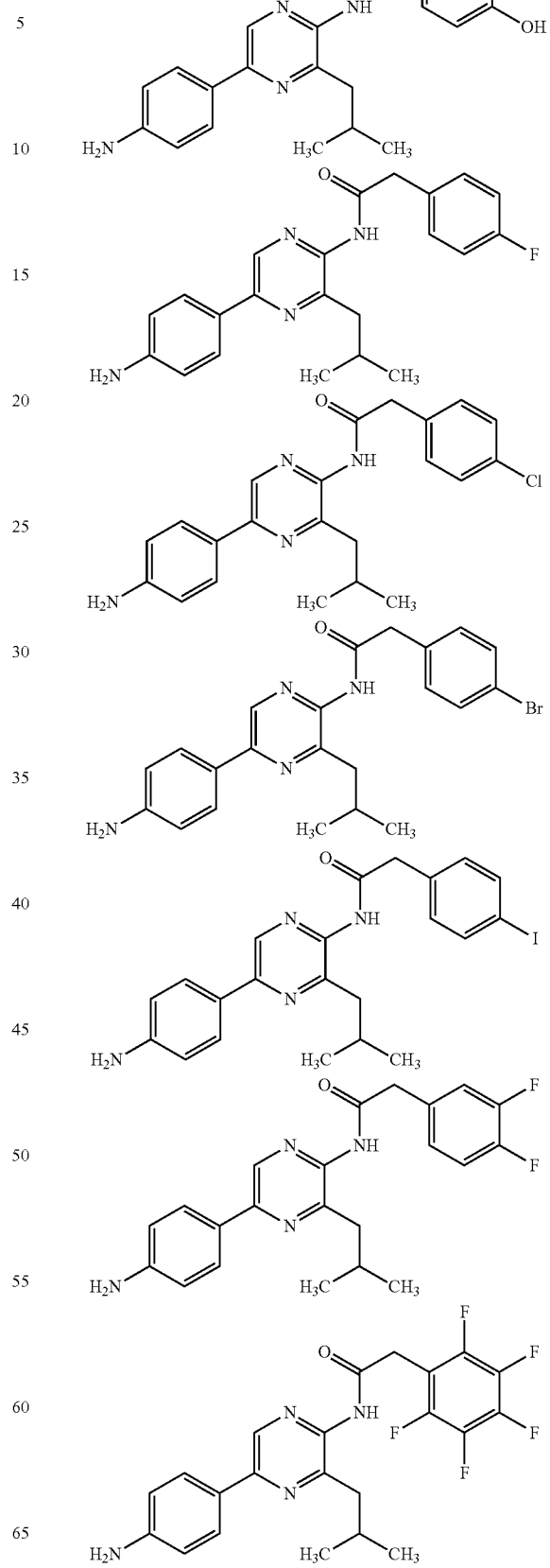

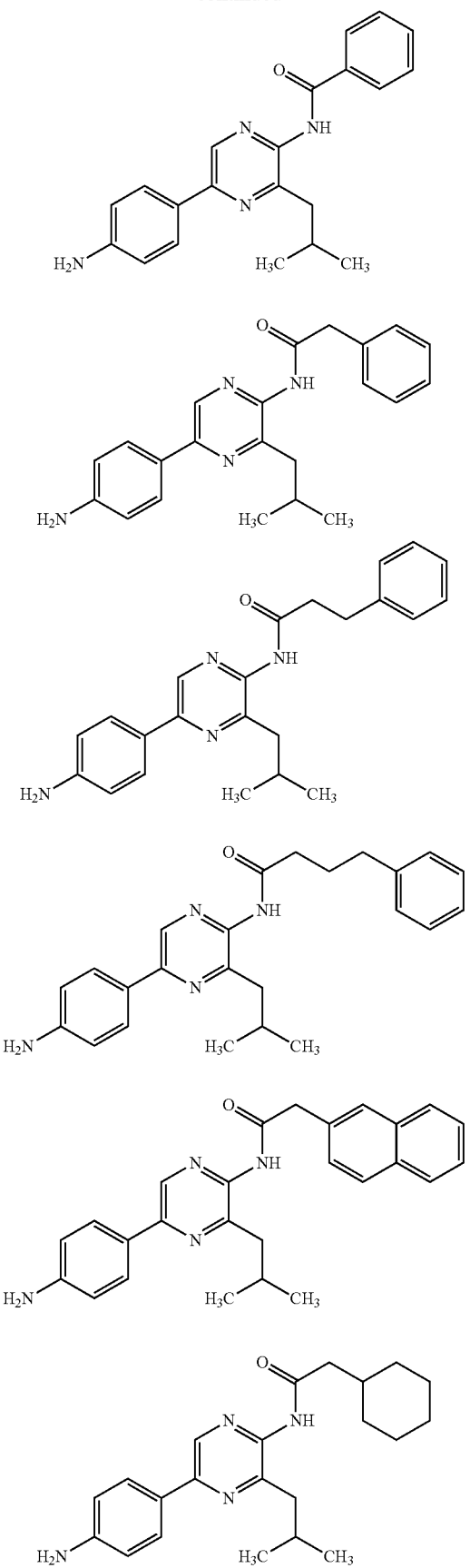
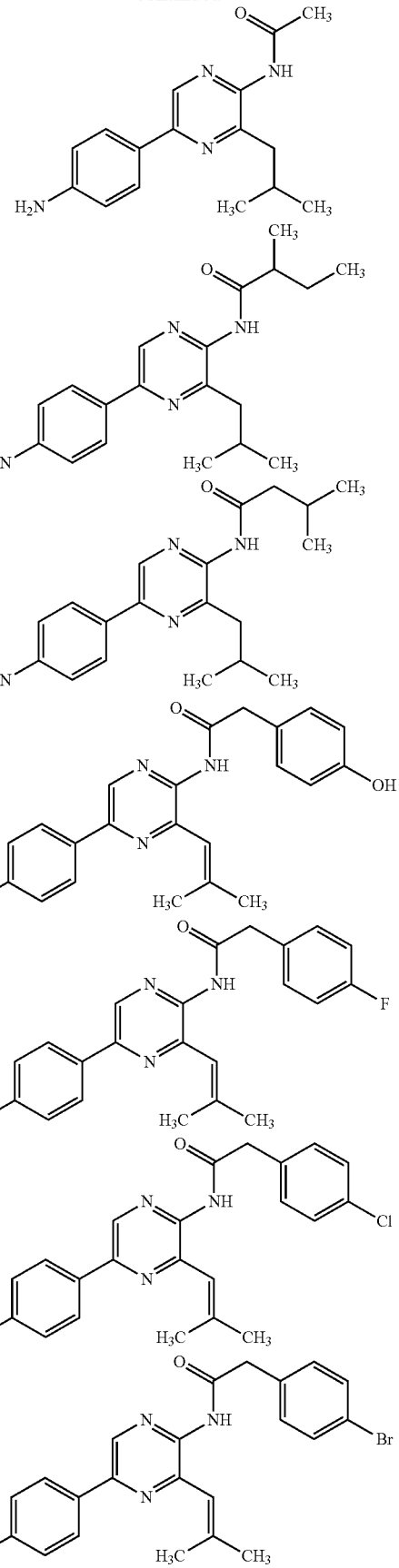

263
-continued
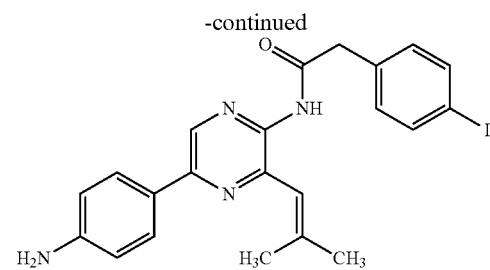
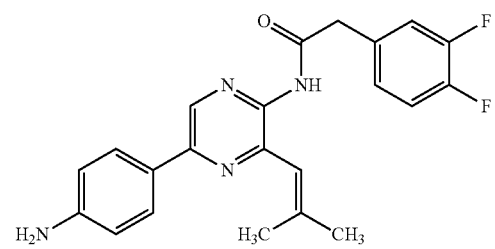
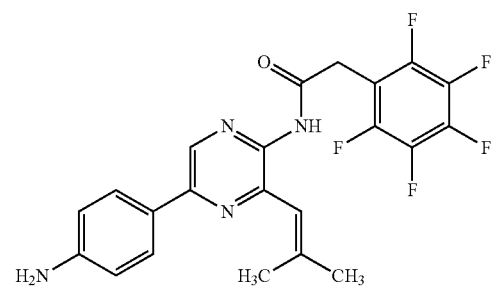
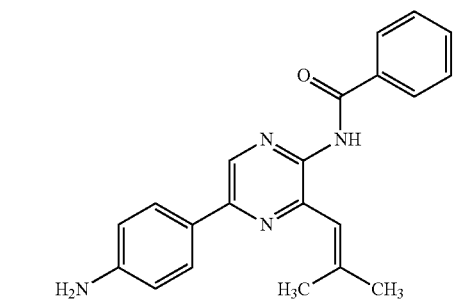
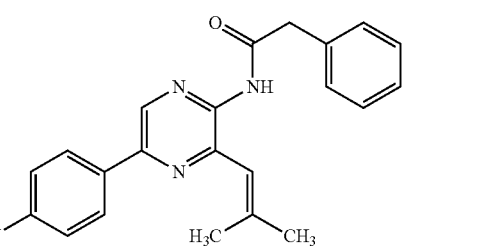
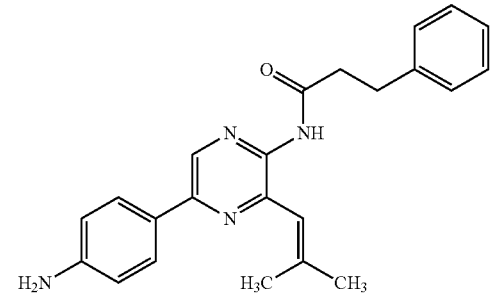
264
-continued
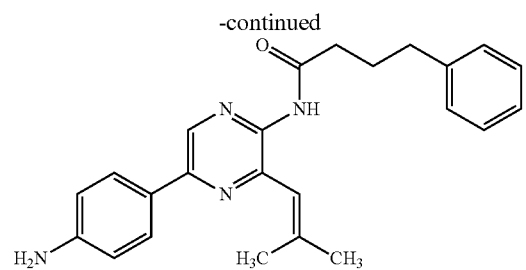
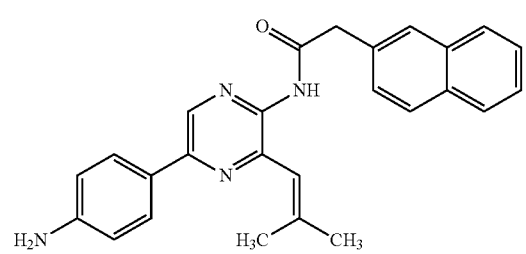
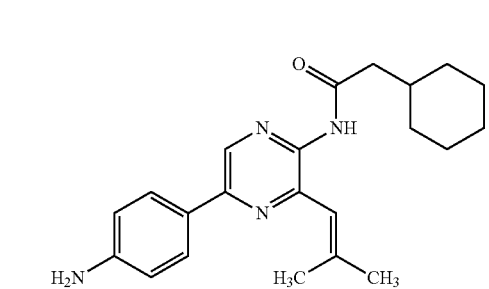
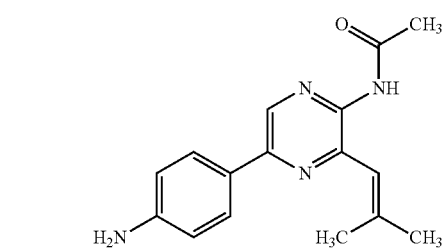
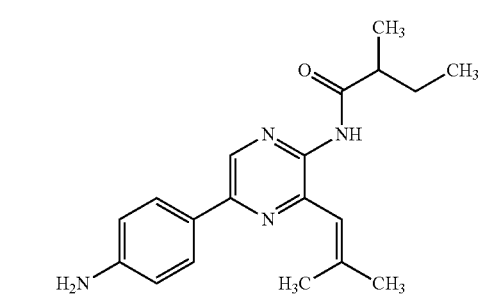
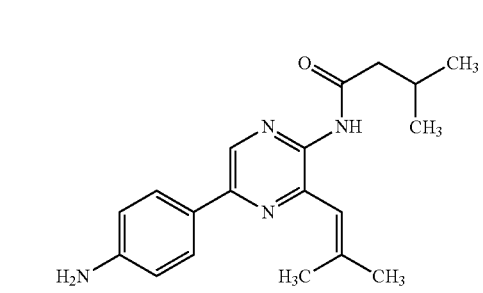

265
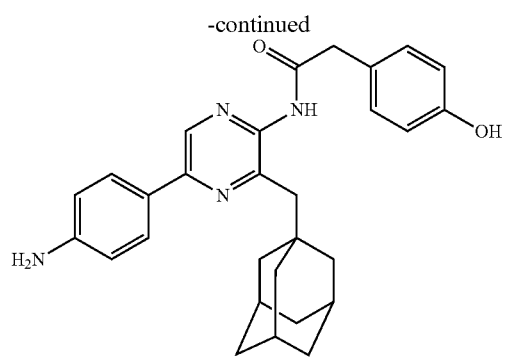
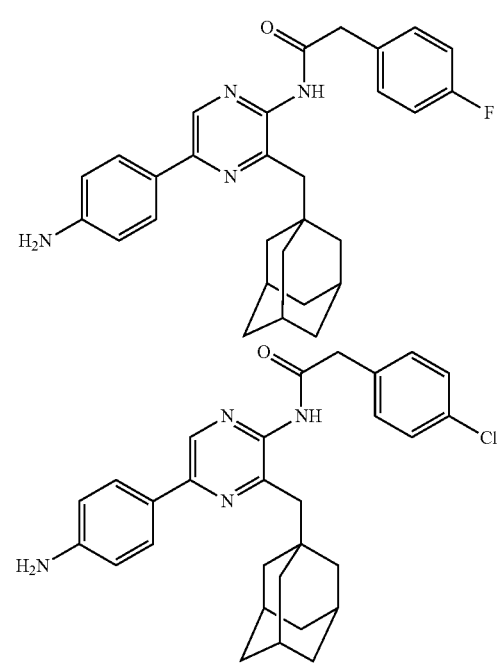
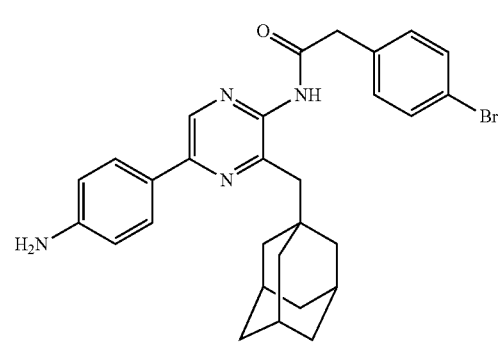
266
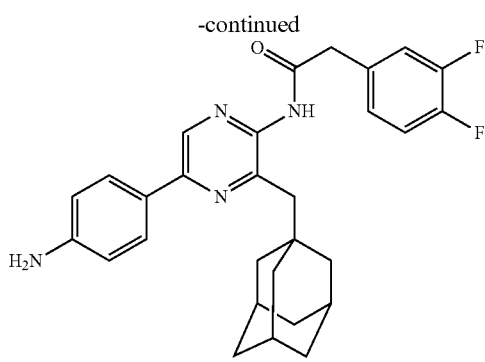
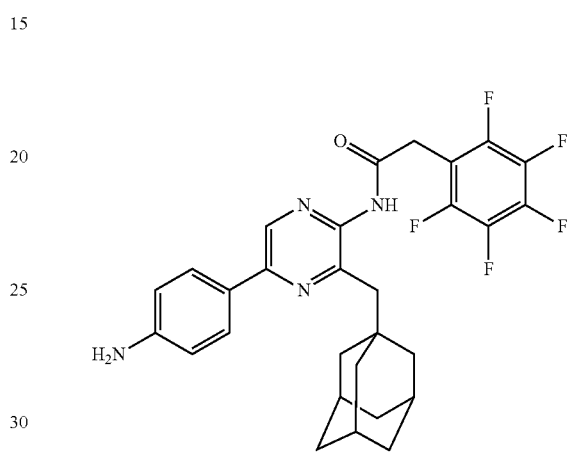

267
-continued
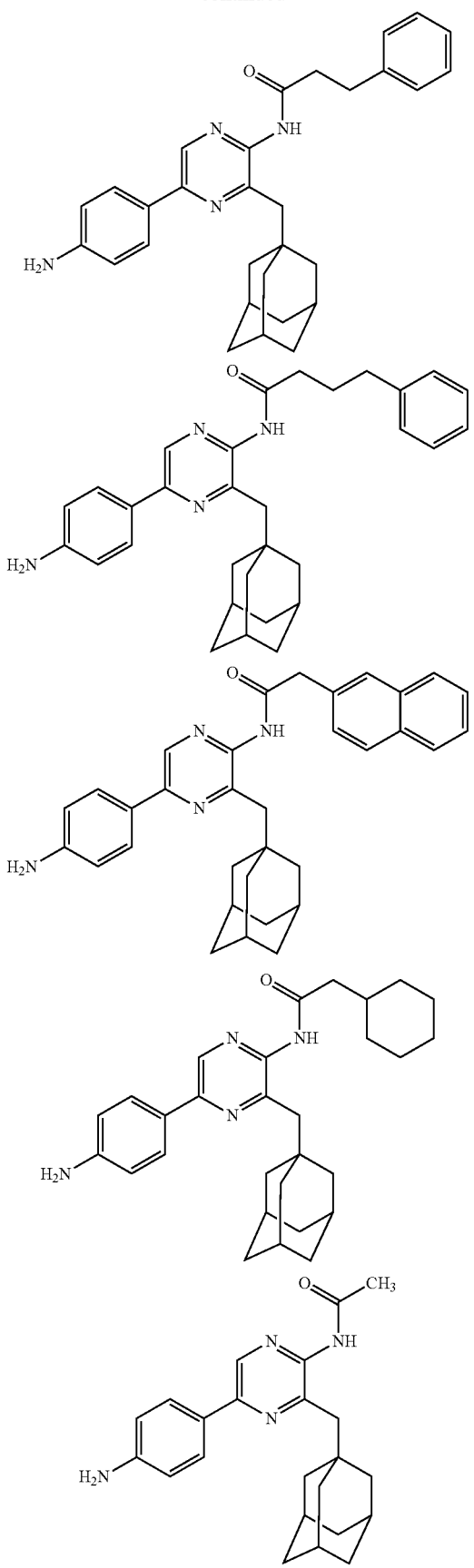
268
-continued
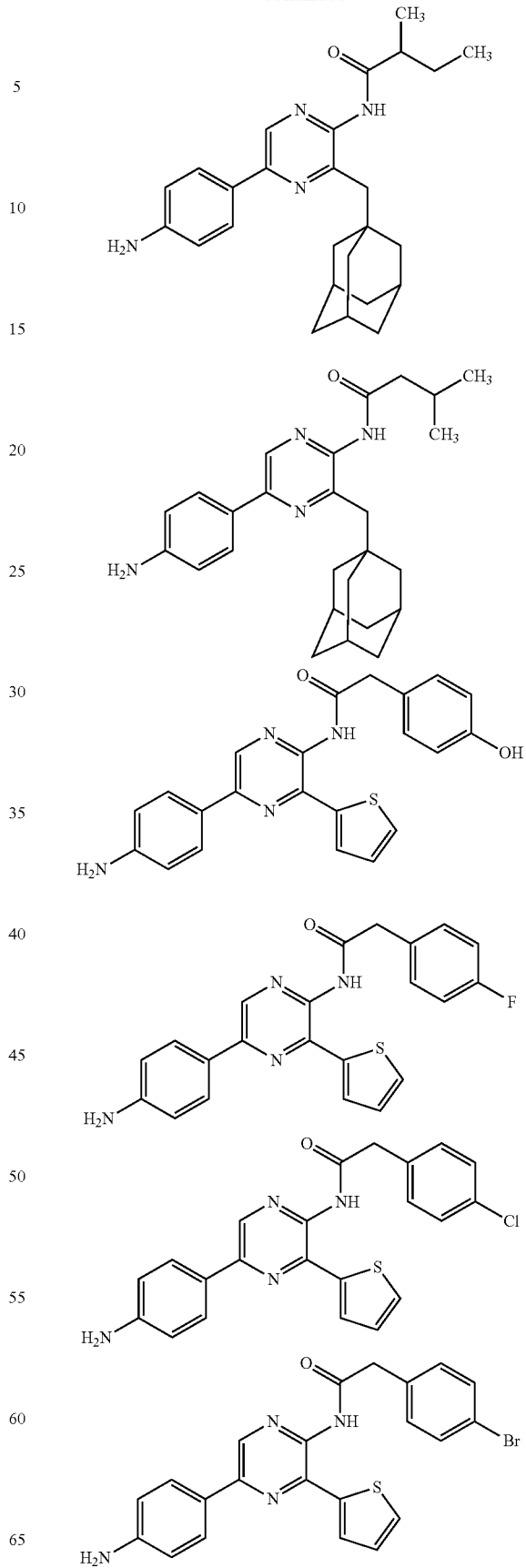

269
-continued
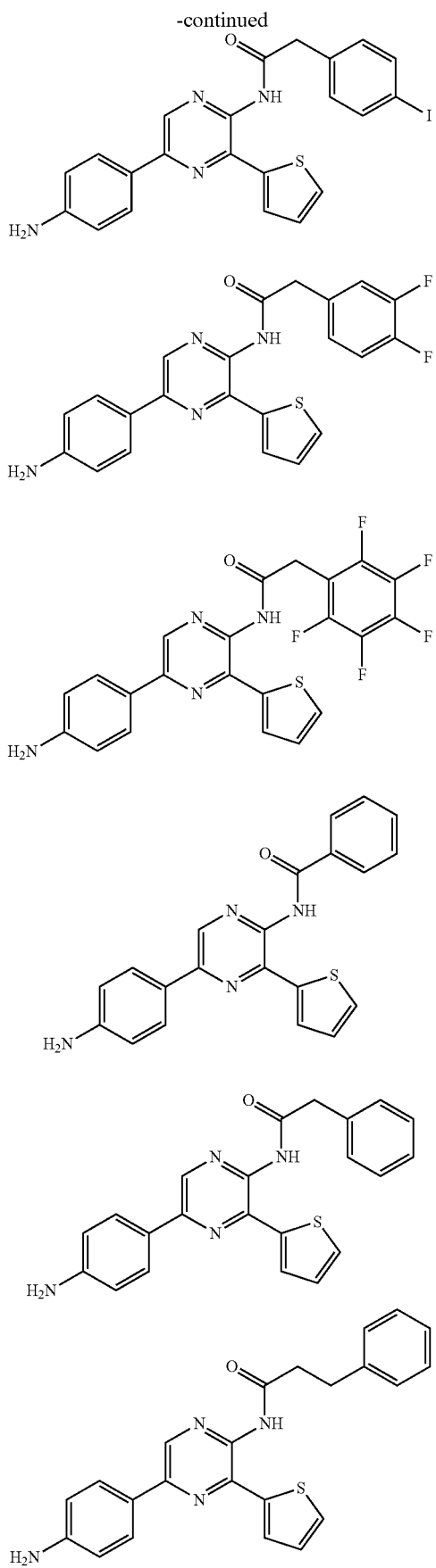
270
-continued
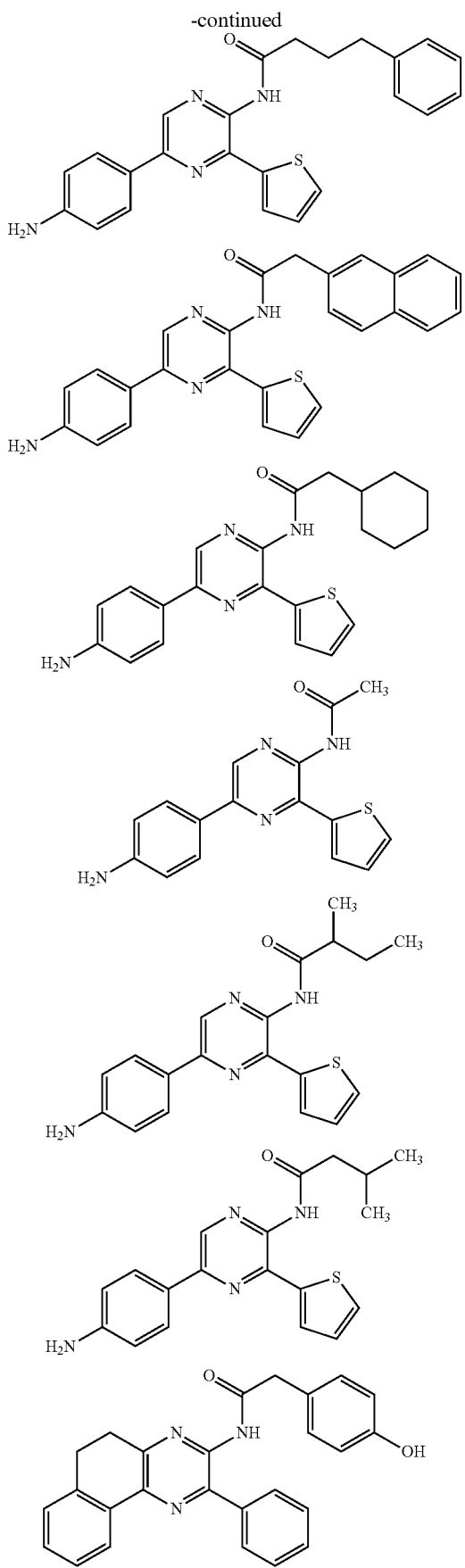

271
-continued
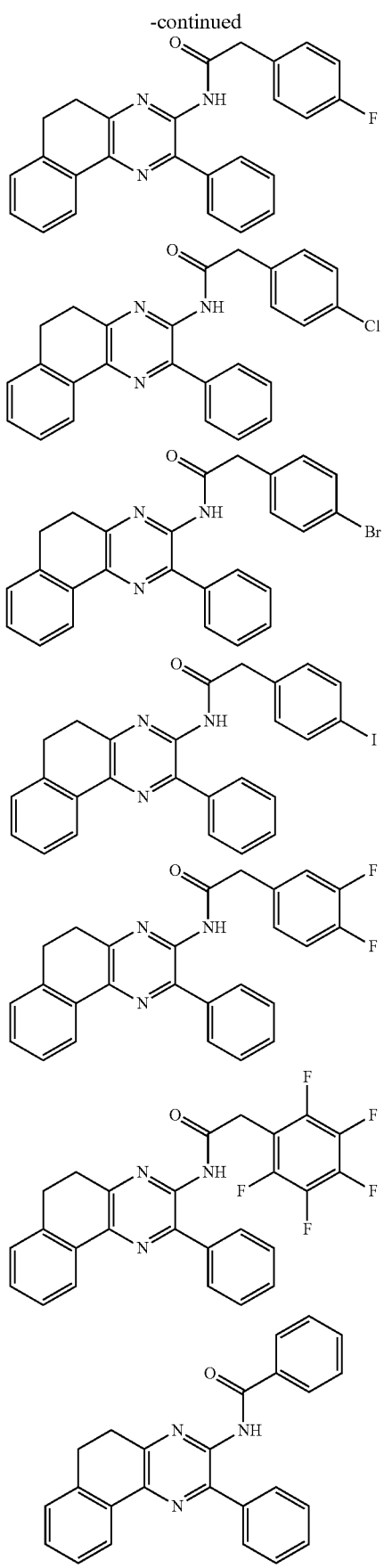
272
-continued
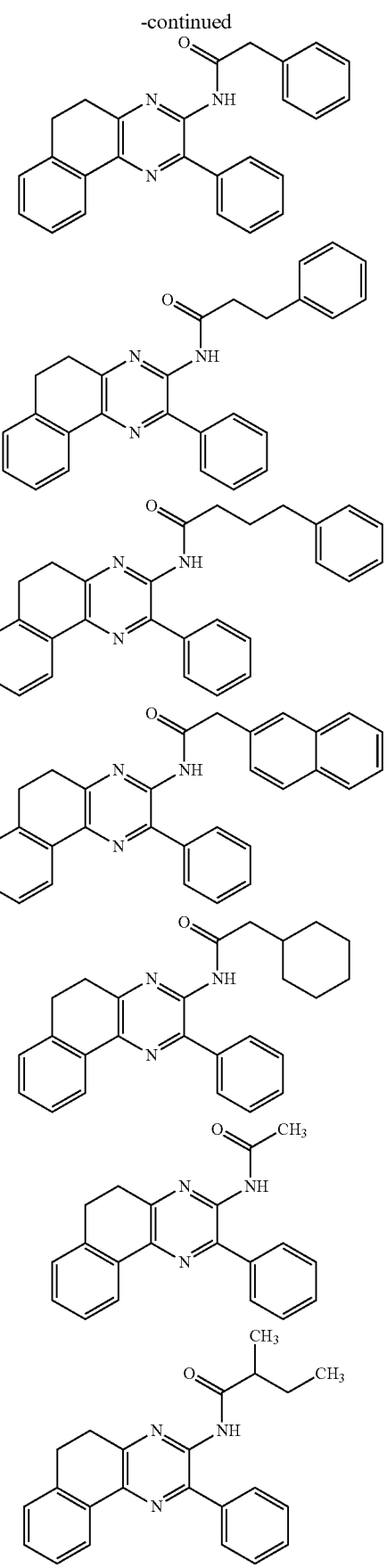

273
-continued
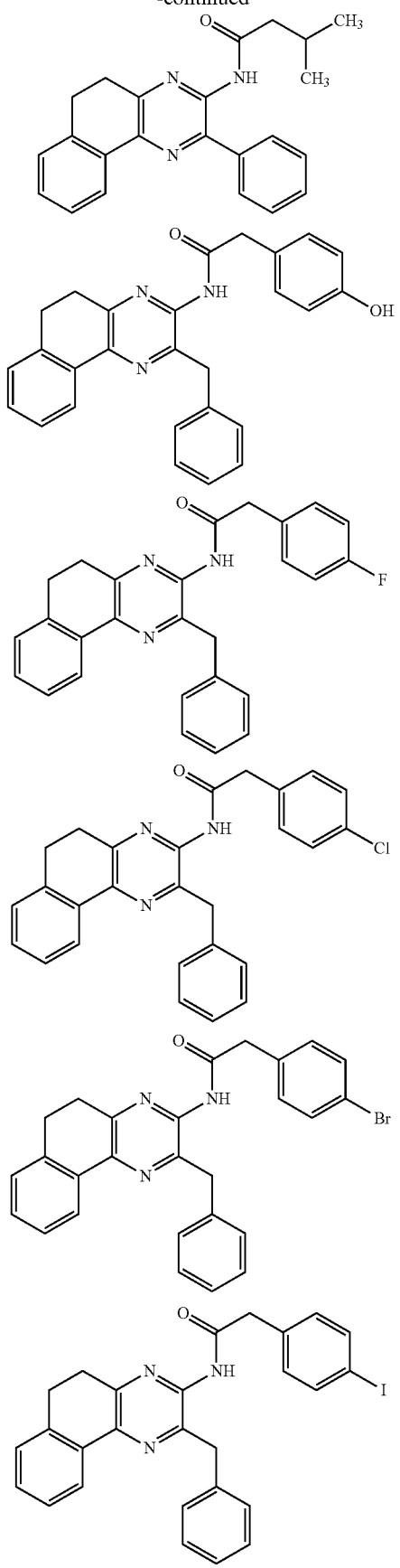
274
-continued
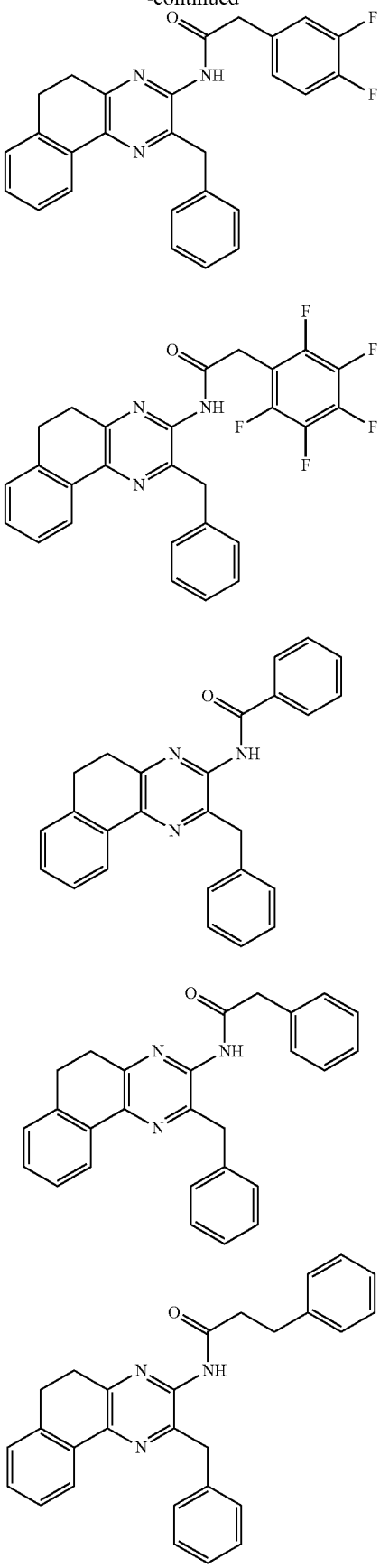

275
-continued
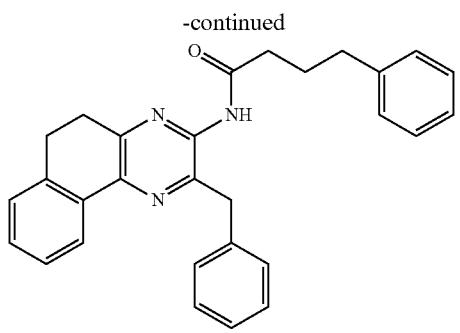
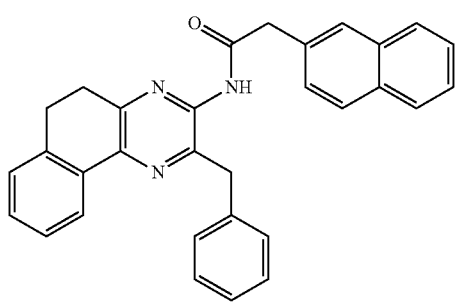
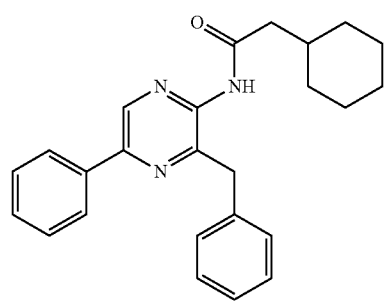
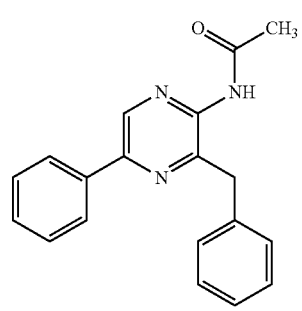
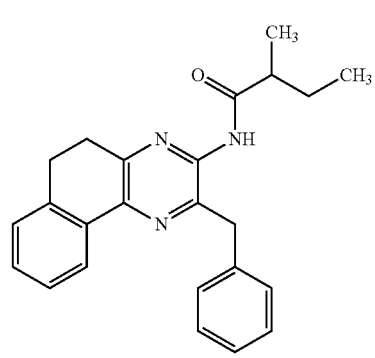
276
-continued
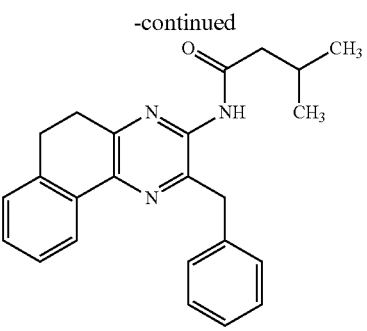
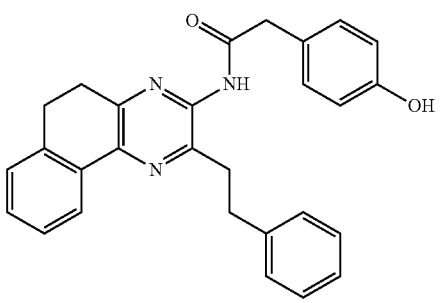
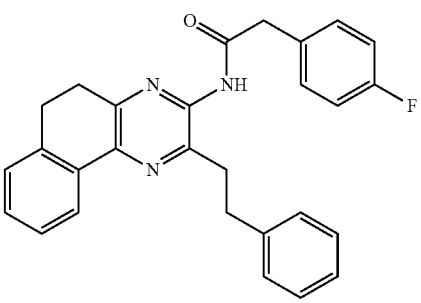
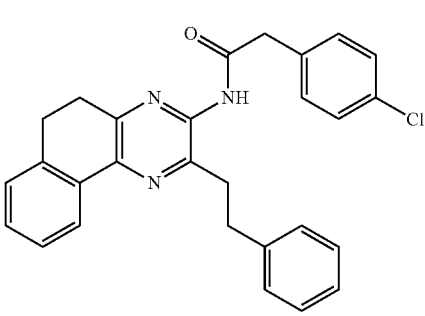
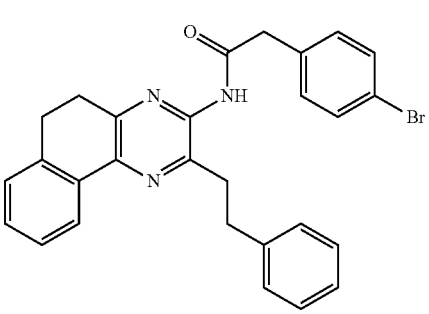

277
-continued
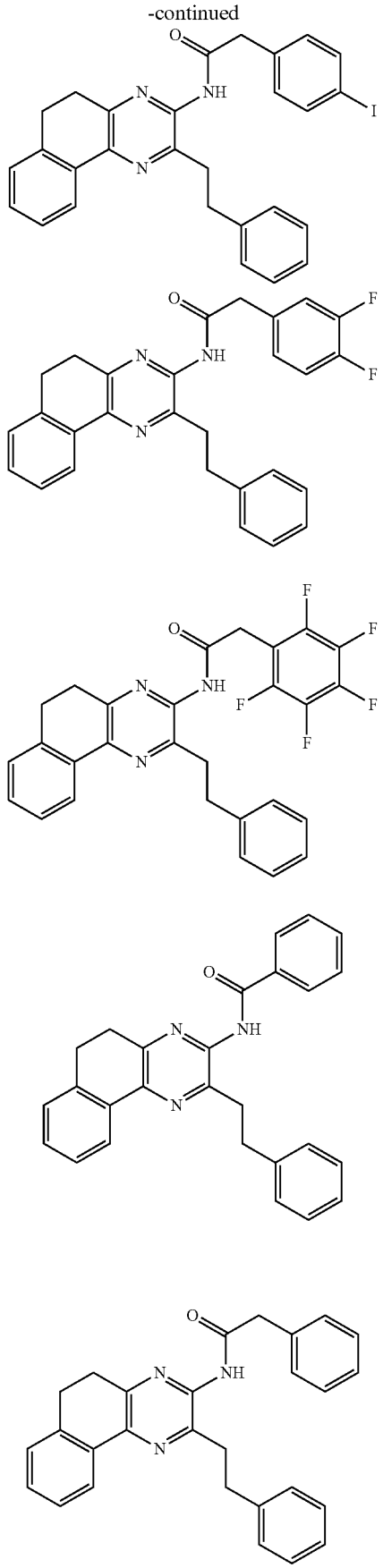
278
-continued
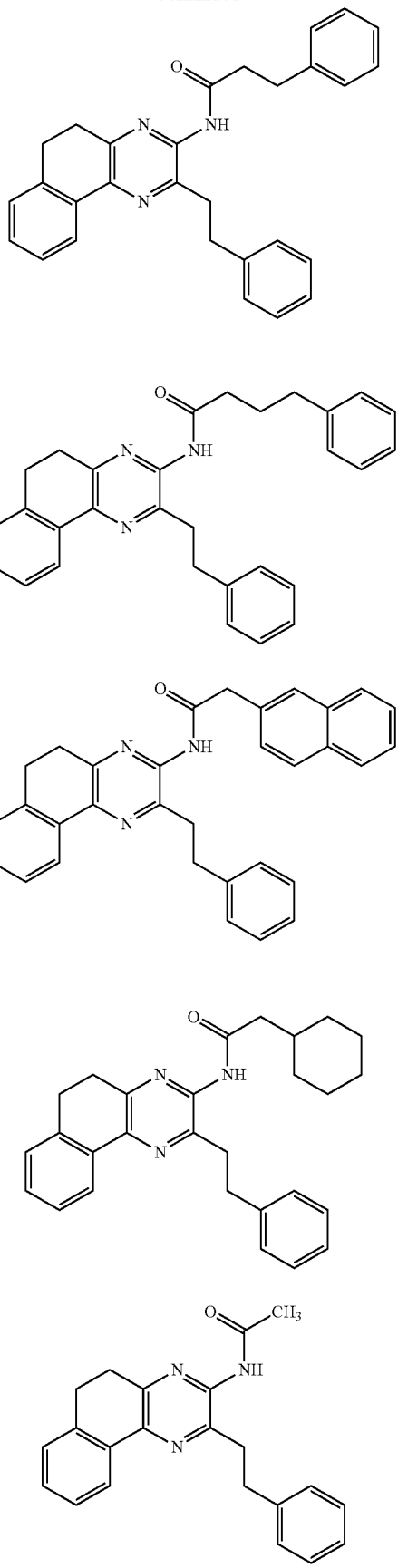

279
-continued
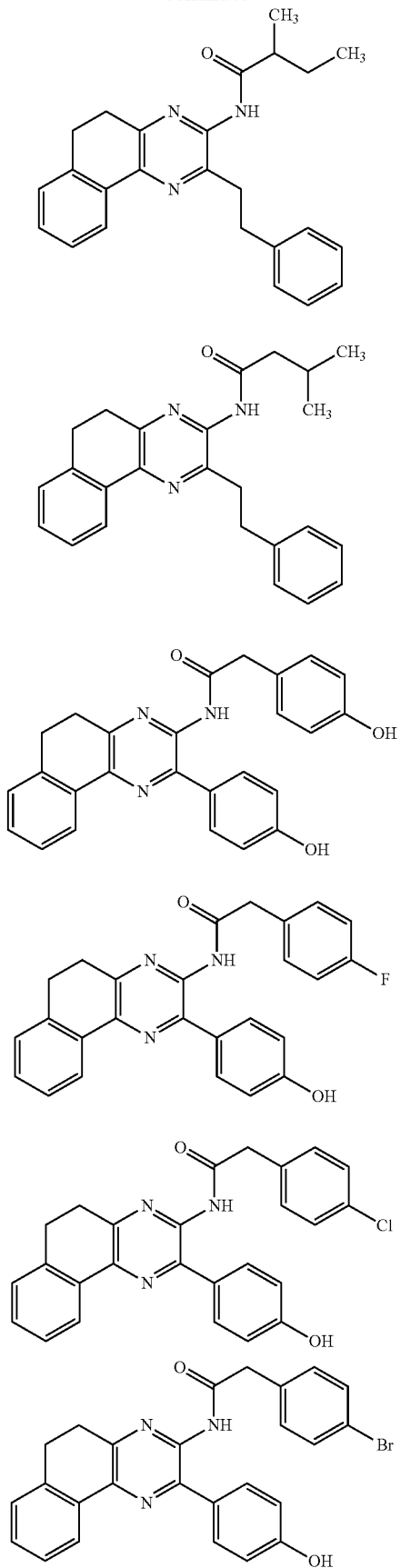
280
-continued
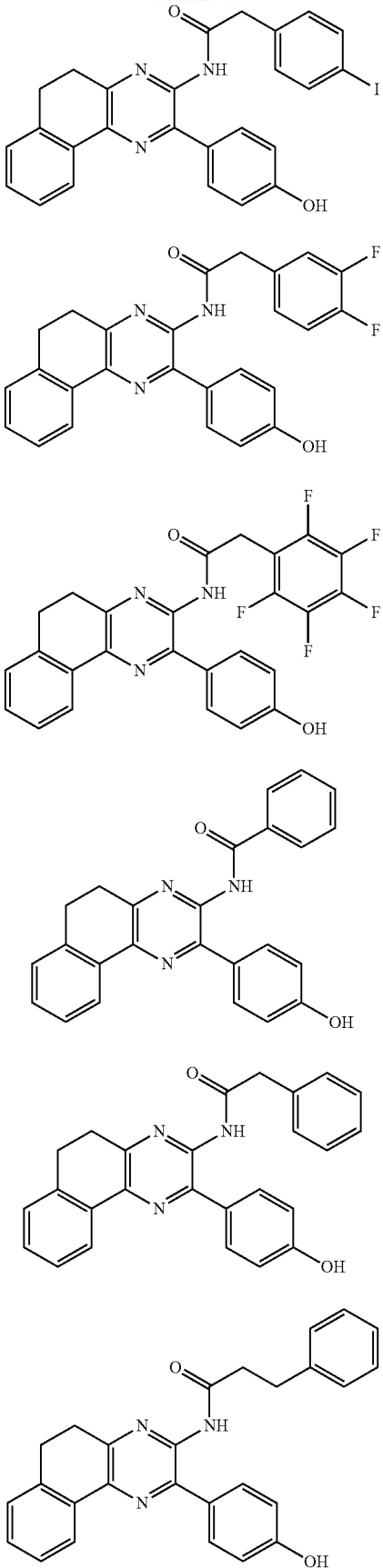

281
-continued
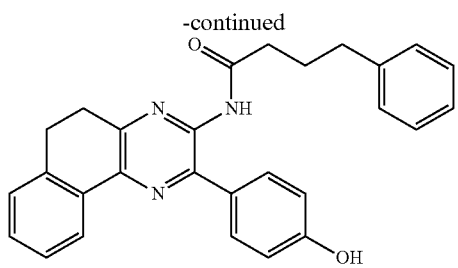
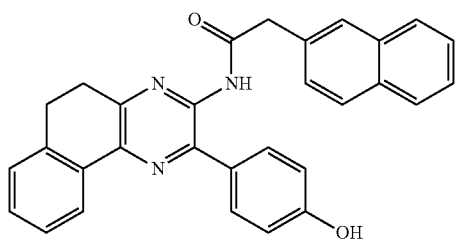
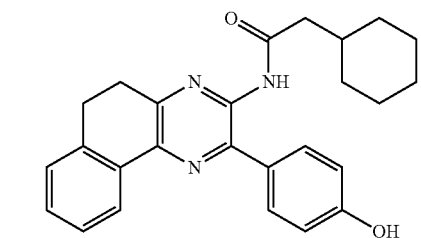
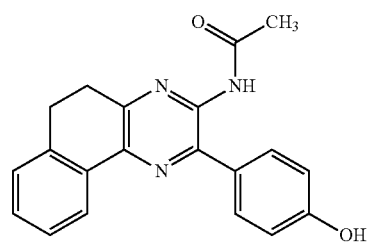
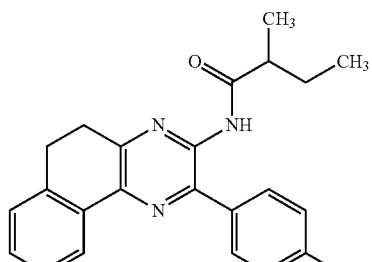
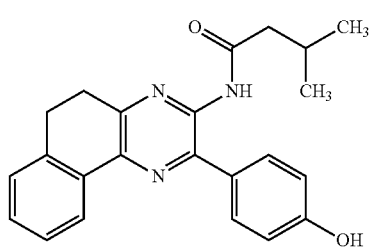
282
-continued
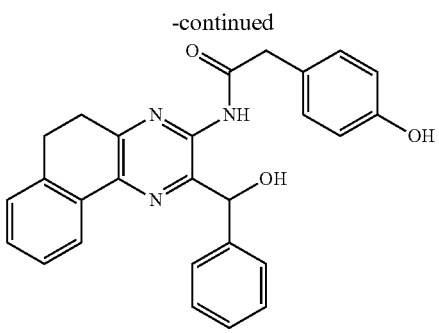
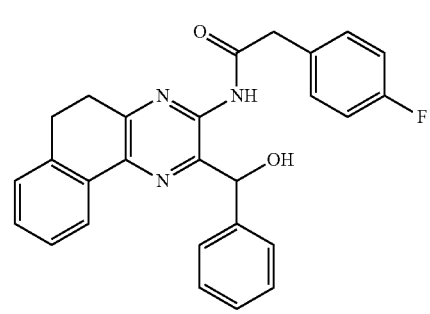
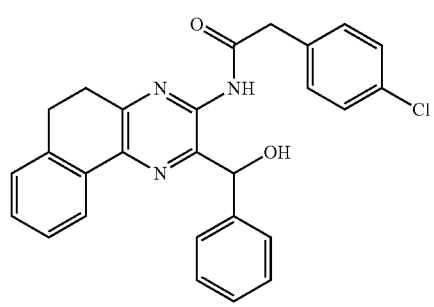
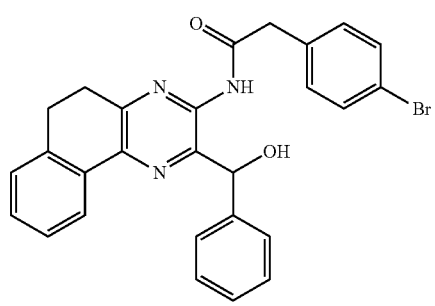
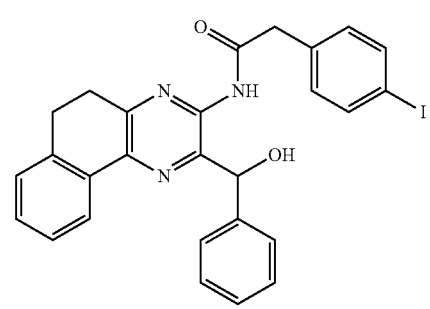

283
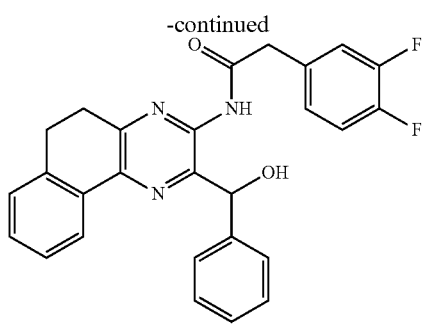
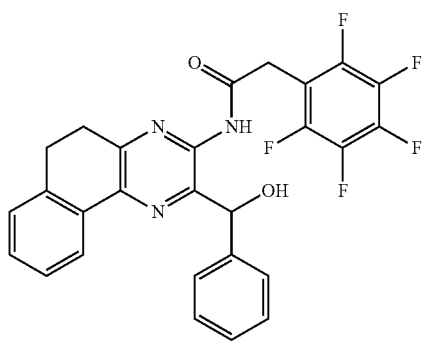
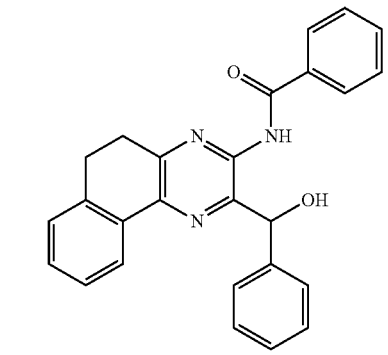
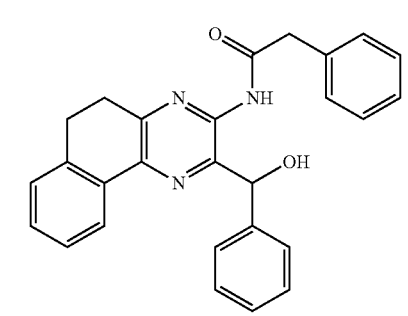
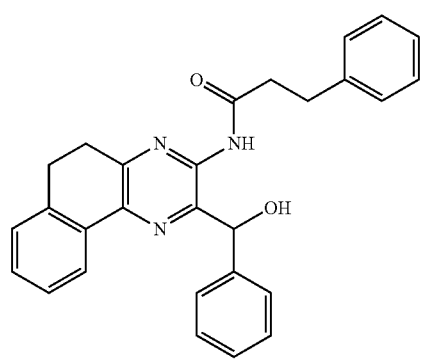
284
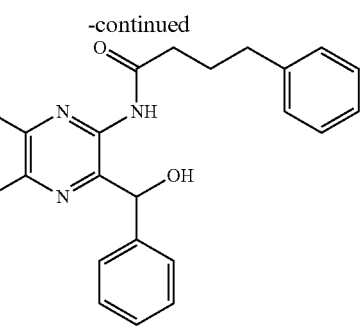
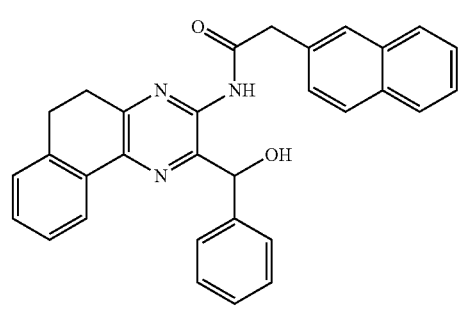
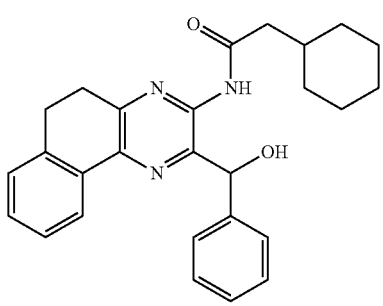
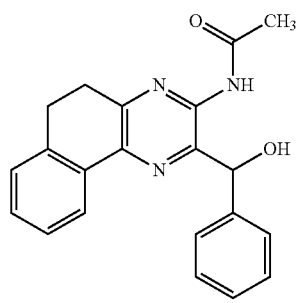
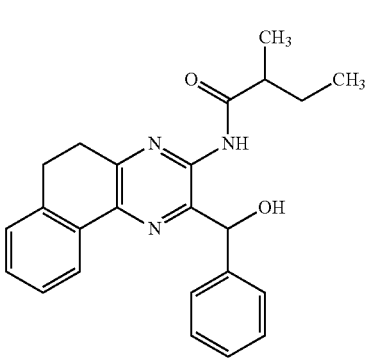

285
-continued
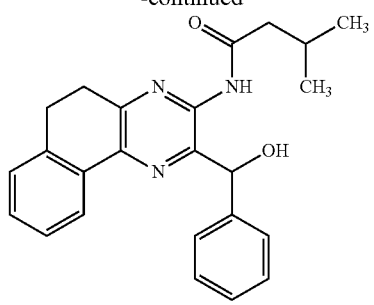
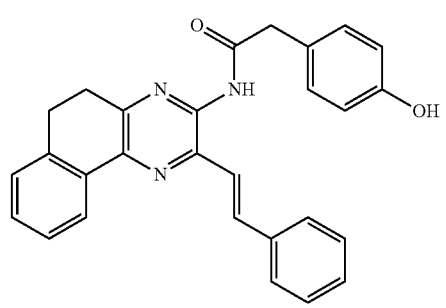
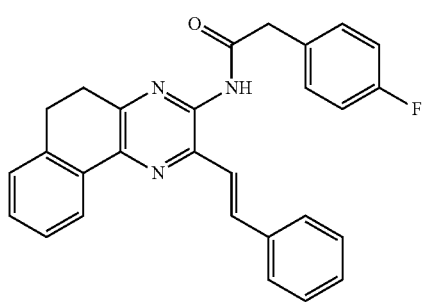
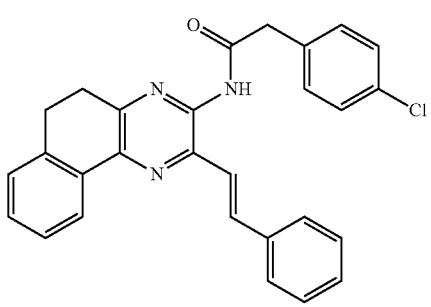
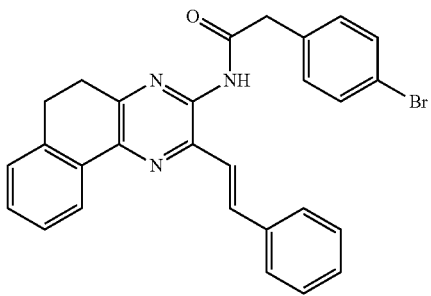
286
-continued
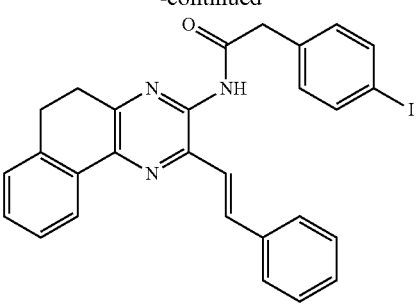
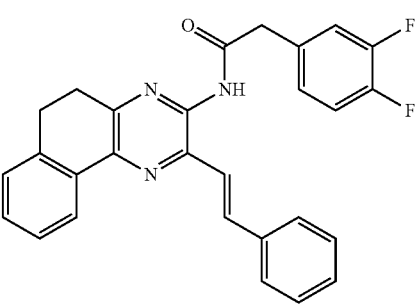
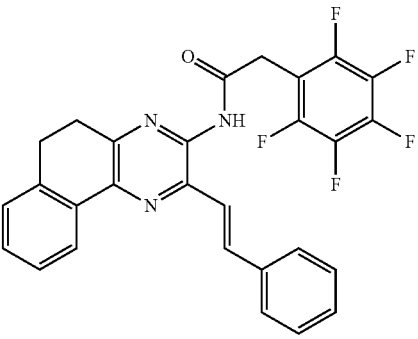
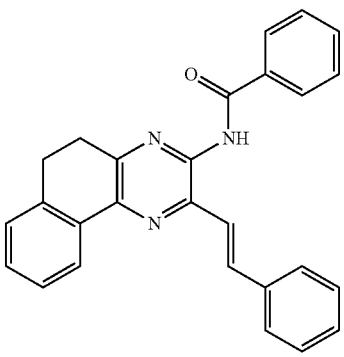
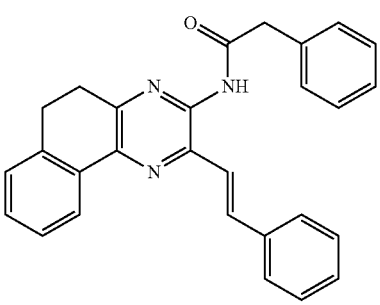

287
-continued
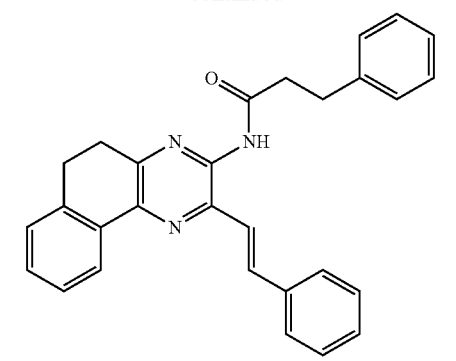
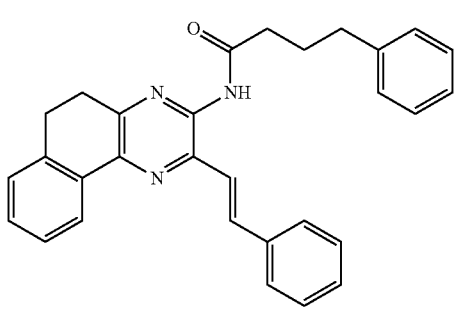
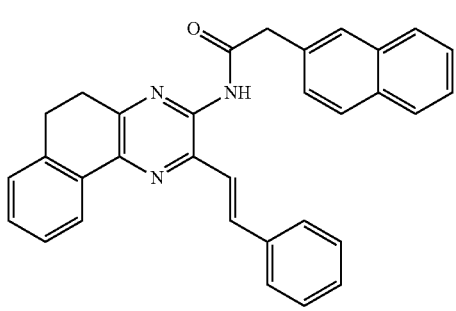
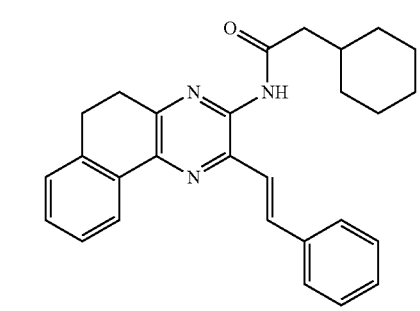
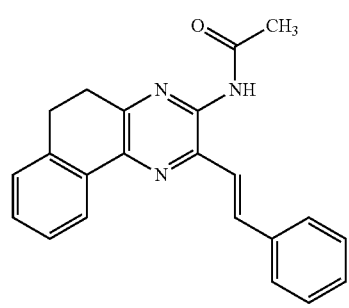
288
-continued
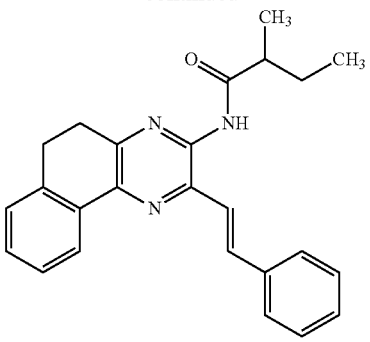
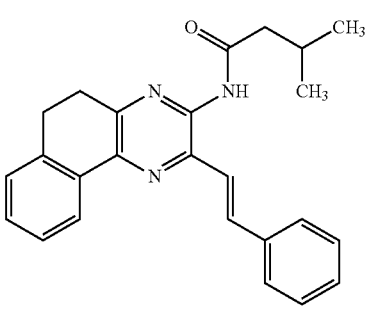
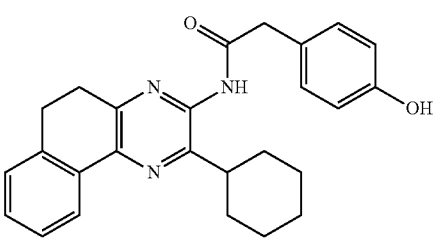
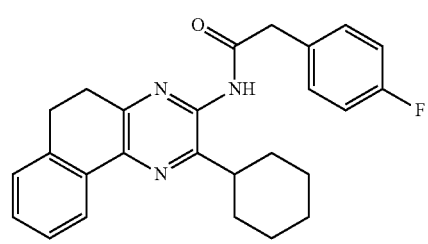
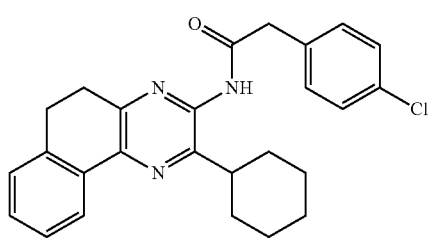
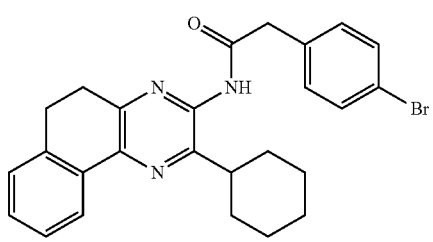

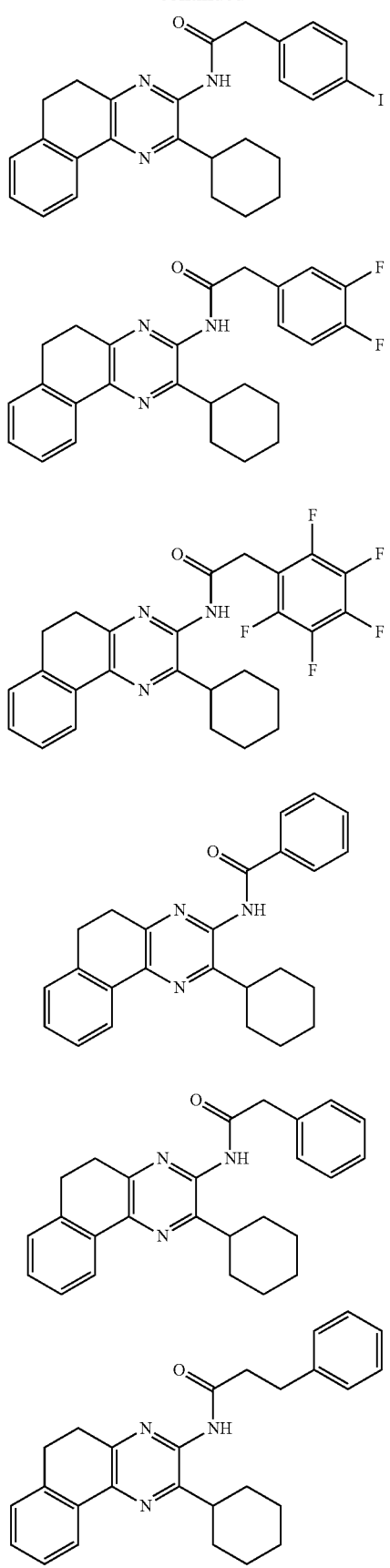
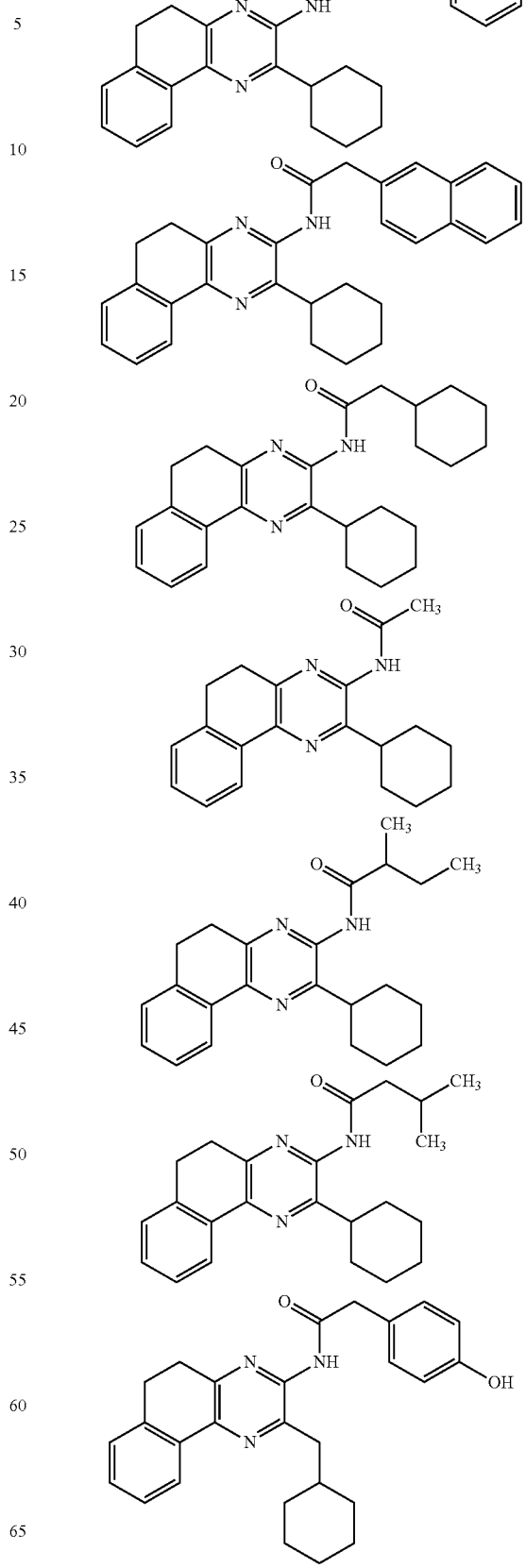

291
-continued
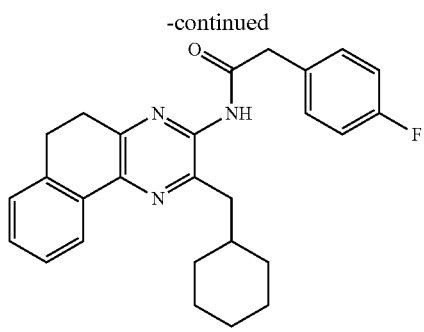
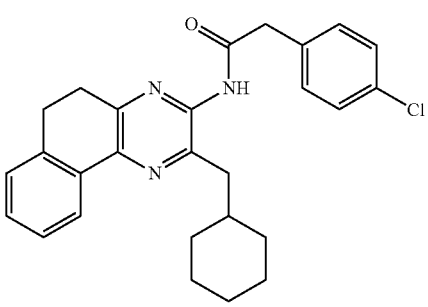
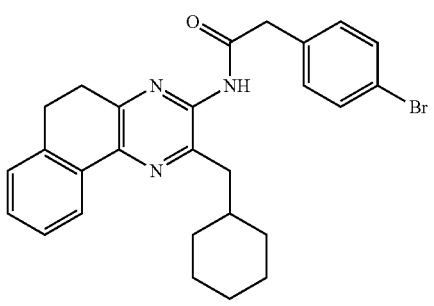
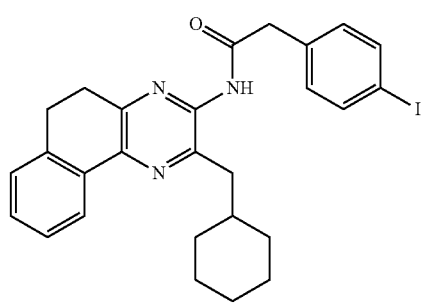
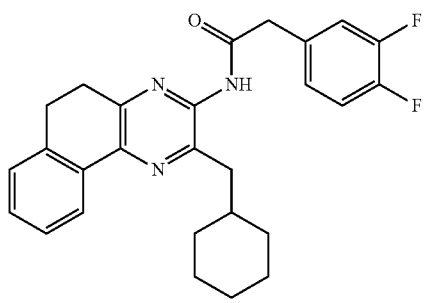
292
-continued
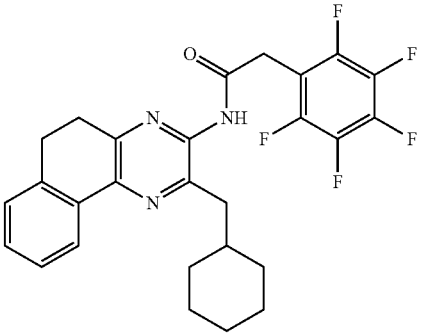
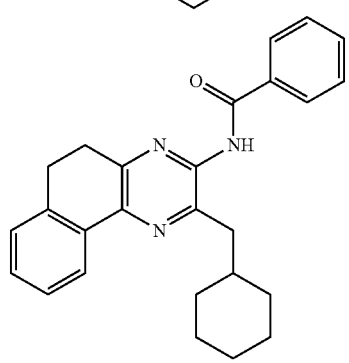
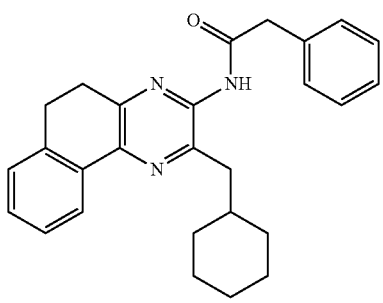
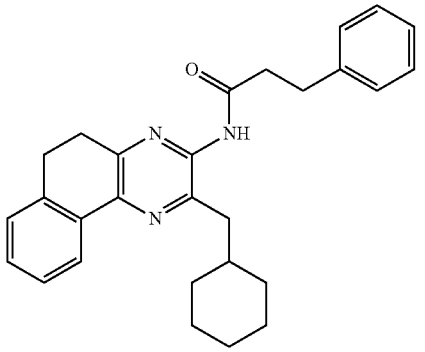
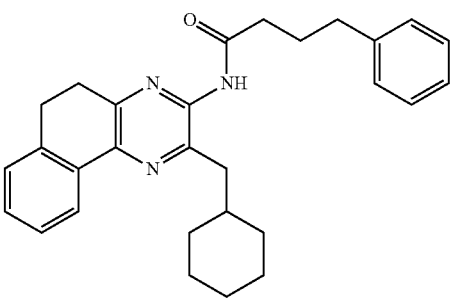

293
-continued
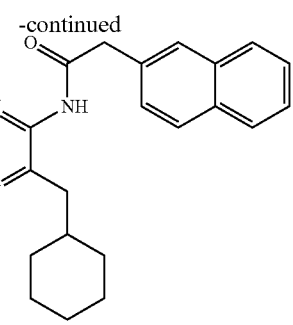
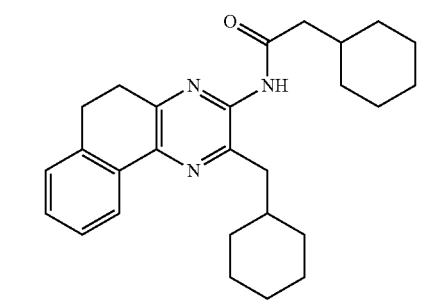
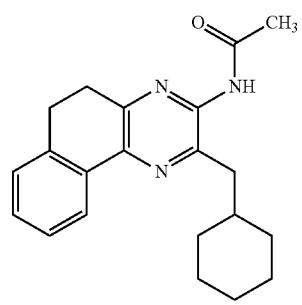
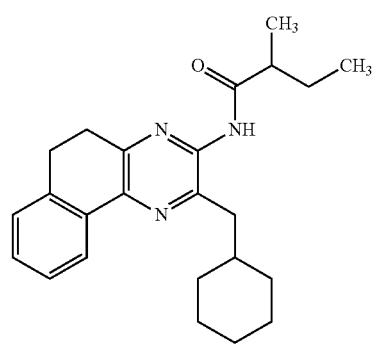
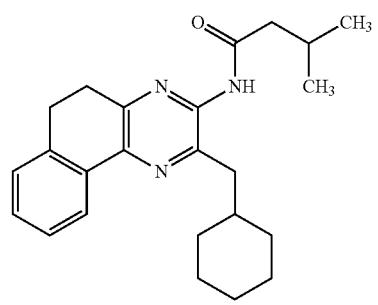
294
-continued
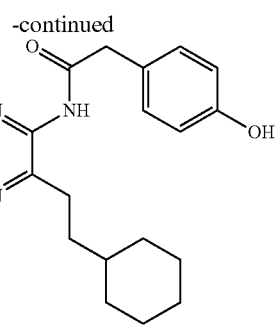
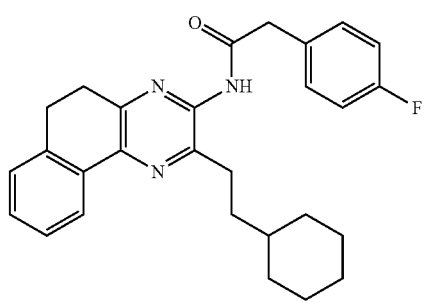
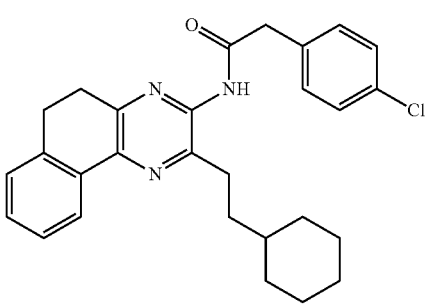
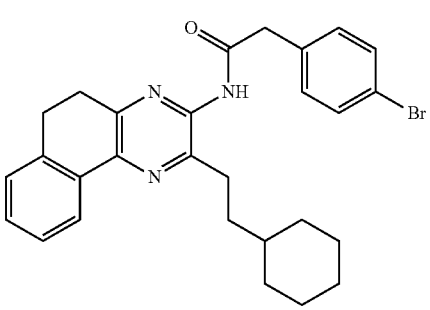
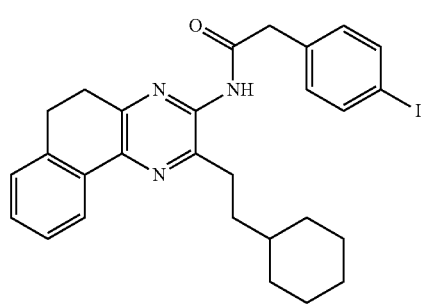

295
-continued
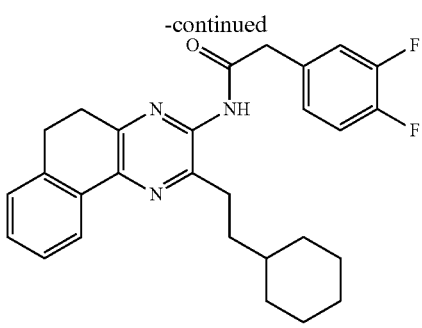
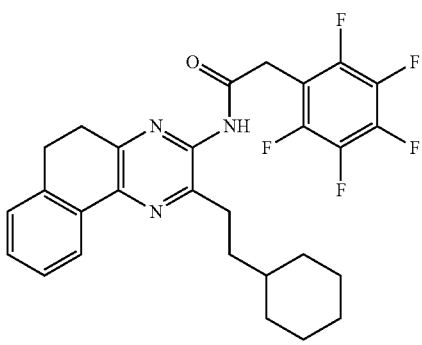
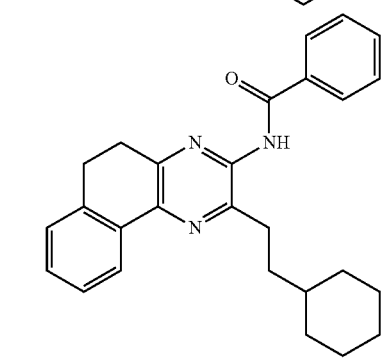
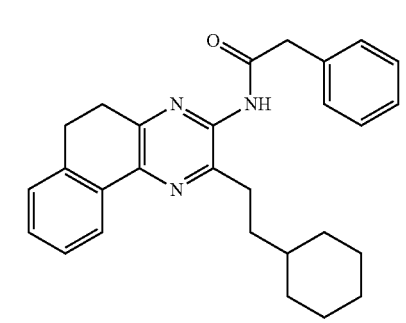
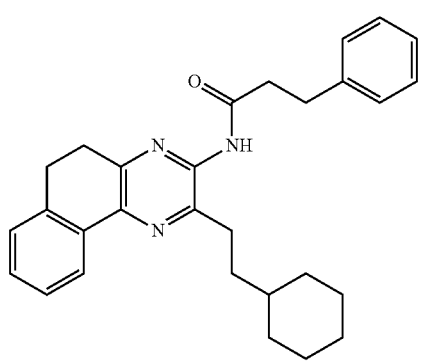
296
-continued
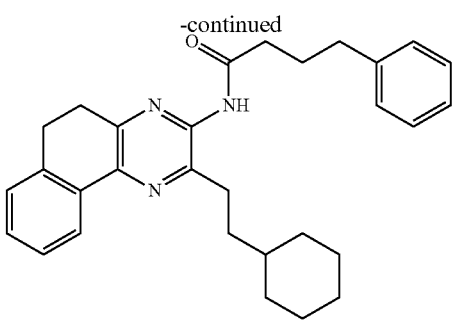
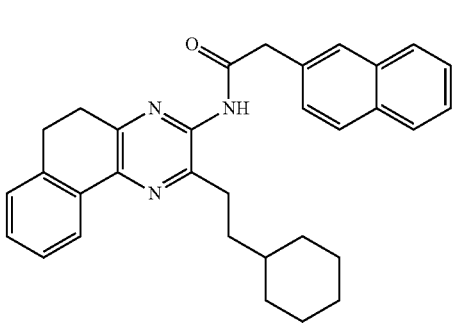
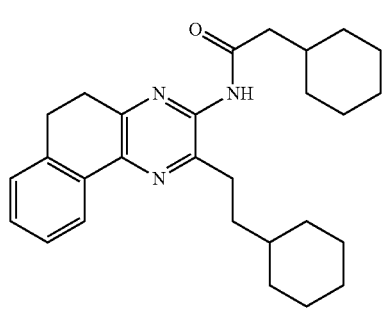
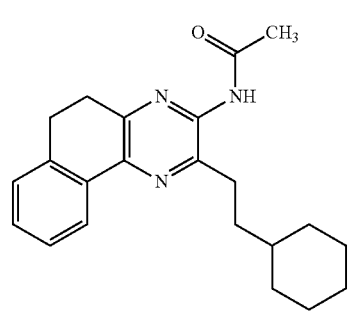
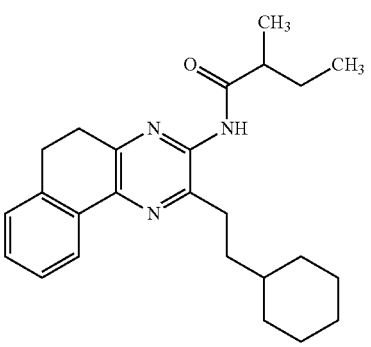

297
-continued
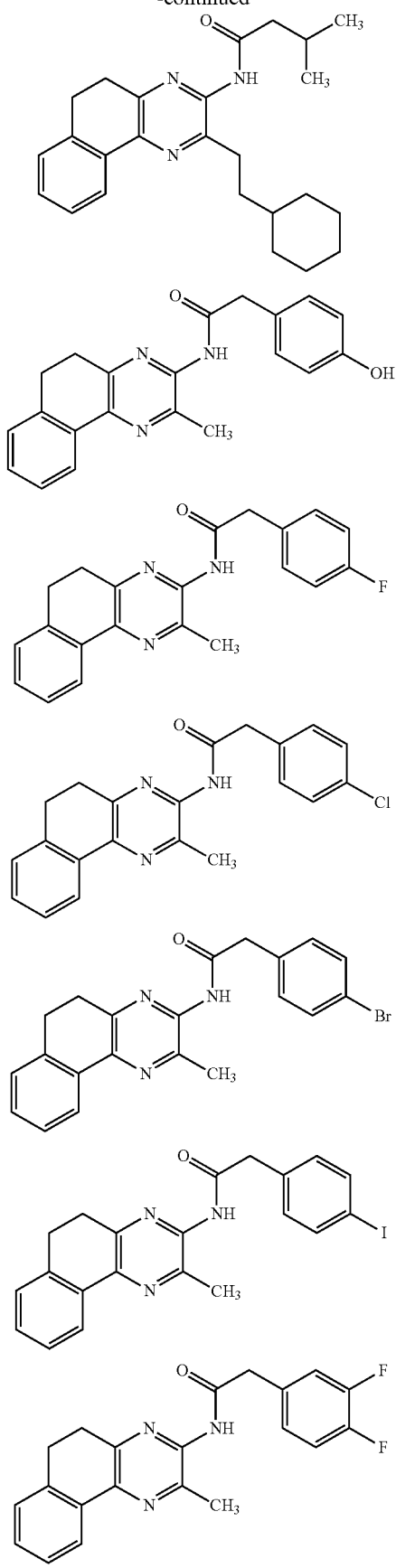
298
-continued
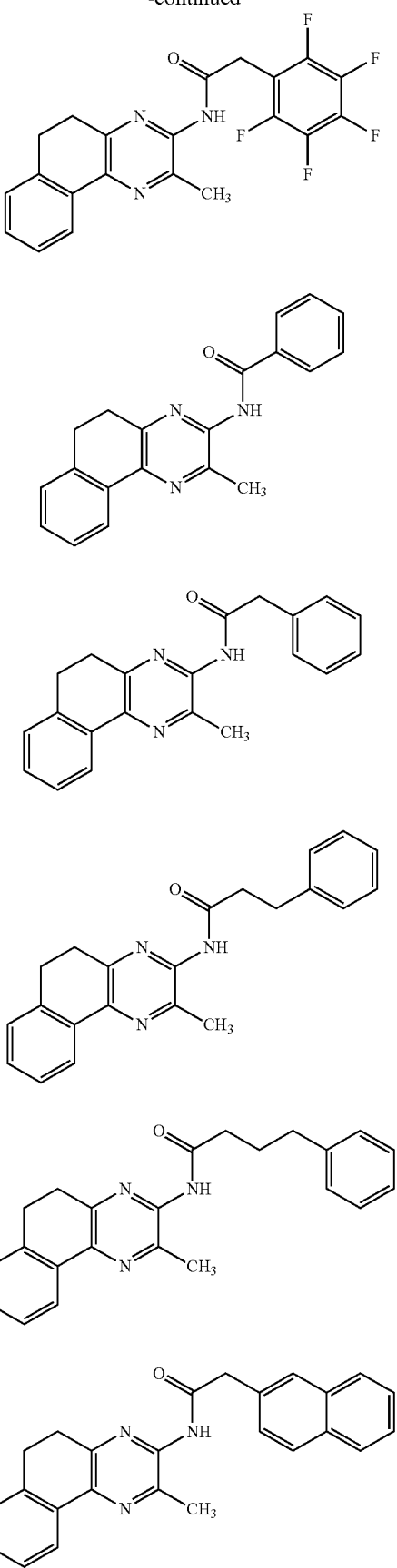

299
-continued
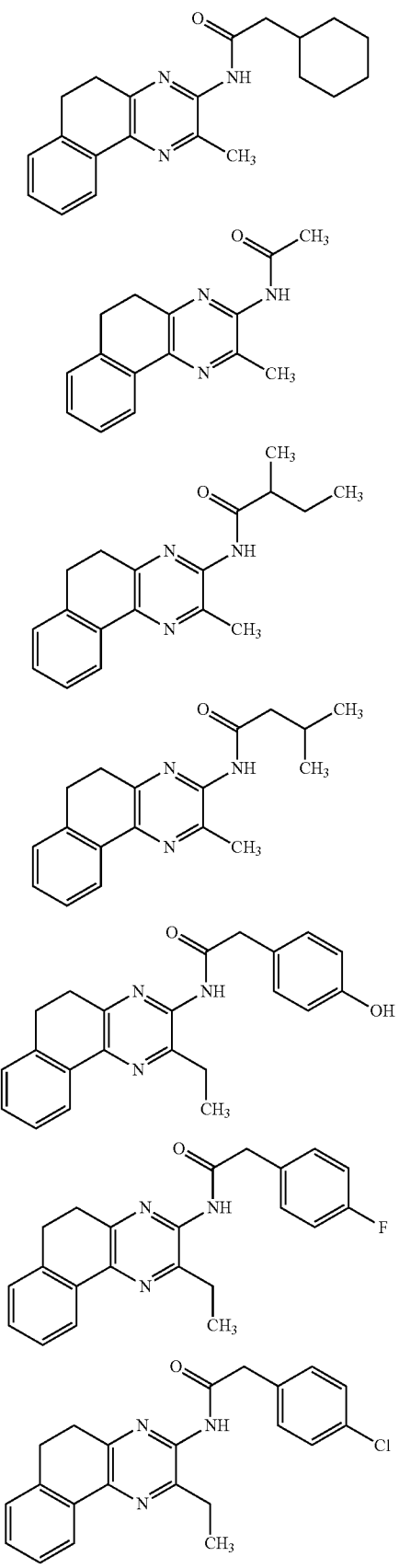
300
-continued
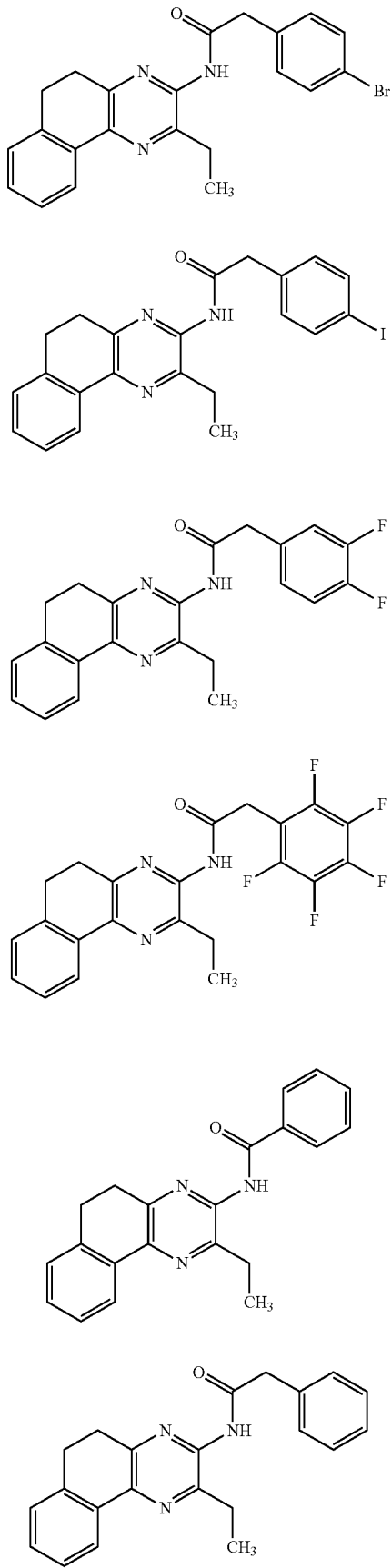

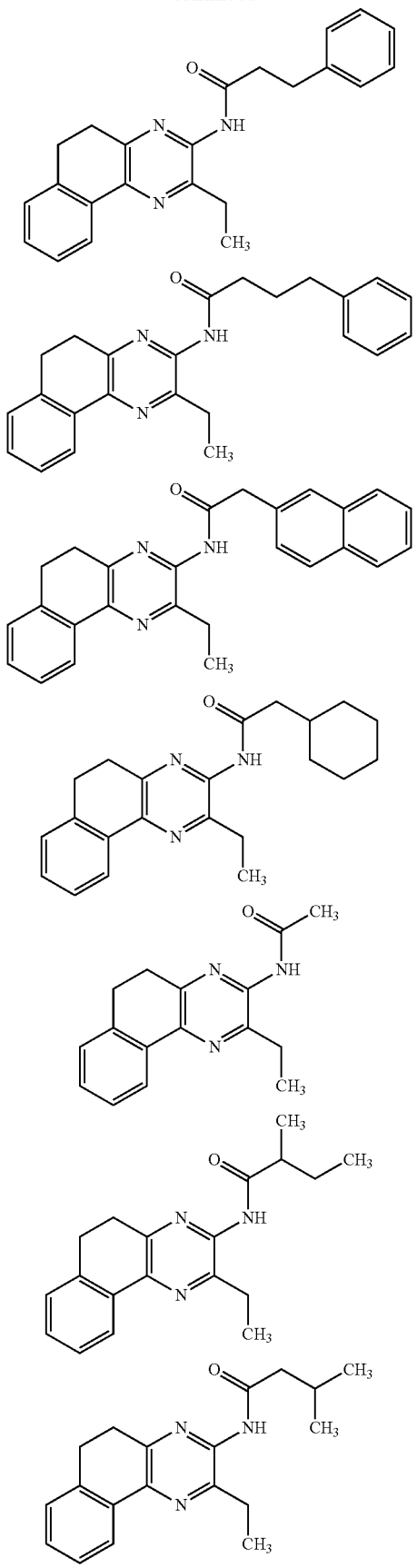
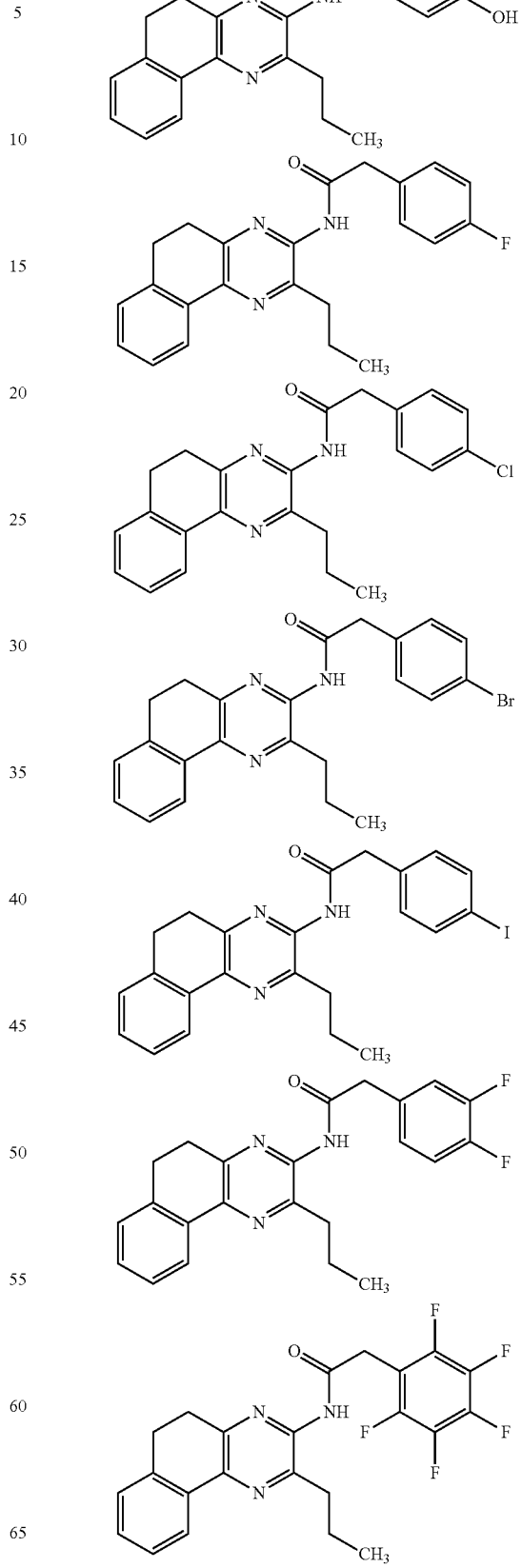

303
-continued
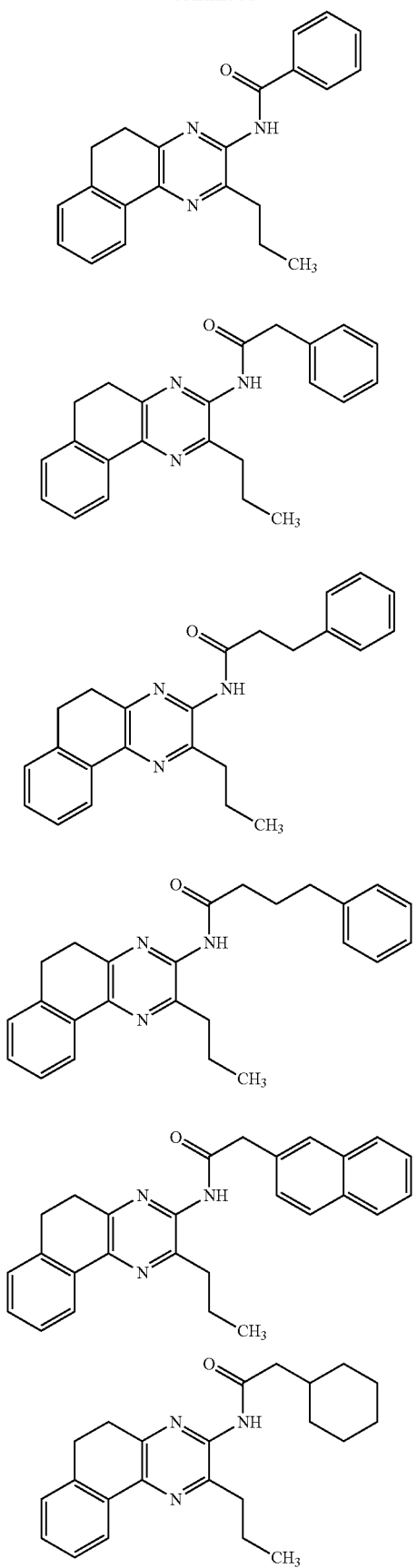
304
-continued
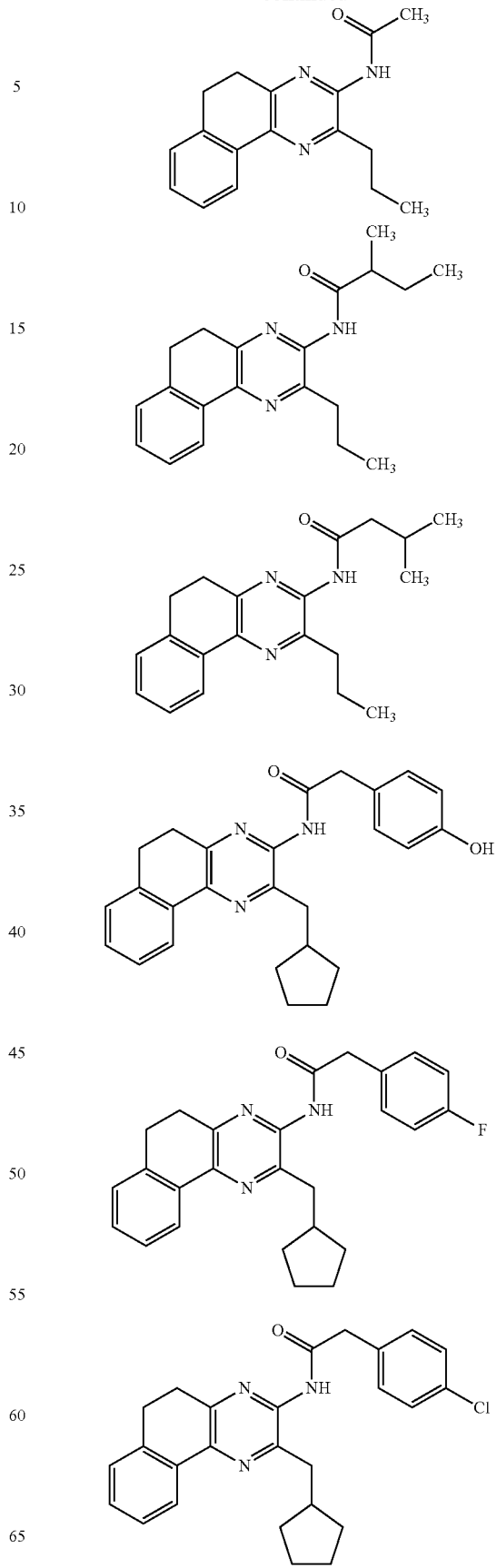

305
-continued
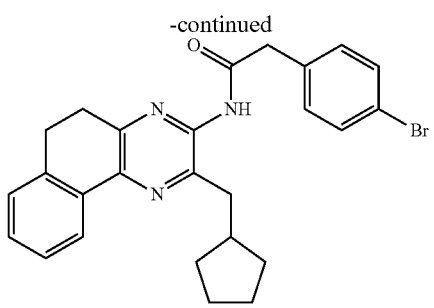
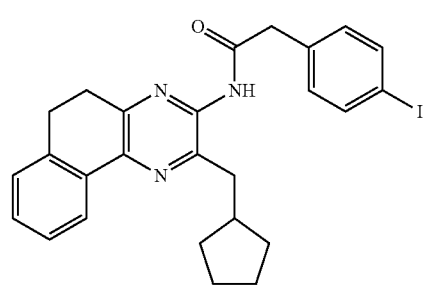

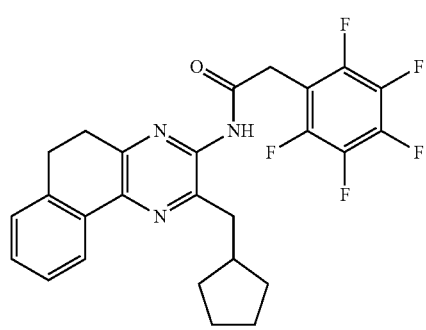
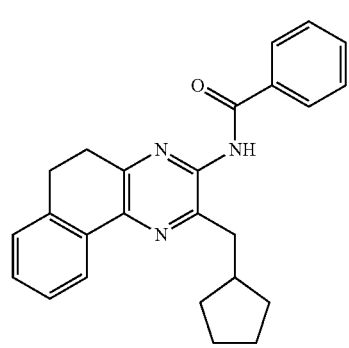
306
-continued
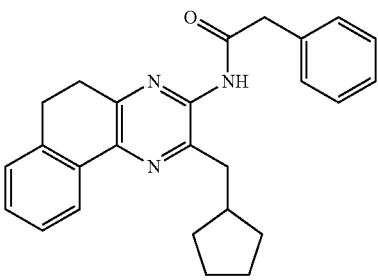
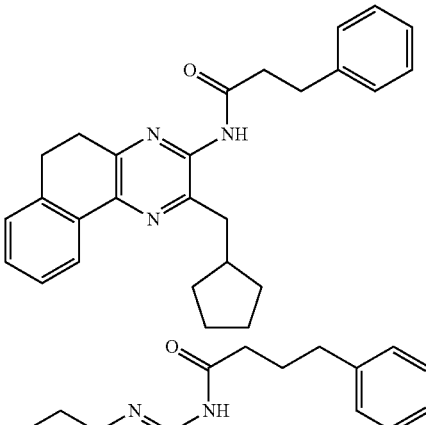
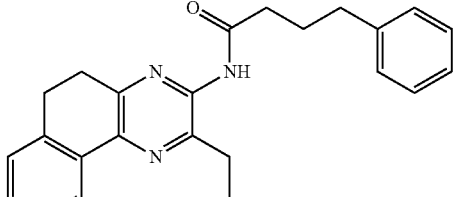
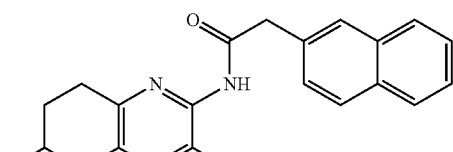
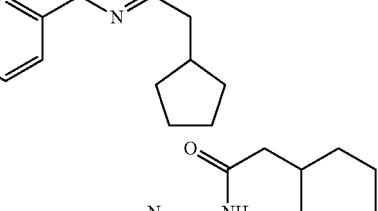
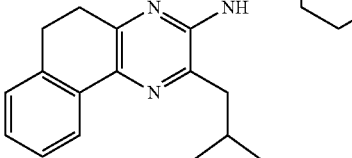
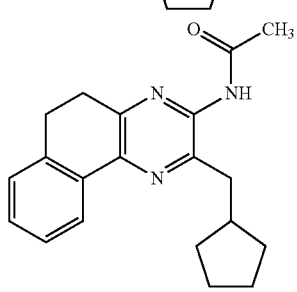

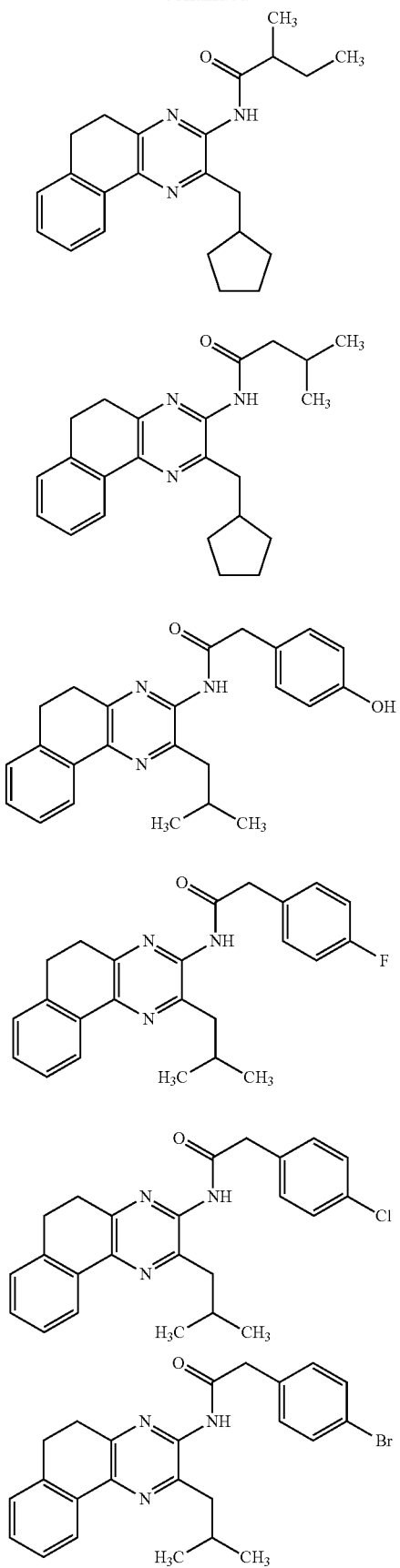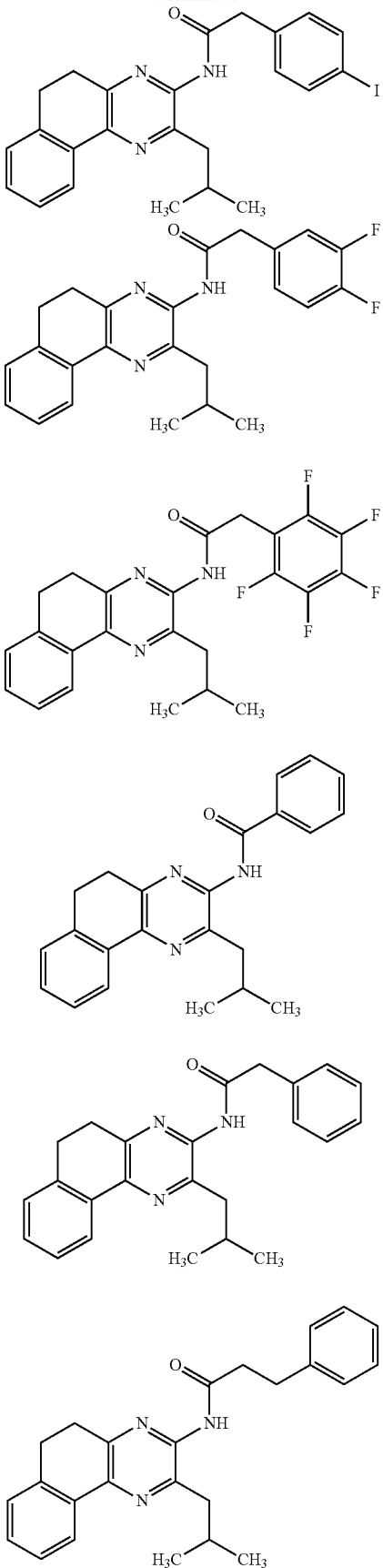

-continued
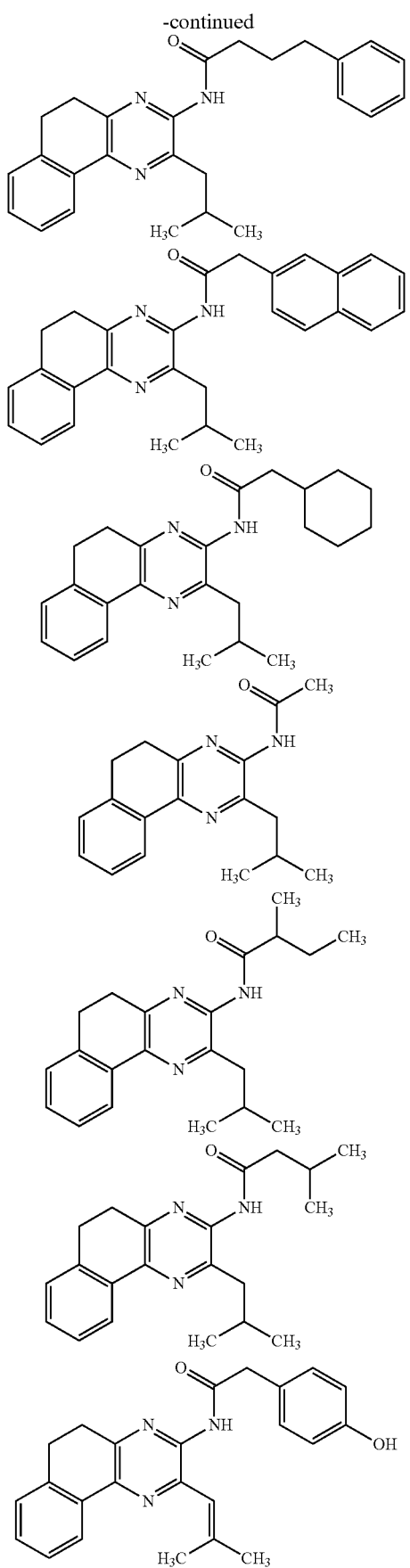
-continued
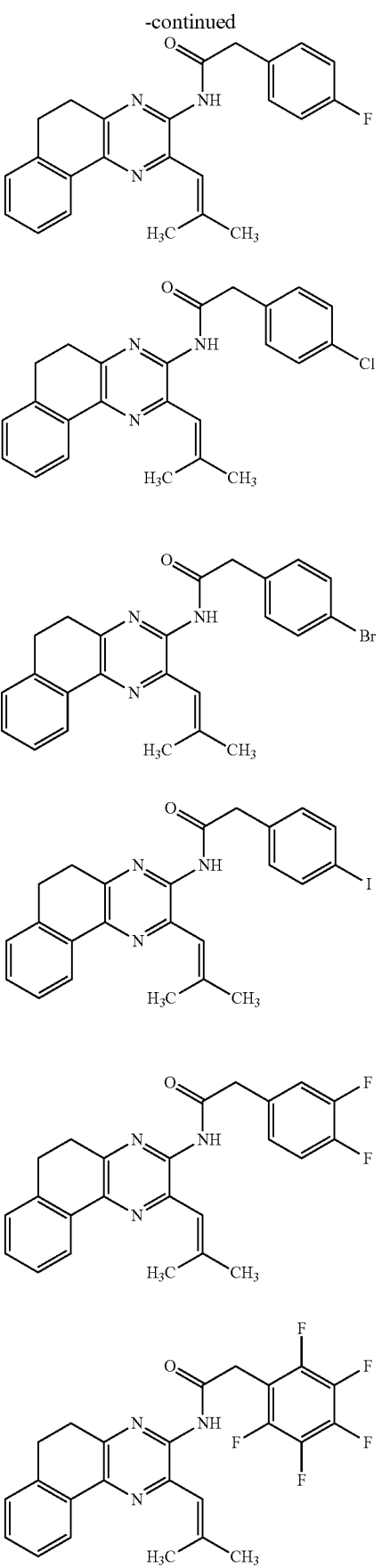

311
-continued
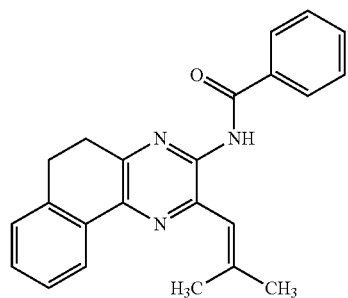
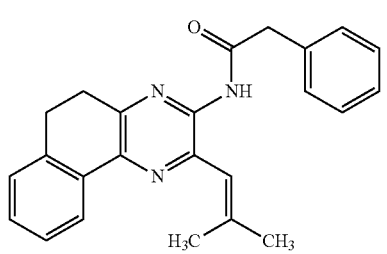
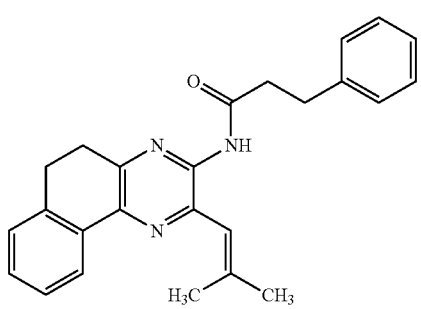
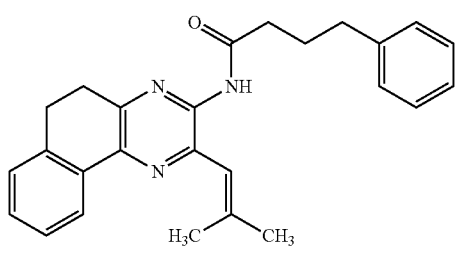
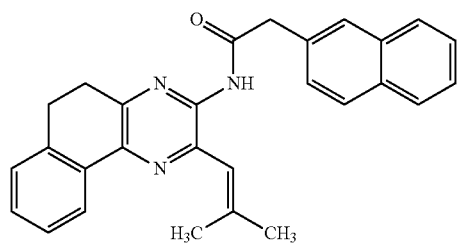
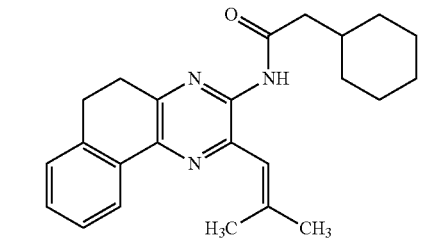
312
-continued
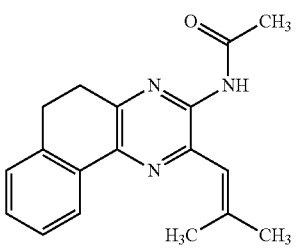
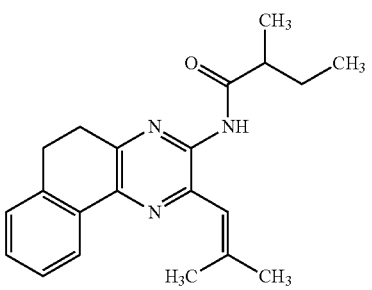
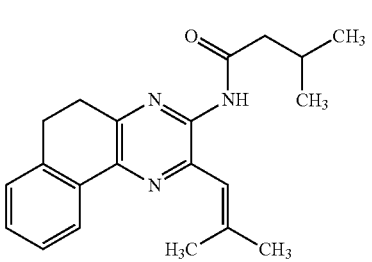
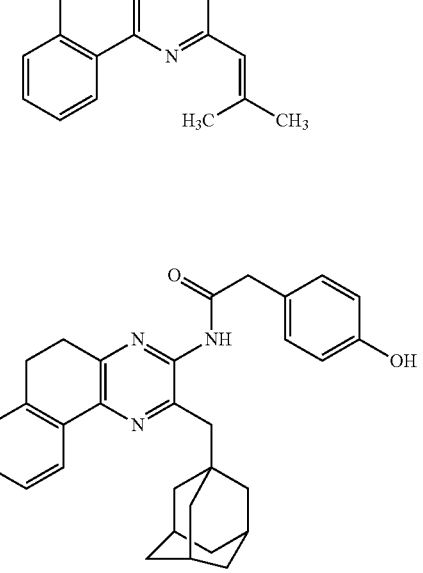
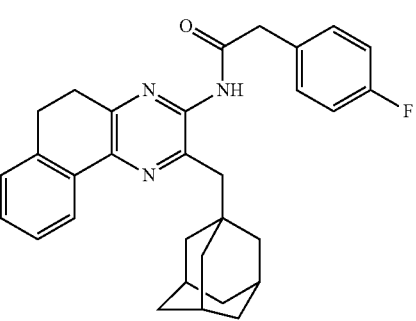

313
-continued
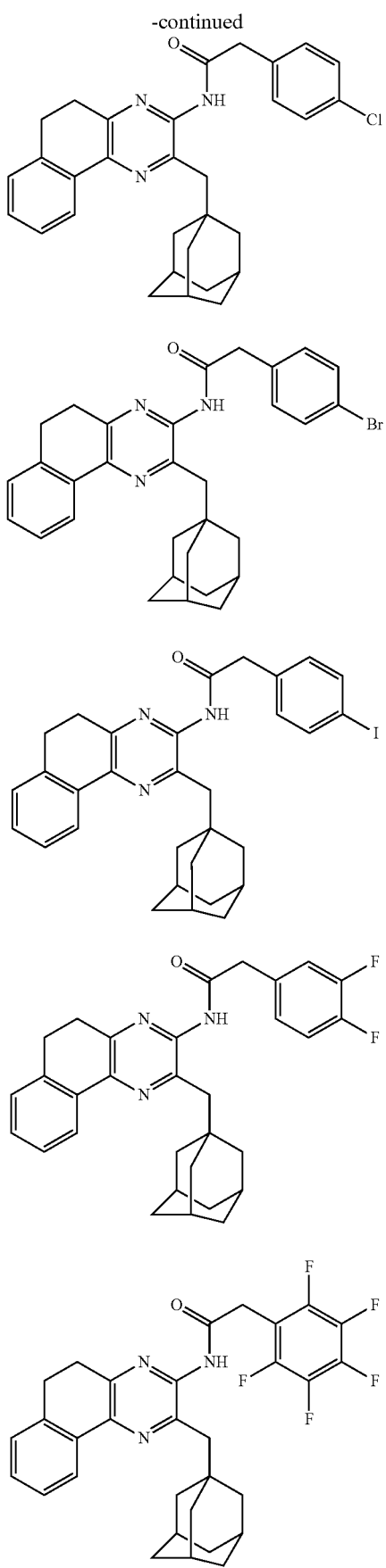
314
-continued
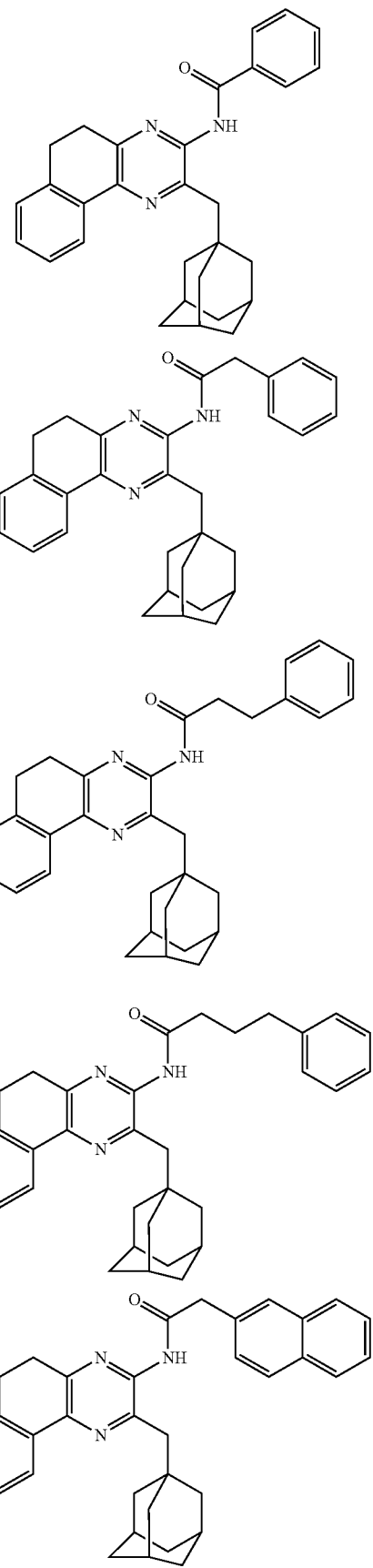

315
-continued
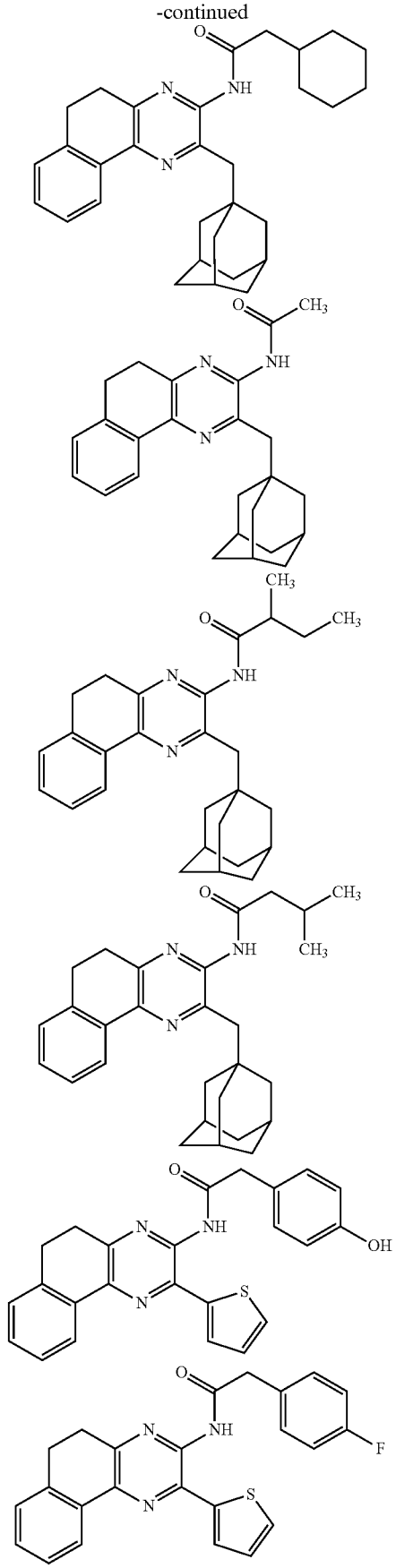
316
-continued
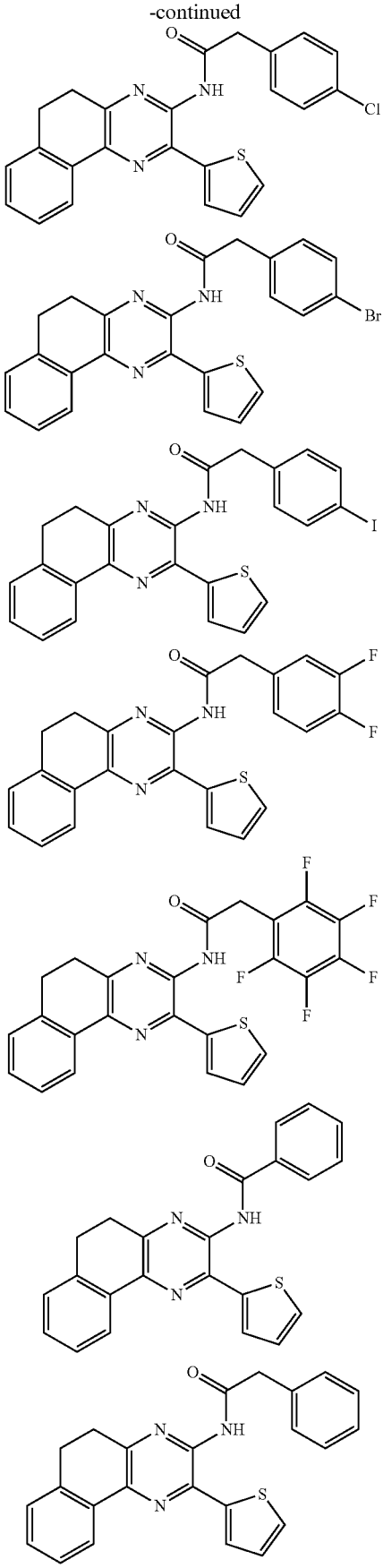

317
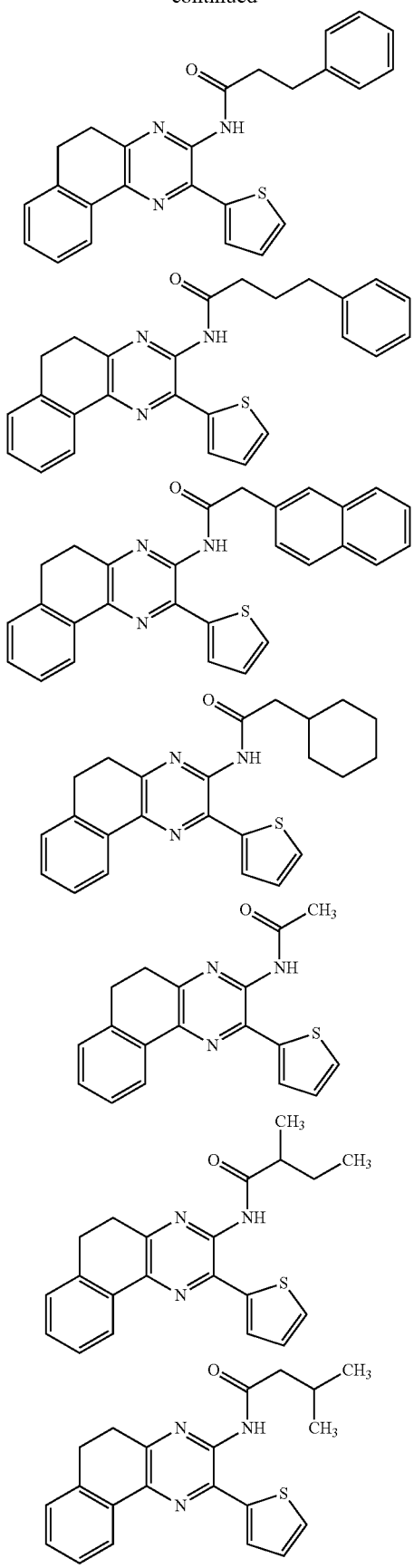
318
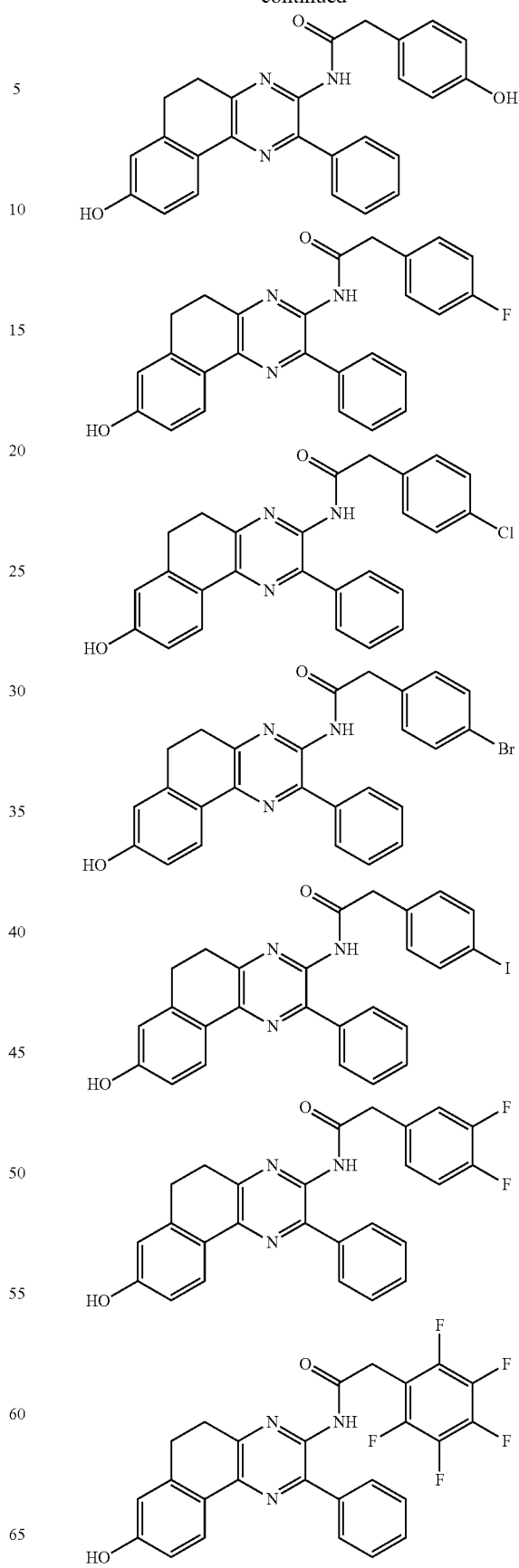

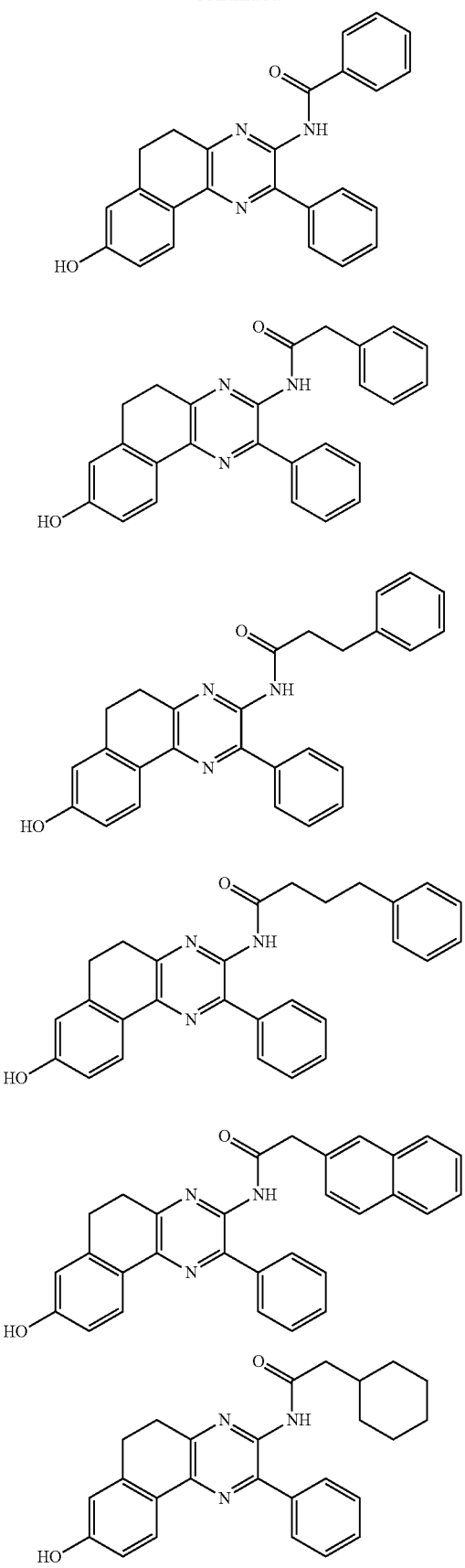
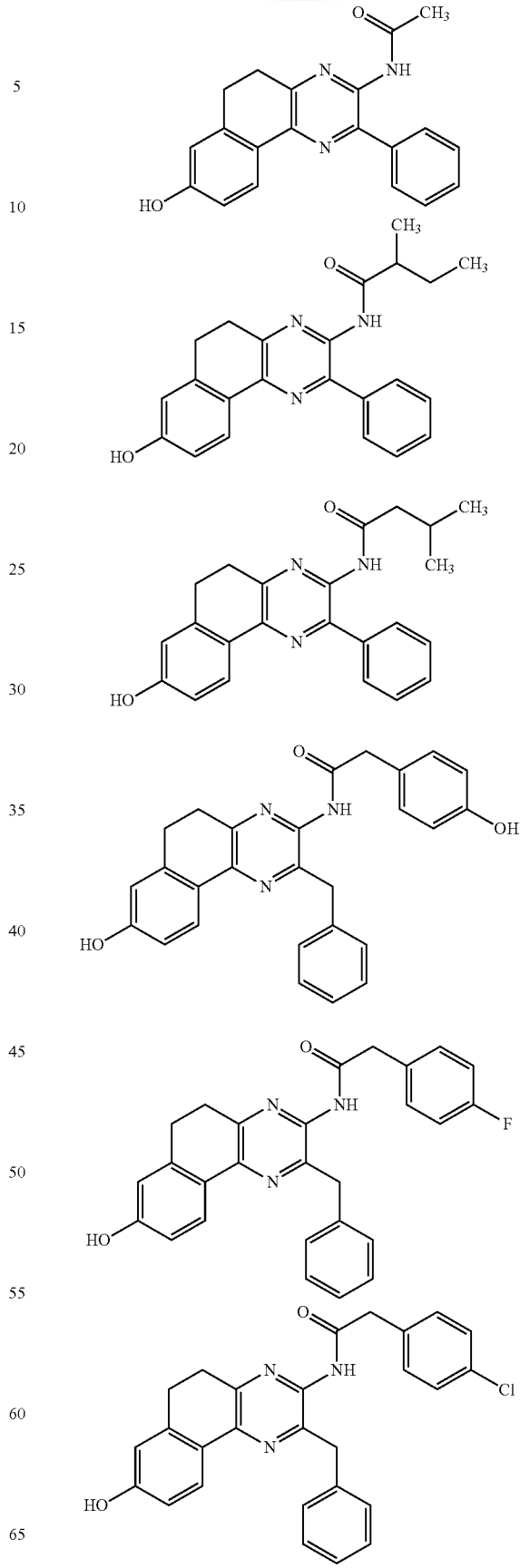

321
-continued
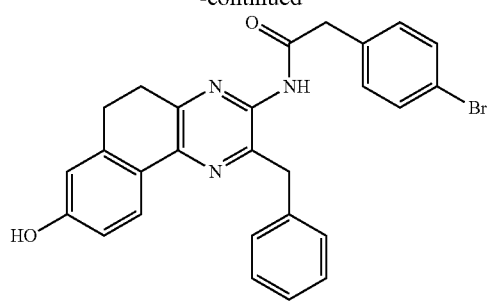
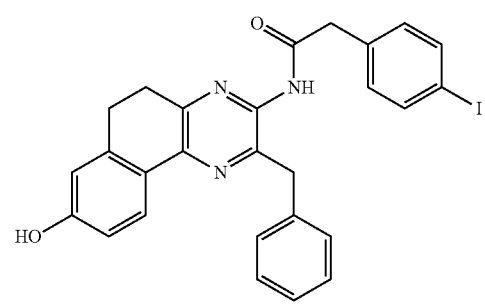
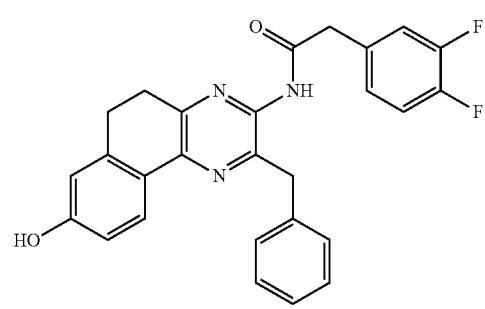
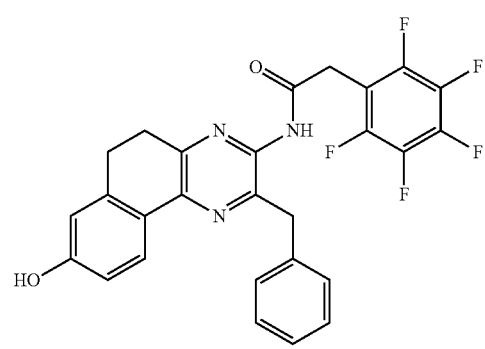
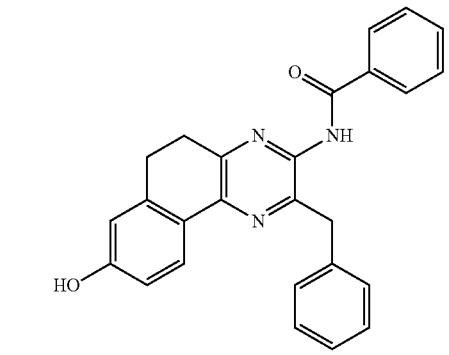
322
-continued
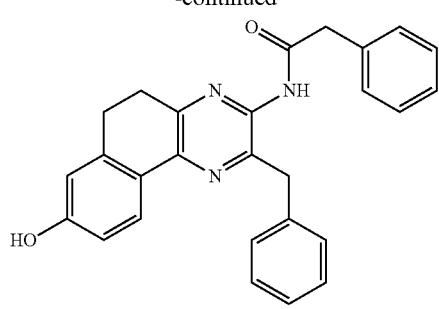
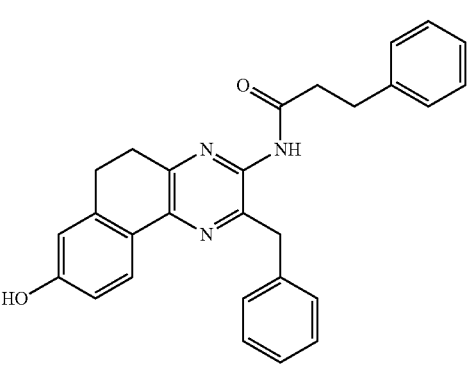
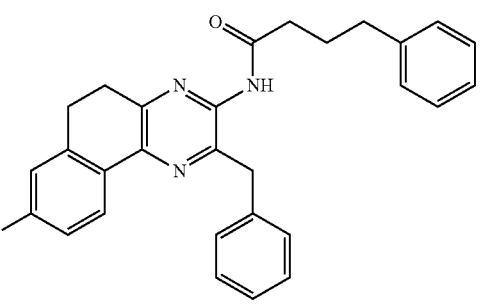
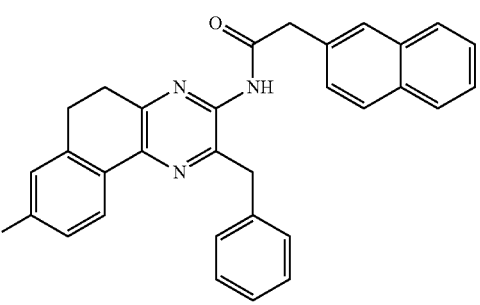
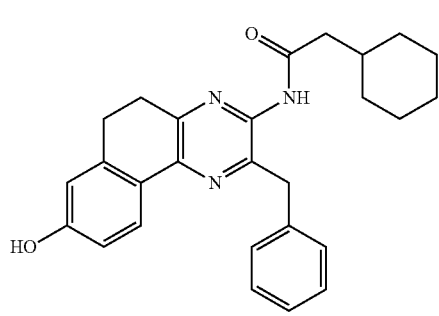

323
-continued
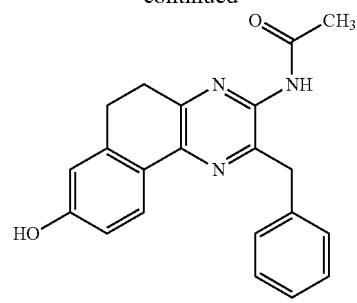
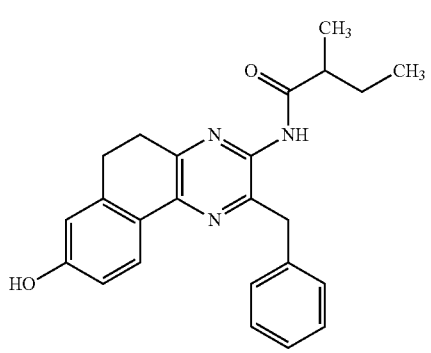
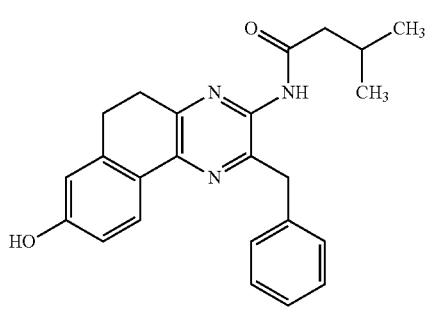
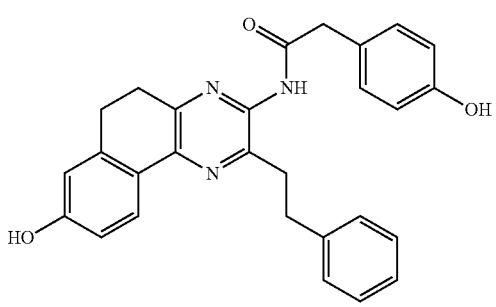
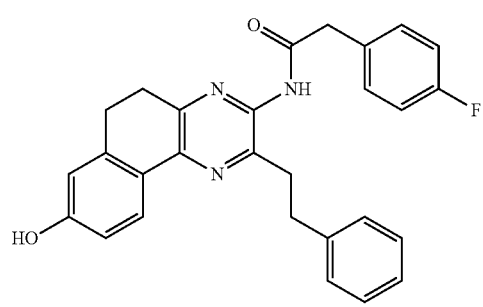
324
-continued
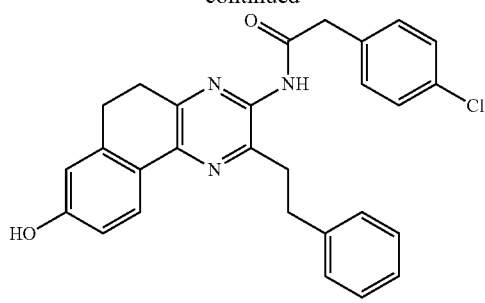
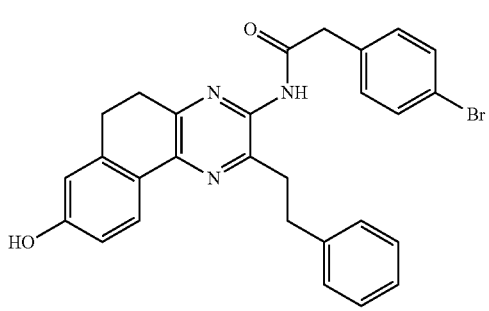
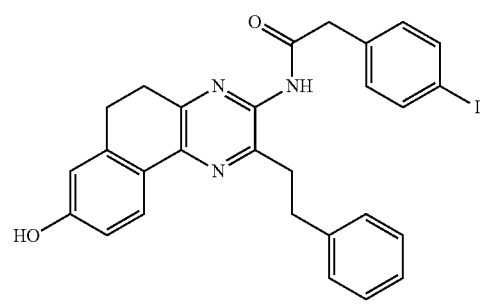
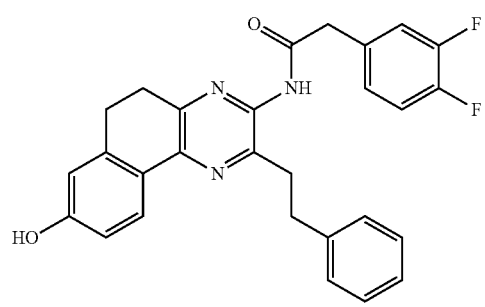
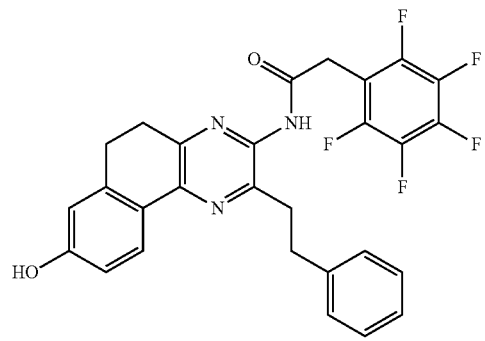

325
-continued
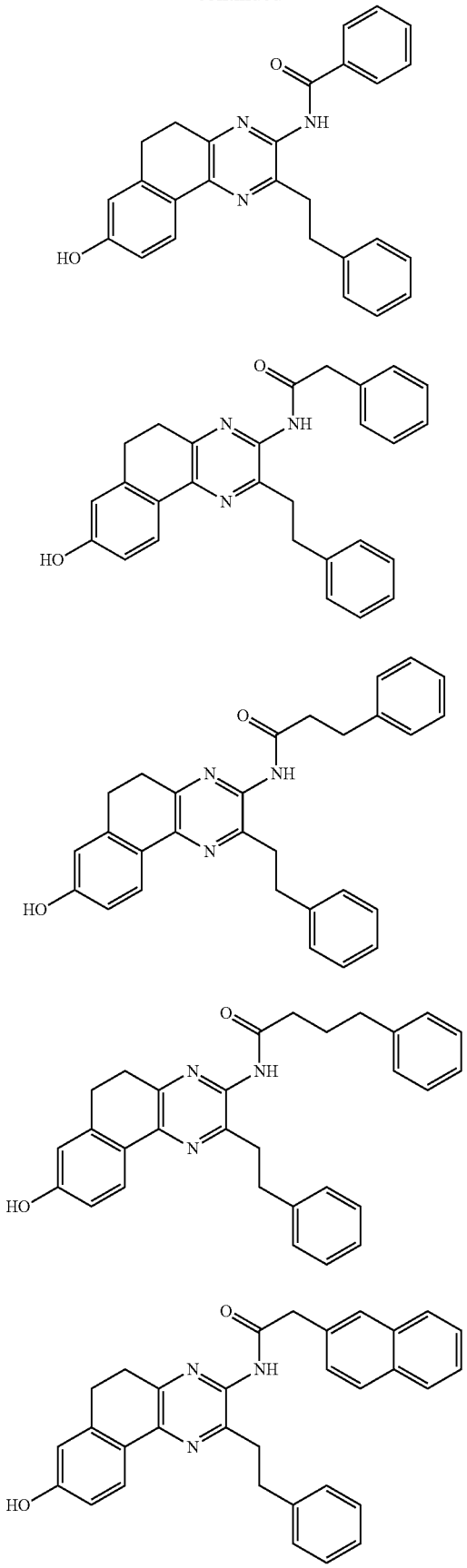
326
-continued
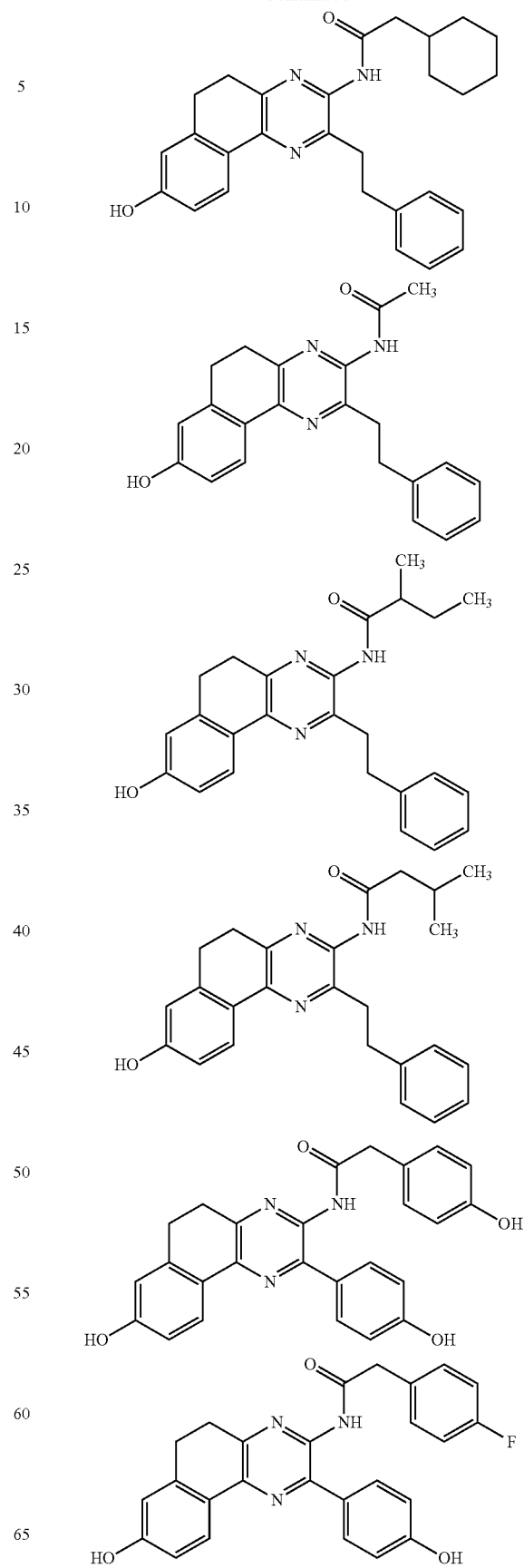

327
-continued
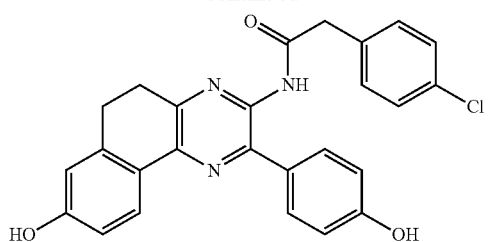
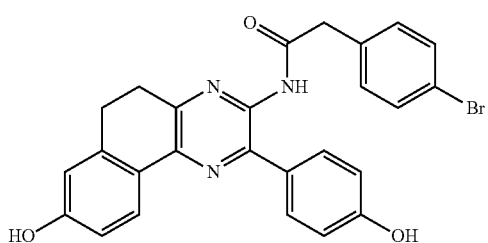
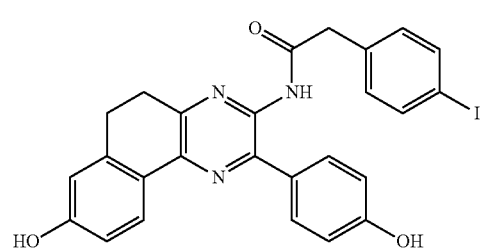
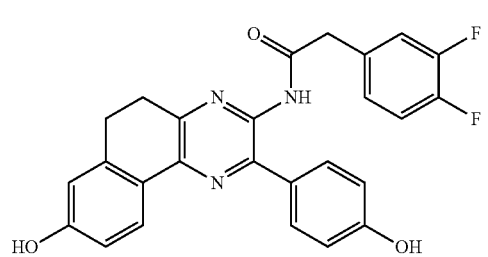
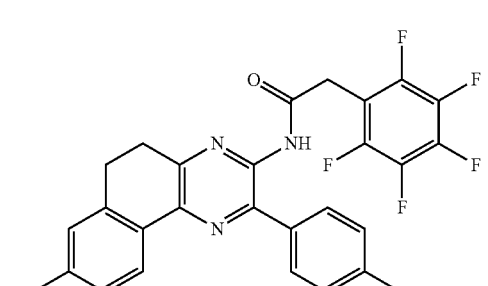
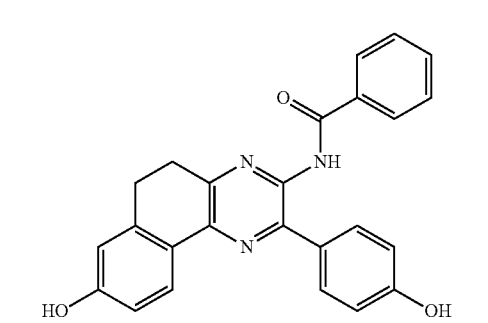
328
-continued
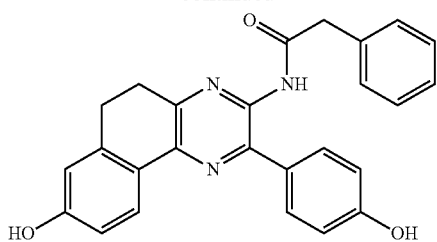
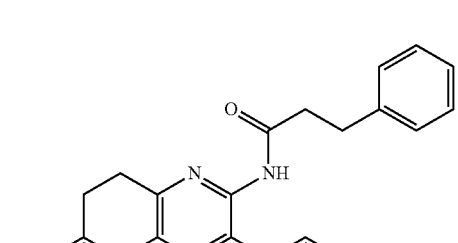
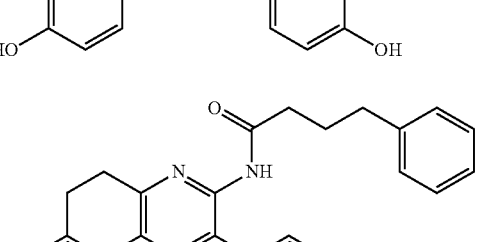
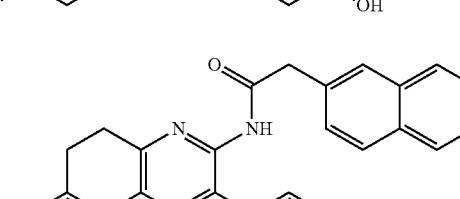
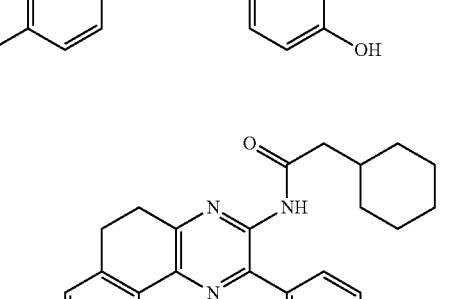
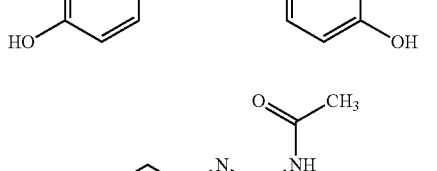
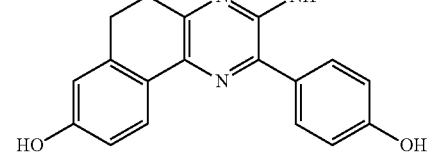

329
-continued
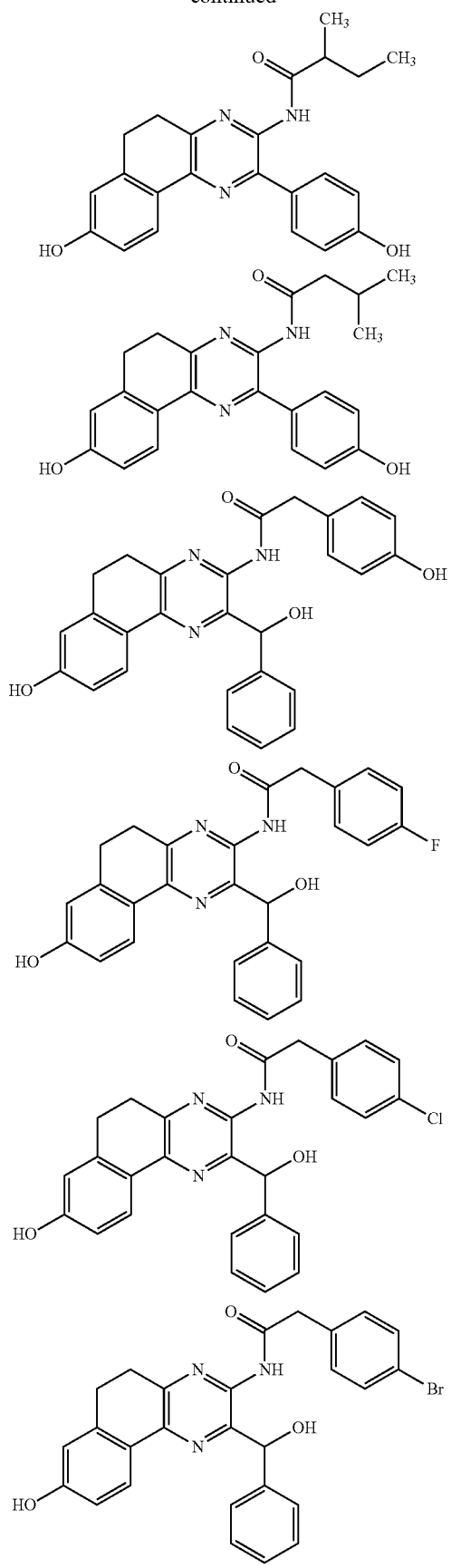
330
-continued
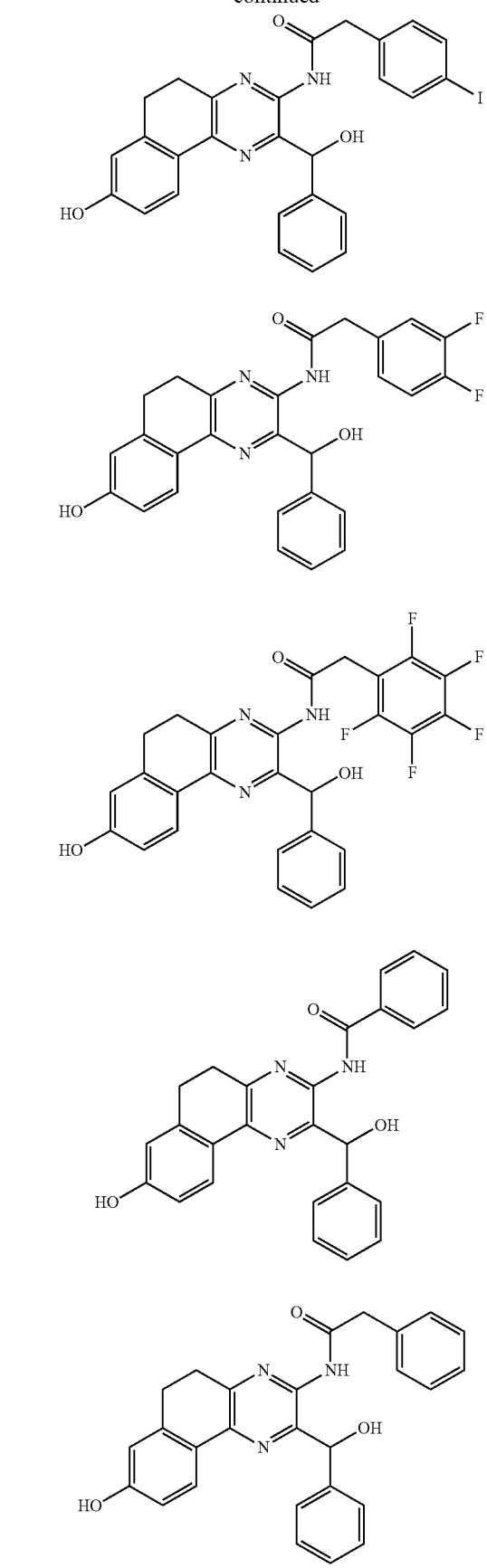

331
-continued
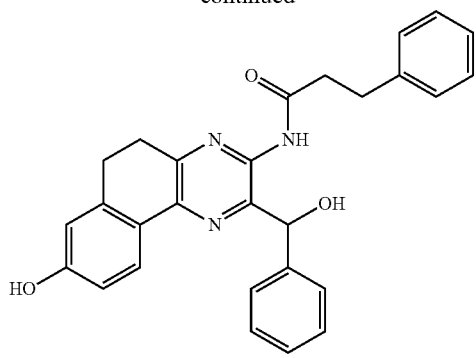
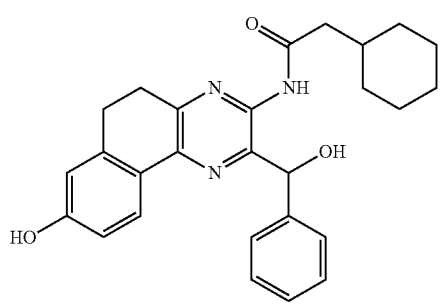
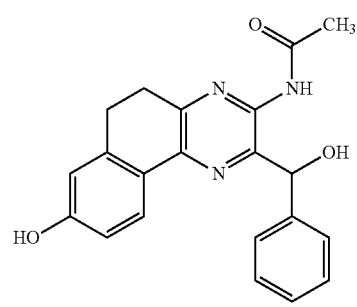
332
-continued
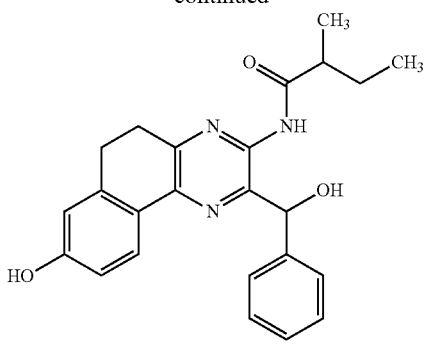
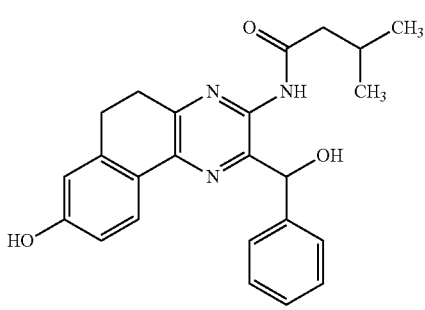
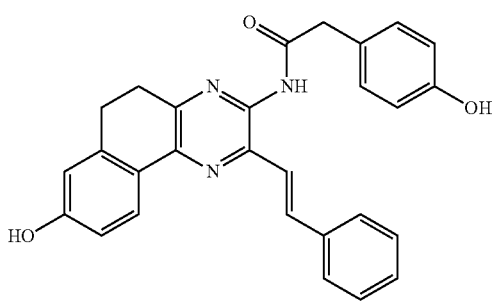
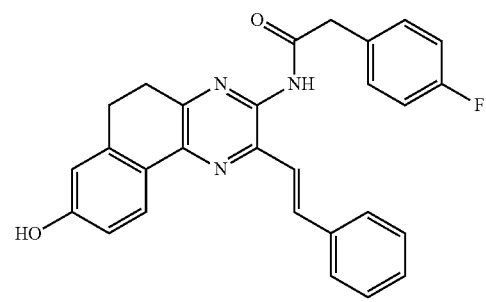
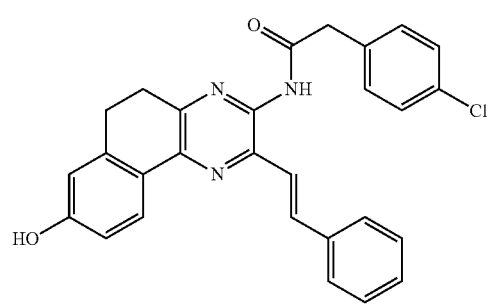

333
-continued
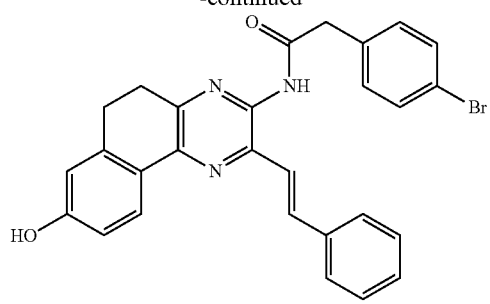
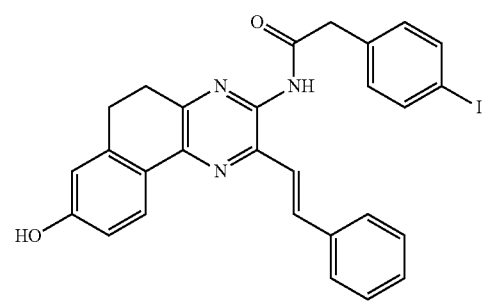
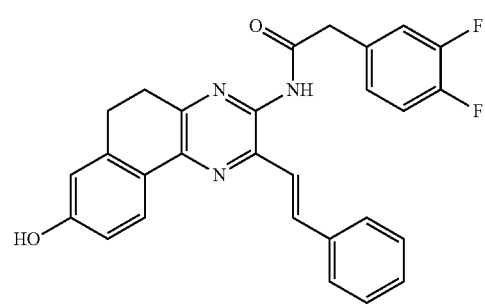
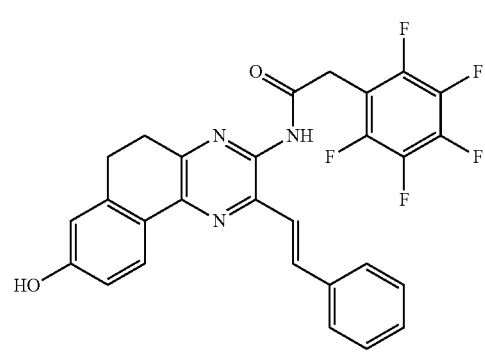
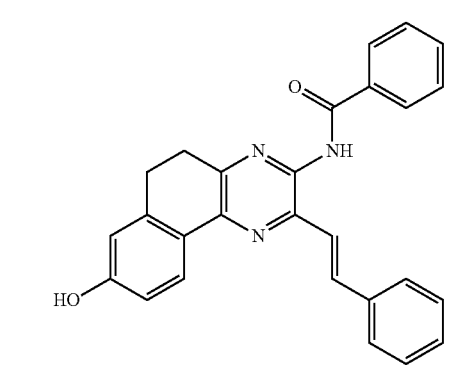
334
-continued
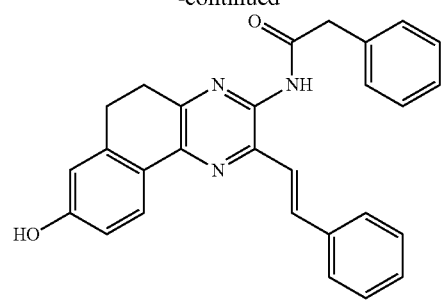
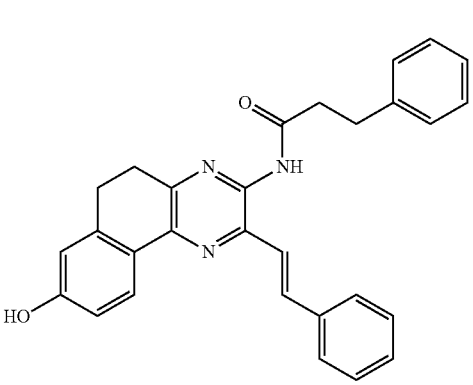
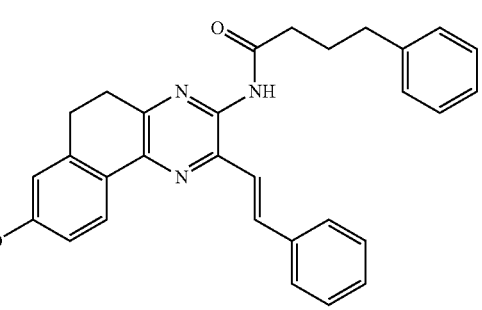
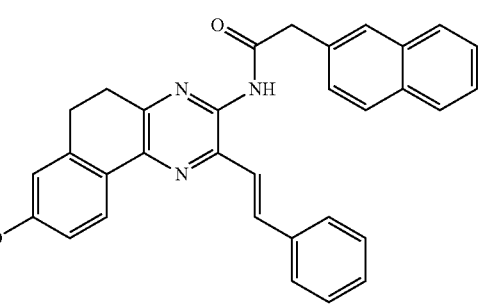
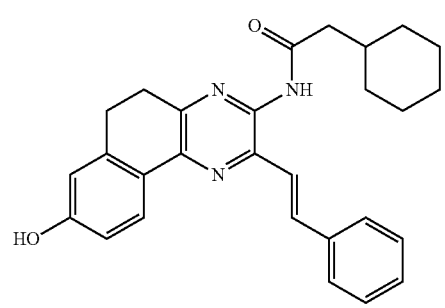

335
-continued
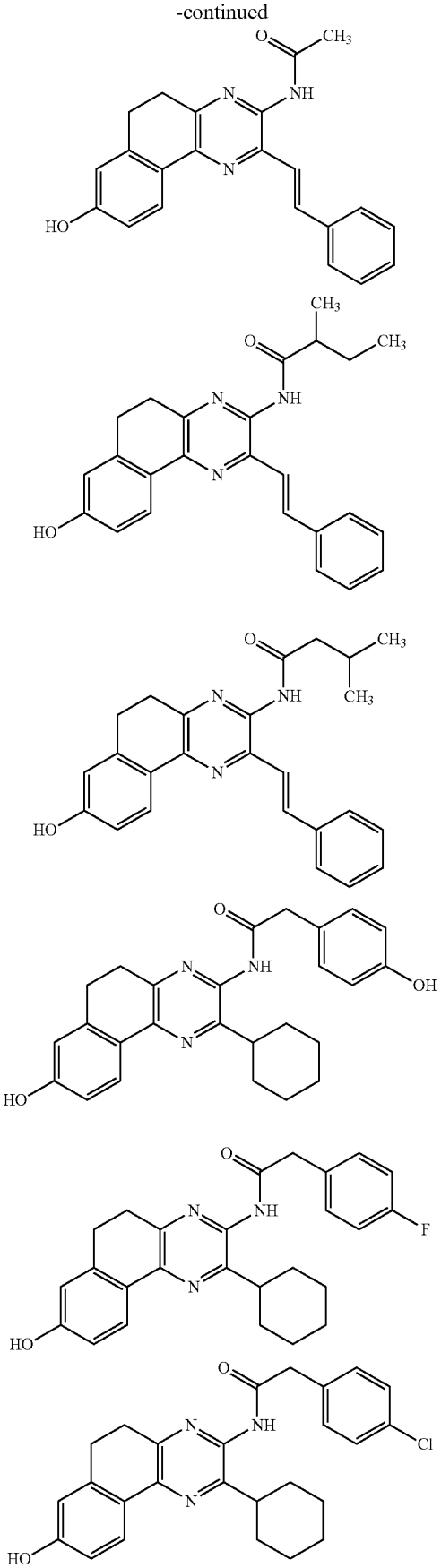
336
-continued
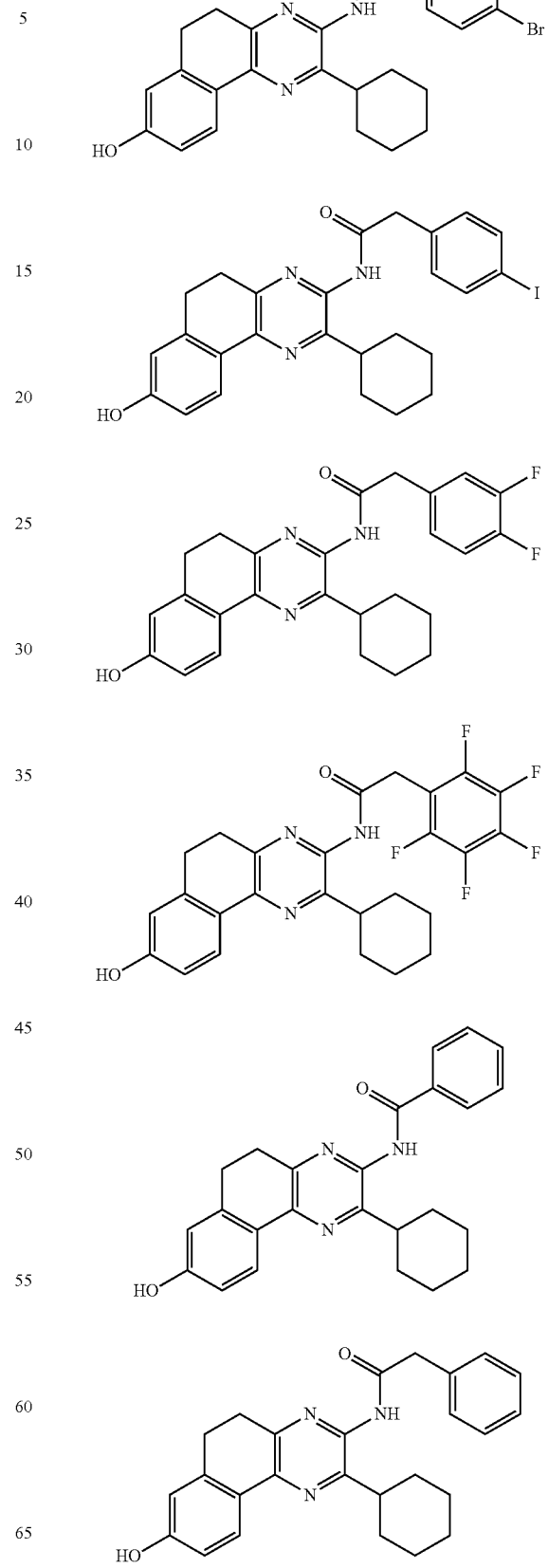

337
-continued
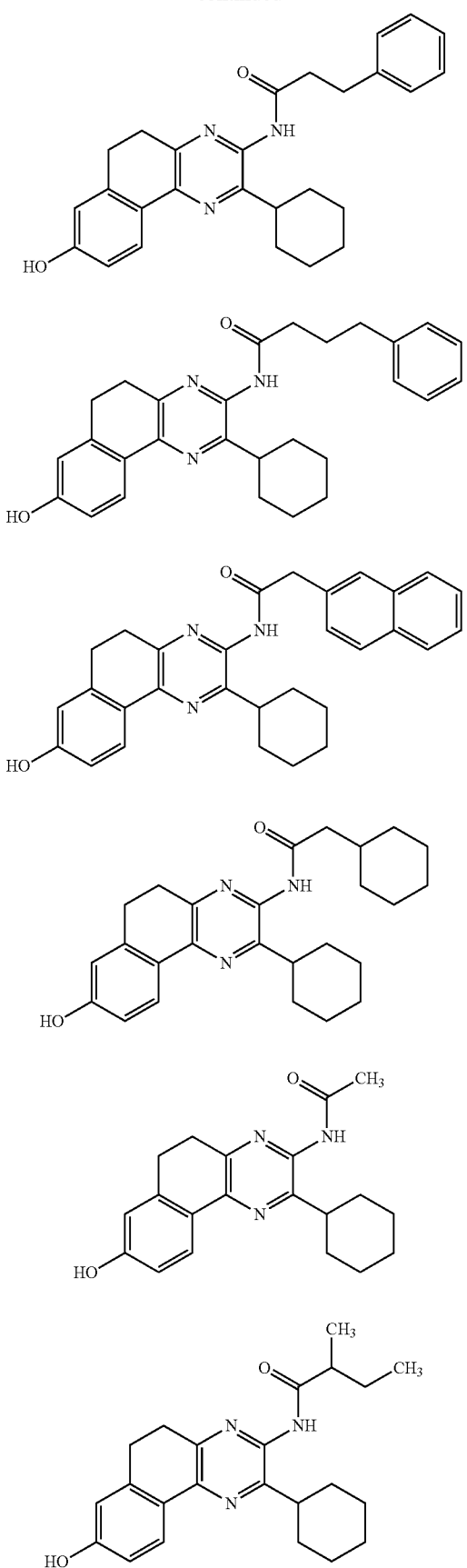
338
-continued
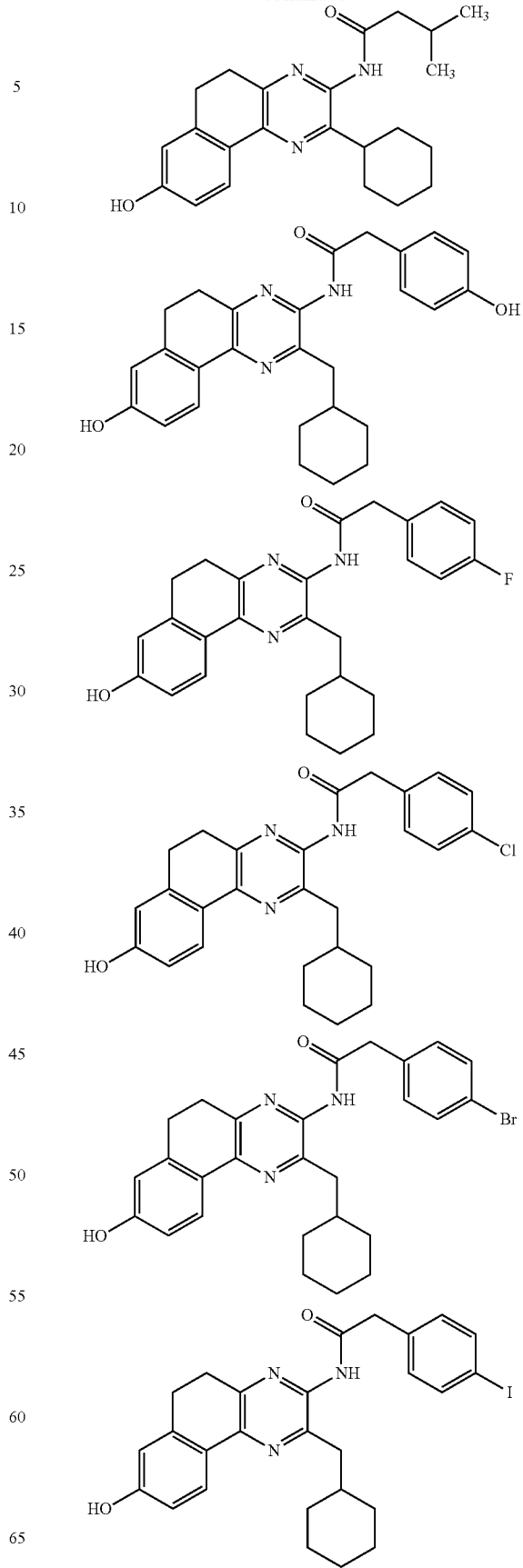

339
-continued
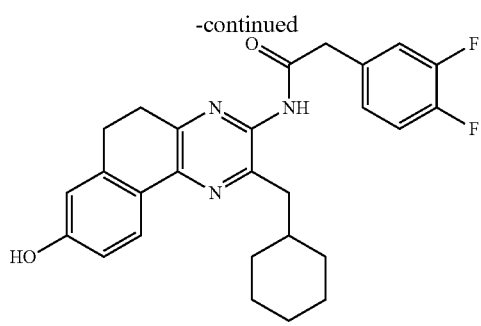
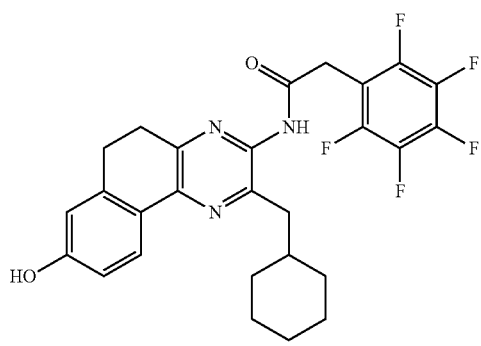
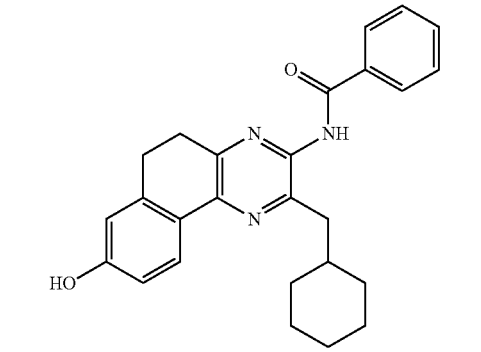
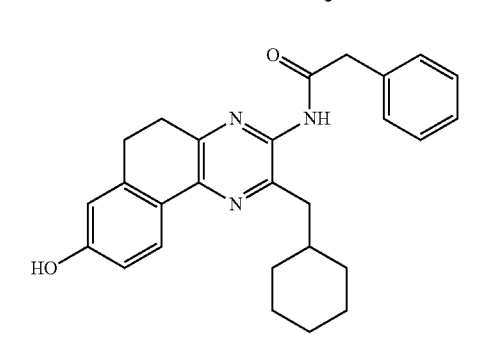
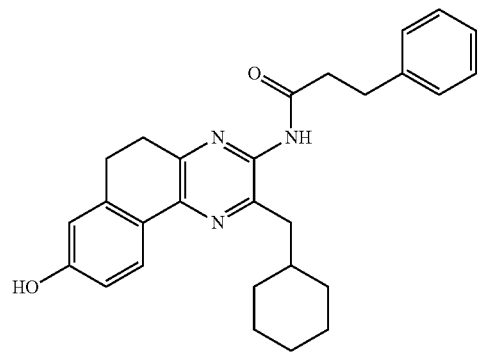
340
-continued
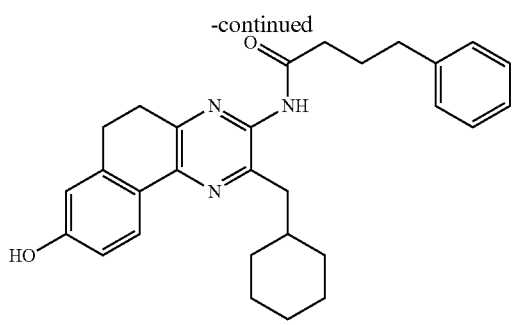
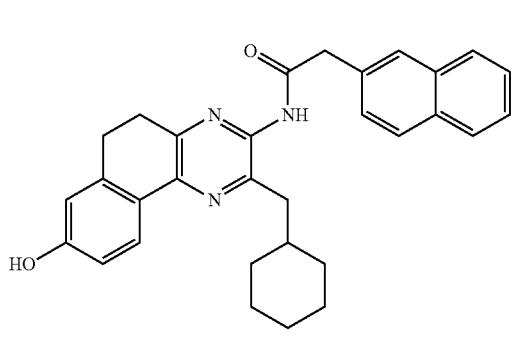
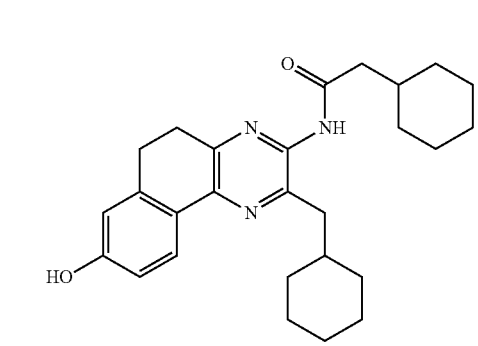
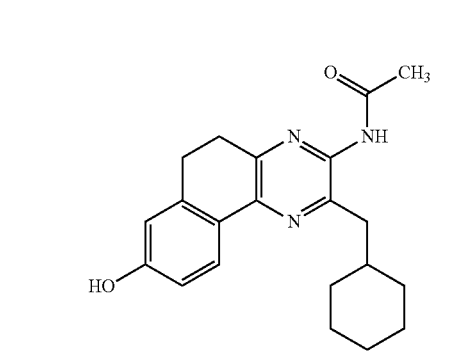
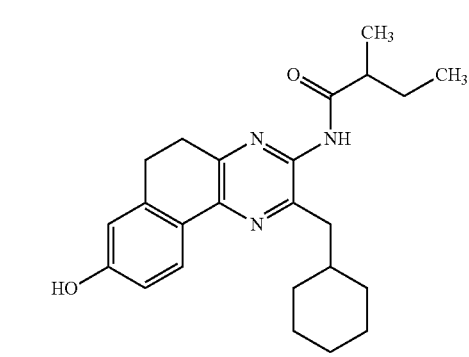

341
-continued
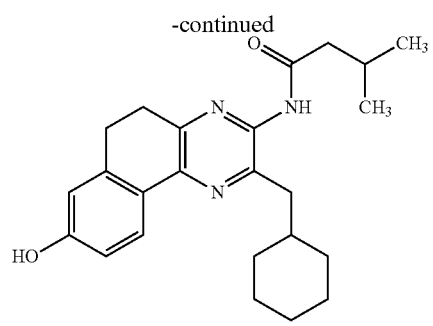
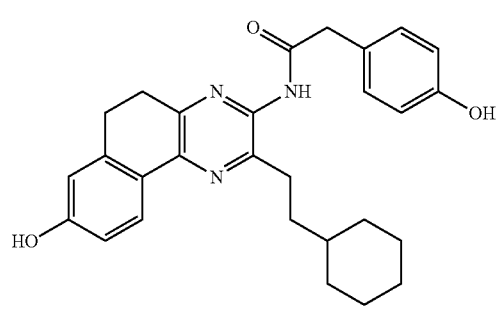
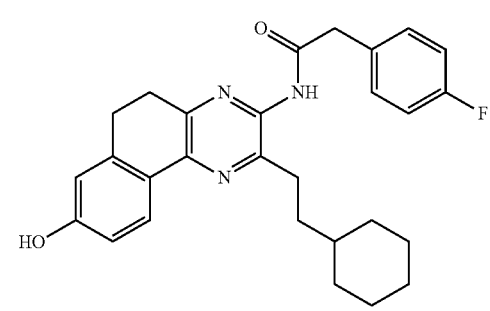
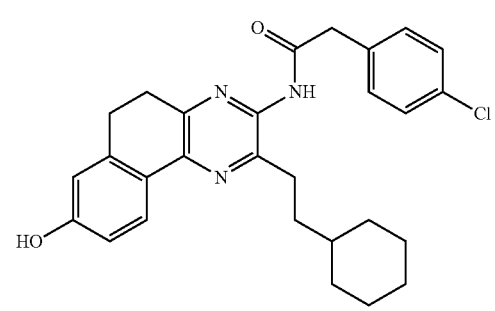
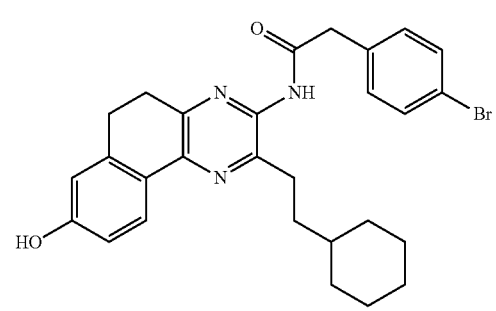
342
-continued
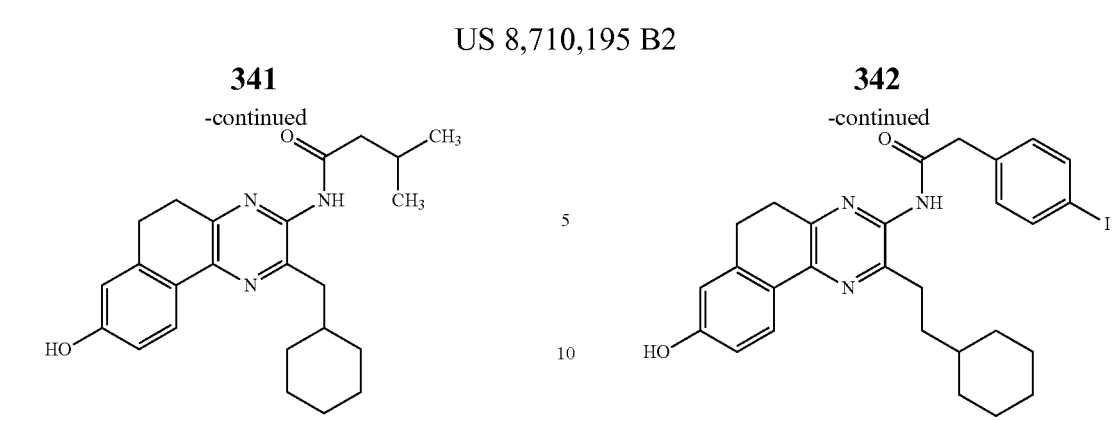
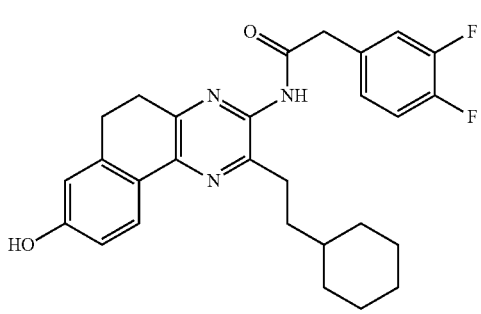
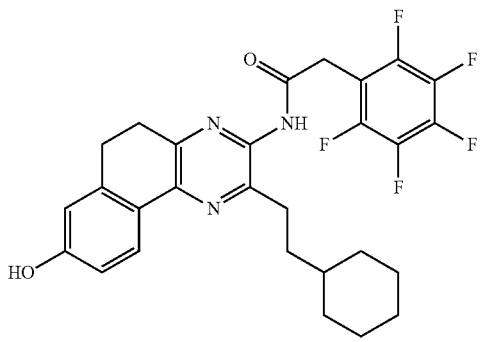
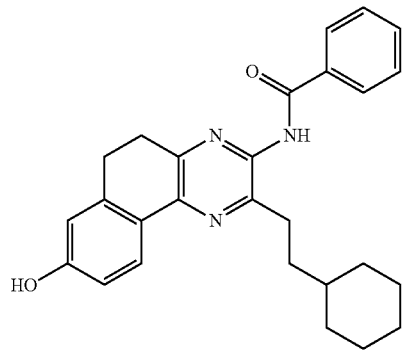
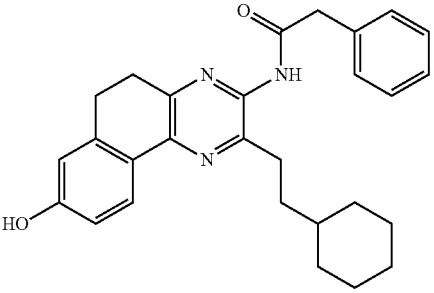

343
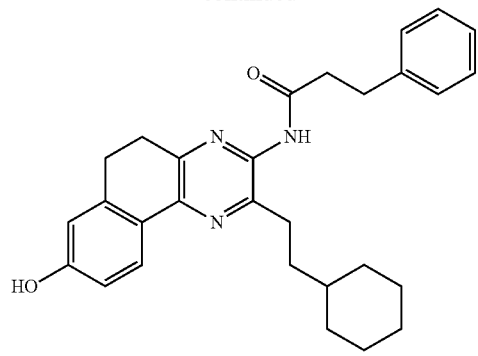
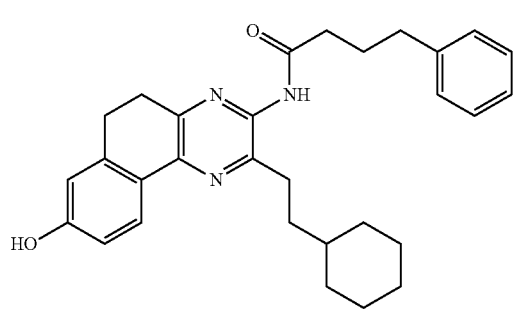
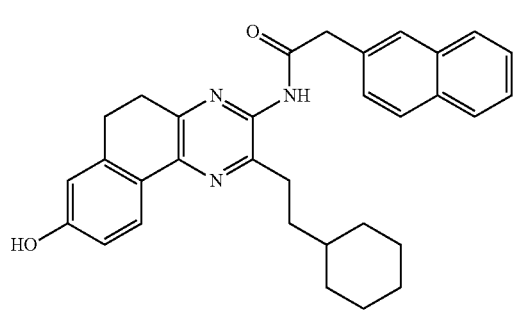
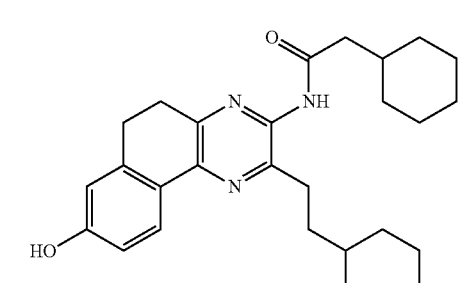
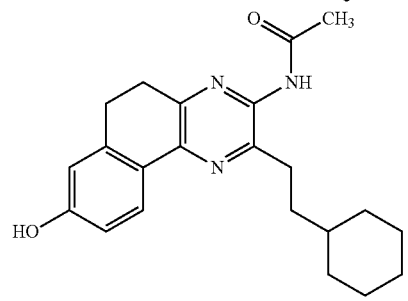
344
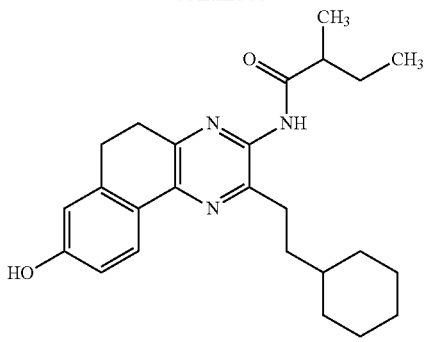
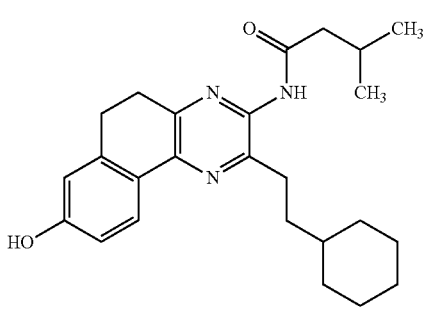
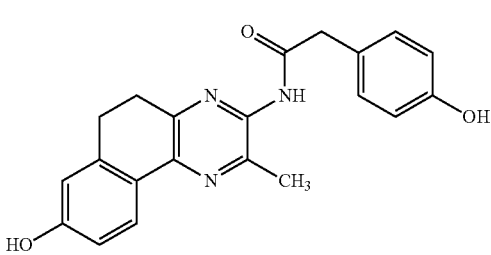
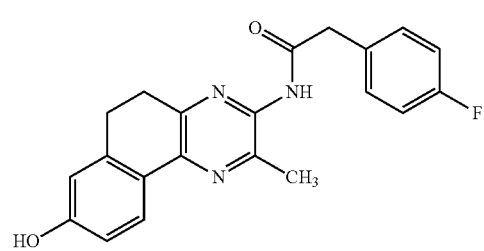
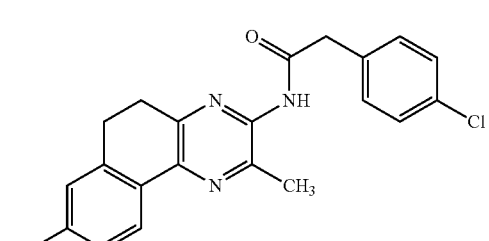
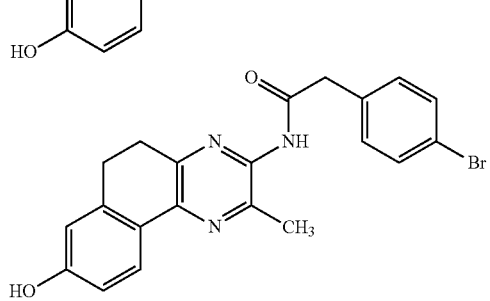

-continued
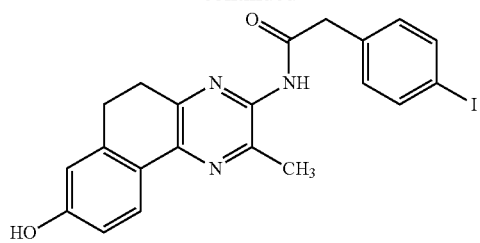
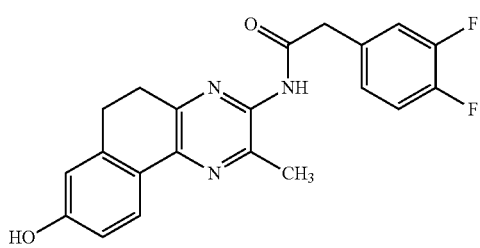
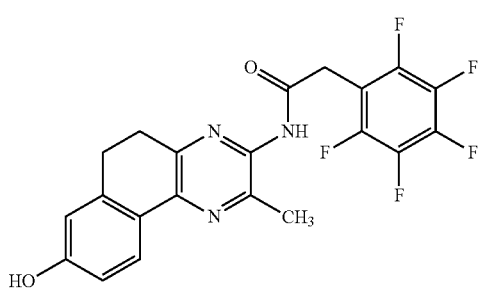
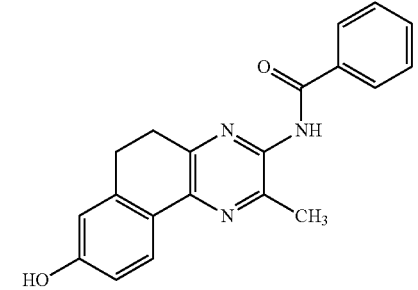
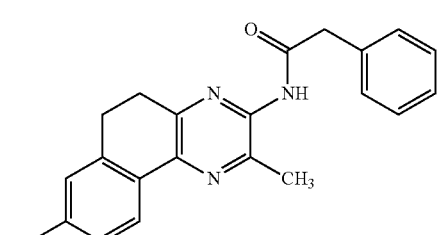
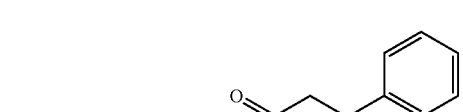
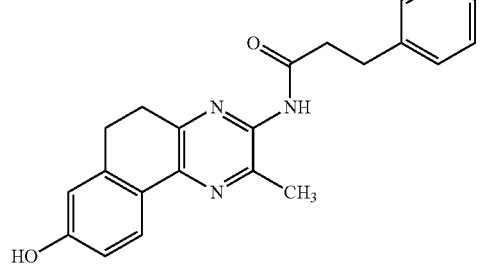
-continued
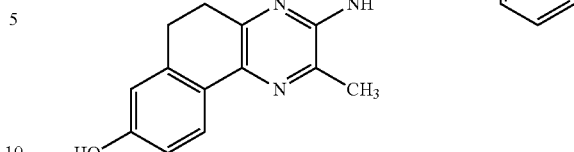
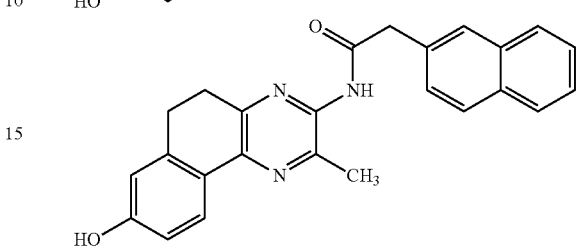
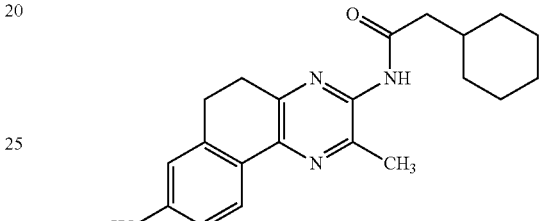
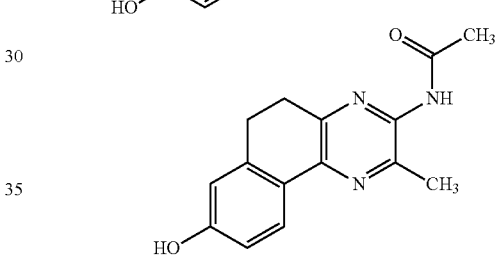
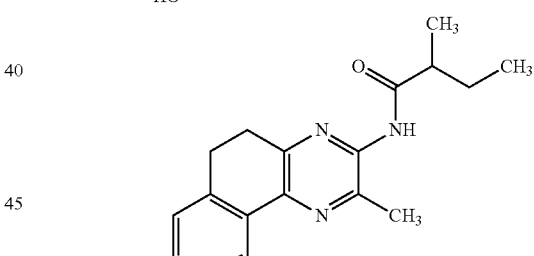
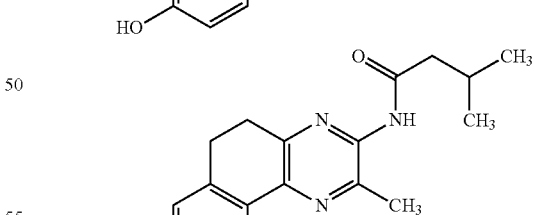
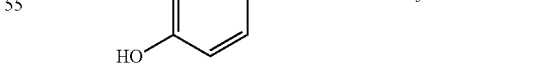
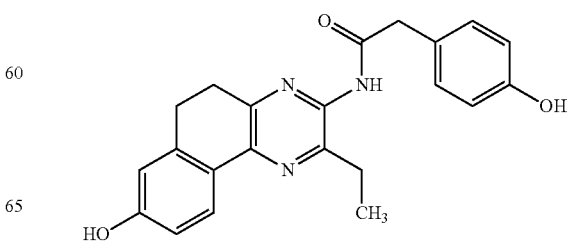

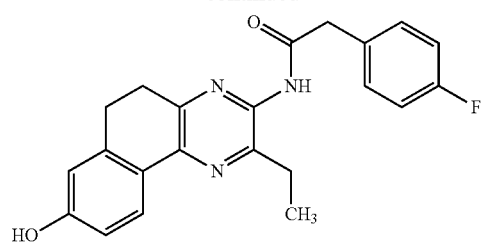
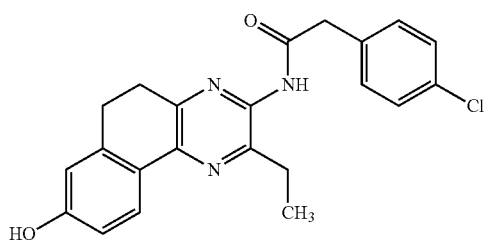
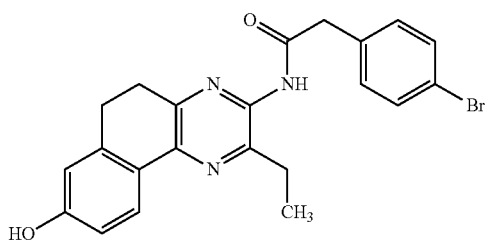
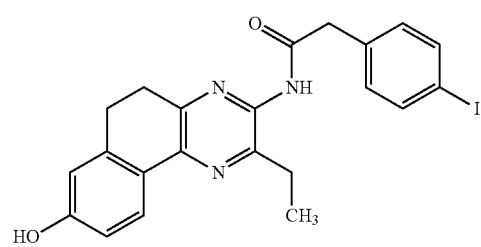
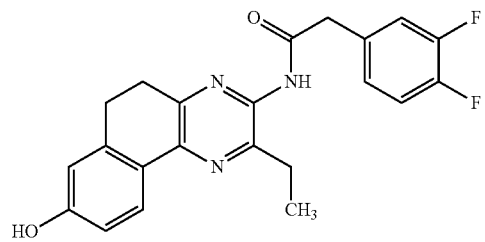
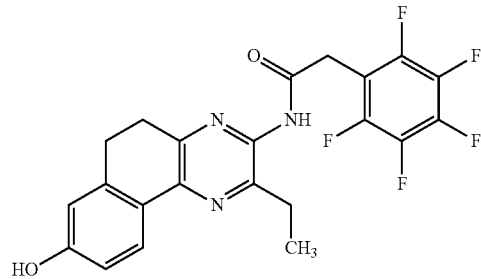
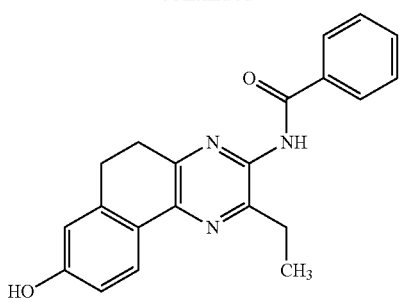
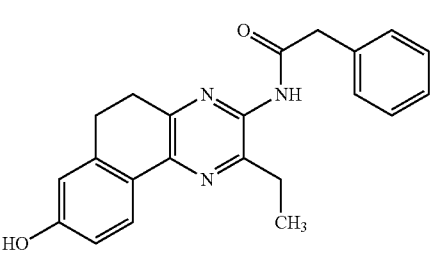
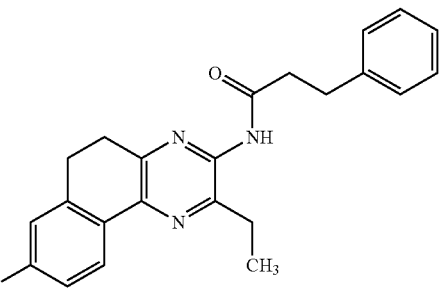
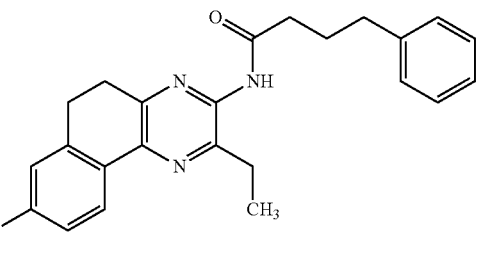
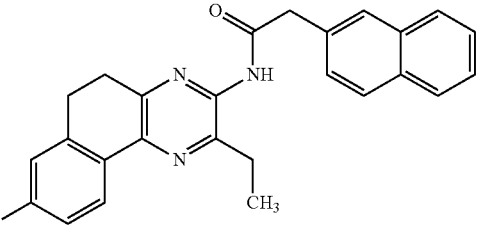
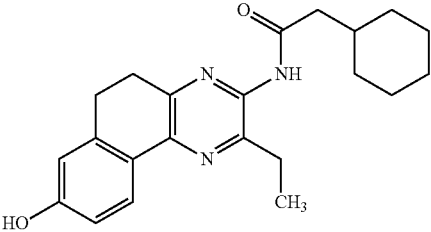

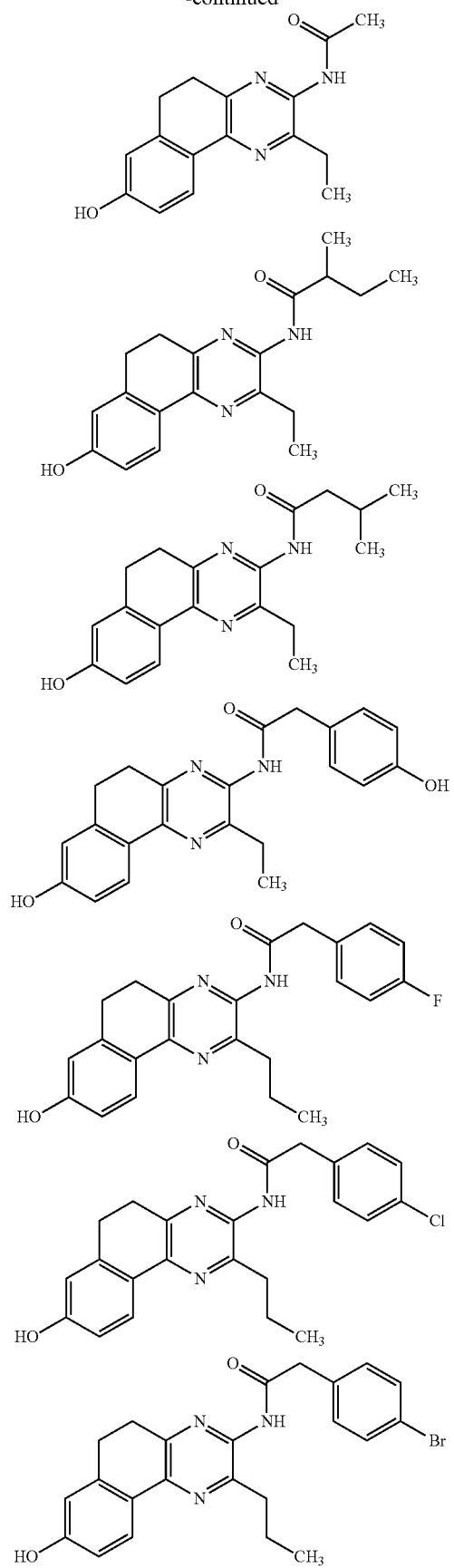
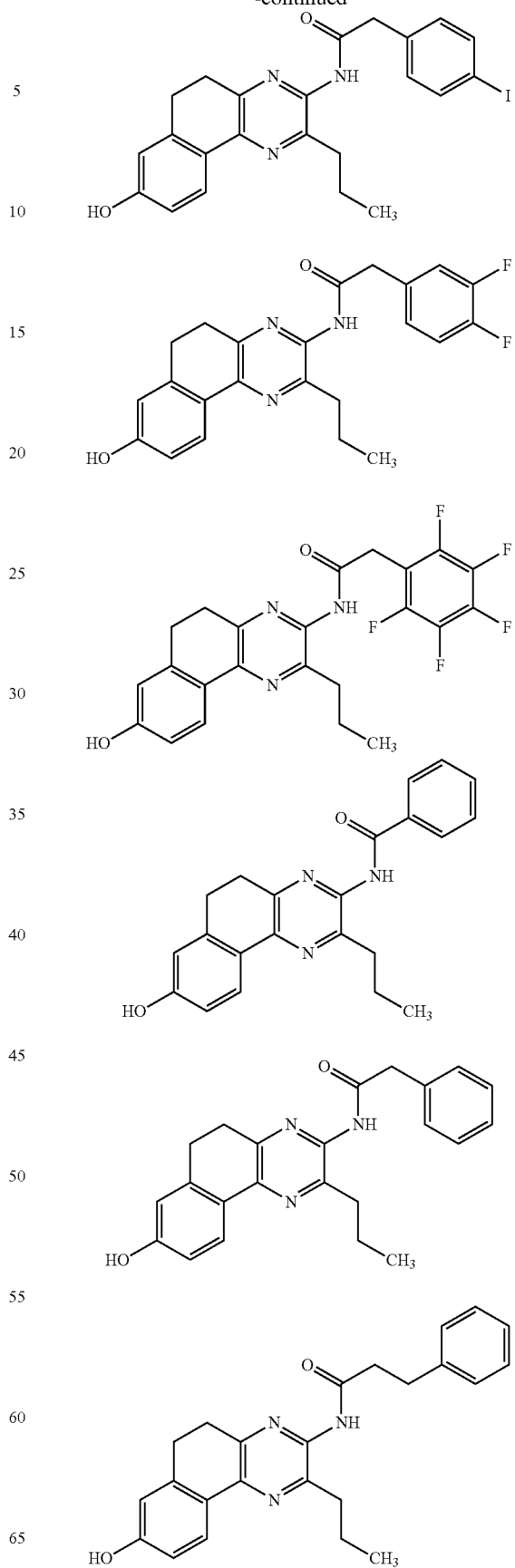

351
-continued
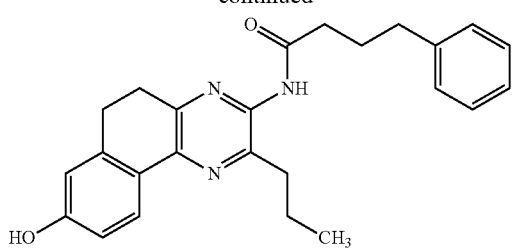
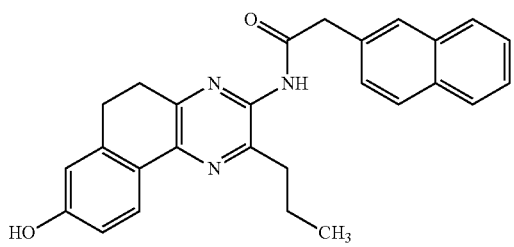
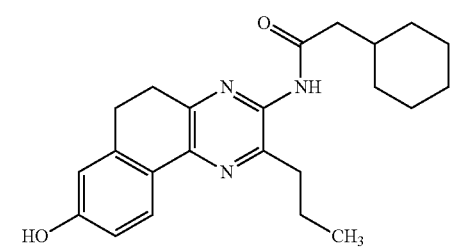
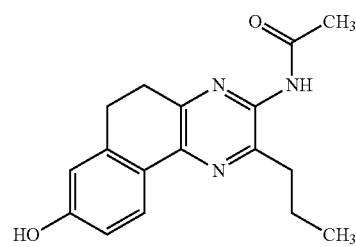
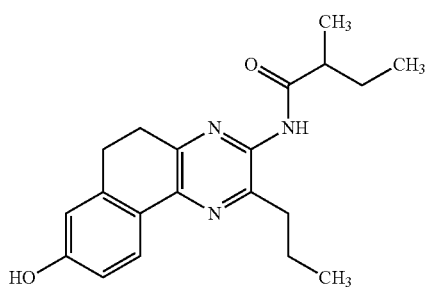
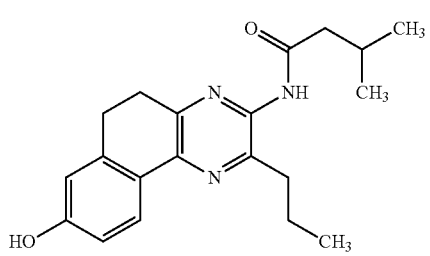
352
-continued
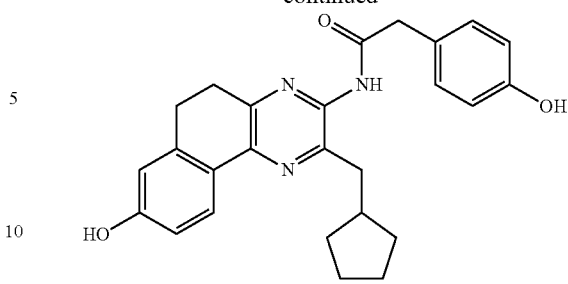
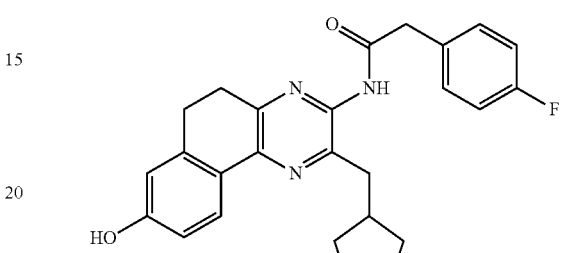
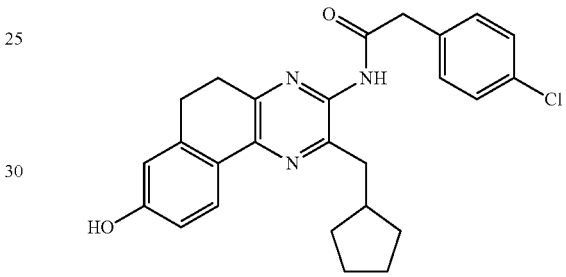
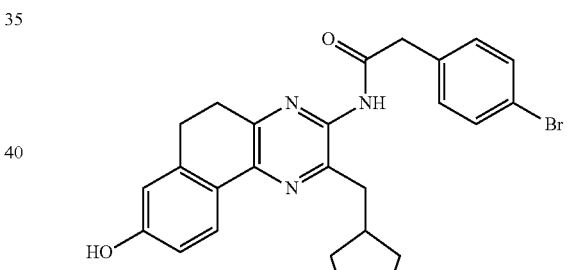
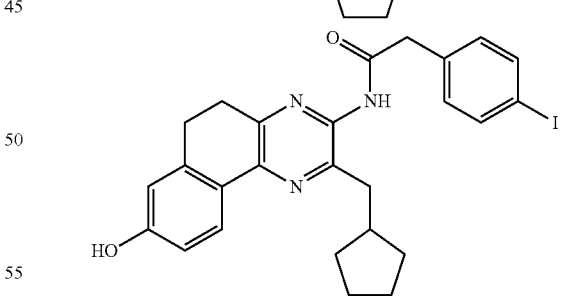
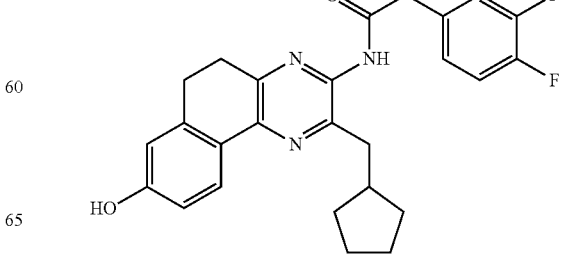

353
-continued
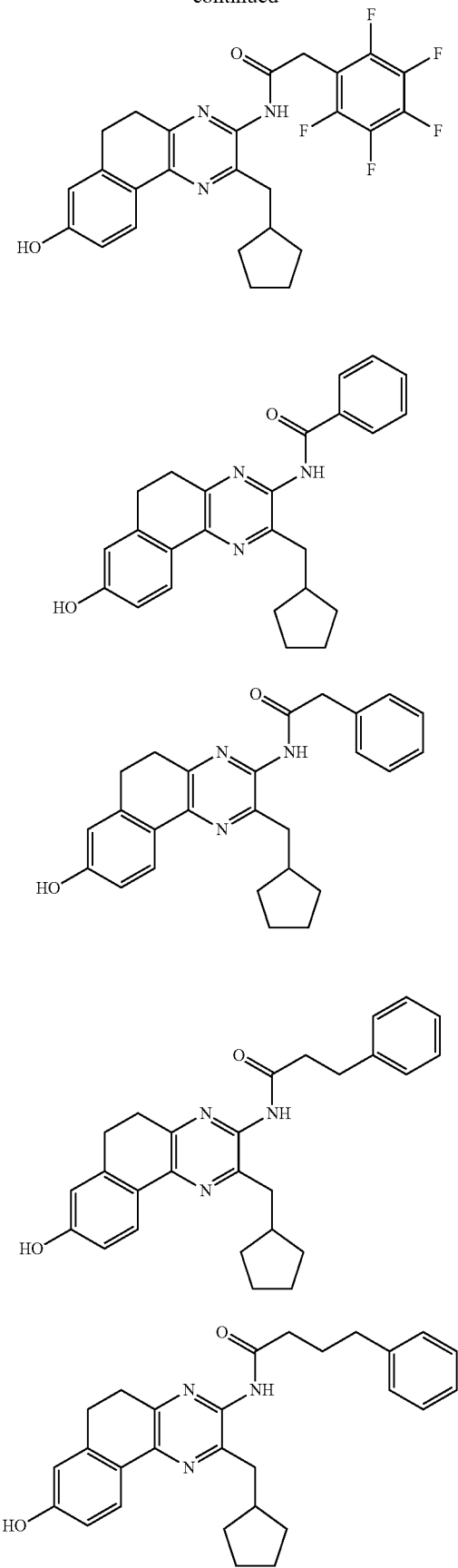
354
-continued
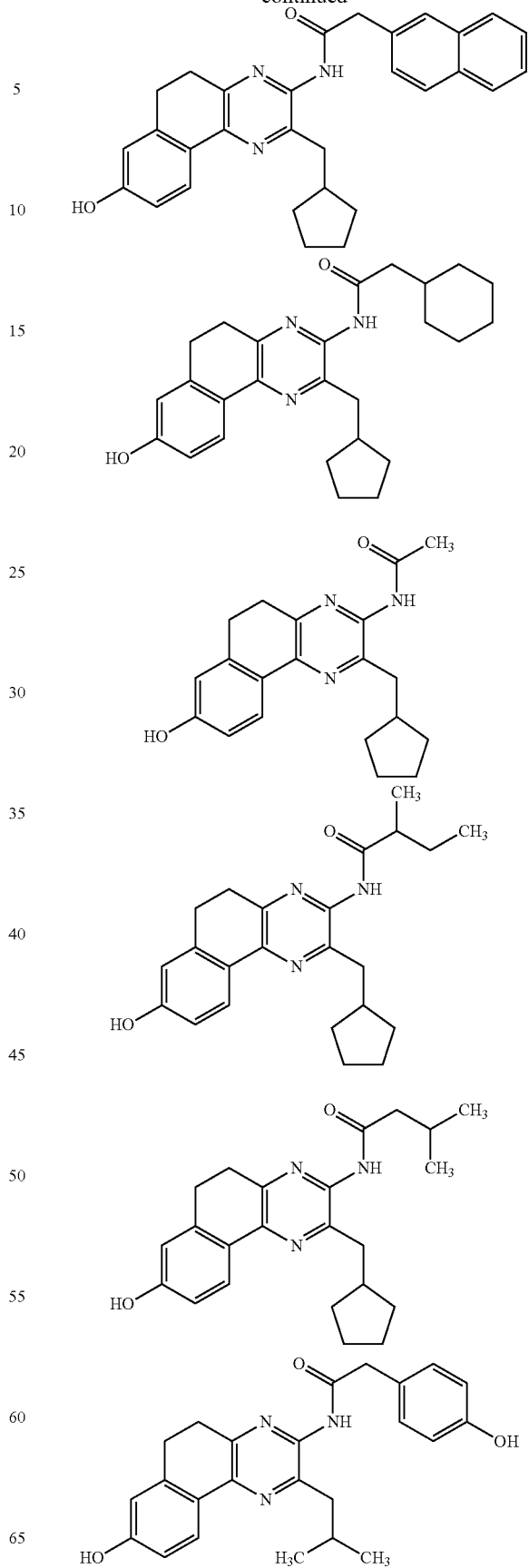

355
-continued
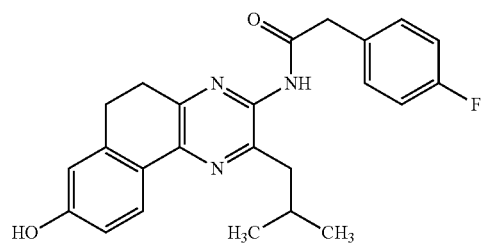
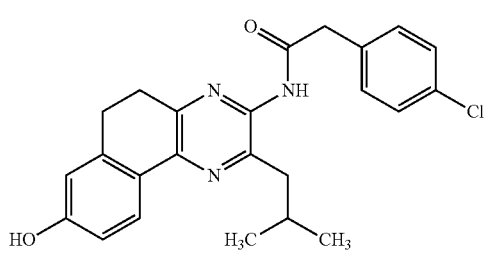
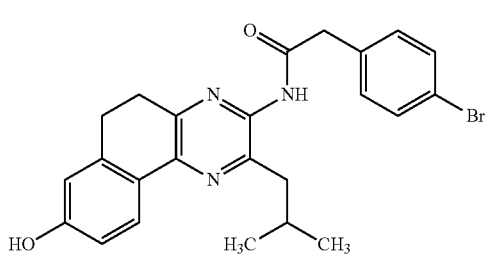
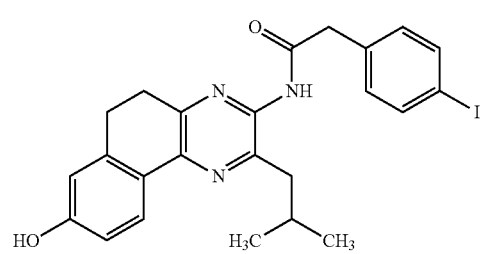
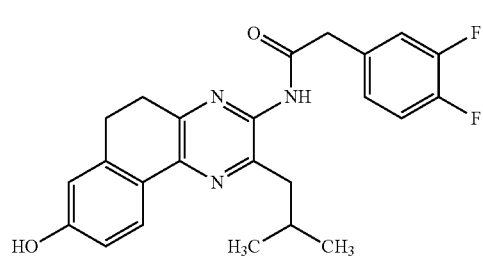
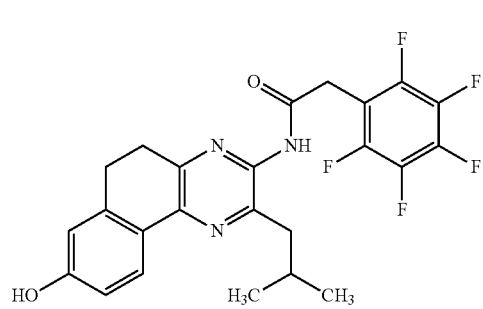
356
-continued
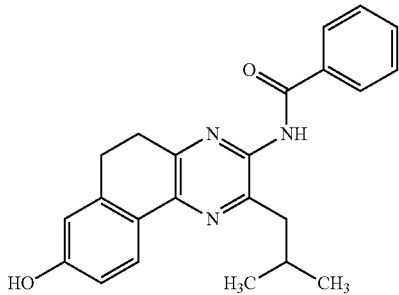
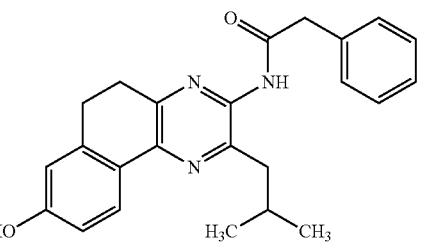
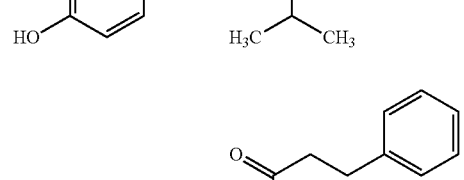
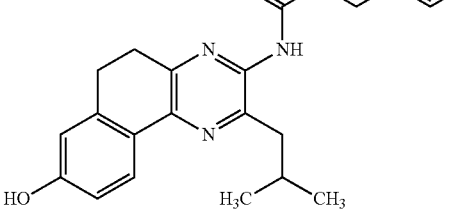
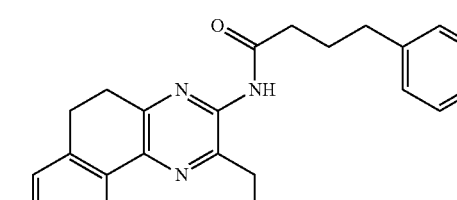
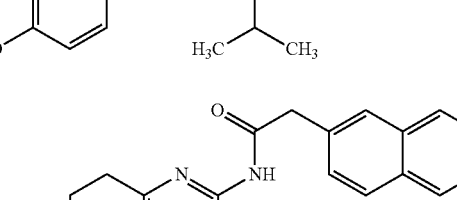
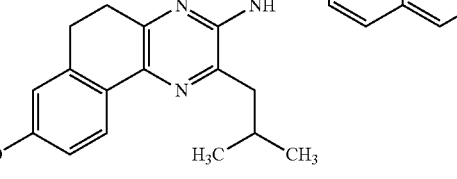
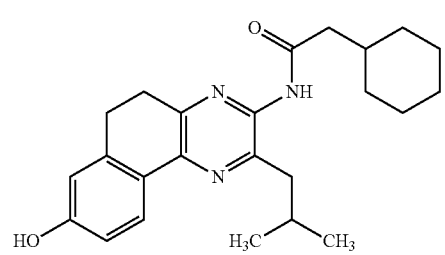

357
-continued
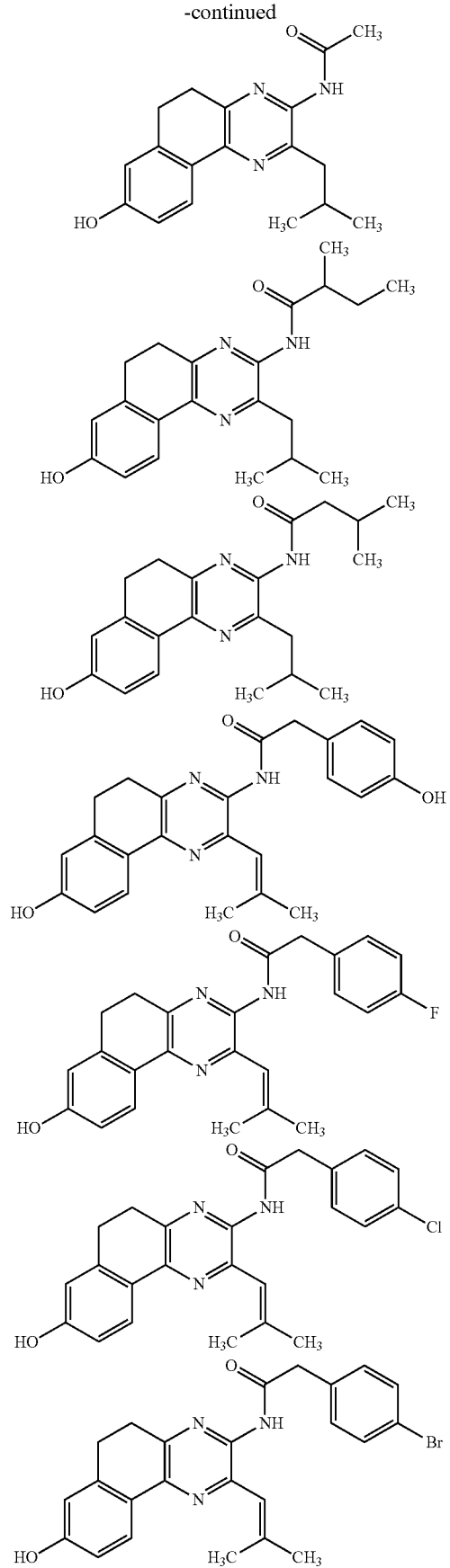
358
-continued
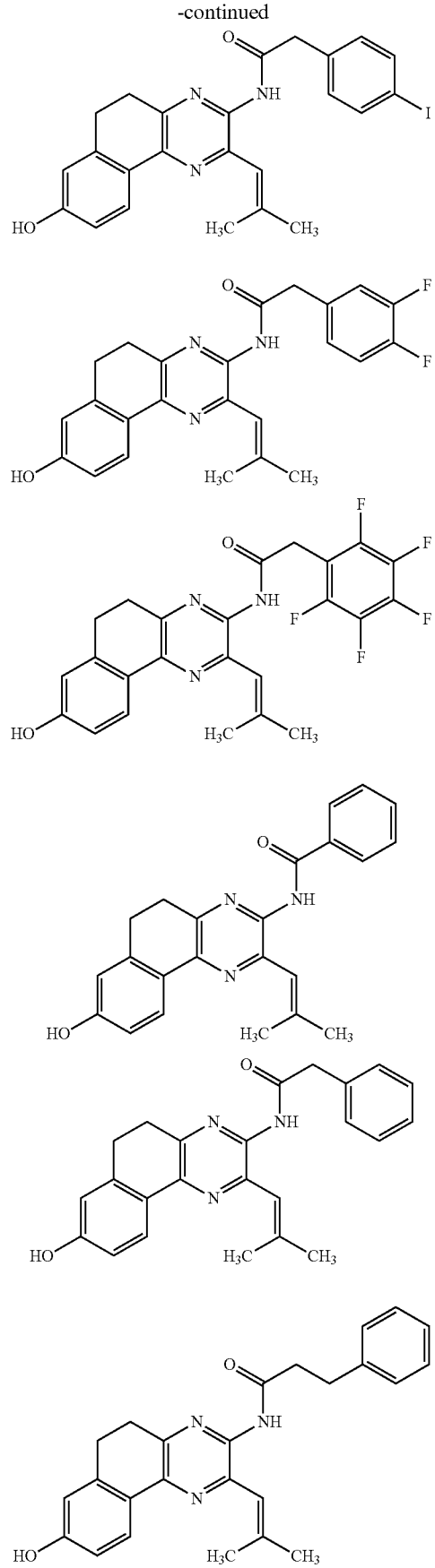

359
-continued
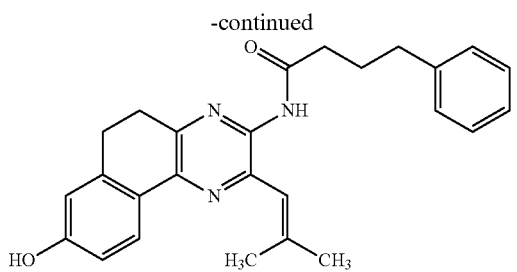
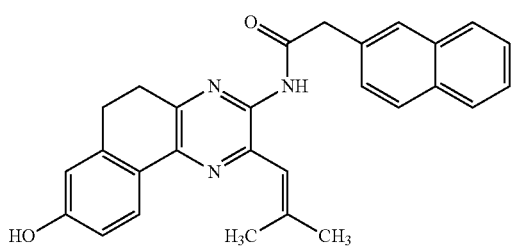
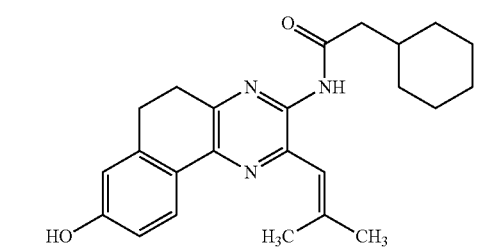
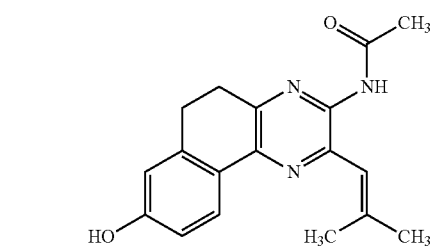
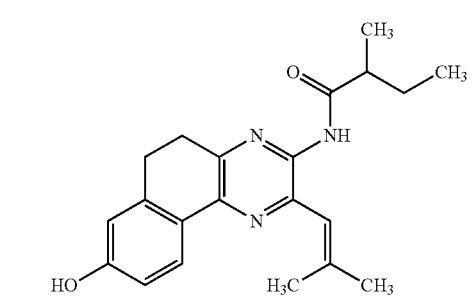
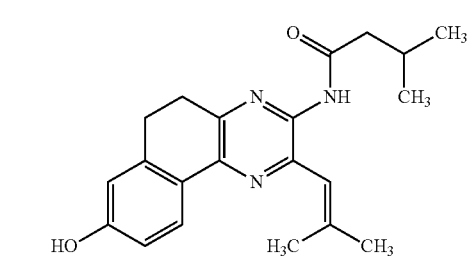
360
-continued
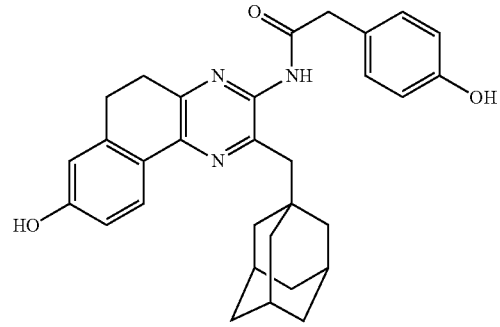
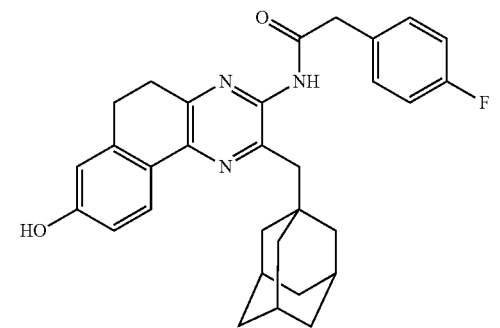
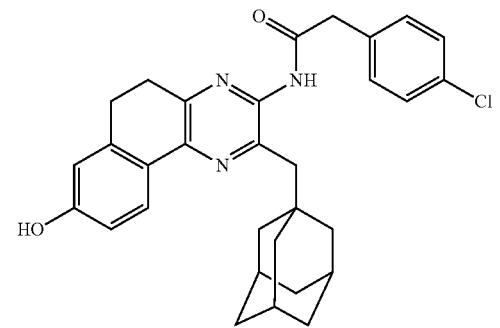
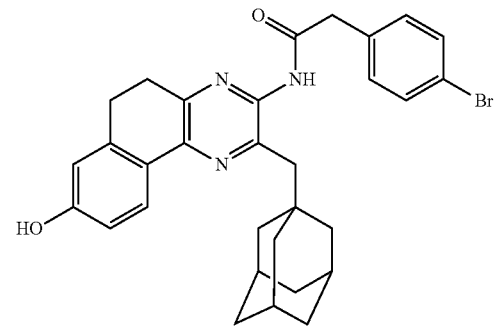
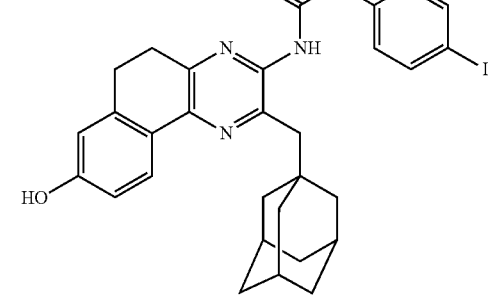

361
-continued
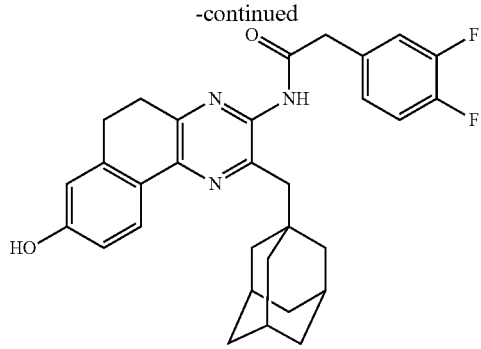
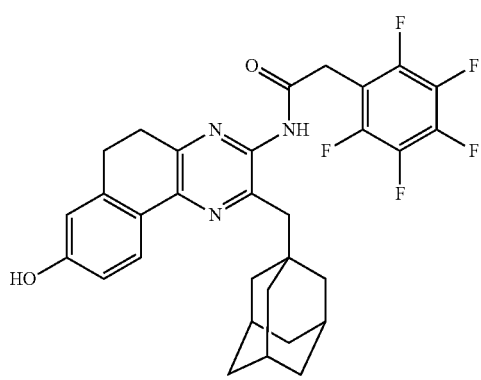
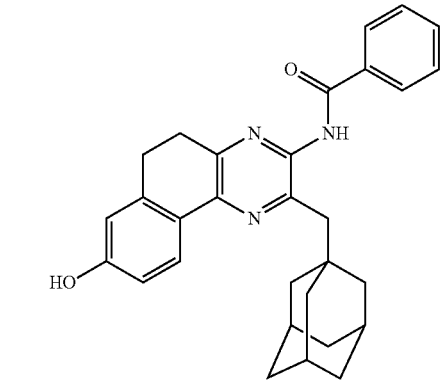
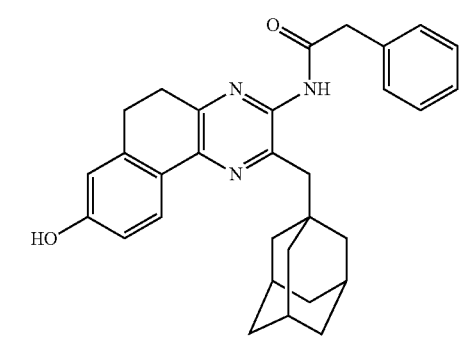
362
-continued
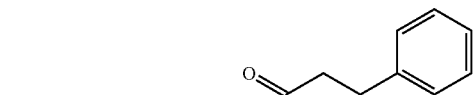
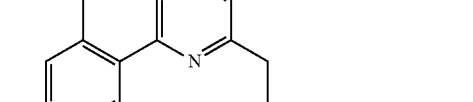
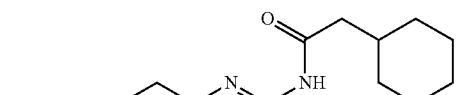
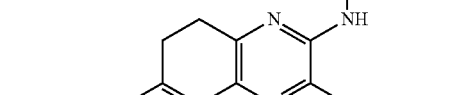

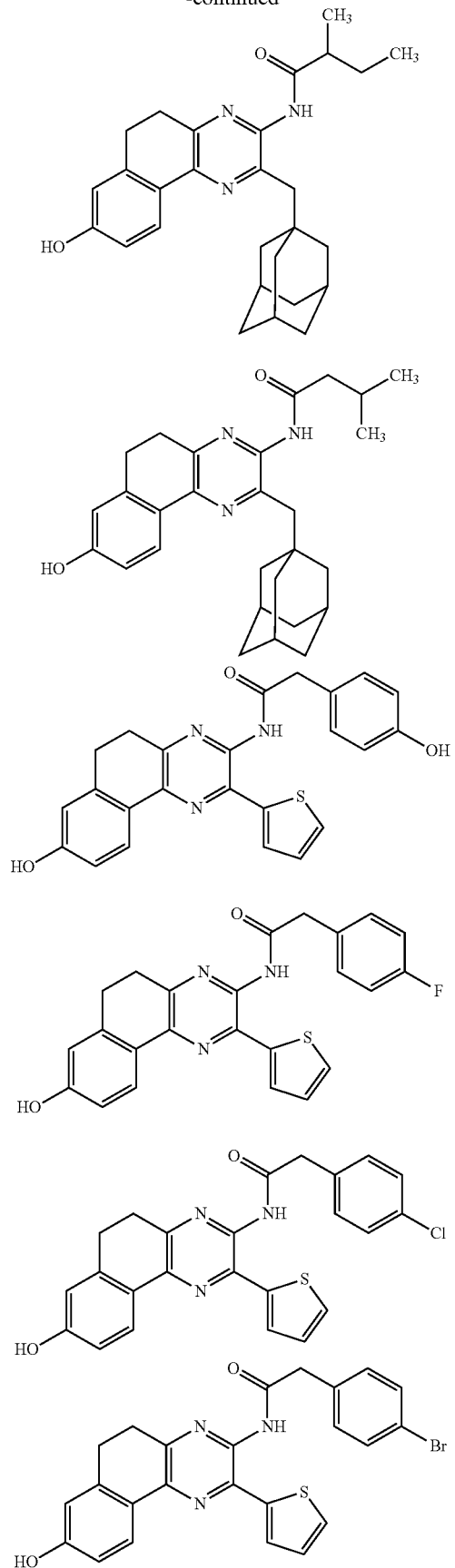
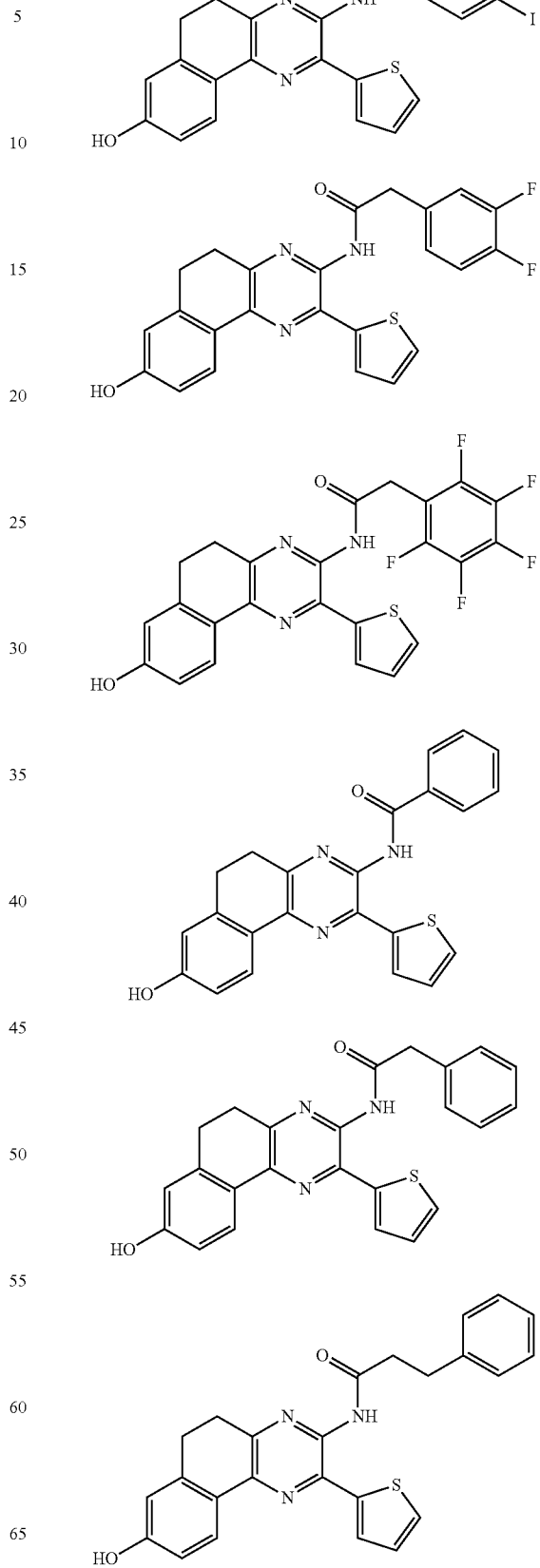

365
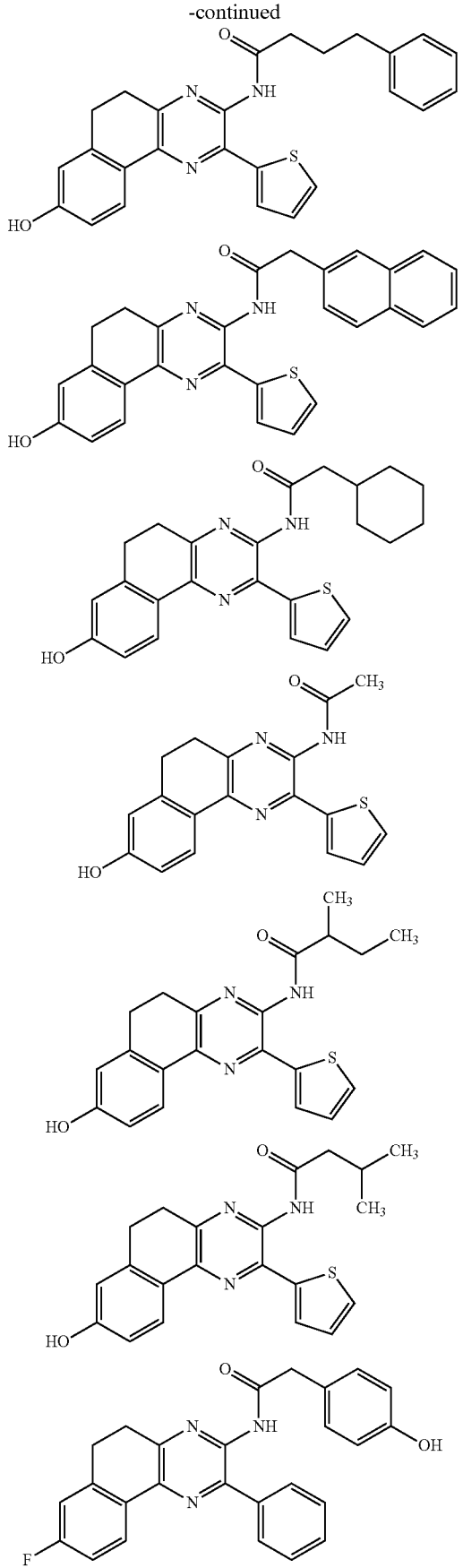
366
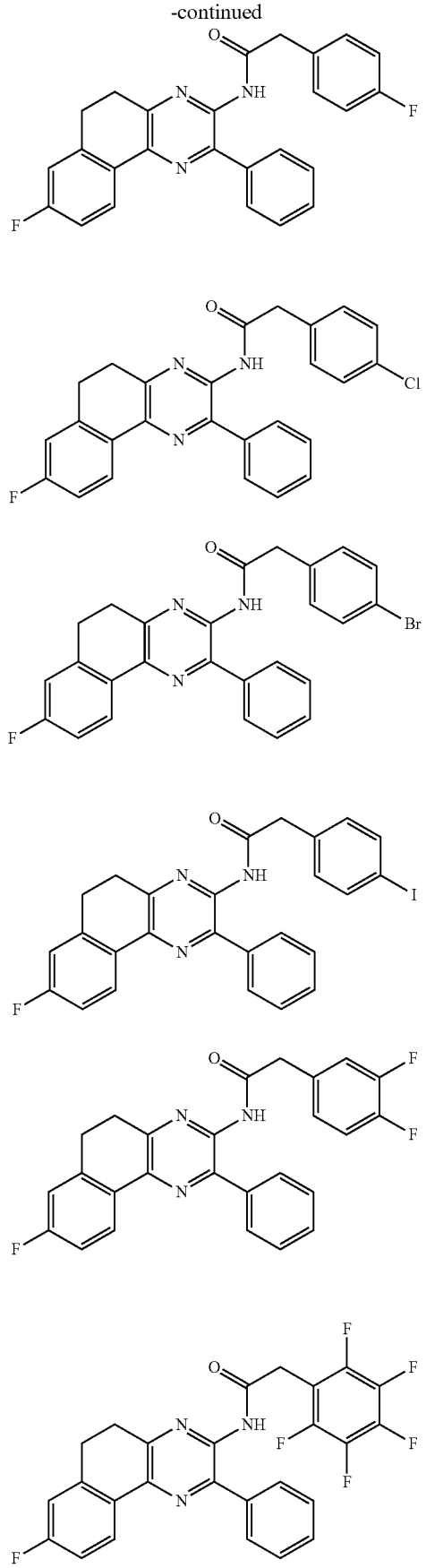

367
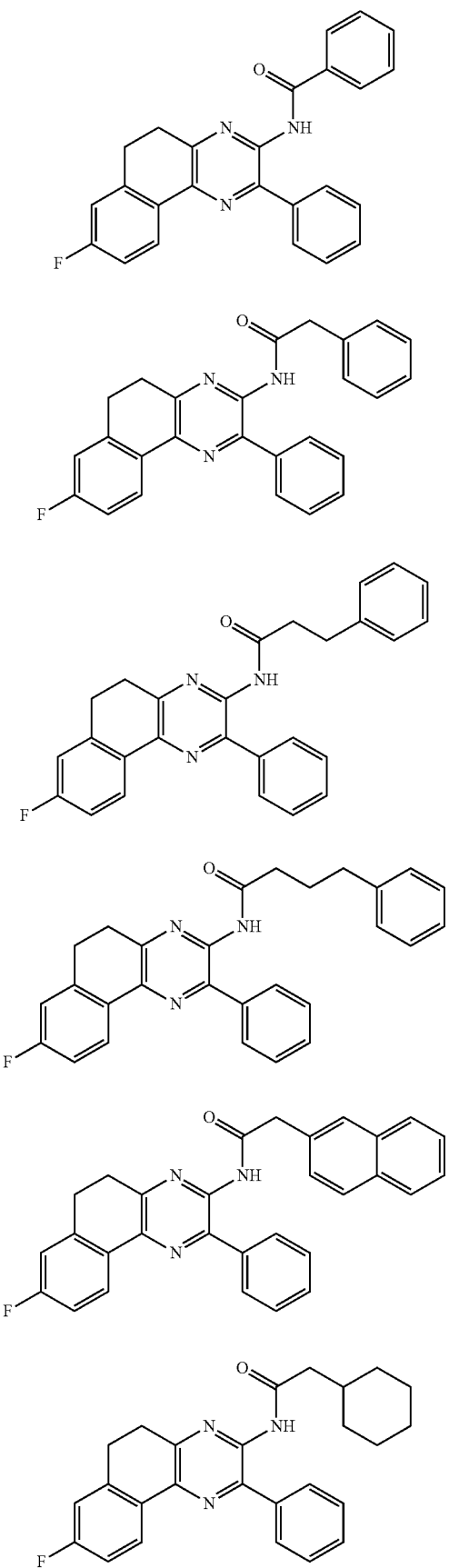
368
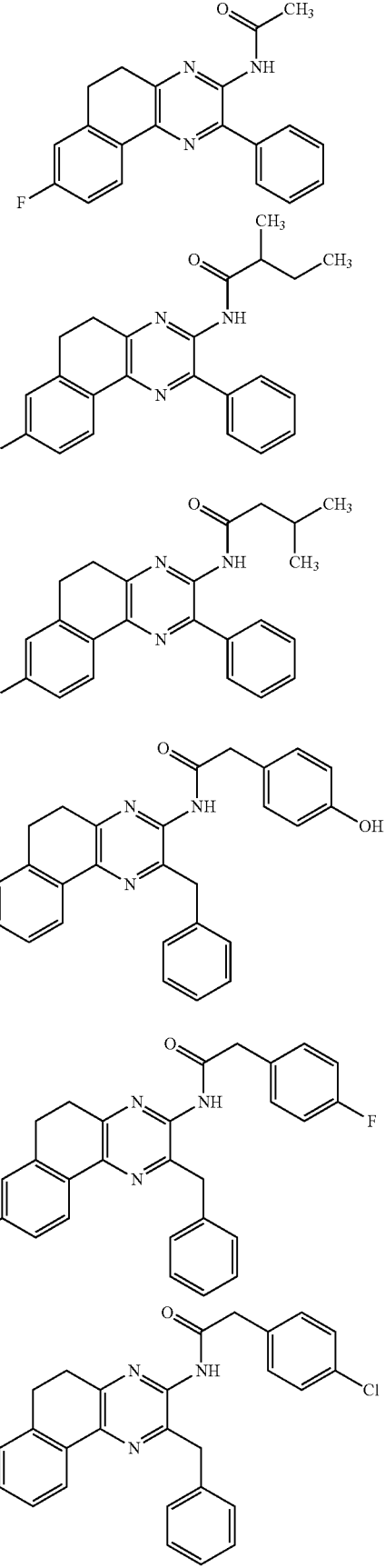

369
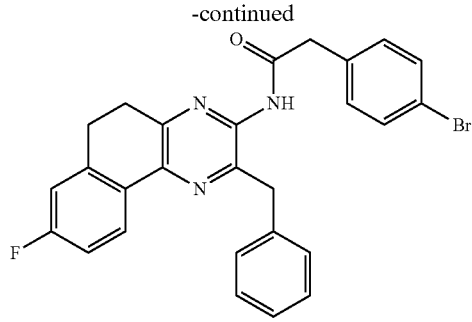
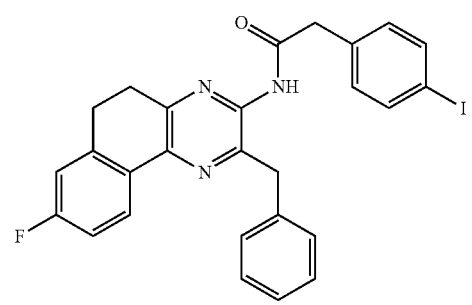
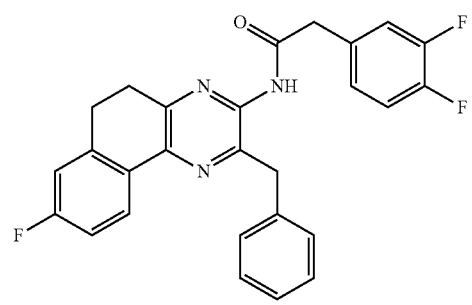
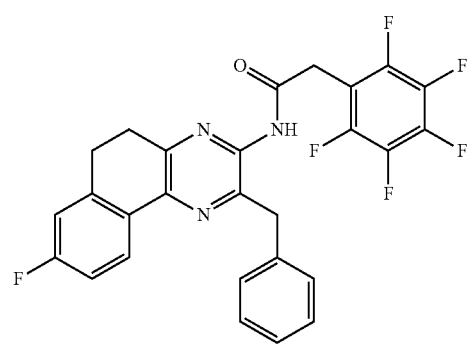
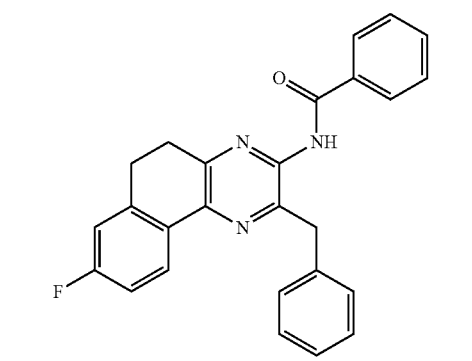
370
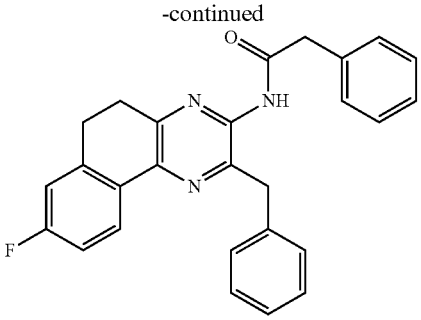
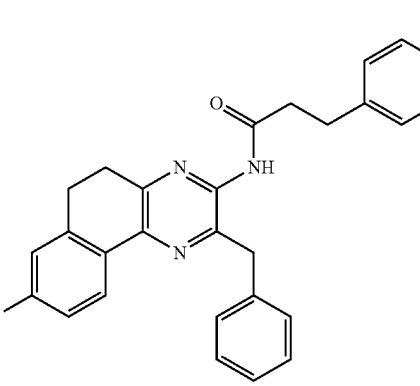
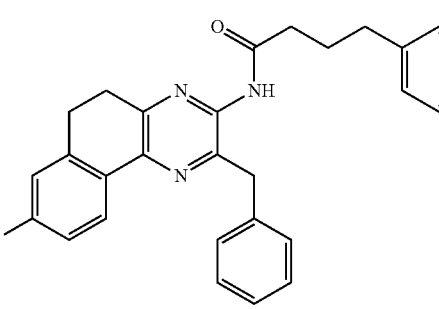
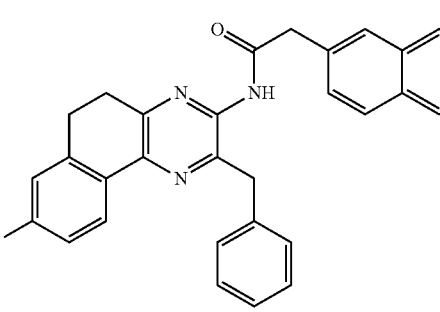
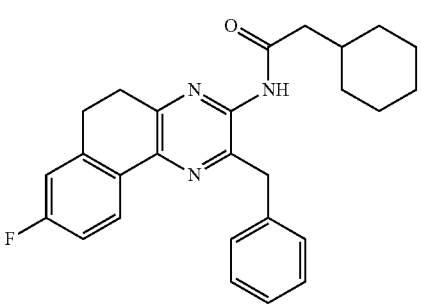

371
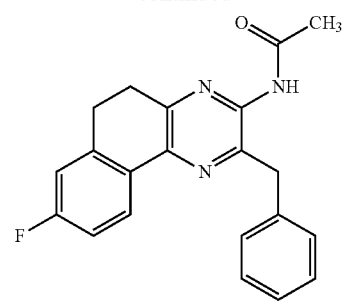
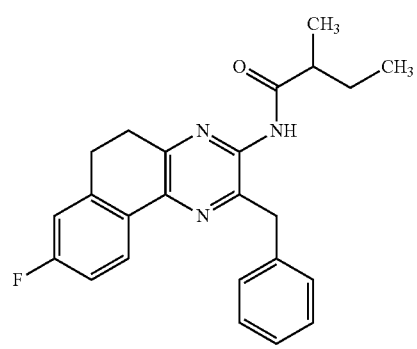
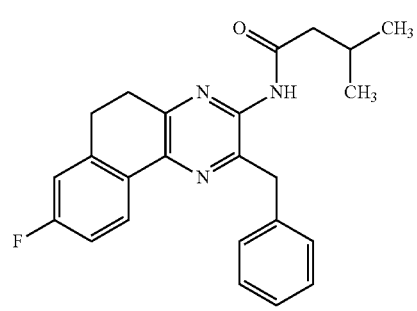
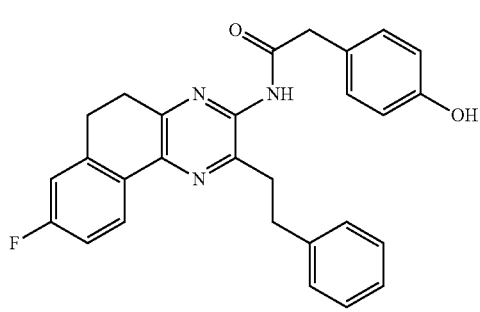
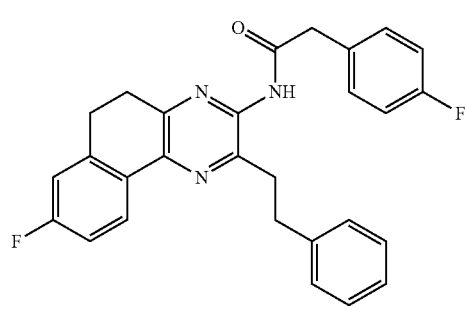
372
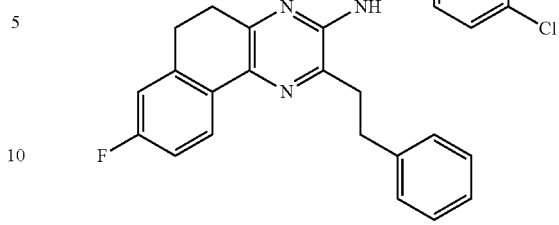
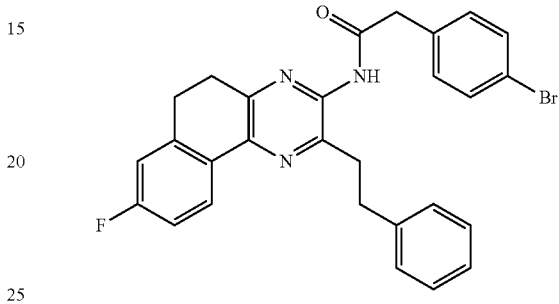
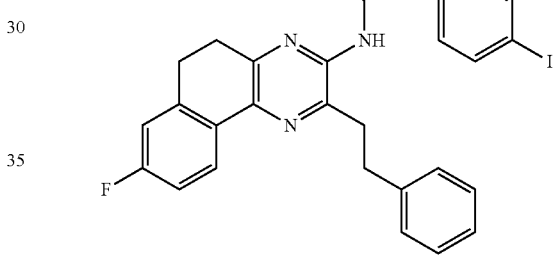
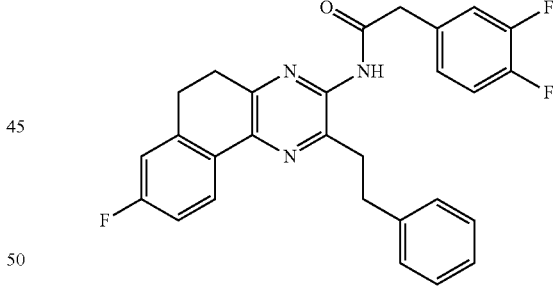
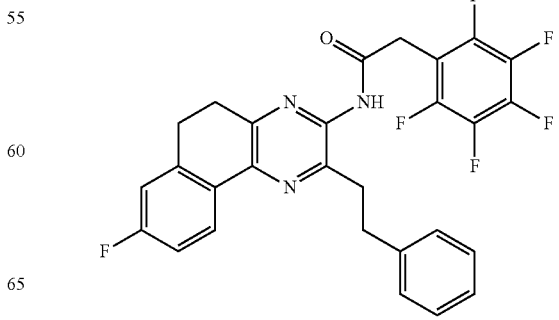

373
-continued
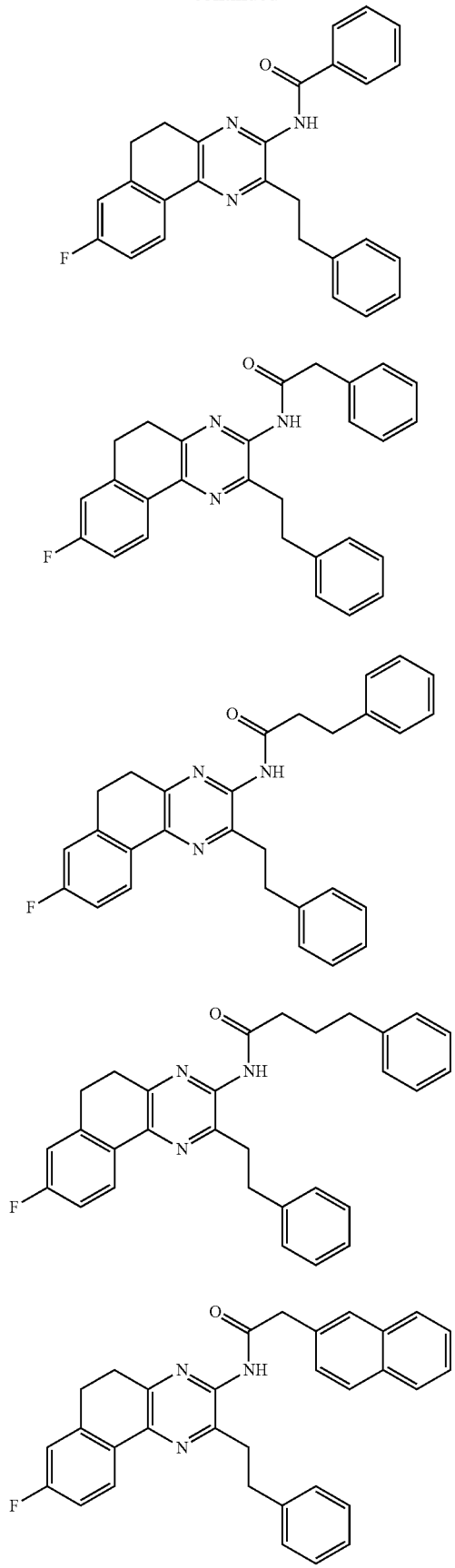
374
-continued
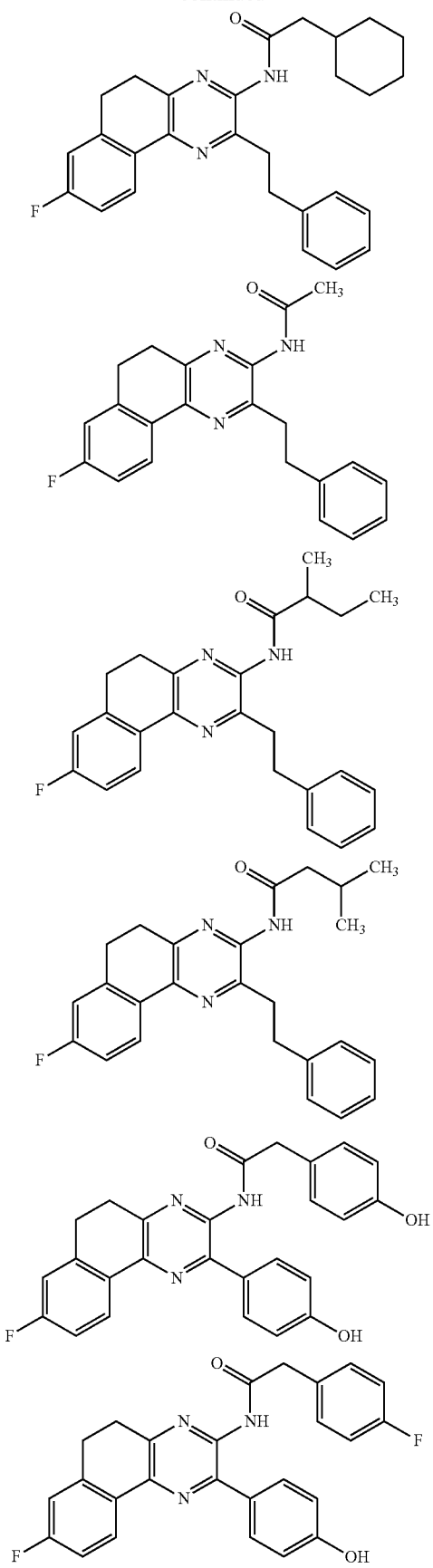

375
-continued
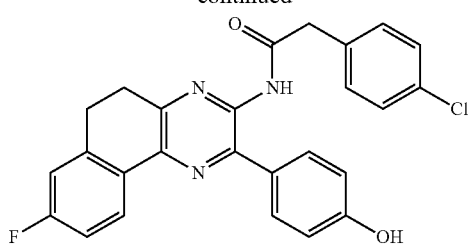
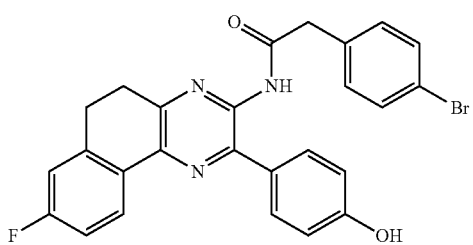
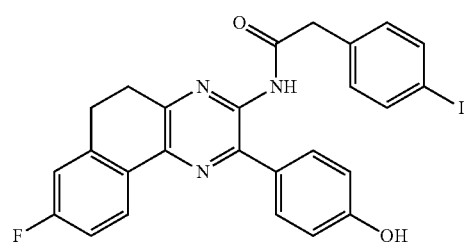
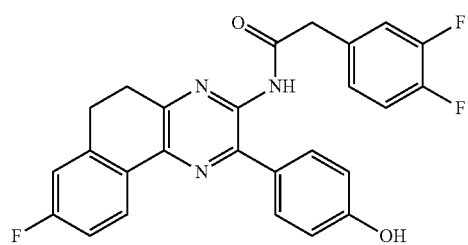
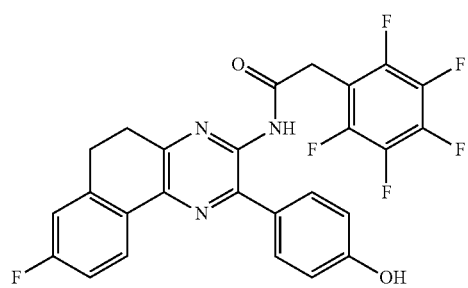
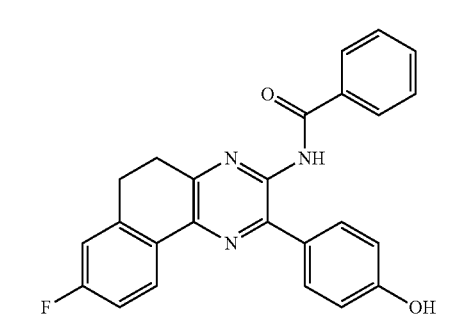 [SMILES: O=C(Nc1ncc(-c2ccc(F)cc2)nc1-c1ccc(O)cc1)c1ccccc1]
376
-continued
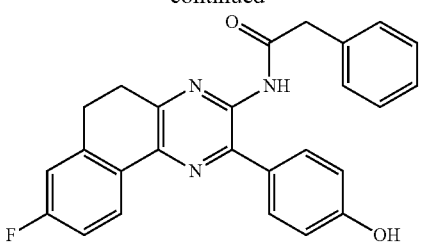
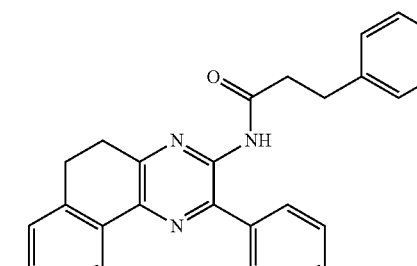
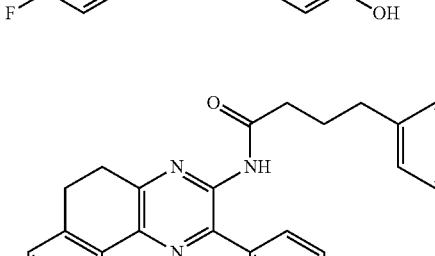
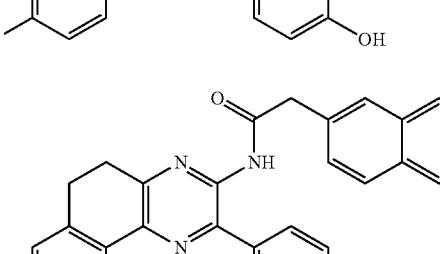
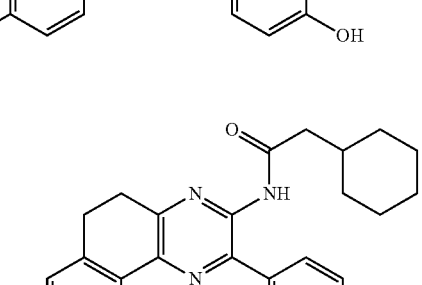
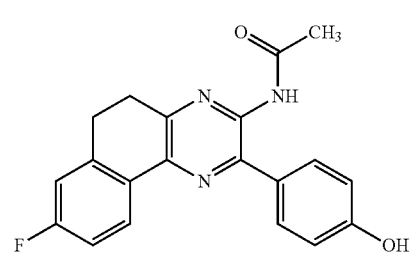

377
-continued
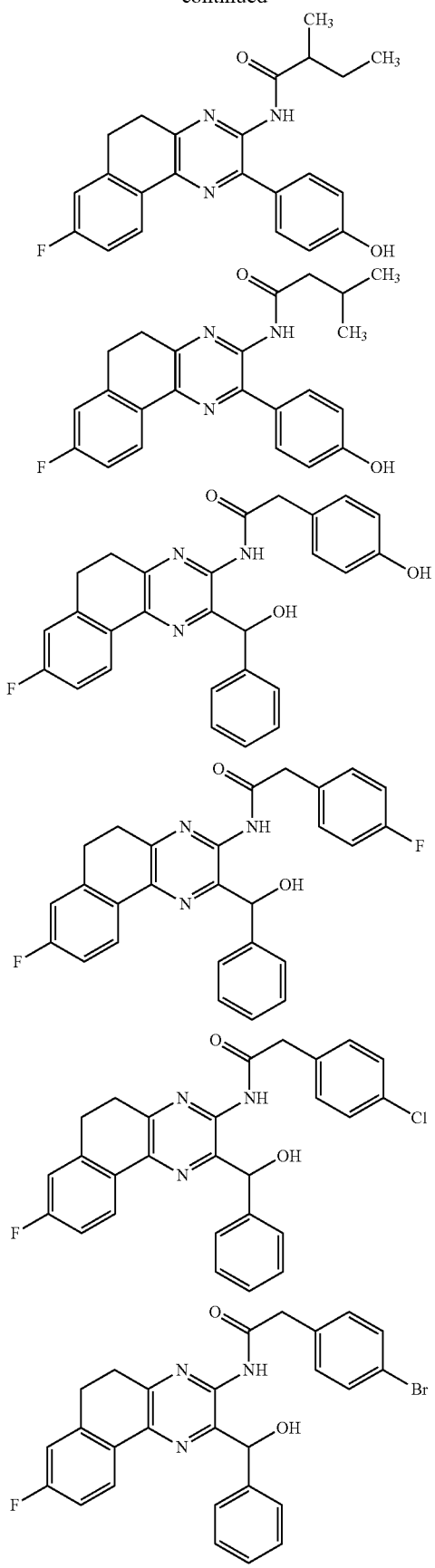
378
-continued
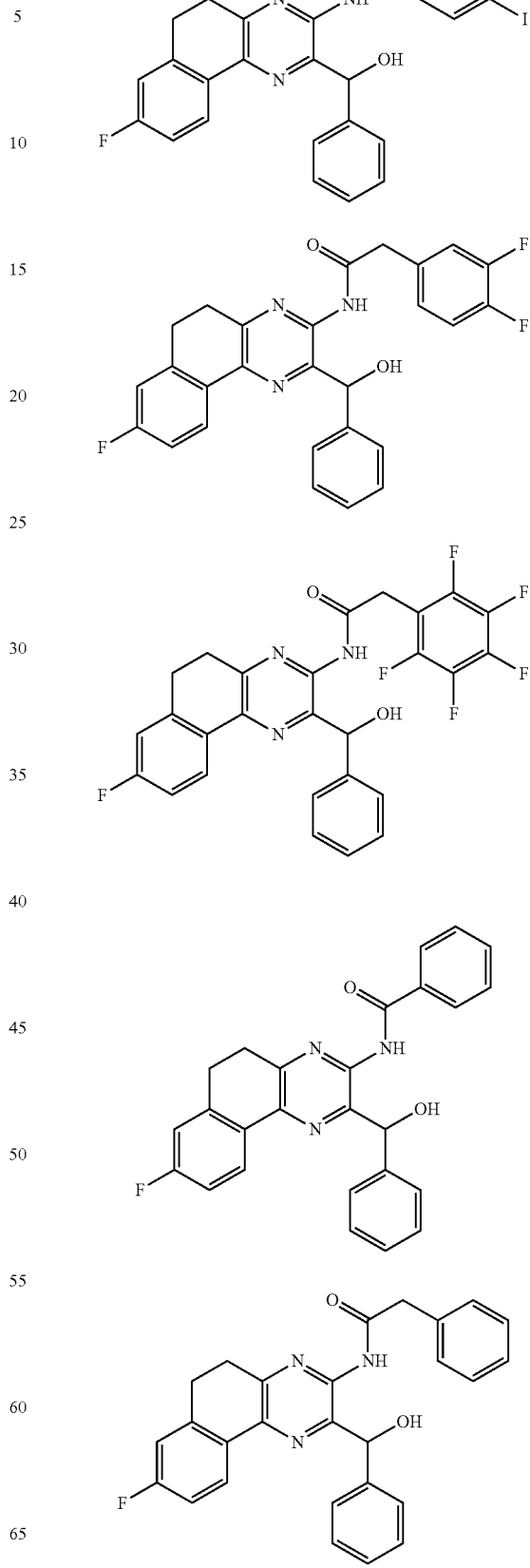

379
-continued
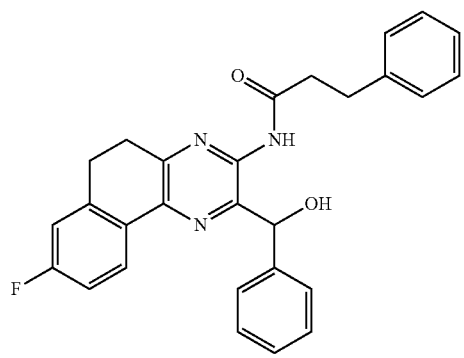
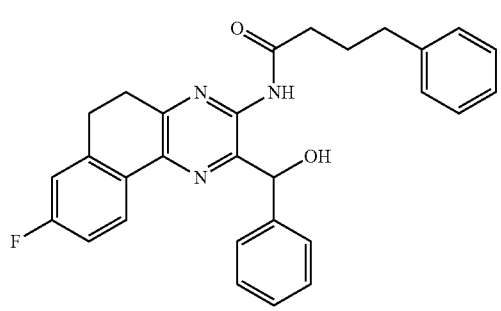
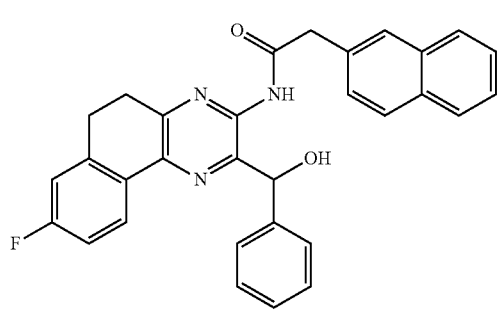
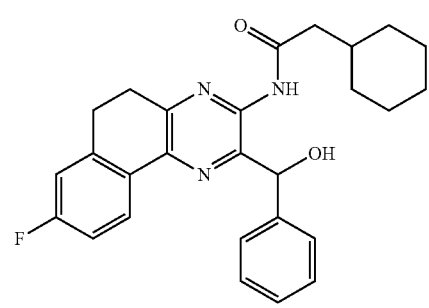
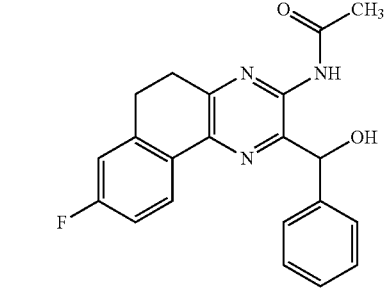
380
-continued
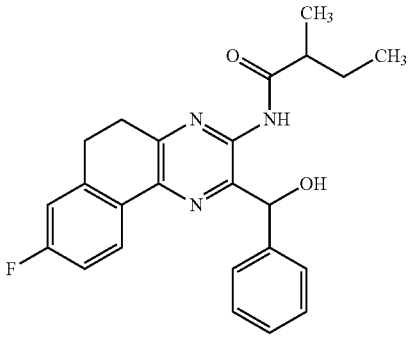
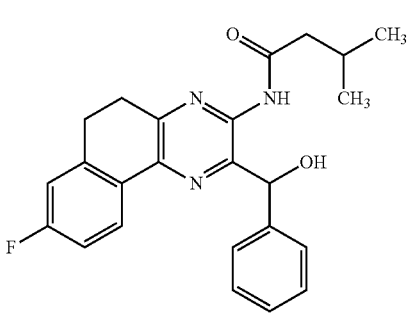
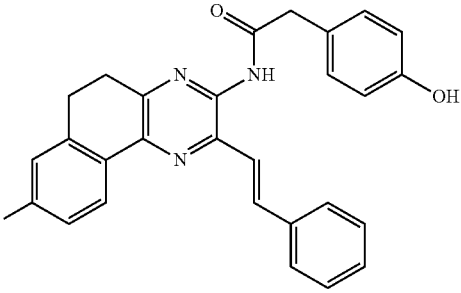
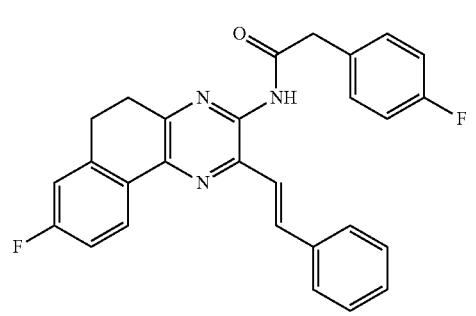
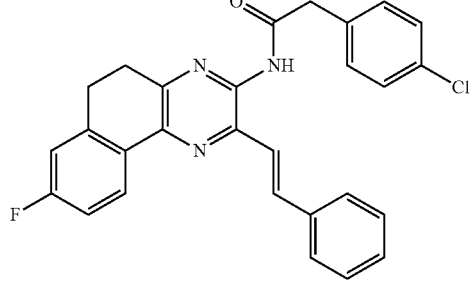

381
-continued
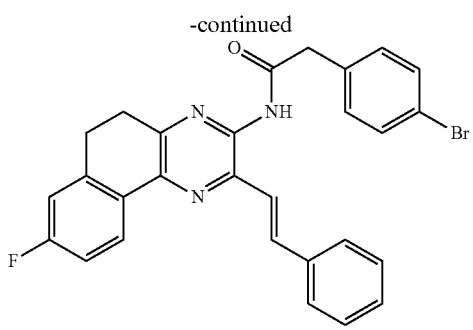
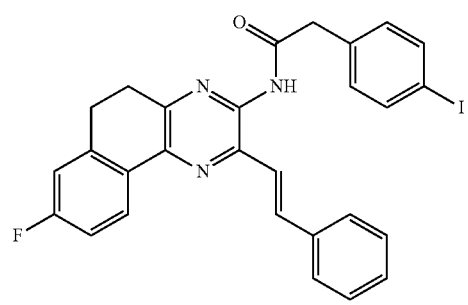
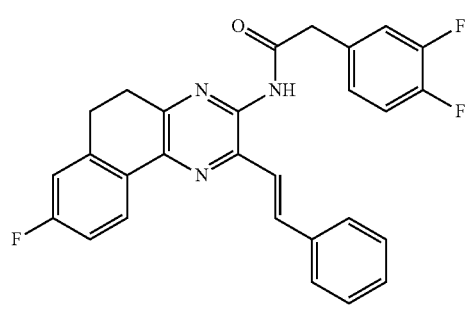
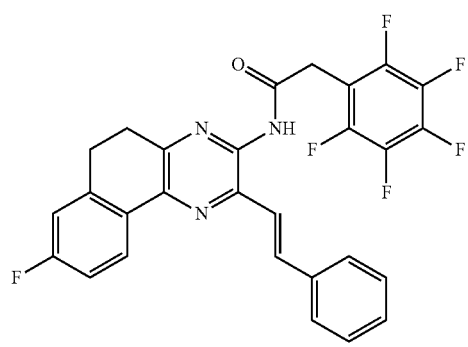
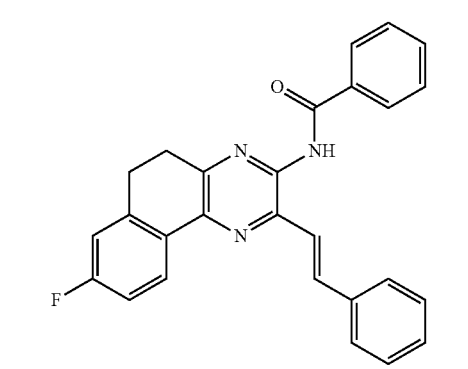
382
-continued
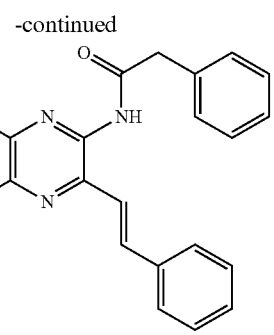
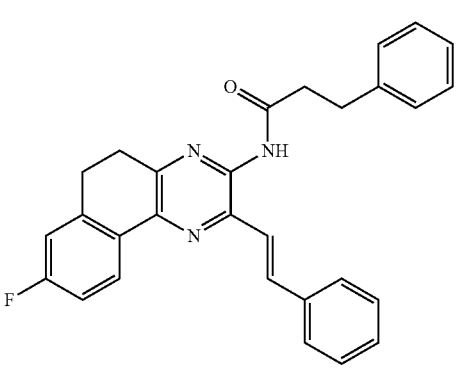
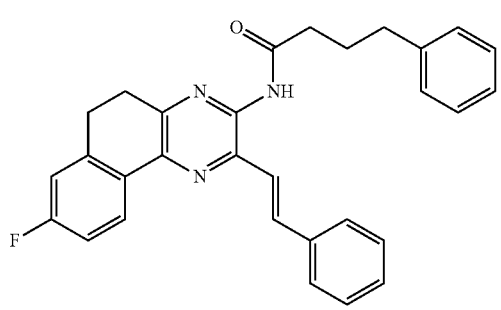
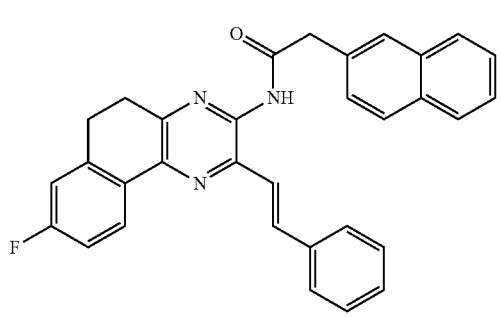
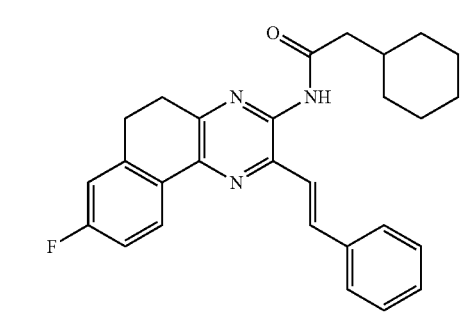

383
-continued
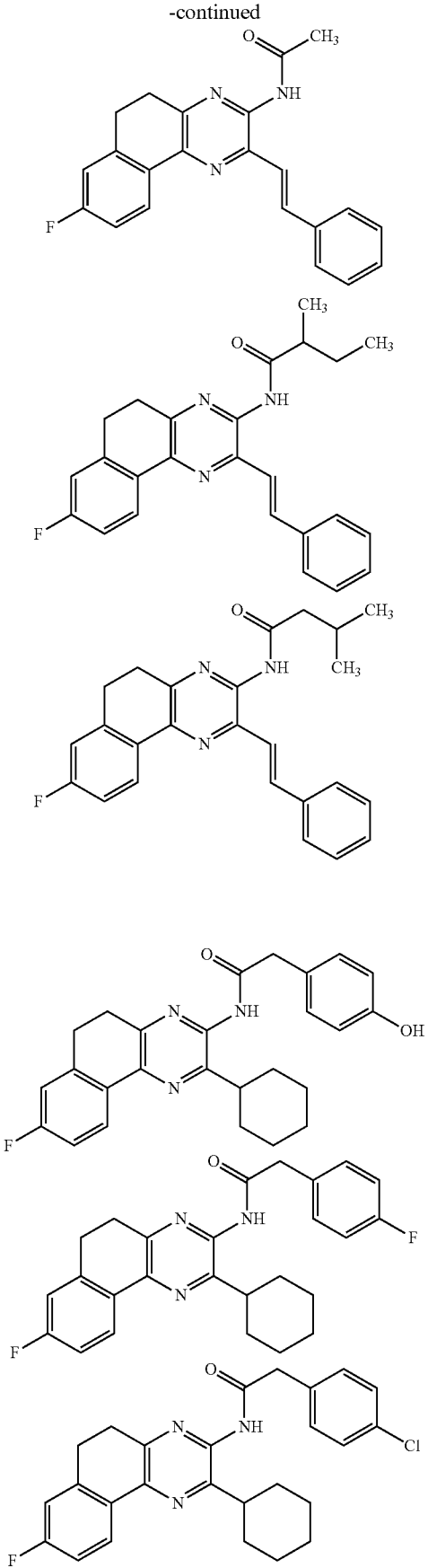
384
-continued
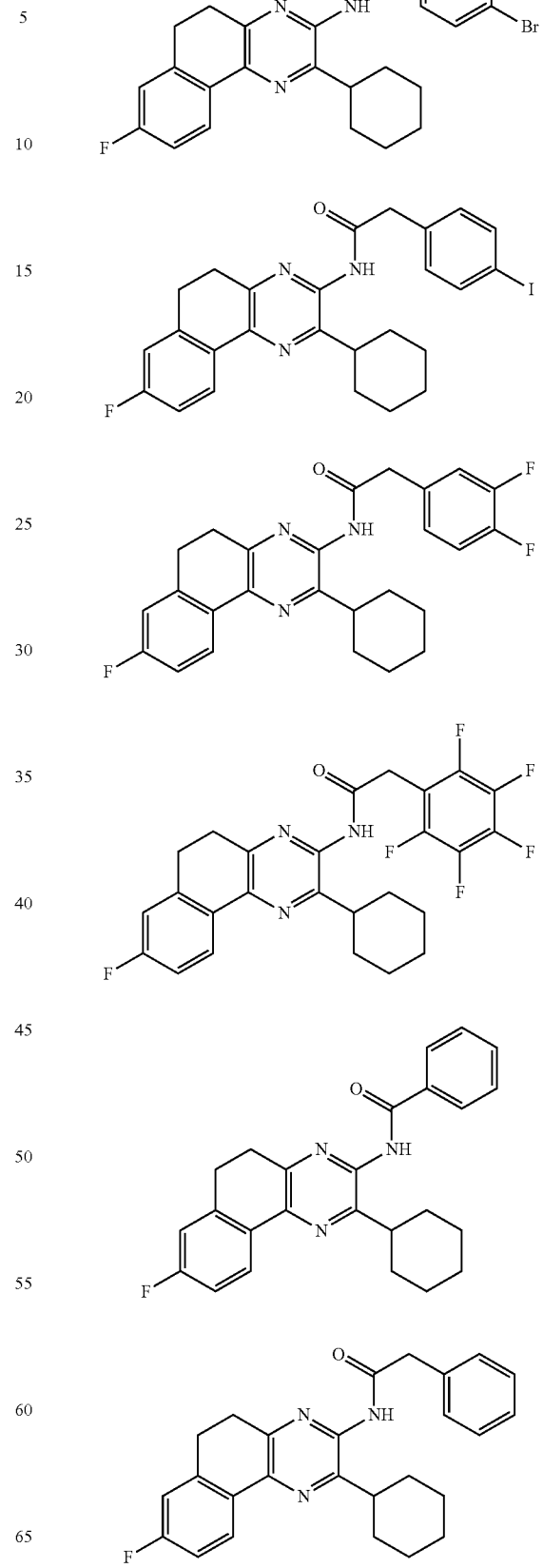

385
-continued
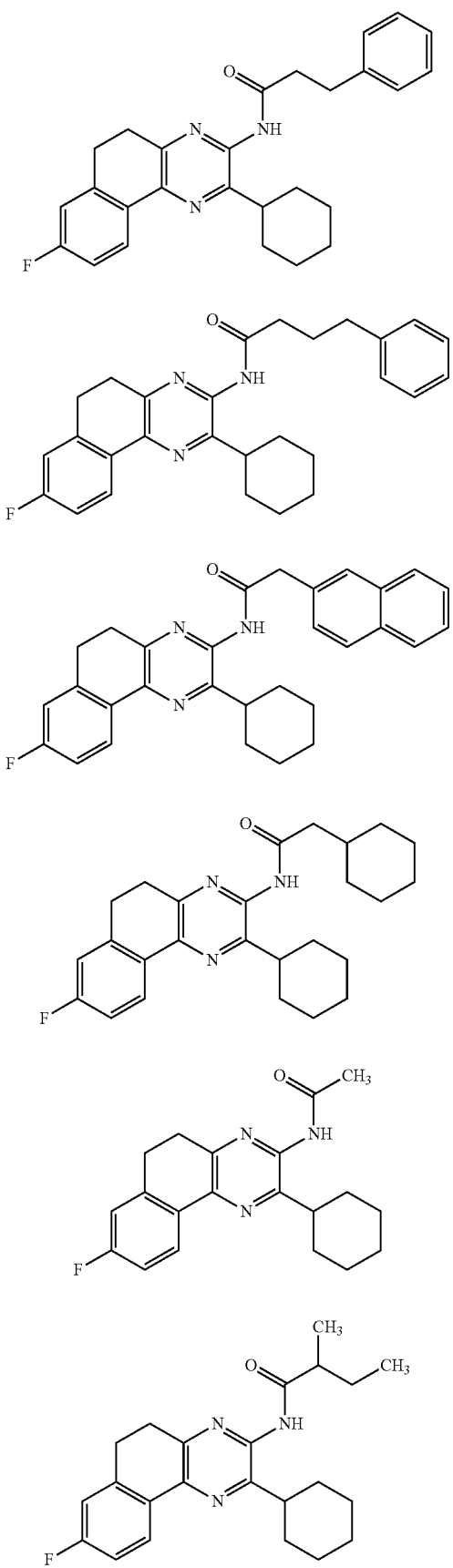
386
-continued
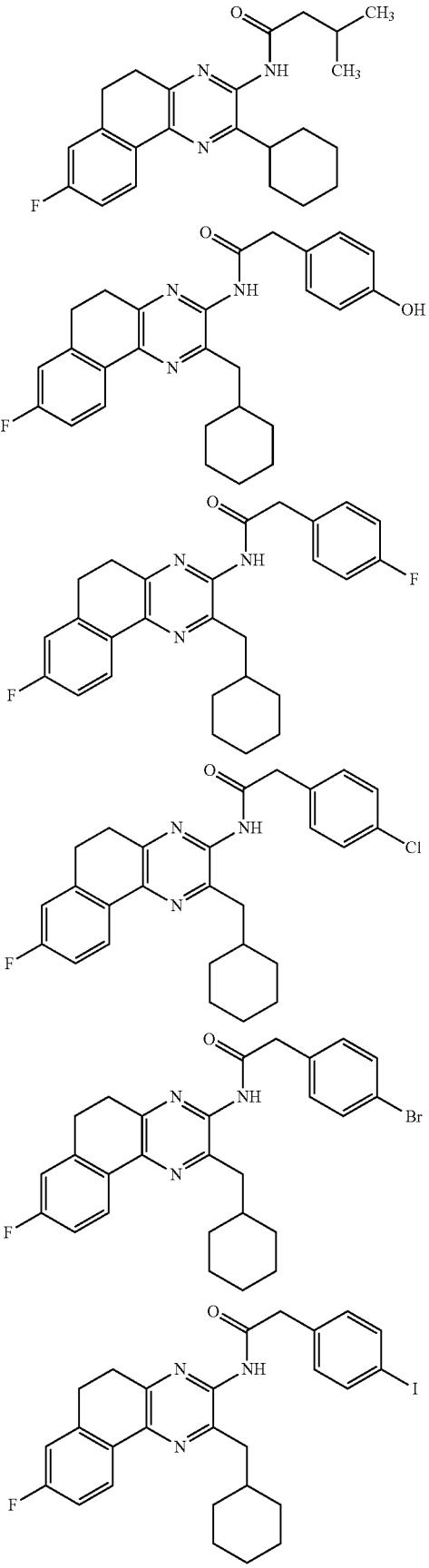

387
-continued
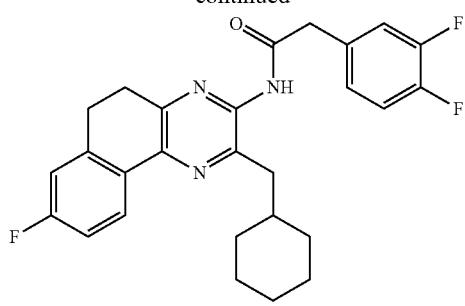
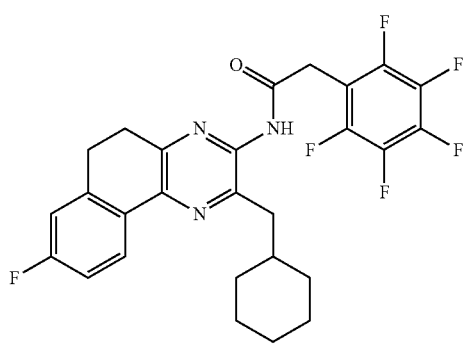
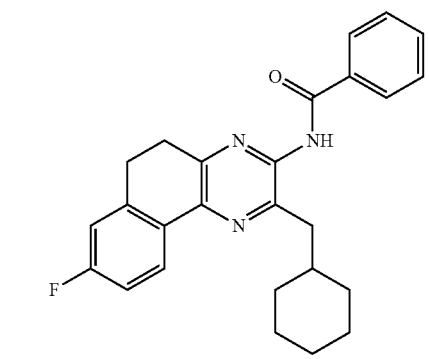
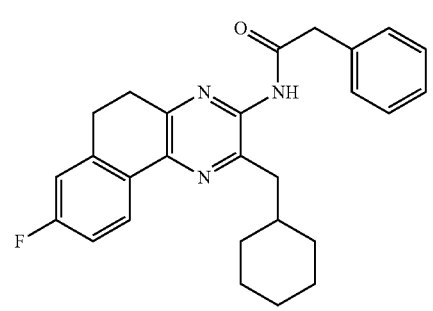
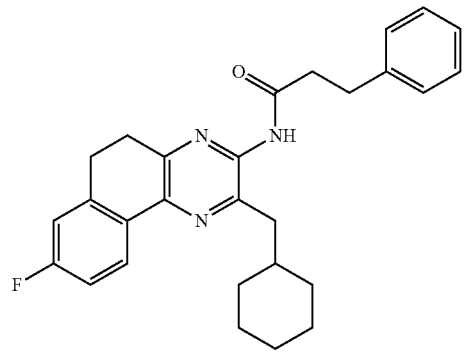
388
-continued
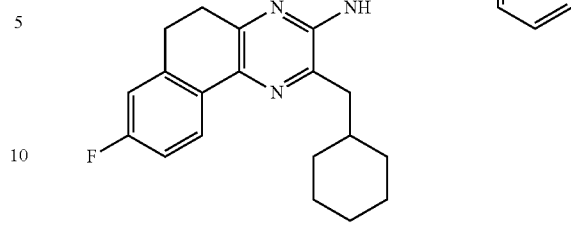
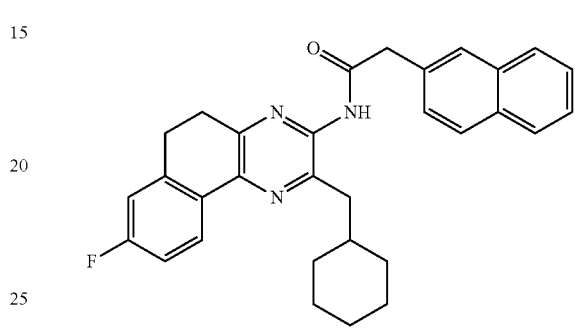
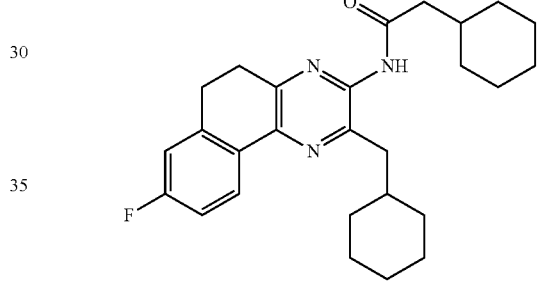
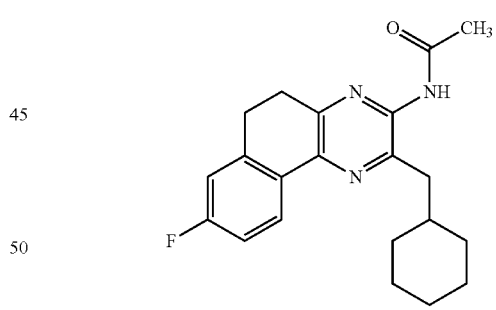
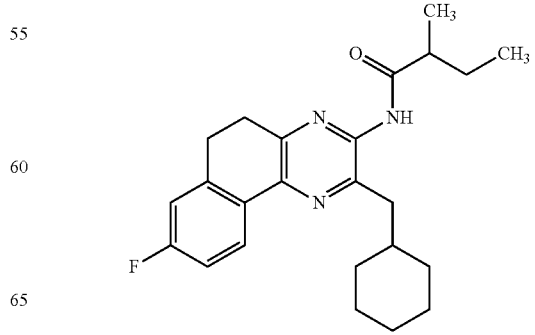

389
-continued
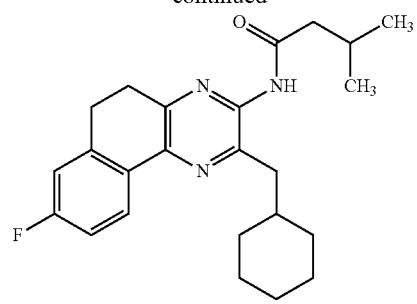
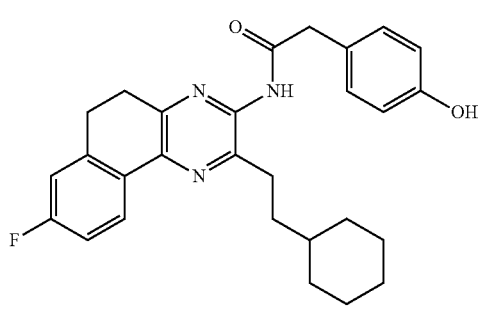
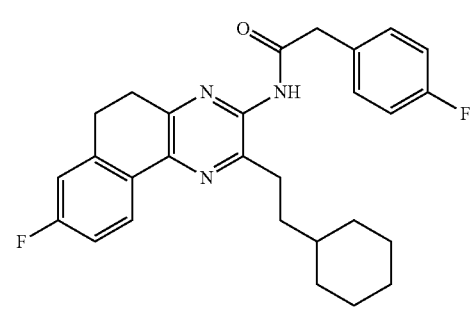
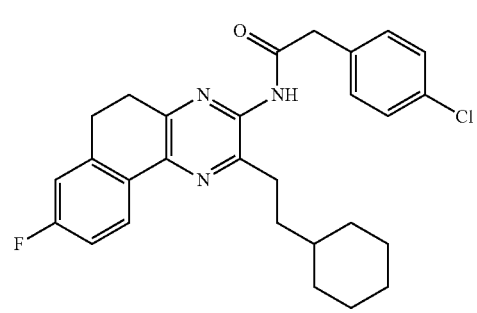
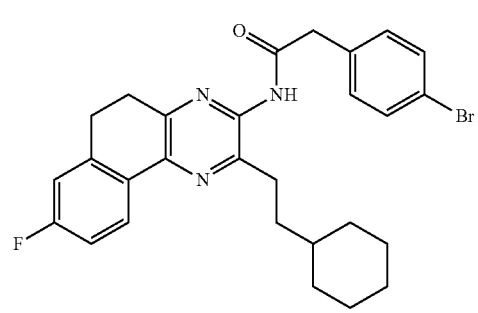
390
-continued
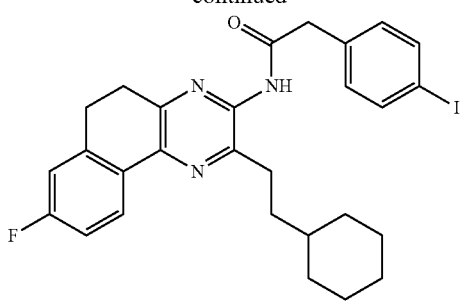
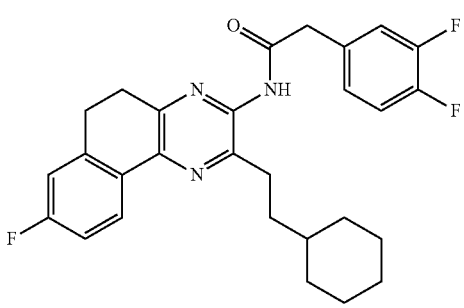
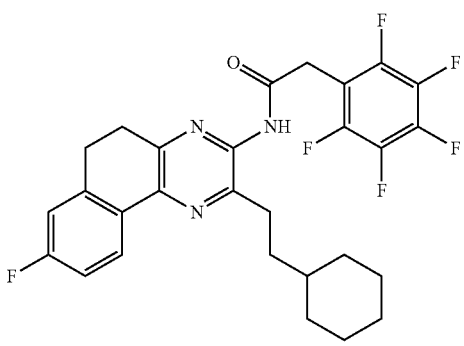
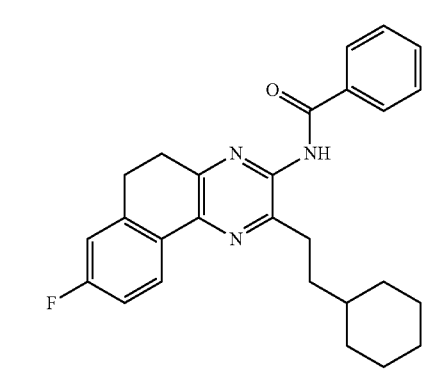
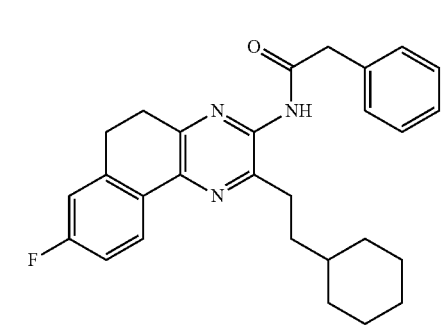

391
-continued
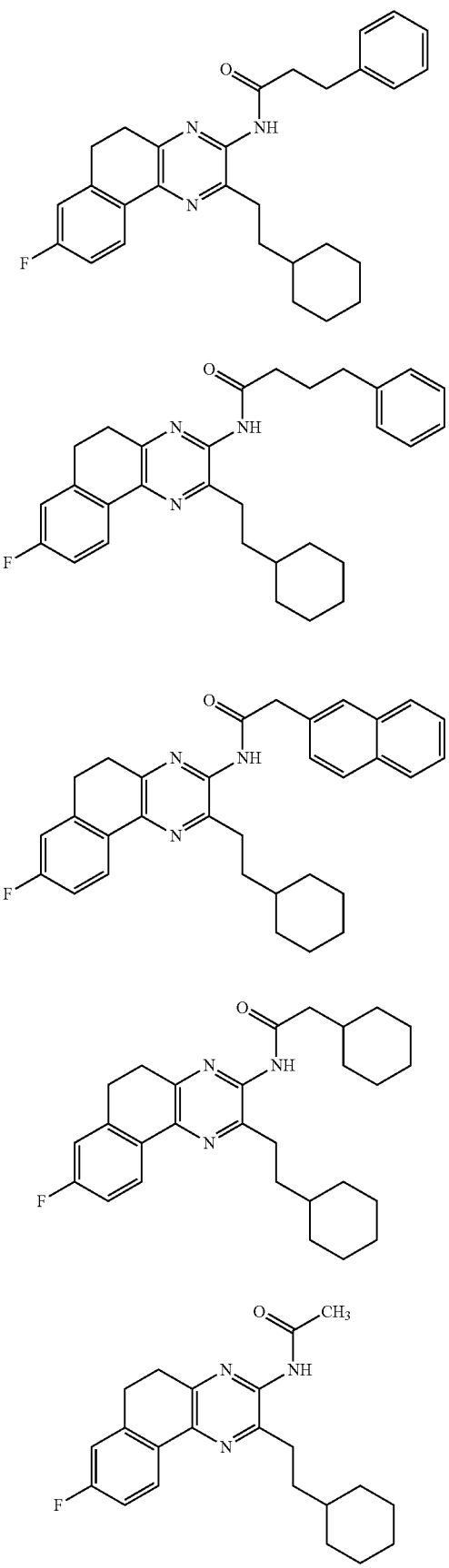
392
-continued
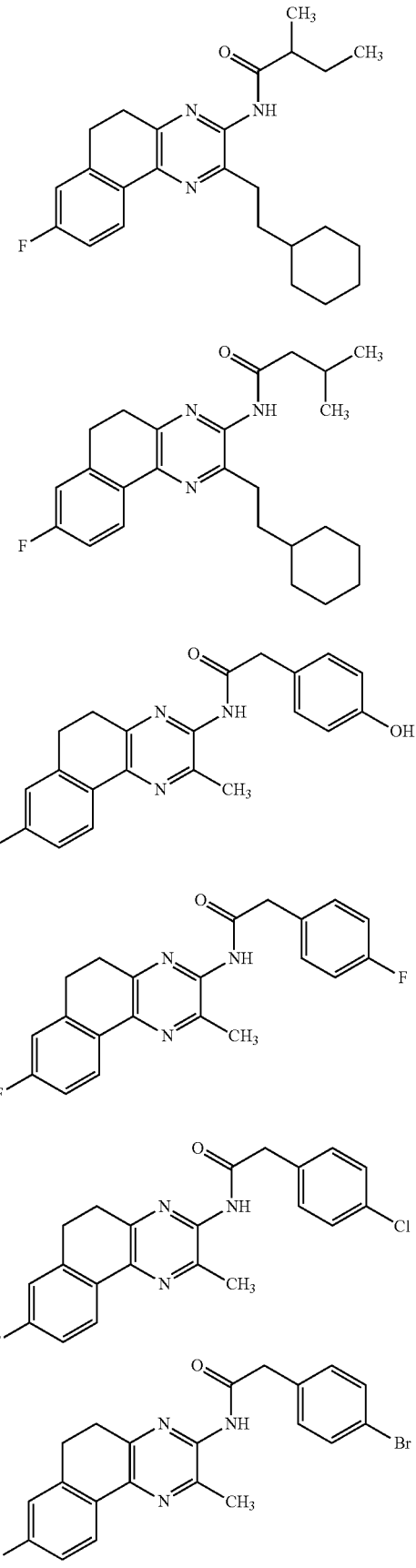

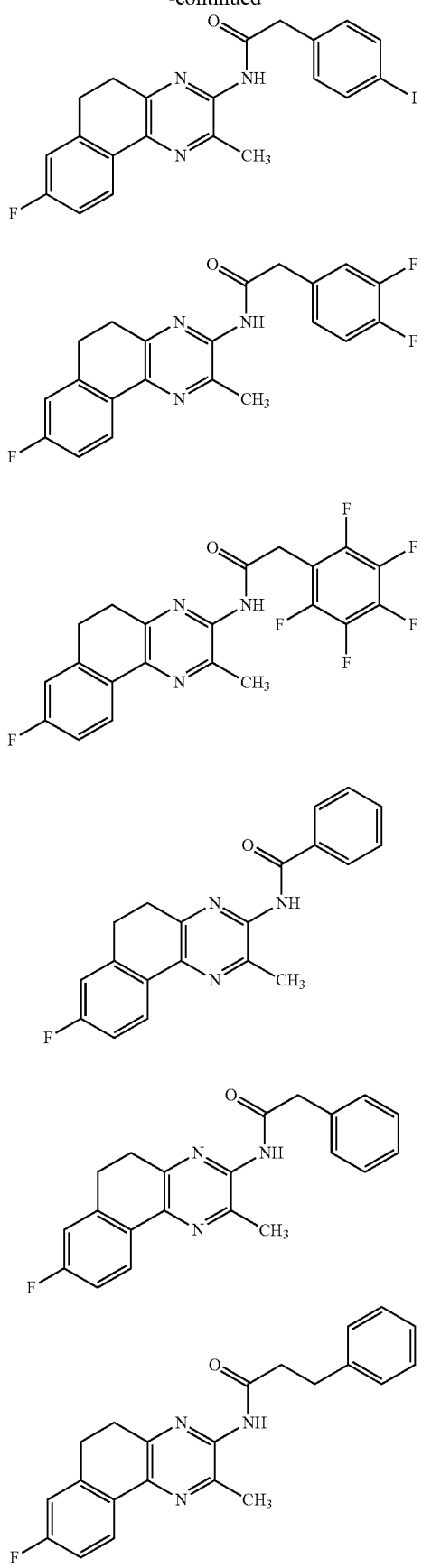
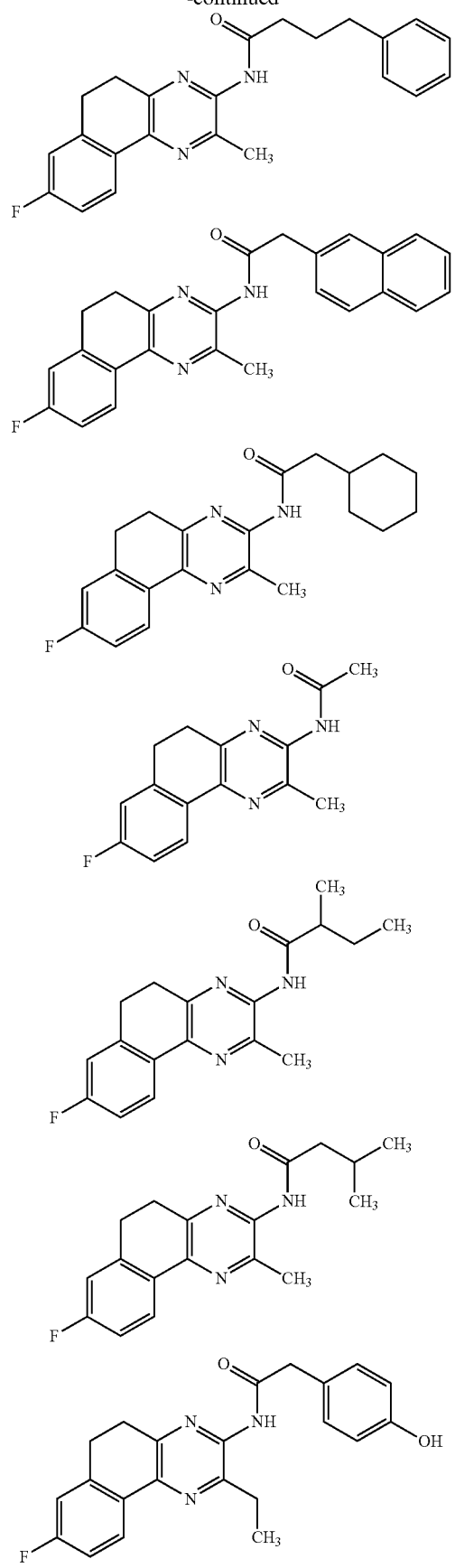

-continued
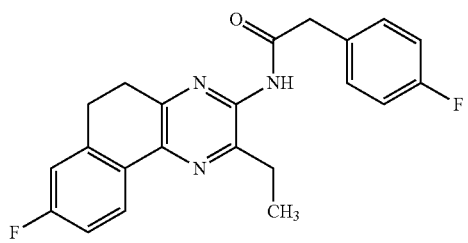
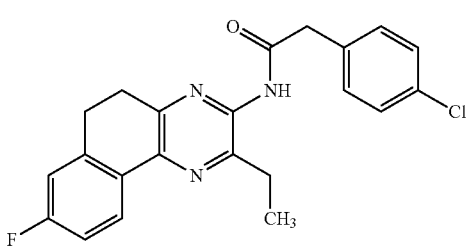
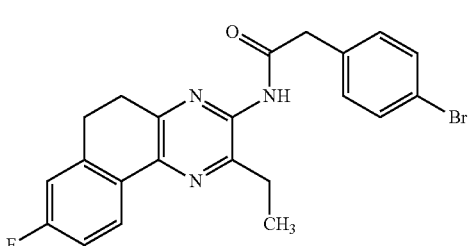
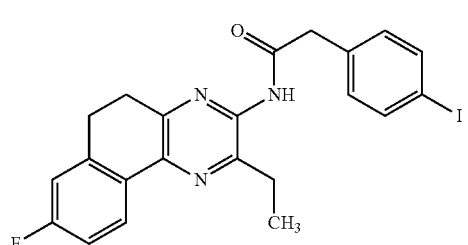
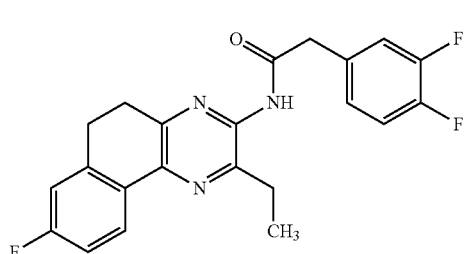
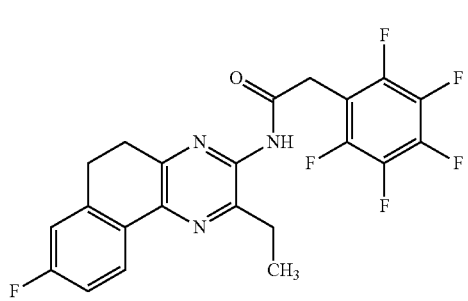
-continued
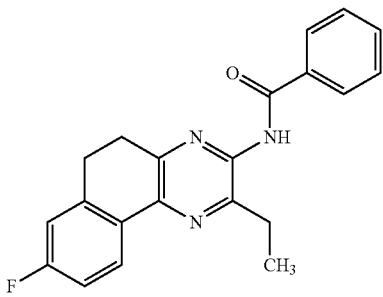
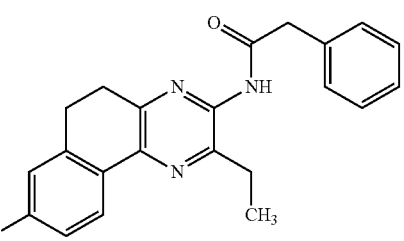
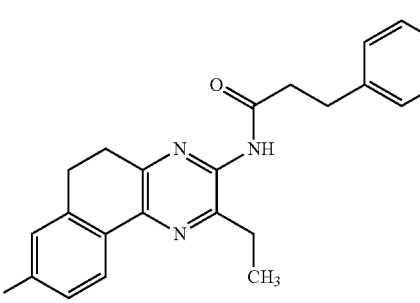
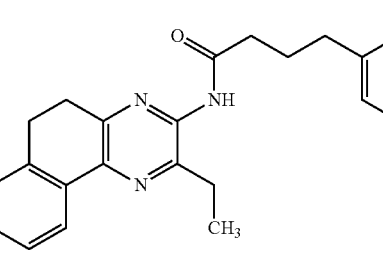
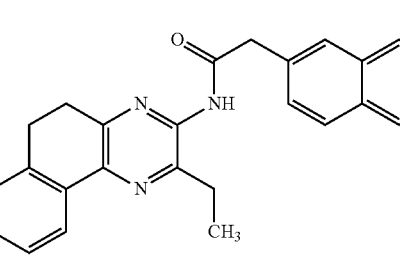
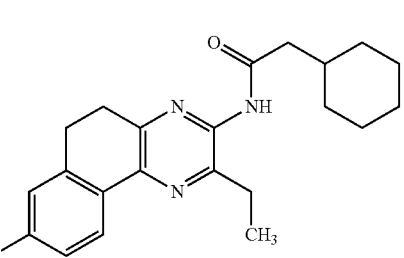

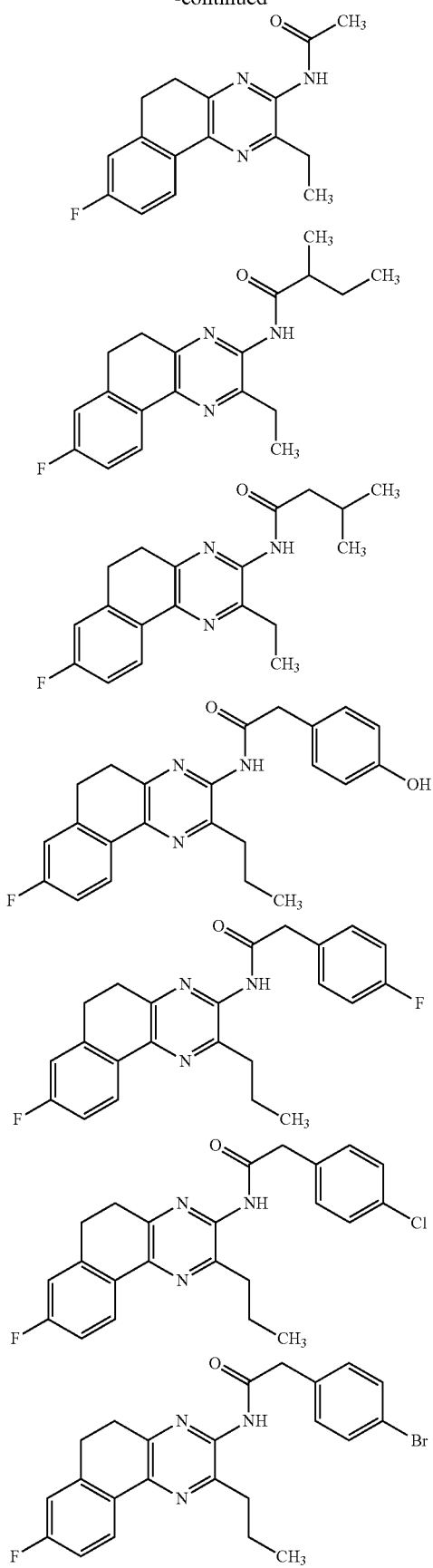
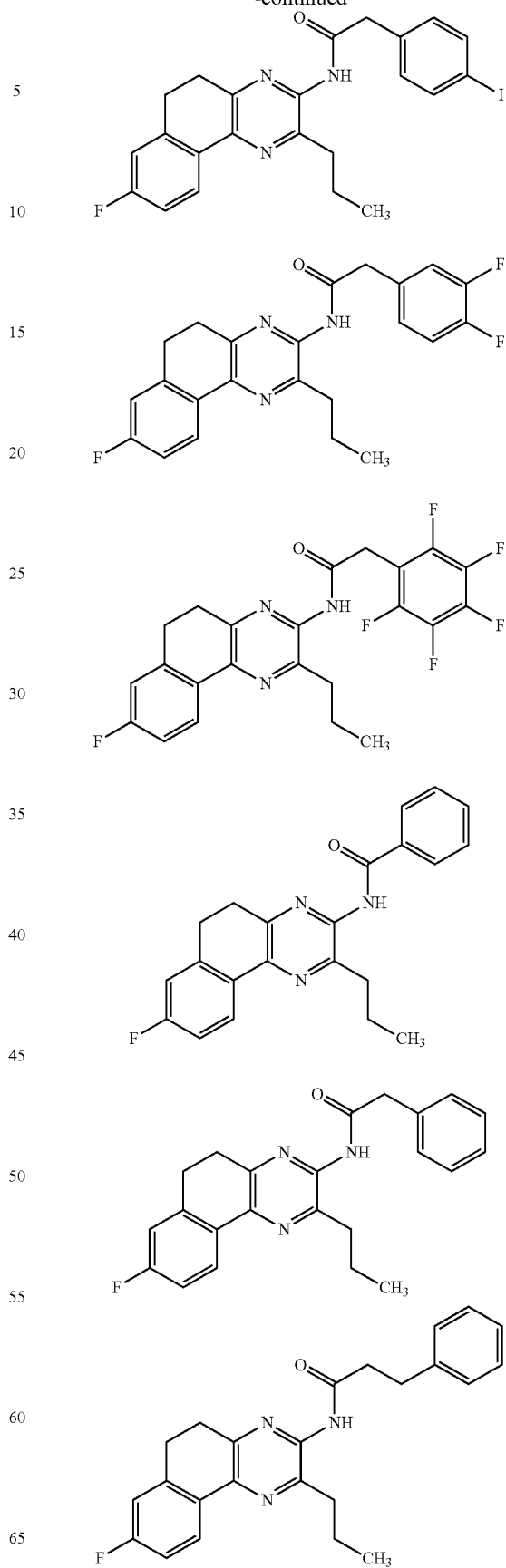

399
-continued
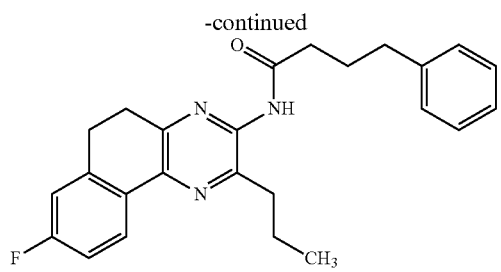
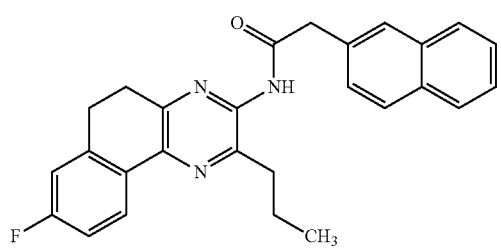
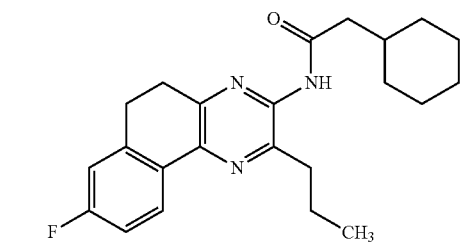
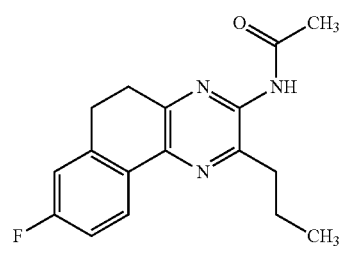
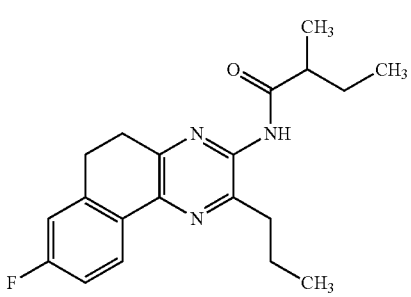
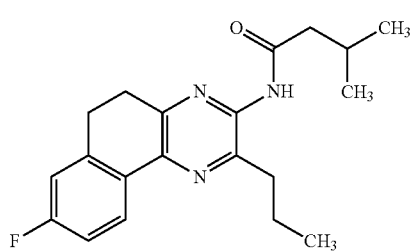
400
-continued
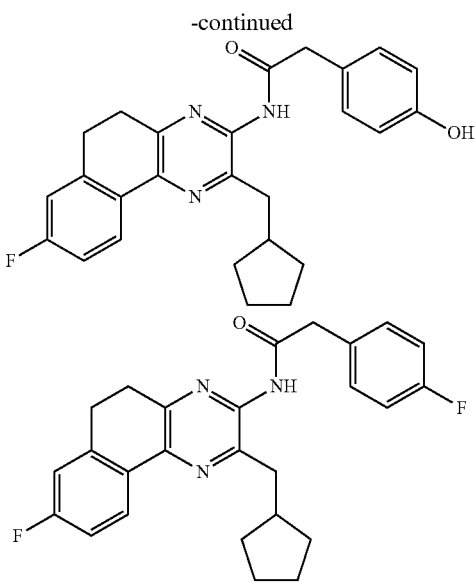
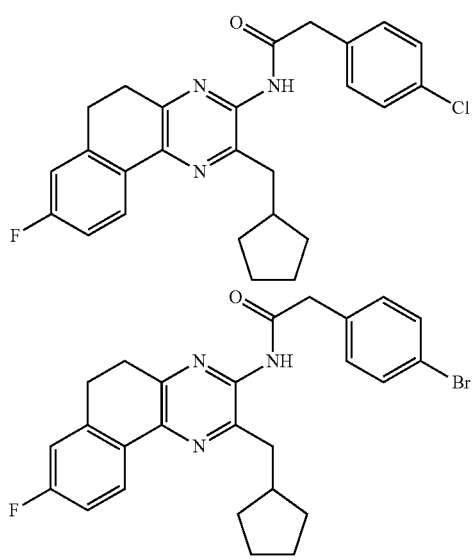
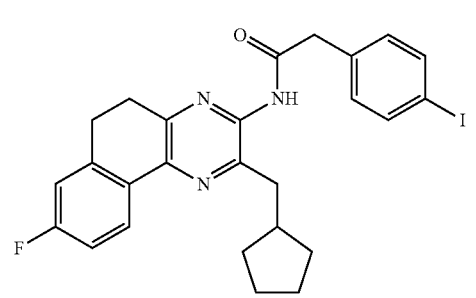
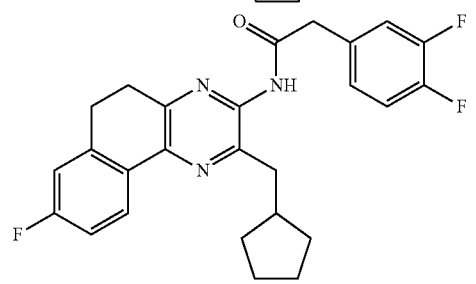

401
-continued
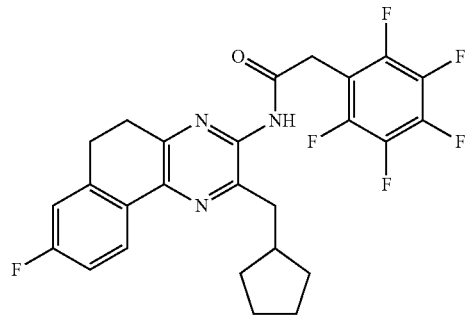
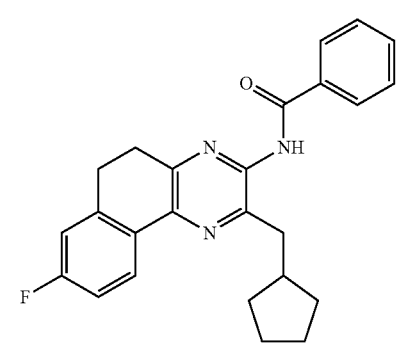
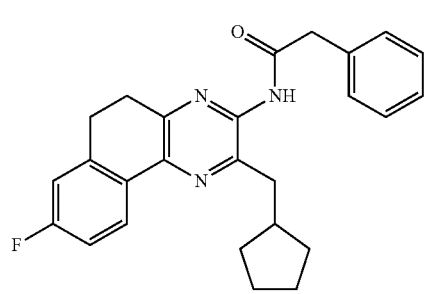
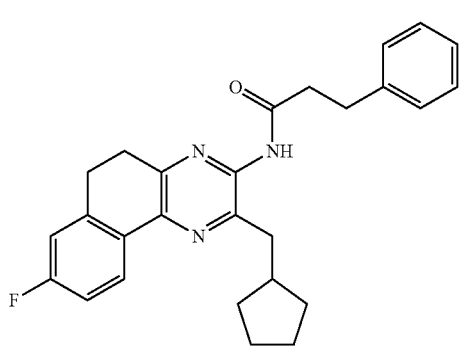
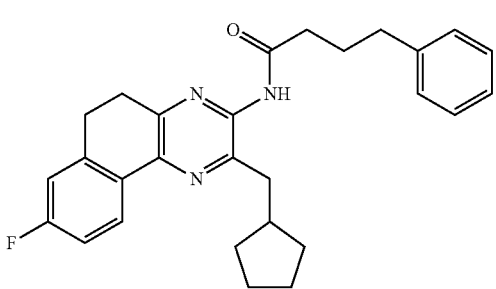
402
-continued
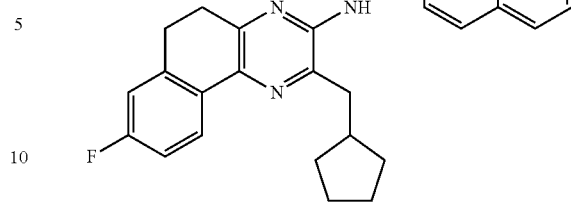
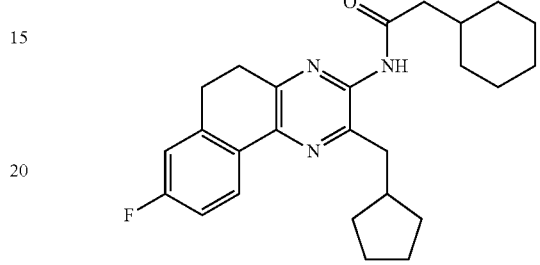
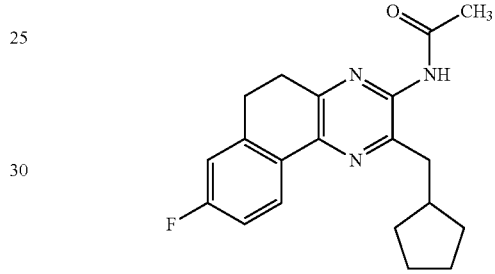
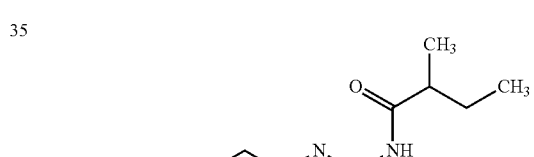
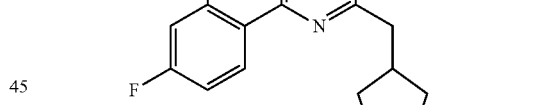
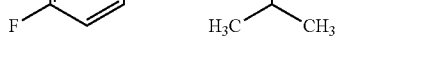

-continued
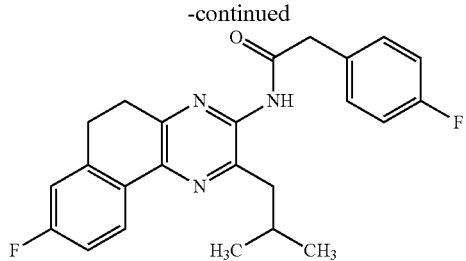
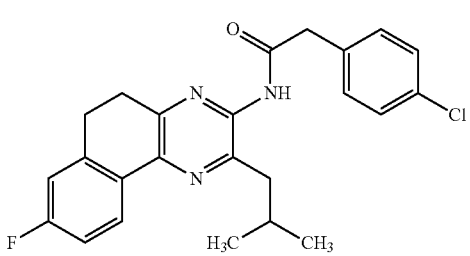
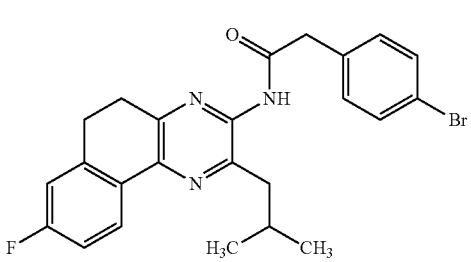
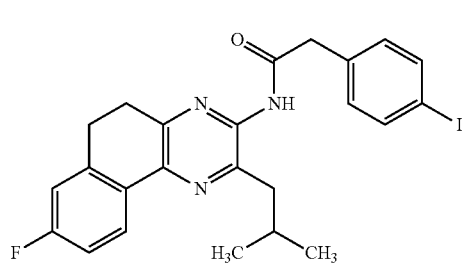
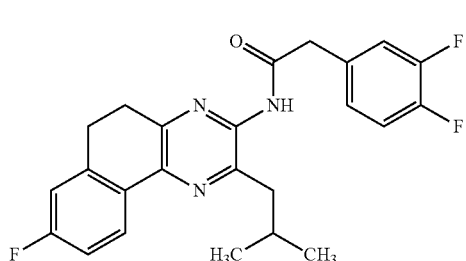
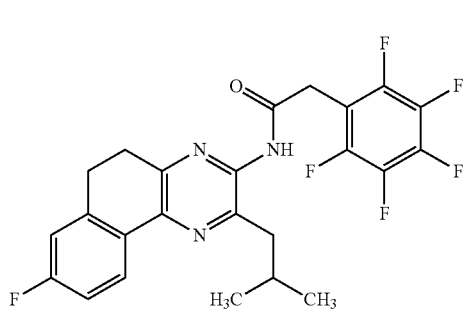
-continued
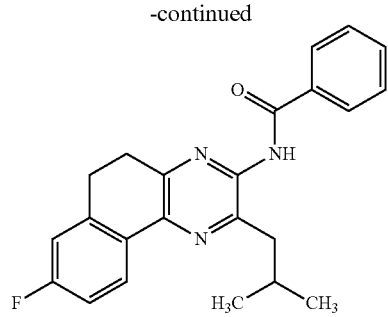
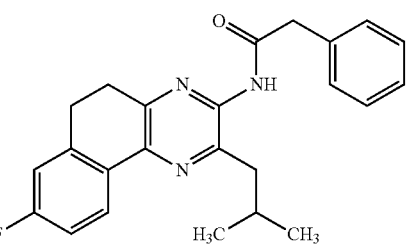
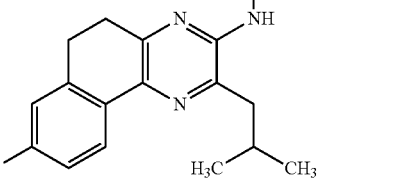
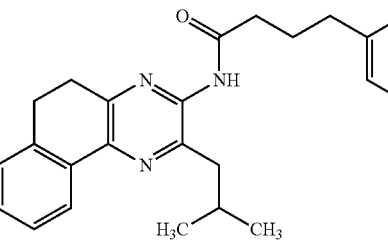
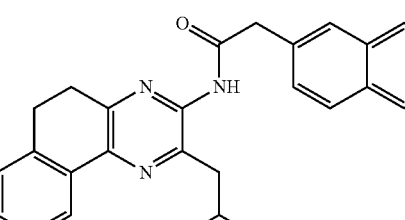
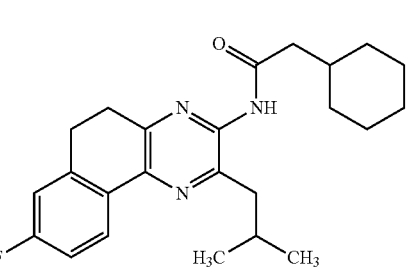

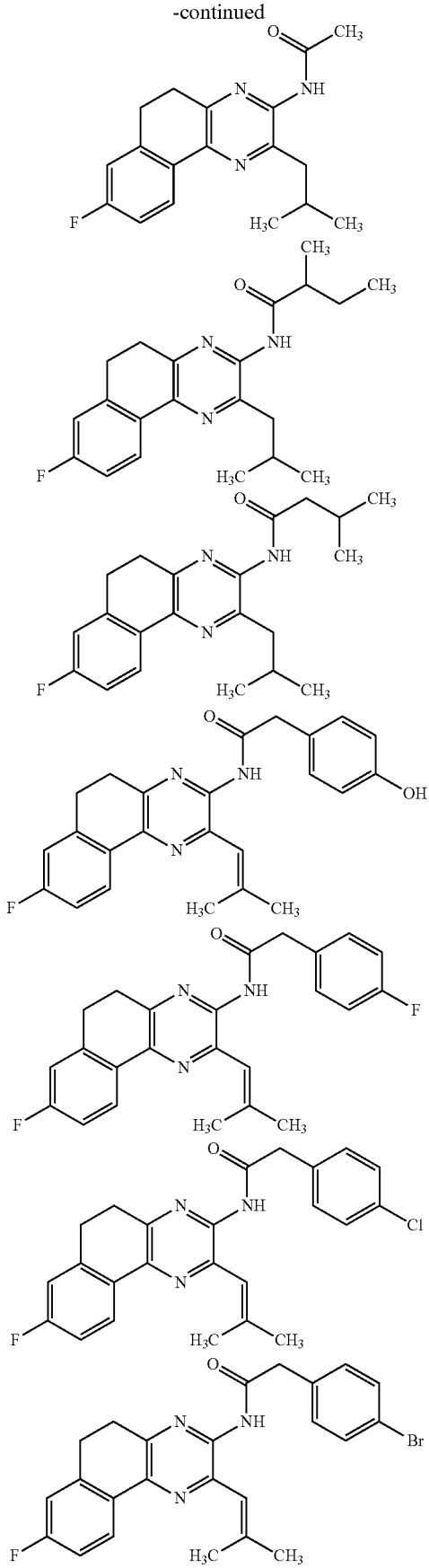
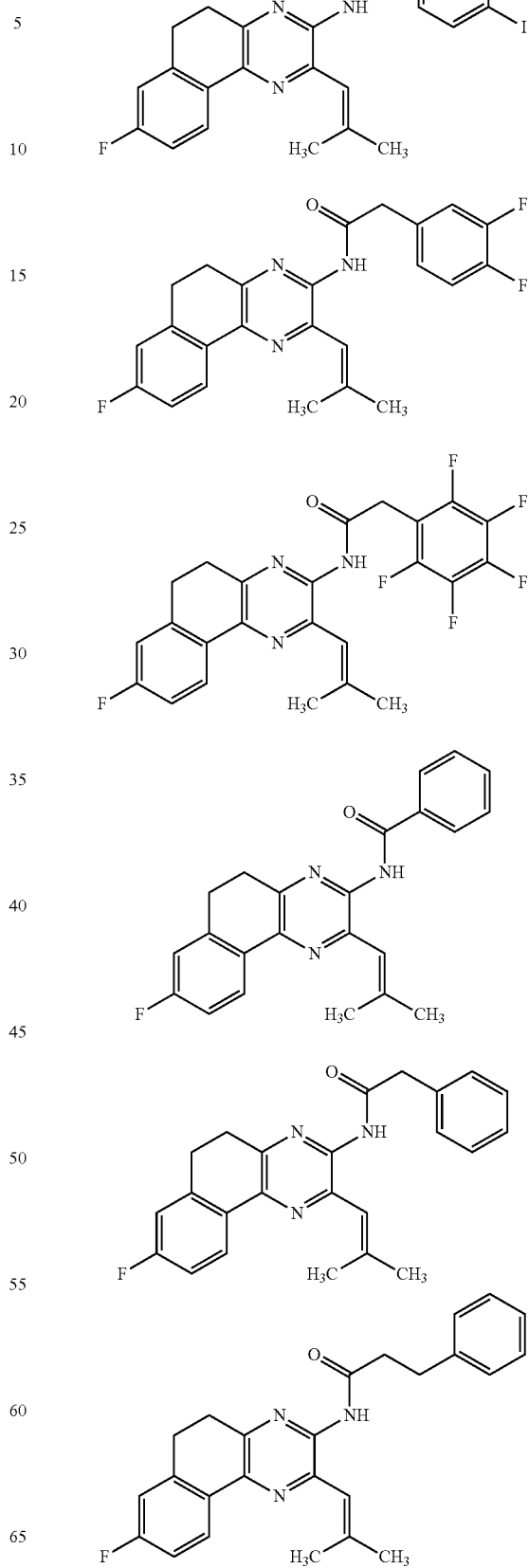

407
-continued
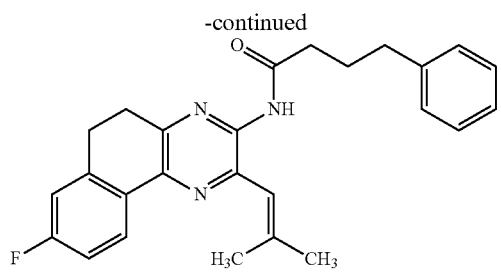
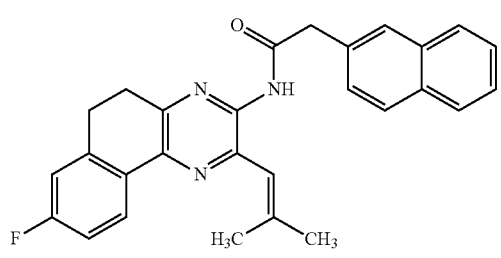
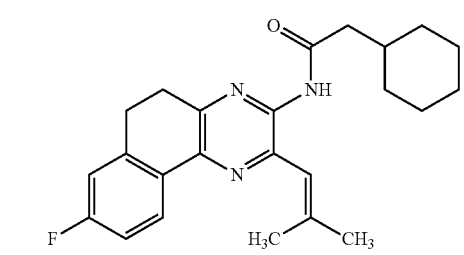
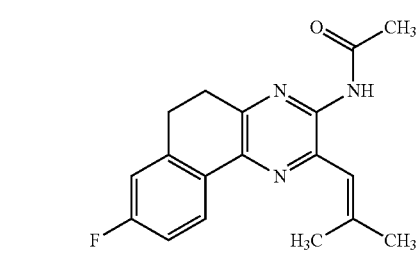
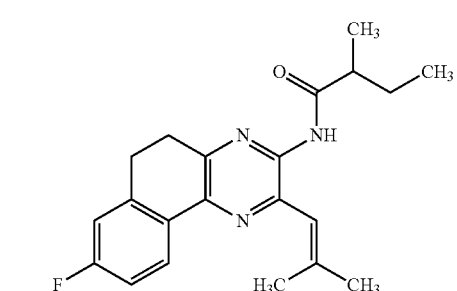
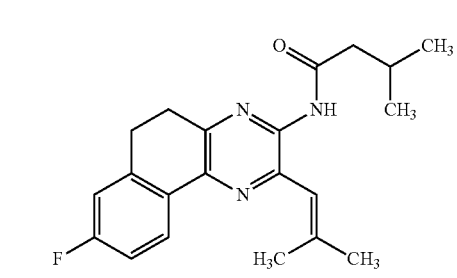
408
-continued
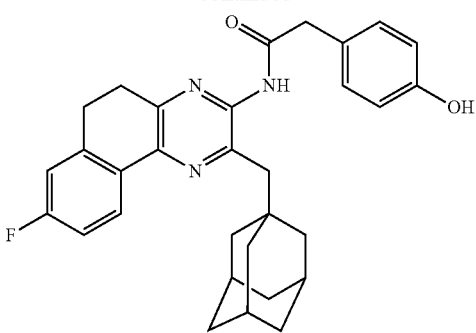
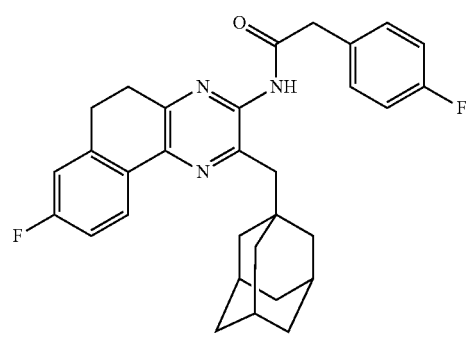
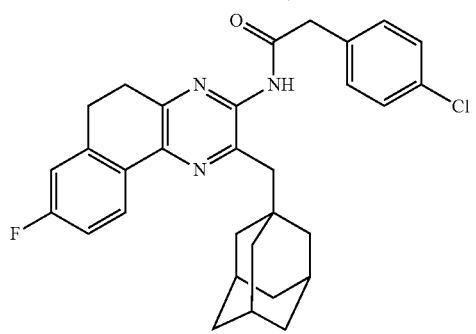
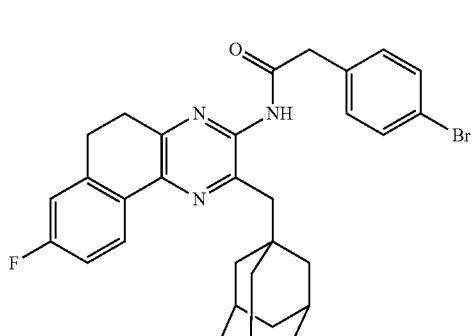
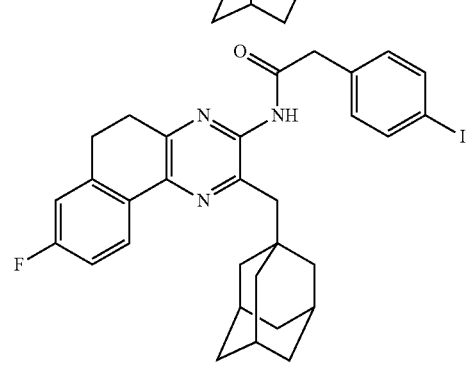

409
-continued
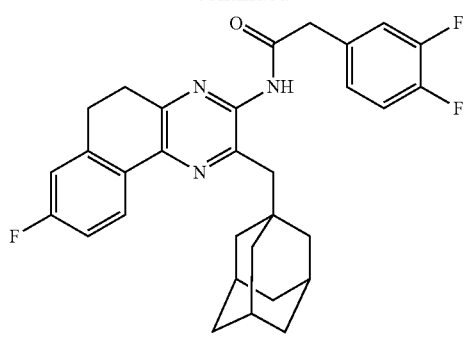
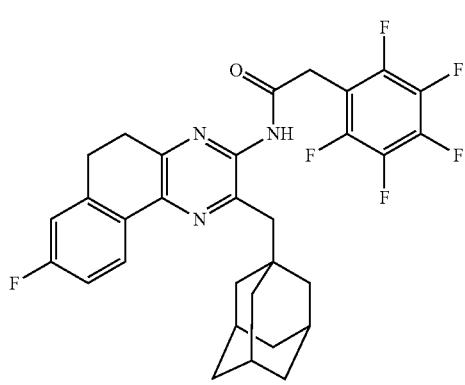
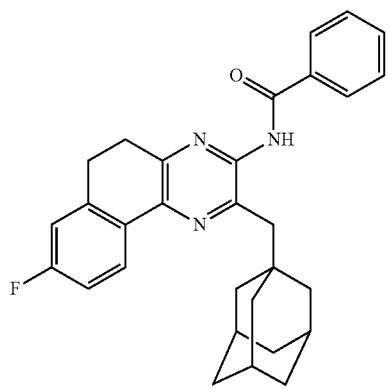
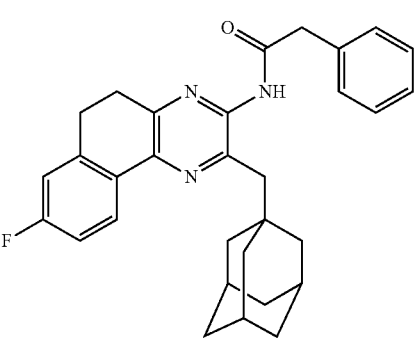
410
-continued
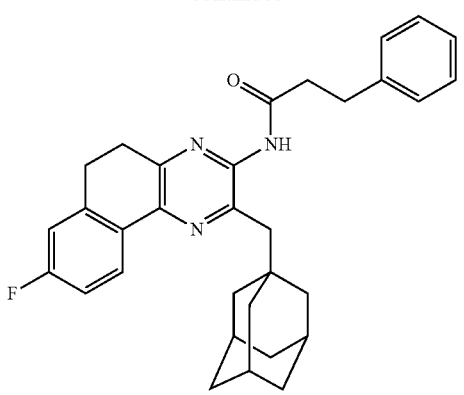
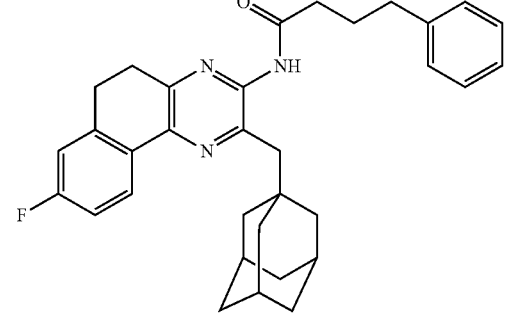
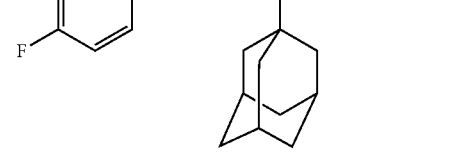
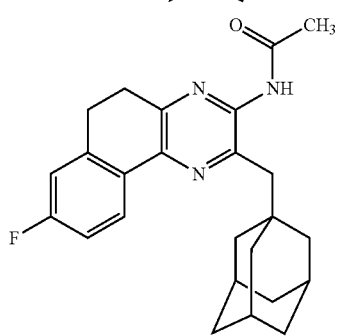

411
-continued
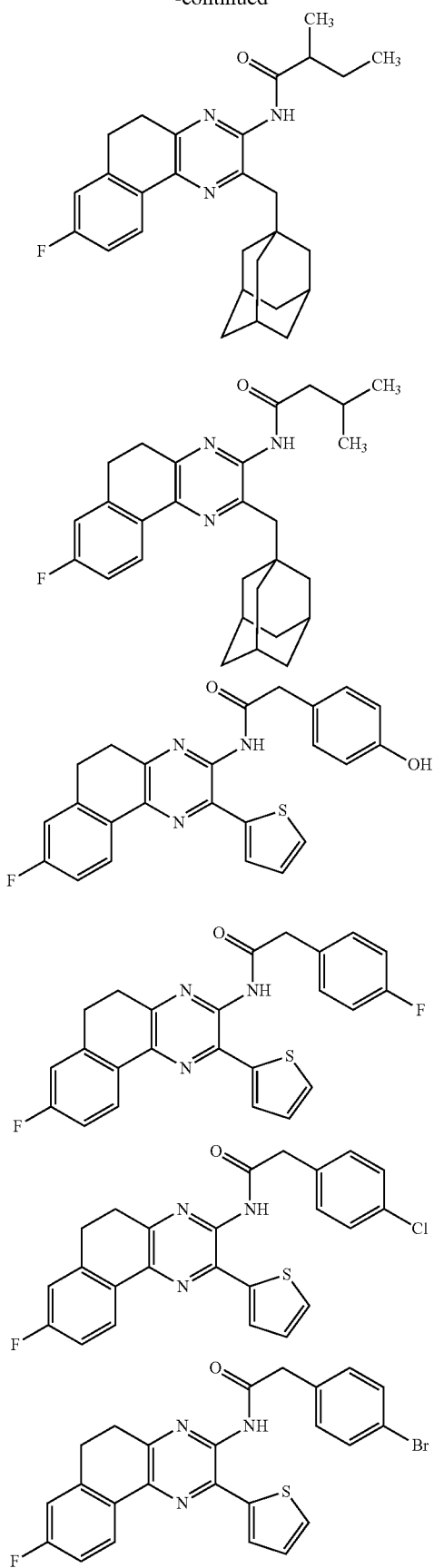
412
-continued
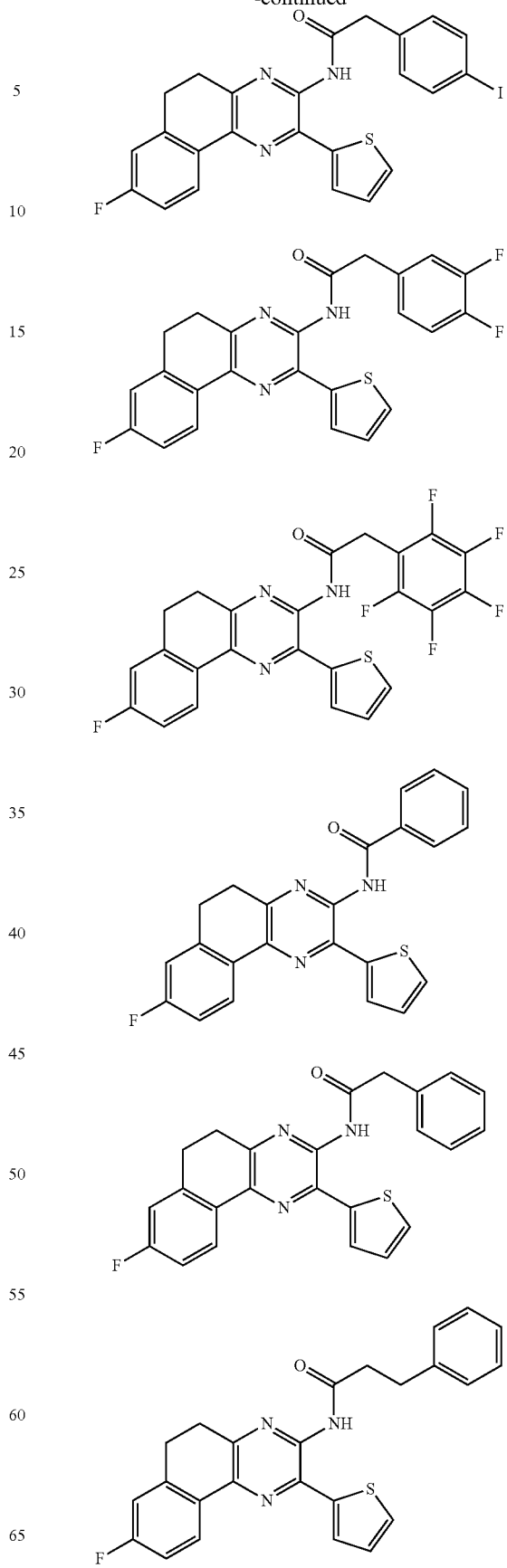

413
-continued
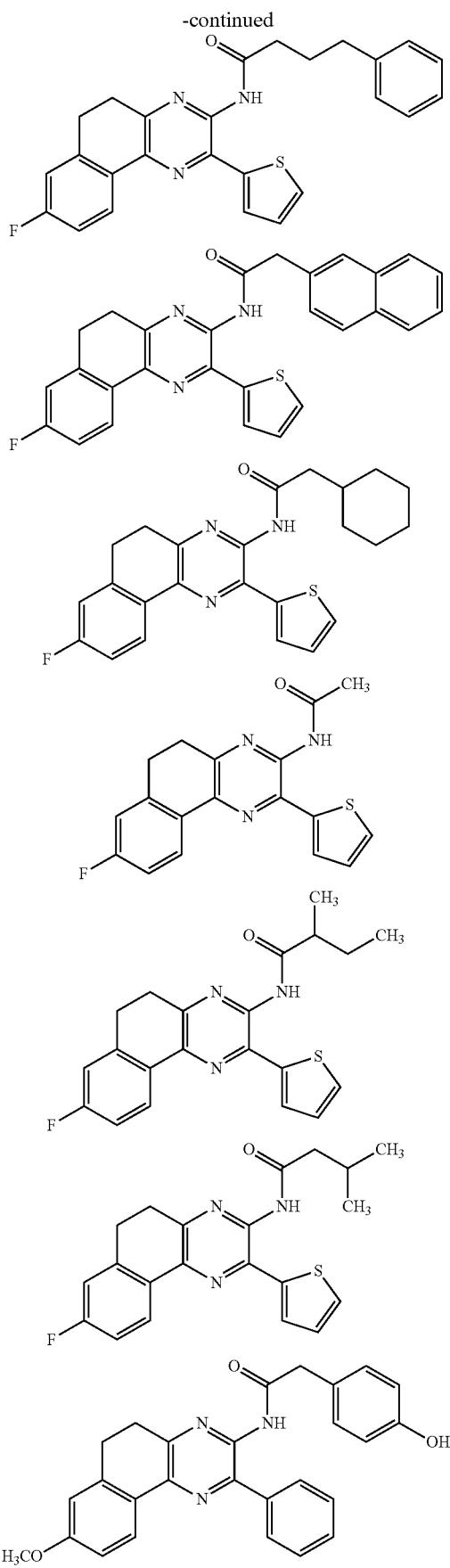
414
-continued
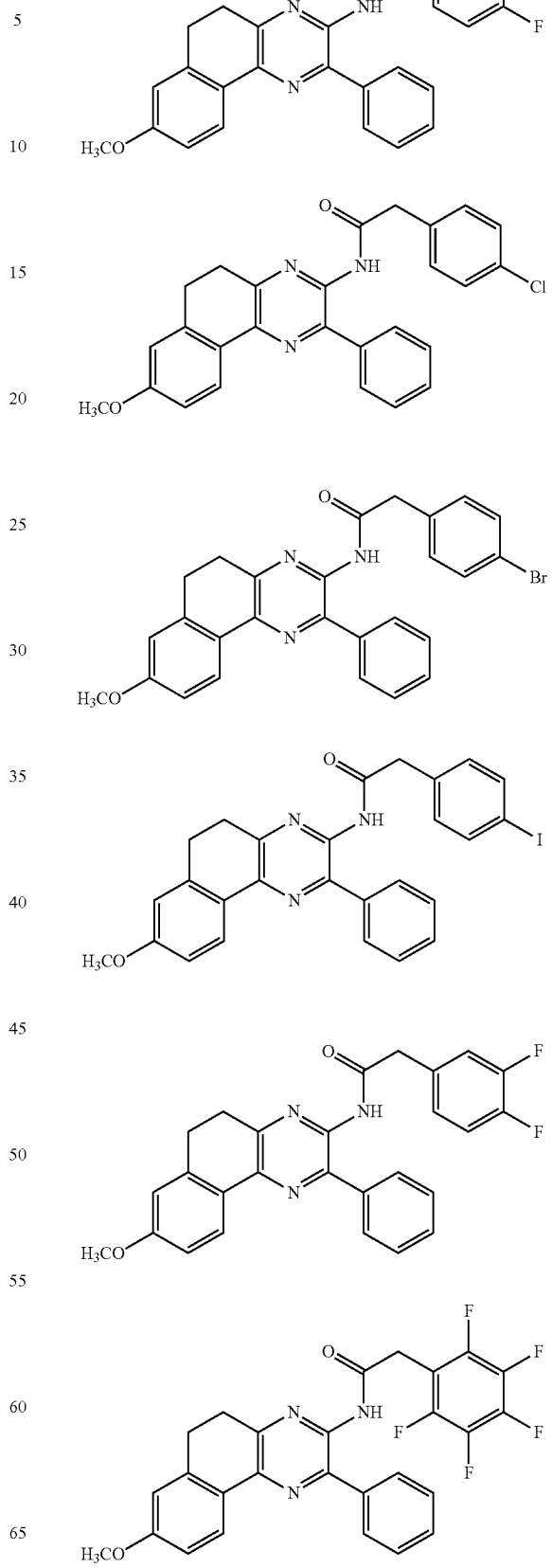

415
-continued
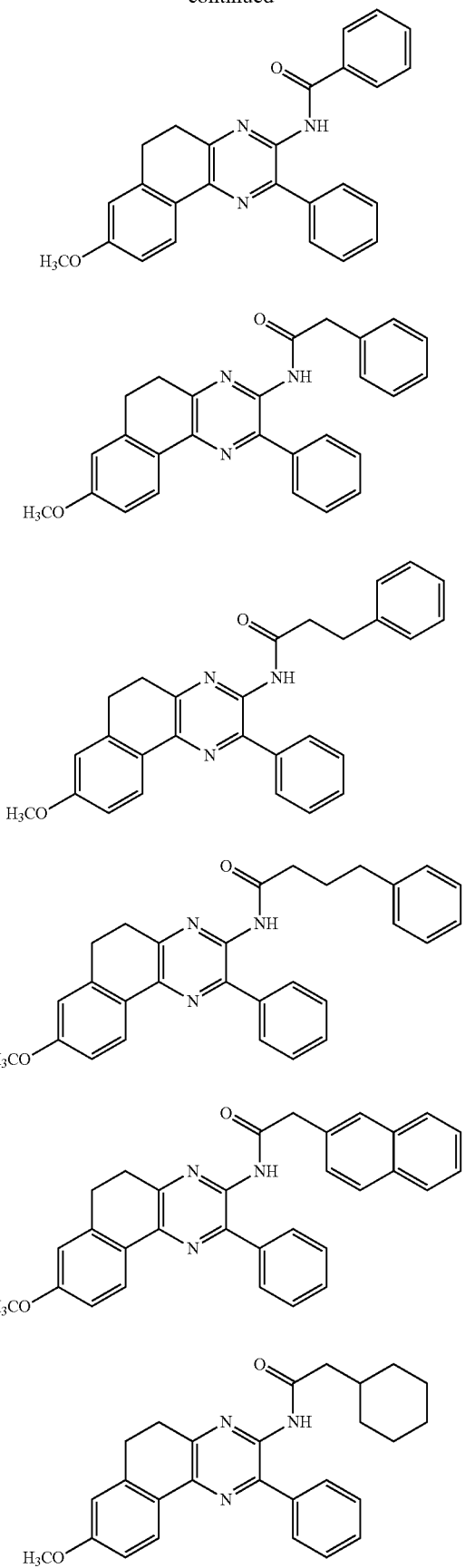
416
-continued
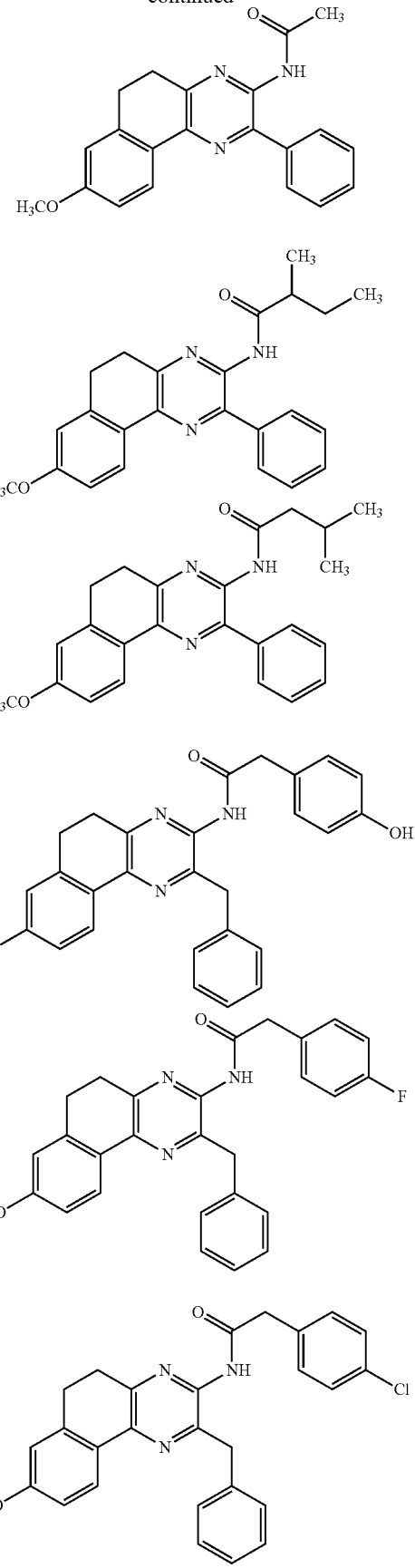

417
-continued
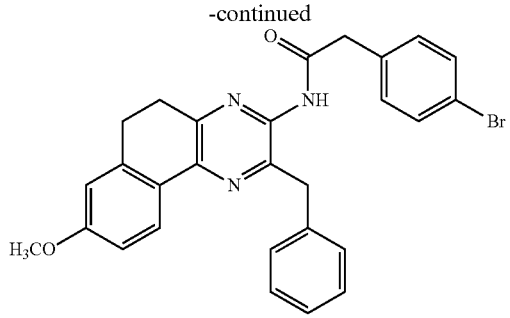
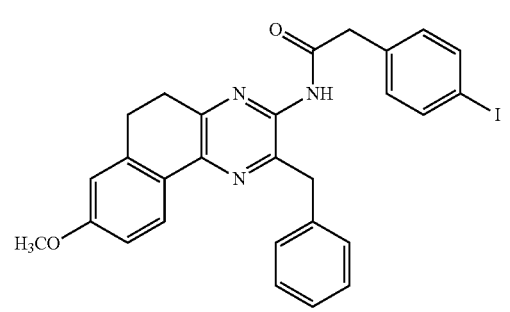
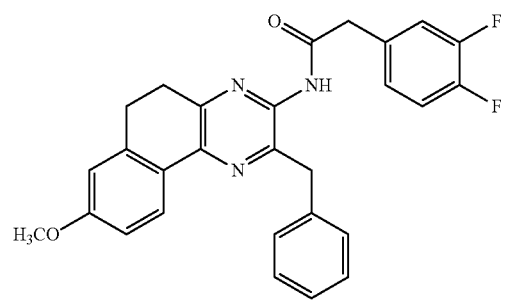
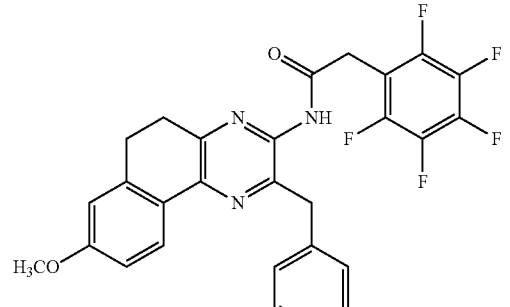
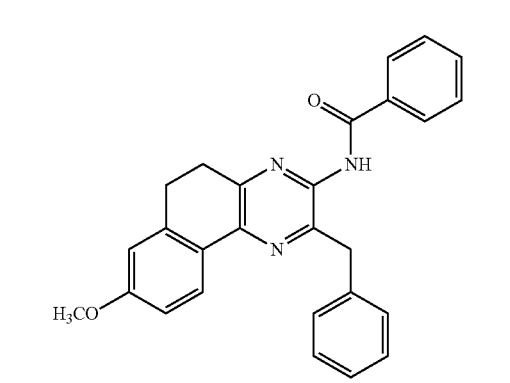
418
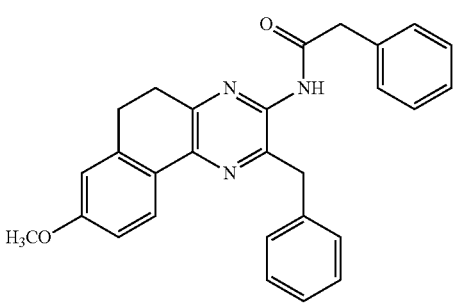
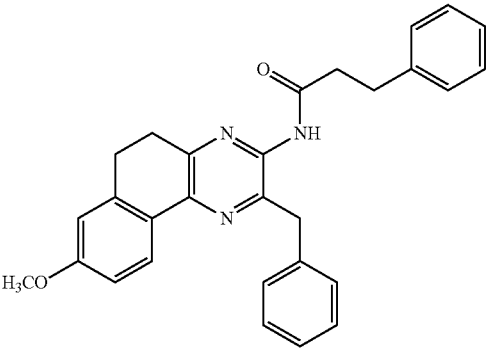
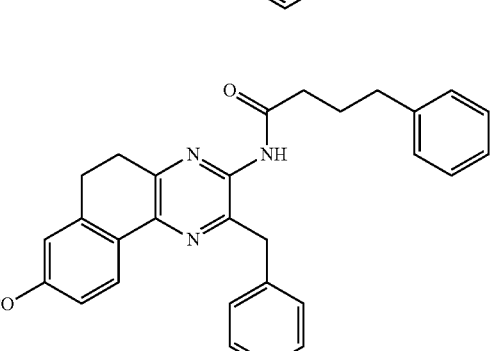
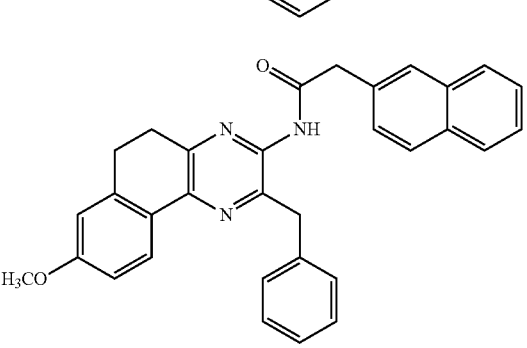
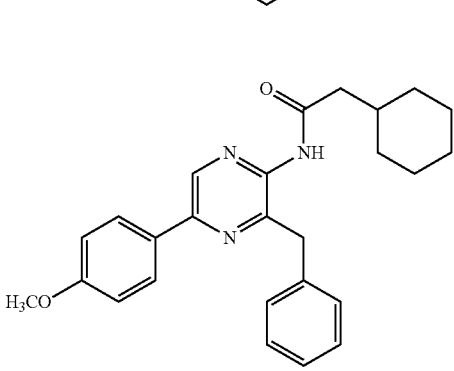

419
-continued
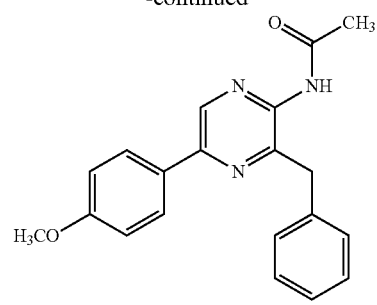
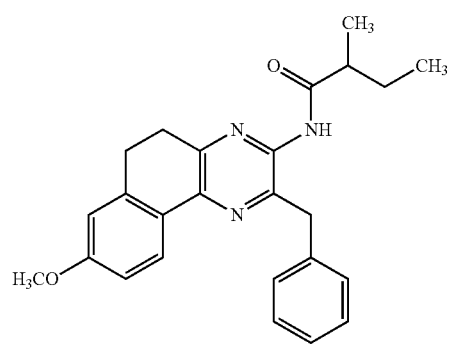
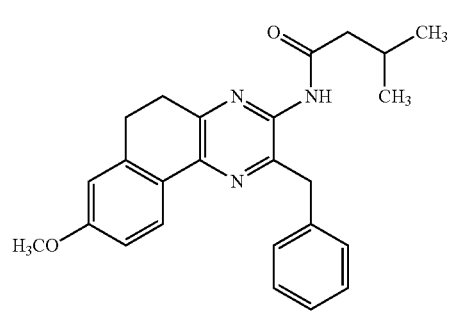
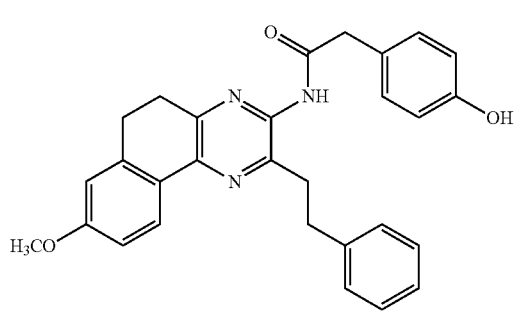
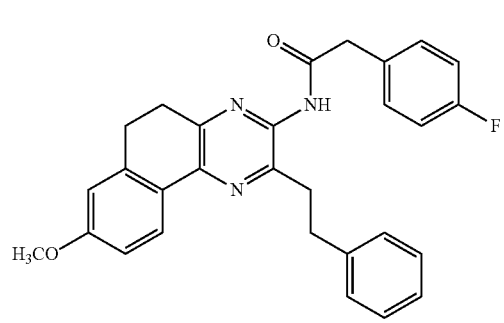
420
-continued
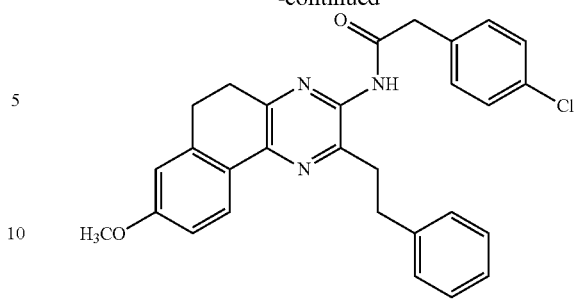
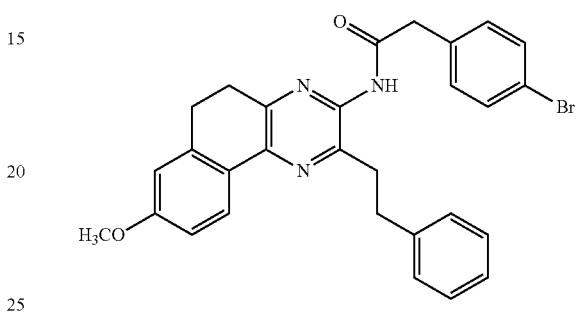
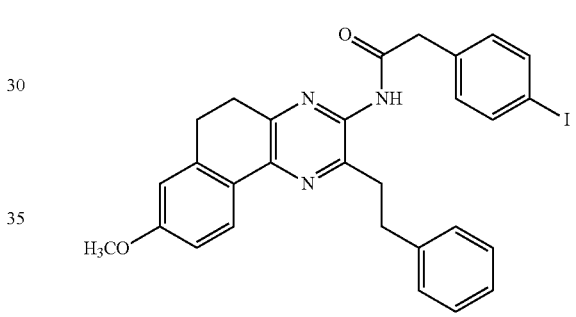
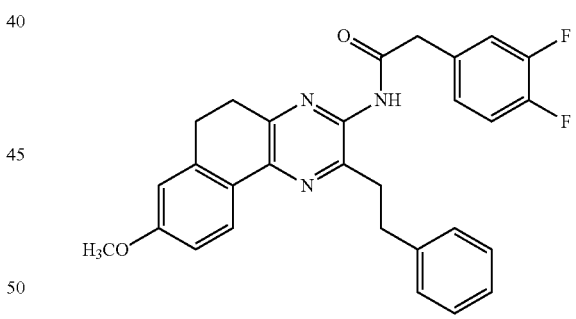
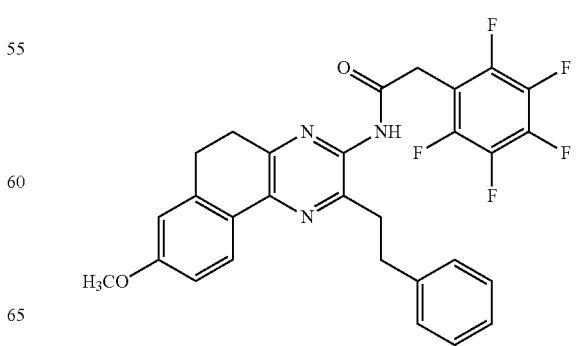

421
-continued
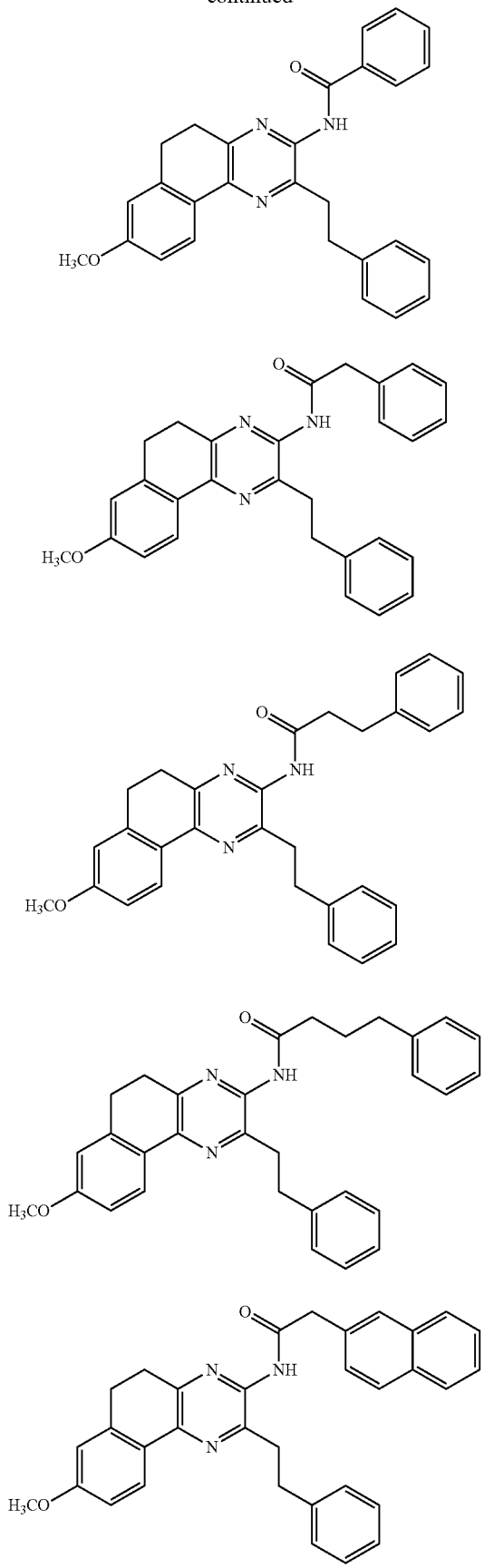
422
-continued
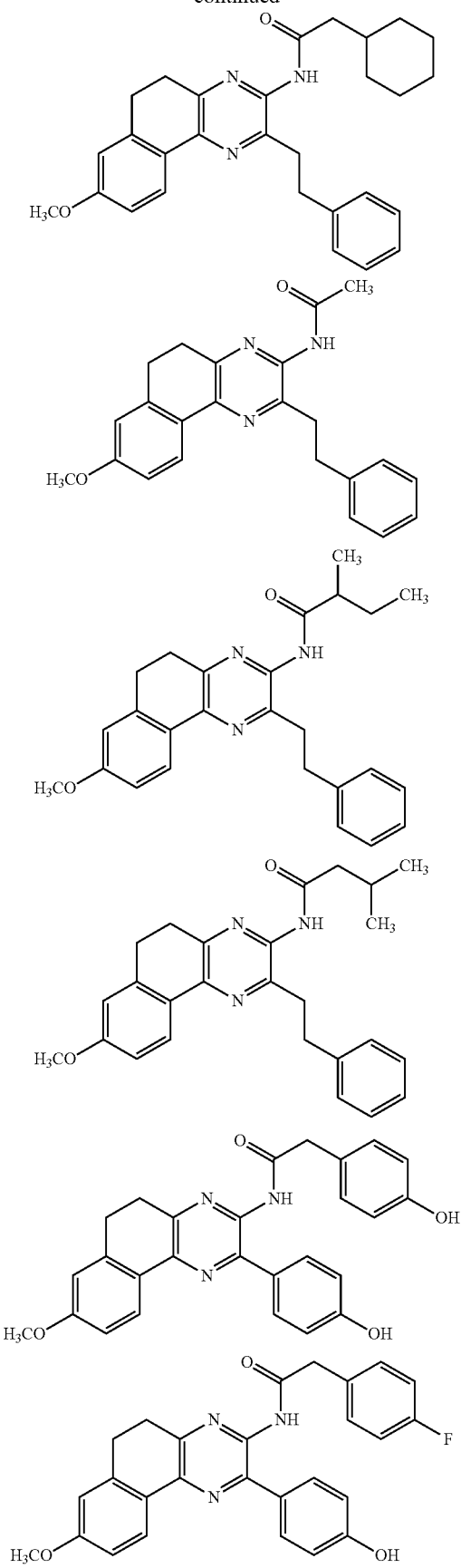

423
-continued
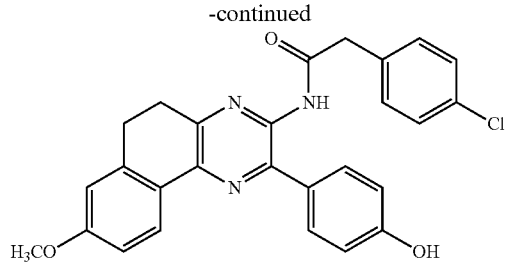
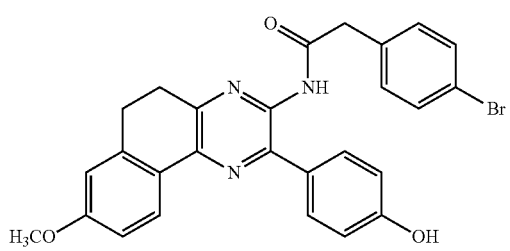
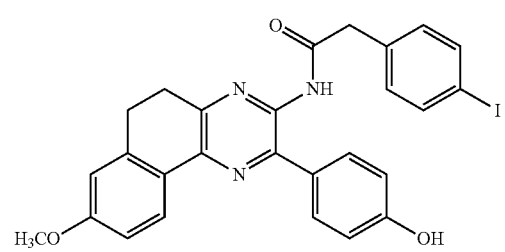
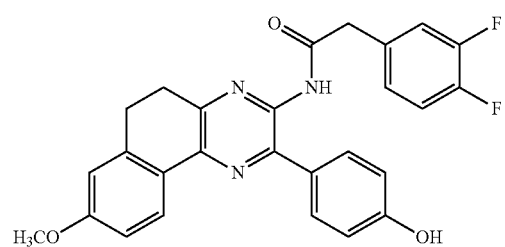
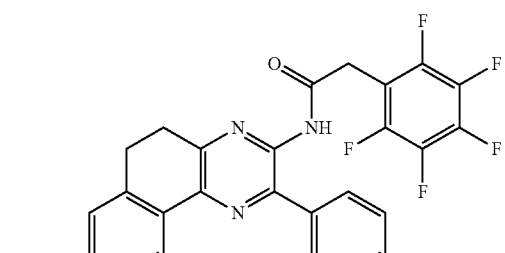
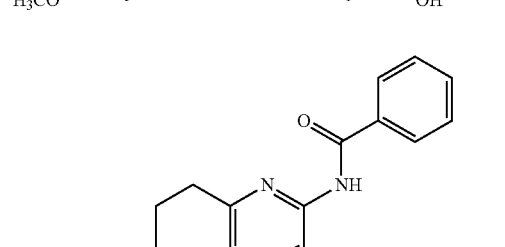
424
-continued
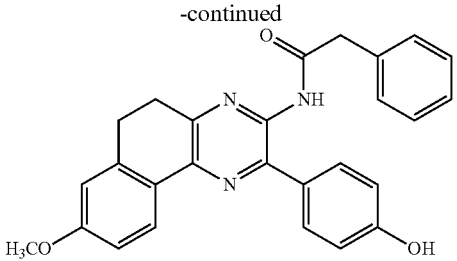
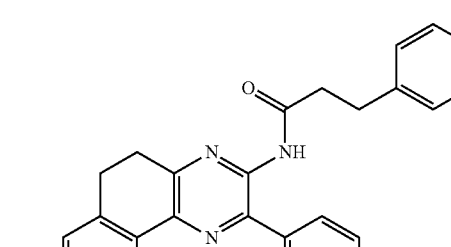
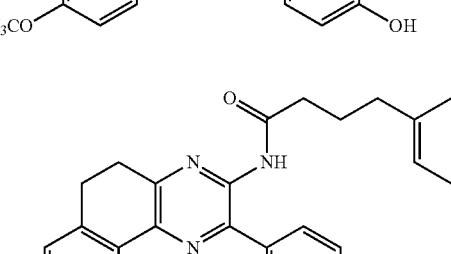
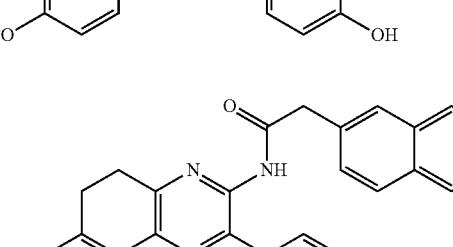
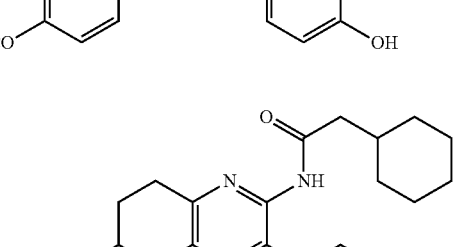
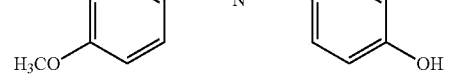

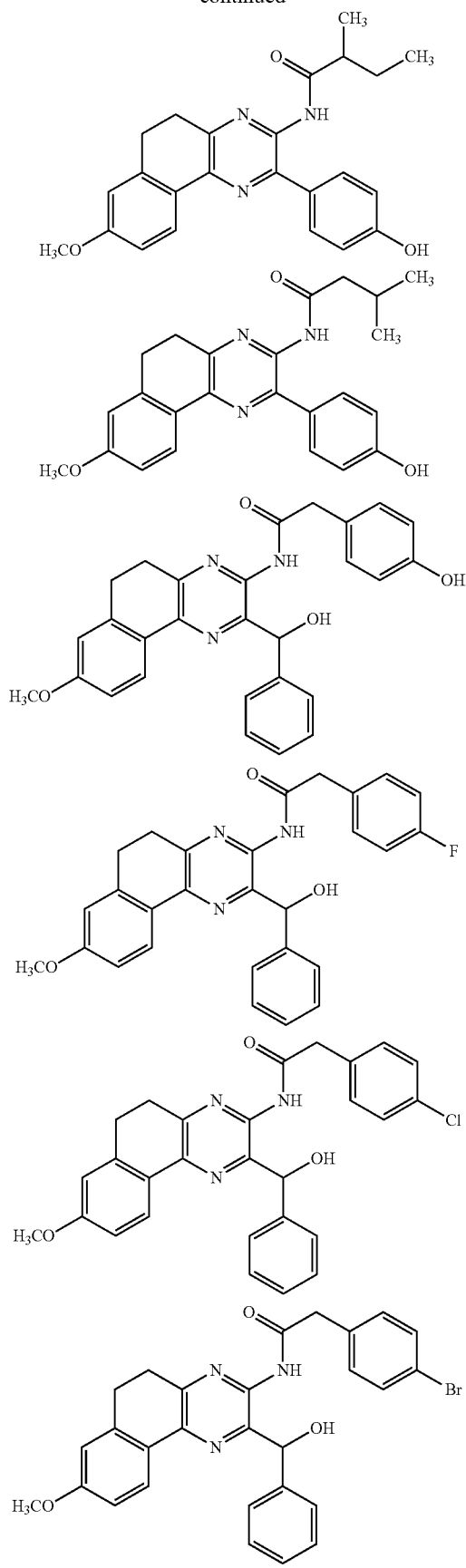
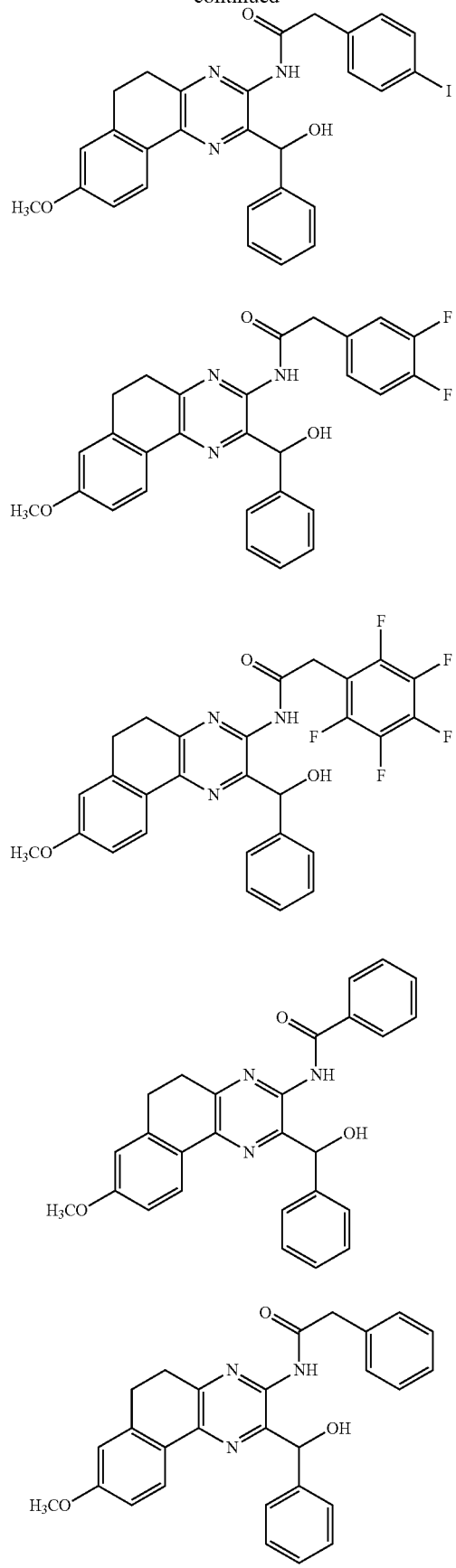

427
-continued
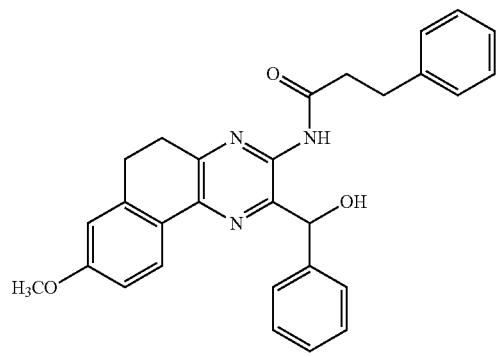
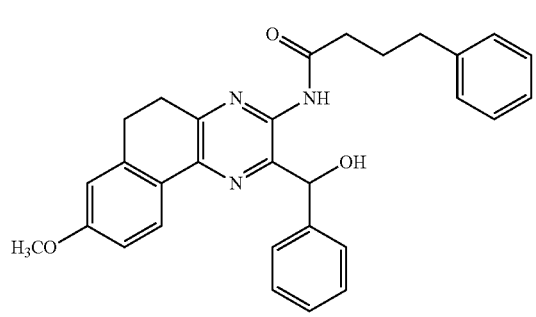
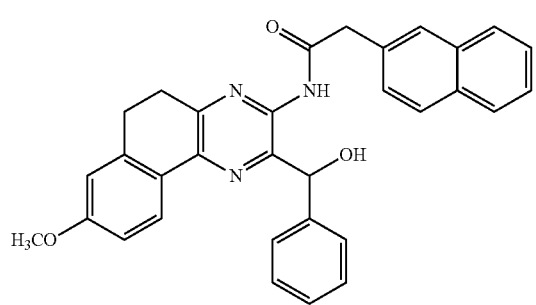
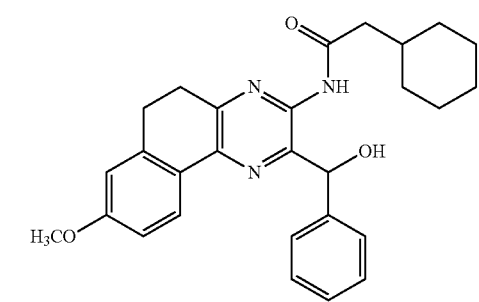
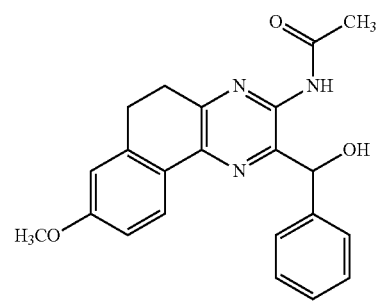
428
-continued
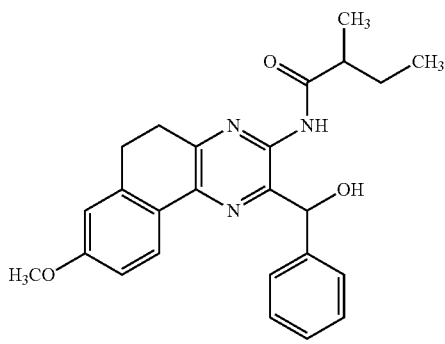
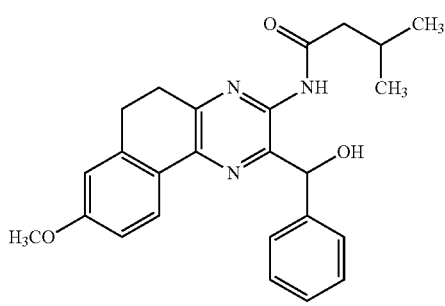
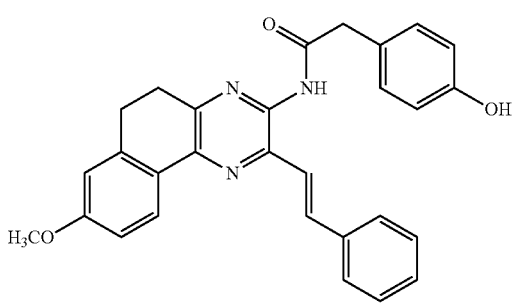
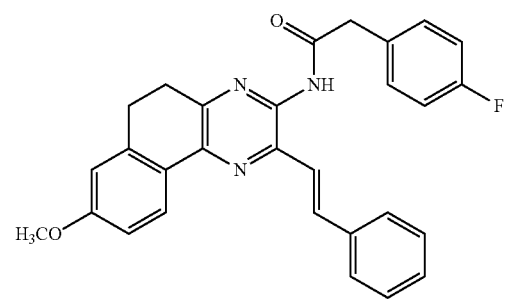
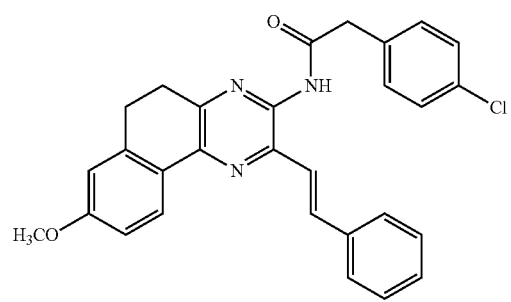

429
-continued
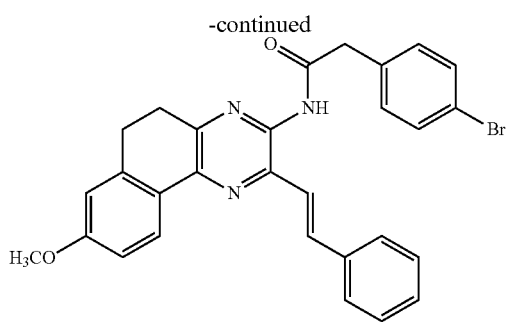
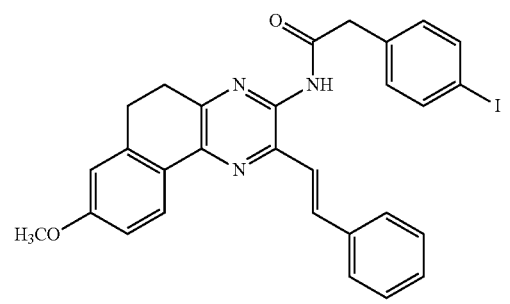
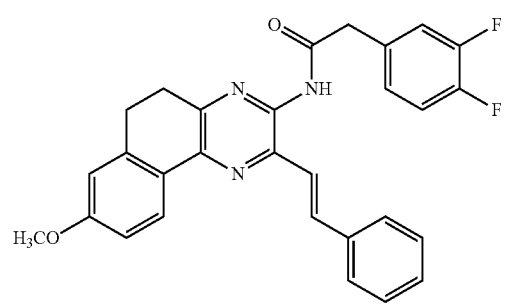
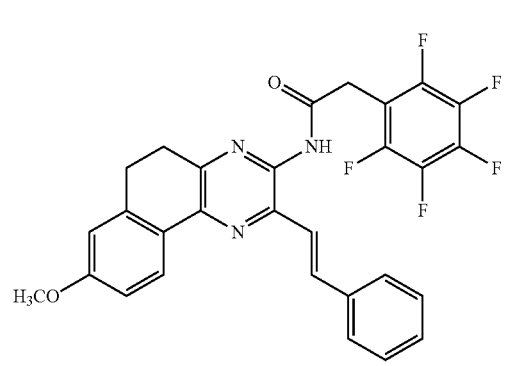
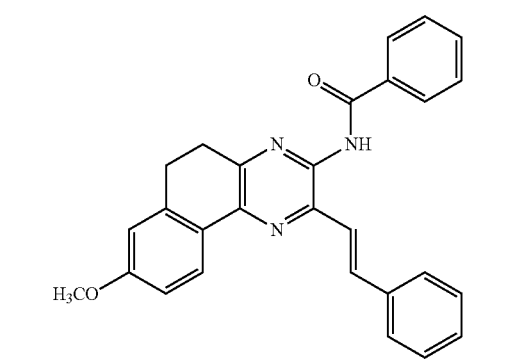
430
-continued
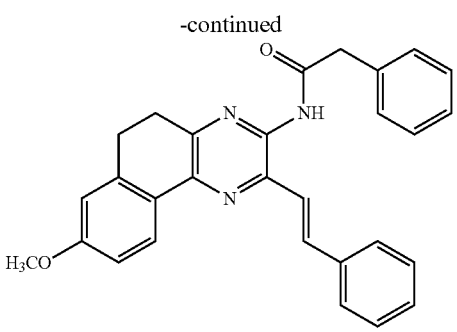
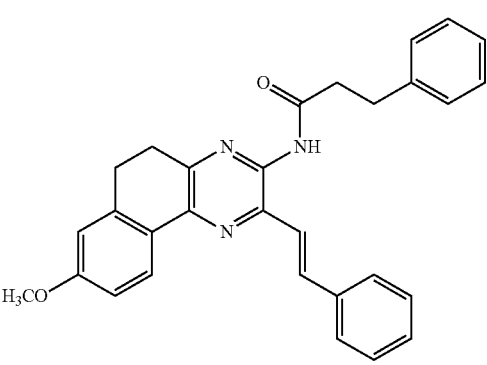
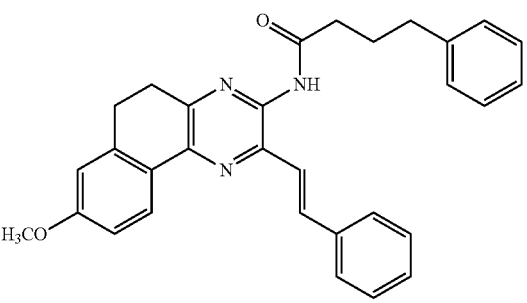
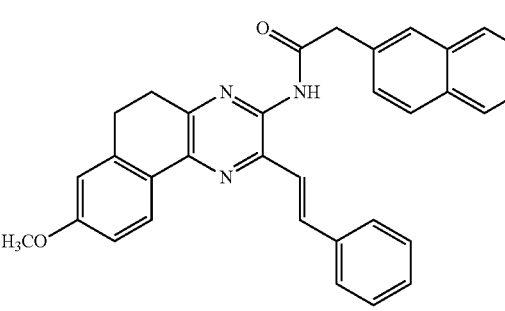
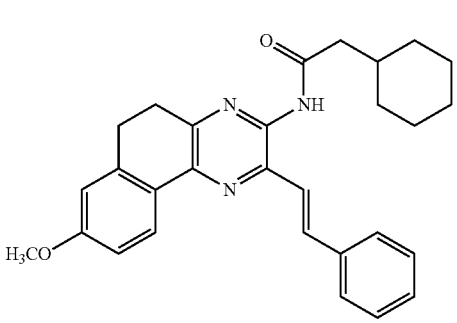

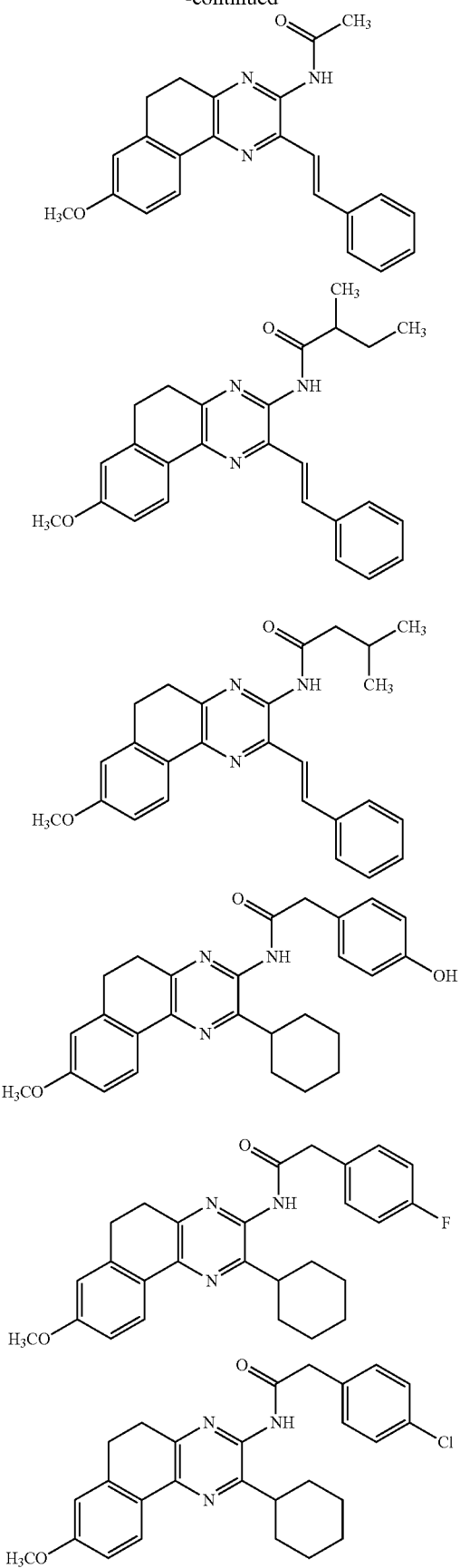
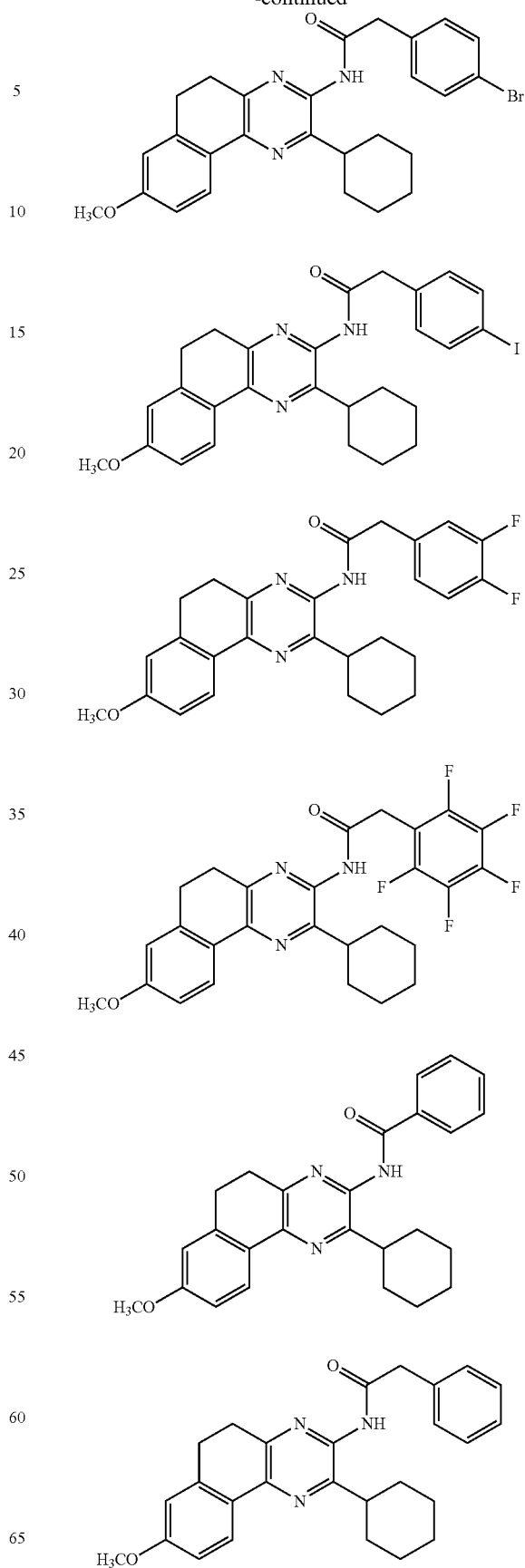

433
-continued
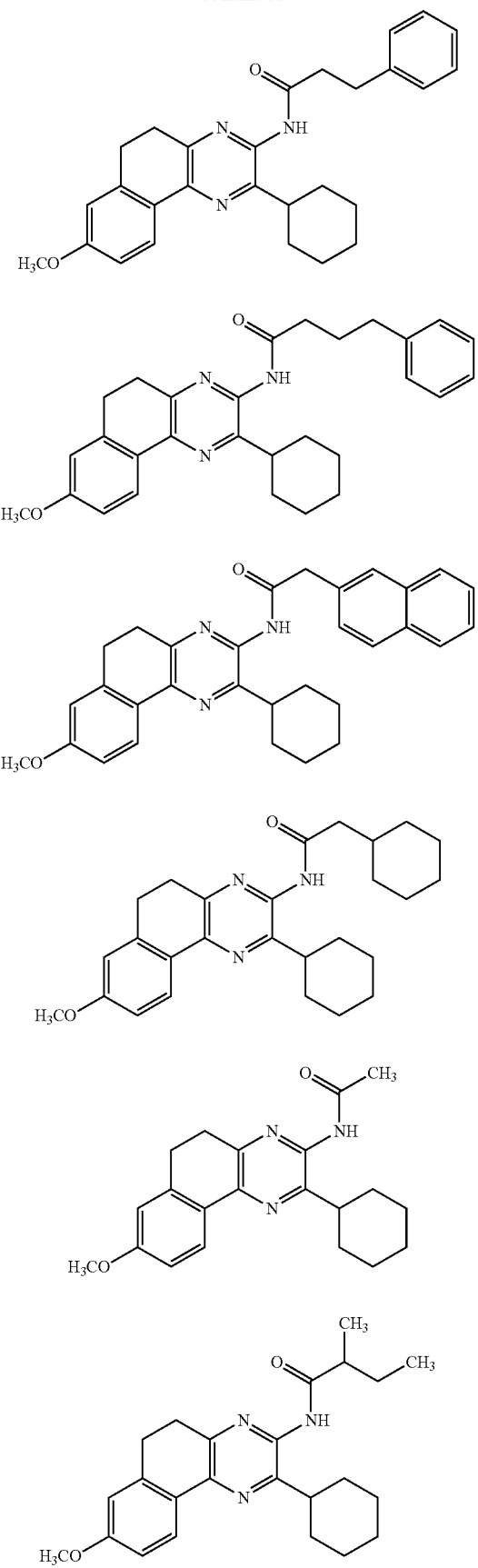
434
-continued
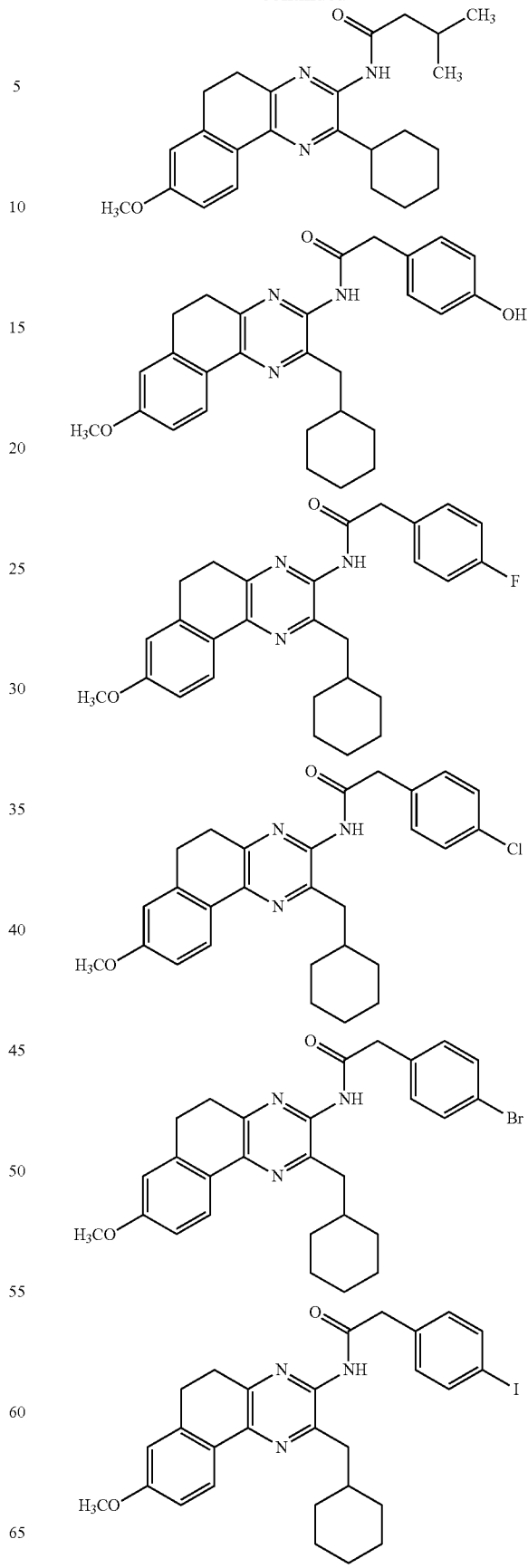

435
-continued
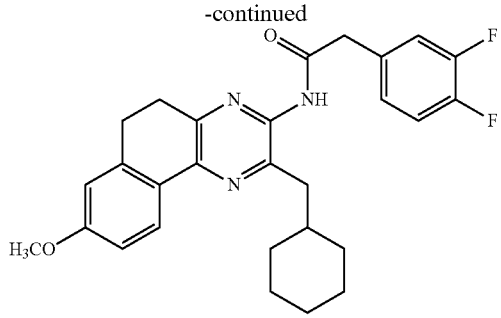
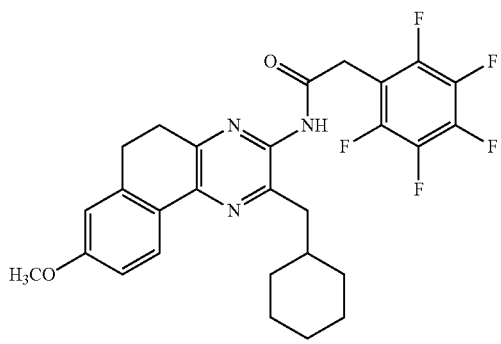
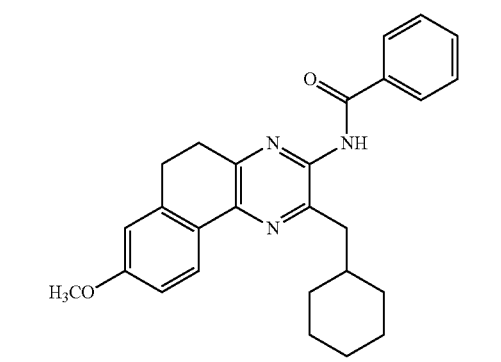
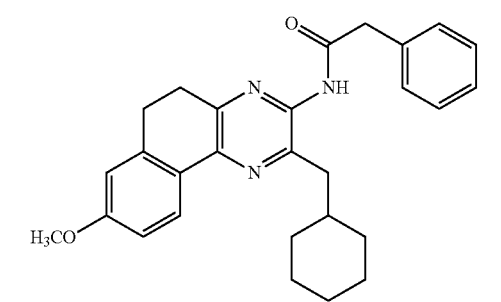
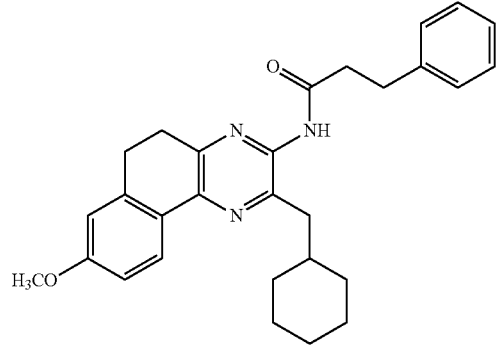
436
-continued
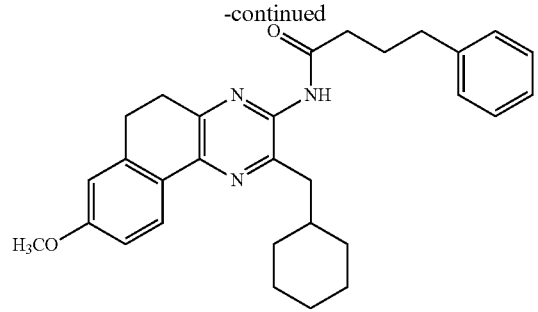
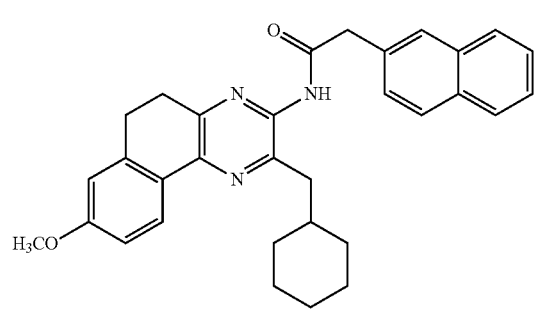
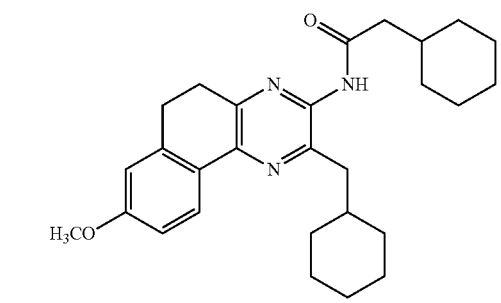
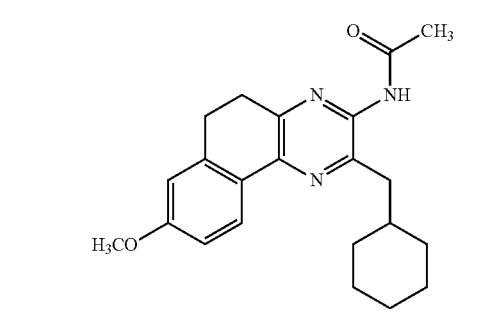
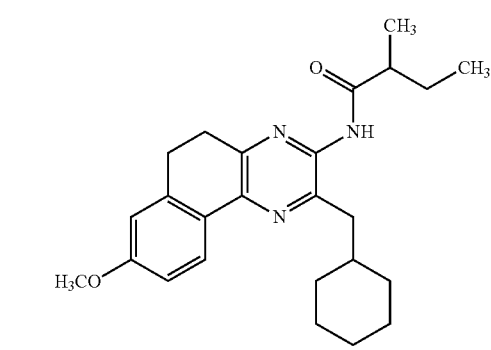

437
-continued
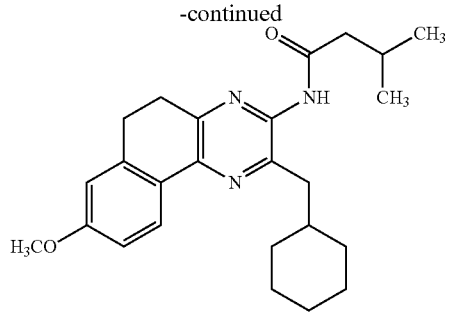
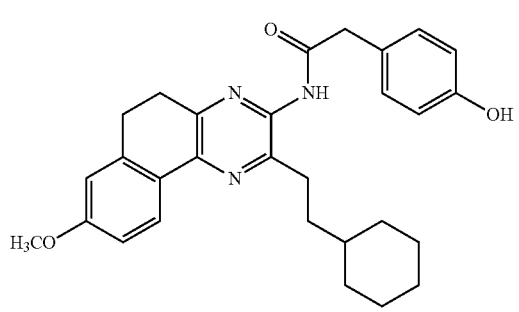
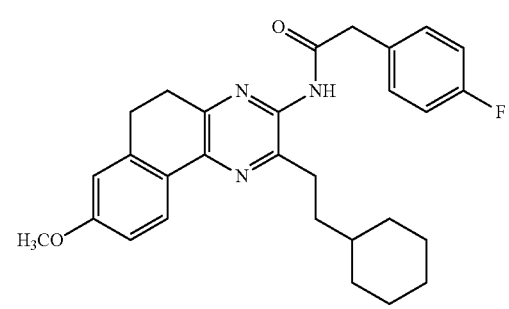
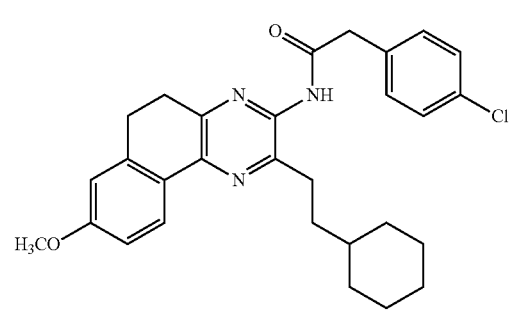
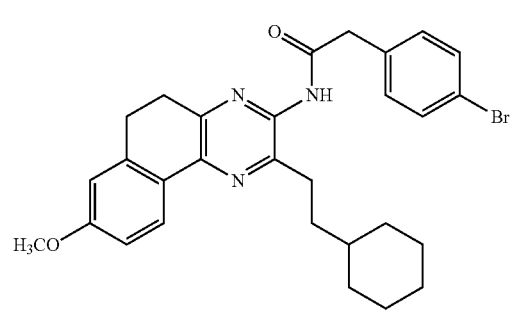
438
-continued
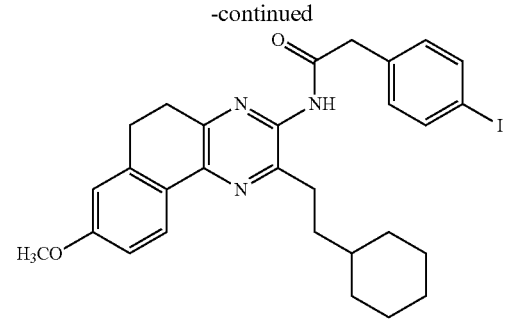
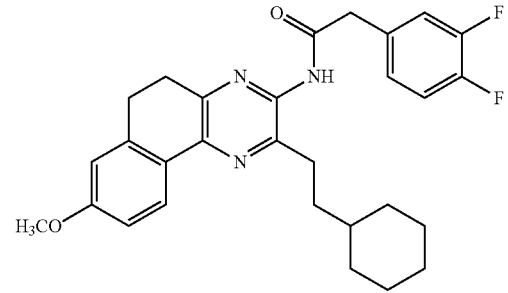
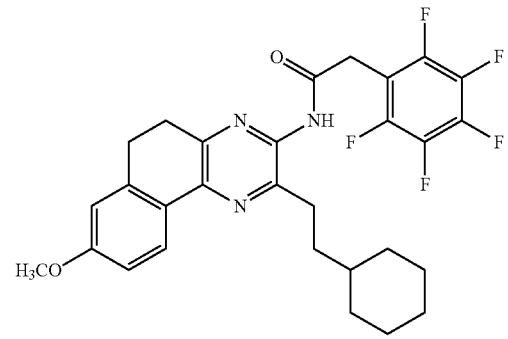
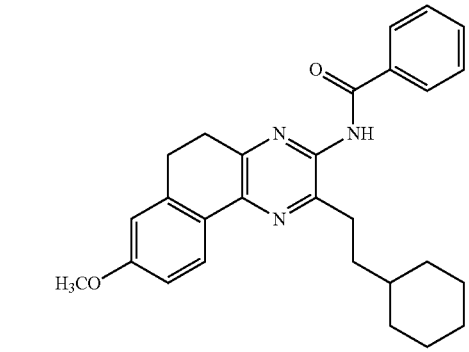
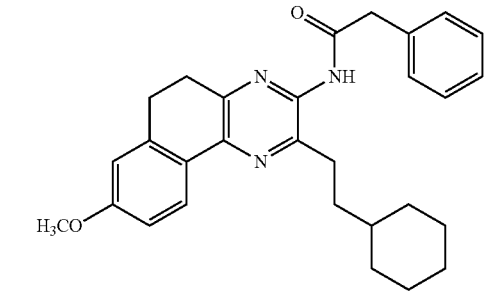

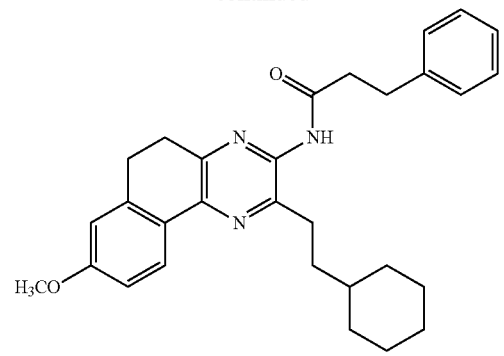
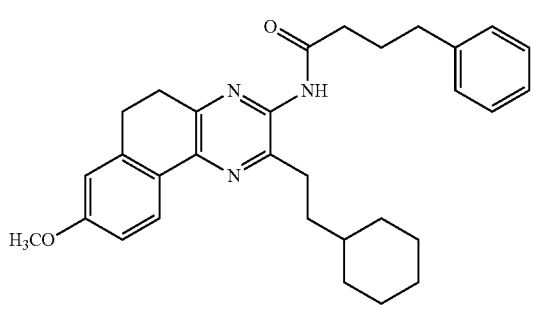
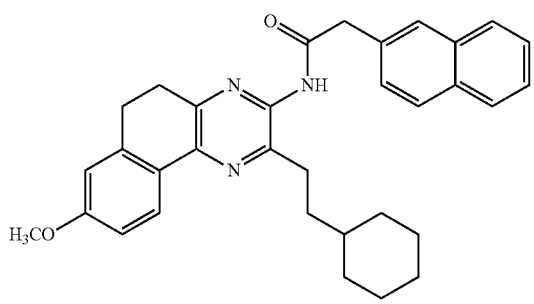
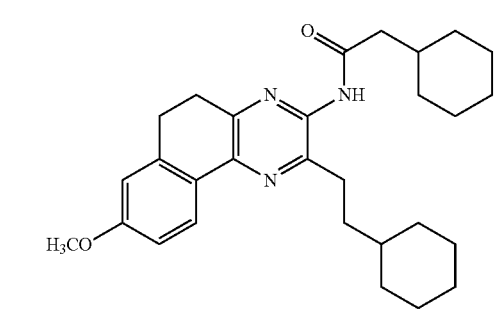
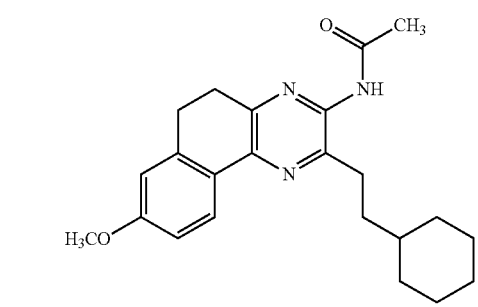
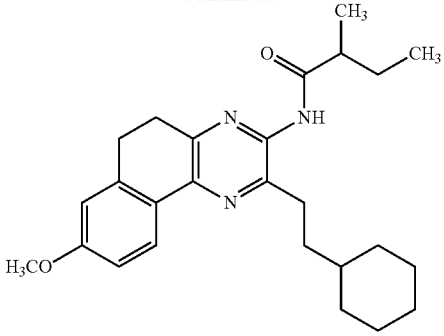
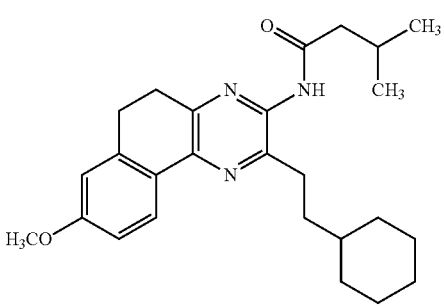
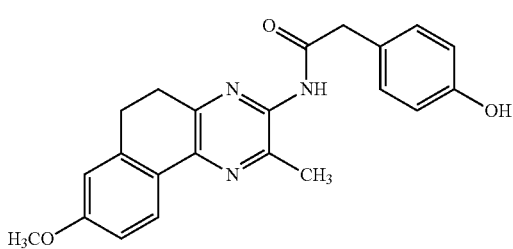
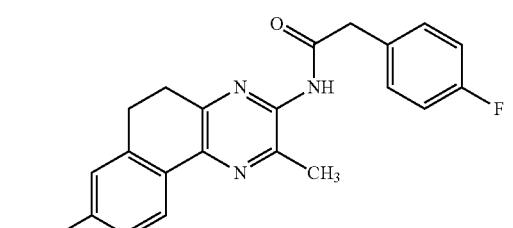
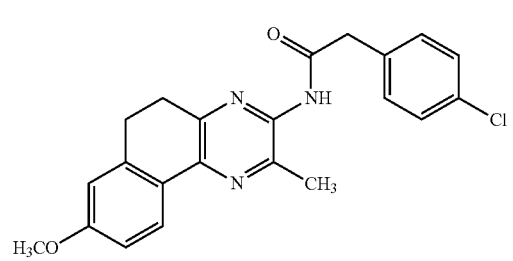
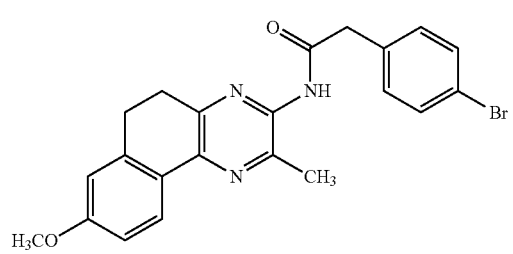

441
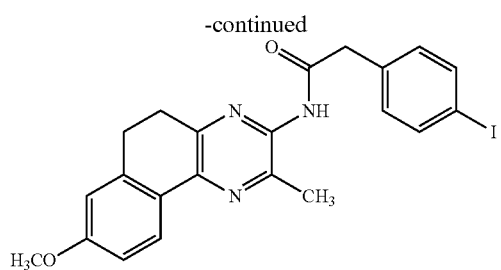
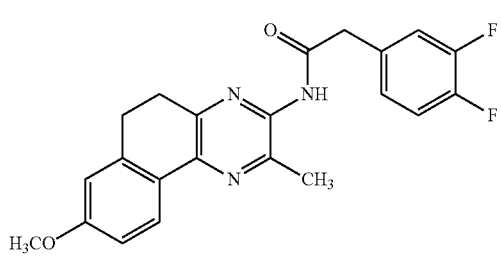
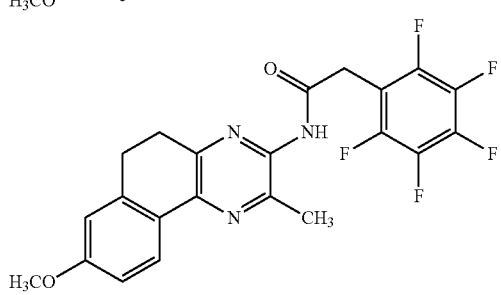
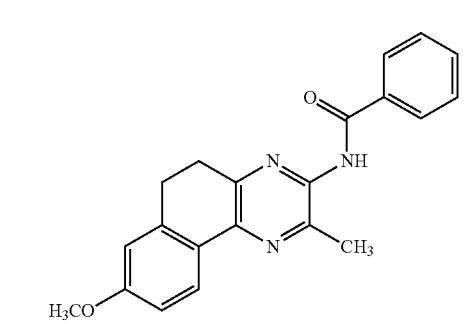
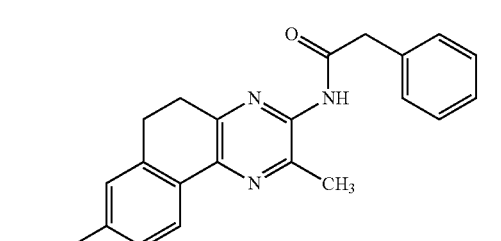
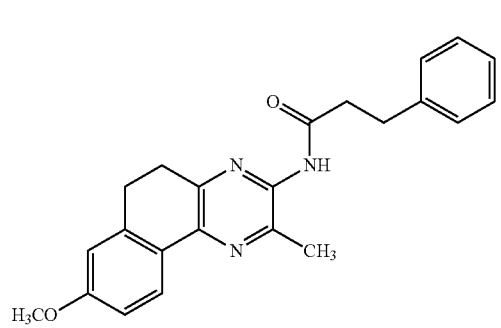
442
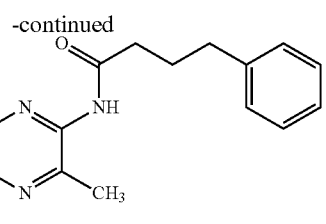
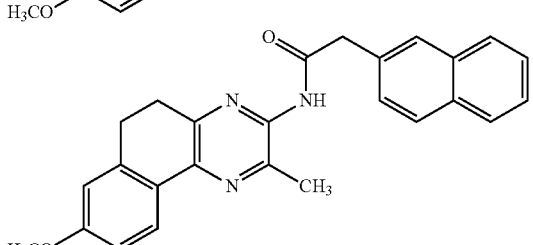
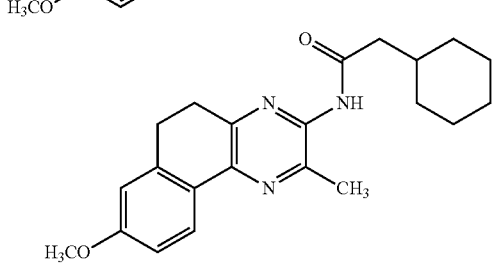
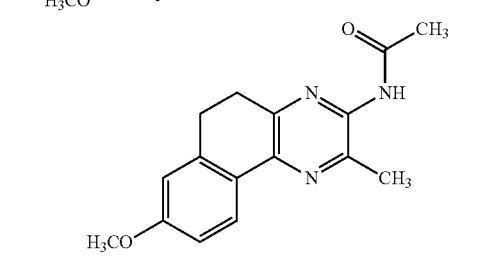
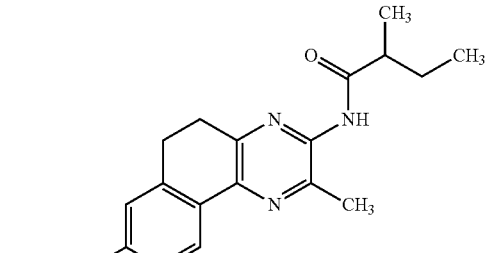
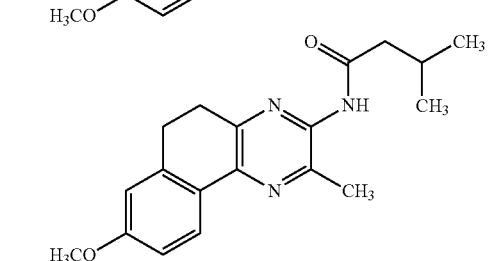
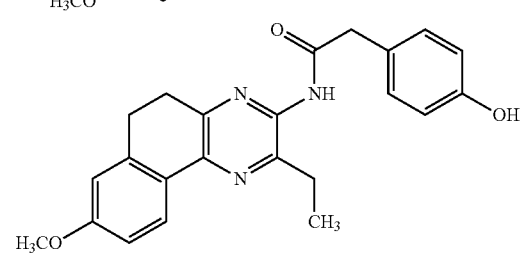

443
-continued
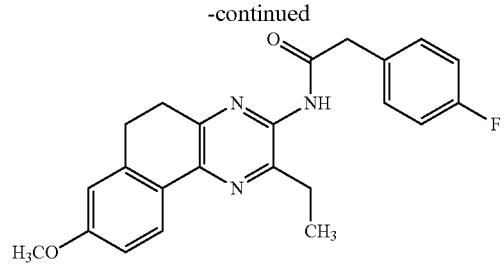
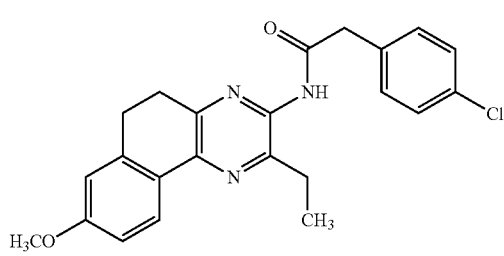
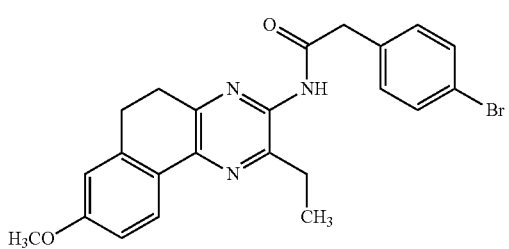
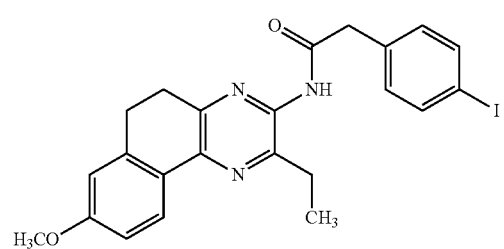
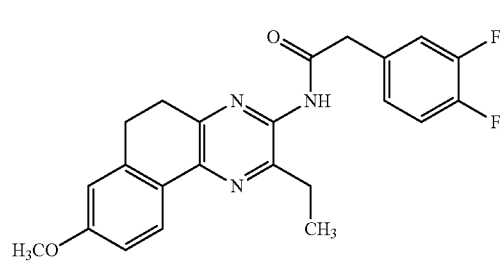
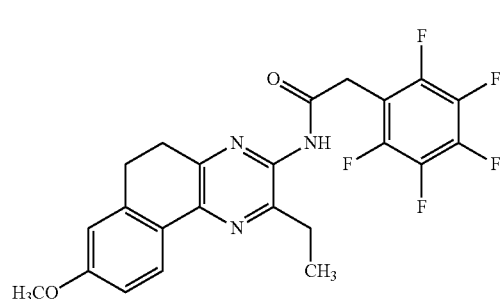
444
-continued
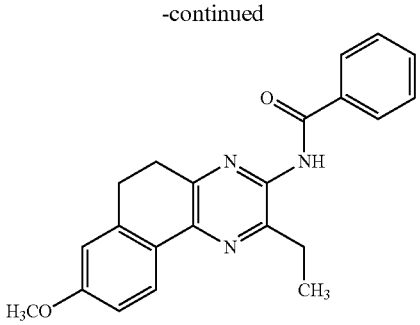
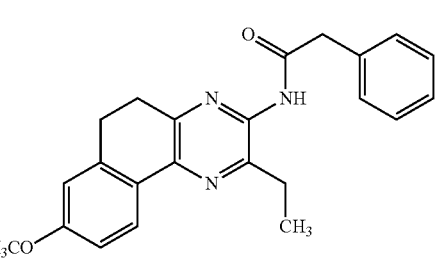
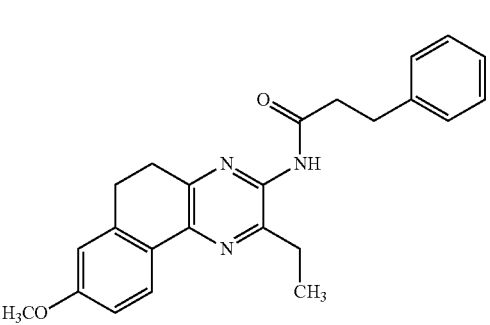
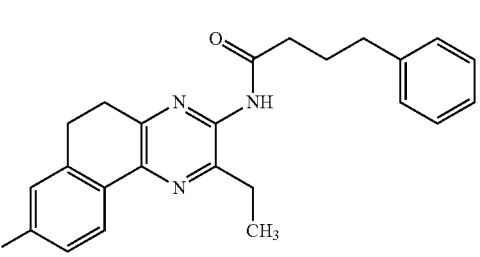
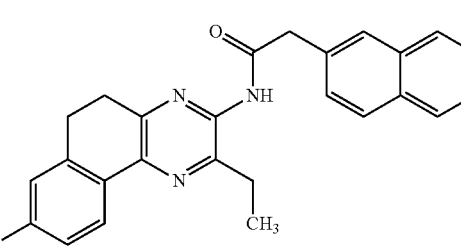
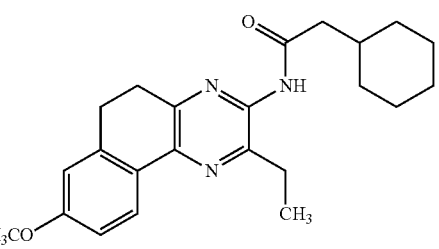

445
-continued
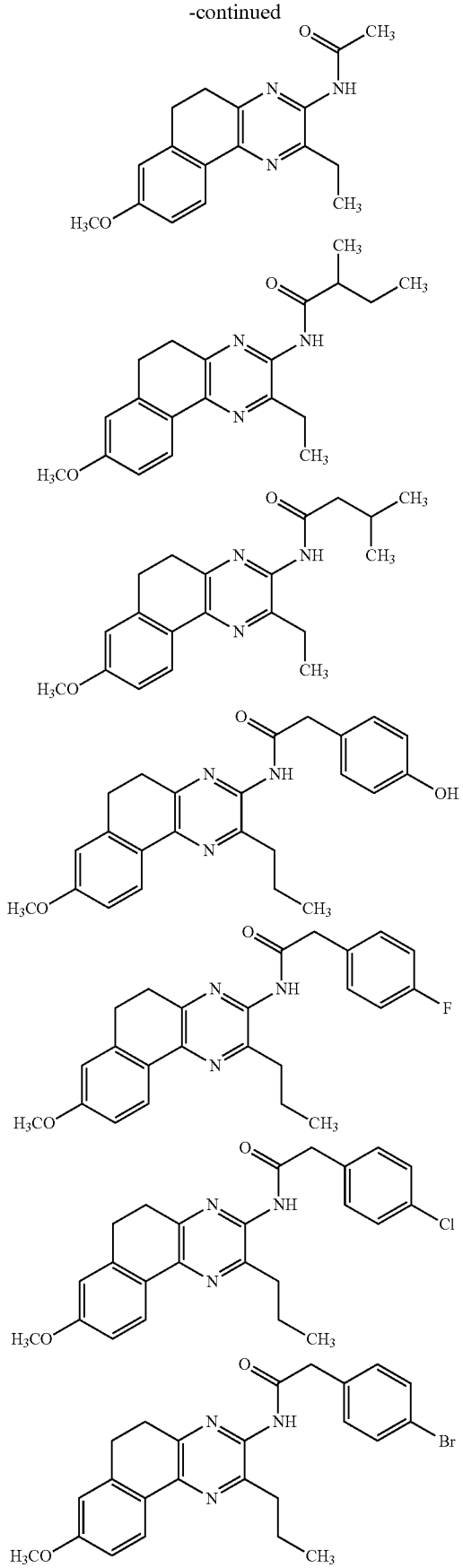
446
-continued
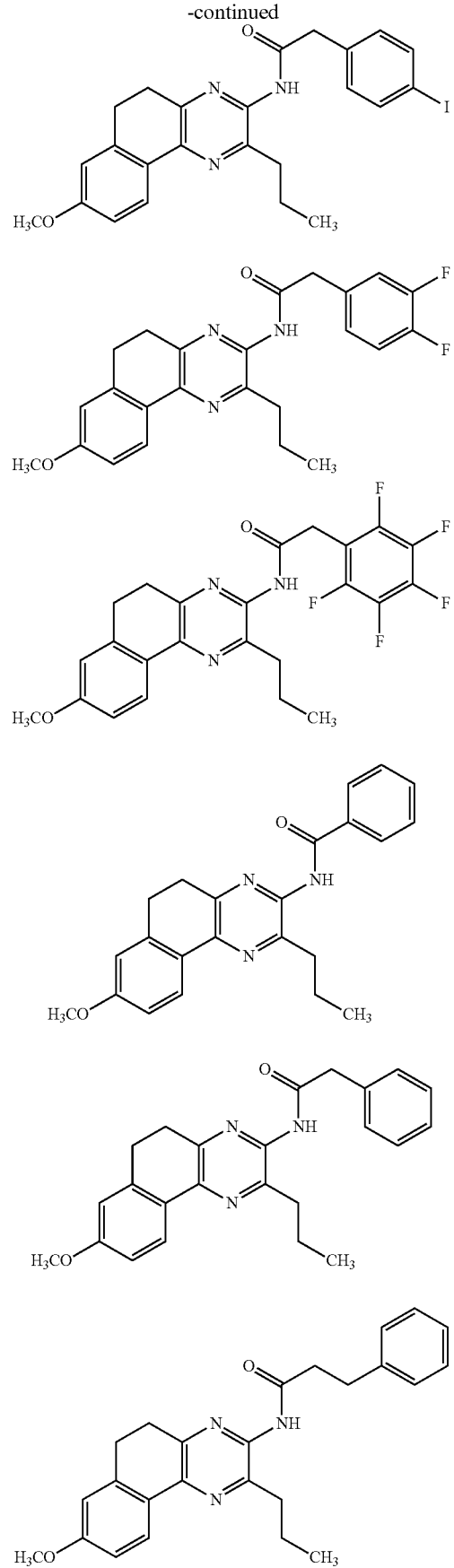

447
-continued
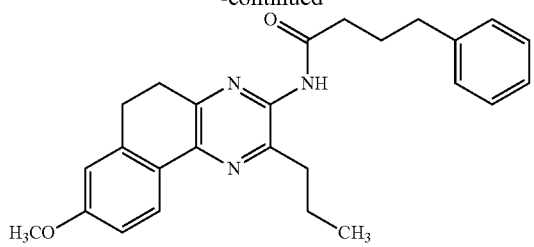
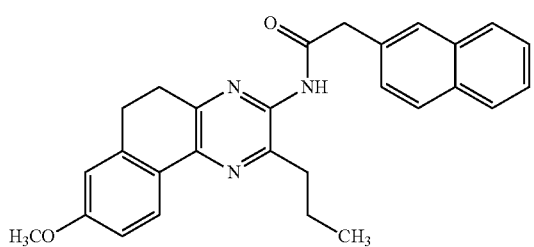
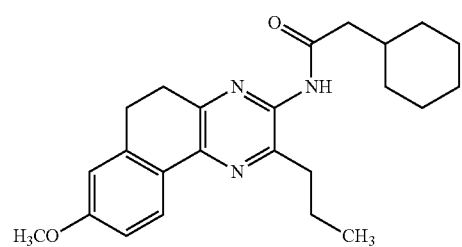
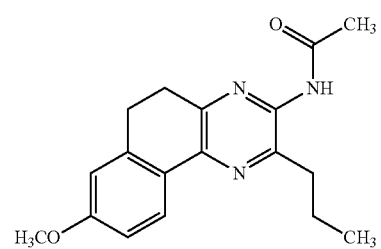
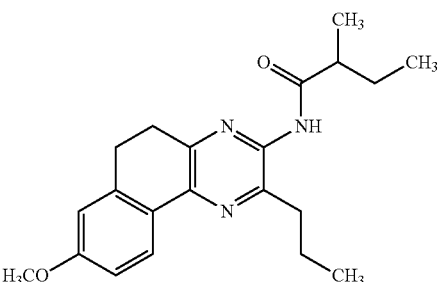
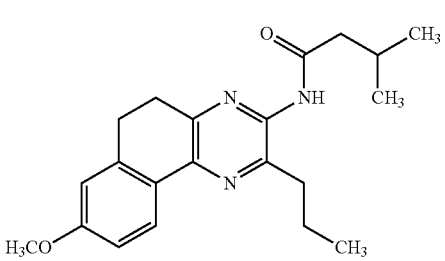
448
-continued
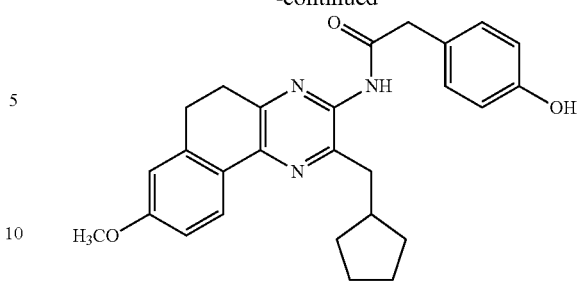
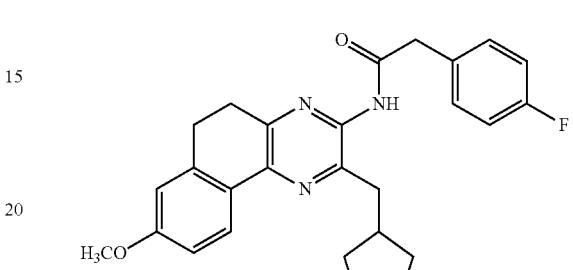
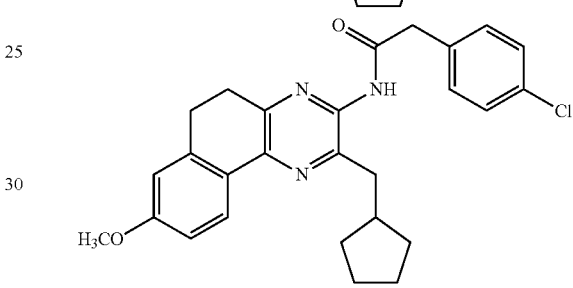
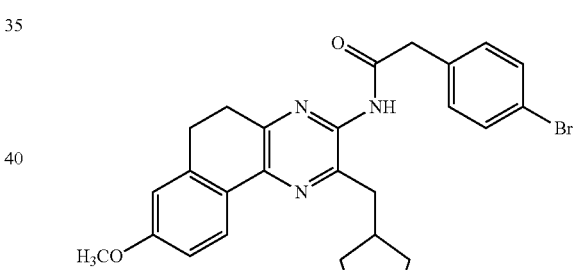
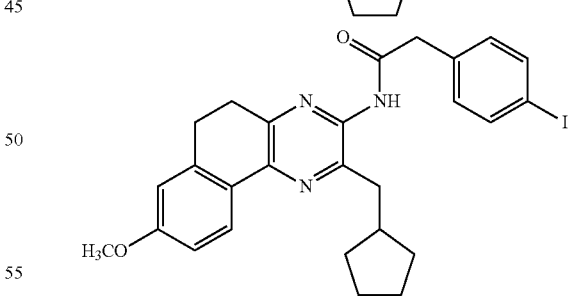
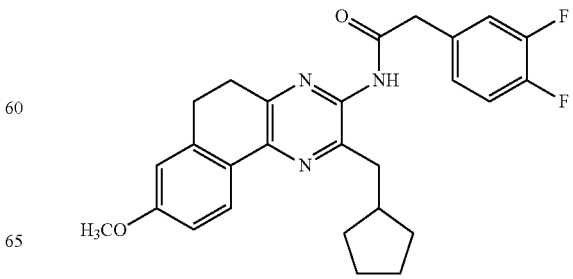

449
-continued
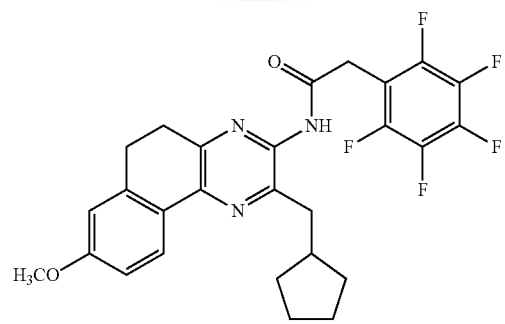
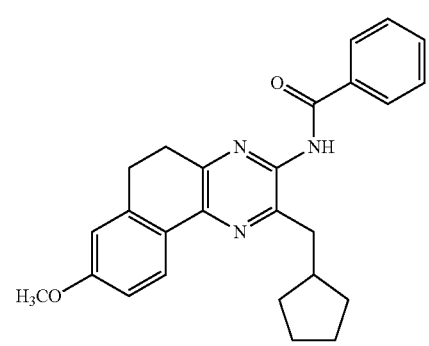
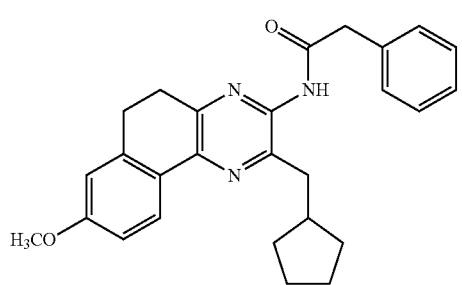
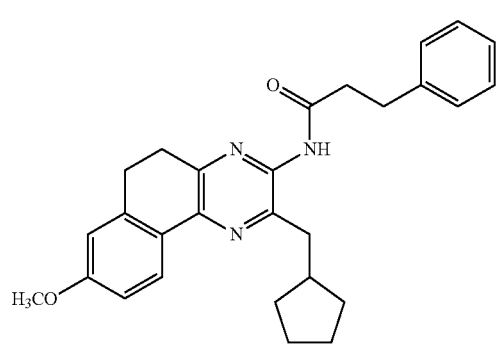
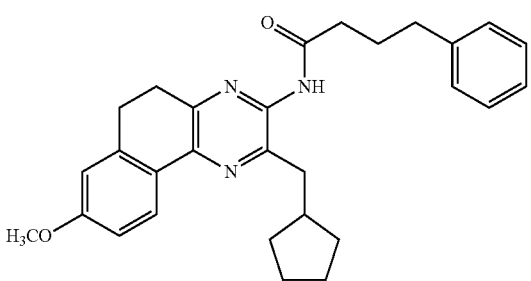
450
-continued
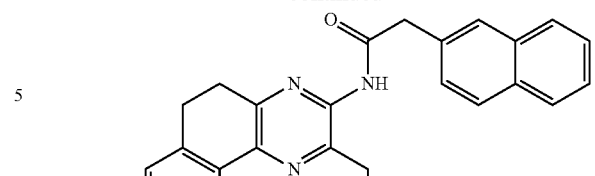
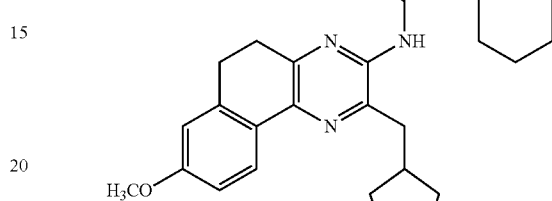
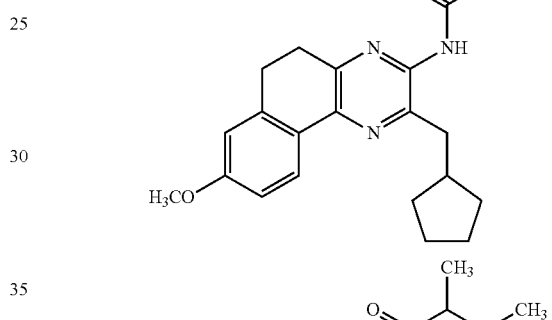
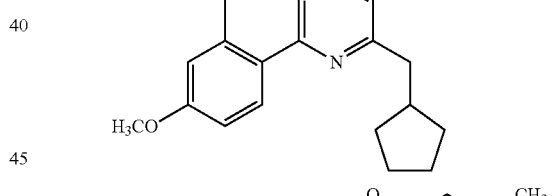
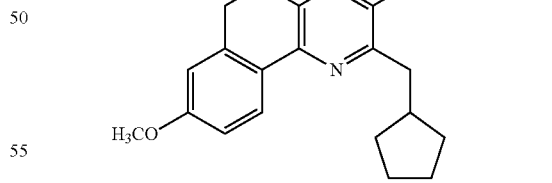
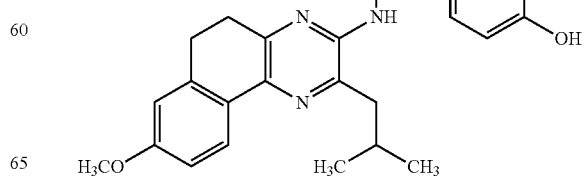

451
-continued
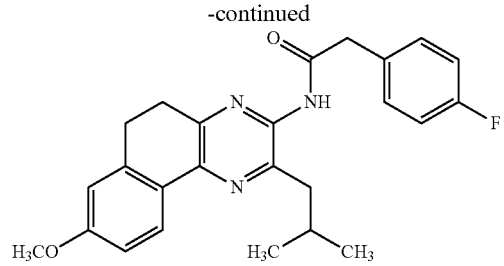
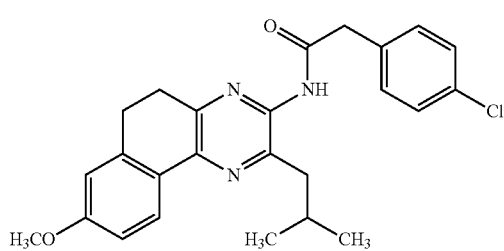
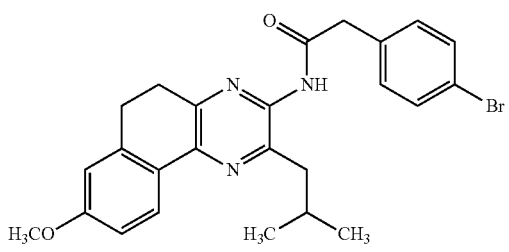
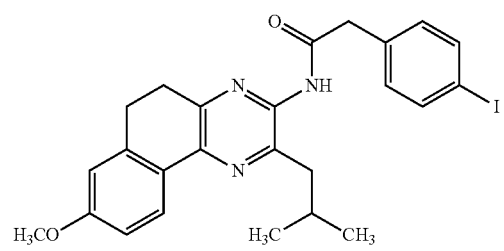
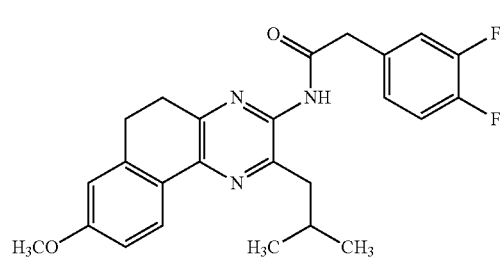
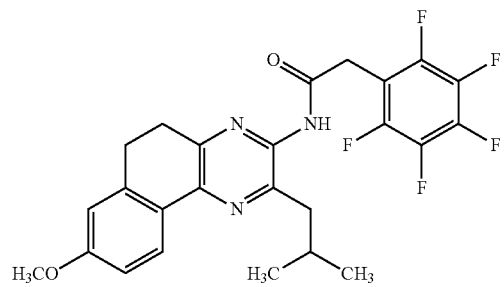
452
-continued
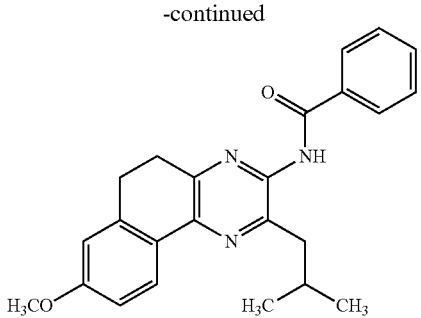
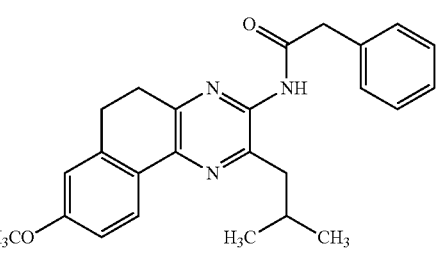
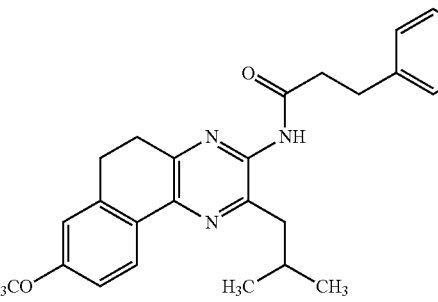
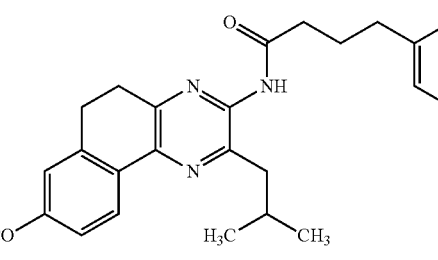
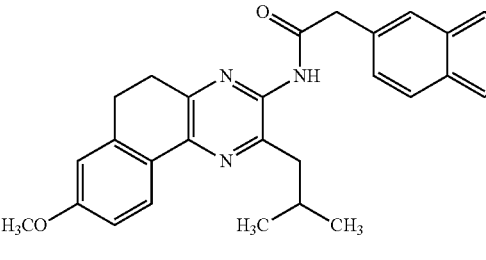
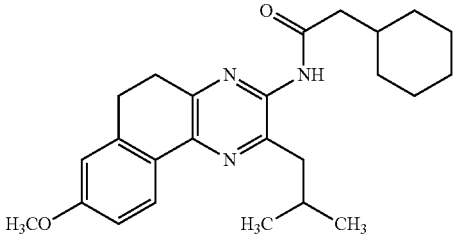

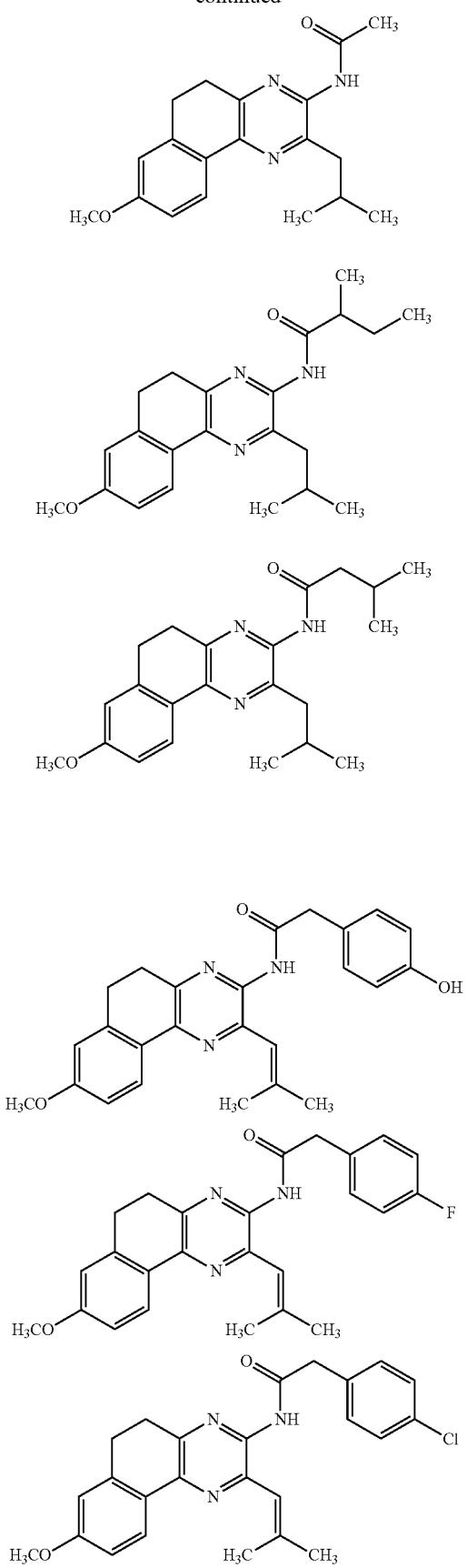
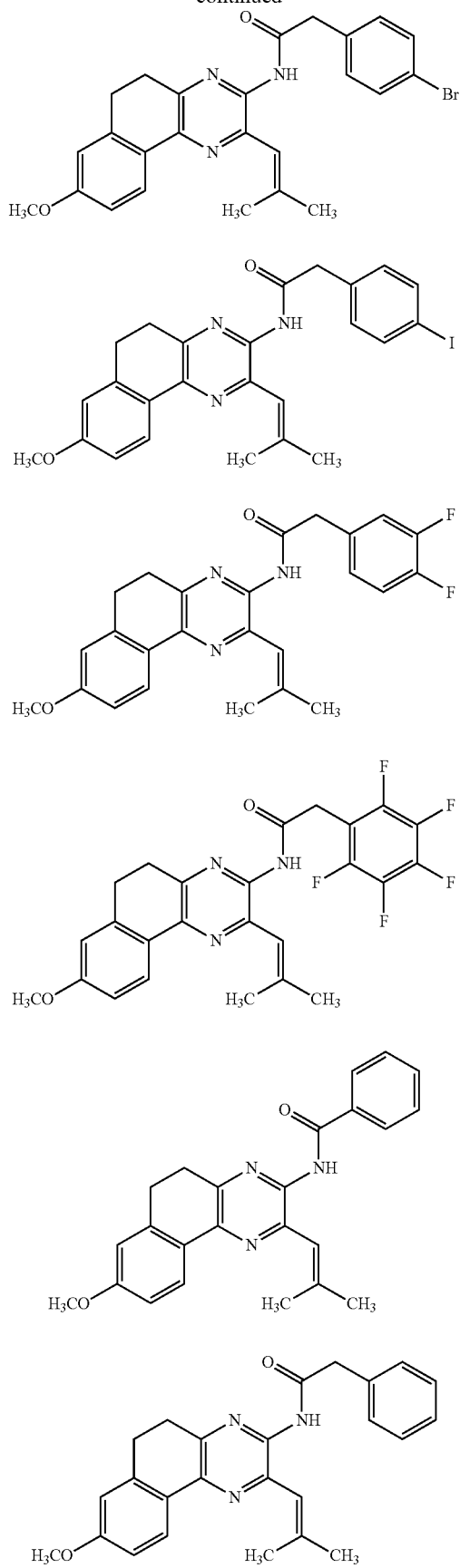

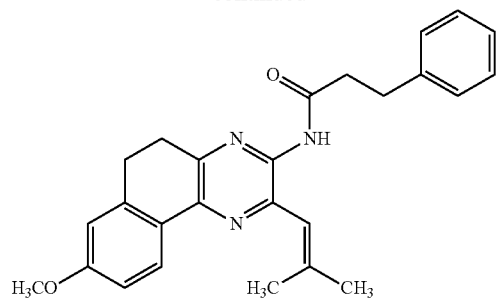
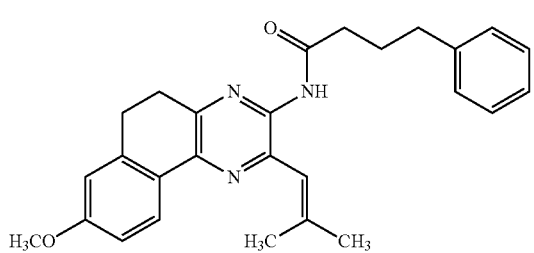
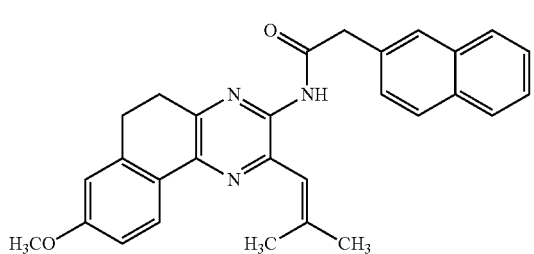
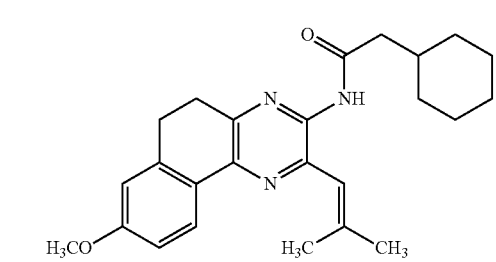
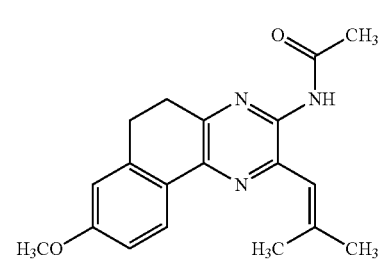
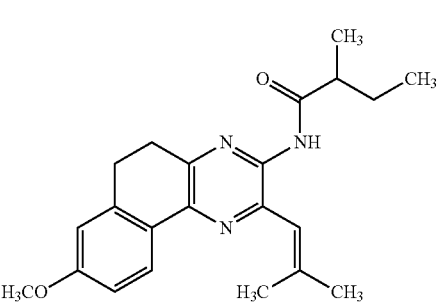
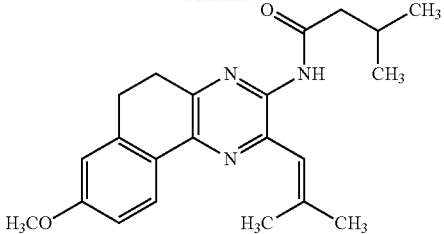
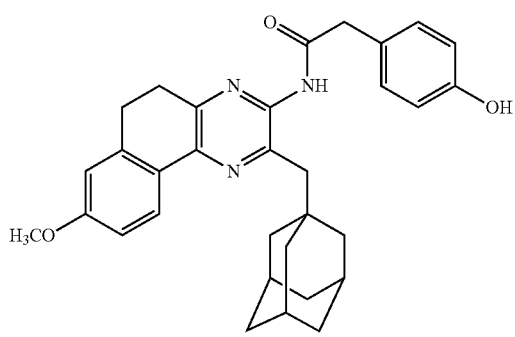
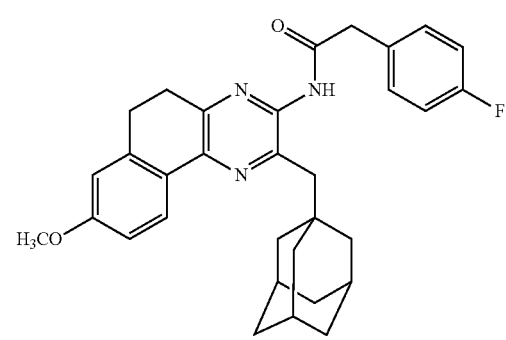
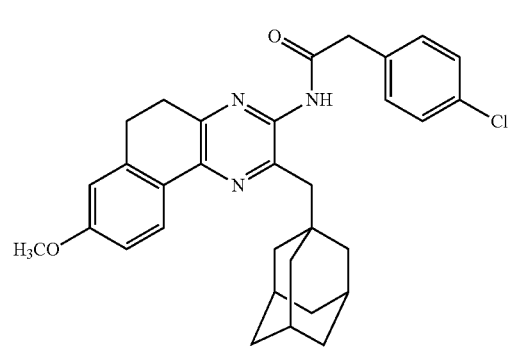
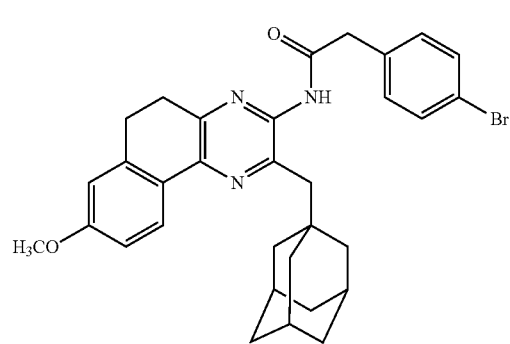

457
-continued
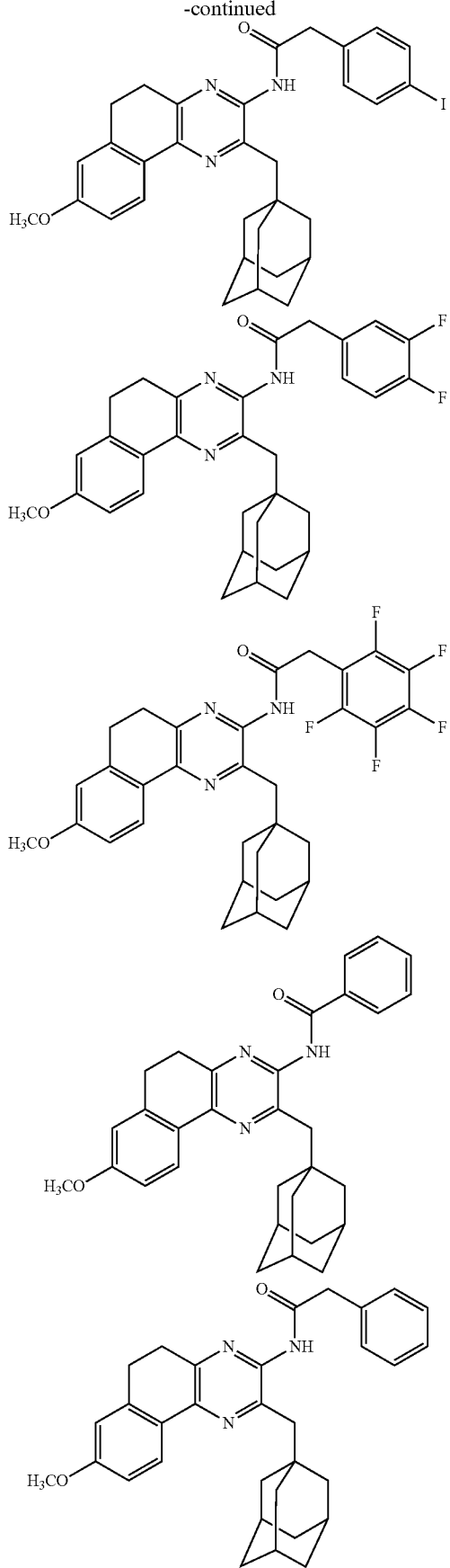
458
-continued
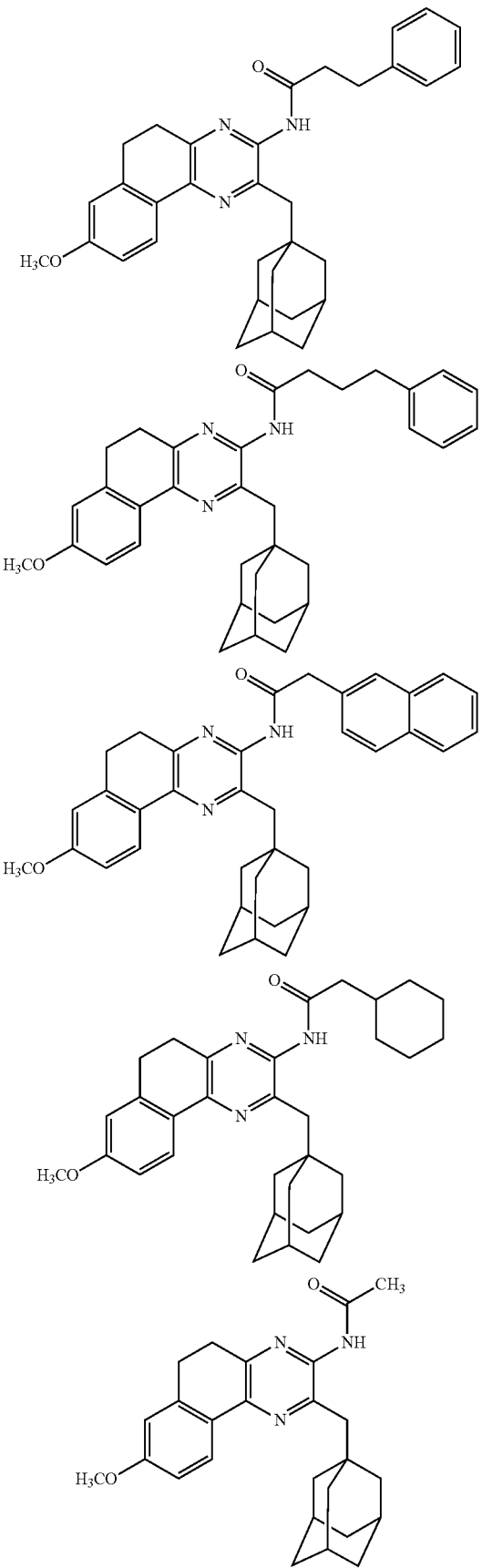

459
-continued
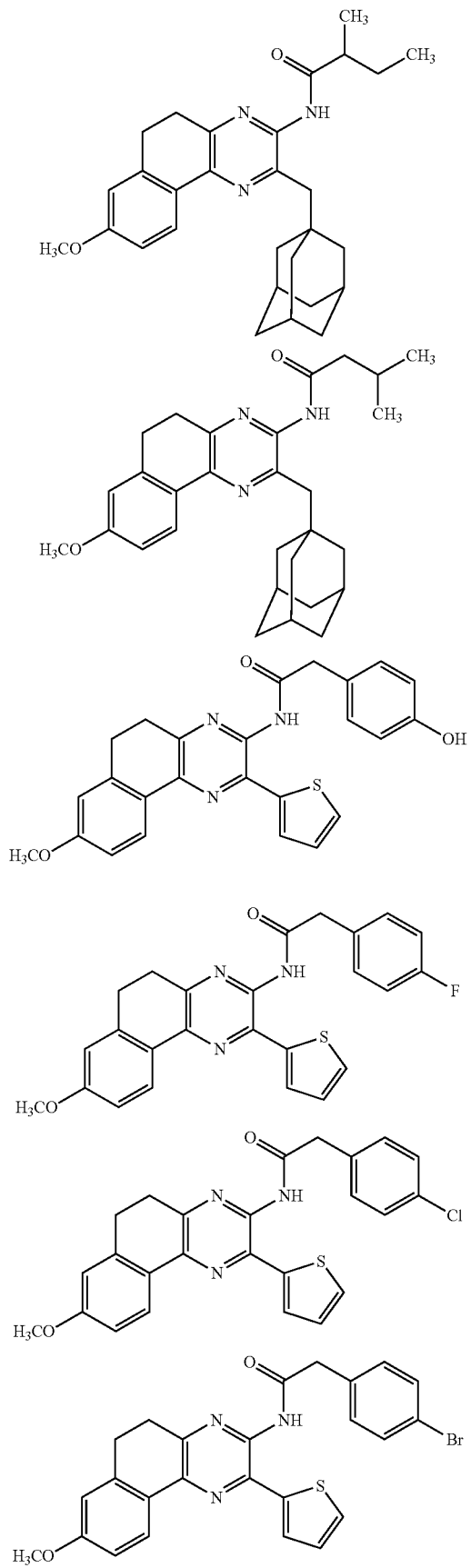
460
-continued
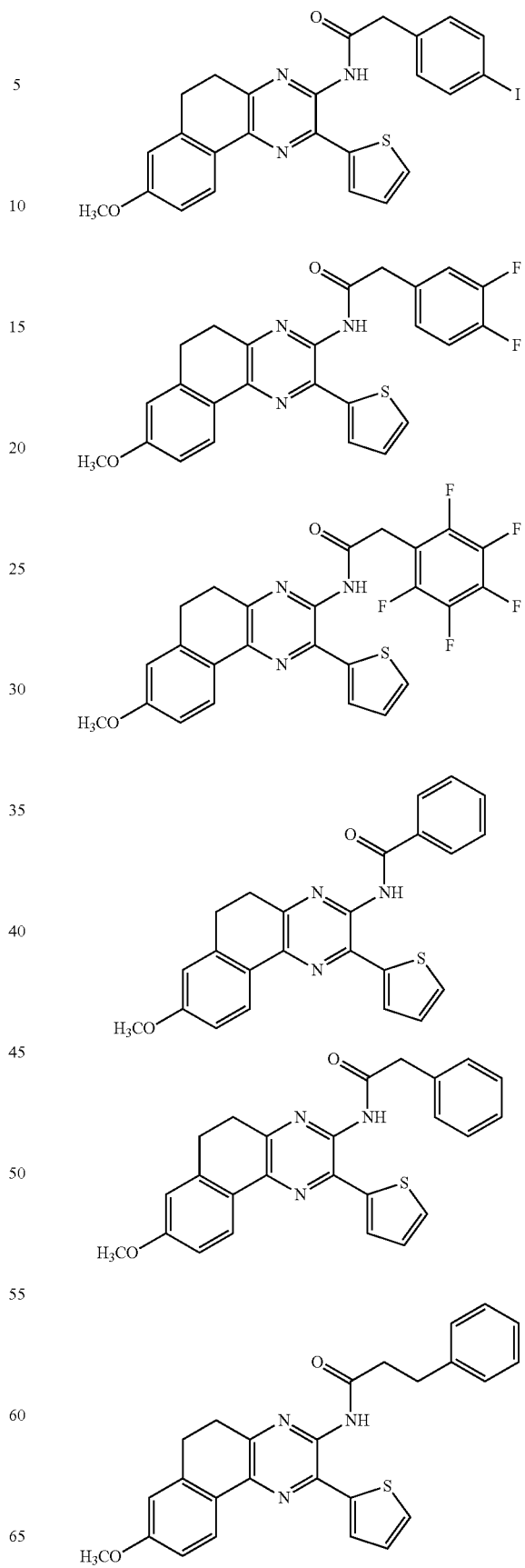

461
-continued
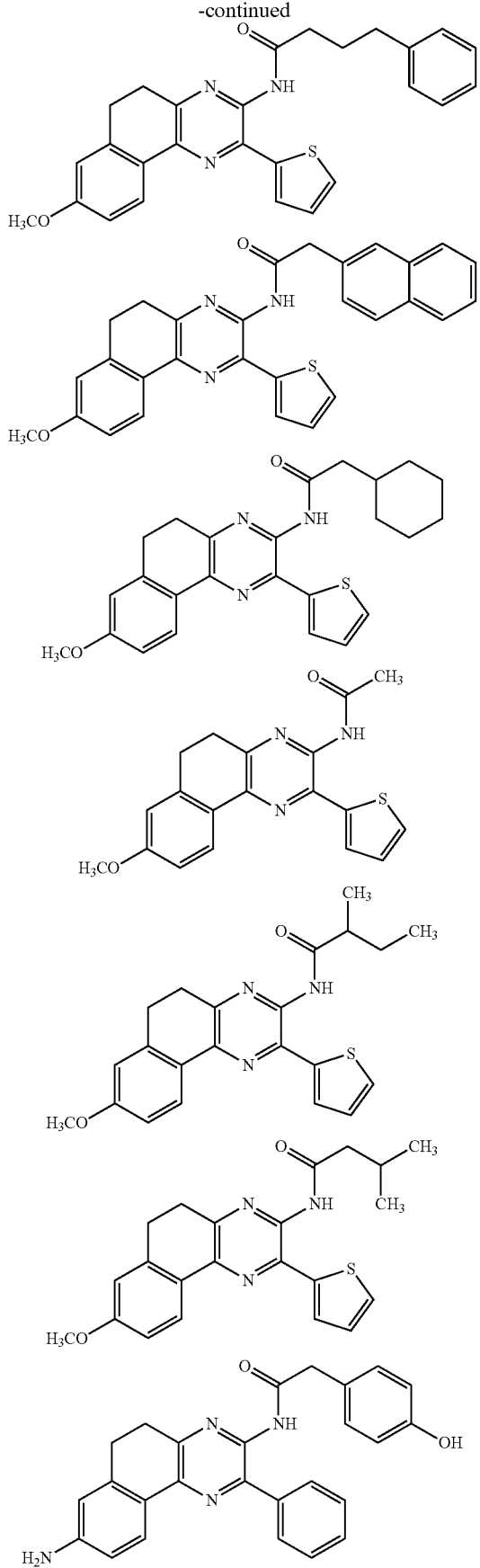
462
-continued
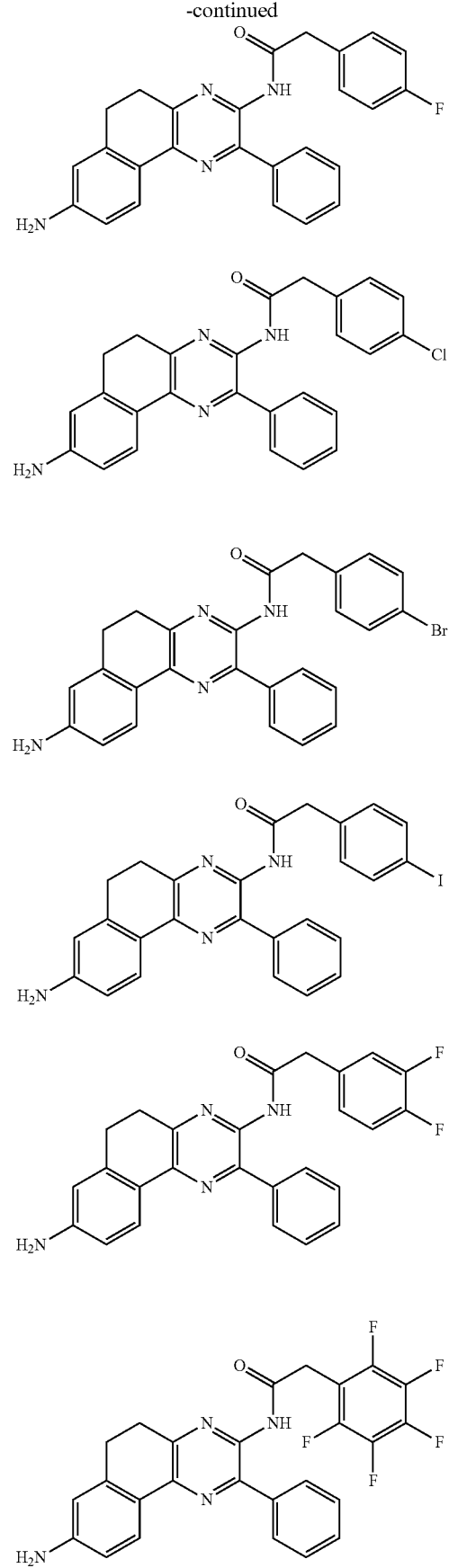

463
-continued
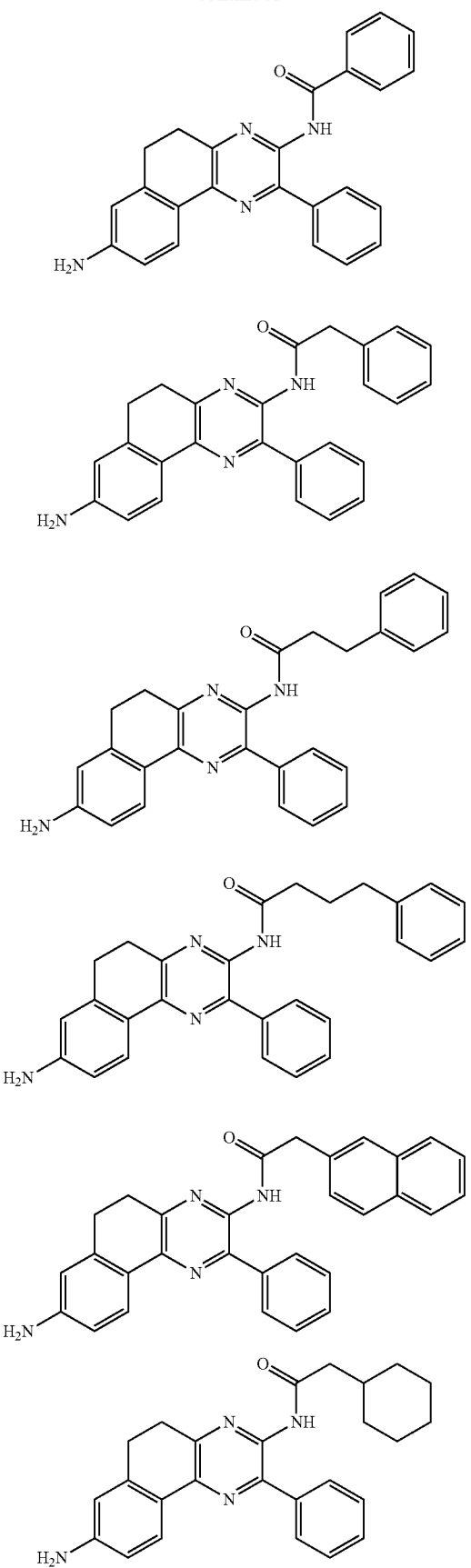
464
-continued
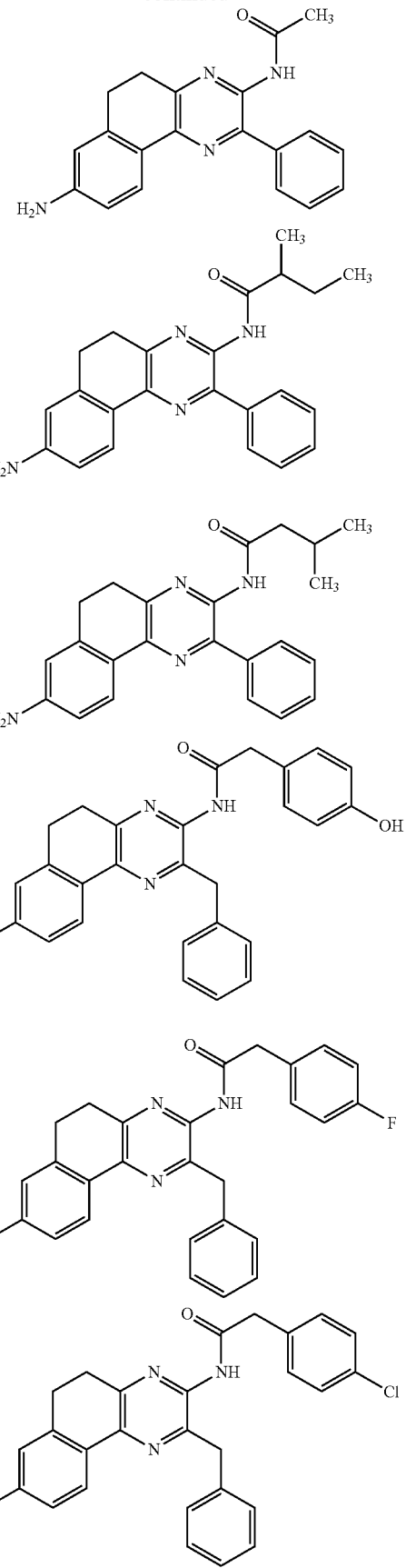

465
-continued
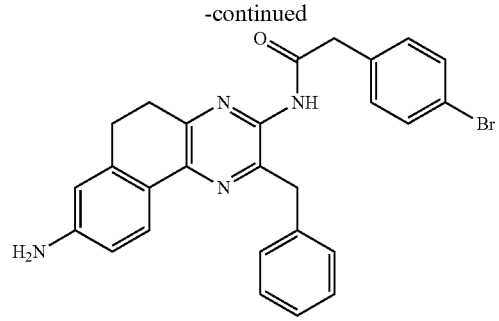
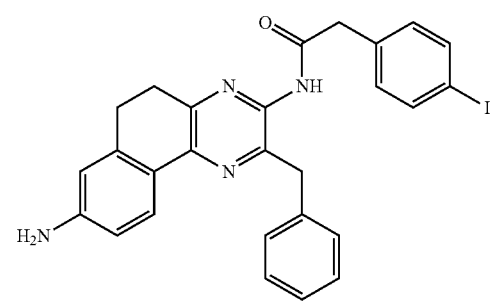
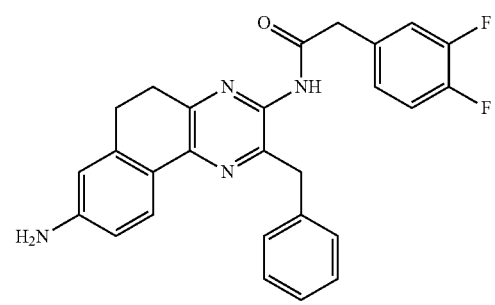
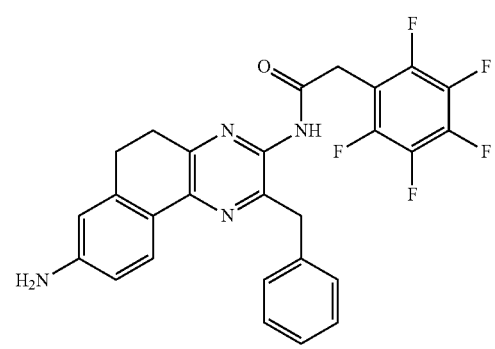
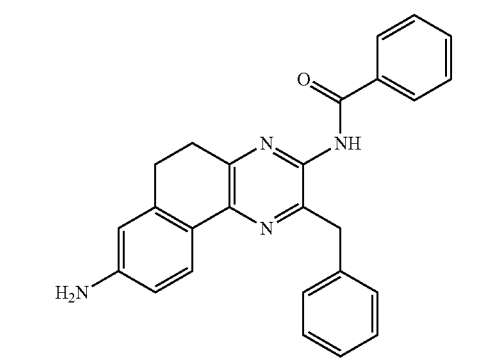
466
-continued
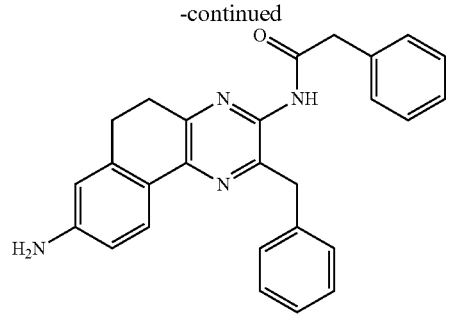
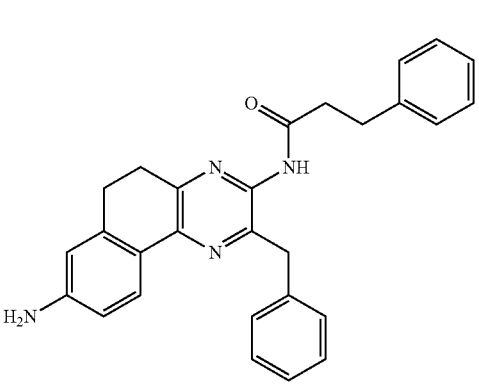
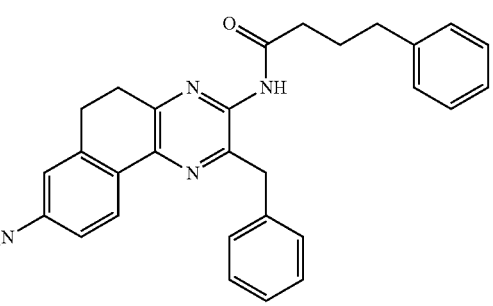
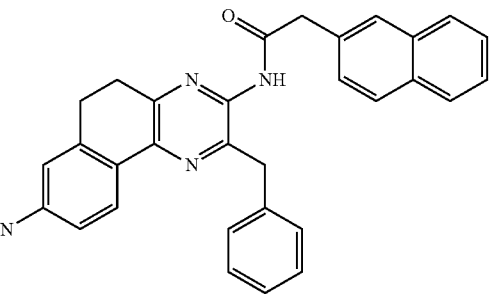
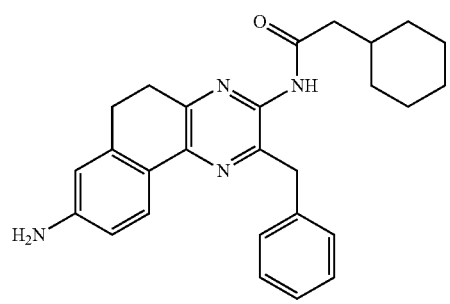

467
-continued
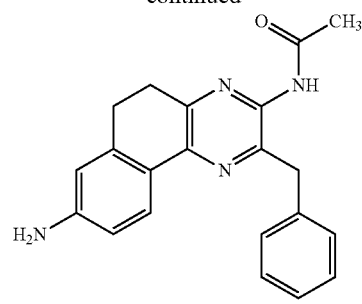
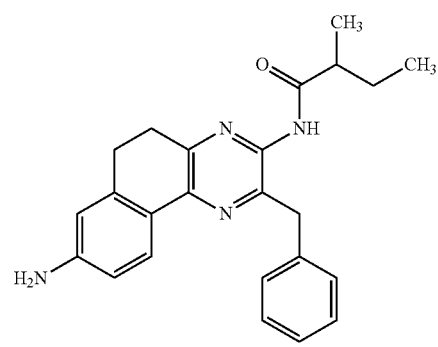
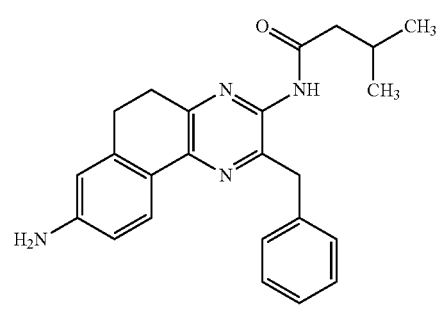
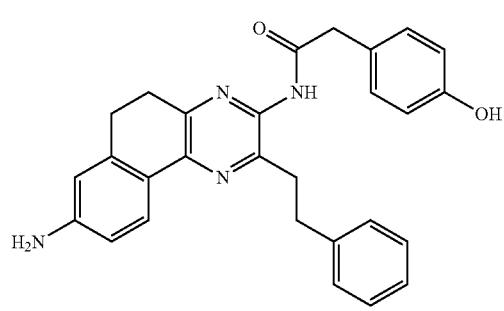
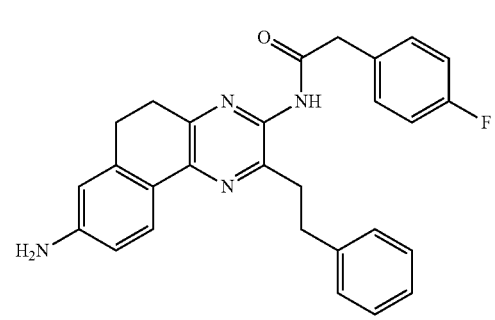
468
-continued
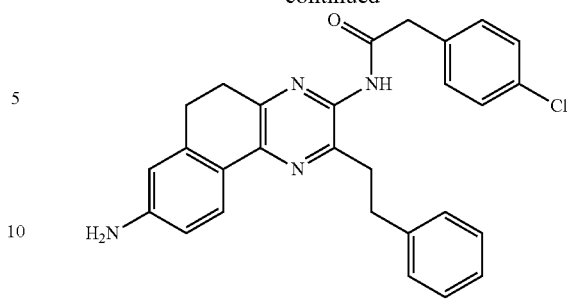
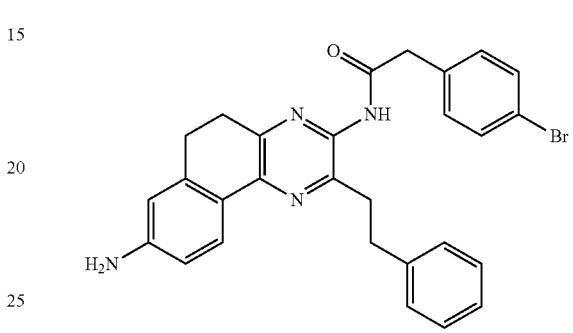
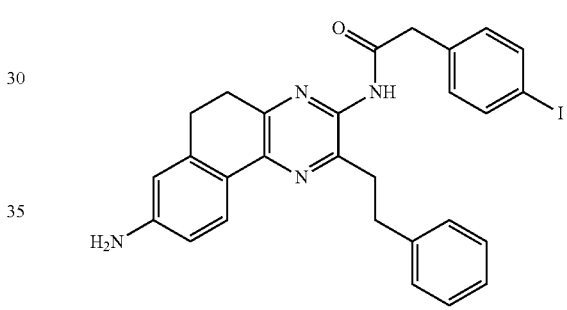
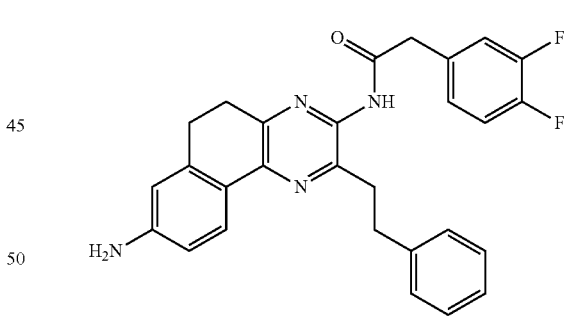
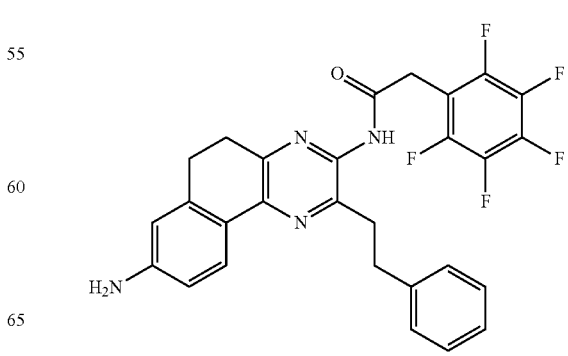

469
-continued
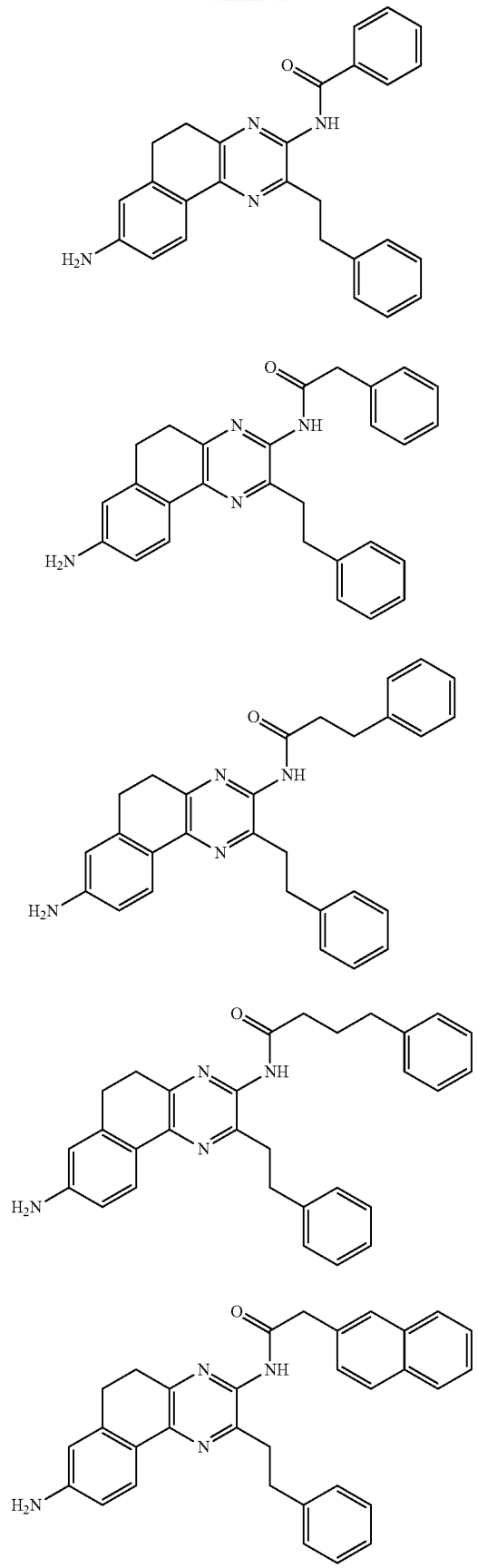
470
-continued
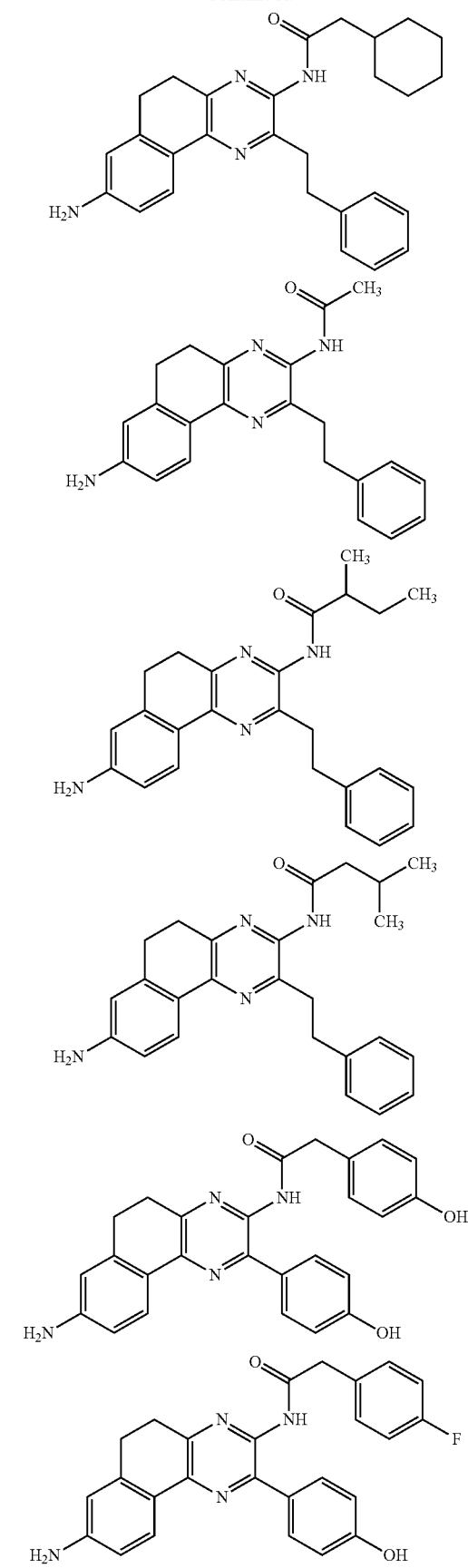

-continued
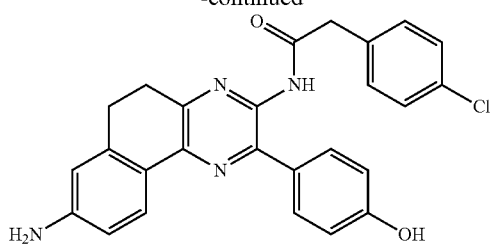
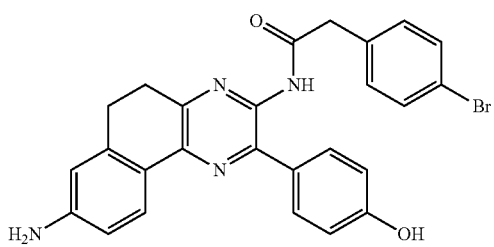
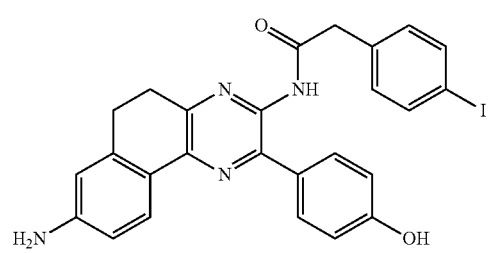
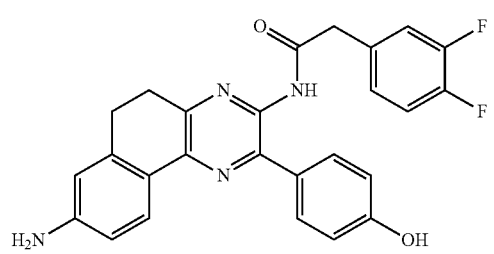
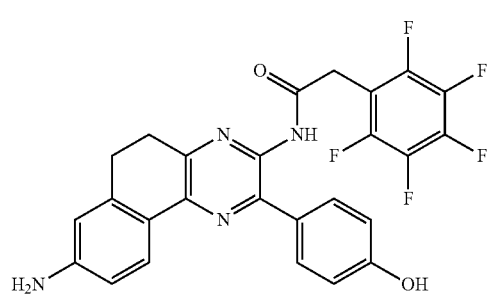
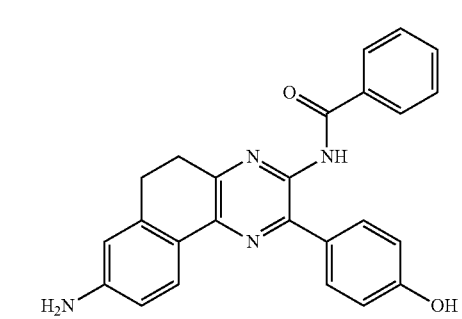
-continued
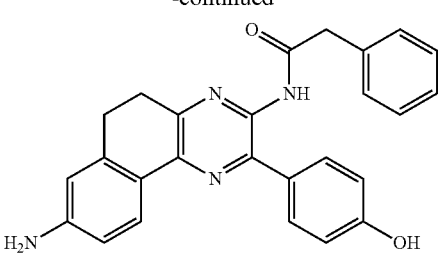
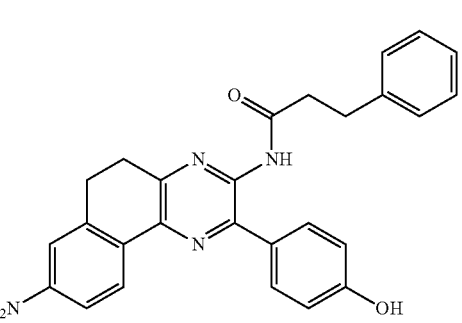
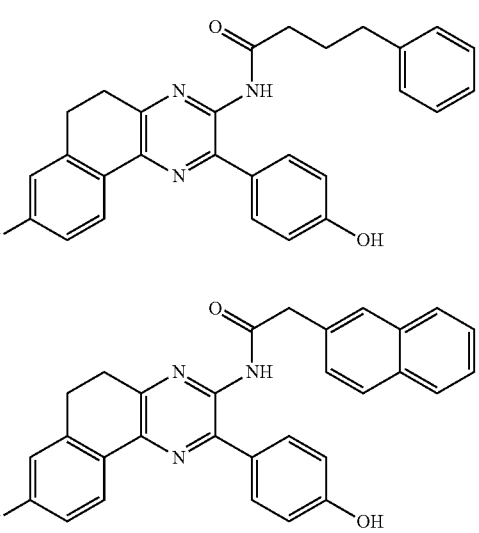
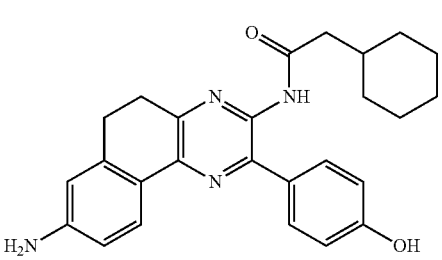
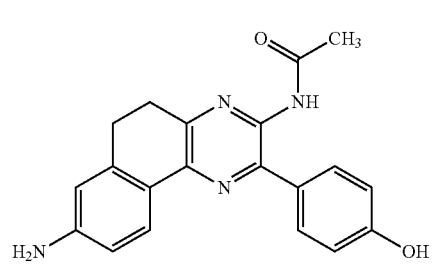

473
-continued
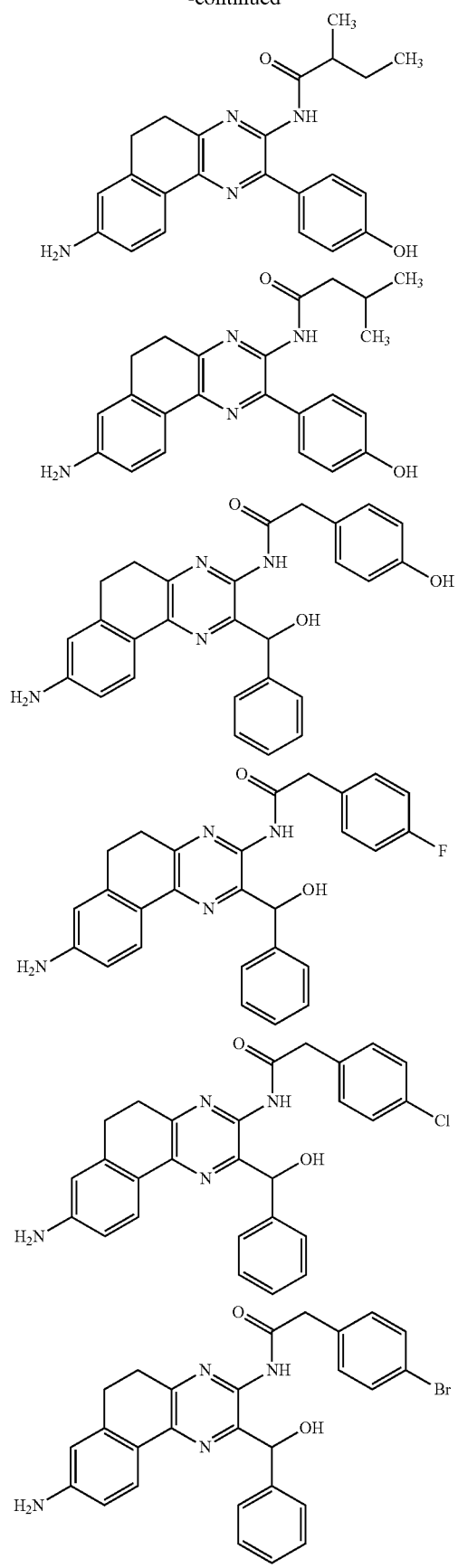
474
-continued
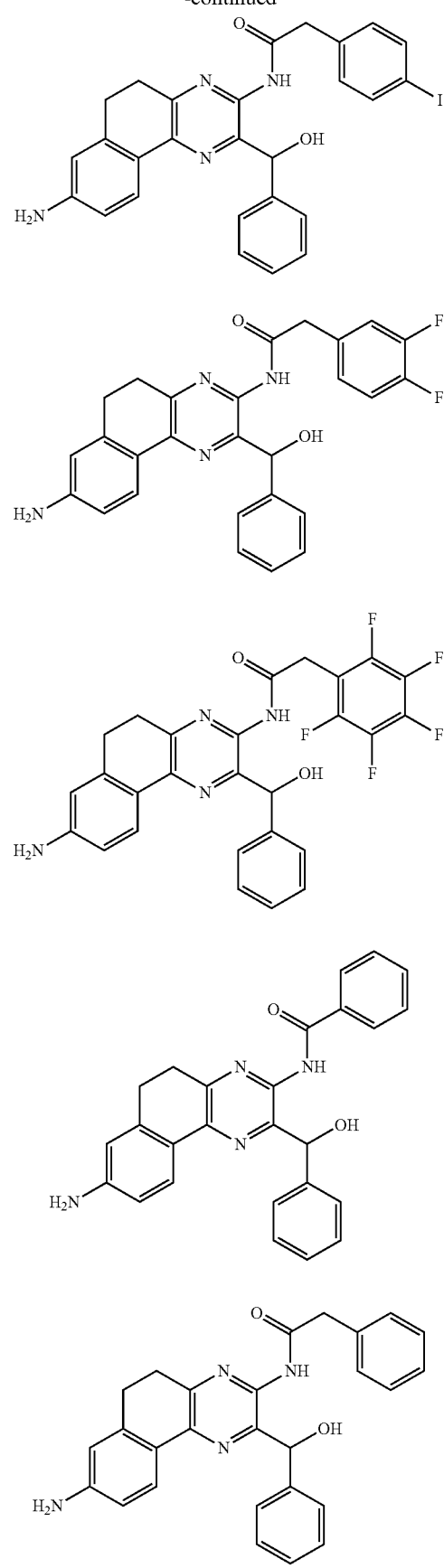

475
-continued
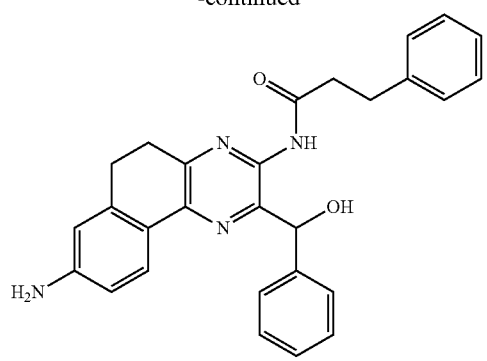
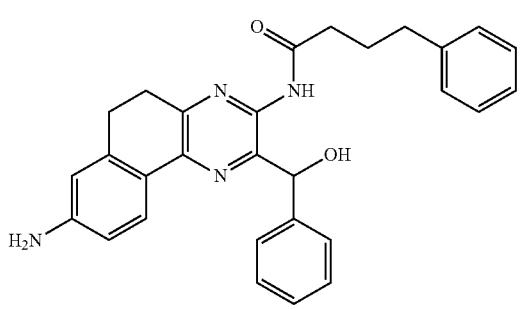
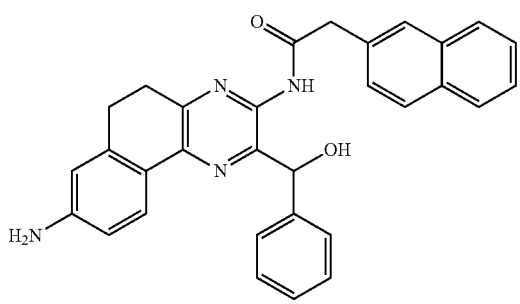
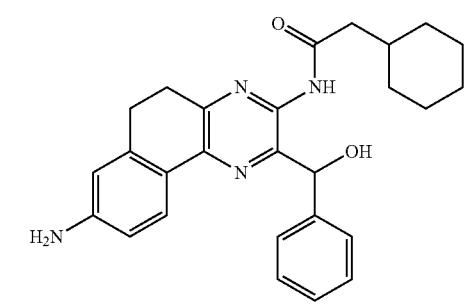
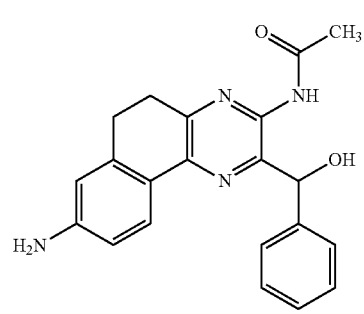
476
-continued
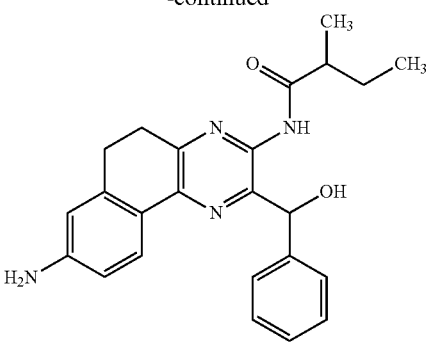
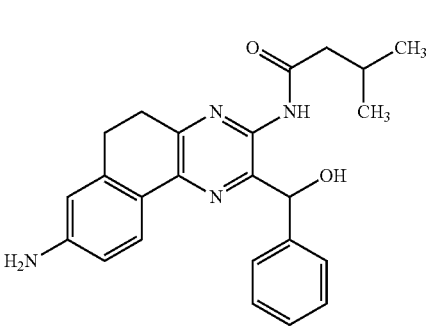
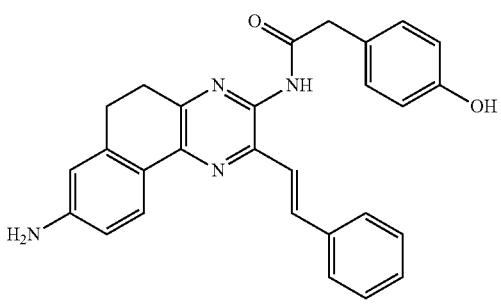
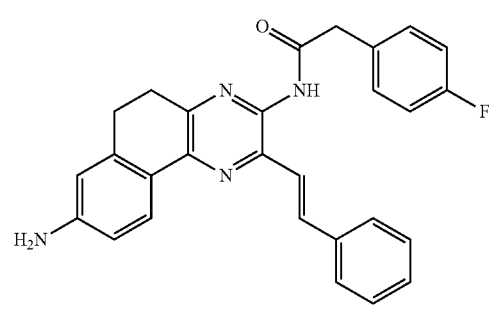
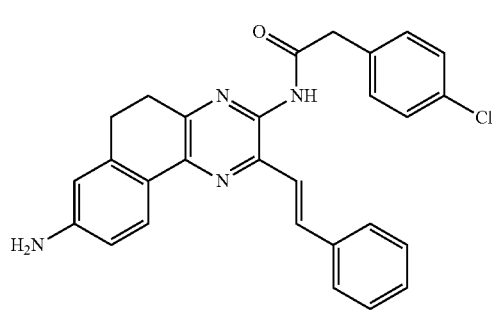

477
-continued
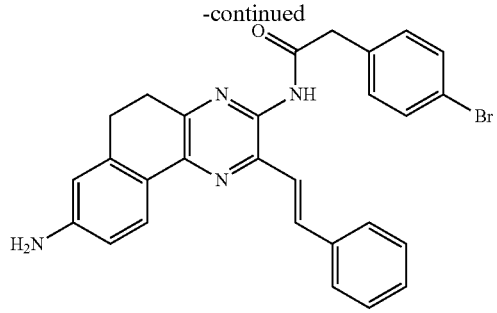
478
-continued
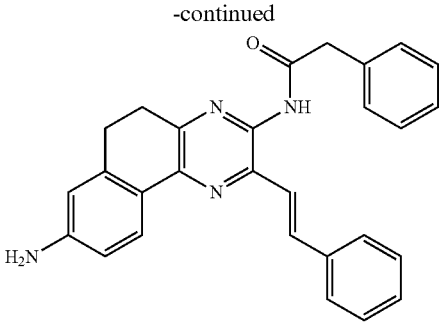
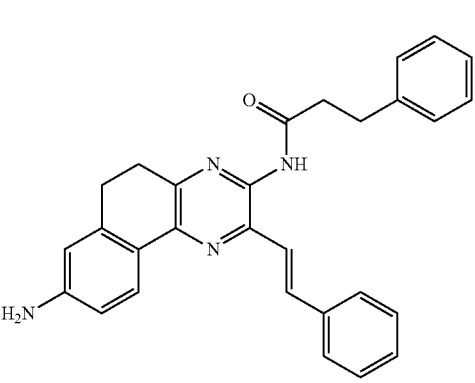
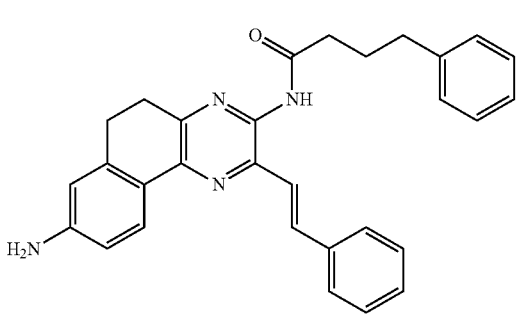
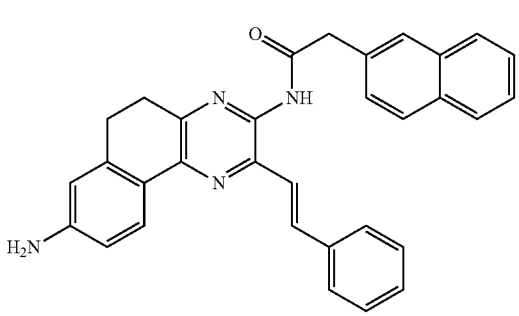
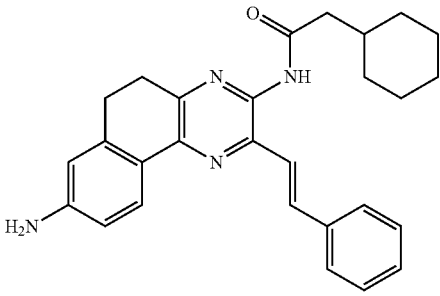

479
-continued
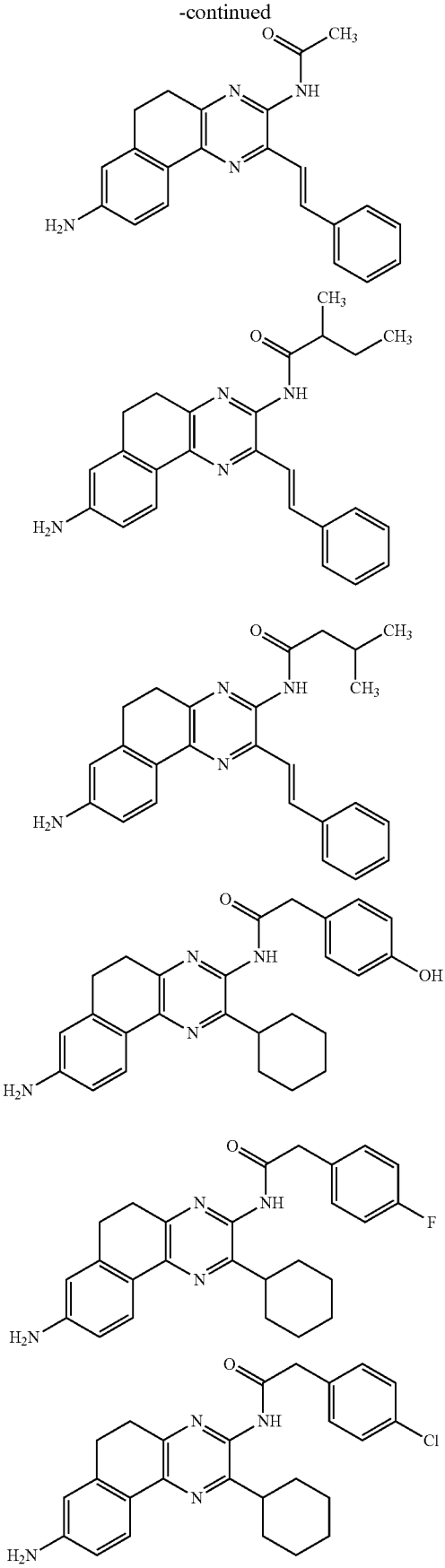
480
-continued
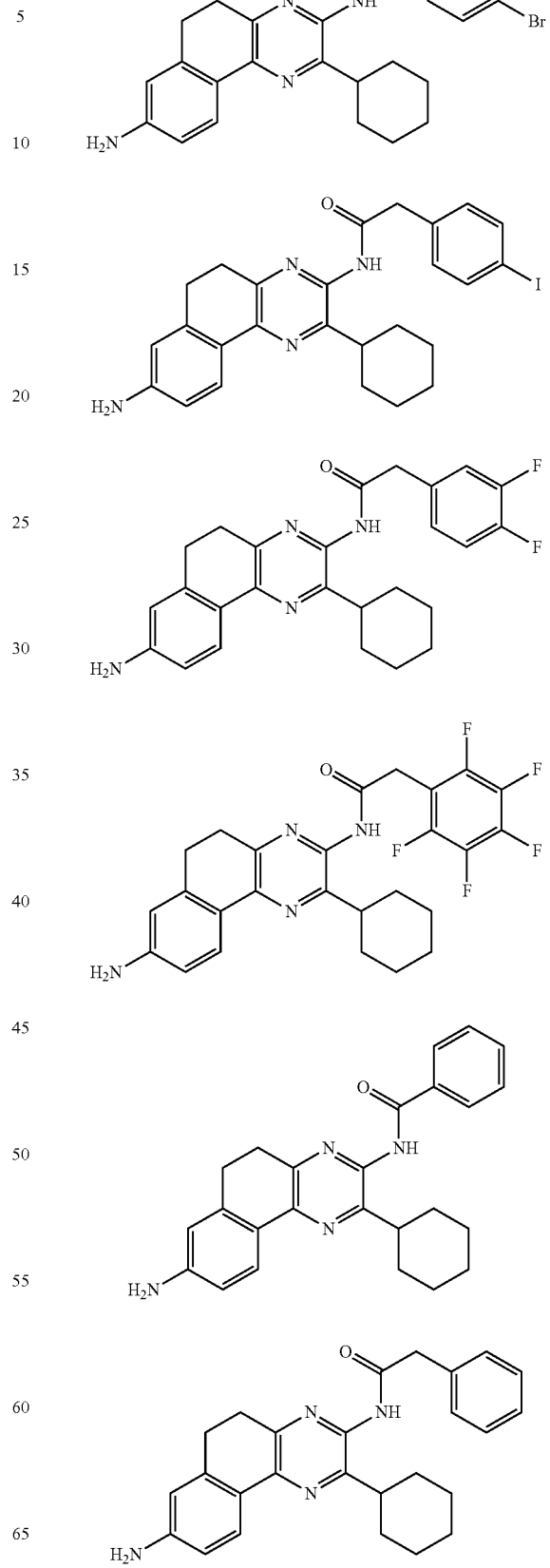

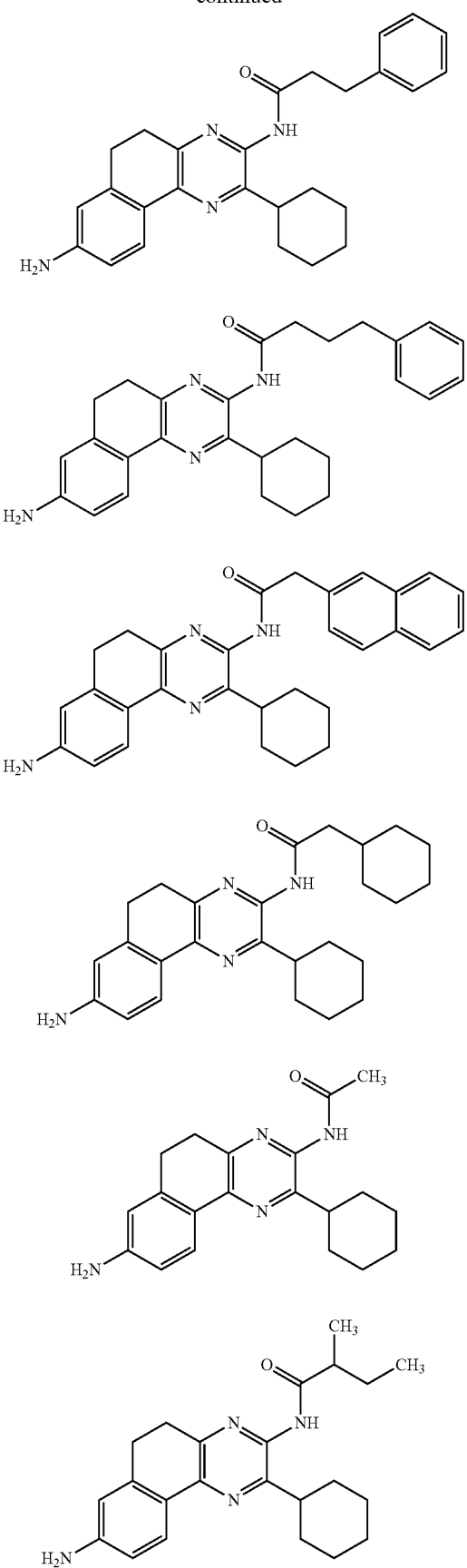
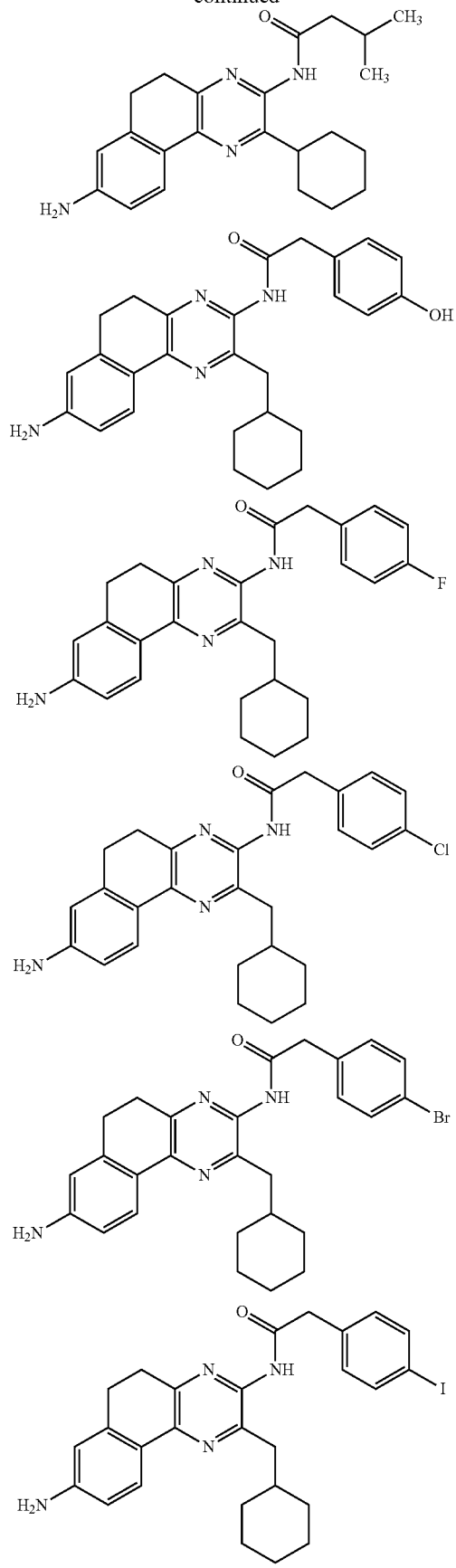

483
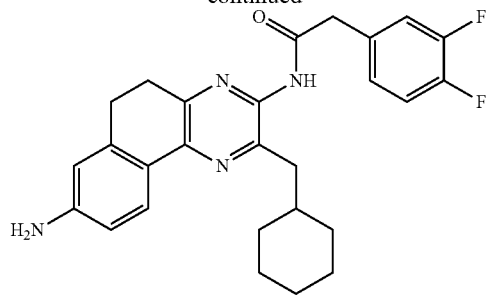
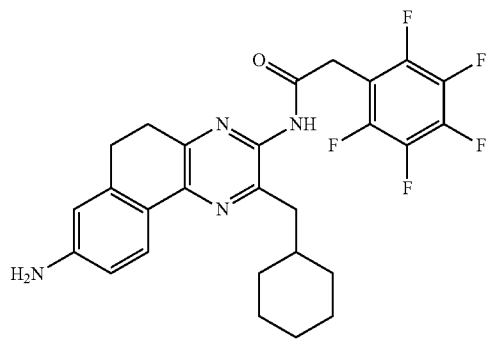
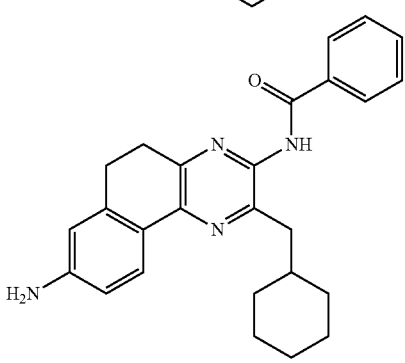
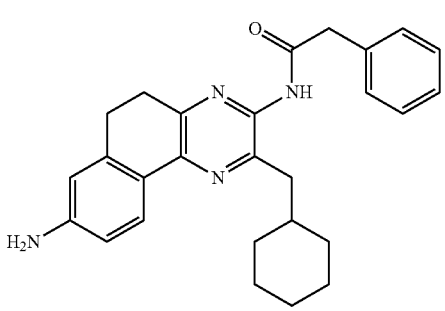
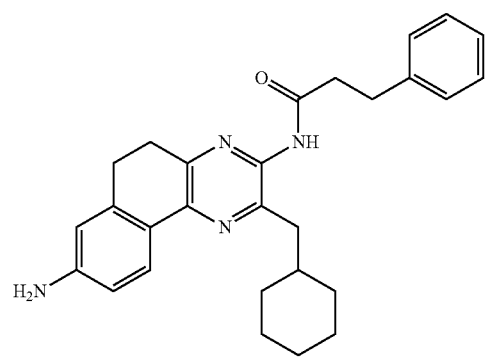
484
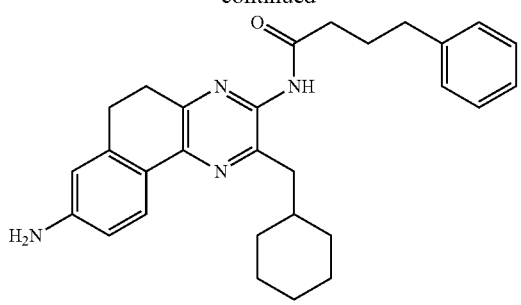
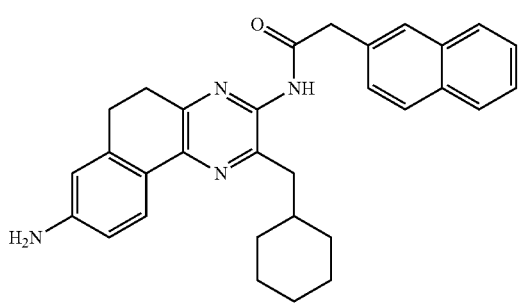
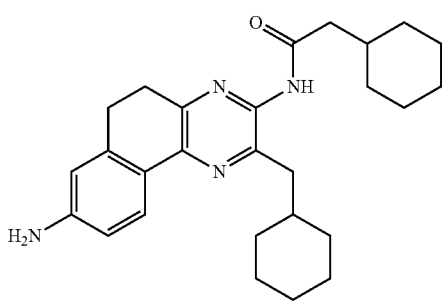
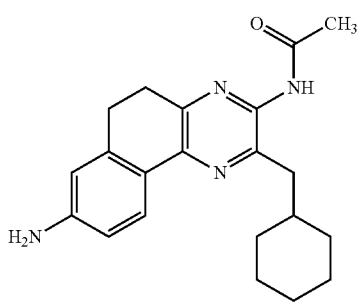
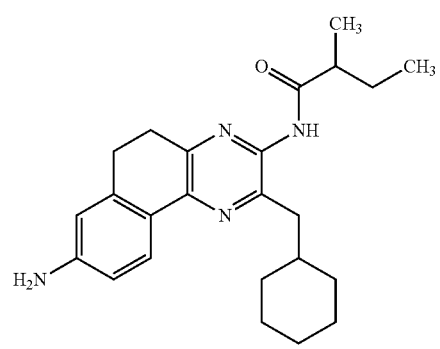

485
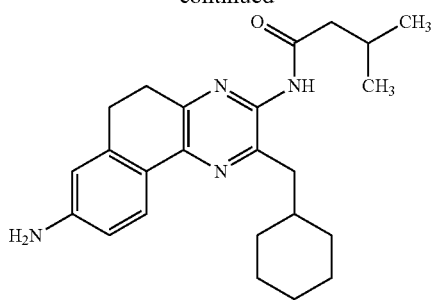
486
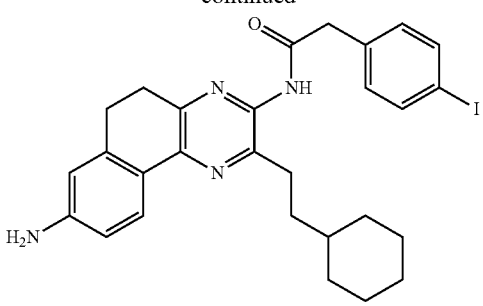

487
-continued
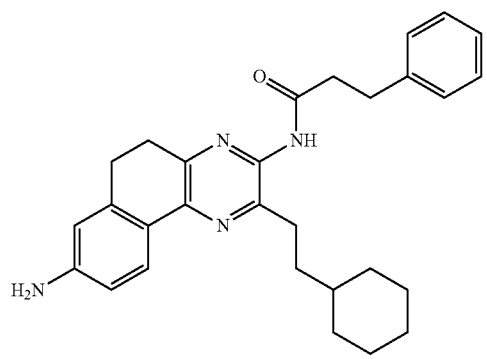
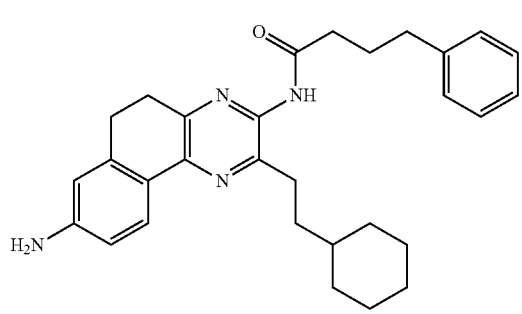
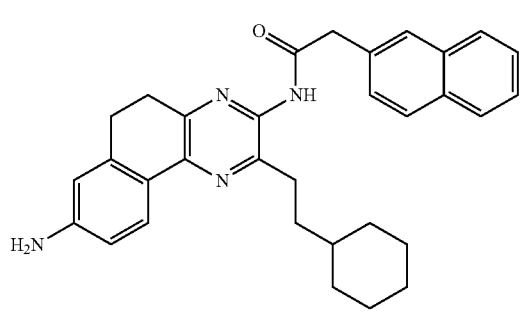
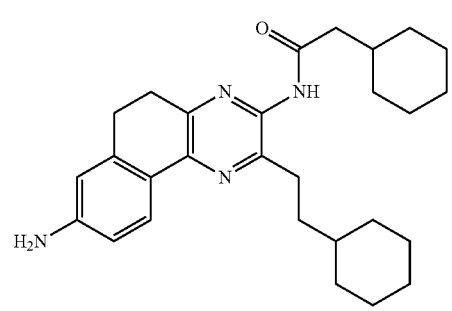
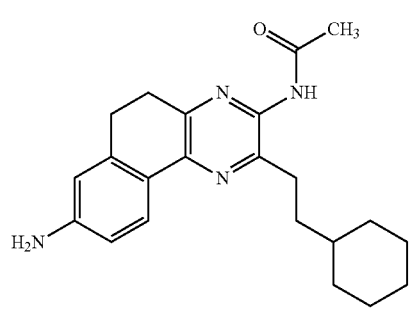
488
-continued
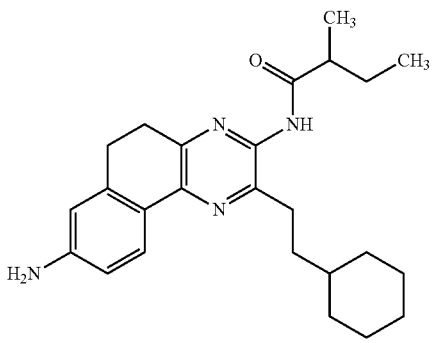
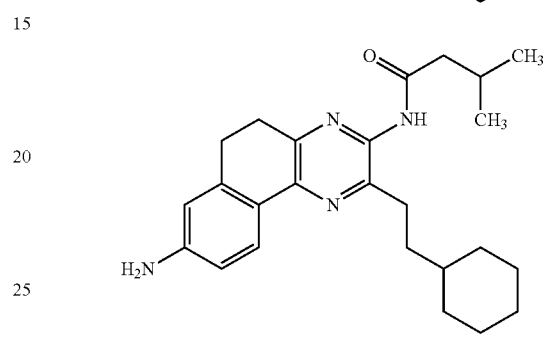
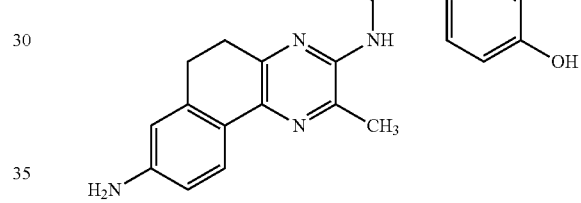
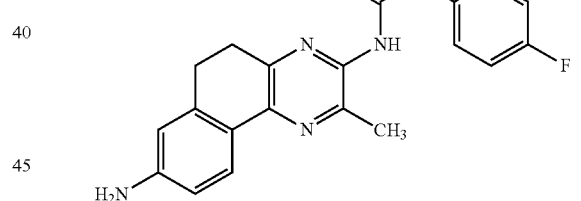
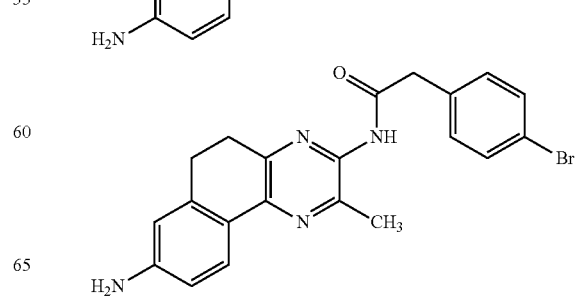

489
-continued
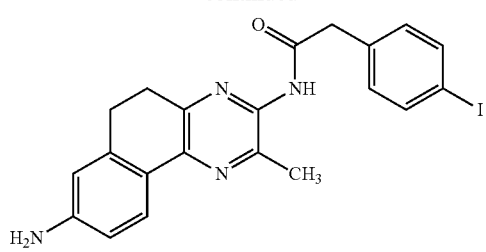
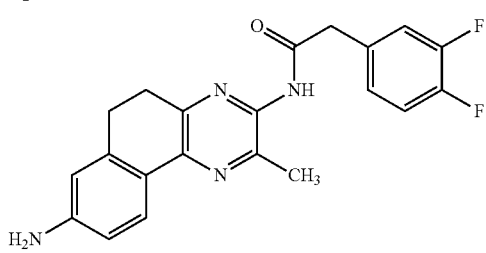
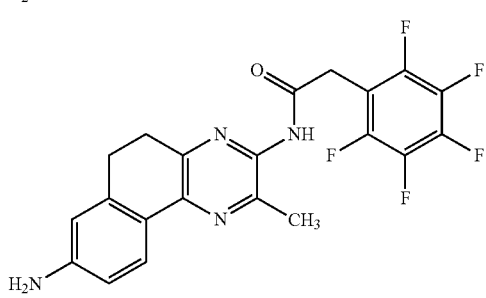
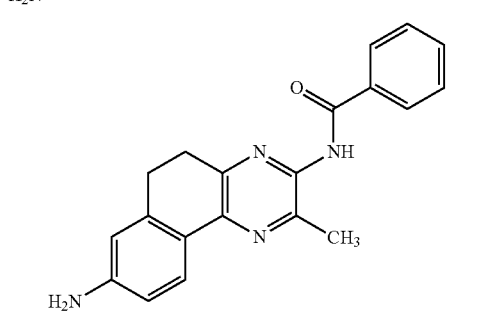
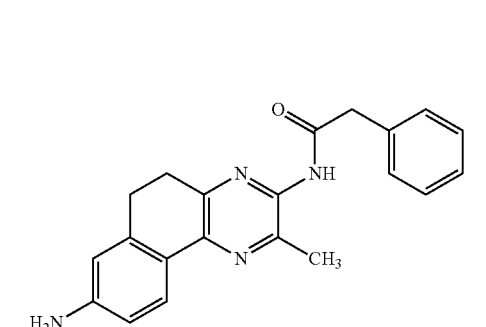
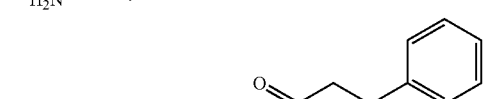
490
-continued
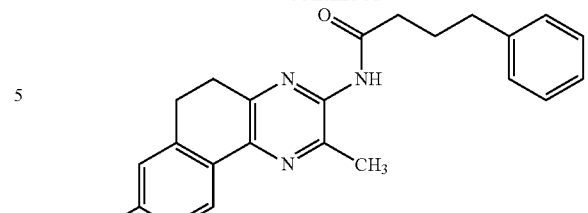
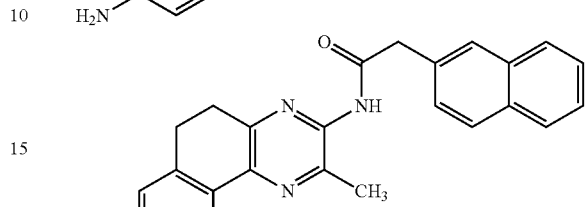
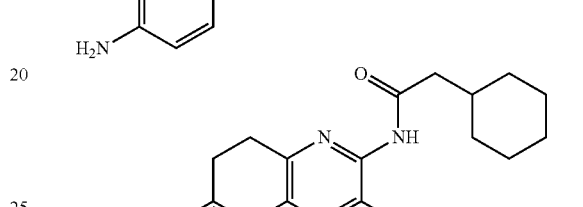
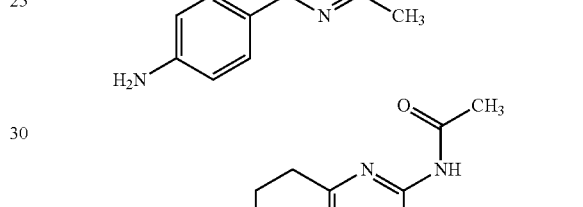
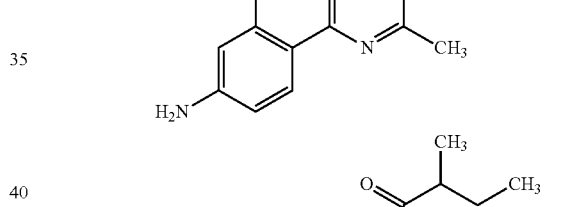
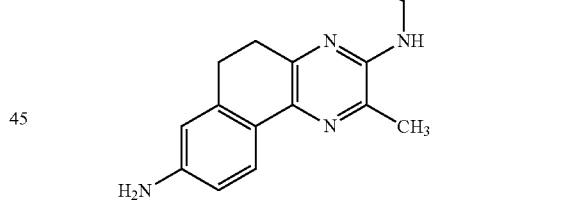
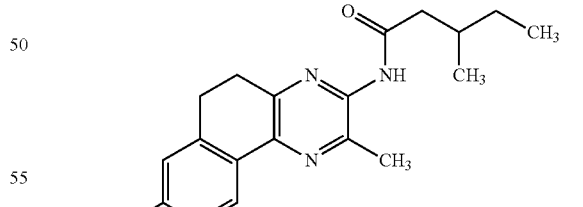
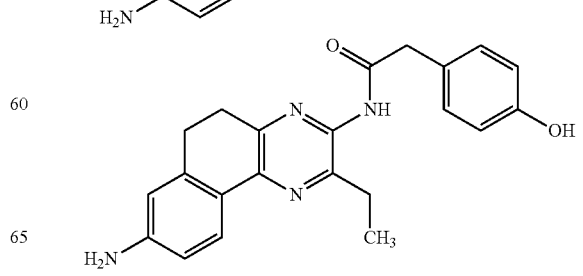

491
-continued
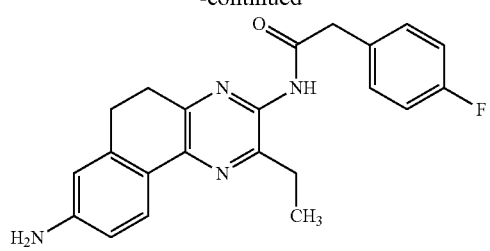
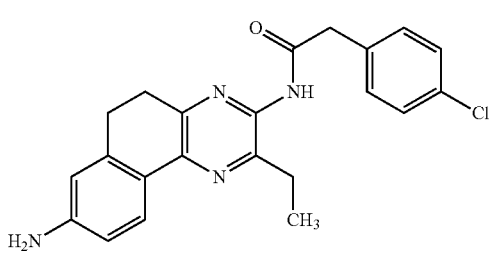
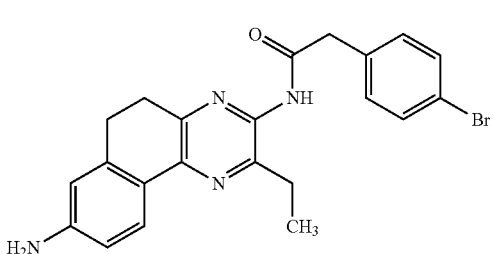
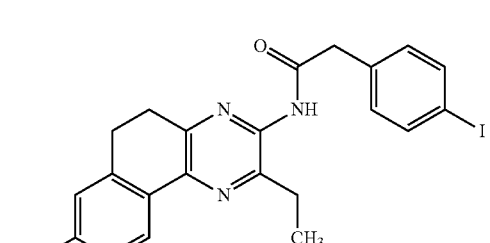
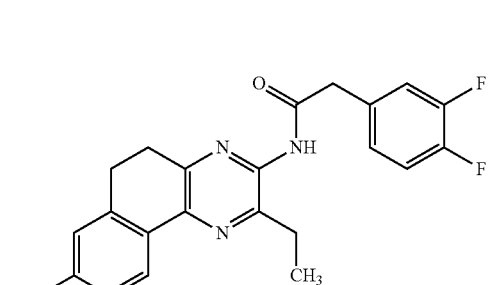
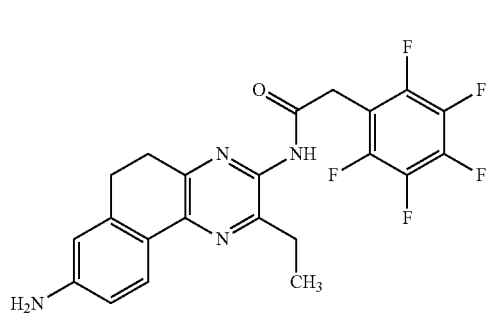
492
-continued
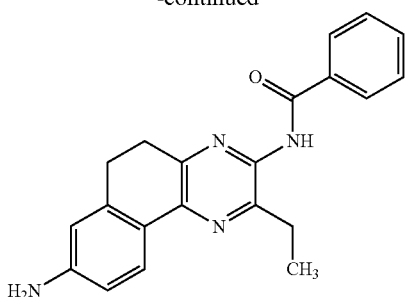
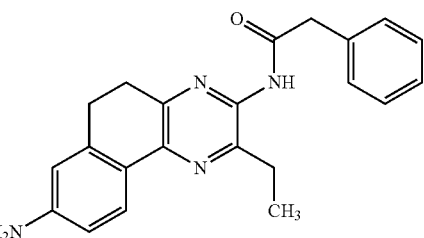
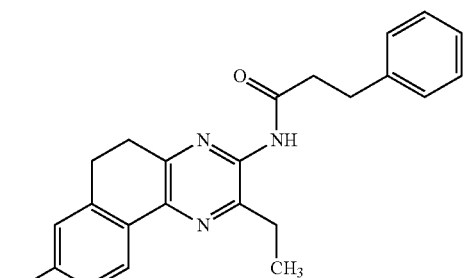
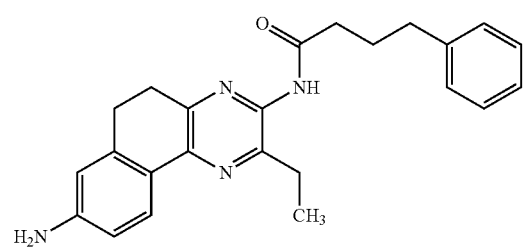
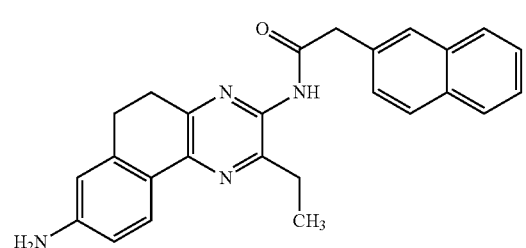
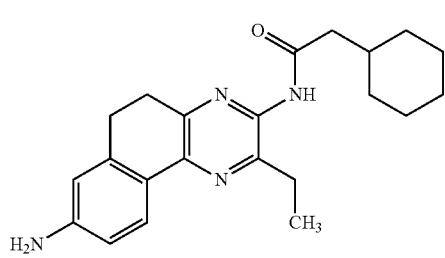

493
-continued
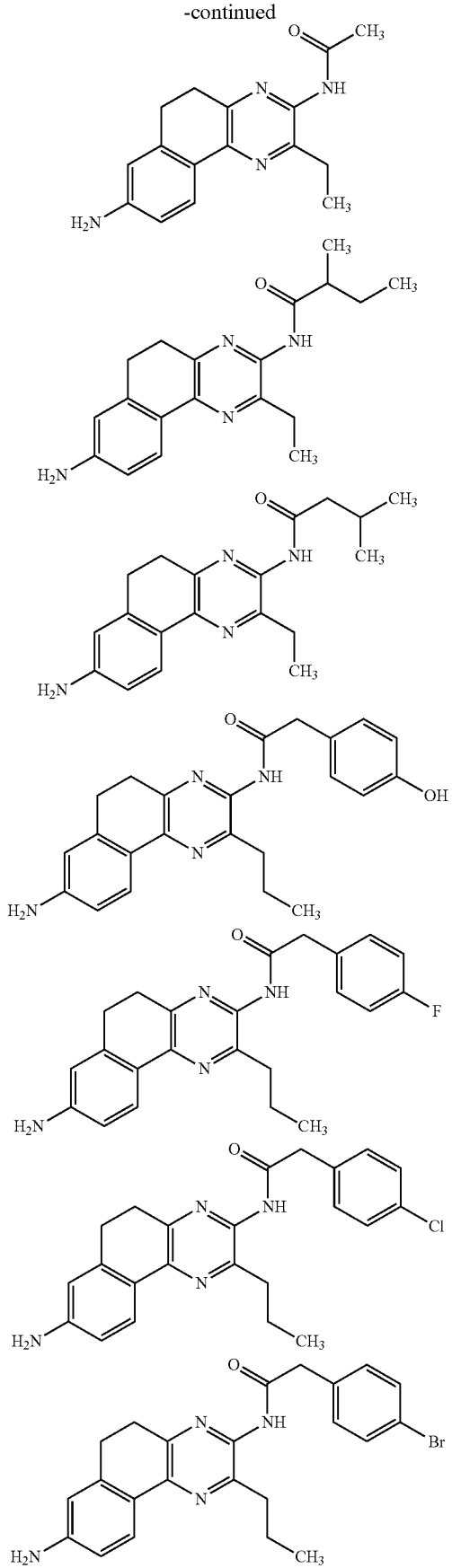
494
-continued
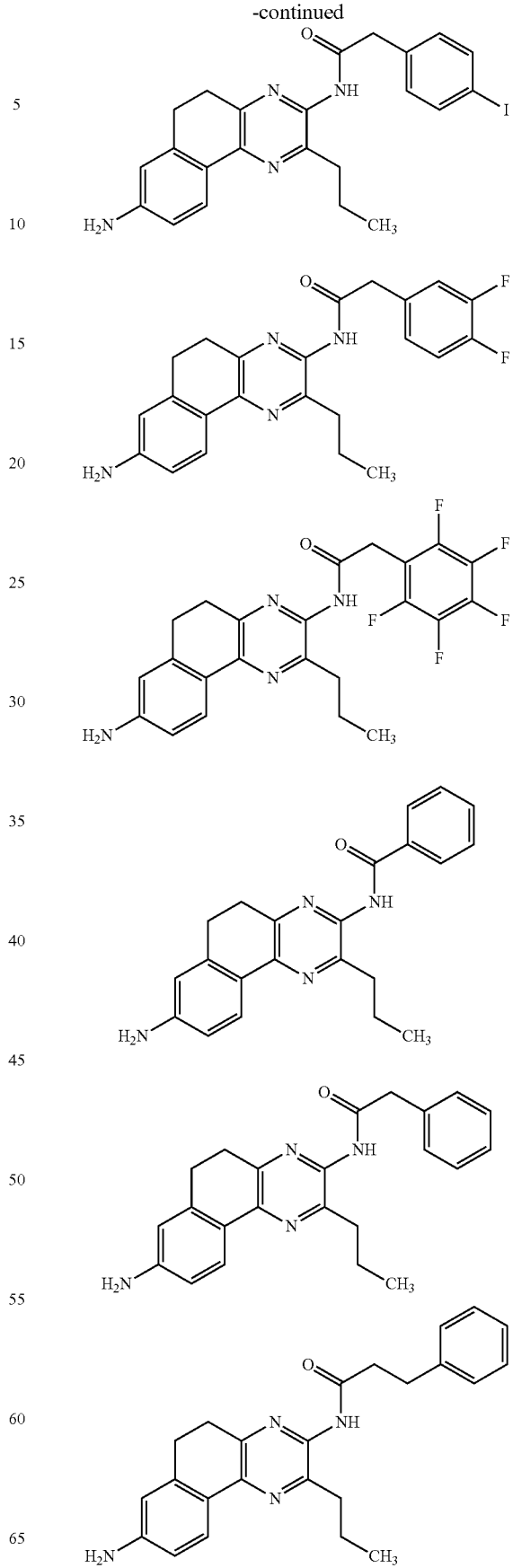

495
-continued
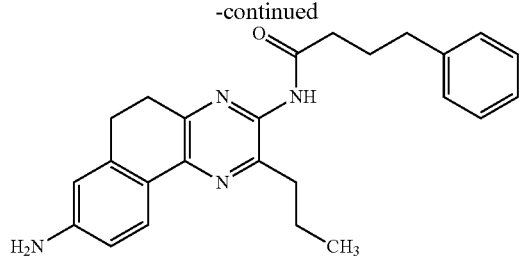
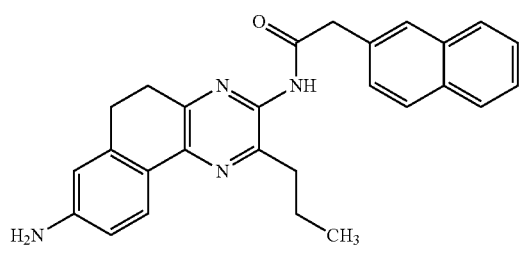
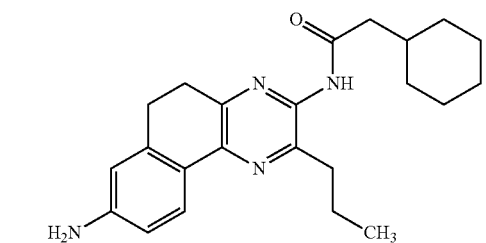
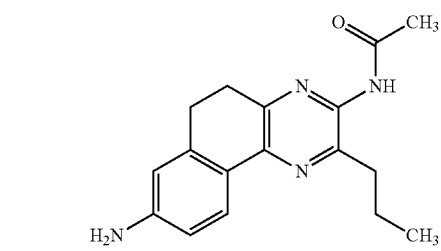
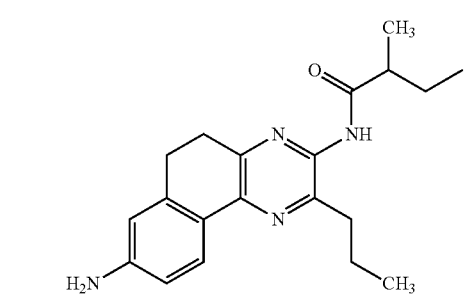
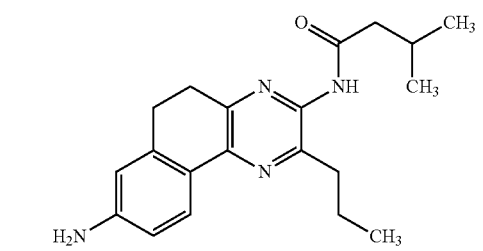
496
-continued
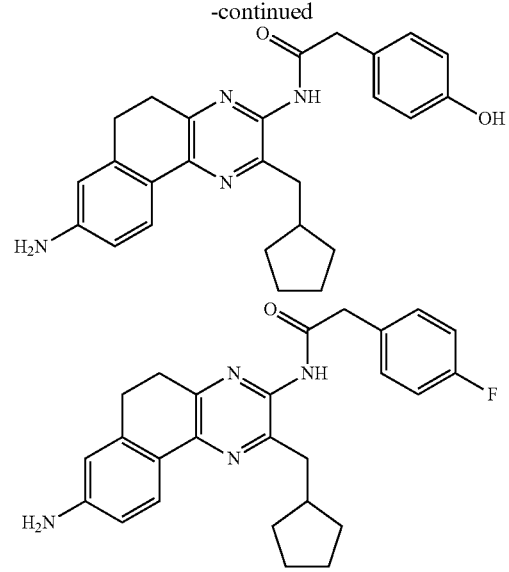
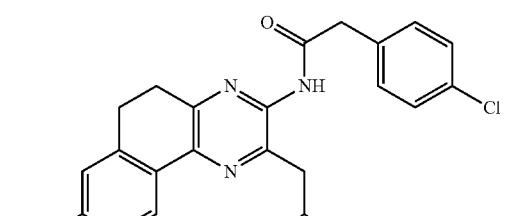
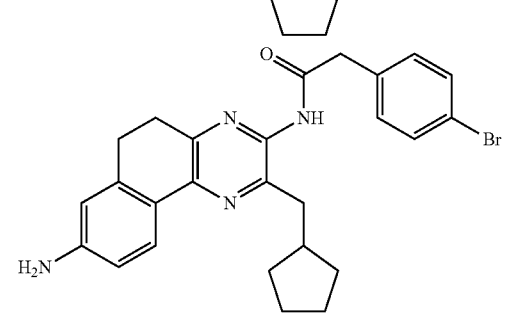
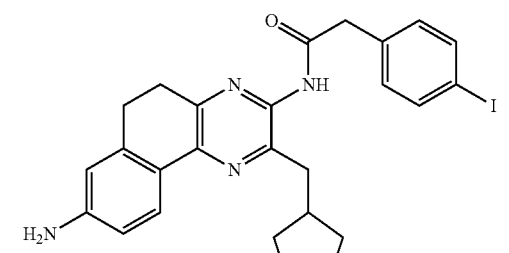
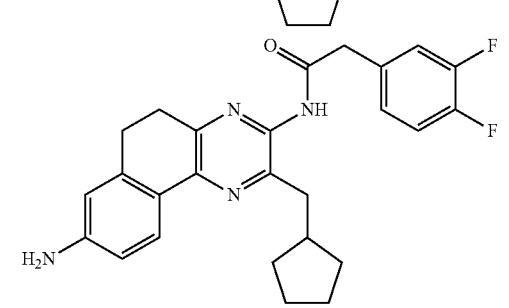

497
-continued
498
-continued
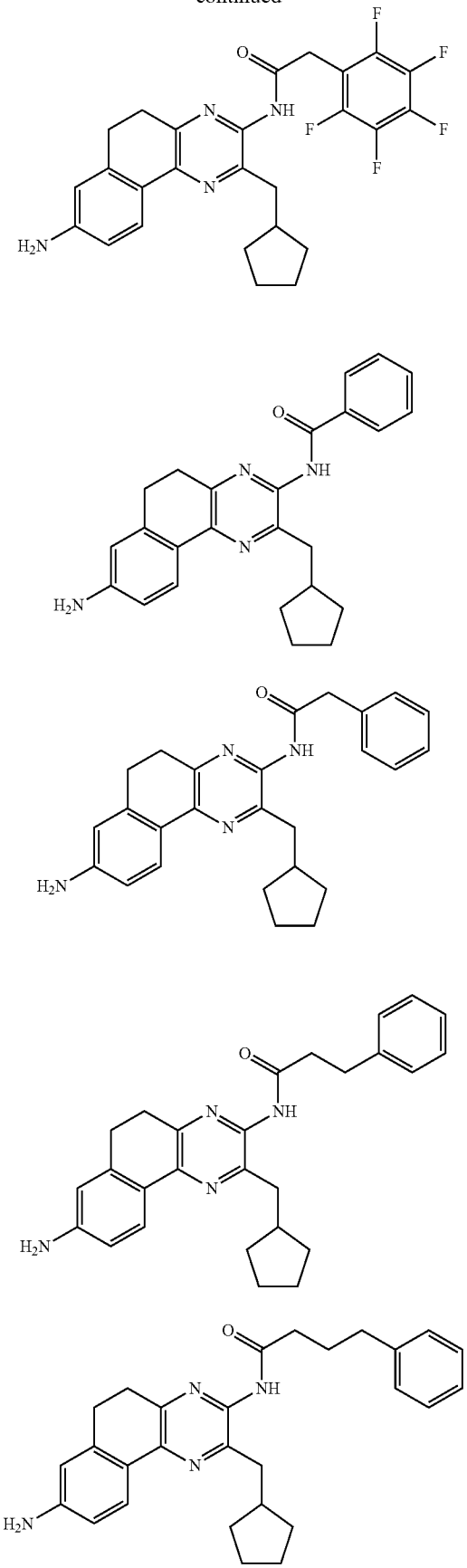
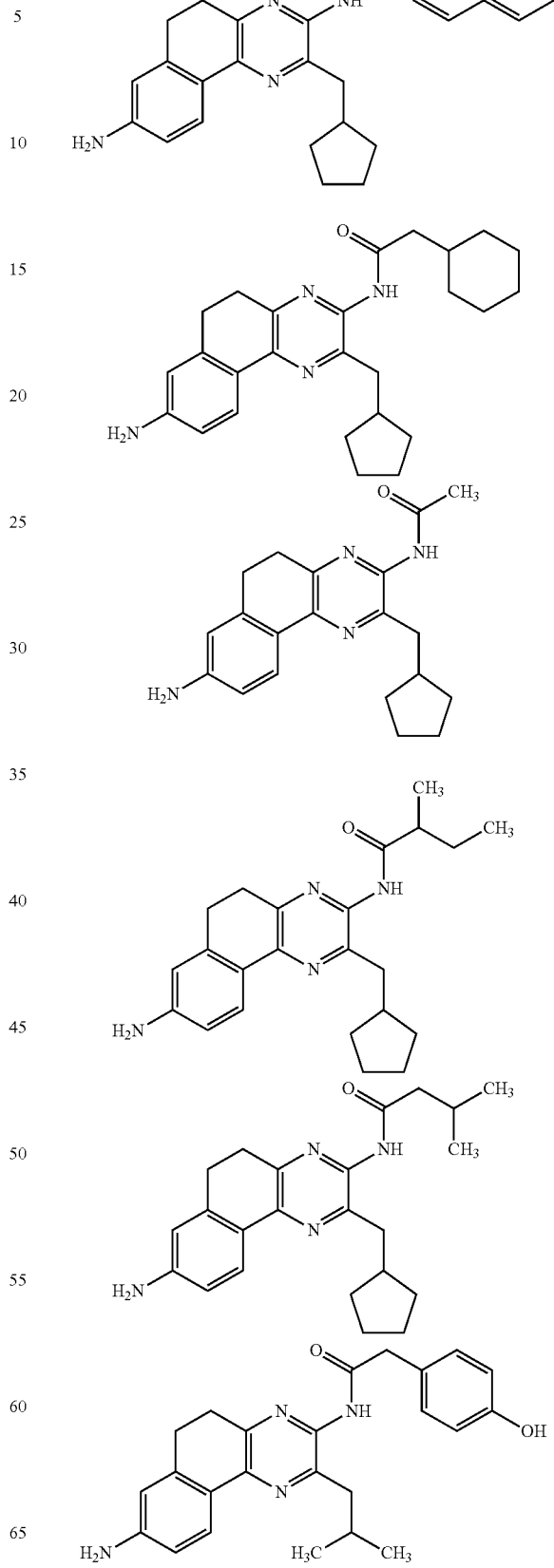

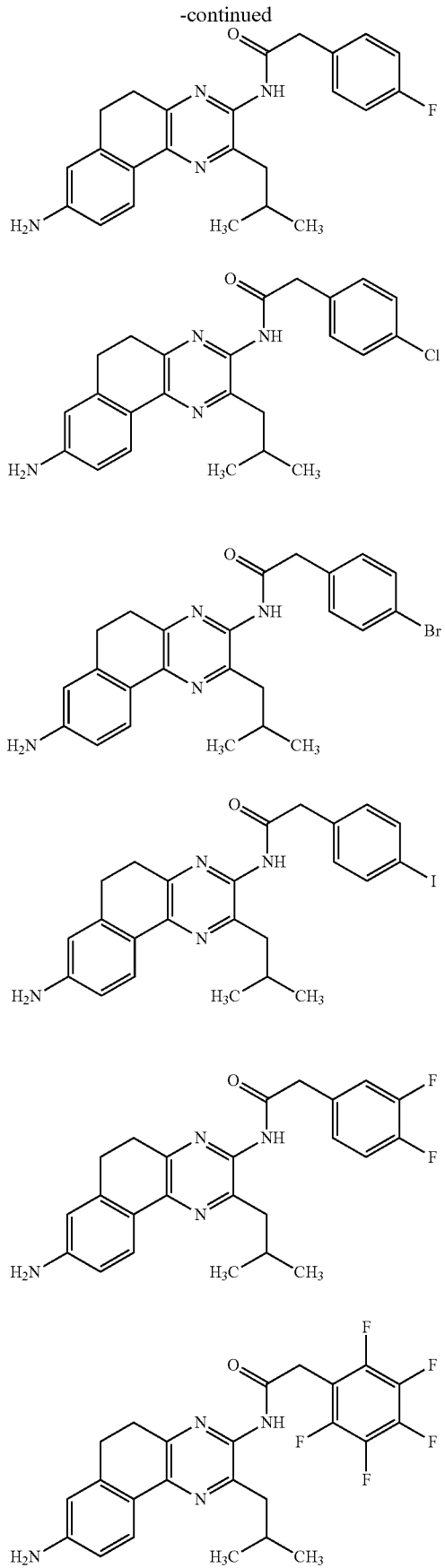
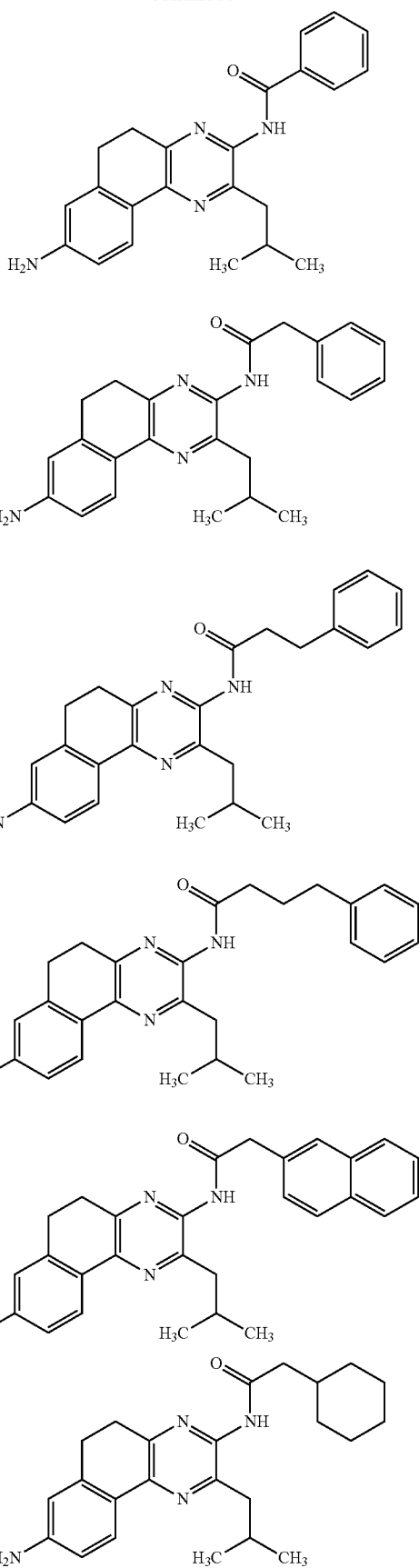

501
-continued
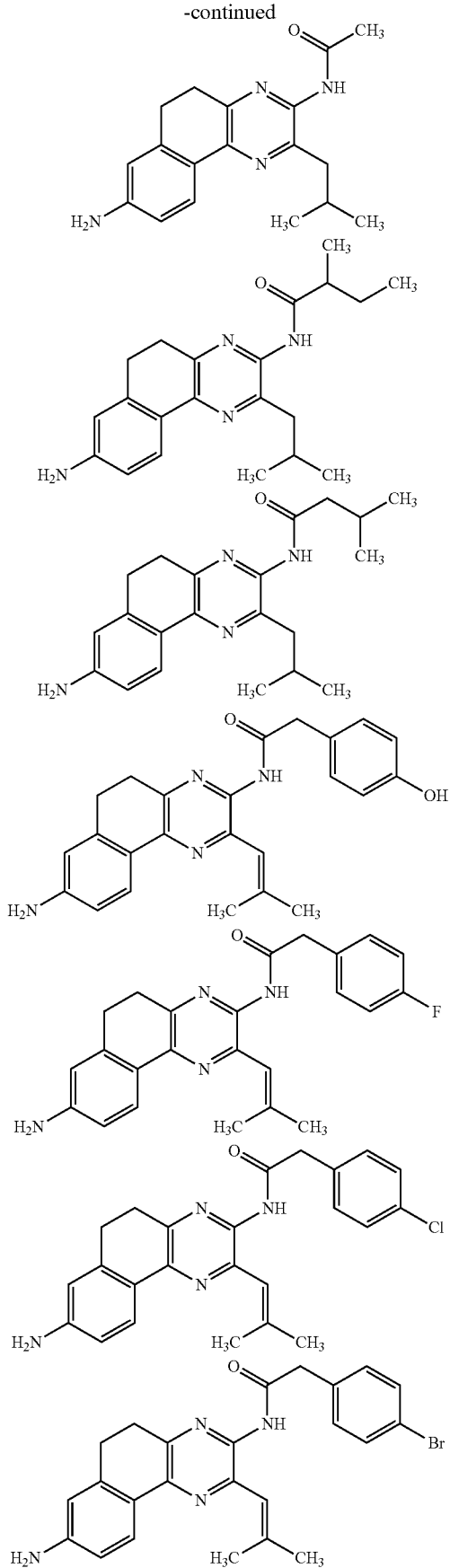
502
-continued
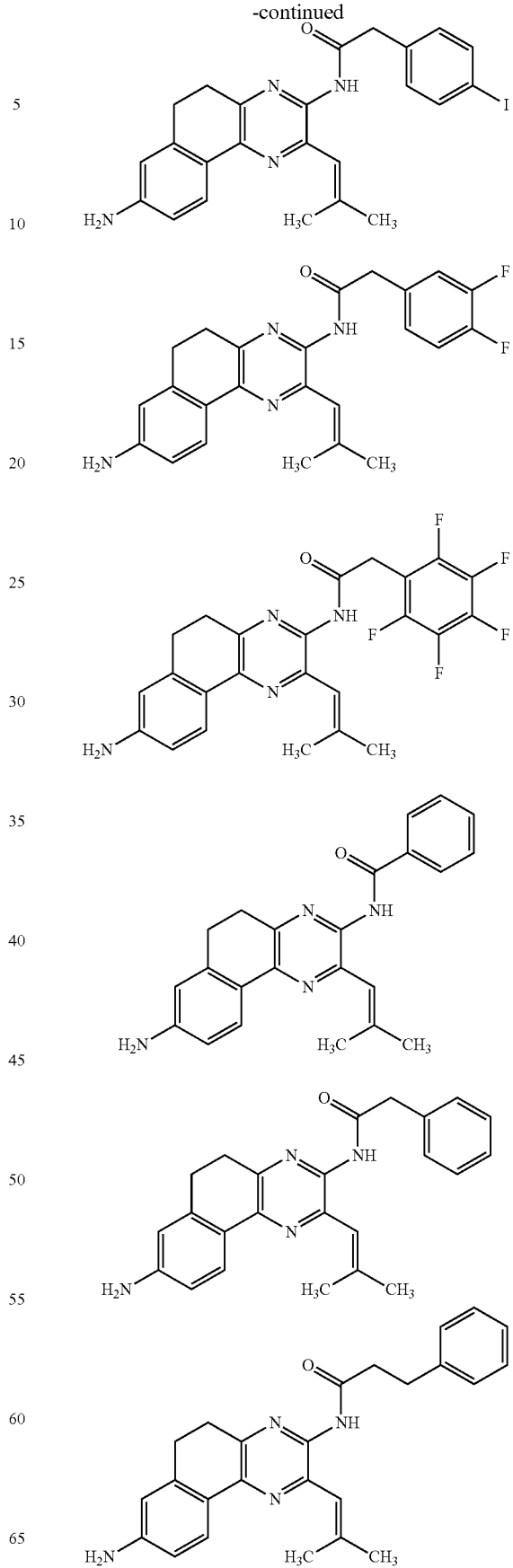

503
-continued
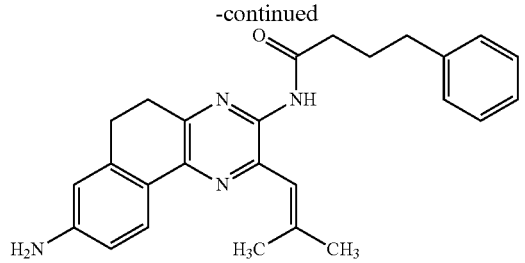
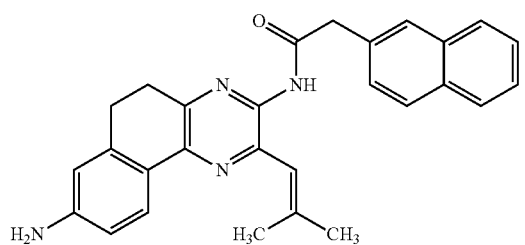
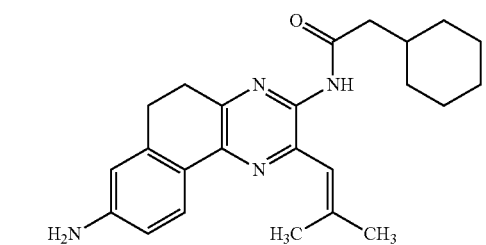
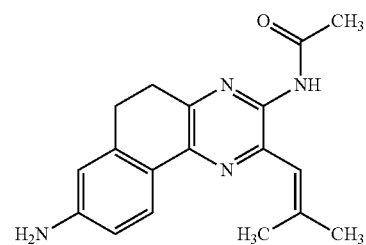
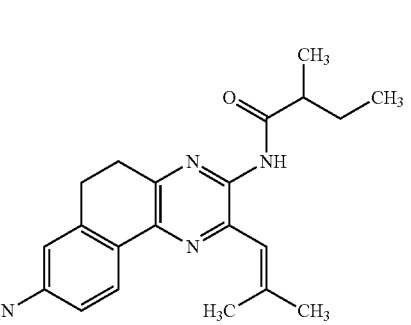
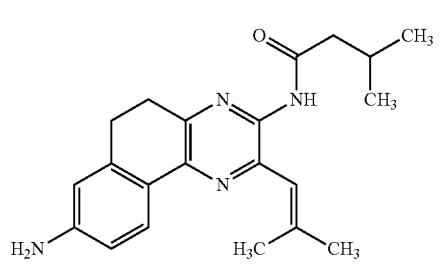
504
-continued
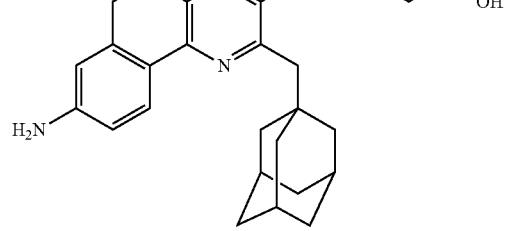
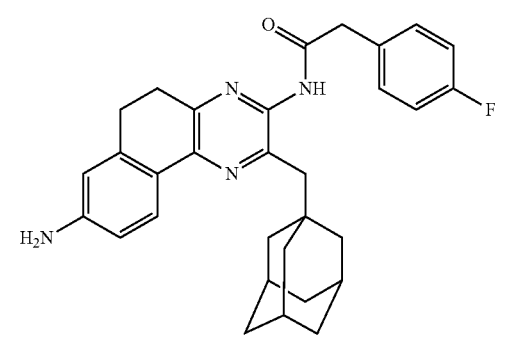
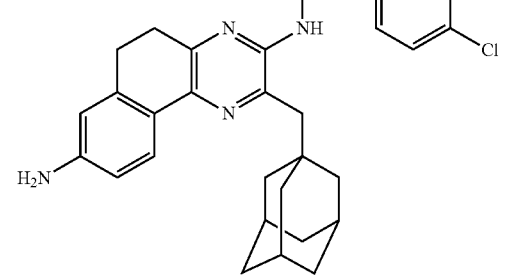
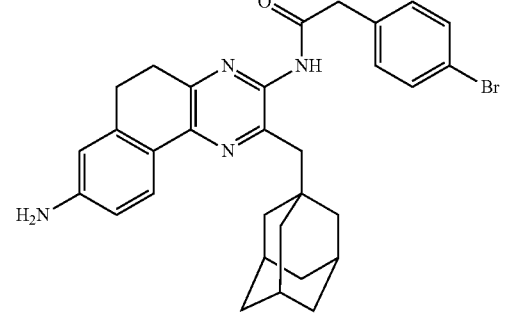
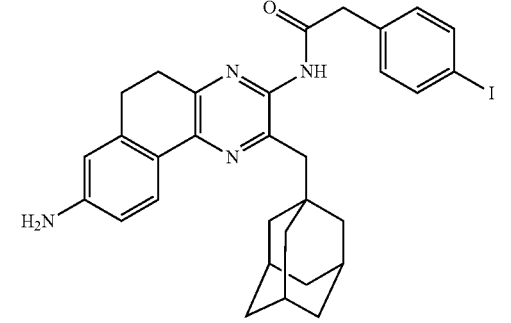

505
-continued
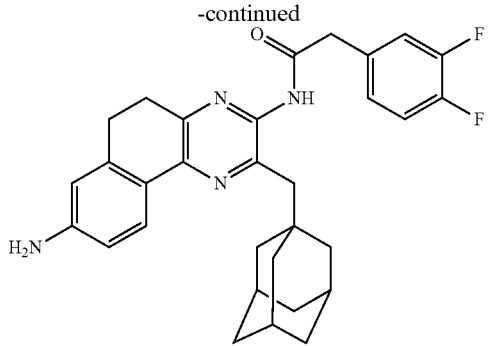
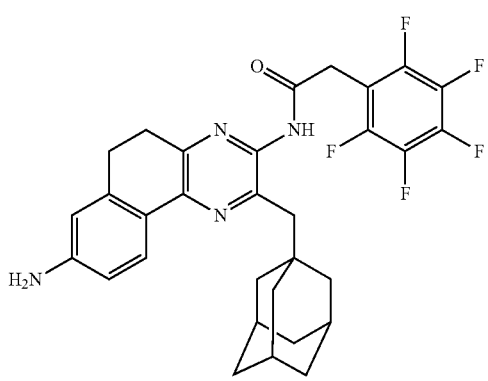
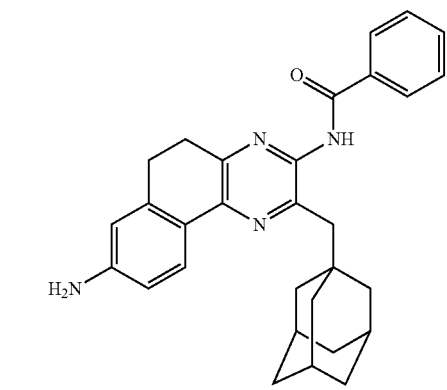
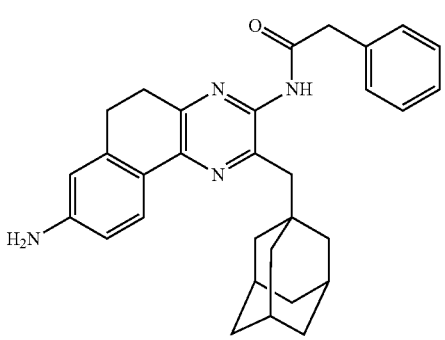
506
-continued
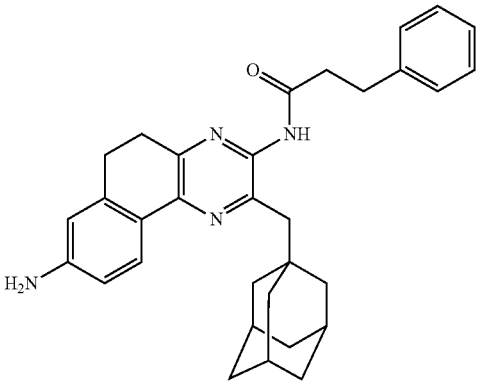
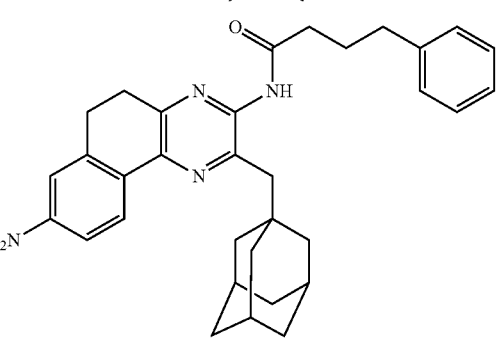
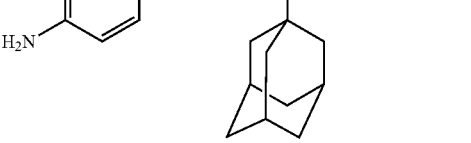
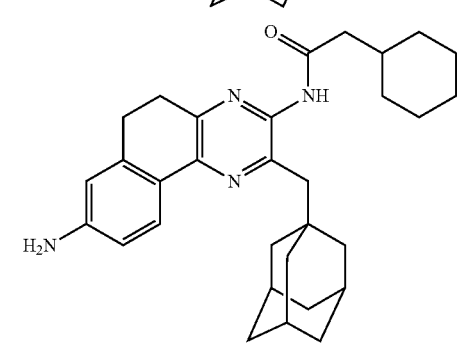
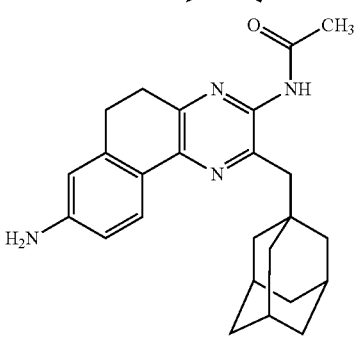

507
-continued
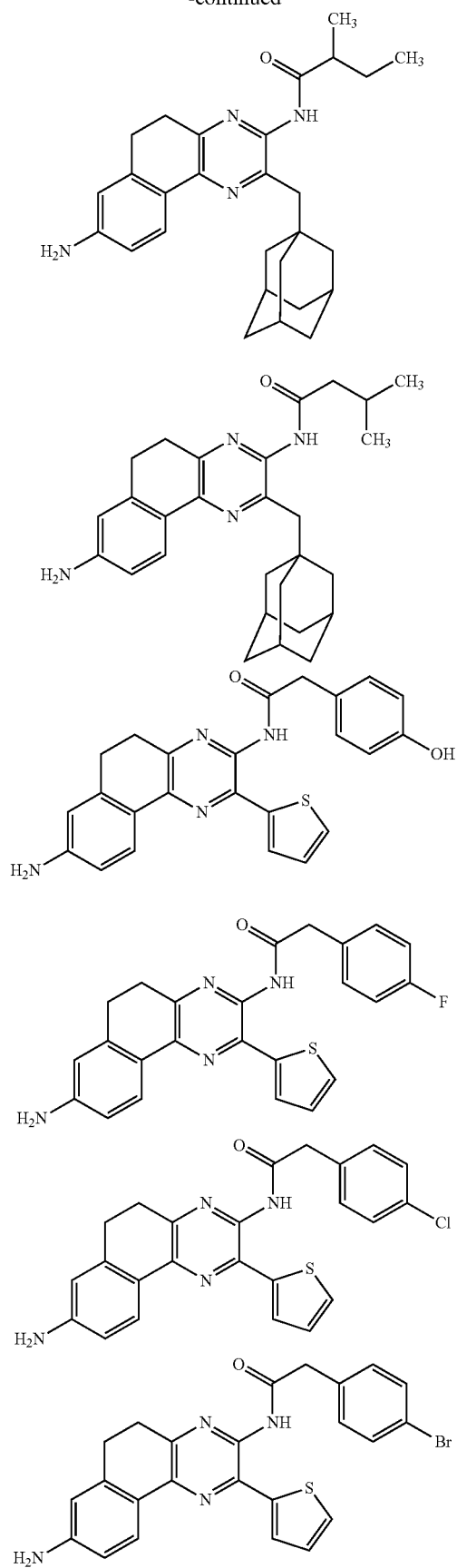
508
-continued
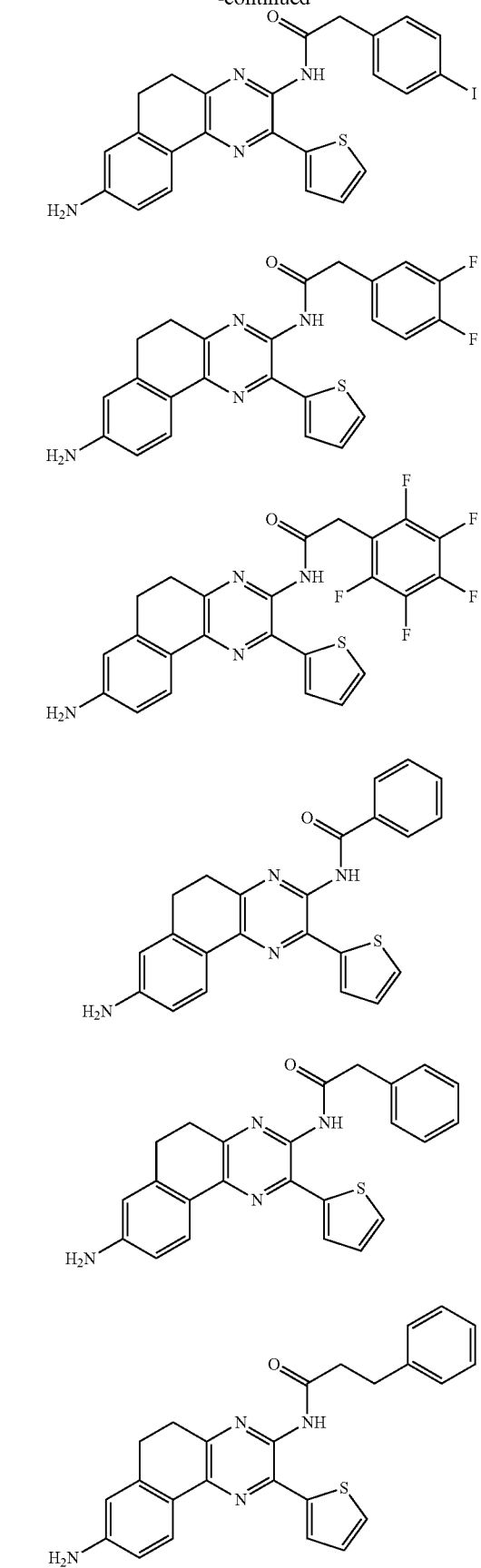

509
-continued
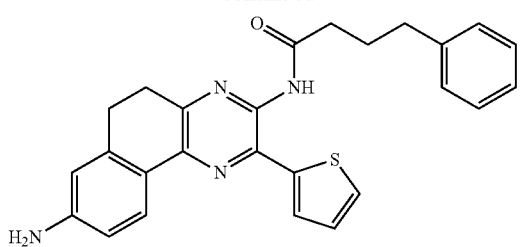
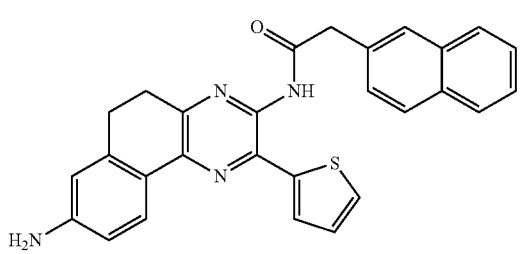
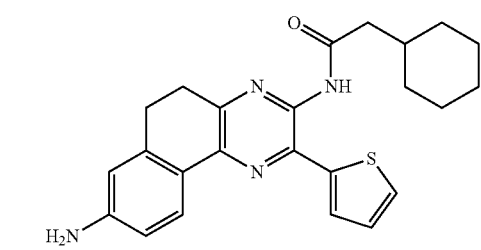
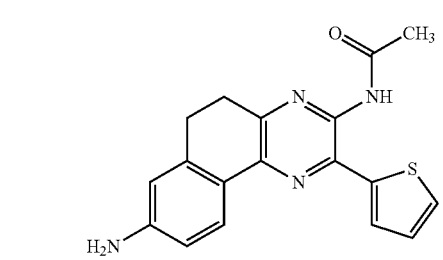
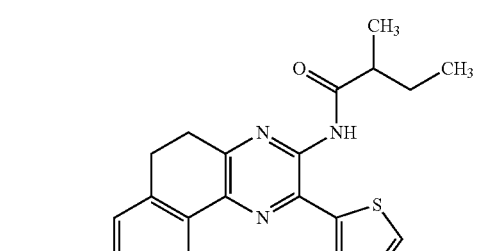
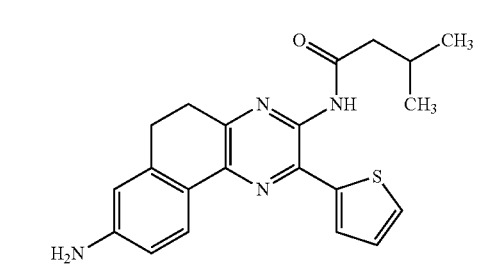
510
-continued
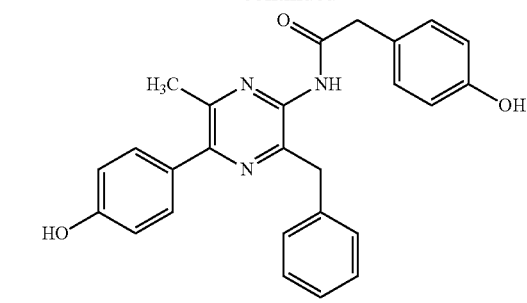
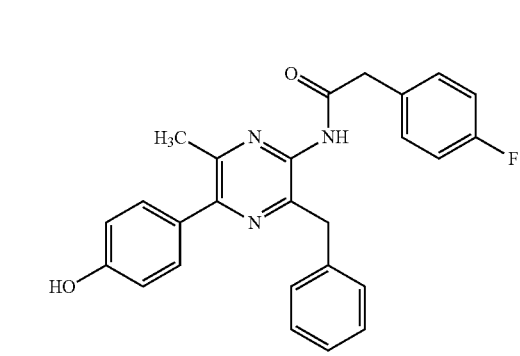
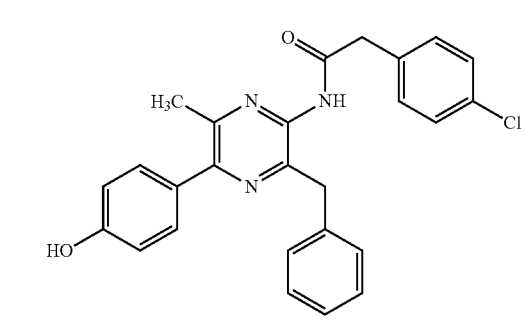
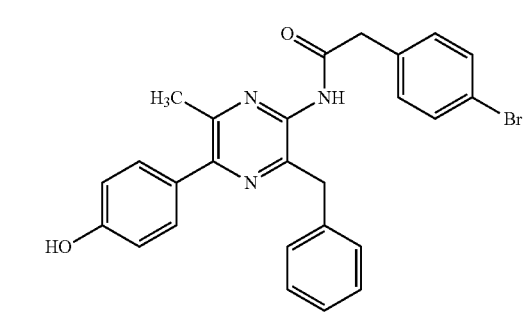
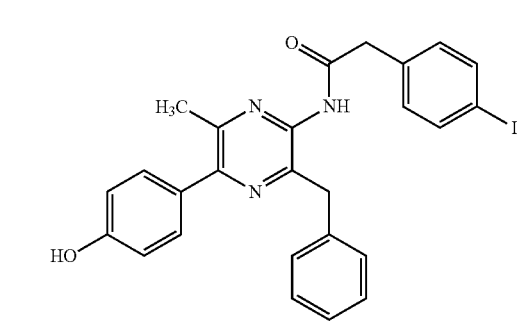

511
-continued
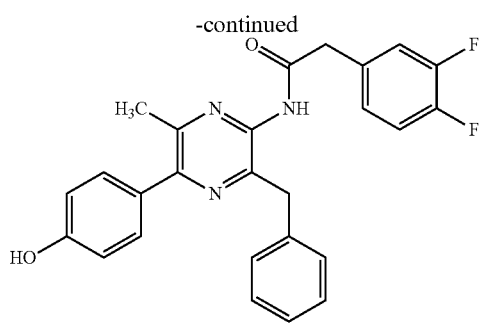
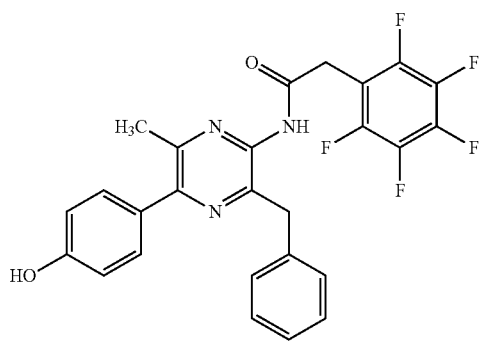
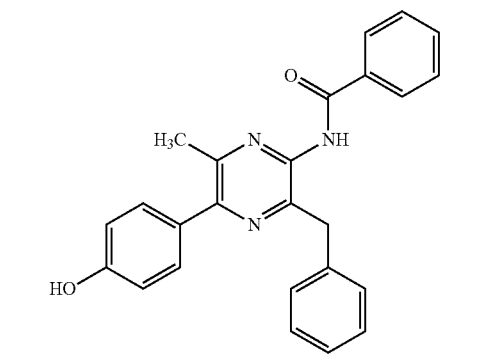
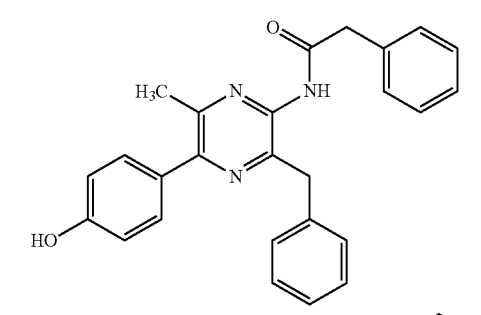
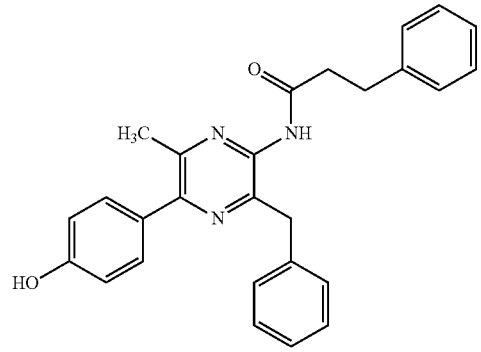
512
-continued
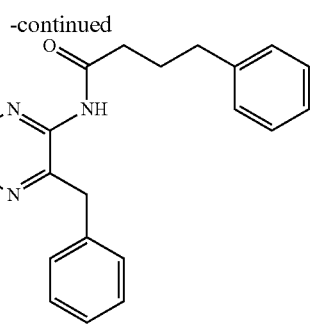
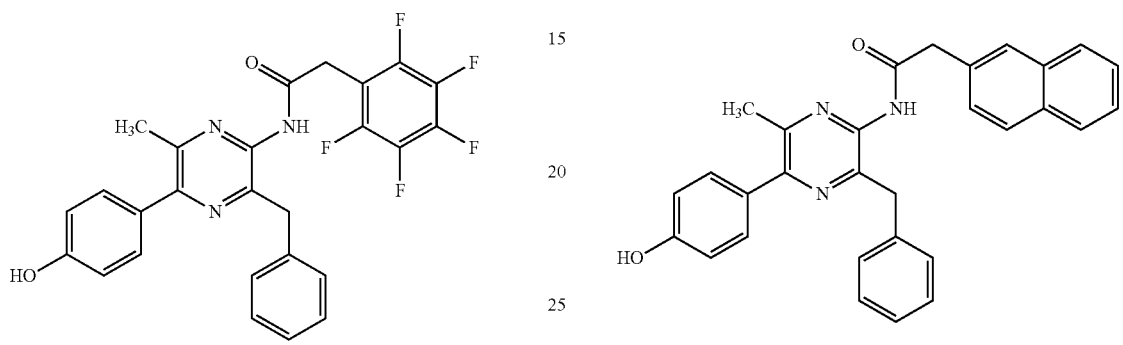
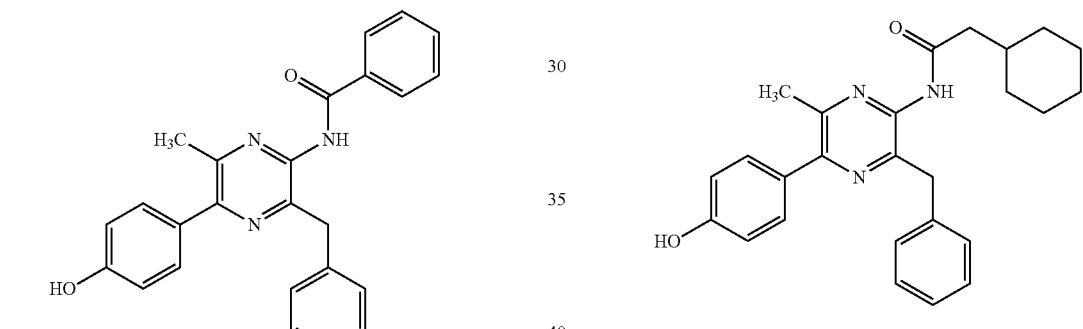
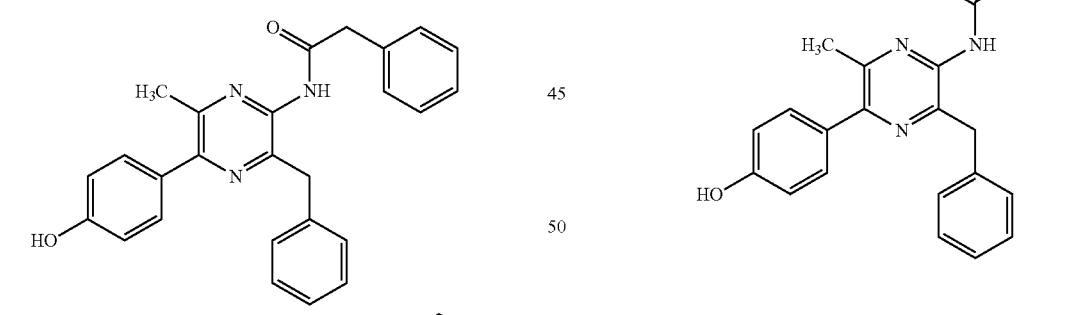
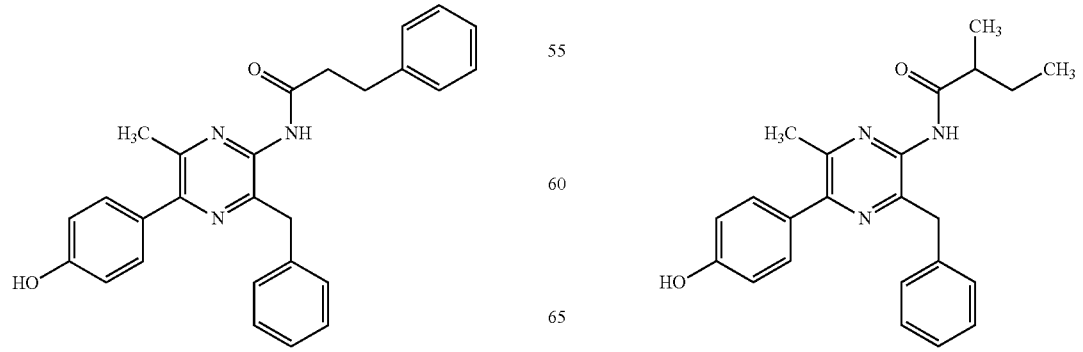

513
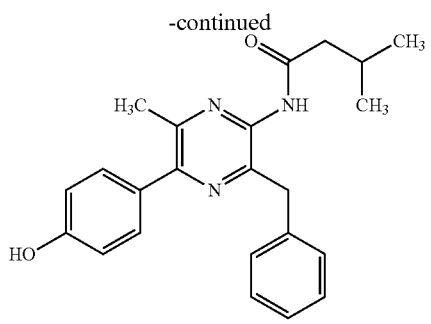
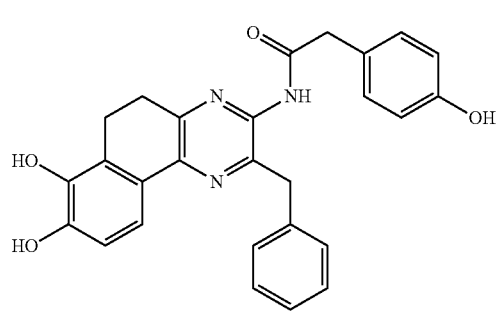
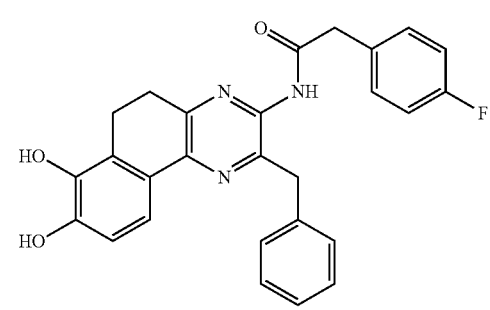
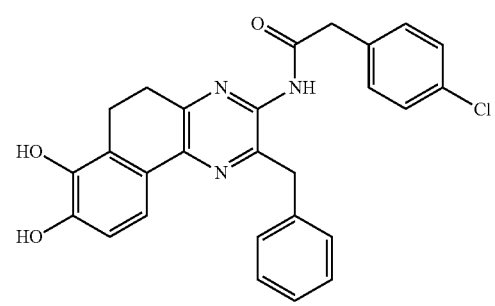
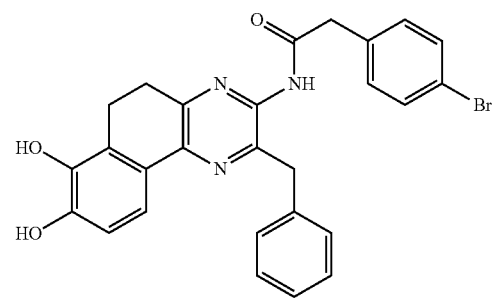
514
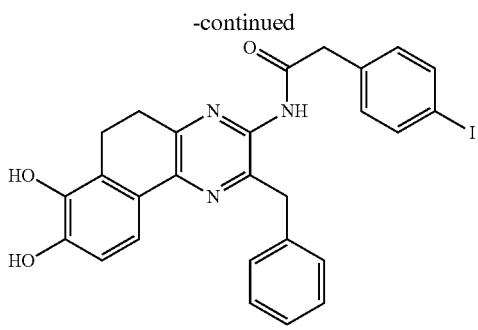
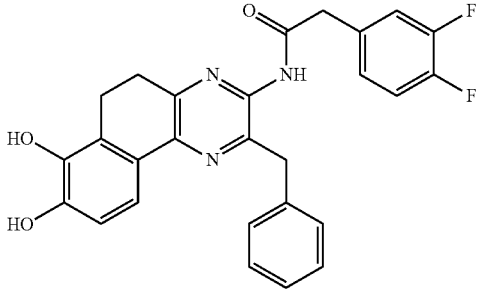
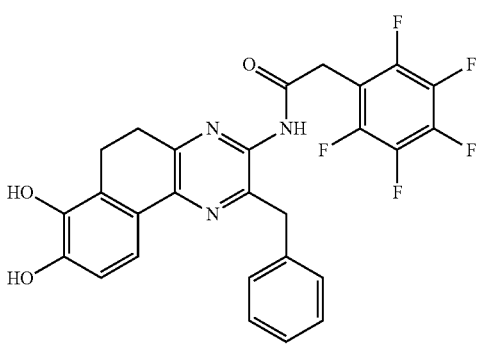
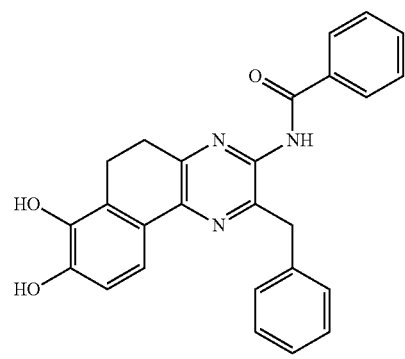
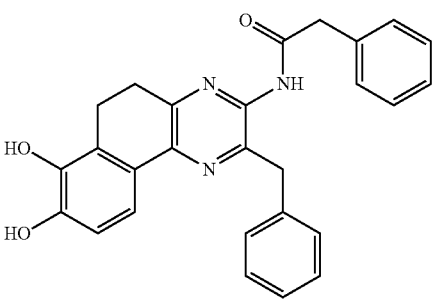

515
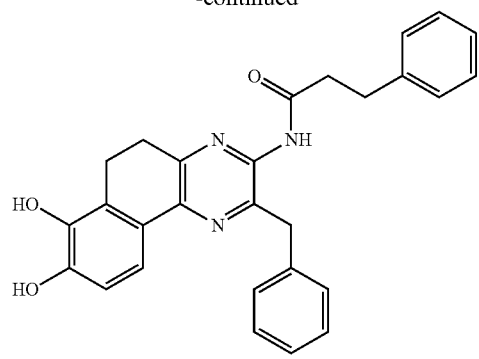
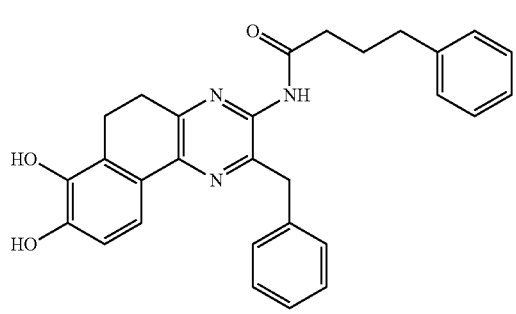
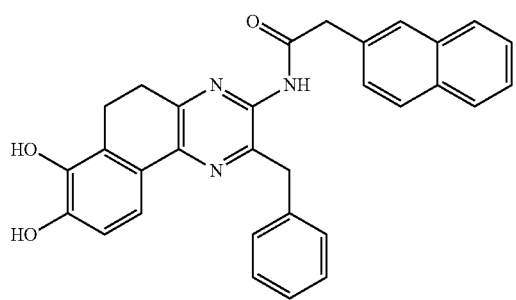
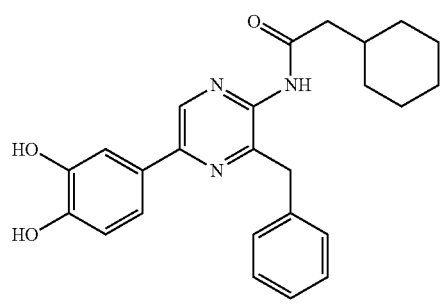
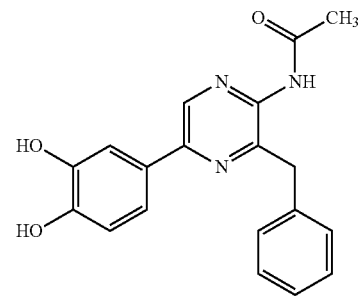
516
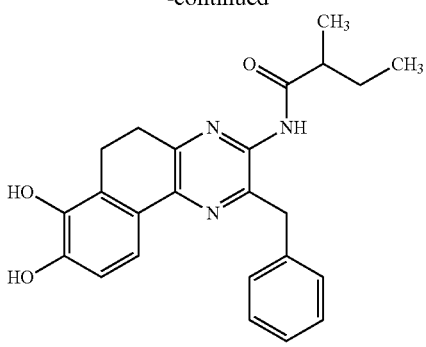
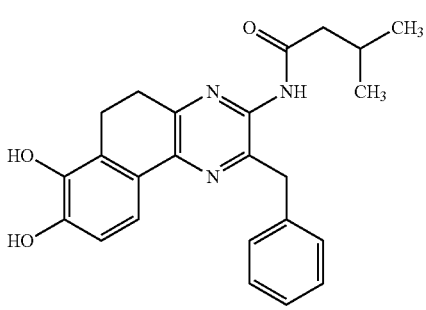
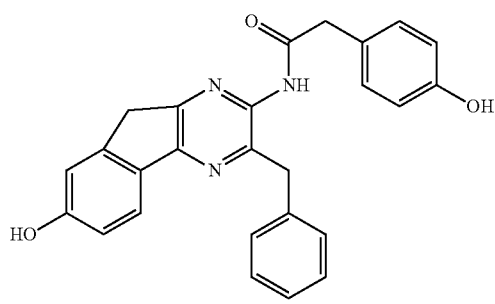
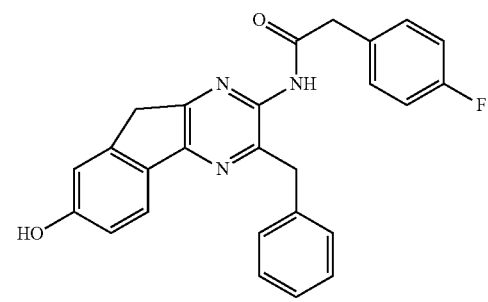
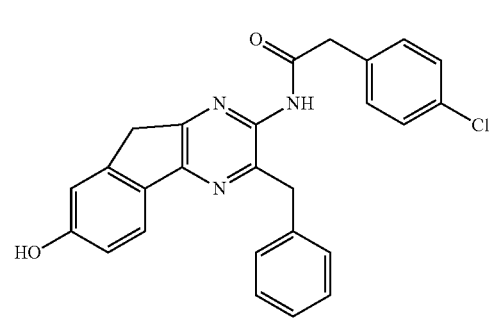

517
-continued
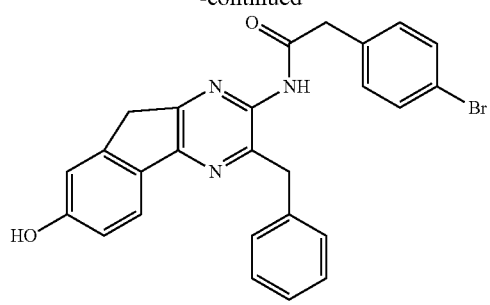
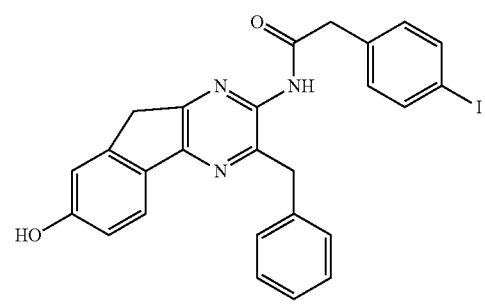
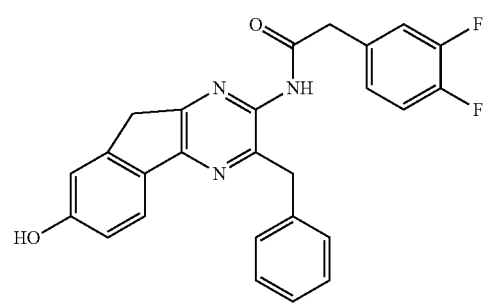
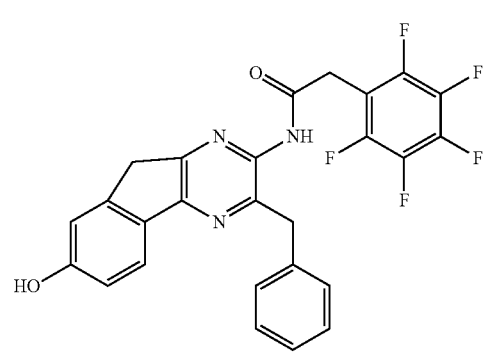
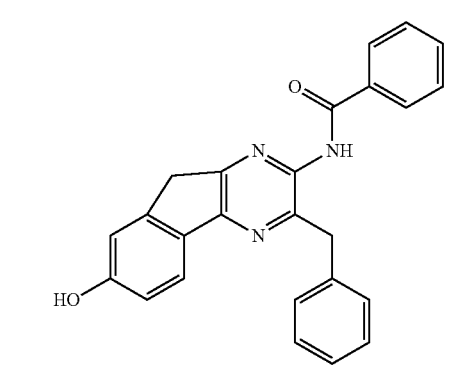
518
-continued
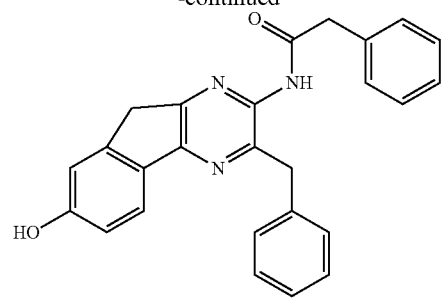
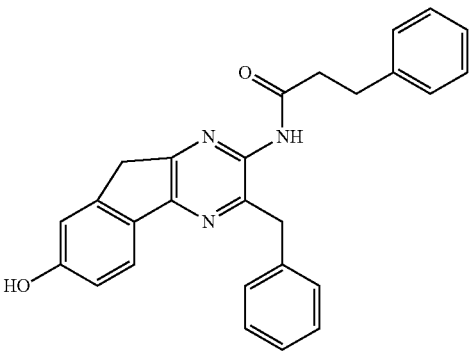
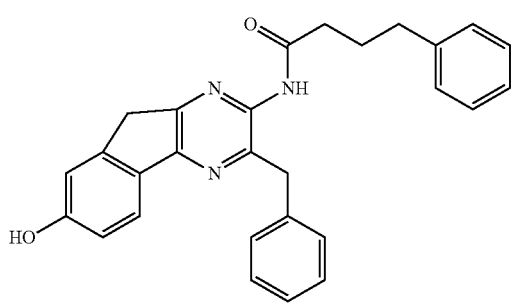
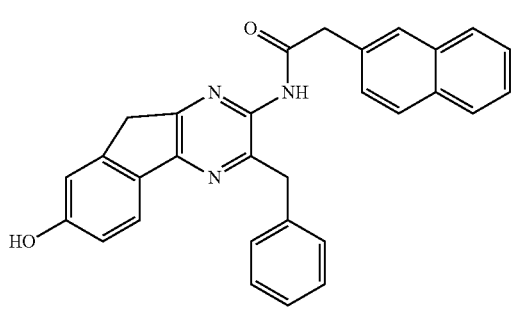
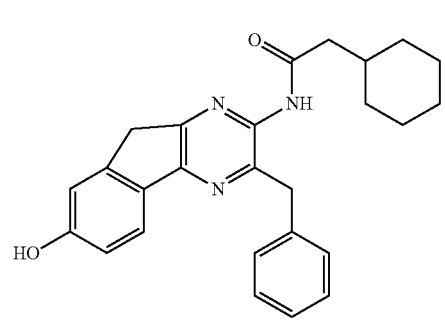

519
-continued
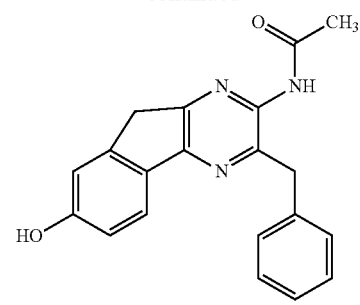
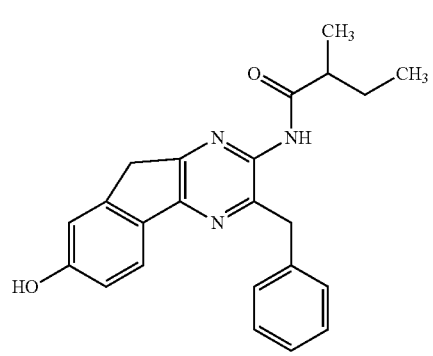
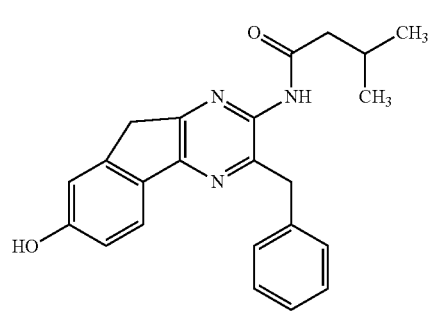
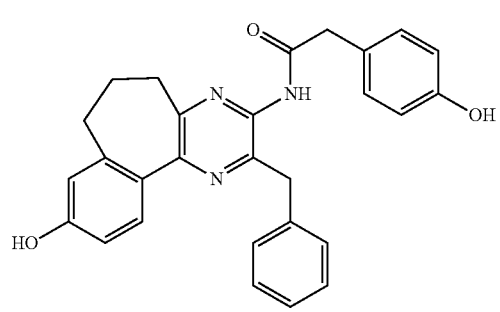
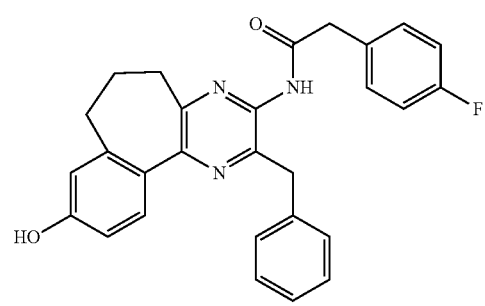
520
-continued
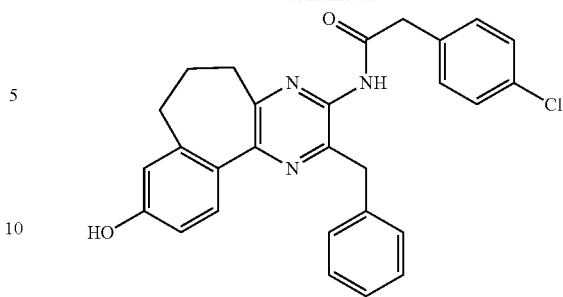
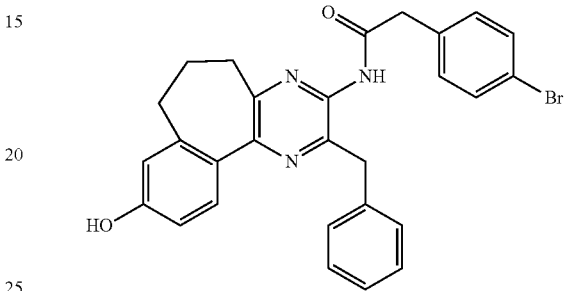
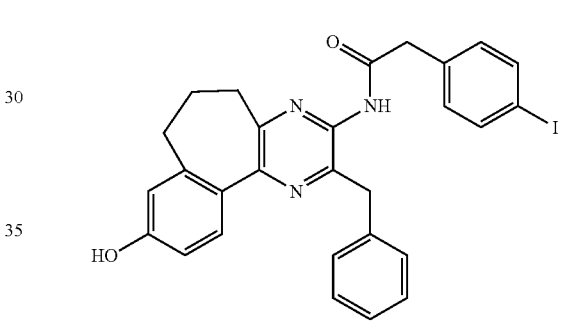
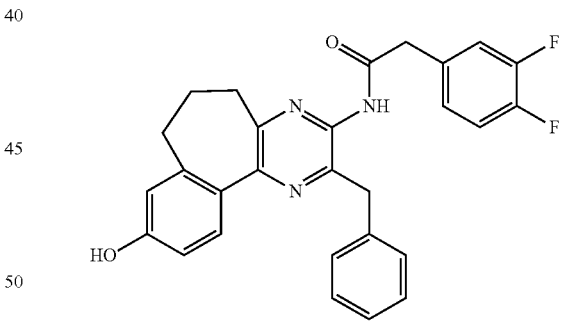
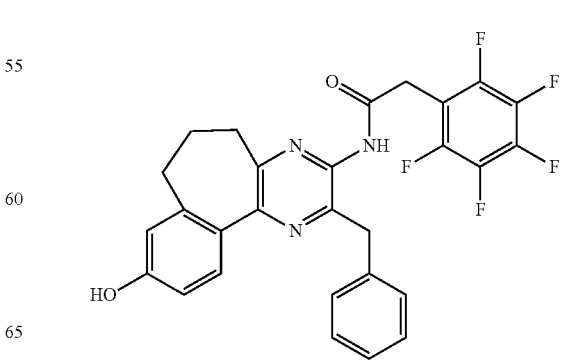

521
-continued
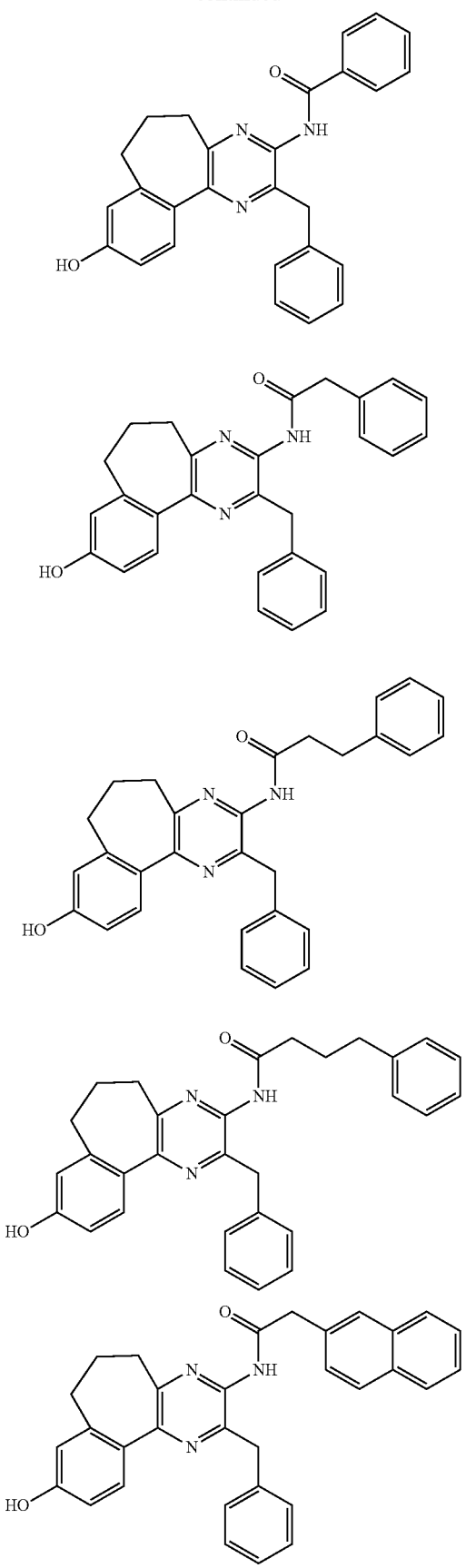
522
-continued
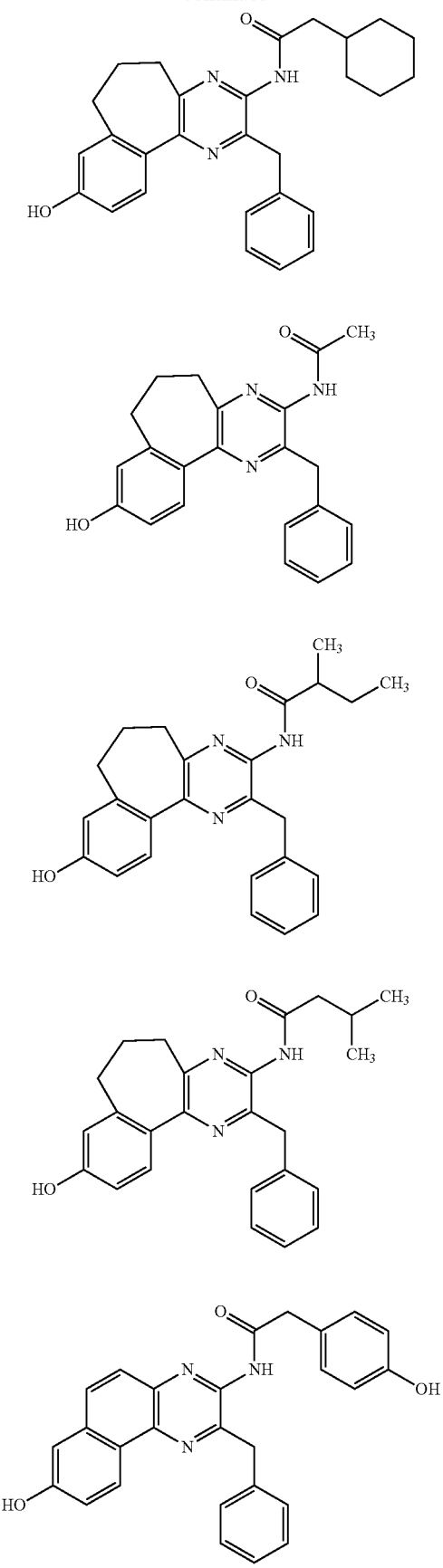

523
-continued
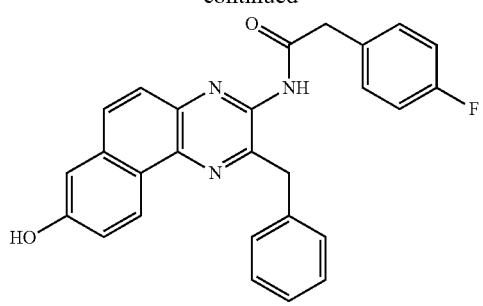
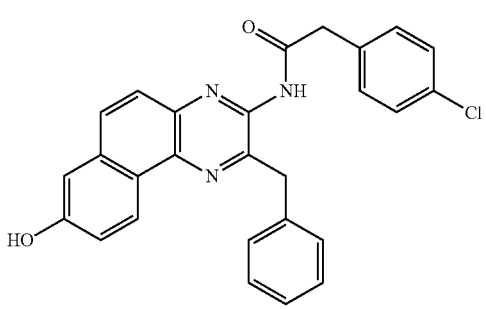
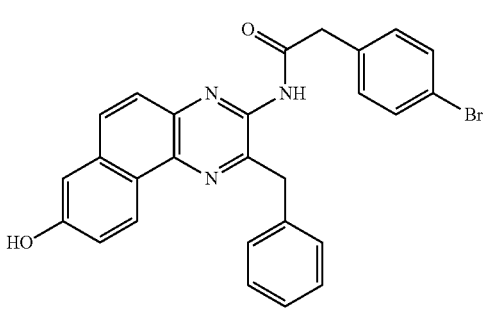
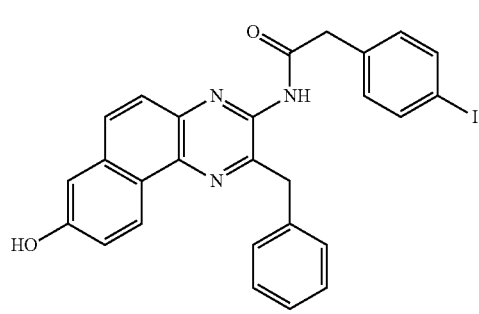
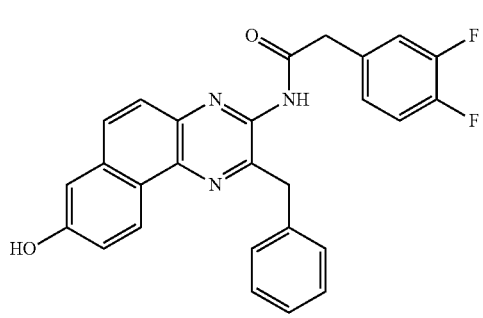
524
-continued
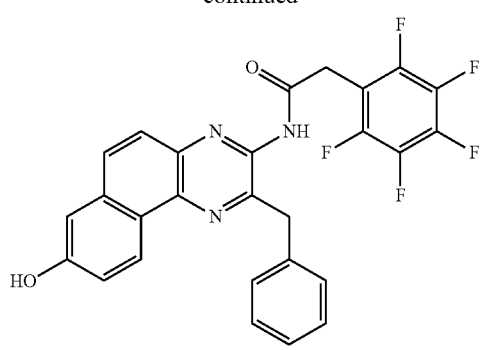
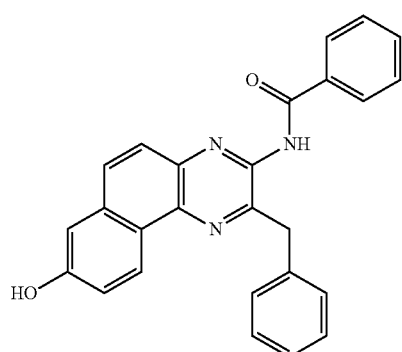
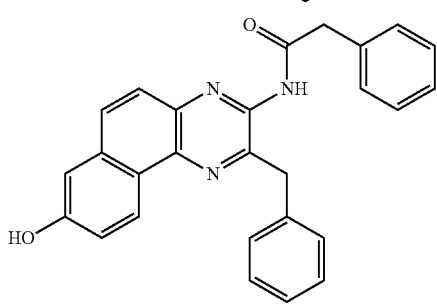
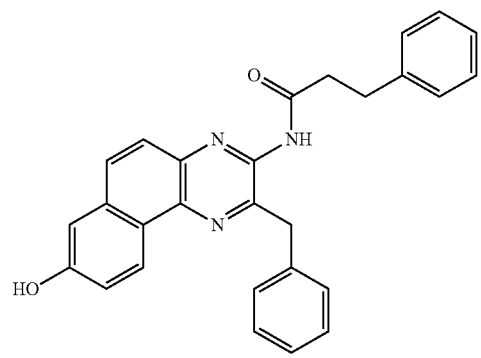
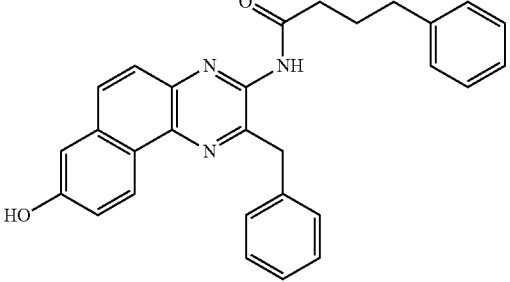

-continued

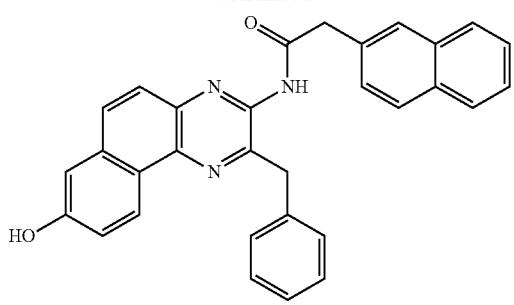

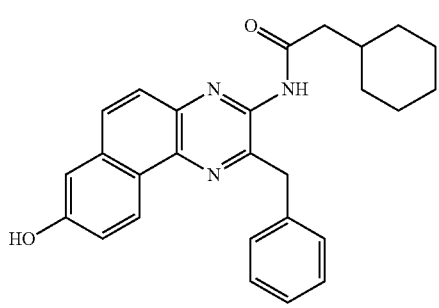

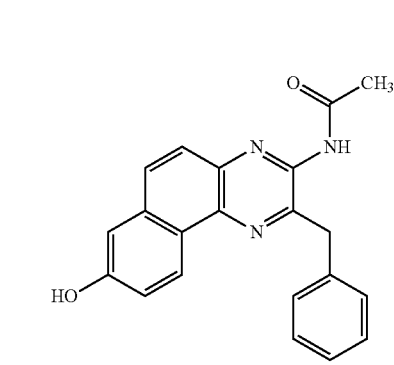

-continued

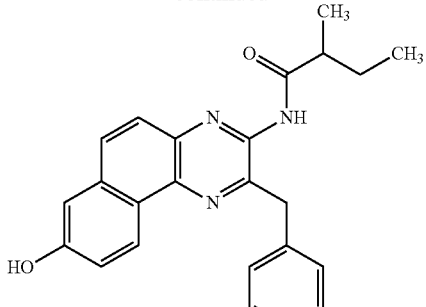

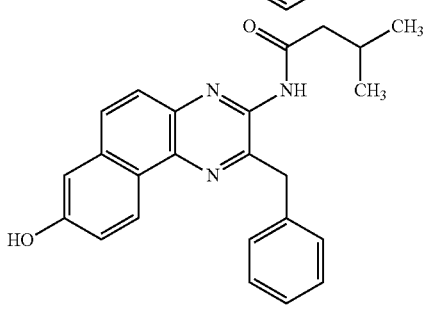

INDUSTRIAL APPLICABILITY

The fluorescent protein having chemiluminescence activity according to the present invention has fluorescence-generating ability together with chemiluminescence activity, which emits light by oxidizing a luminescent substrate as a catalyst. This fluorescent protein can be used, for example, as a photogen in the field of amusement, or a marker in biological experiments. By using one or both of chemiluminescence and fluorescence as a marker, applications in wide range of fields can be expected.

The fluorescent substance (gFP) that does not contain calcium etc. of the present invention can be converted immediately into a calcium-binding photoprotein by reacting with coelenterazine. It can be applied to wide-ranging fields as a marker by detecting one or both of instantaneous luminescence and fluorescence due to calcium in biological experiments.

---

The invention claimed is:

1. An isolated fluorescent protein having chemiluminescence activity, comprising in a complex an apoprotein that is a component of a calcium-binding photoprotein, a coelenteramide or an analog thereof, and a calcium ion or a divalent or trivalent ion that can be substituted for the calcium ion;
   wherein the coelenteramide remains coordinated inside the apoprotein,
   wherein the calcium ion or the divalent or trivalent ion that can be substituted for the calcium ion is bound to EF-hand of the apoprotein, and
   wherein the sulfhydryl groups of the cysteine residues of the apoprotein exists without forming a disulfide bond such that the isolated fluorescent protein maintains chemiluminescence activity.

2. The fluorescent protein having chemiluminescence activity of claim 1, wherein, in the complex of the apoprotein and the coelenteramid or the analog thereof, the ratio of the number of molecules of the apoprotein to the number of molecules of the coelenteramid or the analog thereof is 1:1; and wherein, in the complex of the apoprotein and the calcium ion or the divalent or trivalent ion that can be substituted for the calcium ion, the ratio of the number of molecules of the apoprotein to the number of molecules of the calcium ion or the divalent or trivalent ion is 1:1 to 1:4.

3. The fluorescent protein having chemiluminescence activity of claim 1, wherein the apoprotein is an protein selected from the group consisting of apoaequorin, apoclytin, apoobelin, apomitrocomin, apomineopsin, and apobervoin.

4. The fluorescent protein having chemiluminescence activity of claim 1, wherein the apoprotein is an apoaequorin having the amino acid sequence shown in SEQ ID NO: 1 or a mutant apoaequorin in which one or more amino acids are deleted, substituted, or added in the sequence shown in SEQ ID NO: 1.

5. The fluorescent protein having chemiluminescence activity of claim 1, wherein the apoprotein is an apoobelin having the amino acid sequence shown in SEQ ID NO: 2 or a mutant apoobelin in which one or more amino acids are deleted, substituted, or added in the sequence shown in SEQ ID NO: 2.

6. The fluorescent protein having chemiluminescence activity of claim 1, wherein the apoprotein is an apoclytin having the amino acid sequence shown in SEQ ID NO: 3 or a mutant apoclytin in which one or more amino acids are deleted, substituted, or added in the sequence shown in SEQ ID NO: 3.

7. The fluorescent protein having chemiluminescence activity of claim 1, wherein the apoprotein is an apomitrocomin having the amino acid sequence shown in SEQ ID NO: 4 or a mutant apomitrocomin in which one or more amino acids are deleted, substituted, or added in, the sequence shown in SEQ ID NO: 4.

8. An isolated fluorescent protein having chemiluminescence activity, comprising in a complex an apoprotein that is a component of a calcium-binding photoprotein, a coelenteramid or an analog thereof, and a calcium ion or a divalent or trivalent ion that can be substituted for the calcium ion,
   wherein the coelenteraminde or the analog thereof is represented by the following formula (1) or (2):

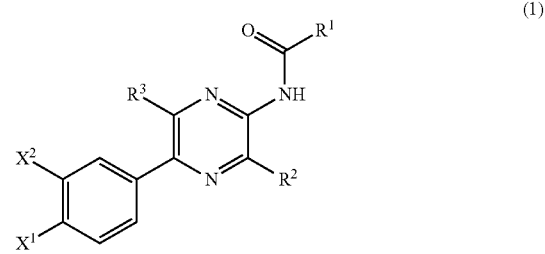

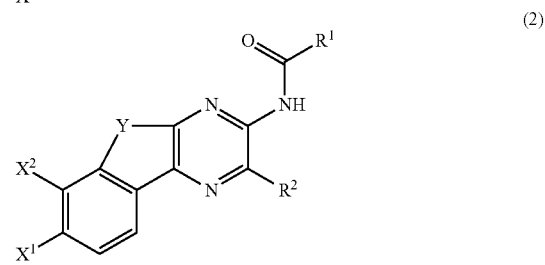

wherein
   $R^1$ is a substituted or unsubstituted aryl group, a substituted or unsubstituted arylated alkyl group, or a straight or branched chain alkyl group that may be substituted by an aliphatic cyclic group;
   $R^2$ is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group;
   $R^3$ is a hydrogen atom, a substituted or unsubstituted alkyl group;
   $X^1$ is a hydrogen atom, a hydroxyl group, a halogen atom, an alkoxyl group, or an amino group;
   $X^2$ is a hydrogen atom or a hydroxyl group; and
   is a divalent hydrocarbon group having 1 to 4 carbon atoms;
   wherein the coelenteraminde remains coordinated inside the apoprotein,
   wherein the calcium ion or the divalent or trivalent ion that can be substituted for the calcium ion is bound to an EF-hand of the apoprotein, and
   wherein the sulfhydryl groups of the cysteine residues of the apoprotein exists without forming a disulfide bond such that the isolated fluorescent protein maintains chemiluminescence activity.

9. The fluorescent protein having chemiluminescence activity of claim 8,
wherein, in the formula (1) or (2),
$R^1$ is an unsubstituted aryl group, an unsubstituted arylated alkyl group, an arylated alkyl group substituted by a hydroxyl group or a halogen atom, or a straight or branched chain alkyl group that may be substituted by a cyclohexyl group;
$R^2$ is an unsubstituted aryl group, an aryl group substituted by a hydroxyl group, an unsubstituted arylated alkyl group, an arylated alkyl group substituted with a hydroxyl group, an unsubstituted aryl alkenyl group, an unsubstituted straight or branched chain alkyl group, a straight chain alkyl group that may be substituted by an aliphatic cyclic group, a branched chain alkenyl group, a heterocyclic group containing sulfur;
$R^3$ is a hydrogen atom, a methyl group, or 2-hydroxyethyl group;
$X^1$ is a hydrogen atom, a hydroxyl group, a fluorine atom, a methoxy group, or an amino group; and
Y is a methylene group, ethylene group, a propylene group, or a vinylene group.

10. The fluorescent protein (bFP) having chemiluminescence activity of claim 8,
wherein, in the formula (1) or (2),
$R^1$ is a phenyl group, a benzyl group, a p-hydroxybenzyl group, a p-fluorobenzyl group, a p-chlorobenzyl group, a p-bromobenzyl group, a p-iodinebenzyl group, a 3,4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group; and
$R^2$ is a phenyl group, a p-hydroxy phenyl group, a benzyl group, an <alpha>-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentyl ethyl group, or a thiophene-2-yl group.

11. The fluorescent protein having chemiluminescence activity of claim 1, wherein the divalent or trivalent ion that can be substituted for the calcium ion is one selected from the group consisting of a strontium ion and a lead ion.

12. A method for detecting a target substance, comprising:
a step of binding a ligand for the target substance to a fluorescent protein having chemiluminescence activity to provide a ligand bound fluorescent protein having chemiluminescence activity, wherein the fluorescent protein comprises in a complex an apoprotein that is a component of a calcium-binding photoprotein, a coelenteramide or an analog thereof, and a calcium ion or a divalent or trivalent ion that can be substituted for the calcium ion,
a step of binding the ligand bound fluorescent protein having chemiluminescence activity to the target substance to be bound via the ligand,
a step of emitting light by adding a coelenterazine or an analog thereof, and
a step of detecting the emitted light;
wherein the coelenteramide remains coordinated inside the apoprotein,
wherein the calcium ion or the divalent or trivalent ion that can be substituted for the calcium ion is bound to an EF-hand of the apoprotein, and
wherein the sulfhydryl groups of the cysteine residues of the apoprotein exists without forming a disulfide bond such that the fluorescent protein maintains chemiluminescence activity.

13. A method for enhancing thermal stability of a fluorescent protein having chemiluminescence activity, wherein the fluorescent protein comprises in a complex an apoprotein that is a component of a calcium-binding photoprotein, a coelenteramide or an analog thereof, and a calcium ion or a divalent or trivalent ion that can be substituted for the calcium ion,
wherein a reducing agent is added to a solution in which the fluorescent protein is dissolved;
wherein the coelenteramide remains coordinated inside the apoprotein; wherein the calcium ion or the divalent or trivalent ion that can be substituted for the calcium ion is bound to an EF-hand of the apoprotein, and
wherein the sulflydryl group of the cysteine residues of the apoprotein exists without forming a disulfide bond such that the fluorescent protein maintains chemiluminescence activity.

14. The method for enhancing thermal stability of claim 13, wherein the reducing agent is dithiothreitol or mercaptoethanol.

15. A chemiluminescence method, comprising a step of reacting a coelenterazine or an analog thereof with a fluorescent protein, wherein the fluorescent protein comprises in a complex an apoprotein that is a component of a calcium-binding photoprotein, a coelenteramide or an analog thereof, and a calcium ion or a divalent or trivalent ion that can be substituted for the calcium ion;
wherein the coelenteramide or the analog thereof remains coordinated inside the apoprotein;
wherein the calcium ion or the divalent or trivalent ion that can be substituted for the calcium ion is bound to an EF-hand of the apoprotein, and
wherein the sulflydryl group of the cysteine residues of the apoprotein exists without forming a disulfide bond such that the fluorescent protein maintains chemiluminescence activity.

16. The chemiluminescence method of claim 15, wherein the coelenterazine or the analog thereof is made to react in the presence of a reducing agent.

17. The chemiluminescence method of claim 15, wherein the coelenterazine or the analog thereof is represented in the following formula (3) or (4):

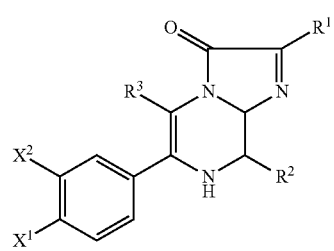

(3)

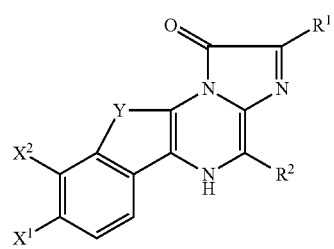

(4)

wherein
$R^1$ is a substituted or unsubstituted aryl group, a substituted or unsubstituted arylated alkyl group, or a straight or branched chain alkyl group that may be substituted by an aliphatic cyclic group;

R² is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group;

R³ is a hydrogen atom, a substituted or unsubstituted alkyl group;

$X^1$ is a hydrogen atom, a hydroxyl group, a halogen atom, an alkoxyl group, or an amino group;

$X^2$ is a hydrogen atom or a hydroxyl group; and

Y is a divalent hydrocarbon group having 1 to 4 carbon atoms.

18. The chemiluminescence method of claim 17, wherein, in the formula (3) or formula (4), R¹ is an unsubstituted aryl group, an unsubstituted arylated alkyl group, an arylated alkyl group substituted by a hydroxyl group or a halogen atom, or a straight or branched chain alkyl group that may be substituted by a cyclohexyl group;

R² is an unsubstituted aryl group, an aryl group substituted by a hydroxyl group, an unsubstituted arylated alkyl group, an arylated alkyl group substituted with a hydroxyl group, an unsubstituted aryl alkenyl group, an unsubstituted straight or branched chain alkyl group, a straight chain alkyl group that may be substituted by an aliphatic cyclic group, a branched chain alkenyl group, a heterocyclic group containing sulfur;

R³ is a hydrogen atom, a methyl group, or 2-hydroxyethyl group;

$X^1$ is a hydrogen atom, a hydroxyl group, a fluorine atom, a methoxy group, or an amino group: and Y is a methylene group, ethylene group, a propylene group, or a vinylene group.

19. The chemiluminescence method of claim 17, wherein, in the formula (3) or (4), R¹ is a phenyl group, a benzyl group, a p-hydroxybenzyl group, a p-fluorobenzyl group, a p-chlorobenzyl group, a p-bromobenzyl group, a p-iodinebenzyl group, a 3,4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group; and R² is a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

20. A luminescence kit comprising the isolated fluorescent protein having chemiluminescence activity of claim 1 and a coelenterazine or an analog thereof.

21. The luminescence kit of claim 20, further comprising a reducing agent.

\* \* \* \* \*

UNITED STATES PATENT AND TRADEMARK OFFICE
CERTIFICATE OF CORRECTION

| | |
|---|---|
| PATENT NO. | : 8,710,195 B2 |
| APPLICATION NO. | : 10/567857 |
| DATED | : April 29, 2014 |
| INVENTOR(S) | : Satoshi Inouye |

Page 1 of 1

It is certified that error appears in the above-identified patent and that said Letters Patent is hereby corrected as shown below:

Title page, item [57] Abstract, Line 15, "emit light" should read as --emits light--.

In the Claims

Claim 3, Col. 531, Line 39, "an protein" should read as --a protein--.

Signed and Sealed this
Sixteenth Day of September, 2014

Michelle K. Lee
*Deputy Director of the United States Patent and Trademark Office*